US010183938B2

(12) United States Patent
Acharya et al.

(10) Patent No.: US 10,183,938 B2
(45) Date of Patent: Jan. 22, 2019

(54) GEMINAL SUBSTITUTED QUINUCLIDINE AMIDE COMPOUNDS AS AGONISTS OF α-7 NICOTONIC ACETYLCHOLINE RECEPTORS

(71) Applicant: AXOVANT SCIENCES GMBH, Basel (CH)

(72) Inventors: Raksha Acharya, Bedford, MA (US); Duane A. Burnett, Wayland, MA (US); Matthew Gregory Bursavich, Needham, MA (US); Andrew Simon Cook, Stow, MA (US); Bryce Alden Harrison, Framingham, MA (US); Gerhard Koenig, Newton, MA (US); Andrew J. Mcriner, Melrose, MA (US)

(73) Assignee: Axovant Sciences GmbH, Basel (CH)

( * ) Notice: Subject to any disclaimer, the term of this patent is extended or adjusted under 35 U.S.C. 154(b) by 0 days.

(21) Appl. No.: 15/536,073

(22) PCT Filed: Dec. 14, 2015

(86) PCT No.: PCT/US2015/065497
§ 371 (c)(1),
(2) Date: Jun. 14, 2017

(87) PCT Pub. No.: WO2016/100184
PCT Pub. Date: Jun. 23, 2016

(65) Prior Publication Data
US 2017/0369486 A1 Dec. 28, 2017

Related U.S. Application Data

(60) Provisional application No. 62/167,706, filed on May 28, 2015, provisional application No. 62/092,702, filed on Dec. 16, 2014.

(51) Int. Cl.
*C07D 453/02* (2006.01)
*A61K 31/519* (2006.01)
*C07D 519/00* (2006.01)

(52) U.S. Cl.
CPC .......... *C07D 453/02* (2013.01); *A61K 31/519* (2013.01); *C07D 519/00* (2013.01)

(58) Field of Classification Search
CPC ................................................... C07D 453/02
USPC ........................................................ 514/305
See application file for complete search history.

(56) References Cited

U.S. PATENT DOCUMENTS

| 3,666,767 A | 5/1972 | Wittekind et al. |
| 3,835,142 A | 9/1974 | Wittekind et al. |
| 4,863,919 A | 9/1989 | Smith |
| 5,444,068 A | 8/1995 | Heitsch et al. |
| 5,635,525 A | 6/1997 | Heitsch et al. |
| 5,889,002 A | 3/1999 | Nielsen et al. |
| 5,935,585 A | 8/1999 | Bernardon et al. |
| 6,171,603 B1 | 1/2001 | Bernardon et al. |
| 6,225,310 B1 | 5/2001 | Nielsen et al. |
| 6,462,036 B1 | 10/2002 | Doyle et al. |
| 6,624,173 B1 | 9/2003 | Crooks et al. |
| 6,727,070 B2 | 4/2004 | Thomas et al. |
| 6,869,958 B2 | 3/2005 | Li |
| 6,911,543 B2 | 6/2005 | Walker et al. |
| 7,019,011 B2 | 3/2006 | Lesuisse et al. |
| 7,071,216 B2 | 7/2006 | Renhowe et al. |
| 7,166,629 B2 | 1/2007 | Lesuisse et al. |
| 7,176,198 B2 | 2/2007 | Piotrowski et al. |
| 7,196,109 B2 | 3/2007 | Lesuisse et al. |
| 7,214,686 B2 | 5/2007 | Bencherif et al. |
| 7,241,773 B2 | 7/2007 | Ji et al. |
| 7,253,196 B2 | 8/2007 | Henriksson et al. |
| 7,371,862 B2 | 5/2008 | Vanotti et al. |
| 7,388,118 B2 | 6/2008 | Romero et al. |
| 7,407,981 B2 | 8/2008 | Lesuisse et al. |
| 7,423,150 B2 | 9/2008 | Costales et al. |
| 7,455,978 B2 | 11/2008 | Thomas et al. |
| 7,514,450 B2 | 4/2009 | Peters et al. |
| 7,582,669 B2 | 9/2009 | Lesuisse et al. |
| 7,629,374 B2 | 12/2009 | Lesuisse et al. |
| 7,652,010 B2 | 1/2010 | Peters et al. |
| 7,674,899 B2 | 3/2010 | Peters et al. |

(Continued)

FOREIGN PATENT DOCUMENTS

| EP | 0327335 | 10/1992 |
| EP | 0327335 B1 | 10/1992 |

(Continued)

OTHER PUBLICATIONS

International Search Report and Written Opinion of the International Searching Authority issued in PCT/US2015/065497, dated Feb. 19. 2016, ISA/US.

(Continued)

*Primary Examiner* — Kahsay Habte
(74) *Attorney, Agent, or Firm* — Jones Day

(57) ABSTRACT

The present invention relates to novel geminal substituted quinuclidine amide compounds, and pharmaceutical compositions of the same, that are suitable as agonists or partial agonists of α7-nAChR, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

15 Claims, 2 Drawing Sheets

(56) References Cited

U.S. PATENT DOCUMENTS

| | | |
|---|---|---|
| 7,683,084 B2 | 3/2010 | Faghih et al. |
| 7,687,515 B2 | 3/2010 | Cai et al. |
| 7,696,238 B2 | 4/2010 | Merle et al. |
| 7,728,010 B2 | 6/2010 | Amiri et al. |
| 7,741,364 B2 | 6/2010 | Faghih et al. |
| 7,750,022 B2 | 7/2010 | Peters et al. |
| 7,786,171 B2 | 8/2010 | Schrimpf et al. |
| 7,795,453 B2 | 9/2010 | Flebner et al. |
| 7,807,700 B2 | 10/2010 | Henriksson et al. |
| 7,872,017 B2 | 1/2011 | Ji et al. |
| 7,897,766 B2 | 3/2011 | Schrimpf et al. |
| 7,902,217 B2 | 3/2011 | Xie et al. |
| 7,902,222 B2 | 3/2011 | Ji et al. |
| 7,994,223 B2 | 8/2011 | Schrimpf et al. |
| 8,076,350 B2 | 12/2011 | Ji et al. |
| 8,163,914 B2 | 4/2012 | Scanio et al. |
| 8,163,915 B2 | 4/2012 | Bunnelle |
| 8,163,916 B2 | 4/2012 | Schrimpf et al. |
| 8,168,791 B2 | 5/2012 | Shi et al. |
| 8,173,667 B2 | 5/2012 | Feuerback et al. |
| 8,273,891 B2 | 9/2012 | Schumacher et al. |
| 8,278,320 B2 | 10/2012 | McDonald et al. |
| 8,288,389 B2 | 10/2012 | Best et al. |
| 8,299,108 B2 | 10/2012 | Amiri et al. |
| 8,309,577 B2 | 11/2012 | Cook et al. |
| 8,314,119 B2 | 11/2012 | Schrimpf et al. |
| 8,383,657 B2 | 2/2013 | Faghih et al. |
| 8,415,382 B2 | 4/2013 | Costales et al. |
| 8,431,575 B2 | 4/2013 | Gohimukkula et al. |
| 8,445,690 B2 | 5/2013 | Bridgewater et al. |
| 8,470,813 B2 | 6/2013 | Faghih et al. |
| 8,481,555 B2 | 7/2013 | Lentz et al. |
| 8,507,516 B2 | 8/2013 | McDonald et al. |
| 8,536,221 B2 | 9/2013 | Mortell et al. |
| 8,541,592 B2 | 9/2013 | Henriksson et al. |
| 8,546,410 B2 | 10/2013 | Liu et al. |
| 8,586,746 B2 | 11/2013 | Schrimpf et al. |
| 8,609,713 B2 | 12/2013 | Faghih et al. |
| 8,614,330 B2 | 12/2013 | Amiri et al. |
| 8,648,085 B2 | 2/2014 | Mittelbiberach et al. |
| 8,686,011 B2 | 4/2014 | Henriksson et al. |
| 8,741,900 B2 | 6/2014 | Gohimukkula et al. |
| 8,778,939 B2 | 7/2014 | Nichols et al. |
| 8,841,289 B2 | 9/2014 | Ratcliffe et al. |
| 8,846,661 B2 | 9/2014 | Schrimpf et al. |
| 8,853,241 B2 | 10/2014 | Ji et al. |
| 8,946,432 B2 | 2/2015 | Sinha et al. |
| 8,980,888 B2 | 3/2015 | Okano et al. |
| 8,980,889 B2 | 3/2015 | Okano et al. |
| 8,987,453 B2 | 3/2015 | Schrimpf et al. |
| 9,012,447 B2 | 4/2015 | Hitchcock et al. |
| 9,045,461 B2 | 6/2015 | Gohimukkula et al. |
| 2002/0028808 A1 | 3/2002 | Hansen |
| 2002/0035106 A1 | 3/2002 | Hansen et al. |
| 2003/0109519 A1 | 3/2003 | Sturis |
| 2003/0125323 A1 | 7/2003 | Sturis |
| 2003/0235583 A1 | 12/2003 | Sturis et al. |
| 2004/0019053 A1 | 1/2004 | Roark |
| 2004/0043983 A1 | 3/2004 | Li |
| 2004/0147522 A1 | 7/2004 | Wong et al. |
| 2004/0192594 A1 | 9/2004 | Reid et al. |
| 2005/0186591 A1 | 8/2005 | Bumcrot et al. |
| 2005/0239853 A1 | 10/2005 | Barf et al. |
| 2005/0245567 A1 | 11/2005 | Peters et al. |
| 2006/0116395 A1 | 6/2006 | Piotrowski et al. |
| 2007/0082350 A1 | 4/2007 | Landfield et al. |
| 2007/0185086 A1 | 8/2007 | Bencherif et al. |
| 2007/0281938 A1 | 12/2007 | Henriksson et al. |
| 2008/0268044 A1 | 10/2008 | Appleby et al. |
| 2009/0005390 A1 | 1/2009 | Peters et al. |
| 2009/0099099 A1 | 4/2009 | Wang et al. |
| 2009/0170869 A1 | 7/2009 | Best et al. |
| 2009/0197860 A1 | 8/2009 | Ji et al. |
| 2009/0312356 A1 | 12/2009 | De Micheli et al. |
| 2010/0298289 A1 | 11/2010 | Raphy et al. |
| 2010/0305089 A1 | 12/2010 | Ji et al. |
| 2011/0014283 A1 | 1/2011 | Clarke et al. |
| 2011/0020447 A1 | 1/2011 | Clarke et al. |
| 2011/0082107 A1 | 4/2011 | Henriksson et al. |
| 2011/0189280 A1 | 8/2011 | Clarke et al. |
| 2011/0262407 A1 | 10/2011 | Bencherif et al. |
| 2012/0035178 A1 | 2/2012 | Cook et al. |
| 2012/0035189 A1 | 2/2012 | Cook et al. |
| 2012/0065219 A1 | 3/2012 | Ji et al. |
| 2012/0190704 A1 | 7/2012 | Schrimpf et al. |
| 2012/0190706 A1 | 7/2012 | Scanio et al. |
| 2012/0196890 A1 | 8/2012 | Bunnelle |
| 2012/0202804 A1 | 8/2012 | Hatfield et al. |
| 2012/0202828 A1 | 8/2012 | Hatfield et al. |
| 2012/0245195 A1 | 9/2012 | Chen et al. |
| 2012/0288501 A1 | 11/2012 | Amiri et al. |
| 2013/0123278 A1 | 5/2013 | Edwards et al. |
| 2013/0131064 A1 | 5/2013 | Cook et al. |
| 2013/0217683 A1 | 8/2013 | Xie et al. |
| 2013/0224195 A1 | 8/2013 | Costales et al. |
| 2013/0225584 A1 | 8/2013 | Andreotti et al. |
| 2013/0231365 A1 | 9/2013 | Koenig |
| 2013/0252901 A1 | 9/2013 | Mediannikov et al. |
| 2013/0310419 A1 | 11/2013 | Sinha et al. |
| 2013/0331387 A1 | 12/2013 | Sinha et al. |
| 2014/0018327 A1 | 1/2014 | Sinha et al. |
| 2014/0024644 A1 | 1/2014 | Hitchcock et al. |
| 2014/0221377 A1 | 8/2014 | Cook et al. |
| 2014/0234270 A1 | 8/2014 | Bencherif et al. |
| 2015/0094309 A1 | 4/2015 | Cook et al. |
| 2015/0132327 A1 | 5/2015 | Okano et al. |
| 2015/0133448 A1 | 5/2015 | Okano et al. |
| 2015/0158867 A1 | 6/2015 | Schrimpf et al. |
| 2015/0166536 A1 | 6/2015 | Okano et al. |
| 2015/0275303 A1 | 10/2015 | Feuerbach et al. |

FOREIGN PATENT DOCUMENTS

| | | |
|---|---|---|
| JP | 3087763 | 9/2000 |
| JP | 2003-267977 | 9/2003 |
| WO | WO 1993/009116 | 5/1993 |
| WO | WO 2001/066546 | 9/2001 |
| WO | WO 2002/100858 | 12/2002 |
| WO | WO 2004/022544 | 3/2004 |
| WO | WO 2004/039366 | 5/2004 |
| WO | WO 2004/039815 | 5/2004 |
| WO | WO-2004039366 A1 | 5/2004 |
| WO | WO 2004/062662 | 7/2004 |
| WO | WO 2007/080191 | 7/2007 |
| WO | WO 2008/000469 | 1/2008 |
| WO | WO 2009/017454 | 2/2009 |
| WO | WO 2009/050227 | 4/2009 |
| WO | WO 2009/083526 | 7/2009 |
| WO | WO 2011/036167 | 3/2011 |
| WO | WO 2012/108490 | 8/2012 |
| WO | WO 2013/132380 | 9/2013 |
| WO | WO 2013/174947 | 11/2013 |
| WO | WO 2013/177024 | 11/2013 |
| WO | WO 2014/072957 | 5/2014 |
| WO | WO 2014/083003 | 6/2014 |
| WO | WO 2014/111839 | 7/2014 |
| WO | WO 2014/141091 | 9/2014 |
| WO | WO 2014/195848 | 12/2014 |
| WO | WO 2014/203150 | 12/2014 |
| WO | WO 2015/066371 | 5/2015 |
| WO | WO 2016/100184 | 6/2016 |

OTHER PUBLICATIONS

International Search Report mailed 19 Feb. 2016 for PCT/US2015/065497 (4 pp.).

International Search Report mailed 16 Aug. 2016 for PCT/US2016/036689 (3 pp.).

International Search Report mailed 27 Oct. 2016 for PCT/US2016/046367 (3 pp.).

International Search Report mailed 10 Jan. 2017 for PCT/US2016/056607 (3 pp.).

(56) References Cited

OTHER PUBLICATIONS

European Search Report mailed 26 Apr. 2018 for Ep 15870786.9 (7 pp.).
Compound Summary for Cid 160186, PubChem Open Chemistry Database, Nih U.S. National Library of Medicine, National Center for Biotechnology Information, Entry Creation Date: 11 Jul. 2005.
Marrero, Mario B. et al. "An a7 Nicotinic Acetylcholine Receptor-Selective Agonist Reduces Weight Gain and Metabolic Changes in a Mouse Model of Diabetes," the Journal of Pharmacology and Experimental Therapeutics, 332:1 (1 Jan. 2010) 173-180.
Mazurov, Anatoly et al. "2-(Arylmethyl)-3-substituted Quinuclidines as Selective a7 Nicotinic Receptor Li_gands," Bioorganic & Medicinal Chemistry Letters, 15:8 (15 Apr. 2005) 2073-2077.
Albuquerque, E. X. et al. "Modulation of Nicotinic Receptor Activity in the Central Nervous System: a Novel Approach to the Treatment of Alzheimer Disease," Alzheimer Disease and Associated Disorders, 15:1 (2001) S19-S25.
D'Andrea, Michael R. et al. "Targeting the Alpha 7 Nicotinic Acetylcholine Receptor to Reduce Amyloid accumulation in Alzheimer's Disease Pyramidal Neurons," Current Pharmaceutical Design, 12 (2006) 677-684.
Deutsch, Stephen I. et al. "Progressive Worsening of Adaptive Functions in Down Syndrome May be Mediated by the Complexing of Soluble a(3 Peptides with the Alpha7 Nicotinic Acetylcholine Receptor: Therapeutic Implications," Clinical Neuropharmacology, 26:51_2003) 277-283.
Haydar, Simon N. et al. "Sar and Biological Evaluation of SEN12333/Vvay-317538: Novel Alpha7 Nicotinic Acetylcholine Receptor Agonist," Bioorganic & Medicinal Chemistry, 17 (2009) 5247-5258.
Jenkins, Jeremy L. et al. "A 3D Similarity Method for Scaffold Hopping from Known Drugs or Natural Ligands to New Chemotypes," J. Med. Chem., 47 (2004) 6144-6159.
Jeyarasasingam, G. et al. "Stimulation of Non-Alpha7 Nicotinic Receptors Partially Protects Dopaminergic Neurons from 1-Methyl-4-Phenylpyridinium-Induced Toxicity in Culture," Neuroscience, 109:2 (2002) 275-285.
Nagele, R. G. et al. "Intracellular Accumulation of p-Amyloid1-42 in Neurons is Facilitated by the Alpha7 Nicotinic Acetylcholine Receptor in Alzheimer's Disease," Neuroscience, 11:2 (2002) 199-211.
Nordberg, Agneta "Neuroprotection in Alzheimer's Disease — New Strategies for Treatment," Neurotoxicity Research, 2 (2000) 157-165.
Wang, Hoau-Yan et al. "Dissociating 13-Amyloid from Alpha7 Nicotinic Acetylcholine Receptor by a Novel Therapeutic Agent, S24795, Normalizes Alpha7 Nicotinic Acetylcholine and Nmda Receptor Function in Alzheimer's Disease Brain," the Journal of Neuroscience, 29:35 (Sep. 2, 2009) 10961-10973.

GEMINAL SUBSTITUTED QUINUCLIDINE AMIDE COMPOUNDS AS AGONISTS OF α-7 NICOTONIC ACETYLCHOLINE RECEPTORS

CROSS REFERENCE TO RELATED APPLICATIONS

This application is a U.S. National Phase Application under 35 U.S.C. 371 of International Application No. PCT/US2015/065497 filed on Dec. 14, 2015 and published as WO 2016/100184 A1 on Jun. 23, 2016. This application is based on and claims the benefit of priority from U.S. Provisional Application No. 62/092,702, filed Dec. 16, 2014, and from U.S. Provisional Application No. 62/167,706, filed May 28, 2015. The entire disclosures of all of the above applications are incorporated herein by reference.

FIELD OF THE INVENTION

The present invention relates to novel geminal substituted quinuclidine amide compounds, and pharmaceutical compositions of the same, that are suitable as agonists or partial agonists of α7-nAChR, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

BACKGROUND OF THE INVENTION

The prevalence of cognitive disease, for example dementia in North America, is approximately 6 to 10% of the population, with Alzheimer's disease accounting for a substantial portion of these cases. Many forms of cognitive disease represent a steadily growing medical and social problem of our aging societies around the World. Some believe the main pathological features may relate to intraneuronal neurofibrillary tangles, formation of amyloid beta plaques and/or neurodegeneration of mainly cholinergic and, in later stages, also serotonergic, noradrenergic, and other neurons, resulting in deficiencies of acetylcholine and other neurotransmitters. Some theories suggest that the gradual development of an acetylcholine signaling deficiency may be responsible for the early clinical manifestations of cognitive disease. Consequently, some believe that compounds that improve cholinergic functioning, such as acetylcholine esterase inhibitors may ameliorate the cognitive deficits in patients with cognitive disease. The most widely used acetylcholine esterase inhibitor is donepezil hydrochloride (Aricept®).

Nicotinic acetylcholine receptors (nAChR) form a large family of ion channels which are activated by the messenger acetylcholine which is produced in the body (Galzi and Changeux, Neuropharmacol. 1995, 34, 563-582). A functional nAChR consists of five subunits which may be different (certain combinations of α1-9 and β1-4,γ,δ,ε subunits) or identical (α7-9). This leads to the formation of a diversity of subtypes which differ in the distribution in the muscles, the nervous system and other organs (McGehee and Role, Annu. Rev. Physiol. 1995, 57, 521-546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, Biol. Psychiatry 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., J. Neurosci. 1993, 13, 596-604). The α7 nAChR has a particularly high permeability for calcium ions, modulates neurotransmission, influences the growth of axons and, in this way, modulates neuronal plasticity (Broide and Leslie, Mol. Neurobiol. 1999, 20, 1-16).

WO 2003/055878 describes a variety of agonists of the alpha7 nAChR said to be useful for improving cognition. WO 2003/055878 suggests that certain agonists of the alpha7 nAChR are useful for improving perception, concentration, learning or memory, especially after cognitive impairments like those occurring for example in situations/diseases/syndromes such as mild cognitive impairment, age-associated learning and memory impairments, age-associated memory loss, Alzheimer's disease, schizophrenia and certain other cognitive disorders.

BRIEF SUMMARY OF THE INVENTION

An aspect of the invention provides a geminal substituted quinuclidine amide compound represented by Formula (I):

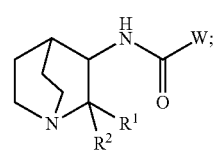

(I)

wherein:
R$^1$ and R$^2$ independently represent a branched or unbranched C$_1$-C$_4$-alkyl radical; or the C(R$^1$)(R$^2$) moiety forms a (3-4 membered)-carbocycle, wherein R$^1$ and R$^2$ taken together represent a C$_2$-C$_3$-alkyl di-radical; wherein the C$_1$-C$_4$-alkyl radical and the C$_2$-C$_3$-alkyl di-radical may be substituted with up to 4 radical substituents comprising: -D, —F, —Cl, —Br, —I, —CN, CH$_3$, CH$_2$CH$_3$, =O, —OR$^3$, or —OCF$_3$;

R$^3$ independently represents —H; a branched or unbranched C$_1$-C$_4$-alkyl radical; C$_3$-C$_4$-cycloalkyl radical; wherein the C$_1$-C$_4$-alkyl radical and the C$_3$-C$_4$-cycloalkyl radical may be substituted with up to 4 radical substituents comprising: -D, —F, —Cl, —Br, —I, —CN, =O, —OH, —OC$_1$-C$_4$-alkyl or —OCF$_3$; and W represents a moiety represented by ring system M-I, M-II, M-III, M-IV, M-V, or M-VI:

M-I

-continued

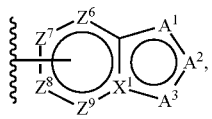
M-II

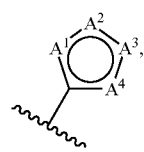
M-III

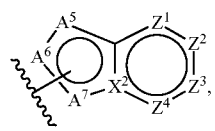
M-IV

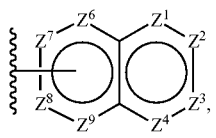
M-V

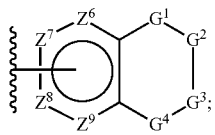
M-VI wherein:
$Z^1$, $Z^2$, $Z^3$, $Z^4$, and $Z^5$ independently represent N or $CR^4$; with the proviso that no more than two of $Z^1$, $Z^2$, $Z^3$, $Z^4$, and $Z^5$ are N;
$R^4$ independently represents —H; -D; —F; —Cl; —Br; —I; —CN; —NO$_2$; —OR$^5$; —N(R$^5$)(R$^6$); —SO$_2$(CH$_2$)$_m$ R$^5$; —(CO)(CH$_2$)$_m$R$^5$; —(CO)N(R$^5$)(R$^6$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; or when adjacent members of $Z^1$, $Z^2$, $Z^3$, $Z^4$, and $Z^5$, is (CR$^4$)(CR$^4$), the (CR$^4$)(CR$^4$) may form a cycle such that the adjacent $R^4$ substituents taken together represents a (3-6 membered)-heteroalkyl di-radical with at least one ring atom of the (3-6 membered)-heteroalkyl di-radical selected from the group consisting of oxygen, nitrogen, and sulfur, with the proviso that when the at least one ring atom is nitrogen, the nitrogen is substituted with —H, a branched or unbranched $C_1$-$C_4$-alkyl radical, a $C_3$-$C_4$-cycloalkyl radical, —(CO)-branched or unbranched $C_1$-$C_4$-alkyl, or —(SO$_2$)-branched or unbranched $C_1$-$C_4$-alkyl, wherein the $C_1$-$C_4$-alkyl radical and the $C_3$-$C_4$-cycloalkyl radical may be substituted with up to 4 radical substituents comprising: -D, halogen, =O, —OH, —OC$_1$-$C_4$-alkyl or —OCF$_3$, and with the further proviso that when the at least one ring atom is sulfur, the sulfur may substituted with 0 or 2=O; wherein the $C_1$-$C_6$-alkyl radical, the (3-6 membered)-heterocycloalkyl radical, the aryl radical, the heteroaryl radical, and the alkyl portion of the (3-6 membered)-heteroalkyl di-radical, may be substituted with up to 4 radical substituents comprising: -D, —F, —Cl, —Br, —I, —CN, —NO$_2$, —OR$^5$, —(CH$_2$)$_m$OR$^5$, —N(R$^5$)(R$^6$), —(CH$_2$)$_m$N(R$^5$)(R$^6$), —SO$_2$(CH$_2$)$_m$R$^5$, —(CO)(CH$_2$)$_m$R$^5$, —(CO)N(R$^5$)(R$^6$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;
$R^5$ and $R^6$ independently represent —H; a branched or unbranched $C_1$-$C_6$-alkyl radical; a $C_3$-$C_6$-cycloalkyl radical; or the N(R$^5$)(R$^6$) moiety forms a cycle, wherein $R^5$ and $R^6$ taken together represent a $C_2$-$C_6$-alkyl di-radical or a (3-6 membered)-heteroalkyl di-radical;
$Z^6$, $Z^7$, $Z^8$, and $Z^9$ independently represent N or $CR^7$; with the proviso that no more than two of $Z^6$, $Z^7$, $Z^8$, and $Z^9$ are N;
$R^7$ independently represents —H; -D; —F; —Cl; —Br; —I; —CN; —NO$_2$; —OR$^8$; —N(R$^8$)(R$^9$); —SO$_2$(CH$_2$)$_m$ R; —(CO)(CH$_2$)$_m$R$^8$; —(CO)N(R$^8$)(R$^9$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^8$, —(CH$_2$)$_m$OR$^8$, —N(R$^8$)(R$^9$), —(CH$_2$)$_m$N(R$^8$)(R$^9$), —SO$_2$(CH$_2$)$_m$R$^8$, —(CO)(CH$_2$)$_m$R$^8$, —(CO)N(R$^8$)(R$^9$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;
$R^8$ and $R^9$ independently represent —H; a branched or unbranched $C_1$-$C_6$-alkyl radical; a $C_3$-$C_6$-cycloalkyl radical; or the N(R$^8$)(R$^9$) moiety forms a cycle, wherein $R^8$ and $R^9$ taken together represent a $C_2$-$C_6$-alkyl di-radical or a (3-6 membered)-heteroalkyl di-radical;
$X^1$ independently represents N or C;
$A^1$, $A^2$, $A^3$ and $A^4$ independently represent N; NR$^{10}$; N(CH$_2$)$_m$R$^{10}$; O; S; or CR$^{11}$; with the proviso that only one $A^1$, $A^2$, $A^3$ and $A^4$ is NR$^{10}$, O, or S; with the further proviso that when $X^1$ is N, then $A^1$, $A^2$, and $A^3$ independently represent N or CR$^{11}$;
$R^{10}$ independently represents —H; -D; —SO$_2$(CH$_2$)$_m$R$^{12}$; —(CO)(CH$_2$)$_m$R$^{12}$; —(CO)N(R$^{12}$)(R$^{13}$); a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^{12}$, —(CH$_2$)$_m$OR$^{12}$, —N(R$^{12}$)(R$^{13}$), —(CH$_2$)$_m$N(R$^{12}$)(R$^{13}$), —SO$_2$(CH$_2$)$_m$R$^{12}$, —(CO)(CH$_2$)$_m$R$^{13}$, —(CO)N(R$^{12}$)(R$^{13}$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;
$R^{11}$ independently represents —H; -D; —F; —Cl; —Br; —I; —CN; —NO$_2$; —OR$^{12}$; —N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —NO$_2$; —OR$^{12}$; —(CH$_2$)$_m$OR$^{12}$; —N(R$^{12}$)(R$^{13}$); —(CH$_2$)$_m$N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$);

—OCF$_3$; a branched or unbranched C$_1$-C$_6$-alkyl radical, a C$_3$-C$_6$-cycloalkyl radical, or a C$_1$-C$_6$-haloalkyl radical;

R$^{12}$ and R$^{13}$ independently represent —H; a branched or unbranched C$_1$-C$_6$-alkyl radical; a C$_3$-C$_6$-cycloalkyl radical; or the N(R$^{12}$)(R$^{13}$) moiety forms a cycle, wherein R$^{12}$ and R$^{13}$ taken together represent a C$_2$-C$_6$-alkyl di-radical or a (3-6 membered)-heteroalkyl di-radical;

X$^2$ independently represents N or C;

A$^5$, A$^6$, and A$^7$ independently represent N; NR$^{14}$; N(CH$_2$)$_m$R$^{14}$; O; S; or CR$^{15}$; with the proviso that only one A$^5$, A$^6$, and A$^7$ is NR$^{14}$, O, or S; with the further proviso that when X$^2$ is N, then A$^5$, A$^6$, and A$^7$ independently represent N or CR$^{15}$;

R$^{14}$ independently represents —H; -D; —(CH$_2$)$_m$N(R$^{16}$)(R$^{17}$); —SO$_2$(CH$_2$)$_m$R$^{16}$; —(CO)(CH$_2$)$_m$R$^{16}$; —(CO)N(R$^{16}$)(R$^{17}$); a C$_1$-C$_6$-alkyl radical; a C$_1$-C$_6$-haloalkyl radical; a C$_3$-C$_6$-cycloalkyl radical; a (3-6 membered)-heterocycloalkyl radical; an aryl radical; a heteroaryl radical; or the bond directly attaching the W moiety with the carbonyl moiety; wherein the C$_1$-C$_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^{16}$, —(CH$_2$)$_m$OR$^{16}$, —N(R$^{16}$)(R$^{17}$), —(CH$_2$)$_m$N(R$^{16}$)(R$^{17}$), —SO$_2$(CH$_2$)$_m$R$^{16}$, —(CO)(CH$_2$)$_m$R$^{16}$, —(CO)N(R$^{16}$)(R$^{17}$), —OCF$_3$, a branched or unbranched C$_1$-C$_6$-alkyl radical, a C$_3$-C$_6$-cycloalkyl radical, or a C$_1$-C$_6$-haloalkyl;

R$^{15}$ independently represents —H; -D; —F; —Cl; —Br; —I; —CN; —NO$_2$; —OR$^{16}$; —N(R$^{16}$)(R$^{17}$); —SO$_2$(CH$_2$)$_m$R$^{16}$; —(CO)(CH$_2$)$_m$R$^{16}$; —(CO)N(R$^{16}$)(R$^{17}$); —OCF$_3$; a C$_1$-C$_6$-alkyl radical; a C$_1$-C$_6$-haloalkyl radical; a C$_3$-C$_6$-cycloalkyl radical; a (3-6 membered)-heterocycloalkyl radical; an aryl radical; a heteroaryl radical; or the bond directly attaching the W moiety with the carbonyl moiety; wherein the C$_1$-C$_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —NO$_2$; —OR$^{16}$; —(CH$_2$)$_m$OR$^{16}$; —N(R$^{16}$)(R$^{17}$); —(CH$_2$)$_m$N(R$^{16}$)(R$^{17}$); —SO$_2$(CH$_2$)$_m$R$^{16}$; —(CO)(CH$_2$)$_m$R$^{16}$; —(CO)N(R$^{16}$)(R$^{17}$); —OCF$_3$; a branched or unbranched C$_1$-C$_6$-alkyl radical, a C$_3$-C$_6$-cycloalkyl radical, or a C$_1$-C$_6$-haloalkyl radical;

R$^{16}$ and R$^{17}$ independently represent —H; a branched or unbranched C$_1$-C$_6$-alkyl radical; a C$_3$-C$_6$-cycloalkyl radical; or the N(R$^{16}$)(R$^{17}$) moiety forms a cycle, wherein R$^{16}$ and R$^{17}$ taken together represent a C$_2$-C$_6$-alkyl di-radical or a (3-6 membered)-heteroalkyl di-radical;

G$^1$, G$^2$, G$^3$, and G$^4$ independently represent C(R$^{18}$)(R$^{18}$); N(R$^{19}$); —N(CH$_2$)$_m$R$^{18}$; O; S; SO$_2$; or (C=O); with the proviso that no more than two of G$^1$, G$^2$, G$^3$, and G$^4$ represent N(R$^{19}$); —N(CH$_2$)$_m$R$^{18}$, O; S; SO$_2$; or (C=O);

R$^{18}$ independently represents —H; -D; —F; —Cl; —Br; —I; —CN; —NO$_2$; —OR$^{19}$; —N(R$^{19}$)(R$^{20}$); —SO$_2$(CH$_2$)$_m$R$^{19}$; —(CO)(CH$_2$)$_m$R$^{19}$; —(CO)N(R$^9$)(R$^{20}$); —OCF$_3$; a C$_1$-C$_6$-alkyl radical; a C$_1$-C$_6$-haloalkyl radical; a C$_3$-C$_6$-cycloalkyl radical; a (3-6 membered)-heterocycloalkyl radical; an aryl radical; or a heteroaryl radical; wherein the C$_1$-C$_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^{19}$, —(CH$_2$)$_m$OR$^{19}$, —N(R$^{19}$)(R$^{20}$), —(CH$_2$)$_m$N(R$^{19}$)(R$^{20}$), —SO$_2$(CH$_2$)$_m$R$^{19}$, —(CO)(CH$_2$)$_m$R$^{19}$, —(CO)N(R$^{19}$)(R$^{20}$), —OCF$_3$, a branched or unbranched C$_1$-C$_6$-alkyl radical, a C$_3$-C$_6$-cycloalkyl radical, or a C$_1$-C$_6$-haloalkyl radical; and R$^{19}$ and R$^{20}$ independently represent —H; a branched or unbranched C$_1$-C$_6$-alkyl radical; a C$_3$-C$_6$-cycloalkyl radical; or the N(R$^{19}$)(R$^{20}$) moiety forms a cycle, wherein R$^{19}$ and R$^{20}$ taken together represent a C$_2$-C$_6$-alkyl di-radical or a (3-6 membered)-heteroalkyl di-radical; or the C(R$^{19}$)(R$^{20}$) moiety forms a cycle, wherein R$^{19}$ and R$^{20}$ taken together represent a C$_2$-C$_6$-alkyl di-radical or a (3-6 membered)-heteroalkyl di-radical;

m independently represents an integer from 1 to 6;

or a single stereoisomer or a pharmaceutically acceptable salt thereof.

An aspect of the invention provides a geminal substituted quinuclidine amide compound represented by Formula (I):

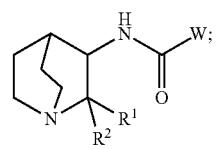

wherein:
R$^1$ and R$^2$ independently represent a branched or unbranched C$_1$-C$_4$-alkyl radical; or the C(R$^1$)(R$^2$) moiety forms a (3-4 membered)-carbocycle, wherein R$^1$ and R$^2$ taken together represent a C$_2$-C$_3$-alkyl di-radical; wherein the C$_1$-C$_4$-alkyl radical and the C$_2$-C$_3$-alkyl di-radical may be substituted with up to 4 radical substituents comprising: -D, —F, —Cl, —Br, —I, —CN, CH$_3$, CH$_2$CH$_3$, =O, —OR$^3$, or —OCF$_3$;

R$^3$ independently represents —H; a branched or unbranched C$_1$-C$_4$-alkyl radical; C$_3$-C$_4$-cycloalkyl radical; wherein the C$_1$-C$_4$-alkyl radical and the C$_3$-C$_4$-cycloalkyl radical may be substituted with up to 4 radical substituents comprising: -D, —F, —Cl, —Br, —I, —CN, =O, —OH, —OC$_1$-C$_4$-alkyl or —OCF$_3$;

W represents a moiety represented by ring system M-I, M-II, M-III, M-IV, M-V, or M-VI:

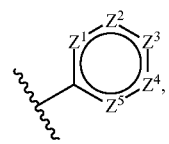

M-I

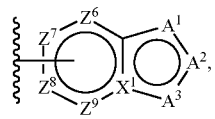

M-II

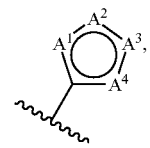

M-III

-continued

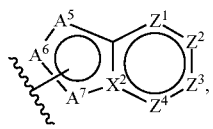

M-IV

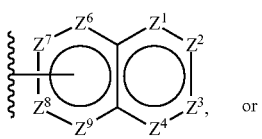

M-V

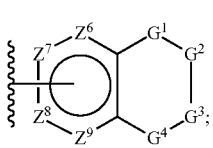

M-VI $Z^1$, $Z^2$, $Z^3$, $Z^4$, and $Z^5$ independently represent N or $CR^4$; with the proviso that no more than two of $Z^1$, $Z^2$, $Z^3$, $Z^4$, and $Z^5$ are N;

$R^4$ independently represents —H; -D; —F; —Cl; —Br; —I; —CN; —NO$_2$; —OR$^5$; —N(R$^5$)(R$^6$); —SO$_2$(CH$_2$)$_m$ R$^5$; —(CO)(CH$_2$)$_m$R$^5$; —(CO)N(R$^5$)(R$^6$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^5$, —(CH$_2$)$_m$OR$^5$, —N(R$^5$)(R$^6$), —(CH$_2$)$_m$N(R$^5$)(R$^6$), —SO$_2$(CH$_2$)$_m$R$^5$, —(CO)(CH$_2$)$_m$R$^5$, —(CO)N(R$^5$)(R$^6$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^5$ and $R^6$ independently represent —H; a branched or unbranched $C_1$-$C_6$-alkyl radical; a $C_3$-$C_6$-cycloalkyl radical; or the N(R$^5$)(R$^6$) moiety forms a cycle, wherein $R^5$ and $R^6$ taken together represent a $C_2$-$C_6$-alkyl di-radical or a (3-6 membered)-heteroalkyl di-radical;

$Z^6$, $Z^7$, $Z^8$, and $Z^9$ independently represent N or $CR^7$; with the proviso that no more than two of $Z^6$, $Z^7$, $Z^8$, and $Z^9$ are N;

$R^7$ independently represents —H; -D; —F; —Cl; —Br; —I; —CN; —NO$_2$; —OR$^8$; —N(R$^8$)(R$^9$); —SO$_2$(CH$_2$)$_m$ R; —(CO)(CH$_2$)$_m$R$^8$; —(CO)N(R$^8$)(R$^9$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^8$, —(CH$_2$)$_m$OR$^8$, —N(R$^8$)(R$^9$), —(CH$_2$)$_m$N(R$^8$)(R$^9$), —SO$_2$(CH$_2$)$_m$R$^8$, —(CO)(CH$_2$)$_m$R$^8$, —(CO)N(R$^8$)(R$^9$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^8$ and $R^9$ independently represent —H; a branched or unbranched $C_1$-$C_6$-alkyl radical; a $C_3$-$C_6$-cycloalkyl radical; or the N(R$^8$)(R$^9$) moiety forms a cycle, wherein $R^8$ and $R^9$ taken together represent a $C_2$-$C_6$-alkyl di-radical or a (3-6 membered)-heteroalkyl di-radical;

$X^1$ independently represents N or C;

$A^1$, $A^2$, $A^3$ and $A^4$ independently represent N; NR$^{10}$; N(CH$_2$)$_m$R$^{10}$; O; S; or CR$^{11}$; with the proviso that only one $A^1$, $A^2$, $A^3$ and $A^4$ is NR$^{10}$, O, or S; with the further proviso that when $X^1$ is N, then $A^1$, $A^2$, and $A^3$ independently represent N or CR$^{11}$;

$R^{10}$ independently represents —H; -D; —SO$_2$(CH$_2$)$_m$R$^{12}$; —(CO)(CH$_2$)$_m$R$^{12}$; —(CO)N(R$^{12}$)(R$^{13}$); a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^{12}$, —(CH$_2$)$_m$OR$^{12}$, —N(R$^{12}$)(R$^{13}$), —(CH$_2$)$_m$N(R$^{12}$)(R$^{13}$), —SO$_2$(CH$_2$)$_m$R$^{12}$, —(CO)(CH$_2$)$_m$R$^{13}$, —(CO)N(R$^{12}$)(R$^{13}$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^{11}$ independently represents —H; -D; —F; —Cl; —Br; —I; —CN; —NO$_2$; —OR$^{12}$; —N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —NO$_2$; —OR$^{12}$; —(CH$_2$)$_m$OR$^{12}$; —N(R$^{12}$)(R$^{13}$); —(CH$_2$)$_m$N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$); —OCF$_3$; a branched or unbranched $C_1$-$C_6$-alkyl radical, a $C_3$-$C_6$-cycloalkyl radical, or a $C_1$-$C_6$-haloalkyl radical;

$R^{12}$ and $R^{13}$ independently represent —H; a branched or unbranched $C_1$-$C_6$-alkyl radical; a $C_3$-$C_6$-cycloalkyl radical; or the N(R$^{12}$)(R$^{13}$) moiety forms a cycle, wherein $R^{12}$ and $R^{13}$ taken together represent a $C_2$-$C_6$-alkyl di-radical or a (3-6 membered)-heteroalkyl di-radical;

$X^2$ independently represents N or C;

$A^5$, $A^6$, and $A^7$ independently represent N; NR$^{14}$; N(CH$_2$)$_m$R$^{14}$; O; S; or CR$^{15}$; with the proviso that only one $A^5$, $A^6$, and $A^7$ is NR$^{14}$, O, or S; with the further proviso that when $X^2$ is N, then $A^5$, $A^6$, and $A^7$ independently represent N or CR$^{15}$;

$R^{14}$ independently represents —H; -D; —(CH$_2$)$_m$N(R$^{16}$)(R$^{17}$); —SO$_2$(CH$_2$)$_m$R$^{16}$; —(CO)(CH$_2$)$_m$R$^{16}$; —(CO)N(R$^{16}$)(R$^{17}$); a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^6$, —(CH$_2$)$_m$OR$^{16}$, —N(R$^{16}$)(R$^{17}$), —(CH$_2$)$_m$N(R$^{16}$)(R$^{17}$), —SO$_2$(CH$_2$)$_m$R$^{16}$, —(CO)(CH$_2$)$_m$R$^{16}$, —(CO)N(R$^{16}$)(R$^{17}$), —OCF$_3$, a branched or unbranched $C_1$-$C_6$-alkyl radical, a $C_3$-$C_6$-cycloalkyl radical, or a $C_1$-$C_6$-haloalkyl;

R¹⁵ independently represents —H; -D; —F; —Cl; —Br; —I; —CN; —NO₂; —OR¹⁶; —N(R¹⁶)(R¹⁷); —SO₂(CH₂)$_m$R¹⁶; —(CO)(CH₂)$_m$R¹⁶; —(CO)N(R¹⁶)(R¹⁷); —OCF₃; a C₁-C₆-alkyl radical; a C₁-C₆-haloalkyl radical; a C₃-C₆-cycloalkyl radical; a (3-6 membered)-heterocycloalkyl radical; an aryl radical; a heteroaryl radical; or the bond directly attaching the W moiety with the carbonyl moiety; wherein the C₁-C₆-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —NO₂; —OR¹⁶; —(CH₂)$_m$OR¹⁶; —N(R¹⁶)(R¹⁷); —(CH₂)$_m$N(R¹⁶)(R¹⁷); —SO₂(CH₂)$_m$R¹⁶; —(CO)(CH₂)$_m$R¹⁶; —(CO)N(R¹⁶)(R¹⁷); —OCF₃; a branched or unbranched C₁-C₆-alkyl radical, a C₃-C₆-cycloalkyl radical, or a C₁-C₆-haloalkyl radical;

R¹⁶ and R¹⁷ independently represent —H; a branched or unbranched C₁-C₆-alkyl radical; a C₃-C₆-cycloalkyl radical; or the N(R¹⁶)(R¹⁷) moiety forms a cycle, wherein R¹⁶ and R¹⁷ taken together represent a C₂-C₆-alkyl di-radical or a (3-6 membered)-heteroalkyl di-radical;

G¹, G², G³, and G⁴ independently represent C(R¹⁸)(R¹⁸); N(R¹⁹); —N(CH₂)$_m$R¹⁸; O; S; SO₂; or (C═O); with the proviso that no more than two of G¹, G², G³, and G⁴ represent N(R¹⁹); —N(CH₂)$_m$R¹⁸, O; S; SO₂; or (C═O);

R¹⁸ independently represents —H; -D; —F; —Cl; —Br; —I; —CN; —NO₂; —OR¹⁹; —N(R¹⁹)(R²⁰); —SO₂(CH₂)$_m$R¹⁹; —(CO)(CH₂)$_m$R¹⁹; —(CO)N(R⁹)(R²⁰); —OCF₃; a C₁-C₆-alkyl radical; a C₁-C₆-haloalkyl radical; a C₃-C₆-cycloalkyl radical; a (3-6 membered)-heterocycloalkyl radical; an aryl radical; or a heteroaryl radical; wherein the C₁-C₆-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO₂, —OR¹⁹, —(CH₂)$_m$OR¹⁹, —N(R¹⁹)(R²⁰), —(CH₂)$_m$N(R¹⁹)(R²⁰), —SO₂(CH₂)$_m$R¹⁹, —(CO)(CH₂)$_m$R¹⁹, —(CO)N(R¹⁹)(R²⁰), —OCF₃, a branched or unbranched C₁-C₆-alkyl radical, a C₃-C₆-cycloalkyl radical, or a C₁-C₆-haloalkyl radical; and R¹⁹ and R²⁰ independently represent —H; a branched or unbranched C₁-C₆-alkyl radical; a C₃-C₆-cycloalkyl radical; or the N(R¹⁹)(R²⁰) moiety forms a cycle, wherein R¹⁹ and R²⁰ taken together represent a C₂-C₆-alkyl di-radical or a (3-6 membered)-heteroalkyl di-radical; or the C(R¹⁹)(R²⁰) moiety forms a cycle, wherein R¹⁹ and R²⁰ taken together represent a C₂-C₆-alkyl di-radical or a (3-6 membered)-heteroalkyl di-radical;

m independently represents an integer from 1 to 6;

or a single stereoisomer or a pharmaceutically acceptable salt thereof.

An aspect of the invention relates to the amide compound represented by Formula (I), wherein R¹ and R² independently represent an unbranched C₁-alkyl radical and said compound is represented by Formula (II):

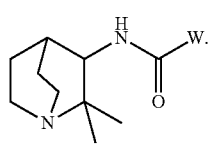

(II)

An aspect of the invention relates to an amide compound represented by Formula (I), wherein R¹ and R² taken together represent a C₂-alkyl di-radical and said compound is represented by Formula (III):

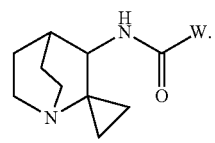

(III)

An aspect of the invention relates to a single stereoisomer of the amide compound represented by Formula (I), Formula (II), or Formula (III), or a pharmaceutically acceptable salt thereof.

An aspect of the invention relates to a single enantiomer or a single diastereomer of the amide compound represented by Formula (I), Formula (II), or Formula (III), or a pharmaceutically acceptable salt thereof.

An aspect of the invention relates to a pharmaceutical composition comprising the amide compound represented by Formula (I), Formula (II), or Formula (III), or a pharmaceutically acceptable salt thereof, and at least one pharmaceutically acceptable carrier, excipient or diluent.

An aspect of the invention relates to a method comprising administering to a patient in need thereof an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating a patient in need thereof, comprising: administering to the patient an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating a patient diagnosed as having a cognitive impairment, comprising: administering to the an effective dose of an amide compound represented by Formula (I), Formula (II), or Formula (III), or a pharmaceutically acceptable salt thereof, or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating a patient in need thereof, comprising: administering to the patient, for example, a patient diagnosed with having a cognitive impairment, Limited Cognitive Impairment, Mild Cognitive Impairment, Alzheimer's disease, and/or schizophrenia, an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent; such that the patient may derive a benefit therefrom.

Another aspect of the invention provides a method of treating one or more symptoms associated with a cognitive impairment, comprising administering to a patient an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent; wherein the patient suffers from, or has been diagnosed as having, a cognitive impairment.

Another aspect of the invention provides a method of improving cognition of a patient in need thereof, comprising: administering to the patient an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of improving cognition in a patient suffering from a cognitive impairment, such as a cognitive impairment associated with either schizophrenia or Alzheimer's disease, for example mild Alzheimer's disease, moderate Alzheimer's disease, severe Alzheimer's disease, or mild-to-moderate Alzheimer's disease, comprising administering an effective dose of an amide compound represented by Formula (I), Formula (II), or Formula (III), or a pharmaceutically acceptable salt thereof; or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating a patient suffering from, diagnosed with having, or suffers from one or more symptoms associated with, a cognitive impairment, for example, Alzheimer's disease, dementia of an Alzheimer's type, MCI, LCI, or schizophrenia, comprising: administering to the patient an effective dose of an amide compound represented by Formula (I), Formula (II), or Formula (III), or a pharmaceutically acceptable salt thereof; or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent. For example, the method of treating a patient suffering from, diagnosed with having, or suffers from one or more symptoms associated with, a cognitive impairment, may provide said patient at least one of the following: (i) treats, minimizes progression of, prevents the deterioration of, or reduces the rate of deterioration of, one or more symptoms associated with the cognitive impairment; (ii) treats the cognitive impairment; (iii) improves cognition in said cognitively impaired patient; (iv) improves one or more behavioral symptoms associated with the cognitive impairment; (v) provides a pro-cognitive effect; (vi) provides a pro-cognitive effect in at least one of the following: visual motor, learning, delayed memory, or executive function, or (vii) provides a positive effect on clinical function in said cognitively impaired patient.

Another aspect of the invention provides a method of treating a patient previously treated, or currently being treated, with an AChEI, that is suffering from, or has been diagnosed with having, a cognitive impairment, for example, Alzheimer's disease, dementia of an Alzheimer's type, MCI, LCI, or schizophrenia, comprising: administering to the patient an effective dose of an amide compound represented by Formula (I), Formula (II), or Formula (III), or a pharmaceutically acceptable salt thereof; or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluents; wherein the method improves one or more symptoms associated with the cognitive impairment in the previously, or currently, AChEI treated patient.

Another aspect of the invention provides a method of treating a patient suffering from, or diagnosed with having a cognitive impairment, comprising: administering to the patient an effective dose of an amide compound represented by Formula (I), Formula (II), or Formula (III), or a pharmaceutically acceptable salt thereof; or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent; wherein the method provides a positive effect on cognition or a positive effect on clinical function in said cognitively impaired patient, and wherein said patient has been previously treated or is currently being treated with an AChEI.

Another aspect of the invention provides a method of improving cognition in a patient diagnosed as having a probable cognitive disease, comprising: administering to the patient an effective dose of an amide compound represented by Formula (I), Formula (II), or Formula (III), or a pharmaceutically acceptable salt thereof; or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of improving or substantially improving one or more symptoms in a cognitive disease patient, comprising: administering to the patient an effective dose of an amide compound represented by Formula (I), Formula (II), or Formula (III), or a pharmaceutically acceptable salt thereof; or administering to the patient an effective dose of a pharmaceutical composition comprising the effective dose of the amide compound represented by Formula (I), Formula (II), or Formula (III), or a pharmaceutically acceptable salt thereof, and at least one pharmaceutically acceptable carrier, excipient or diluent.

Another aspect of the invention provides a method of slowing the rate of deterioration of at least one symptom in a cognitive disease patient, comprising: administering to the patient an effective dose of an amide compound represented by Formula (I), Formula (II), or Formula (III), or a pharmaceutically acceptable salt thereof; or administering to the patient the pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating one or more symptoms associated with a cognitive disease in a patient suffering therefrom, comprising: administering to the patient an effective dose of an amide compound represented by Formula (I), Formula (II), or Formula (III), or a pharmaceutically acceptable salt thereof; or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent Another aspect provides a method of minimizing or substantially halting the rate of progression of one or more cognitive diseases in a patient suffering from a cognitive disease, comprising: administering to the patient an effective dose of an amide compound represented by Formula (I), Formula (II), or Formula (III), or a pharmaceutically acceptable salt thereof, or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of substantially stopping or reversing progression of one or more cognitive diseases, in a patient suffering therefrom, comprising: administering to the patient an effective dose of an amide compound represented by Formula (I), Formula (II), or Formula (III), or a pharmaceutically acceptable salt thereof; or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating dementia, comprising: administering to a patient in need thereof an effective amount of an amide compound represented by Formula (I), Formula (II), or Formula (III), or a pharmaceutically acceptable salt thereof, or administering to the patient an effective dose of a pharmaceutical composition comprising the effective amount of the amide compound represented by Formula (I), Formula (II), or Formula (III), or a pharmaceutically acceptable salt thereof, and at least one pharmaceutically acceptable carrier, excipient or diluent; wherein said effective amount is administered in an effective dose.

Another aspect of the invention provides a method of treating dementia, comprising: administering to a patient in need thereof an effective amount of an amide compound represented by Formula (I), Formula (II), or Formula (III), or a pharmaceutically acceptable salt thereof, or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent.

Another aspect of the invention provides a method of treating dementia, comprising: administering to a patient in need thereof an effective amount of an amide compound represented by Formula (I), Formula (II), or Formula (III), or a pharmaceutically acceptable salt thereof, wherein the amide compound represented by Formula (I), Formula (II), or Formula (III), or a pharmaceutically acceptable salt thereof, is administered in the form of a pharmaceutical composition comprising at least one pharmaceutically acceptable carrier, excipient or diluent.

Another aspect of the invention provides a method of treating dementia, comprising: administering to a patient in need thereof an effective amount of an amide compound represented by Formula (I), Formula (II), or Formula (III), or a pharmaceutically acceptable salt thereof; or administering to the patient an effective dose of a pharmaceutical composition comprising the amide compound represented by Formula (I), Formula (II), or Formula (III), or a pharmaceutically acceptable salt thereof, and at least one pharmaceutically acceptable carrier, excipient or diluent; wherein the pharmaceutical composition is in the form of a tablet.

Another aspect of the invention provides a method of treating a patient having a cognitive disease and being administered an acetylcholine esterase inhibitor, comprising: administering to a patient in need thereof an effective amount of an amide compound represented by Formula (I), Formula (II), or Formula (III), or a pharmaceutically acceptable salt thereof; or administering to the patient an effective dose of a pharmaceutical composition comprising an amide compound represented by Formula (I), Formula (II), or Formula (III), or a pharmaceutically acceptable salt thereof, and at least one pharmaceutically acceptable carrier, excipient or diluent; wherein the treatment comprises halting the administration of the acetylcholine esterase inhibitor prior to treating with the amide compound represented by Formula (I), Formula (II), or Formula (III), or a pharmaceutically acceptable salt thereof.

DETAILED DESCRIPTION OF THE INVENTION

Figure 1:
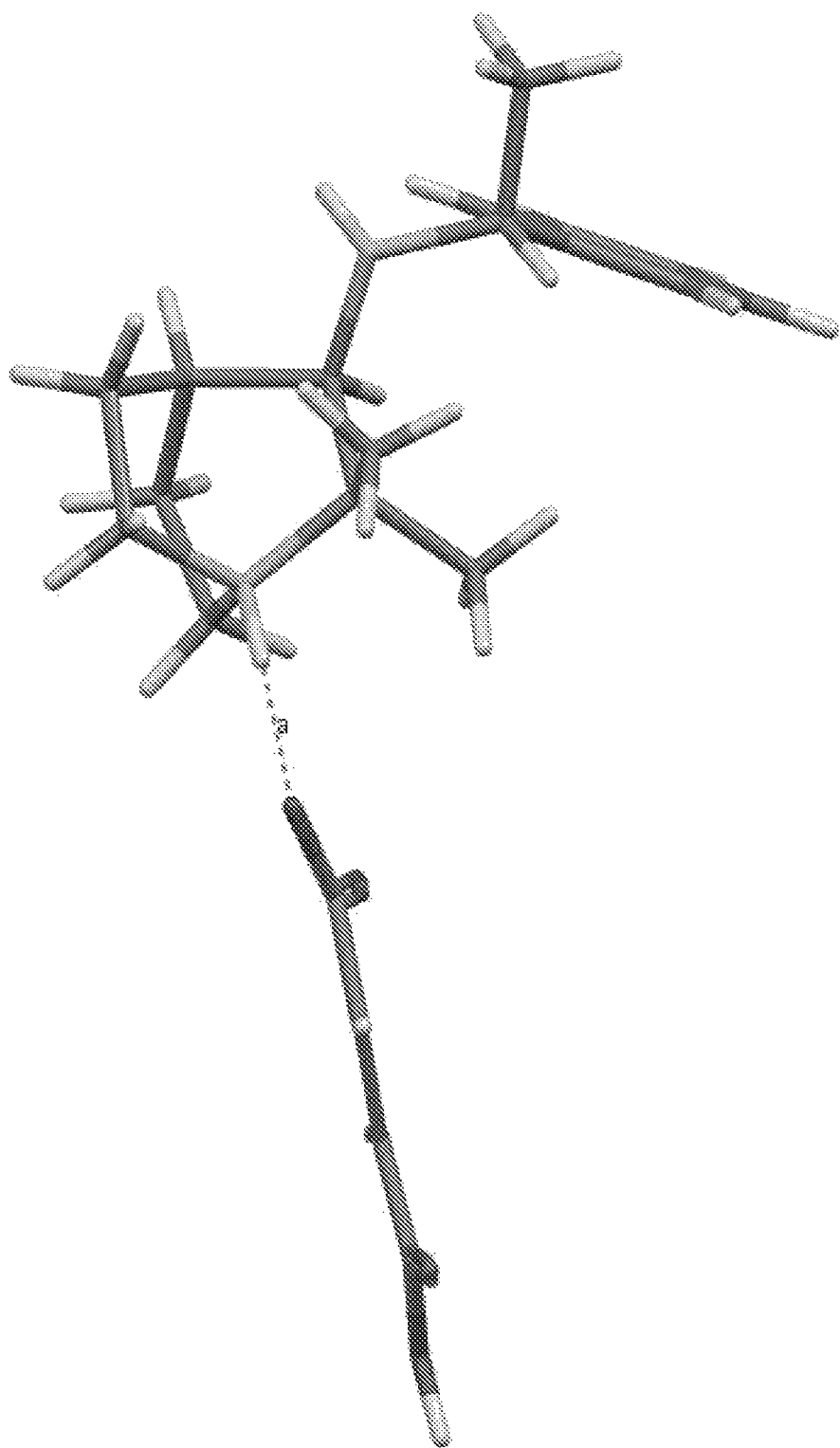
FIG. 1: Illustrates a 3-D representation of the formed crystal of (R)-2,2-dimethyl-N—((R)-1-phenylethyl)quinuclidin-3-amine fumarate.

An embodiment of the present invention provides a geminal substituted quinuclidine amide compound represented by Formula (I):

(I)

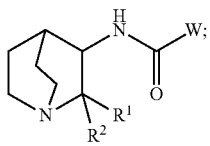

wherein:
  $R^1$ and $R^2$ independently represent a branched or unbranched $C_1$-$C_4$-alkyl radical; or the $C(R^1)(R^2)$ moiety forms a (3-4 membered)-carbocycle, wherein $R^1$ and $R^2$ taken together represent a $C_2$-$C_3$-alkyl di-radical; wherein the $C_1$-$C_4$-alkyl radical and the $C_2$-$C_3$-alkyl di-radical may be substituted with up to 4 radical substituents comprising: -D, —F, —Cl, —Br, —I, —CN, $CH_3$, $CH_2CH_3$, =O, —$OR^3$, or —$OCF_3$;
  $R^3$ independently represents —H; a branched or unbranched $C_1$-$C_4$-alkyl radical; $C_3$-$C_4$-cycloalkyl radical; wherein the $C_1$-$C_4$-alkyl radical and the $C_3$-$C_4$-cycloalkyl radical may be substituted with up to 4 radical substituents comprising: -D, —F, —Cl, —Br, —I, —CN, =O, —OH, —O$C_1$-$C_4$-alkyl or —$OCF_3$; and
  W represents a moiety represented by ring system M-I, M-II, M-III, M-IV, M-V, or M-VI:

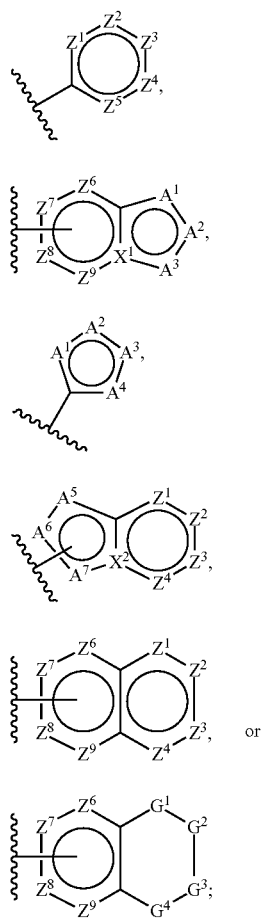

wherein:
  $Z^1$, $Z^2$, $Z^3$, $Z^4$, and $Z^5$ independently represent N or $CR^4$; with the proviso that no more than two of $Z^1$, $Z^2$, $Z^3$, $Z^4$, and $Z^5$ are N;
  $R^4$ independently represents —H; -D; —F; —Cl; —Br; —I; —CN; —$NO_2$; —$OR^5$; —$N(R^5)(R^6)$; —$SO_2(CH_2)_m$ $R^5$; —$(CO)(CH_2)_mR^5$; —$(CO)N(R^5)(R^6)$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; or when adjacent members of $Z^1$, $Z^2$, $Z^3$, $Z^4$, and $Z^5$, is $(CR^4)(CR^4)$, the $(CR^4)(CR^4)$ may form a cycle such that the adjacent $R^4$ substituents taken together represents a (3-6 membered)-heteroalkyl di-radical with at least one ring atom of the (3-6 membered)-heteroalkyl di-radical selected from the group consisting of oxygen, nitrogen, and sulfur, with the proviso that when the at least one ring atom is nitrogen, the nitrogen is substituted with —H, a branched or unbranched $C_1$-$C_4$-alkyl radical, a $C_3$-$C_4$-cycloalkyl radical, —(CO)-branched or unbranched $C_1$-$C_4$-alkyl, or —($SO_2$)-branched or unbranched $C_1$-$C_4$-alkyl, wherein the $C_1$-$C_4$-alkyl radical and the $C_3$-$C_4$-cycloalkyl radical may be substituted with up to 4 radical substituents comprising: -D, halogen, =O, —OH, —O$C_1$-$C_4$-alkyl or —$OCF_3$, and with the further proviso that when the at least one ring atom is sulfur, the sulfur may substituted with 0 or 2=O; wherein the $C_1$-$C_6$-alkyl radical, the (3-6 membered)-heterocycloalkyl radical, the aryl radical, the heteroaryl radical, and the alkyl portion of the (3-6 membered)-heteroalkyl di-radical, may be substituted with up to 4 radical substituents comprising: -D, —F, —Cl, —Br, —I, —CN, —$NO_2$, —$OR^5$, —$(CH_2)_mOR^5$, —$N(R^5)(R^6)$, —$(CH_2)_mN(R^5)(R^6)$, —$SO_2(CH_2)_mR^5$, —(CO)$(CH_2)_mR^5$, —$(CO)N(R^5)(R^6)$, —$OCF_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;
  $R^5$ and $R^6$ independently represent —H; a branched or unbranched $C_1$-$C_6$-alkyl radical; a $C_3$-$C_6$-cycloalkyl radical; or the $N(R^5)(R^6)$ moiety forms a cycle, wherein $R^5$ and $R^6$ taken together represent a $C_2$-$C_6$-alkyl di-radical or a (3-6 membered)-heteroalkyl di-radical;
  $Z^6$, $Z^7$, $Z^8$, and $Z^9$ independently represent N or $CR^7$; with the proviso that no more than two of $Z^6$, $Z^7$, $Z^8$, and $Z^9$ are N;
  $R^7$ independently represents —H; -D; —F; —Cl; —Br; —I; —CN; —$NO_2$; —$OR^8$; —$N(R^8)(R^9)$; —$SO_2(CH_2)_m$ $R^8$; —$(CO)(CH_2)_mR^8$; —$(CO)N(R^8)(R^9)$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^8$, —$(CH_2)_mOR^8$, —$N(R^8)(R^9)$, —$(CH_2)_mN(R^8)(R^9)$, —$SO_2(CH_2)_mR^8$, —$(CO)(CH_2)_mR^8$, —$(CO)N(R^8)(R^9)$, —$OCF_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;
  $R^8$ and $R^9$ independently represent —H; a branched or unbranched $C_1$-$C_6$-alkyl radical; a $C_3$-$C_6$-cycloalkyl radical; or the $N(R^8)(R^9)$ moiety forms a cycle, wherein $R^8$ and $R^9$ taken together represent a $C_2$-$C_6$-alkyl di-radical or a (3-6 membered)-heteroalkyl di-radical;

$X^1$ independently represents N or C;

$A^1$, $A^2$, $A^3$ and $A^4$ independently represent N; $NR^{10}$; $N(CH_2)_m R^{10}$; O; S; or $CR^{11}$; with the proviso that only one $A^1$, $A^2$, $A^3$ and $A^4$ is $NR^{10}$, O, or S; with the further proviso that when $X^1$ is N, then $A^1$, $A^2$, and $A^3$ independently represent N or $CR^{11}$;

$R^{10}$ independently represents —H; -D; —$SO_2(CH_2)_m R^{12}$; —$(CO)(CH_2)_m R^{12}$; —$(CO)N(R^{12})(R^{13})$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^{12}$, —$(CH_2)_m OR^{12}$, —$N(R^{12})(R^{13})$, —$(CH_2)_m N(R^{12})(R^{13})$, —$SO_2(CH_2)_m R^{12}$, —$(CO)(CH_2)_m R^{13}$, —$(CO)N(R^{12})(R^{13})$, —$OCF_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^{11}$ independently represents —H; -D; —F; —Cl; —Br; —I; —CN; —$NO_2$; —$OR^{12}$; —$N(R^{12})(R^{13})$; —$SO_2(CH_2)_m R^{12}$; —$(CO)(CH_2)_m R^{12}$; —$(CO)N(R^{12})(R^{13})$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —$NO_2$; —$OR^{12}$; —$(CH_2)_m OR^{12}$; —$N(R^{12})(R^{13})$; —$(CH_2)_m N(R^{12})(R^{13})$; —$SO_2(CH_2)_m R^{12}$; —$(CO)(CH_2)_m R^{12}$; —$(CO)N(R^{12})(R^{13})$; —$OCF_3$; a branched or unbranched $C_1$-$C_6$-alkyl radical, a $C_3$-$C_6$-cycloalkyl radical, or a $C_1$-$C_6$-haloalkyl radical;

$R^{12}$ and $R^{13}$ independently represent —H; a branched or unbranched $C_1$-$C_6$-alkyl radical; a $C_3$-$C_6$-cycloalkyl radical; or the $N(R^{12})(R^{13})$ moiety forms a cycle, wherein $R^{12}$ and $R^{13}$ taken together represent a $C_2$-$C_6$-alkyl di-radical or a (3-6 membered)-heteroalkyl di-radical;

$X^2$ independently represents N or C;

$A^5$, $A^6$, and $A^7$ independently represent N; $NR^{14}$; $N(CH_2)_m R^{14}$; O; S; or $CR^{15}$; with the proviso that only one $A^5$, $A^6$, and $A^7$ is $NR^{14}$, O, or S; with the further proviso that when $X^2$ is N, then $A^5$, $A^6$, and $A^7$ independently represent N or $CR^{15}$;

$R^{14}$ independently represents —H; -D; —$(CH_2)_m N(R^{16})(R^{17})$; —$SO_2(CH_2)_m R^{16}$; —$(CO)(CH_2)_m R^6$; —$(CO)N(R^{16})(R^{17})$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^{16}$, —$(CH_2)_m OR^{16}$, —$N(R^{16})(R^{17})$, —$(CH_2)_m N(R^{16})(R^{17})$, —$SO_2(CH_2)_m R^{16}$, —$(CO)(CH_2)_m R^{16}$, —$(CO)N(R^{16})(R^{17})$, —$OCF_3$, a branched or unbranched $C_1$-$C_6$-alkyl radical, a $C_3$-$C_6$-cycloalkyl radical, or a $C_1$-$C_6$-haloalkyl;

$R^{15}$ independently represents —H; -D; —F; —Cl; —Br; —I; —CN; —$NO_2$; —$OR^{16}$; —$N(R^{16})(R^{17})$; —$SO_2(CH_2)_m R^{16}$; —$(CO)(CH_2)_m R^{16}$; —$(CO)N(R^{16})(R^{17})$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —$NO_2$; —$OR^{16}$; —$(CH_2)_m OR^{16}$; —$N(R^{16})(R^{17})$; —$(CH_2)_m N(R^{16})(R^{17})$; —$SO_2(CH_2)_m R^{16}$; —$(CO)(CH_2)_m R^{16}$; —$(CO)N(R^{16})(R^{17})$; —$OCF_3$; a branched or unbranched $C_1$-$C_6$-alkyl radical, a $C_3$-$C_6$-cycloalkyl radical, or a $C_1$-$C_6$-haloalkyl radical;

$R^{16}$ and $R^{17}$ independently represent —H; a branched or unbranched $C_1$-$C_6$-alkyl radical; a $C_3$-$C_6$-cycloalkyl radical; or the $N(R^{16})(R^{17})$ moiety forms a cycle, wherein $R^{16}$ and $R^{17}$ taken together represent a $C_2$-$C_6$-alkyl di-radical or a (3-6 membered)-heteroalkyl di-radical;

$G^1$, $G^2$, $G^3$, and $G^4$ independently represent $C(R^{18})(R^{18})$; $N(R^{19})$; —$N(CH_2)_m R^{18}$; O; S; $SO_2$; or (C=O); with the proviso that no more than two of $G^1$, $G^2$, $G^3$, and $G^4$ represent $N(R^{19})$; —$N(CH_2)_m R^{18}$, O; S; $SO_2$; or (C=O);

$R^{18}$ independently represents —H; -D; —F; —Cl; —Br; —I; —CN; —$NO_2$; —$OR^{19}$; —$N(R^{19})(R^{20})$; —$SO_2(CH_2)_m R^{19}$; —$(CO)(CH_2)_m R^{19}$; —$(CO)N(R^9)(R^{20})$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^{19}$, —$(CH_2)_m OR^{19}$, —$N(R^{19})(R^{20})$, —$(CH_2)_m N(R^{19})(R^{20})$, —$SO_2(CH_2)_m R^{19}$, —$(CO)(CH_2)_m R^{19}$, —$(CO)N(R^{19})(R^{20})$, —$OCF_3$, a branched or unbranched $C_1$-$C_6$-alkyl radical, a $C_3$-$C_6$-cycloalkyl radical, or a $C_1$-$C_6$-haloalkyl radical; and $R^{19}$ and $R^{20}$ independently represent —H; a branched or unbranched $C_1$-$C_6$-alkyl radical; a $C_3$-$C_6$-cycloalkyl radical; or the $N(R^{19})(R^{20})$ moiety forms a cycle, wherein $R^{19}$ and $R^{20}$ taken together represent a $C_2$-$C_6$-alkyl di-radical or a (3-6 membered)-heteroalkyl di-radical; or the $C(R^{19})(R^{20})$ moiety forms a cycle, wherein $R^{19}$ and $R^{20}$ taken together represent a $C_2$-$C_6$-alkyl di-radical or a (3-6 membered)-heteroalkyl di-radical;

m independently represents an integer from 1 to 6;

or a single stereoisomer or a pharmaceutically acceptable salt thereof.

In certain embodiments, the amide compound represented by Formula (I), (II), or (III), may comprise the W representing the moiety represented by the ring system M-I. In certain embodiments, the amide compound represented by Formula (I), (II), or (III), may comprise the W representing the moiety represented by the ring system M-I, wherein, for example, the $Z^1$ represents N, and $Z^2$, $Z^3$, $Z^4$, and $Z^5$ each independently represent $CR^4$; $Z^2$ represents N, and $Z^1$, $Z^3$, $Z^4$, and $Z^5$ each independently represent $CR^4$; $Z^3$ represents N, and $Z^1$, $Z^2$, $Z^4$, and $Z^5$ each independently represent $CR^4$; $Z^1$ and $Z^2$ each represent N, and $Z^3$, $Z^4$, and $Z^5$ each independently represent $CR^4$; $Z^1$ and $Z^3$ each represent N, and $Z^2$, $Z^4$, and $Z^5$ each independently represent $CR^4$; $Z^1$ and $Z^4$ each represent N, and $Z^2$, $Z^3$, and $Z^5$ each independently represent $CR^4$; $Z^1$ and $Z^5$ each represent N, and $Z^2$, $Z^3$, and $Z^4$ each independently represent $CR^4$; $Z^2$ and $Z^3$ each represent N, and $Z^1$, $Z^4$, and $Z^5$ each independently represent $CR^4$; or $Z^2$ and $Z^4$ each represent N, and $Z^1$, $Z^3$, and $Z^5$ each independently represent $CR^4$.

In certain embodiments, the amide compound represented by Formula (I), (II), or (III), may comprise the W representing the moiety represented by the ring system M-I, wherein at least one or two of $Z^1$, $Z^2$, $Z^3$, $Z^4$, and $Z^5$, represent $CR^4$ with said $R^4$ representing -D; —F; —Cl; —Br; —I; —CN; —$NO_2$; —$OR^5$; —$N(R^5)(R^6)$; —$SO_2(CH_2)_mR^5$; —$(CO)(CH_2)_mR^5$; —$(CO)N(R^5)(R^6)$; —$OCF_3$; a $C_1$-$C_6$-alkyl radical; a $C_1$-$C_6$-haloalkyl radical; a $C_3$-$C_6$-cycloalkyl radical; or a (3-6 membered)-heterocycloalkyl radical; wherein the $C_1$-$C_6$-alkyl radical and the (3-6 membered)-heterocycloalkyl radical, may be substituted with up to 4 radical substituents comprising: -D, —F, —Cl, —Br, —I, —CN, —$NO_2$, —$OR^5$, —$(CH_2)_mOR^5$, —$N(R^5)(R^6)$, —$(CH_2)_mN(R^5)(R^6)$, —$SO_2(CH_2)_mR^5$, —$(CO)(CH_2)_mR^5$, —$(CO)N(R^5)(R^6)$, —$OCF_3$, a branched or unbranched $C_1$-$C_6$-alkyl radical, a $C_3$-$C_6$-cycloalkyl radical, or a $C_1$-$C_6$-haloalkyl radical.

In certain embodiments, the amide compound represented by Formula (I), (II), or (III), may comprise the W representing the moiety represented by the ring system M-I, wherein the at least one or two of $Z^1$, $Z^2$, $Z^3$, $Z^4$, and $Z^5$, represent $CR^4$ with said $R^4$ representing —F; —Cl; —Br; —I; or —CN.

In certain embodiments, the amide compound represented by Formula (I), (II), or (III), may comprise the W representing the moiety represented by the ring system M-I, wherein the at least one or two of $Z^1$, $Z^2$, $Z^3$, $Z^4$, and $Z^5$, represent $CR^4$ with said $R^4$ representing an aryl radical or a heteroaryl radical; wherein the aryl radical and the heteroaryl radical may be substituted with up to 4 radical substituents comprising: -D, —F, —Cl, —Br, —I, —CN, —$NO_2$, —$OR^5$, —$(CH_2)_mOR^5$, —$N(R^5)(R^6)$, —$(CH_2)_mN(R^5)(R^6)$, —$SO_2(CH_2)_mR^5$, —$(CO)(CH_2)_mR^5$, —$(CO)N(R^5)(R^6)$, —$OCF_3$, a branched or unbranched $C_1$-$C_6$-alkyl radical, a $C_3$-$C_6$-cycloalkyl radical, or a $C_1$-$C_6$-haloalkyl radical.

In certain embodiments, the amide compound represented by Formula (I), (II), or (III), may comprise the W representing the moiety represented by the ring system M-I, wherein $Z^1$, $Z^2$, $Z^3$, $Z^4$, and $Z^5$, each independently represent $CR^4$ with said $R^4$ representing —H; -D; —F; —Cl; —Br; —I; —$OCH_3$; —$OCF_3$; a $C_1$-$C_3$-alkyl radical; —$CF_3$; or a $C_3$-$C_4$-cycloalkyl radical; wherein the $C_1$-$C_3$-alkyl radical may be substituted with up to 4 radical substituents comprising: -D, —F, —Cl, a branched or unbranched $C_1$-$C_3$-alkyl radical, a $C_3$-$C_4$-cycloalkyl radical, or a $C_1$-$C_3$-haloalkyl radical. For example, in certain embodiments, $Z^1$, $Z^2$, $Z^4$, and $Z^5$ independently represent $CR^4$ with said $R^4$ representing —H or -D; and $Z^3$ independently represents $CR^4$ with said $R^4$ representing —H; -D; —F; —Cl; —Br; —I; —$OCH_3$; —$OCF_3$; a $C_1$-$C_3$-alkyl radical; —$CF_3$; or a $C_3$-$C_4$-cycloalkyl radical; wherein the $C_1$-$C_3$-alkyl radical may be substituted with up to 4 radical substituents comprising: -D, —F, —Cl, a branched or unbranched $C_1$-$C_3$-alkyl radical, a $C_3$-$C_4$-cycloalkyl radical, or a $C_1$-$C_3$-haloalkyl radical.

In certain embodiments, the amide compound represented by Formula (I), (II), or (III), may comprise the W representing the moiety represented by the ring system M-I, wherein $Z^1$, $Z^2$, $Z^4$, and $Z^5$ independently represent $CR^4$ with said $R^4$ representing —H or -D; and $Z^3$ independently represents $CR^4$ with said $R^4$ representing —Cl; —$OCH_3$; —$OCF_3$; a $C_1$-$C_3$-alkyl radical; —$CF_3$; or a $C_3$-$C_4$-cycloalkyl radical.

In certain embodiments, the amide compound represented by Formula (I), (II), or (III), may comprise the W representing the moiety represented by the ring system M-II. In certain embodiments, the amide compound represented by Formula (I), (II), or (III), may comprise the W representing the moiety represented by the ring system M-II, wherein $X^1$ represents C. For example, the amide compound represented by Formula (I), (II), or (III), may comprise the W representing the moiety represented by the ring system M-II, wherein M-II represents a moiety represented by one of the following:

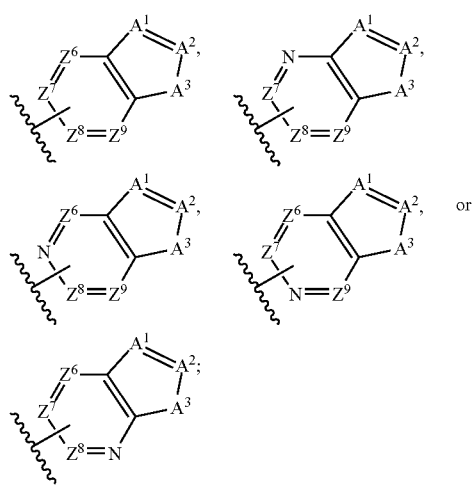

wherein $A^1$ and $A^2$ independently represent N or $CR^{11}$, and $A^3$ independently represents $NR^{10}$, O, or S. In certain embodiments, the amide compound represented by Formula (I), (II), or (III), may comprise the W representing the moiety represented by the ring system M-II, wherein either $Z^6$ or $Z^7$ represents $CR^7$ with said $R^7$ representing the bond directly attaching the W moiety with the carbonyl moiety, or wherein either $Z^8$ or $Z^9$ represents $CR^7$ with said $R^7$ representing the bond directly attaching the W moiety with the carbonyl moiety.

For example, in certain embodiments, the amide compound represented by Formula (I), (II), or (III), may comprise the W representing the moiety represented by the ring system M-II with $X^1$ representing C, wherein M-II represents a moiety represented by:

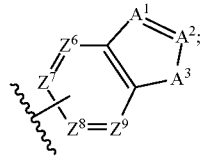

wherein $A^1$ and $A^2$ independently represent N or $CR^{11}$; $A^3$ independently represents $NR^{10}$, O, or S; and $Z^6$, $Z^7$, $Z^8$, and $Z^9$ represent $CR^7$, with one of said $R^7$ of $Z^6$, $Z^7$, $Z^8$, and $Z^9$ representing the bond directly attaching the W moiety with the carbonyl moiety.

In certain embodiments, for example, the amide compound represented by Formula (I), (II), or (III), may comprise the W representing the moiety represented by the ring system M-II-1 with $X^1$ representing C, said $R^7$ of $Z^7$ represents the bond directly attaching the W moiety with the carbonyl moiety:

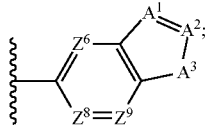

M-II-1 wherein $A^1$ and $A^2$ independently represent N or $CR^{11}$; $A^3$ independently represents $NR^{10}$, O, or S; and $Z^6$, $Z^8$, and $Z^9$ independently represent $CR^7$. For example, in certain embodiments, the amide compound represented by Formula (I), (II), or (III), may comprise the W representing the moiety represented by the ring system M-II-1, wherein $A^1$ and $A^2$ independently represent $CR^u$, and $A^3$ represents $NR^{10}$, O, or S, such as wherein $A^1$ and $A^2$ independently represent $CR^u$, for example $A^1$ and $A^2$ independently represent wherein $R^{11}$ independently represents —H, —F, —Cl, a $C_1$-$C_4$-alkyl radical, —$CF_3$, or a $C_3$-$C_4$-cycloalkyl radical, and $A^3$ represents 0; or wherein $A^1$ represents N and $A^2$ represents $CR^{11}$, and $A^3$ represents $NR^{10}$, O, or S.

In certain embodiments, for example, the amide compound represented by Formula (I), (II), or (III), may comprise the W representing the moiety represented by the ring system M-II-2 with $X^1$ representing C, said $R^7$ of $Z^8$ represents the bond directly attaching the W moiety with the carbonyl moiety:

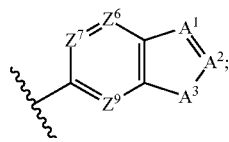

M-II-2 wherein $A^1$ and $A^2$ independently represent N or $CR^{11}$; $A^3$ independently represents $NR^{10}$, O, or S; and $Z^6$, $Z^7$, and $Z^9$ independently represent $CR^7$. For example, in certain embodiments, the amide compound represented by Formula (I), (II), or (III), may comprise the W representing the moiety represented by the ring system M-II-2, wherein $A^1$ and $A^2$ independently represent $CR^u$, and $A^3$ represents $NR^{10}$, O, or S, such as wherein $A^1$ and $A^2$ independently represent $CR^u$, for example $A^1$ and $A^2$ independently represent wherein $R^{11}$ independently represents —H, —F, —Cl, —Br, —CN, —$OR^{12}$, —$OCF_3$, a $C_1$-$C_4$-alkyl radical, —$CF_3$, or a $C_3$-$C_4$-cycloalkyl radical, and $A^3$ represents $NR^{10}$, O, or S; or wherein $A^1$ represents N and $A^2$ represents $CR^{11}$, and $A^3$ represents $NR^{10}$, O, or S.

For example, in certain embodiments, the amide compound represented by Formula (I), (II), or (III), may comprise the W representing the moiety represented by the ring system M-II with $X^1$ representing C, wherein M-II represents a moiety represented by:

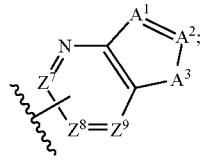

wherein $A^1$ and $A^2$ independently represent N or $CR^{11}$; $A^3$ independently represents $NR^{10}$, O, or S; and $Z^7$, $Z^8$, and $Z^9$ independently represent $CR^7$, with one of said $R^7$ of $Z^7$, $Z^8$, and $Z^9$ representing the bond directly attaching the W moiety with the carbonyl moiety.

In certain embodiments, for example, the amide compound represented by Formula (I), (II), or (III), may comprise the W representing the moiety represented by the ring system M-II-3 with $X^1$ representing C, said $R^7$ of $Z^7$ represents the bond directly attaching the W moiety with the carbonyl

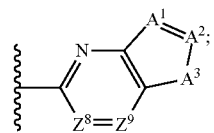

M-II-3 wherein $A^1$ and $A^2$ independently represent N or $CR^{11}$; $A^3$ independently represents $NR^{10}$, O, or S; and $Z^8$ and $Z^9$ independently represent $CR^7$. For example, in certain embodiments, the amide compound represented by Formula (I), (II), or (III), may comprise the W representing the moiety represented by the ring system M-II-3, wherein $A^1$ and $A^2$ independently represent $CR^{11}$, and $A^3$ represents $NR^{10}$, O, or S; or wherein $A^1$ represents N and $A^2$ represents $CR^{11}$, and $A^3$ represents $NR^{10}$, O, or S.

In certain embodiments, for example, the amide compound represented by Formula (I), (II), or (III), may comprise the W representing the moiety represented by the ring system M-II-4 with $X^1$ representing C, said $R^7$ of $Z^8$ represents the bond directly attaching the W moiety with the carbonyl moiety:

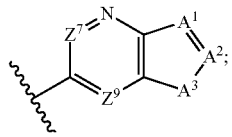

M-II-4 wherein $A^1$ and $A^2$ independently represent N or $CR^{11}$; $A^3$ independently represents $NR^{10}$, O, or S; and $Z^7$ and $Z^9$ independently represent $CR^7$. For example, in certain embodiments, the amide compound represented by Formula (I), (II), or (III), may comprise the W representing the moiety represented by the ring system M-II-4, wherein $A^1$ and $A^2$ independently represent $CR^{11}$, and $A^3$ represents $NR^{10}$, O, or S; or wherein $A^1$ represents N and $A^2$ represents $CR^{11}$, and $A^3$ represents $NR^{10}$, O, or S.

For example, in certain embodiments, the amide compound represented by Formula (I), (II), or (III), may comprise the W representing the moiety represented by the ring system M-II with $X^1$ representing C, wherein M-II represents a moiety represented by:

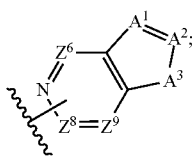

wherein A$^1$ and A$^2$ independently represent N or CR$^{11}$; A$^3$ independently represents NR$^{10}$, O, or S; and Z$^6$, Z$^8$, and Z$^9$ independently represent CR$^7$, with one of said R$^7$ of Z$^6$, Z$^8$, and Z$^9$ representing the bond directly attaching the W moiety with the carbonyl moiety.

In certain embodiments, for example, the amide compound represented by Formula (I), (II), or (III), may comprise the W representing the moiety represented by the ring system M-II-5 with X$^1$ representing C, said R$^7$ of Z$^8$ represents the bond directly attaching the W moiety with the carbonyl moiety:

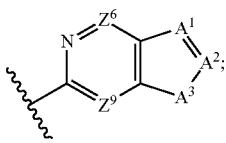

M-II-5 wherein A$^1$ and A$^2$ independently represent N or CR$^{11}$; A$^3$ independently represents NR$^{10}$, O, or S; and Z$^6$ and Z$^9$ independently represent CR$^7$. For example, in certain embodiments, the amide compound represented by Formula (I), (II), or (III), may comprise the W representing the moiety represented by the ring system M-II-5, wherein A$^1$ and A$^2$ independently represent CR$^{11}$, and A$^3$ represents NR$^{10}$, O, or S; or wherein A$^1$ represents N and A$^2$ represents CR$^{11}$, and A$^3$ represents NR$^{10}$, O, or S.

For example, in certain embodiments, the amide compound represented by Formula (I), (II), or (III), may comprise the W representing the moiety represented by the ring system M-II with X$^1$ representing C, wherein M-II represents a moiety represented by:

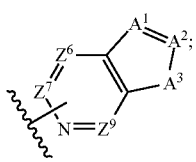

wherein A$^1$ and A$^2$ independently represent N or CR$^{11}$; A$^3$ independently represents NR$^{10}$, O, or S; and Z$^6$, Z$^7$, and Z$^9$ independently represent CR$^7$, with one of said R$^7$ of Z$^6$, Z$^7$, and Z$^9$ representing the bond directly attaching the W moiety with the carbonyl moiety.

In certain embodiments, for example, the amide compound represented by Formula (I), (II), or (III), may comprise the W representing the moiety represented by the ring system M-II-6 with X$^1$ representing C, said R$^7$ of Z$^7$ represents the bond directly attaching the W moiety with the carbonyl moiety:

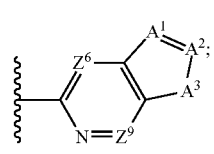

M-II-6 wherein A$^1$ and A$^2$ independently represent N or CR$^{11}$; A$^3$ independently represents NR$^{10}$, O, or S; and Z$^6$ and Z$^9$ independently represent CR$^7$. For example, in certain embodiments, the amide compound represented by Formula (I), (II), or (III), may comprise the W representing the moiety represented by the ring system M-II-6, wherein A$^1$ and A$^2$ independently represent CR$^{11}$, for example, wherein R$^{11}$ independently represents —H, —F, —Cl, —OCF$_3$, a C$_1$-C$_4$-alkyl radical, —CF$_3$, or a C$_3$-C$_4$-cycloalkyl radical, such as wherein R$^{11}$ independently represents —H, and A$^3$ represents NR$^{10}$, O, or S, for example, wherein A$^3$ represents O; or wherein A$^1$ represents N and A$^2$ represents CR$^{11}$, and A$^3$ represents NR$^{10}$, O, or S.

For example, in certain embodiments, the amide compound represented by Formula (I), (II), or (III), may comprise the W representing the moiety represented by the ring system M-II with X$^1$ representing C, wherein M-II represents a moiety represented by:

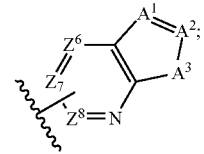

wherein A$^1$ and A$^2$ independently represent N or CR$^{11}$; A$^3$ independently represents NR$^{10}$, O, or S; and Z$^6$, Z$^7$, and Z$^8$ independently represent CR$^7$, with one of said R$^7$ of Z$^6$, Z$^7$, and Z$^8$ representing the bond directly attaching the W moiety with the carbonyl moiety.

In certain embodiments, for example, the amide compound represented by Formula (I), (II), or (III), may comprise the W representing the moiety represented by the ring system M-II-7 with X$^1$ representing C, said R$^7$ of Z$^7$ represents the bond directly attaching the W moiety with the carbonyl moiety:

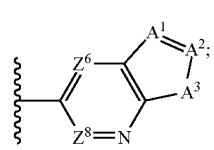

M-II-7 wherein A$^1$ and A$^2$ independently represent N or CR$^{11}$; A$^3$ independently represents NR$^{10}$, O, or S; and Z$^6$ and Z$^8$ independently represent CR$^7$. For example, in certain embodiments, the amide compound represented by Formula (I), (II), or (III), may comprise the W representing the moiety represented by the ring system M-II-7, wherein A$^1$ and A$^2$ independently represent CR$^{u}$, and A$^3$ represents NR$^{10}$, O, or S; or wherein A$^1$ represents N and A$^2$ represents CR$^{11}$, and A$^3$ represents NR$^{10}$, O, or S.

In certain embodiments, for example, the amide compound represented by Formula (I), (II), or (III), may comprise the W representing the moiety represented by the ring system M-II-8 with $X^1$ representing C, said $R^7$ of $Z^8$ represents the bond directly attaching the W moiety with the carbonyl moiety:

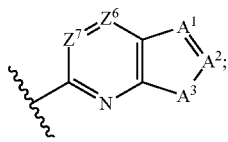

M-II-8 wherein $A^1$ and $A^2$ independently represent N or $CR^{11}$; $A^3$ independently represents $NR^{10}$, O, or S; and $Z^6$ and $Z^7$ independently represent $CR^7$. For example, in certain embodiments, the amide compound represented by Formula (I), (II), or (III), may comprise the W representing the moiety represented by the ring system M-II-8, wherein $A^1$ and $A^2$ independently represent $CR^u$, and $A^3$ represents $NR^{10}$, O, or S; or wherein $A^1$ represents N and $A^2$ represents $CR^{11}$, and $A^3$ represents $NR^{10}$, O, or S.

In certain embodiments, for example, the amide compound represented by Formula (I), (II), or (III), may comprise the W representing the moiety represented by any one of ring systems M-II-1 to M-II-8, wherein $R^7$ independently represents —H; -D; —F; —Cl; —Br; —I; —CN; —$OR^8$; —$OCF_3$; a $C_1$-$C_6$-alkyl radical; a $C_1$-$C_6$-haloalkyl radical; a $C_3$-$C_6$-cycloalkyl radical; wherein the $C_1$-$C_6$-alkyl radical may be substituted with up to 4 radical substituents comprising: -D, —F, —Cl, —Br, —I, —CN, —$NO_2$, —$OR^8$, —$(CH_2)_mOR^8$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical; for example, wherein $R^7$ independently represents —H or -D.

In certain embodiments, for example, the amide compound represented by Formula (I), (II), or (III), may comprise the W representing the moiety represented by any one of ring systems M-II-1 to M-II-8, wherein $R^{11}$ independently represents —H; —F; —Cl; —Br; —I; —CN; —$OR^2$; —$(CH_2)_mOR^{12}$; —$OCF_3$; a $C_1$-$C_6$-alkyl radical; a $C_1$-$C_6$-haloalkyl radical; or a $C_3$-$C_6$-cycloalkyl radical; for example, wherein $R^{11}$ independently represents —H; —F; —Cl; —Br; —I; —CN; —$OR^2$; —$(CH_2)_mOR^2$; —$OCF_3$; a $C_1$-$C_4$-alkyl radical; or a $C_1$-$C_2$-haloalkyl radical; for example, wherein $R^{11}$ independently represents —H; —F; —Cl; —Br; —I; —CN; —$OR^2$; —$OCF_3$; a $C_1$-$C_4$-alkyl radical; —$CF_3$; or a $C_3$-$C_4$-cycloalkyl radical.

In certain embodiments, for example, the amide compound represented by Formula (I), (II), or (III), may comprise the W representing the moiety represented by any one of ring systems M-II-1 to M-II-8, wherein $R^{12}$ independently represents —H, a branched or unbranched $C_1$-$C_4$-alkyl radical, or a $C_3$-$C_6$-cycloalkyl radical.

In certain embodiments, the amide compound represented by Formula (I), (II), or (III), may comprise the W representing the moiety represented by the ring system M-II. In certain embodiments, the amide compound represented by Formula (I), (II), or (III), may comprise the W representing the moiety represented by the ring system M-II, wherein $X^1$ represents N. For example, the amide compound represented by Formula (I), (II), or (III), may comprise the W representing the moiety represented by the ring system M-II, wherein M-II represents a moiety represented by one of the following:

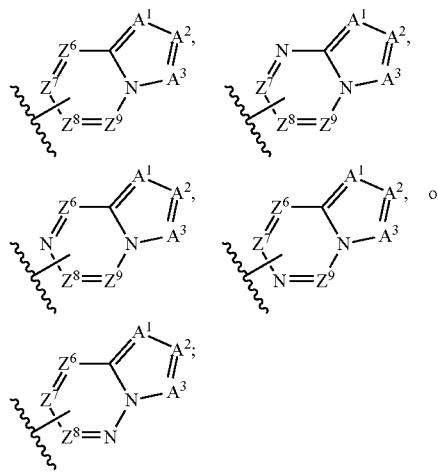

wherein $A^1$, $A^2$, and $A^3$, independently represent N or $CR^{11}$. In certain embodiments, for example, the amide compound represented by Formula (I), (II), or (III), may comprise the W representing the moiety represented by the ring system M-II, wherein $A^1$ independently represents $CR^{11}$; and $A^2$ and $A^3$ independently represent N or $CR^{11}$; for example, wherein $A^2$ independently represents $CR^{11}$; and $A^1$ and $A^3$ independently represent N or $CR^{11}$; for example, wherein $A^3$ independently represents $CR^{10}$; and $A^1$ and $A^2$ independently represent N or $CR^{11}$; or in certain embodiments, for example, wherein each of $A^1$, $A^2$, and $A^3$, represents N. In certain embodiments, the amide compound represented by Formula (I), (II), or (III), may comprise the W representing the moiety represented by the ring system M-II, wherein either $Z^6$ or $Z^7$ represents $CR^7$ with said $R^7$ representing the bond directly attaching the W moiety with the carbonyl moiety, or wherein either $Z^8$ or $Z^9$ represents $CR^7$ with said $R^7$ representing the bond directly attaching the W moiety with the carbonyl moiety.

In certain embodiments, the amide compound represented by Formula (I), (II), or (III), may comprise the W representing the moiety represented by the ring system M-III. In certain embodiments, the amide compound represented by Formula (I), (II), or (III), may comprise the W representing the moiety represented by the ring system M-III, wherein M-III represents a moiety represented by one of the following ring systems:

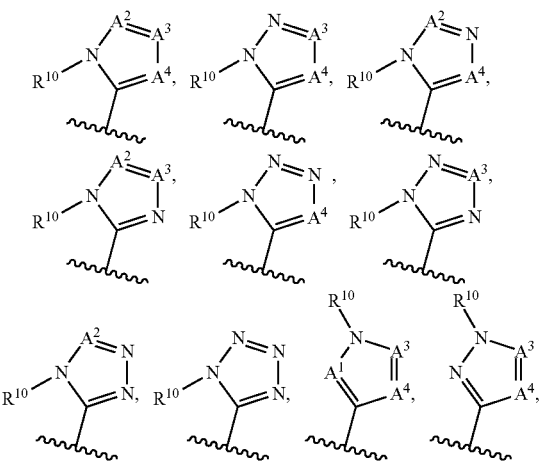

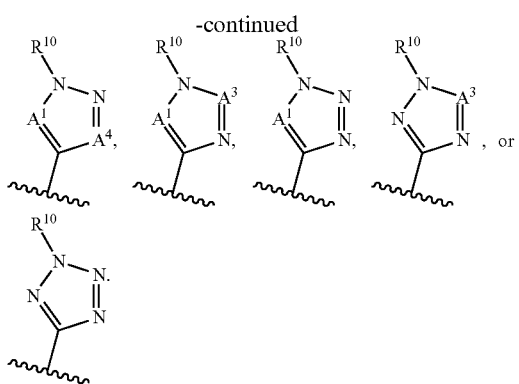

In certain embodiments, the amide compound represented by Formula (I), (II), or (III), may comprise the W representing the moiety represented by the ring system M-III, wherein M-III represents a moiety represented by one of the following:

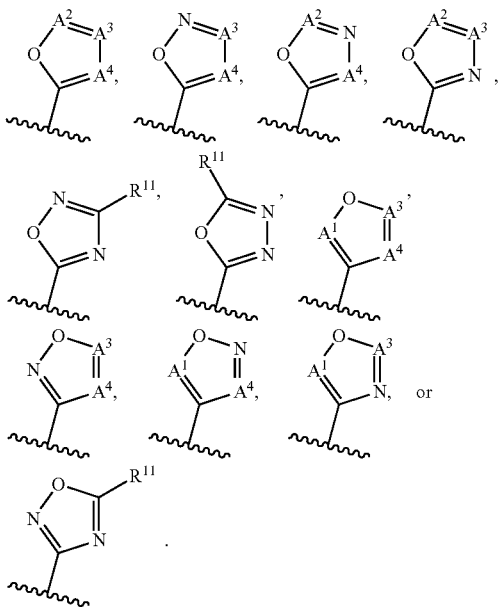

In certain embodiments, the amide compound represented by Formula (I), (II), or (III), may comprise the W representing the moiety represented by the ring system M-III, wherein M-III represents a moiety represented by one of the following:

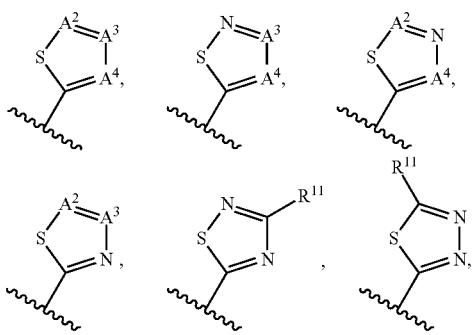

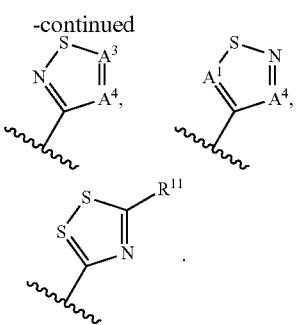

For example, in certain embodiments, the amide compound represented by Formula (I), (II), or (III), may comprise the W representing the moiety represented by the ring system M-III, wherein M-III represents a moiety represented by one of the following:

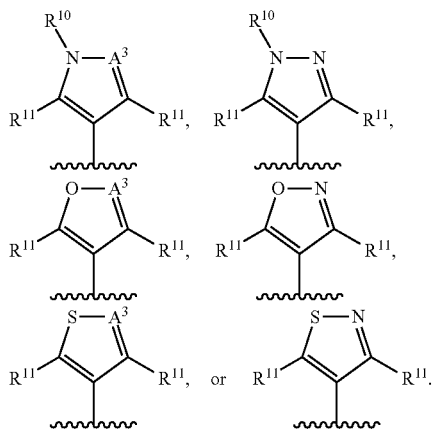

In certain embodiments, the amide compound represented by Formula (I), (II), or (III), may comprise the W representing the moiety represented by the ring system M-IV.

In certain embodiments, the amide compound represented by Formula (I), (II), or (III), may comprise the W representing the moiety represented by the ring system M-IV, wherein $X^2$ represents C. For example, the amide compound represented by Formula (I), (II), or (III), comprising W representing the moiety represented by the ring system M-IV, may comprise a moiety represented by one of the following:

M-IV-1

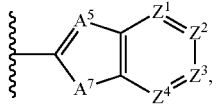

M-IV-2

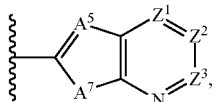

M-IV-3

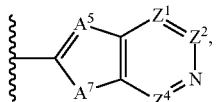

-continued

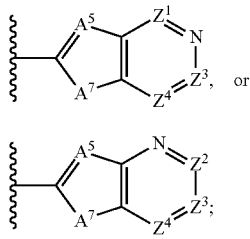

M-IV-4

M-IV-5 wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S.

In certain embodiments, the amide compound represented by Formula (I), (II), or (III), may comprise the W representing the moiety represented by the ring system M-IV, wherein M-IV represents a moiety represented by ring system M-IV-1:

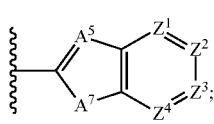

M-IV-1 wherein $Z^1$, $Z^2$, $Z^3$, and $Z^4$ independently represent $CR^4$. For example, in certain embodiments, the amide compound represented by Formula (I), (II), or (III), may comprise the W representing the moiety represented by the ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $R^4$ independently represents —H; -D; —F; —Cl; —Br; —I; —CN; —NO$_2$; —OR$^5$; —N(R$^5$)(R$^6$); —SO$_2$(CH$_2$)$_m$R$^5$; —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; or a heteroaryl radical; wherein the $C_1$-$C_6$-alkyl radical, the (3-6 membered)-heterocycloalkyl radical, and the heteroaryl radical may be substituted with up to 4 radical substituents comprising: -D, —F, —Cl, —Br, —I, —CN, —NO$_2$, —OR$^5$, —N(R$^5$)(R$^6$), —SO$_2$(CH$_2$)$_m$R$^5$, —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical. For example, in certain embodiments, the amide compound represented by Formula (I), (II), or (III), may comprise the W representing the moiety represented by the ring system M-IV-1, wherein $R^5$ and $R^6$ independently represent —H; a branched or unbranched $C_1$-$C_3$-alkyl radical; or a $C_3$-$C_6$-cycloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$ and $Z^2$ independently represent CH; and $Z^3$ and $Z^4$ independently represent $CR^4$, wherein $R^4$ independently represents —H; -D; —F; —Cl; —Br; —CN; —OR$^5$; —N(R$^5$)(R$^6$); —SO$_2$(CH$_2$)$_m$R$^5$; —OCF$_3$; a $C_1$-$C_4$-alkyl radical; —CF$_3$; a $C_3$-$C_4$-cycloalkyl radical; a 6 membered-heterocycloalkyl radical; or a heteroaryl radical; wherein the $C_1$-$C_4$-alkyl radical, the 6 membered-heterocycloalkyl radical, and the heteroaryl radical may be substituted with up to 4 radical substituents comprising: -D, —F, —Cl, —Br, —I, —CN, —NO$_2$, —OR$^5$, —N(R$^5$)(R$^6$), —SO$_2$(CH$_2$)$_m$R$^5$, —OCF$_3$, a branched or unbranched $C_1$-$C_4$-alkyl radical, a $C_3$-$C_4$-cycloalkyl radical, a $C_1$-$C_4$-hydroxyalkyl radical, or a $C_1$-$C_2$-haloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^4$ independently represent CH; and $Z^3$ independently represent $CR^4$, wherein $R^4$ independently represents —H; -D; —F; —Cl; —Br; —CN; —OR$^5$; —N(R$^5$)(R$^6$); —SO$_2$(CH$_2$)$_m$R$^5$; —OCF$_3$; a $C_1$-$C_4$-alkyl radical; —CF$_3$; a $C_3$-$C_4$-cycloalkyl radical; a 6 membered-heterocycloalkyl radical; or a heteroaryl radical; wherein the $C_1$-$C_4$-alkyl radical, the 6 membered-heterocycloalkyl radical, and the heteroaryl radical may be substituted with up to 4 radical substituents comprising: -D, —F, —Cl, —Br, —I, —CN, —NO$_2$, —OR$^5$, —N(R$^5$)(R$^6$), —SO$_2$(CH$_2$)$_m$R$^5$, —OCF$_3$, a branched or unbranched $C_1$-$C_4$-alkyl radical, a $C_3$-$C_4$-cycloalkyl radical, a $C_1$-$C_4$-hydroxyalkyl radical, or a $C_1$-$C_2$-haloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^4$ independently represent CH; and $Z^3$ independently represent $CR^4$, wherein $R^4$ independently represents —H; -D; —F; —Cl; —Br; —OR$^5$; —N(R$^5$)(R$^6$); —OCF$_3$; a $C_1$-$C_4$-alkyl radical; —CF$_3$; or a $C_3$-$C_4$-cycloalkyl radical; wherein the $C_1$-$C_4$-alkyl radical may be substituted with up to 4 radical substituents comprising: -D, —F, a branched or unbranched $C_1$-$C_4$-alkyl radical, a $C_3$-$C_4$-cycloalkyl radical, a $C_1$-$C_4$-hydroxyalkyl radical, or a $C_1$-$C_2$-haloalkyl radical; and wherein $R^5$ and $R^6$ independently represent —H; a branched or unbranched $C_1$-$C_3$-alkyl radical; or a $C_3$-$C_6$-cycloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S, for example, $A^7$ represents S; and wherein $Z^1$, $Z^2$, and $Z^4$ independently represent CH; and $Z^3$ independently represent $CR^4$, wherein $R^4$ independently represents —H; -D; —F; —Cl; —Br; —OCH$_3$; —NH$_2$; —CH$_3$; —CF$_3$; or a cyclopropyl radical, for example, wherein $R^4$ independently represents —H, -D, —F, —Cl, —Br, —OCH$_3$, —CH$_3$, or a cyclopropyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^3$ independently represent CH; and $Z^4$ independently represent $CR^4$, wherein $R^4$ independently represents —H; -D; —F; —Cl; —Br; —CN; —$OR^5$; —$N(R^5)(R^6)$; —$SO_2(CH_2)_mR^5$; —$OCF_3$; a $C_1$-$C_4$-alkyl radical; —$CF_3$; a $C_3$-$C_4$-cycloalkyl radical; a 6 membered-heterocycloalkyl radical; or a heteroaryl radical; wherein the $C_1$-$C_4$-alkyl radical, the 6 membered-heterocycloalkyl radical, and the heteroaryl radical may be substituted with up to 4 radical substituents comprising: -D, —F, —Cl, —Br, —I, —CN, —$NO_2$, —$OR^5$, —$N(R^5)(R^6)$, —$SO_2(CH_2)_mR^5$, —$OCF_3$, a branched or unbranched $C_1$-$C_4$-alkyl radical, a $C_3$-$C_4$-cycloalkyl radical, a $C_1$-$C_4$-hydroxyalkyl radical, or a $C_1$-$C_2$-haloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^3$ independently represent CH; and $Z^4$ independently represent $CR^4$, wherein $R^4$ independently represents —H; -D; —F; —Cl; —Br; —$OR^5$; —$N(R^5)(R^6)$; —$OCF_3$; a $C_1$-$C_4$-alkyl radical; —$CF_3$; or a $C_3$-$C_4$-cycloalkyl radical; wherein the $C_1$-$C_4$-alkyl radical may be substituted with up to 4 radical substituents comprising: -D, —F, a branched or unbranched $C_1$-$C_4$-alkyl radical, a $C_3$-$C_4$-cycloalkyl radical, a $C_1$-$C_4$-hydroxyalkyl radical, or a $C_1$-$C_2$-haloalkyl radical; and wherein $R^5$ and $R^6$ independently represent —H; a branched or unbranched $C_1$-$C_3$-alkyl radical; or a $C_3$-$C_6$-cycloalkyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^3$ independently represent CH; and $Z^4$ independently represent $CR^4$, wherein $R^4$ independently represents —H; -D; —F; —Cl; —Br; —$OCH_3$; —$NH_2$; —$CH_3$; —$CF_3$; or a cyclopropyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^3$ independently represent CH; and $Z^4$ independently represent $CR^4$, wherein $R^4$ independently represents —F; —Cl; —$OCH_3$; —$CH_3$; —$CF_3$; or a cyclopropyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$, $Z^2$, and $Z^3$ independently represent CH; and $Z^4$ independently represent $CR^4$, wherein $R^4$ independently represents —H; —F; —Cl; —CN; —$OCH_3$; —$OCH_2CH_3$; —$OCF_3$; or a cyclopropyl radical, for example, wherein $R^4$ independently represents —H; —F; —CN; —$OCH_2CH_3$; —$OCF_3$; or a cyclopropyl radical.

In certain embodiments, the amide compound represented by Formula (I), (II), or (III), may comprise the W representing the moiety represented by the ring system M-IV, wherein M-IV represents a moiety represented by ring system M-IV-1, wherein $A^5$ represents N or $CR^{15}$, preferably $A^5$ represents $CR^{15}$, wherein $R^{15}$ preferably represents —H; and $A^7$ represents $NR^{14}$, $N(CH_2)_mR^{14}$, O, or S, preferably $A^7$ represents O or S; and wherein $Z^1$ independently represents CH; $Z^2$ independently represents $CR^4$, wherein $R^4$ independently represents —H or —F; $Z^3$ independently represents $CR^4$, wherein $R^4$ independently represents —H; -D; —Cl; —Br; —$OCH_3$; —$CH_3$; or a cyclopropyl radical; and $Z^4$ independently represents $CR^4$, wherein $R^4$ independently represents —H; -D; —F; —Cl; —CN; —$OCH_2CH_3$; —$OCF_3$; or a cyclopropyl radical; for example, wherein $Z^1$ and $Z^2$ independently represent CH; $Z^3$ independently represents $CR^4$, wherein $R^4$ independently represents —Cl or —$CH_3$; and $Z^4$ independently represents $CR^4$, wherein $R^4$ independently represents —F or —Cl.

In certain embodiments, the amide compound represented by Formula (I), (II), or (III), may comprise the W representing the moiety represented by the ring system M-IV, wherein $X^2$ represents C. For example, the amide compound represented by Formula (I), (II), or (III), comprising W representing the moiety represented by the ring system M-IV, may comprise a moiety represented by one of the following:

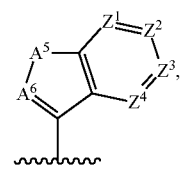

M-IV-6

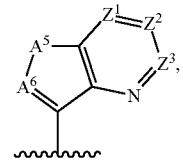

M-IV-7

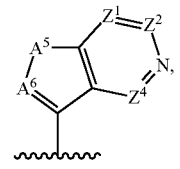

M-IV-8

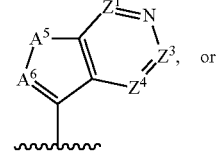

M-IV-9 or

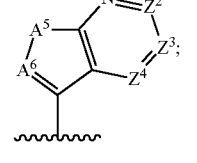

M-IV-10 wherein $A^5$ represents $NR^{14}$; O; or S, preferably $A^5$ represents O or S.

In certain embodiments, the amide compound represented by Formula (I), (II), or (III), may comprise the W representing the moiety represented by the ring system M-IV, wherein $X^2$ represents N. For example, the amide compound represented by Formula (I), (II), or (III), comprising W representing the moiety represented by the ring system M-IV, may comprise a moiety represented by one of the following:

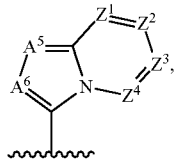

M-IV-11

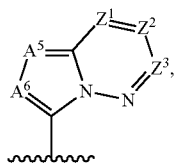

M-IV-12

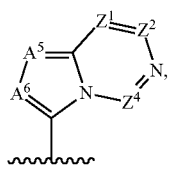

M-IV-13

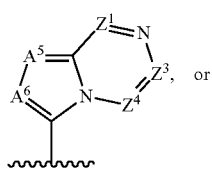

M-IV-14 or

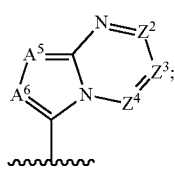

M-IV-15 wherein $A^5$ and $A^6$ independently represent N or $CR^{15}$, preferably $A^5$ and $A^6$ represents $CR^{15}$, wherein $R^{15}$ preferably represents —H.

In certain embodiments, the amide compound represented by Formula (I), (II), or (III), may comprise the W representing the moiety represented by the ring system M-IV, wherein $X^2$ represents N. For example, the amide compound represented by Formula (I), (II), or (III), comprising W representing the moiety represented by the ring system M-IV, may comprise a moiety represented by one of the following:

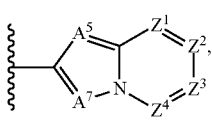

M-IV-16

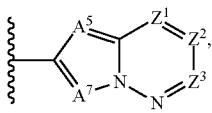

M-IV-17

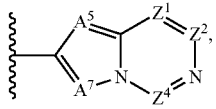

M-IV-18

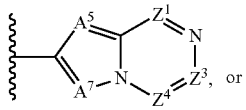

M-IV-19 or

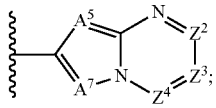

M-IV-20 wherein $A^5$ and $A^7$ independently represent N or $CR^{15}$.

In certain embodiments, the amide compound represented by Formula (I), (II), or (III), may comprise the W representing the moiety represented by the ring system M-IV, wherein $X^2$ represents N. For example, the amide compound represented by Formula (I), (II), or (III), comprising W representing the moiety represented by the ring system M-IV, may comprise a moiety represented by one of the following:

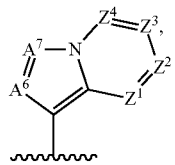

M-IV-21

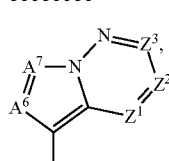

M-IV-22

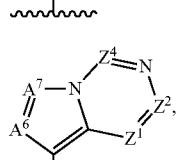

M-IV-23

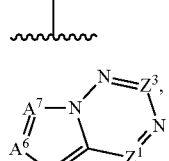

M-IV-24 or

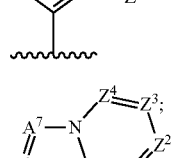

M-IV-25 wherein $A^6$ and $A^7$ independently represent N or $CR^{15}$.

For example, in certain embodiments, the amide compound represented by Formula (I), (II), or (III), may comprise the W representing the moiety represented by the ring system M-IV-22:

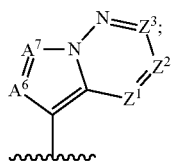

M-IV-22 wherein $Z^1$, $Z^2$, and $Z^3$ independently represent $CR^4$; $A^6$ represents $CR^5$; and $A^7$ represents N.

In certain embodiments, the amide compound represented by Formula (I), (II), or (III), may comprise the W representing the moiety represented by the ring system M-V. For example, in certain embodiments, the amide compound represented by Formula (I), (II), or (III), may comprise the W representing the moiety represented by the ring system M-V, wherein M-V represents a moiety represented by one of the following:

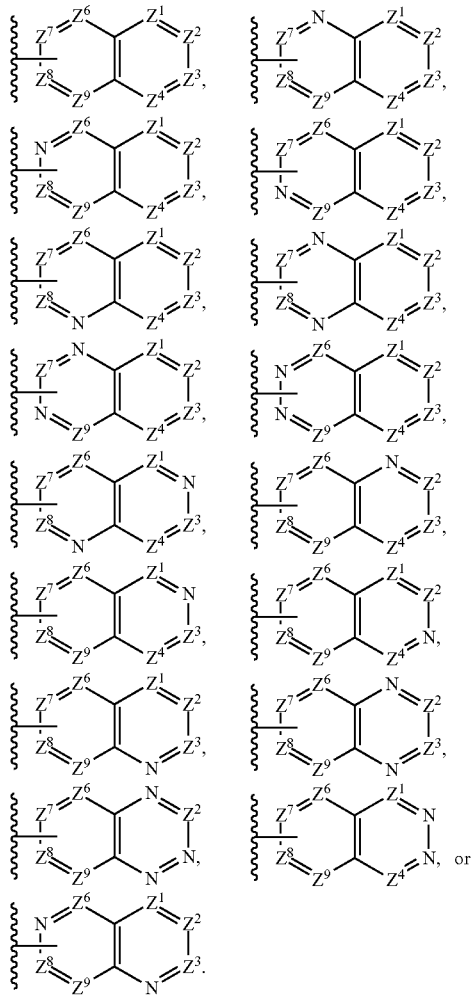

In certain embodiments, the amide compound represented by Formula (I), (II), or (III), may comprise the W representing the moiety represented by the ring system M-VI. For example, in certain embodiments, the amide compound represented by Formula (I), (II), or (III), may comprise the W representing the moiety represented by the ring system M-VI, wherein M-VI represents a moiety represented by one of the following:

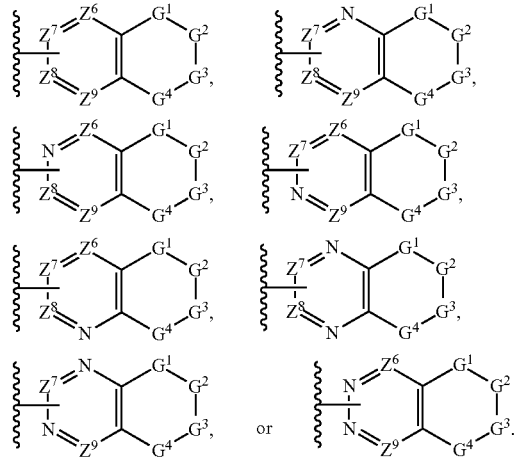

In certain embodiments, for example, the amide compound represented by Formula (I), (II), or (III), may comprise the W representing the moiety represented by the ring system M-VI, wherein M-VI represents a moiety represented by one of the following:

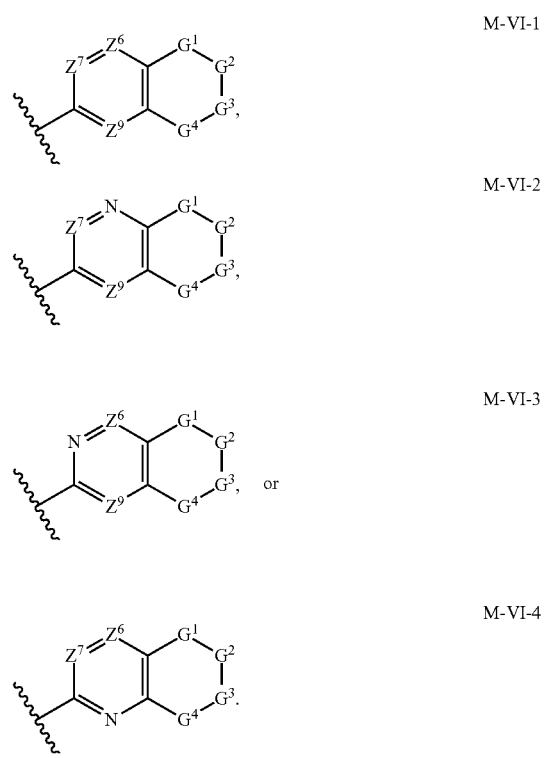

M-VI-1

M-VI-2

M-VI-3

M-VI-4

In certain embodiments, for example, the amide compound represented by Formula (I), (II), or (III), may comprise the W representing the moiety represented by the ring system M-VI, wherein M-VI represents a moiety represented by ring system M-VI-1:

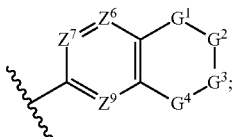

M-VI-1 wherein $Z^6$, $Z^7$, and $Z^9$ independently represent $CR^7$. For example, in certain embodiments, the amide compound represented by Formula (I), (II), or (III), may comprise the W representing the moiety represented by the ring system M-VI-1, wherein $G^1$ and $G^4$ independently represent —NH or O; and $G^2$ and $G^3$ independently represent $C(R^{18})(R^{18})$; for example, wherein $G^1$ and $G^4$ independently represent O; and $G^2$ and $G^3$ independently represent $C(R^{18})(R^{18})$, wherein $R^{18}$ independently represents —H.

In certain embodiments, for example, the amide compound represented by Formula (I), (II), or (III), may comprise the W representing the moiety represented by the ring system M-VI, wherein M-VI represents a moiety represented by ring system M-VI-3:

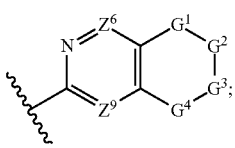

M-VI-3 wherein $Z^6$ and $Z^9$ independently represent $CR^7$. For example, in certain embodiments, the amide compound represented by Formula (I), (II), or (III), may comprise the W representing the moiety represented by the ring system M-VI-1, wherein $G^1$ and $G^4$ independently represent —NH or O; and $G^2$ and $G^3$ independently represent $C(R^{18})(R^{18})$; for example, wherein $G^1$ and $G^4$ independently represent O; and $G^2$ and $G^3$ independently represent $C(R^{18})(R^{18})$, wherein $R^{18}$ independently represents —H.

In certain embodiments, the amide compound represented by Formula (I), (II), or (III), may comprise the W representing the moiety represented by the ring system M-I, M-IV, or M-V, wherein adjacent members of $Z^1$, $Z^2$, $Z^3$, $Z^4$, and $Z^5$, is $(CR^4)(CR^4)$, and the $(CR^4)(CR^4)$ forms a cycle such that the adjacent $R^4$ substitutents taken together represents a (3-6 membered)-heteroalkyl di-radical with at least one ring atom of the (3-6 membered)-heteroalkyl di-radical selected from the group consisting of oxygen, nitrogen, and sulfur, with the proviso that when the at least one ring atom is nitrogen, the nitrogen is unsubstituted (specifically is —N(H)—) or is substituted with a branched or unbranched $C_1$-$C_4$-alkyl radical, a $C_3$-$C_4$-cycloalkyl radical, —(CO)-branched or unbranched $C_1$-$C_4$-alkyl, or —($SO_2$)-branched or unbranched $C_1$-$C_4$-alkyl, wherein the $C_1$-$C_4$-alkyl radical and the $C_3$-$C_4$-cycloalkyl radical may be substituted with up to 4 radical substituents comprising: -D, halogen, =O, —OH, —$OC_1$-$C_4$-alkyl or —$OCF_3$, and with the further proviso that when the at least one ring atom is sulfur, the sulfur may substituted with 0 or 2 =O; and wherein the alkyl portion of said (3-6 membered)-heteroalkyl di-radical may be substituted with up to 4 radical substituents comprising: -D, —F, —Cl, —Br, —I, —$OR^5$, —$(CH_2)_mOR^5$, —$N(R^5)(R^6)$, —$(CH_2)_mN(R^5)(R^6)$, —$SO_2(CH_2)_mR^5$, —$(CO)(CH_2)_mR^5$, —$(CO)N(R^5)(R^6)$, —$OCF_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical. For example, in certain embodiments, the amide compound represented by Formula (I), (II), or (III), may comprise the W representing the moiety represented by the ring system M-I, M-IV, or M-V, wherein adjacent members of $Z^1$, $Z^2$, $Z^3$, $Z^4$, and $Z^5$, is $(CR^4)(CR^4)$, such as adjacent members $Z^1$ and $Z^2$ is $(CR^4)(CR^4)$, adjacent members $Z^2$ and $Z^3$ is $(CR^4)(CR^4)$, adjacent members $Z^3$ and $Z^4$ is $(CR^4)(CR^4)$, or adjacent members $Z^4$ and $Z^5$ is $(CR^4)(CR^4)$, and the $(CR^4)(CR^4)$ forms a cycle such that the adjacent $R^4$ substitutents taken together represents a (3-6 membered)-heteroalkyl di-radical with at least one ring atom of the (3-6 membered)-heteroalkyl di-radical selected from the group consisting of oxygen, nitrogen, and sulfur, for example, at least two ring atoms of the (3-6 membered)-heteroalkyl di-radical are independently selected from the group consisting of oxygen, nitrogen, and sulfur, with the proviso that when the at least one ring atom is, or at least two ring atoms are independently, nitrogen, then the nitrogen is unsubstituted (specifically is —N(H)—) or is substituted with a branched or unbranched $C_1$-$C_4$-alkyl radical, a $C_3$-$C_4$-cycloalkyl radical, —(CO)-branched or unbranched $C_1$-$C_4$-alkyl, or —($SO_2$)-branched or unbranched $C_1$-$C_4$-alkyl, wherein the $C_1$-$C_4$-alkyl radical and the $C_3$-$C_4$-cycloalkyl radical may be substituted with up to 4 radical substituents comprising: -D, halogen, =O, —OH, —$OC_1$-$C_4$-alkyl or —$OCF_3$. For example, in certain embodiments, adjacent members of $Z^1$, $Z^2$, $Z^3$, $Z^4$, and $Z^5$, is $(CR^4)(CR^4)$, and the $(CR^4)(CR^4)$ forms a cycle such that the adjacent $R^4$ substitutents taken together represents a (3-6 membered)-heteroalkyl di-radical, and the (3-6 membered)-heteroalkyl di-radical comprises: —$OCH_2CH_2CH_2$—, —$OCH_2CH_2N(H)$—, —$OCH_2CH_2N(C_1$-$C_4$-alkyl)-, such as —$OCH_2CH_2N(Me)$-; —$CH_2CH_2CH_2N(CO)(C_1$-$C_4$-alkyl)-, —$N(H)CH_2CH_2O$—, —$N(C_1$-$C_4$-alkyl)$CH_2CH_2O$—, such as —$N(Me)CH_2CH_2O$—; —$OCH_2CH_2O$—; —$OCF_2O$—; or —$CH_2CH_2CH_2O$—. For purposes described herein, when the (3-6 membered)-heteroalkyl di-radical is specified, it is both referenced and attached on the ring system M-I, M-IV, or M-V, in order from lowest to highest of adjacent members of $Z^1$, $Z^2$, $Z^3$, $Z^4$, and $Z^5$. For example, by way of illustration, the resulting ring system of W representing the moiety represented by the ring system M-IV-1, wherein $A^7$ is S, and the adjacent members $Z^1$ and $Z^2$ is $(CR^4)(CR^4)$, and the $(CR^4)(CR^4)$ forms a cycle such that the adjacent $R^4$ substitutents taken together represents a (3-6 membered)-heteroalkyl di-radical, and the (3-6 membered)-heteroalkyl di-radical is: (i) —$OCH_2CH_2CH_2$—, (ii) —$OCH_2CH_2N(H)$—; (iii) —$N(H)CH_2CH_2O$—; (iv) —$OCH_2CH_2O$—; (v) —$OCF_2O$—; or (vi) —$CH_2CH_2CH_2O$—, would be represented by the following structures:

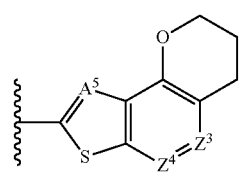

(i)

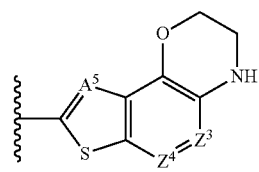

(ii)

-continued

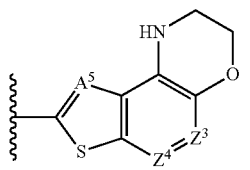
(iii)

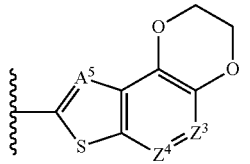
(iv)

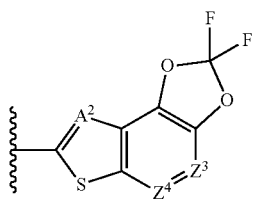
(v)

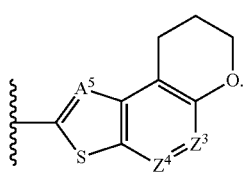
(vi)

In certain embodiments, the amide compound represented by Formula (I), (II), or (III), for example, may comprise the W representing the moiety represented by the ring system M-I to M-VI, wherein $R^1$ and $R^2$ independently represent an unbranched $C_1$-alkyl radical, and said compound is represented by Formula (II):

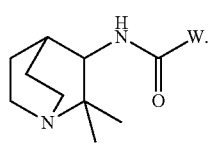
(II)

In certain embodiments, the amide compound represented by Formula (I), (II), or (III), for example, may comprise the W representing the moiety represented by the ring system M-I to M-VI, wherein $R^1$ and $R^2$ taken together represent a $C_2$-alkyl di-radical and said compound is represented by Formula (III):

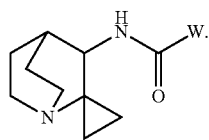
(III)

In certain embodiments, the amide compound represented by Formula (I), (II), or (III), may comprise racemic mixture of enantiomers, a mixture of diastereomers, a single enantiomer, or a single diastereomer, of the compound, or a pharmaceutically acceptable salt thereof. In certain embodiments, the amide compound represented by Formula (I), (II), or (III), may comprise a mixture of tautomers, substantially a single tautomer form, or a single tautomer form, such as a tautomer contained within W, for example, a tautomer may be contained within a W containing a heteroaryl ring nitrogen adjacent to a heteroaryl ring carbon substituted with a hydroxyl group.

The chemical names and structure diagrams used herein to describe the compounds of the present invention, supra and infra, were created with the use of ChemBioDraw Ultra® Version 12.0 (available from CambridgeSoft Corp., Cambridge, Mass.).

In certain embodiments, specific examples of the amide compound represented by Formula (I) may include, collectively or individually, the compounds listed below, and single enantiomers and pharmaceutically acceptable salts thereof:

N-(2,2-dimethylquinuclidin-3-yl)benzo[b]thiophene-2-carboxamide;
4-chloro-N-(2,2-dimethylquinuclidin-3-yl)benzamide;
7-chloro-N-(2,2-dimethylquinuclidin-3-yl)benzo[b]thiophene-2-carboxamide;
N-(2,2-dimethylquinuclidin-3-yl)-7-fluoro-benzo[b]thiophene-2-carboxamide;
N-(2,2-dimethylquinuclidin-3-yl)benzo[b]thiophene-6-carboxamide;
N-(2,2-dimethylquinuclidin-3-yl)benzofuran-5-carboxamide;
N-(2,2-dimethylquinuclidin-3-yl)-7-(trifluoromethyl)benzo[b]thiophene-2-carboxamide;
N-(2,2-dimethylquinuclidin-3-yl)-6-fluorobenzo[b]thiophene-2-carboxamide;
6-cyano-N-(2,2-dimethylquinuclidin-3-yl)benzo[b]thiophene-2-carboxamide;
N-(2,2-dimethylquinuclidin-3-yl)-6-(trifluoromethyl)benzo[b]thiophene-2-carboxamide;
N-(2,2-dimethylquinuclidin-3-yl)-5-fluorobenzo[b]thiophene-2-carboxamide;
6-chloro-N-(2,2-dimethylquinuclidin-3-yl)benzo[b]thiophene-2-carboxamide;
5-chloro-N-(2,2-dimethylquinuclidin-3-yl)benzo[b]thiophene-2-carboxamide;
5,6-dichloro-N-(2,2-dimethylquinuclidin-3-yl)benzo[b]thiophene-2-carboxamide;
N-(2,2-dimethylquinuclidin-3-yl)-6-methylbenzo[b]thiophene-2-carboxamide;
N-(2,2-dimethylquinuclidin-3-yl)-5-methylbenzo[b]thiophene-2-carboxamide;
N-(2,2-dimethylquinuclidin-3-yl)-5-(trifluoromethyl)benzo[b]thiophene-2-carboxamide;
6-cyclopropyl-N-(2,2-dimethylquinuclidin-3-yl)benzo[b]thiophene-2-carboxamide;
5-cyclopropyl-N-(2,2-dimethylquinuclidin-3-yl)benzo[b]thiophene-2-carboxamide;
N-(2,2-dimethylquinuclidin-3-yl)-6-methoxybenzo[b]thiophene-2-carboxamide;
N-(2,2-dimethylquinuclidin-3-yl)-5-methoxybenzo[b]thiophene-2-carboxamide;
N-(2,2-dimethylquinuclidin-3-yl)furo[2,3-c]pyridine-5-carboxamide;
N-(2,2-dimethylquinuclidin-3-yl)-2,3-dihydro-[1,4]dioxino[2,3-c]pyridine-7-carboxamide;
N-(2,2-dimethylquinuclidin-3-yl)-3-methylbenzo[b]thiophene-5-carboxamide;
N-(2,2-dimethylquinuclidin-3-yl)-3-methylbenzo[b]thiophene-6-carboxamide;

N-(2,2-dimethylquinuclidin-3-yl)-1H-indole-6-carboxamide;
N-(2,2-dimethylquinuclidin-3-yl)pyrazolo[1,5-b]pyridazine-3-carboxamide;
N-(2,2-dimethylquinuclidin-3-yl)thieno[2,3-b]pyridine-2-carboxamide;
N-(2,2-dimethylquinuclidin-3-yl)benzo[d]thiazole-2-carboxamide;
N-(2,2-dimethylquinuclidin-3-yl)benzo[b]thiophene-5-carboxamide;
N-(2,2-dimethylquinuclidin-3-yl)benzofuran-6-carboxamide;
N-(2,2-dimethylquinuclidin-3-yl)-2-methylbenzo[d]oxazole-5-carboxamide;
N-(2,2-dimethylquinuclidin-3-yl)-2-methylbenzo[d]oxazole-6-carboxamide;
N-(2,2-dimethylquinuclidin-3-yl)-2-methylbenzo[d]thiazole-5-carboxamide;
N-(2,2-dimethylquinuclidin-3-yl)-2-methylbenzo[d]thiazole-6-carboxamide;
N-(2,2-dimethylquinuclidin-3-yl)furo[2,3-b]pyridine-5-carboxamide;
N-(2,2-dimethylquinuclidin-3-yl)furo[3,2-b]pyridine-5-carboxamide;
N-(2,2-dimethylquinuclidin-3-yl)-2-methylbenzofuran-5-carboxamide;
2-chloro-N-(2,2-dimethylquinuclidin-3-yl)benzofuran-5-carboxamide;
N-(2,2-dimethylquinuclidin-3-yl)-3-methylbenzofuran-5-carboxamide;
3-chloro-N-(2,2-dimethylquinuclidin-3-yl)benzofuran-5-carboxamide;
N-(2,2-dimethylquinuclidin-3-yl)-1-methyl-1H-benzo[d]imidazole-5-carboxamide;
N-(2,2-dimethylquinuclidin-3-yl)thieno[2,3-c]pyridine-5-carboxamide;
N-(2,2-dimethylquinuclidin-3-yl)-6-morpholinobenzo[b]thiophene-2-carboxamide;
6-(4,4-difluoropiperidin-1-yl)-N-(2,2-dimethylquinuclidin-3-yl)benzo[b]thiophene-2-carboxamide;
6-bromo-N-(2,2-dimethylquinuclidin-3-yl)benzo[b]thiophene-2-carboxamide;
N-(2,2-dimethylquinuclidin-3-yl)-6-isopropoxybenzo[b]thiophene-2-carboxamide;
N-(2,2-dimethylquinuclidin-3-yl)-6-(methylsulfonyl)benzo[b]thiophene-2-carboxamide;
N-(2,2-dimethylquinuclidin-3-yl)-6-nitrobenzo[b]thiophene-2-carboxamide;
6-amino-N-(2,2-dimethylquinuclidin-3-yl)benzo[b]thiophene-2-carboxamide;
N-(2,2-dimethylquinuclidin-3-yl)-6-(tetrahydro-2H-pyran-4-yl)benzo[b]thiophene-2-carboxamide;
N-(2,2-dimethylquinuclidin-3-yl)-7-fluoro-6-methoxybenzo[b]thiophene-2-carboxamide;
7-chloro-N-(2,2-dimethylquinuclidin-3-yl)-6-methylbenzo[b]thiophene-2-carboxamide;
N-(2,2-dimethylquinuclidin-3-yl)-7-fluoro-6-methylbenzo[b]thiophene-2-carboxamide;
N-(1'-azaspiro[cyclopropane-1,2'-bicyclo[2.2.2]octan]-3'-yl)benzo[b]thiophene-2-carboxamide;
4-chloro-N-(1'-azaspiro[cyclopropane-1,2'-bicyclo[2.2.2]octan]-3'-yl)benzamide;
7-chloro-N-(1'-azaspiro[cyclopropane-1,2'-bicyclo[2.2.2]octan]-3'-yl)benzo[b]thiophene-2-carboxamide;
7-fluoro-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)benzo[b]thiophene-6-carboxamide;
N-(1'-azaspiro[cyclopropane-1,2'-bicyclo[2.2.2]octan]-3'-yl)benzofuran-5-carboxamide;
N-(1'-azaspiro[cyclopropane-1,2'-bicyclo[2.2.2]octan]-3'-yl)-7-(trifluoromethyl)benzo[b]thiophene-2-carboxamide;
6-fluoro-N-(1'-azaspiro[cyclopropane-1,2'-bicyclo[2.2.2]octan]-3'-yl)benzo[b]thiophene-2-carboxamide;
6-nitro-N-(1'-azaspiro[cyclopropane-1,2'-bicyclo[2.2.2]octan]-3'-yl)benzo[b]thiophene-2-carboxamide;
6-amino-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-6-(trifluoromethyl)benzo[b]thiophene-2-carboxamide;
5-fluoro-N-(1'-azaspiro[cyclopropane-1,2'-bicyclo[2.2.2]octan]-3'-yl)benzo[b]thiophene-2-carboxamide;
6-chloro-N-(1'-azaspiro[cyclopropane-1,2'-bicyclo[2.2.2]octan]-3'-yl)benzo[b]thiophene-2-carboxamide;
5-chloro-N-(1'-azaspiro[cyclopropane-1,2'-bicyclo[2.2.2]octan]-3'-yl)benzo[b]thiophene-2-carboxamide;
5,6-dichloro-N-(1'-azaspiro[cyclopropane-1,2'-bicyclo[2.2.2]octan]-3'-yl)benzo[b]thiophene-2-carboxamide;
6-methyl-N-(1'-azaspiro[cyclopropane-1,2'-bicyclo[2.2.2]octan]-3'-yl)benzo[b]thiophene-2-carboxamide;
5-methyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-5-(trifluoromethyl)benzo[b]thiophene-2-carboxamide;
6-cyclopropyl-N-(1'-azaspiro[cyclopropane-1,2'-bicyclo[2.2.2]octan]-3'-yl)benzo[b]thiophene-2-carboxamide;
5-cyclopropyl-N-(1'-azaspiro[cyclopropane-1,2'-bicyclo[2.2.2]octan]-3'-yl)benzo[b]thiophene-2-carboxamide;
6-methoxy-N-(1'-azaspiro[cyclopropane-1,2'-bicyclo[2.2.2]octan]-3'-yl)benzo[b]thiophene-2-carboxamide;
5-methoxy-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)furo[2,3-c]pyridine-5-carboxamide;
N-(1'-azaspiro[cyclopropane-1,2'-bicyclo[2.2.2]octan]-3'-yl)-2,3-dihydro-[1,4]dioxino[2,3-c]pyridine-7-carboxamide;
3-methyl-N-(1'-azaspiro[cyclopropane-1,2'-bicyclo[2.2.2]octan]-3'-yl)benzo[b]thiophene-5-carboxamide;
3-methyl-N-(1'-azaspiro[cyclopropane-1,2'-bicyclo[2.2.2]octan]-3'-yl)benzo[b]thiophene-6-carboxamide;
N-(1'-azaspiro[cyclopropane-1,2'-bicyclo[2.2.2]octan]-3'-yl)-1H-indole-6-carboxamide;
N-(1'-azaspiro[cyclopropane-1,2'-bicyclo[2.2.2]octan]-3'-yl)pyrazolo[1,5-b]pyridazine-3-carboxamide;
N-(1'-azaspiro[cyclopropane-1,2'-bicyclo[2.2.2]octan]-3'-yl)thieno[2,3-b]pyridine-2-carboxamide;
N-(1'-azaspiro[cyclopropane-1,2'-bicyclo[2.2.2]octan]-3'-yl)benzo[d]thiazole-2-carboxamide;
N-(1'-azaspiro[cyclopropane-1,2'-bicyclo[2.2.2]octan]-3'-yl)benzo[b]thiophene-5-carboxamide;
N-(1'-azaspiro[cyclopropane-1,2'-bicyclo[2.2.2]octan]-3'-yl)benzofuran-6-carboxamide;
2-methyl-N-(1'-azaspiro[cyclopropane-1,2'-bicyclo[2.2.2]octan]-3'-yl)benzo[d]oxazole-5-carboxamide;
2-methyl-N-(1'-azaspiro[cyclopropane-1,2'-bicyclo[2.2.2]octan]-3'-yl)benzo[d]oxazole-6-carboxamide;
2-methyl-N-(1'-azaspiro[cyclopropane-1,2'-bicyclo[2.2.2]octan]-3'-yl)benzo[d]thiazole-5-carboxamide;

2-methyl-N-(1'-azaspiro[cyclopropane-1,2'-bicyclo[2.2.2]octan]-3'-yl)benzo[d]thiazole-6-carboxamide;
N-(1'-azaspiro[cyclopropane-1,2'-bicyclo[2.2.2]octan]-3'-yl)furo[2,3-b]pyridine-5-carboxamide;
N-(1'-azaspiro[cyclopropane-1,2'-bicyclo[2.2.2]octan]-3'-yl)furo[3,2-b]pyridine-5-carboxamide;
2-methyl-N-(1'-azaspiro[cyclopropane-1,2'-bicyclo[2.2.2]octan]-3'-yl)benzofuran-5-carboxamide;
2-chloro-N-(1'-azaspiro[cyclopropane-1,2'-bicyclo[2.2.2]octan]-3'-yl)benzofuran-5-carboxamide;
3-methyl-N-(1'-azaspiro[cyclopropane-1,2'-bicyclo[2.2.2]octan]-3'-yl)benzofuran-5-carboxamide;
3-chloro-N-(1'-azaspiro[cyclopropane-1,2'-bicyclo[2.2.2]octan]-3'-yl)benzofuran-5-carboxamide;
1-methyl-N-(1'-azaspiro[cyclopropane-1,2'-bicyclo[2.2.2]octan]-3'-yl)-1H-benzo[d]imidazole-5-carboxamide;
1-methyl-N-(1'-azaspiro[cyclopropane-1,2'-bicyclo[2.2.2]octan]-3'-yl)-1H-benzo[d]imidazole-6-carboxamide;
N-(1'-azaspiro[cyclopropane-1,2'-bicyclo[2.2.2]octan]-3'-yl)thieno[2,3-c]pyridine-5-carboxamide;
N-(1'-azaspiro[cyclopropane-1,2'-bicyclo[2.2.2]octan]-3'-yl)-6-(1H-1,2,3-triazol-1-yl)benzo[b]thiophene-2-carboxamide;
6-morpholino-N-(1'-azaspiro[cyclopropane-1,2'-bicyclo[2.2.2]octan]-3'-yl)benzo[b]thiophene-2-carboxamide;
6-(4,4-difluoropiperidin-1-yl)-N-(1'-azaspiro[cyclopropane-1,2'-bicyclo[2.2.2]octan]-3'-yl)benzo[b]thiophene-2-carboxamide;
6-bromo-N-(1'-azaspiro[cyclopropane-1,2'-bicyclo[2.2.2]octan]-3'-yl)benzo[b]thiophene-2-carboxamide;
6-isopropoxy-N-(1'-azaspiro[cyclopropane-1,2'-bicyclo[2.2.2]octan]-3'-yl)benzo[b]thiophene-2-carboxamide;
6-(methylsulfonyl)-N-(1'-azaspiro[cyclopropane-1,2'-bicyclo[2.2.2]octan]-3'-yl)benzo[b]thiophene-2-carboxamide;
6-cyano-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-6-(tetrahydro-2H-pyran-4-yl)benzo[b]thiophene-2-carboxamide;
7-fluoro-6-methyl-N-(1'-azaspiro[cyclopropane-1,2'-bicyclo[2.2.2]octan]-3'-yl)benzo[b]thiophene-2-carboxamide; and
N-(1'-azaspiro[cyclopropane-1,2'-bicyclo[2.2.2]octan]-3'-yl)-2,3-dihydrobenzo[b][1,4]dioxine-6-carboxamide.

In certain embodiments, specific examples of the amide compound represented by Formula (I) may include, collectively or individually, the compounds listed below, and single enantiomers and pharmaceutically acceptable salts thereof:

2-amino-N-(2,2-dimethylquinuclidin-3-yl)thieno[2,3-d]pyrimidine-6-carboxamide;
6,7-dichloro-N-(2,2-dimethylquinuclidin-3-yl)benzo[b]thiophene-2-carboxamide;
6-chloro-N-(2,2-dimethylquinuclidin-3-yl)-7-fluorobenzo[b]thiophene-2-carboxamide;
6-chloro-N-(2,2-dimethylquinuclidin-3-yl)-7-(trifluoromethyl)benzo[b]thiophene-2-carboxamide;
7-chloro-N-(2,2-dimethylquinuclidin-3-yl)-6-methoxybenzo[b]thiophene-2-carboxamide;
N-(2,2-dimethylquinuclidin-3-yl)-6-methyl-7-(trifluoromethyl)benzo[b]thiophene-2-carboxamide;
7-chloro-N-(2,2-dimethylquinuclidin-3-yl)-6-fluorobenzo[b]thiophene-2-carboxamide;
7-cyano-N-(2,2-dimethylquinuclidin-3-yl)benzo[b]thiophene-2-carboxamide;
N-(2,2-dimethylquinuclidin-3-yl)-7-methoxybenzo[b]thiophene-2-carboxamide;
N-(2,2-dimethylquinuclidin-3-yl)-6,7-difluorobenzo[b]thiophene-2-carboxamide;
7-cyclopropyl-N-(2,2-dimethylquinuclidin-3-yl)benzo[b]thiophene-2-carboxamide;
N-(2,2-dimethylquinuclidin-3-yl)-7-isopropylbenzo[b]thiophene-2-carboxamide;
N-(2,2-dimethylquinuclidin-3-yl)-7-(trifluoromethoxy)benzo[b]thiophene-2-carboxamide;
N-(2,2-dimethylquinuclidin-3-yl)-7-(tetrahydro-2H-pyran-4-yl)benzo[b]thiophene-2-carboxamide;
N-(2,2-dimethylquinuclidin-3-yl)-1H-indole-2-carboxamide;
6-chloro-N-(2,2-dimethylquinuclidin-3-yl)-5-fluorobenzo[b]thiophene-2-carboxamide;
N-(2,2-dimethylquinuclidin-3-yl)-5-fluoro-6-methoxybenzo[b]thiophene-2-carboxamide;
6-chloro-N-(2,2-dimethylquinuclidin-3-yl)-5,7-difluorobenzo[b]thiophene-2-carboxamide;
N-(2,2-dimethylquinuclidin-3-yl)-7-methylbenzo[b]thiophene-2-carboxamide;
N-(2,2-dimethylquinuclidin-3-yl)-7-(2,2,2-trifluoroethyl)benzo[b]thiophene-2-carboxamide;
7-(dimethylamino)-N-(2,2-dimethylquinuclidin-3-yl)benzo[b]thiophene-2-carboxamide;
N-(2,2-dimethylquinuclidin-3-yl)-7-(thiazol-2-yl)benzo[b]thiophene-2-carboxamide;
N-(2,2-dimethylquinuclidin-3-yl)isoquinoline-3-carboxamide;
7-(tert-butyl)-N-(2,2-dimethylquinuclidin-3-yl)benzo[b]thiophene-2-carboxamide;
N-(2,2-dimethylquinuclidin-3-yl)-7-phenylbenzo[b]thiophene-2-carboxamide;
N-(2,2-dimethylquinuclidin-3-yl)-7-(1-methylcyclopropyl)benzo[b]thiophene-2-carboxamide;
N-(2,2-dimethylquinuclidin-3-yl)-6-ethoxybenzo[b]thiophene-2-carboxamide;
N-(2,2-dimethylquinuclidin-3-yl)-7-ethoxybenzo[b]thiophene-2-carboxamide;
N-(2,2-dimethylquinuclidin-3-yl)-7-propoxybenzo[b]thiophene-2-carboxamide;
6-chloro-N-(2,2-dimethylquinuclidin-3-yl)-7-methoxybenzo[b]thiophene-2-carboxamide;
N-(2,2-dimethylquinuclidin-3-yl)-7-methoxy-6-methylbenzo[b]thiophene-2-carboxamide;
N-(2,2-dimethylquinuclidin-3-yl)-1H-indazole-3-carboxamide;
7-cyclopropyl-N-(2,2-dimethylquinuclidin-3-yl)-6-methylbenzo[b]thiophene-2-carboxamide;
N-(2,2-dimethylquinuclidin-3-yl)-6-fluoro-7-methoxybenzo[b]thiophene-2-carboxamide;
7-cyano-N-(2,2-dimethylquinuclidin-3-yl)-6-methylbenzo[b]thiophene-2-carboxamide;
N-(2,2-dimethylquinuclidin-3-yl)-7-(methoxymethyl)benzo[b]thiophene-2-carboxamide;
N-(2,2-dimethylquinuclidin-3-yl)-3,4-dihydro-2H-thieno[3,2-h]chromene-8-carboxamide;
N-(2,2-dimethylquinuclidin-3-yl)-8,9-dihydro-7H-thieno[2,3-f]chromene-2-carboxamide;
N-(2,2-dimethylquinuclidin-3-yl)-2-methylbenzo[b]thiophene-6-carboxamide;
2-chloro-N-(2,2-dimethylquinuclidin-3-yl)benzo[b]thiophene-6-carboxamide;
6-chloro-N-(2,2-dimethylquinuclidin-3-yl)-7-methylbenzo[b]thiophene-2-carboxamide;
2-amino-N-(1'-azaspiro[cyclopropane-1,2'-bicyclo[2.2.2]octan]-3'-yl)thieno[2,3-d]pyrimidine-6-carboxamide;

6,7-dichloro-N-(1'-azaspiro[cyclopropane-1,2'-bicyclo[2.2.2]octan]-3'-yl)benzo[b]thiophene-2-carboxamide;
6-chloro-7-fluoro-N-(1'-azaspiro[cyclopropane-1,2'-bicyclo[2.2.2]octan]-3'-yl)benzo[b]thiophene-2-carboxamide;
6-chloro-N-(1'-azaspiro[cyclopropane-1,2'-bicyclo[2.2.2]octan]-3'-yl)-7-(trifluoromethyl)benzo[b]thiophene-2-carboxamide;
6-fluoro-N-(1'-azaspiro[cyclopropane-1,2'-bicyclo[2.2.2]octan]-3'-yl)-7-(trifluoromethyl)benzo[b]thiophene-2-carboxamide;
7-chloro-6-methoxy-N-(1'-azaspiro[cyclopropane-1,2'-bicyclo[2.2.2]octan]-3'-yl)benzo[b]thiophene-2-carboxamide;
7-fluoro-6-methoxy-N-(1'-azaspiro[cyclopropane-1,2'-bicyclo[2.2.2]octan]-3'-yl)benzo[b]thiophene-2-carboxamide;
7-chloro-6-methyl-N-(1'-azaspiro[cyclopropane-1,2'-bicyclo[2.2.2]octan]-3'-yl)benzo[b]thiophene-2-carboxamide;
6-methyl-N-(1'-azaspiro[cyclopropane-1,2'-bicyclo[2.2.2]octan]-3'-yl)-7-(trifluoromethyl)benzo[b]thiophene-2-carboxamide;
7-chloro-6-fluoro-N-(1'-azaspiro[cyclopropane-1,2'-bicyclo[2.2.2]octan]-3'-yl)benzo[b]thiophene-2-carboxamide;
6-cyclopropyl-7-fluoro-N-(1'-azaspiro[cyclopropane-1,2'-bicyclo[2.2.2]octan]-3'-yl)benzo[b]thiophene-2-carboxamide;
7-cyano-N-(1'-azaspiro[cyclopropane-1,2'-bicyclo[2.2.2]octan]-3'-yl)benzo[b]thiophene-2-carboxamide;
7-methoxy-N-(1'-azaspiro[cyclopropane-1,2'-bicyclo[2.2.2]octan]-3'-yl)benzo[b]thiophene-2-carboxamide;
6,7-difluoro-N-(1'-azaspiro[cyclopropane-1,2'-bicyclo[2.2.2]octan]-3'-yl)benzo[b]thiophene-2-carboxamide;
6-chloro-N-(1'-azaspiro[cyclopropane-1,2'-bicyclo[2.2.2]octan]-3'-yl)benzofuran-2-carboxamide;
7-chloro-N-(1'-azaspiro[cyclopropane-1,2'-bicyclo[2.2.2]octan]-3'-yl)benzofuran-2-carboxamide;
7-cyclopropyl-N-(1'-azaspiro[cyclopropane-1,2'-bicyclo[2.2.2]octan]-3'-yl)benzo[b]thiophene-2-carboxamide;
7-isopropyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-7-(trifluoromethoxy)benzo[b]thiophene-2-carboxamide;
N-(1'-azaspiro[cyclopropane-1,2'-bicyclo[2.2.2]octan]-3'-yl)-7-(tetrahydro-2H-pyran-4-yl)benzo[b]thiophene-2-carboxamide;
N-(1'-azaspiro[cyclopropane-1,2'-bicyclo[2.2.2]octan]-3'-yl)benzo[d]oxazole-2-carboxamide;
N-(1'-azaspiro[cyclopropane-1,2'-bicyclo[2.2.2]octan]-3'-yl)-1H-indole-2-carboxamide;
N-(1'-azaspiro[cyclopropane-1,2'-bicyclo[2.2.2]octan]-3'-yl)thieno[2,3-c]pyridine-2-carboxamide;
6-chloro-5-fluoro-N-(1'-azaspiro[cyclopropane-1,2'-bicyclo[2.2.2]octan]-3'-yl)benzo[b]thiophene-2-carboxamide;
5-fluoro-6-methoxy-N-(1'-azaspiro[cyclopropane-1,2'-bicyclo[2.2.2]octan]-3'-yl)benzo[b]thiophene-2-carboxamide;
5,6-difluoro-N-(1'-azaspiro[cyclopropane-1,2'-bicyclo[2.2.2]octan]-3'-yl)benzo[b]thiophene-2-carboxamide;
6-chloro-5,7-difluoro-N-(1'-azaspiro[cyclopropane-1,2'-bicyclo[2.2.2]octan]-3'-yl)benzo[b]thiophene-2-carboxamide;
7-methyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-7-(2,2,2-trifluoroethyl)benzo[b]thiophene-2-carboxamide;
7-(dimethylamino)-N-(1'-azaspiro[cyclopropane-1,2'-bicyclo[2.2.2]octan]-3'-yl)benzo[b]thiophene-2-carboxamide;
7-(methylsulfonyl)-N-(1'-azaspiro[cyclopropane-1,2'-bicyclo[2.2.2]octan]-3'-yl)benzo[b]thiophene-2-carboxamide;
7-morpholino-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-7-(thiazol-2-yl)benzo[b]thiophene-2-carboxamide;
N-(1'-azaspiro[cyclopropane-1,2'-bicyclo[2.2.2]octan]-3'-yl)isoquinoline-3-carboxamide;
2-cyclopropyl-N-(1'-azaspiro[cyclopropane-1,2'-bicyclo[2.2.2]octan]-3'-yl)benzofuran-5-carboxamide;
7-(tert-butyl)-N-(1'-azaspiro[cyclopropane-1,2'-bicyclo[2.2.2]octan]-3'-yl)benzo[b]thiophene-2-carboxamide;
7-(2-hydroxypropan-2-yl)-N-(1'-azaspiro[cyclopropane-1,2'-bicyclo[2.2.2]octan]-3'-yl)benzo[b]thiophene-2-carboxamide;
7-phenyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-7-(1-(trifluoromethyl)cyclopropyl)benzo[b]thiophene-2-carboxamide;
7-(1-methylcyclopropyl)-N-(1'-azaspiro[cyclopropane-1,2'-bicyclo[2.2.2]octan]-3'-yl)benzo[b]thiophene-2-carboxamide;
6-ethoxy-N-(1'-azaspiro[cyclopropane-1,2'-bicyclo[2.2.2]octan]-3'-yl)benzo[b]thiophene-2-carboxamide;
7-ethoxy-N-(1'-azaspiro[cyclopropane-1,2'-bicyclo[2.2.2]octan]-3'-yl)benzo[b]thiophene-2-carboxamide;
7-propoxy-N-(1'-azaspiro[cyclopropane-1,2'-bicyclo[2.2.2]octan]-3'-yl)benzo[b]thiophene-2-carboxamide;
6-chloro-7-methoxy-N-(1'-azaspiro[cyclopropane-1,2'-bicyclo[2.2.2]octan]-3'-yl)benzo[b]thiophene-2-carboxamide;
7-methoxy-6-methyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-1H-indazole-3-carboxamide;
1-methyl-N-(1'-azaspiro[cyclopropane-1,2'-bicyclo[2.2.2]octan]-3'-yl)-1H-indole-6-carboxamide;
7-cyclopropyl-6-methyl-N-(1'-azaspiro[cyclopropane-1,2'-bicyclo[2.2.2]octan]-3'-yl)benzo[b]thiophene-2-carboxamide;
6-fluoro-7-methoxy-N-(1'-azaspiro[cyclopropane-1,2'-bicyclo[2.2.2]octan]-3'-yl)benzo[b]thiophene-2-carboxamide;
7-cyano-6-methyl-N-(1'-azaspiro[cyclopropane-1,2'-bicyclo[2.2.2]octan]-3'-yl)benzo[b]thiophene-2-carboxamide;
7-(methoxymethyl)-N-(1'-azaspiro[cyclopropane-1,2'-bicyclo[2.2.2]octan]-3'-yl)benzo[b]thiophene-2-carboxamide;
6-(methoxymethyl)-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-3,4-dihydro-2H-thieno[3,2-h]chromene-8-carboxamide;
2-methyl-N-(1'-azaspiro[cyclopropane-1,2'-bicyclo[2.2.2]octan]-3'-yl)benzo[b]thiophene-6-carboxamide;
2-chloro-N-(1'-azaspiro[cyclopropane-1,2'-bicyclo[2.2.2]octan]-3'-yl)benzo[b]thiophene-6-carboxamide;
N-(1'-azaspiro[cyclopropane-1,2'-bicyclo[2.2.2]octan]-3'-yl)-8,9-dihydro-7H-thieno[2,3-f]chromene-2-carboxamide;
6-chloro-7-methyl-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-1-methyl-1H-benzo[d]imidazole-6-carboxamide;
6-(tert-butyl)-N-(2,2-dimethylquinuclidin-3-yl)benzo[b]thiophene-2-carboxamide;
N-(2,2-dimethylquinuclidin-3-yl)-6-(1H-1,2,3-triazol-1-yl)benzo[b]thiophene-2-carboxamide;

N-(2,2-dimethylquinuclidin-3-yl)-6-(trifluoromethoxy)benzo[b]thiophene-2-carboxamide;
N-(2,2-dimethylquinuclidin-3-yl)-6-(oxetan-3-yl)benzo[b]thiophene-2-carboxamide;
N-(2,2-dimethylquinuclidin-3-yl)-6-fluoro-7-(trifluoromethyl)benzo[b]thiophene-2-carboxamide;
N-(2,2-dimethylquinuclidin-3-yl)-6-methoxy-7-(trifluoromethyl)benzo[b]thiophene-2-carboxamide;
6-cyclopropyl-N-(2,2-dimethylquinuclidin-3-yl)-7-fluorobenzo[b]thiophene-2-carboxamide;
7-chloro-6-cyclopropyl-N-(2,2-dimethylquinuclidin-3-yl)benzo[b]thiophene-2-carboxamide;
N-(2,2-dimethylquinuclidin-3-yl)-2,3-dihydrobenzo[b][1,4]dioxine-6-carboxamide;
6-chloro-N-(2,2-dimethylquinuclidin-3-yl)benzofuran-2-carboxamide;
7-chloro-N-(2,2-dimethylquinuclidin-3-yl)benzofuran-2-carboxamide;
N-(2,2-dimethylquinuclidin-3-yl)benzo[d]oxazole-2-carboxamide;
N-(2,2-dimethylquinuclidin-3-yl)-1H-benzo[d]imidazole-2-carboxamide;
N-(2,2-dimethylquinuclidin-3-yl)-1-methyl-1H-benzo[d]imidazole-2-carboxamide;
N-(2,2-dimethylquinuclidin-3-yl)-1-methyl-1H-indole-2-carboxamide;
N-(2,2-dimethylquinuclidin-3-yl)thieno[2,3-c]pyridine-2-carboxamide;
3,4-dichloro-N-(2,2-dimethylquinuclidin-3-yl)benzamide;
N-(2,2-dimethylquinuclidin-3-yl)-4-methoxy-3-methylbenzamide;
N-(2,2-dimethylquinuclidin-3-yl)imidazo[1,2-a]pyrazine-6-carboxamide;
N-(2,2-dimethylquinuclidin-3-yl)-5,6-difluorobenzo[b]thiophene-2-carboxamide;
N-(2,2-dimethylquinuclidin-3-yl)-7-(methylsulfonyl)benzo[b]thiophene-2-carboxamide;
N-(2,2-dimethylquinuclidin-3-yl)-7-morpholinobenzo[b]thiophene-2-carboxamide;
N-(2,2-dimethylquinuclidin-3-yl)quinoline-3-carboxamide;
N-(2,2-dimethylquinuclidin-3-yl)quinoline-7-carboxamide;
N-(2,2-dimethylquinuclidin-3-yl)quinoline-6-carboxamide;
2-cyclopropyl-N-(2,2-dimethylquinuclidin-3-yl)benzofuran-5-carboxamide;
N-(2,2-dimethylquinuclidin-3-yl)-7-(2-hydroxypropan-2-yl)benzo[b]thiophene-2-carboxamide;
N-(2,2-dimethylquinuclidin-3-yl)-7-(1-(trifluoromethyl)cyclopropyl)benzo[b]thiophene-2-carboxamide;
N-(2,2-dimethylquinuclidin-3-yl)-1H-indole-5-carboxamide;
6-cyclopropyl-N-(2,2-dimethylquinuclidin-3-yl)-7-methoxybenzo[b]thiophene-2-carboxamide;
N-(2,2-dimethylquinuclidin-3-yl)benzo[d]isoxazole-5-carboxamide;
N-(2,2-dimethylquinuclidin-3-yl)benzo[d]isoxazole-6-carboxamide;
N-(2,2-dimethylquinuclidin-3-yl)-2,2-difluorobenzo[d][1,3]dioxole-5-carboxamide;
N-(2,2-dimethylquinuclidin-3-yl)-1-methyl-1H-indazole-3-carboxamide;
N-(2,2-dimethylquinuclidin-3-yl)benzo[d]isoxazole-3-carboxamide;
N-(2,2-dimethylquinuclidin-3-yl)-1-methyl-1H-indole-5-carboxamide;
N-(2,2-dimethylquinuclidin-3-yl)-1-methyl-1H-indole-6-carboxamide;
6-(dimethylamino)-N-(2,2-dimethylquinuclidin-3-yl)benzo[b]thiophene-2-carboxamide;
N-(2,2-dimethylquinuclidin-3-yl)-6-(methoxymethyl)benzo[b]thiophene-2-carboxamide;
N-(2,2-dimethylquinuclidin-3-yl)-4,5,6,7-tetrahydrobenzo[b]thiophene-2-carboxamide;
6-(tert-butyl)-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-6-(trifluoromethoxy)benzo[b]thiophene-2-carboxamide;
6-(oxetan-3-yl)-N-(1'-azaspiro[cyclopropane-1,2'-bicyclo[2.2.2]octan]-3'-yl)benzo[b]thiophene-2-carboxamide;
6-methoxy-N-(1'-azaspiro[cyclopropane-1,2'-bicyclo[2.2.2]octan]-3'-yl)-7-(trifluoromethyl)benzo[b]thiophene-2-carboxamide;
7-chloro-6-cyclopropyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-1H-benzo[d]imidazole-2-carboxamide;
1-methyl-N-(1'-azaspiro[cyclopropane-1,2'-bicyclo[2.2.2]octan]-3'-yl)-1H-benzo[d]imidazole-2-carboxamide;
1-methyl-N-(1'-azaspiro[cyclopropane-1,2'-bicyclo[2.2.2]octan]-3'-yl)-1H-indole-2-carboxamide;
3,4-dichloro-N-(1'-azaspiro[cyclopropane-1,2'-bicyclo[2.2.2]octan]-3'-yl)benzamide;
4-methoxy-3-methyl-N-(1'-azaspiro[cyclopropane-1,2'-bicyclo[2.2.2]octan]-3'-yl)benzamide;
N-(1'-azaspiro[cyclopropane-1,2'-bicyclo[2.2.2]octan]-3'-yl)imidazo[1,2-a]pyrazine-6-carboxamide;
N-(1'-azaspiro[cyclopropane-1,2'-bicyclo[2.2.2]octan]-3'-yl)quinoline-3-carboxamide;
N-(1'-azaspiro[cyclopropane-1,2'-bicyclo[2.2.2]octan]-3'-yl)quinoline-7-carboxamide;
N-(1'-azaspiro[cyclopropane-1,2'-bicyclo[2.2.2]octan]-3'-yl)quinoline-6-carboxamide;
N-(1'-azaspiro[cyclopropane-1,2'-bicyclo[2.2.2]octan]-3'-yl)-1H-indole-5-carboxamide;
6-cyclopropyl-7-methoxy-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)benzo[d]isoxazole-5-carboxamide;
N-(1'-azaspiro[cyclopropane-1,2'-bicyclo[2.2.2]octan]-3'-yl)benzo[d]isoxazole-6-carboxamide;
2,2-difluoro-N-(1'-azaspiro[cyclopropane-1,2'-bicyclo[2.2.2]octan]-3'-yl)benzo[d][1,3]dioxole-5-carboxamide;
1-methyl-N-(1'-azaspiro[cyclopropane-1,2'-bicyclo[2.2.2]octan]-3'-yl)-1H-indazole-3-carboxamide;
N-(1'-azaspiro[cyclopropane-1,2'-bicyclo[2.2.2]octan]-3'-yl)benzo[d]isoxazole-3-carboxamide;
1-methyl-N-(1'-azaspiro[cyclopropane-1,2'-bicyclo[2.2.2]octan]-3'-yl)-1H-indole-5-carboxamide;
6-(dimethylamino)-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-4,5,6,7-tetrahydrobenzo[b]thiophene-2-carboxamide.
N-(2,2-dimethylquinuclidin-3-yl)-7-(oxetan-3-yl)benzo[b]thiophene-2-carboxamide;
6-cyclopropoxy-N-(2,2-dimethylquinuclidin-3-yl)benzo[b]thiophene-2-carboxamide;
7-(oxetan-3-yl)-N-(1'-azaspiro[cyclopropane-1,2'-bicyclo[2.2.2]octan]-3'-yl)benzo[b]thiophene-2-carboxamide; and
6-cyclopropoxy-N-(1'-azaspiro[cyclopropane-1,2'-bicyclo[2.2.2]octan]-3'-yl)benzo[b]thiophene-2-carboxamide.

In certain embodiments, specific examples of the amide compound represented by Formula (I) may include, collectively or individually, the single enantiomers listed below, and pharmaceutically acceptable salts thereof:

7-cyclobutyl-N-(2,2-dimethylquinuclidin-3-yl)benzo[b]thiophene-2-carboxamide;
7-cyclobutyl-N-(1'-azaspiro[cyclopropane-1,2'-bicyclo[2.2.2]octan]-3'-yl)benzo[b]thiophene-2-carboxamide;
7-cyclopropyl-N-(2,2-dimethylquinuclidin-3-yl)-6-methoxybenzo[b]thiophene-2-carboxamide;
7-cyclopropyl-6-methoxy-N-(1'-azaspiro[cyclopropane-1,2'-bicyclo[2.2.2]octan]-3'-yl)benzo[b]thiophene-2-carboxamide;
7-cyclopropoxy-N-(2,2-dimethylquinuclidin-3-yl)benzo[b]thiophene-2-carboxamide;
7-cyclopropoxy-N-(1'-azaspiro[cyclopropane-1,2'-bicyclo[2.2.2]octan]-3'-yl)benzo[b]thiophene-2-carboxamide;
6-cyclopropoxy-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-7-(2,2,2-trifluoroethoxy)benzo[b]thiophene-2-carboxamide;
N-(1'-azaspiro[cyclopropane-1,2'-bicyclo[2.2.2]octan]-3'-yl)-7-(2,2,2-trifluoroethoxy)benzo[b]thiophene-2-carboxamide;
N-(2,2-dimethylquinuclidin-3-yl)-6-fluoro-7-methylbenzo[b]thiophene-2-carboxamide;
6-fluoro-7-methyl-N-(1'-azaspiro[cyclopropane-1,2'-bicyclo[2.2.2]octan]-3'-yl)benzo[b]thiophene-2-carboxamide;
7-chloro-5-fluoro-N-(1'-azaspiro[cyclopropane-1,2'-bicyclo[2.2.2]octan]-3'-yl)benzo[b]thiophene-2-carboxamide;
4-chloro-N-(1'-azaspiro[cyclopropane-1,2'-bicyclo[2.2.2]octan]-3'-yl)benzo[b]thiophene-2-carboxamide;
6-chloro-7-cyclopropyl-N-(1'-azaspiro[cyclopropane-1,2'-bicyclo[2.2.2]octan]-3'-yl)benzo[b]thiophene-2-carboxamide;
7-chloro-N-(2,2-dimethylquinuclidin-3-yl)-5-fluorobenzo[b]thiophene-2-carboxamide;
6-fluoro-N-(1'-azaspiro[cyclopropane-1,2'-bicyclo[2.2.2]octan]-3'-yl)-7-(trifluoromethoxy)benzo[b]thiophene-2-carboxamide;
N-(2,2-dimethylquinuclidin-3-yl)-6-fluoro-7-(trifluoromethoxy)benzo[b]thiophene-2-carboxamide;
N-(2,2-dimethylquinuclidin-3-yl)-6-methyl-7-(thiazol-2-yl)benzo[b]thiophene-2-carboxamide;
6-methyl-N-(1'-azaspiro[cyclopropane-1,2'-bicyclo[2.2.2]octan]-3'-yl)-7-(thiazol-2-yl)benzo[b]thiophene-2-carboxamide;
7-cyano-N-(2,2-dimethylquinuclidin-3-yl)-6-fluorobenzo[b]thiophene-2-carboxamide;
6-chloro-7-cyclopropyl-N-(2,2-dimethylquinuclidin-3-yl)benzo[b]thiophene-2-carboxamide;
6-chloro-7-cyano-N-(2,2-dimethylquinuclidin-3-yl)benzo[b]thiophene-2-carboxamide;
7-(tert-butoxy)-N-(2,2-dimethylquinuclidin-3-yl)benzo[b]thiophene-2-carboxamide;
7-(tert-butoxy)-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-2,3-dihydro-1H-thieno[2',3':3,4]benzo[1,2-b][1,4]oxazine-8-carboxamide;
N-(2,2-dimethylquinuclidin-3-yl)-1-methyl-2,3-dihydro-1H-thieno[2',3':3,4]benzo[1,2-b][1,4]oxazine-8-carboxamide;
N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
1-methyl-N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
2-cyclopropyl-N-(2,2-dimethylquinuclidin-3-yl)benzo[b]thiophene-6-carboxamide;
2-cyclopropyl-N-(1'-azaspiro[cyclopropane-1,2'-bicyclo[2.2.2]octan]-3'-yl)benzo[b]thiophene-6-carboxamide;
7-(difluoromethyl)-N-(2,2-dimethylquinuclidin-3-yl)benzo[b]thiophene-2-carboxamide;
7-(difluoromethyl)-N-(1'-azaspiro[cyclopropane-1,2'-bicyclo[2.2.2]octan]-3'-yl)benzo[b]thiophene-2-carboxamide;
7-(oxetan-3-yl)-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-7-(oxetan-3-yl)benzo[b]thiophene-2-carboxamide;
6-chloro-N-(2,2-dimethylquinuclidin-3-yl)-7-isopropoxybenzo[b]thiophene-2-carboxamide;
7-cyclobutoxy-N-(2,2-dimethylquinuclidin-3-yl)benzo[b]thiophene-2-carboxamide;
6-chloro-N-(2,2-dimethylquinuclidin-3-yl)-7-ethoxybenzo[b]thiophene-2-carboxamide;
6-chloro-7-cyano-N-(1'-azaspiro[cyclopropane-1,2'-bicyclo[2.2.2]octan]-3'-yl)benzo[b]thiophene-2-carboxamide;
7-cyano-6-fluoro-N-(1'-azaspiro[cyclopropane-1,2'-bicyclo[2.2.2]octan]-3'-yl)benzo[b]thiophene-2-carboxamide;
6-chloro-7-isopropoxy-N-(1'-azaspiro[cyclopropane-1,2'-bicyclo[2.2.2]octan]-3'-yl)benzo[b]thiophene-2-carboxamide;
6-chloro-7-ethoxy-N-(1'-azaspiro[cyclopropane-1,2'-bicyclo[2.2.2]octan]-3'-yl)benzo[b]thiophene-2-carboxamide;
7-cyclobutoxy-N-(1'-azaspiro[cyclopropane-1,2'-bicyclo[2.2.2]octan]-3'-yl)benzo[b]thiophene-2-carboxamide;
6,7-dimethyl-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-7-ethoxy-6-fluorobenzo[b]thiophene-2-carboxamide;
7-isopropoxy-6-methyl-N-(1'-azaspiro[cyclopropane-1,2'-bicyclo[2.2.2]octan]-3'-yl)benzo[b]thiophene-2-carboxamide;
7-ethoxy-6-fluoro-N-(1'-azaspiro[cyclopropane-1,2'-bicyclo[2.2.2]octan]-3'-yl)benzo[b]thiophene-2-carboxamide;
7-cyclopropyl-N-(2,2-dimethylquinuclidin-3-yl)-6-fluorobenzo[b]thiophene-2-carboxamide;
7-cyclopropyl-6-fluoro-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-7-isopropoxy-6-methylbenzo[b]thiophene-2-carboxamide;
N-(2,2-dimethylquinuclidin-3-yl)-7-ethoxy-6-methylbenzo[b]thiophene-2-carboxamide;
7-ethoxy-6-methyl-N-(1'-azaspiro[cyclopropane-1,2'-bicyclo[2.2.2]octan]-3'-yl)benzo[b]thiophene-2-carboxamide;
N-(2,2-dimethylquinuclidin-3-yl)-6,7-dimethylbenzo[b]thiophene-2-carboxamide;
N-(2,2-dimethylquinuclidin-3-yl)-5-fluoro-6-methylbenzo[b]thiophene-2-carboxamide;
5-fluoro-6-methyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)thieno[3,2-c]pyridine-6-carboxamide;
N-(2,2-dimethylquinuclidin-3-yl)thieno[3,2-c]pyridine-6-carboxamide;
N-(2,2-dimethylquinuclidin-3-yl)-2,3-dihydrothieno[3,2-g]benzofuran-7-carboxamide;
N-(1'-azaspiro[cyclopropane-1,2'-bicyclo[2.2.2]octan]-3'-yl)-2,3-dihydrothieno[3,2-g]benzofuran-7-carboxamide;

N-(2,2-dimethylquinuclidin-3-yl)-5,7-difluorobenzo[b]thiophene-2-carboxamide;
5,7-difluoro-N-(1'-azaspiro[cyclopropane-1,2'-bicyclo[2.2.2]octan]-3'-yl)benzo[b]thiophene-2-carboxamide;
7-chloro-N-(2,2-dimethylquinuclidin-3-yl)pyrrolo[1,2-c]pyrimidine-3-carboxamide;
7-chloro-N-(1'-azaspiro[cyclopropane-1,2'-bicyclo[2.2.2]octan]-3'-yl)pyrrolo[1,2-c]pyrimidine-3-carboxamide;
N-(2,2-dimethylquinuclidin-3-yl)pyrrolo[1,2-c]pyrimidine-3-carboxamide;
N-(2,2-dimethylquinuclidin-3-yl)-6-fluoro-7-(2,2,2-trifluoroethoxy)benzo[b]thiophene-2-carboxamide;
6-fluoro-N-(1'-azaspiro[cyclopropane-1,2'-bicyclo[2.2.2]octan]-3'-yl)-7-(2,2,2-trifluoroethoxy)benzo[b]thiophene-2-carboxamide;
6-cyclopropyl-N-(2,2-dimethylquinuclidin-3-yl)-5-fluorobenzo[b]thiophene-2-carboxamide;
N-(2,2-dimethylquinuclidin-3-yl)-3,4-dihydro-2H-thieno[3',2':5,6]benzo[1,2-b][1,4]oxazine-8-carboxamide;
N-(2,2-dimethylquinuclidin-3-yl)-4-methyl-3,4-dihydro-2H-thieno[3',2':5,6]benzo[1,2-b][1,4]oxazine-8-carboxamide;
6-chloro-N-(2,2-dimethylquinuclidin-3-yl)-7-(2,2,2-trifluoroethyl)benzo[b]thiophene-2-carboxamide;
N-(2,2-dimethylquinuclidin-3-yl)-6-methyl-7-(2,2,2-trifluoroethyl)benzo[b]thiophene-2-carboxamide;
N-(2,2-dimethylquinuclidin-3-yl)-2,2-difluorothieno[2',3':3,4]benzo[1,2-d][1,3]dioxole-7-carboxamide;
N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
4-methyl-N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
6-chloro-N-(1'-azaspiro[cyclopropane-1,2'-bicyclo[2.2.2]octan]-3'-yl)-7-(2,2,2-trifluoroethyl)benzo[b]thiophene-2-carboxamide;
6-methyl-N-(1'-azaspiro[cyclopropane-1,2'-bicyclo[2.2.2]octan]-3'-yl)-7-(2,2,2-trifluoroethyl)benzo[b]thiophene-2-carboxamide;
2,2-difluoro-N-(1'-azaspiro[cyclopropane-1,2'-bicyclo[2.2.2]octan]-3'-yl)thieno[2',3':3,4]benzo[1,2-d][1,3]dioxole-7-carboxamide;
N-(1'-azaspiro[cyclopropane-1,2'-bicyclo[2.2.2]octan]-3'-yl)-7,8-dihydrothieno[2,3-e]benzofuran-2-carboxamide;
6-fluoro-N-(1'-azaspiro[cyclopropane-1,2'-bicyclo[2.2.2]octan]-3'-yl)-7-(thiazol-2-yl)benzo[b]thiophene-2-carboxamide;
6-chloro-N-(1'-azaspiro[cyclopropane-1,2'-bicyclo[2.2.2]octan]-3'-yl)-7-(thiazol-2-yl)benzo[b]thiophene-2-carboxamide;
N-(2,2-dimethylquinuclidin-3-yl)-7,8-dihydrothieno[2,3-e]benzofuran-2-carboxamide;
N-(2,2-dimethylquinuclidin-3-yl)-6-fluoro-7-(thiazol-2-yl)benzo[b]thiophene-2-carboxamide;
6-chloro-N-(2,2-dimethylquinuclidin-3-yl)-7-(thiazol-2-yl)benzo[b]thiophene-2-carboxamide;
5,7-difluoro-6-methyl-N-(1'-azaspiro[cyclopropane-1,2'-bicyclo[2.2.2]octan]-3'-yl)benzo[b]thiophene-2-carboxamide;
6-methoxy-N-(1'-azaspiro[cyclopropane-1,2'-bicyclo[2.2.2]octan]-3'-yl)-7-(trifluoromethoxy)benzo[b]thiophene-2-carboxamide;
7-cyclopropyl-5-fluoro-N-(1'-azaspiro[cyclopropane-1,2'-bicyclo[2.2.2]octan]-3'-yl)benzo[b]thiophene-2-carboxamide;
6-cyclopropyl-5-fluoro-N-(1'-azaspiro[cyclopropane-1,2'-bicyclo[2.2.2]octan]-3'-yl)benzo[b]thiophene-2-carboxamide;
7-chloro-5-fluoro-6-methyl-N-(1'-azaspiro[cyclopropane-1,2'-bicyclo[2.2.2]octan]-3'-yl)benzo[b]thiophene-2-carboxamide;
4-fluoro-N-(1'-azaspiro[cyclopropane-1,2'-bicyclo[2.2.2]octan]-3'-yl)furo[2,3-c]pyridine-5-carboxamide;
3-fluoro-N-(1'-azaspiro[cyclopropane-1,2'-bicyclo[2.2.2]octan]-3'-yl)furo[2,3-c]pyridine-5-carboxamide;
2-fluoro-N-(1'-azaspiro[cyclopropane-1,2'-bicyclo[2.2.2]octan]-3'-yl)furo[2,3-c]pyridine-5-carboxamide;
4-methyl-N-(1'-azaspiro[cyclopropane-1,2'-bicyclo[2.2.2]octan]-3'-yl)furo[2,3-c]pyridine-5-carboxamide;
7-methyl-N-(1'-azaspiro[cyclopropane-1,2'-bicyclo[2.2.2]octan]-3'-yl)furo[2,3-c]pyridine-5-carboxamide;
N-(2,2-dimethylquinuclidin-3-yl)-5,7-difluoro-6-methylbenzo[b]thiophene-2-carboxamide;
N-(2,2-dimethylquinuclidin-3-yl)-6-methoxy-7-(trifluoromethoxy)benzo[b]thiophene-2-carboxamide;
7-cyclopropyl-N-(2,2-dimethylquinuclidin-3-yl)-5-fluorobenzo[b]thiophene-2-carboxamide;
7-chloro-N-(2,2-dimethylquinuclidin-3-yl)-5-fluoro-6-methylbenzo[b]thiophene-2-carboxamide;
N-(2,2-dimethylquinuclidin-3-yl)-4-fluorofuro[2,3-c]pyridine-5-carboxamide;
N-(2,2-dimethylquinuclidin-3-yl)-3-fluorofuro[2,3-c]pyridine-5-carboxamide;
N-(2,2-dimethylquinuclidin-3-yl)-2-fluorofuro[2,3-c]pyridine-5-carboxamide;
N-(2,2-dimethylquinuclidin-3-yl)-4-methylfuro[2,3-c]pyridine-5-carboxamide;
N-(2,2-dimethylquinuclidin-3-yl)-7-methylfuro[2,3-c]pyridine-5-carboxamide;
7-(1-fluorocyclopropyl)-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-6,8-dihydrothieno[2,3-e]isobenzofuran-2-carboxamide;
7-cyclopropoxy-6-fluoro-N-(1'-azaspiro[cyclopropane-1,2'-bicyclo[2.2.2]octan]-3'-yl)benzo[b]thiophene-2-carboxamide;
7-cyclopropoxy-6-methyl-N-(1'-azaspiro[cyclopropane-1,2'-bicyclo[2.2.2]octan]-3'-yl)benzo[b]thiophene-2-carboxamide;
6-chloro-7-cyclopropoxy-N-(1'-azaspiro[cyclopropane-1,2'-bicyclo[2.2.2]octan]-3'-yl)benzo[b]thiophene-2-carboxamide;
6-methyl-N-(1'-azaspiro[cyclopropane-1,2'-bicyclo[2.2.2]octan]-3'-yl)-7-(2,2,2-trifluoroethoxy)benzo[b]thiophene-2-carboxamide;
5,6-difluoro-7-methyl-N-(1'-azaspiro[cyclopropane-1,2'-bicyclo[2.2.2]octan]-3'-yl)benzo[b]thiophene-2-carboxamide;
3-methyl-N-(1'-azaspiro[cyclopropane-1,2'-bicyclo[2.2.2]octan]-3'-yl)furo[2,3-c]pyridine-5-carboxamide;
3-chloro-N-(1'-azaspiro[cyclopropane-1,2'-bicyclo[2.2.2]octan]-3'-yl)furo[2,3-c]pyridine-5-carboxamide;
N-(1'-azaspiro[cyclopropane-1,2'-bicyclo[2.2.2]octan]-3'-yl)pyrrolo[1,2-a]pyrazine-3-carboxamide;
N-(1'-azaspiro[cyclopropane-1,2'-bicyclo[2.2.2]octan]-3'-yl)pyrrolo[1,2-c]pyrimidine-3-carboxamide;
N-(1'-azaspiro[cyclopropane-1,2'-bicyclo[2.2.2]octan]-3'-yl)indolizine-6-carboxamide;
6-methyl-N-(1'-azaspiro[cyclopropane-1,2'-bicyclo[2.2.2]octan]-3'-yl)pyrrolo[1,2-a]pyrazine-3-carboxamide;

N-(1'-azaspiro[cyclopropane-1,2'-bicyclo[2.2.2]octan]-3'-yl)-1H-pyrrolo[3,2-c]pyridine-6-carboxamide;
N-(2,2-dimethylquinuclidin-3-yl)-7-(1-fluorocyclopropyl)benzo[b]thiophene-2-carboxamide;
N-(2,2-dimethylquinuclidin-3-yl)-6,8-dihydrothieno[2,3-e]isobenzofuran-2-carboxamide;
7-cyclopropoxy-N-(2,2-dimethylquinuclidin-3-yl)-6-fluorobenzo[b]thiophene-2-carboxamide;
7-cyclopropoxy-N-(2,2-dimethylquinuclidin-3-yl)-6-methylbenzo[b]thiophene-2-carboxamide;
6-chloro-7-cyclopropoxy-N-(2,2-dimethylquinuclidin-3-yl)benzo[b]thiophene-2-carboxamide;
N-(2,2-dimethylquinuclidin-3-yl)-6-methyl-7-(2,2,2-trifluoroethoxy)benzo[b]thiophene-2-carboxamide;
N-(2,2-dimethylquinuclidin-3-yl)-5,6-difluoro-7-methyl-benzo[b]thiophene-2-carboxamide;
N-(2,2-dimethylquinuclidin-3-yl)-3-methylfuro[2,3-c]pyridine-5-carboxamide;
3-chloro-N-(2,2-dimethylquinuclidin-3-yl)furo[2,3-c]pyridine-5-carboxamide;
N-(2,2-dimethylquinuclidin-3-yl)pyrrolo[1,2-a]pyrazine-3-carboxamide;
N-(2,2-dimethylquinuclidin-3-yl)indolizine-6-carboxamide;
N-(2,2-dimethylquinuclidin-3-yl)-6-methylpyrrolo[1,2-a]pyrazine-3-carboxamide; and
N-(2,2-dimethylquinuclidin-3-yl)-1H-pyrrolo[3,2-c]pyridine-6-carboxamide;

In certain embodiments, specific examples of the amide compound represented by Formula (I) may include, collectively or individually, the compounds listed below, and single enantiomers and pharmaceutically acceptable salts thereof:
N-(2,2-dimethylquinuclidin-3-yl)benzo[b]thiophene-2-carboxamide;
N-(2,2-dimethylquinuclidin-3-yl)-7-fluoro-benzo[b]thiophene-2-carboxamide;
N-(2,2-dimethylquinuclidin-3-yl)benzofuran-5-carboxamide;
6-chloro-N-(2,2-dimethylquinuclidin-3-yl)benzo[b]thiophene-2-carboxamide;
N-(2,2-dimethylquinuclidin-3-yl)furo[2,3-c]pyridine-5-carboxamide;
7-chloro-N-(2,2-dimethylquinuclidin-3-yl)-6-methylbenzo[b]thiophene-2-carboxamide;
N-(2,2-dimethylquinuclidin-3-yl)-7-fluoro-6-methylbenzo[b]thiophene-2-carboxamide;
N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)benzo[b]thiophene-6-carboxamide;
N-(1'-azaspiro[cyclopropane-1,2'-bicyclo[2.2.2]octan]-3'-yl)benzofuran-5-carboxamide;
6-chloro-N-(1'-azaspiro[cyclopropane-1,2'-bicyclo[2.2.2]octan]-3'-yl)benzo[b]thiophene-2-carboxamide;
6-methyl-N-(1'-azaspiro[cyclopropane-1,2'-bicyclo[2.2.2]octan]-3'-yl)benzo[b]thiophene-2-carboxamide;
6-cyclopropyl-N-(1'-azaspiro[cyclopropane-1,2'-bicyclo[2.2.2]octan]-3'-yl)benzo[b]thiophene-2-carboxamide;
6-methoxy-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)furo[2,3-c]pyridine-5-carboxamide;
N-(1'-azaspiro[cyclopropane-1,2'-bicyclo[2.2.2]octan]-3'-yl)-1H-indole-6-carboxamide;
2-chloro-N-(1'-azaspiro[cyclopropane-1,2'-bicyclo[2.2.2]octan]-3'-yl)benzofuran-5-carboxamide;
6-bromo-N-(1'-azaspiro[cyclopropane-1,2'-bicyclo[2.2.2]octan]-3'-yl)benzo[b]thiophene-2-carboxamide;
7-fluoro-6-methyl-N-(1'-azaspiro[cyclopropane-1,2'-bicyclo[2.2.2]octan]-3'-yl)benzo[b]thiophene-2-carboxamide;
6,7-dichloro-N-(1'-azaspiro[cyclopropane-1,2'-bicyclo[2.2.2]octan]-3'-yl)benzo[b]thiophene-2-carboxamide;
6-chloro-7-fluoro-N-(1'-azaspiro[cyclopropane-1,2'-bicyclo[2.2.2]octan]-3'-yl)benzo[b]thiophene-2-carboxamide;
7-cyano-N-(1'-azaspiro[cyclopropane-1,2'-bicyclo[2.2.2]octan]-3'-yl)benzo[b]thiophene-2-carboxamide;
7-cyclopropyl-N-(1'-azaspiro[cyclopropane-1,2'-bicyclo[2.2.2]octan]-3'-yl)benzo[b]thiophene-2-carboxamide;
N-(1'-azaspiro[cyclopropane-1,2'-bicyclo[2.2.2]octan]-3'-yl)-7-(trifluoromethoxy)benzo[b]thiophene-2-carboxamide;
5-fluoro-6-methoxy-N-(1'-azaspiro[cyclopropane-1,2'-bicyclo[2.2.2]octan]-3'-yl)benzo[b]thiophene-2-carboxamide;
7-ethoxy-N-(1'-azaspiro[cyclopropane-1,2'-bicyclo[2.2.2]octan]-3'-yl)benzo[b]thiophene-2-carboxamide; and
2-chloro-N-(1'-azaspiro[cyclopropane-1,2'-bicyclo[2.2.2]octan]-3'-yl)benzo[b]thiophene-6-carboxamide.

In certain embodiments, specific examples of the amide compound represented by Formula (I) may include, collectively or individually, the single enantiomers listed below, and pharmaceutically acceptable salts thereof:
(R)—N-(2,2-dimethylquinuclidin-3-yl)benzo[b]thiophene-2-carboxamide;
(S)—N-(2,2-dimethylquinuclidin-3-yl)benzo[b]thiophene-2-carboxamide;
(R)-4-chloro-N-(2,2-dimethylquinuclidin-3-yl)benzamide;
(S)-4-chloro-N-(2,2-dimethylquinuclidin-3-yl)benzamide;
(R)-7-chloro-N-(2,2-dimethylquinuclidin-3-yl)benzo[b]thiophene-2-carboxamide;
(S)-7-chloro-N-(2,2-dimethylquinuclidin-3-yl)benzo[b]thiophene-2-carboxamide;
(R)—N-(2,2-dimethylquinuclidin-3-yl)-7-fluoro-benzo[b]thiophene-2-carboxamide;
(S)—N-(2,2-dimethylquinuclidin-3-yl)-7-fluoro-benzo[b]thiophene-2-carboxamide;
(R)—N-(2,2-dimethylquinuclidin-3-yl)benzo[b]thiophene-6-carboxamide;
(S)—N-(2,2-dimethylquinuclidin-3-yl)benzo[b]thiophene-6-carboxamide;
(R)—N-(2,2-dimethylquinuclidin-3-yl)benzofuran-5-carboxamide;
(S)—N-(2,2-dimethylquinuclidin-3-yl)benzofuran-5-carboxamide;
(R)—N-(2,2-dimethylquinuclidin-3-yl)-7-(trifluoromethyl)benzo[b]thiophene-2-carboxamide;
(S)—N-(2,2-dimethylquinuclidin-3-yl)-7-(trifluoromethyl)benzo[b]thiophene-2-carboxamide;
(R)—N-(2,2-dimethylquinuclidin-3-yl)-6-fluorobenzo[b]thiophene-2-carboxamide;
(S)—N-(2,2-dimethylquinuclidin-3-yl)-6-fluorobenzo[b]thiophene-2-carboxamide;
(R)-6-cyano-N-(2,2-dimethylquinuclidin-3-yl)benzo[b]thiophene-2-carboxamide;
(S)-6-cyano-N-(2,2-dimethylquinuclidin-3-yl)benzo[b]thiophene-2-carboxamide;
(R)—N-(2,2-dimethylquinuclidin-3-yl)-6-(trifluoromethyl)benzo[b]thiophene-2-carboxamide;
(S)—N-(2,2-dimethylquinuclidin-3-yl)-6-(trifluoromethyl)benzo[b]thiophene-2-carboxamide;
(R)—N-(2,2-dimethylquinuclidin-3-yl)-5-fluorobenzo[b]thiophene-2-carboxamide;
(S)—N-(2,2-dimethylquinuclidin-3-yl)-5-fluorobenzo[b]thiophene-2-carboxamide;

(R)-6-chloro-N-(2,2-dimethylquinuclidin-3-yl)benzo[b]thiophene-2-carboxamide;
(S)-6-chloro-N-(2,2-dimethylquinuclidin-3-yl)benzo[b]thiophene-2-carboxamide;
(R)-5-chloro-N-(2,2-dimethylquinuclidin-3-yl)benzo[b]thiophene-2-carboxamide;
(S)-5-chloro-N-(2,2-dimethylquinuclidin-3-yl)benzo[b]thiophene-2-carboxamide;
(R)-5,6-dichloro-N-(2,2-dimethylquinuclidin-3-yl)benzo[b]thiophene-2-carboxamide;
(S)-5,6-dichloro-N-(2,2-dimethylquinuclidin-3-yl)benzo[b]thiophene-2-carboxamide;
(R)—N-(2,2-dimethylquinuclidin-3-yl)-6-methylbenzo[b]thiophene-2-carboxamide;
(S)—N-(2,2-dimethylquinuclidin-3-yl)-6-methylbenzo[b]thiophene-2-carboxamide;
(R)—N-(2,2-dimethylquinuclidin-3-yl)-5-methylbenzo[b]thiophene-2-carboxamide;
(S)—N-(2,2-dimethylquinuclidin-3-yl)-5-methylbenzo[b]thiophene-2-carboxamide;
(R)—N-(2,2-dimethylquinuclidin-3-yl)-5-(trifluoromethyl)benzo[b]thiophene-2-carboxamide;
(S)—N-(2,2-dimethylquinuclidin-3-yl)-5-(trifluoromethyl)benzo[b]thiophene-2-carboxamide;
(R)-6-cyclopropyl-N-(2,2-dimethylquinuclidin-3-yl)benzo[b]thiophene-2-carboxamide;
(S)-6-cyclopropyl-N-(2,2-dimethylquinuclidin-3-yl)benzo[b]thiophene-2-carboxamide;
(R)-5-cyclopropyl-N-(2,2-dimethylquinuclidin-3-yl)benzo[b]thiophene-2-carboxamide;
(S)-5-cyclopropyl-N-(2,2-dimethylquinuclidin-3-yl)benzo[b]thiophene-2-carboxamide;
(R)—N-(2,2-dimethylquinuclidin-3-yl)-6-methoxybenzo[b]thiophene-2-carboxamide;
(S)—N-(2,2-dimethylquinuclidin-3-yl)-6-methoxybenzo[b]thiophene-2-carboxamide;
(R)—N-(2,2-dimethylquinuclidin-3-yl)-5-methoxybenzo[b]thiophene-2-carboxamide;
(S)—N-(2,2-dimethylquinuclidin-3-yl)-5-methoxybenzo[b]thiophene-2-carboxamide;
(R)—N-(2,2-dimethylquinuclidin-3-yl)furo[2,3-c]pyridine-5-carboxamide;
(S)—N-(2,2-dimethylquinuclidin-3-yl)furo[2,3-c]pyridine-5-carboxamide;
(R)—N-(2,2-dimethylquinuclidin-3-yl)-2,3-dihydro-[1,4]dioxino[2,3-c]pyridine-7-carboxamide;
(S)—N-(2,2-dimethylquinuclidin-3-yl)-2,3-dihydro-[1,4]dioxino[2,3-c]pyridine-7-carboxamide;
(R)—N-(2,2-dimethylquinuclidin-3-yl)-3-methylbenzo[b]thiophene-5-carboxamide;
(S)—N-(2,2-dimethylquinuclidin-3-yl)-3-methylbenzo[b]thiophene-5-carboxamide;
(R)—N-(2,2-dimethylquinuclidin-3-yl)-3-methylbenzo[b]thiophene-6-carboxamide;
(S)—N-(2,2-dimethylquinuclidin-3-yl)-3-methylbenzo[b]thiophene-6-carboxamide;
(R)—N-(2,2-dimethylquinuclidin-3-yl)-1H-indole-6-carboxamide;
(S)—N-(2,2-dimethylquinuclidin-3-yl)-1H-indole-6-carboxamide;
(R)—N-(2,2-dimethylquinuclidin-3-yl)pyrazolo[1,5-b]pyridazine-3-carboxamide;
(S)—N-(2,2-dimethylquinuclidin-3-yl)pyrazolo[1,5-b]pyridazine-3-carboxamide;
(R)—N-(2,2-dimethylquinuclidin-3-yl)thieno[2,3-b]pyridine-2-carboxamide;
(S)—N-(2,2-dimethylquinuclidin-3-yl)thieno[2,3-b]pyridine-2-carboxamide;
(R)—N-(2,2-dimethylquinuclidin-3-yl)benzo[d]thiazole-2-carboxamide;
(S)—N-(2,2-dimethylquinuclidin-3-yl)benzo[d]thiazole-2-carboxamide;
(R)—N-(2,2-dimethylquinuclidin-3-yl)benzo[b]thiophene-5-carboxamide;
(S)—N-(2,2-dimethylquinuclidin-3-yl)benzo[b]thiophene-5-carboxamide;
(R)—N-(2,2-dimethylquinuclidin-3-yl)benzofuran-6-carboxamide;
(S)—N-(2,2-dimethylquinuclidin-3-yl)benzofuran-6-carboxamide;
(R)—N-(2,2-dimethylquinuclidin-3-yl)-2-methylbenzo[d]oxazole-5-carboxamide;
(S)—N-(2,2-dimethylquinuclidin-3-yl)-2-methylbenzo[d]oxazole-5-carboxamide;
(R)—N-(2,2-dimethylquinuclidin-3-yl)-2-methylbenzo[d]oxazole-6-carboxamide;
(S)—N-(2,2-dimethylquinuclidin-3-yl)-2-methylbenzo[d]oxazole-6-carboxamide;
(R)—N-(2,2-dimethylquinuclidin-3-yl)-2-methylbenzo[d]thiazole-5-carboxamide;
(S)—N-(2,2-dimethylquinuclidin-3-yl)-2-methylbenzo[d]thiazole-5-carboxamide;
(R)—N-(2,2-dimethylquinuclidin-3-yl)-2-methylbenzo[d]thiazole-6-carboxamide;
(S)—N-(2,2-dimethylquinuclidin-3-yl)-2-methylbenzo[d]thiazole-6-carboxamide;
(R)—N-(2,2-dimethylquinuclidin-3-yl)furo[2,3-b]pyridine-5-carboxamide;
(S)—N-(2,2-dimethylquinuclidin-3-yl)furo[2,3-b]pyridine-5-carboxamide;
(R)—N-(2,2-dimethylquinuclidin-3-yl)furo[3,2-b]pyridine-5-carboxamide;
(S)—N-(2,2-dimethylquinuclidin-3-yl)furo[3,2-b]pyridine-5-carboxamide;
(R)—N-(2,2-dimethylquinuclidin-3-yl)-2-methylbenzofuran-5-carboxamide;
(S)—N-(2,2-dimethylquinuclidin-3-yl)-2-methylbenzofuran-5-carboxamide;
(R)-2-chloro-N-(2,2-dimethylquinuclidin-3-yl)benzofuran-5-carboxamide;
(S)-2-chloro-N-(2,2-dimethylquinuclidin-3-yl)benzofuran-5-carboxamide;
(R)—N-(2,2-dimethylquinuclidin-3-yl)-3-methylbenzofuran-5-carboxamide;
(S)—N-(2,2-dimethylquinuclidin-3-yl)-3-methylbenzofuran-5-carboxamide;
(R)-3-chloro-N-(2,2-dimethylquinuclidin-3-yl)benzofuran-5-carboxamide;
(S)-3-chloro-N-(2,2-dimethylquinuclidin-3-yl)benzofuran-5-carboxamide;
(R)—N-(2,2-dimethylquinuclidin-3-yl)-1-methyl-1H-benzo[d]imidazole-5-carboxamide;
(S)—N-(2,2-dimethylquinuclidin-3-yl)-1-methyl-1H-benzo[d]imidazole-5-carboxamide;
(R)—N-(2,2-dimethylquinuclidin-3-yl)thieno[2,3-c]pyridine-5-carboxamide;
(S)—N-(2,2-dimethylquinuclidin-3-yl)thieno[2,3-c]pyridine-5-carboxamide;
(R)—N-(2,2-dimethylquinuclidin-3-yl)-6-morpholinobenzo[b]thiophene-2-carboxamide;
(S)—N-(2,2-dimethylquinuclidin-3-yl)-6-morpholinobenzo[b]thiophene-2-carboxamide;

(R)-6-(4,4-difluoropiperidin-1-yl)-N-(2,2-dimethylquinuclidin-3-yl)benzo[b]thiophene-2-carboxamide;
(S)-6-(4,4-difluoropiperidin-1-yl)-N-(2,2-dimethylquinuclidin-3-yl)benzo[b]thiophene-2-carboxamide;
(R)-6-bromo-N-(2,2-dimethylquinuclidin-3-yl)benzo[b]thiophene-2-carboxamide;
(S)-6-bromo-N-(2,2-dimethylquinuclidin-3-yl)benzo[b]thiophene-2-carboxamide;
(R)—N-(2,2-dimethylquinuclidin-3-yl)-6-isopropoxybenzo[b]thiophene-2-carboxamide;
(S)—N-(2,2-dimethylquinuclidin-3-yl)-6-isopropoxybenzo[b]thiophene-2-carboxamide;
(R)—N-(2,2-dimethylquinuclidin-3-yl)-6-(methylsulfonyl)benzo[b]thiophene-2-carboxamide;
(S)—N-(2,2-dimethylquinuclidin-3-yl)-6-(methylsulfonyl)benzo[b]thiophene-2-carboxamide;
(R)—N-(2,2-dimethylquinuclidin-3-yl)-6-nitrobenzo[b]thiophene-2-carboxamide;
(S)—N-(2,2-dimethylquinuclidin-3-yl)-6-nitrobenzo[b]thiophene-2-carboxamide;
(R)-6-amino-N-(2,2-dimethylquinuclidin-3-yl)benzo[b]thiophene-2-carboxamide;
(S)-6-amino-N-(2,2-dimethylquinuclidin-3-yl)benzo[b]thiophene-2-carboxamide;
(R)—N-(2,2-dimethylquinuclidin-3-yl)-6-(tetrahydro-2H-pyran-4-yl)benzo[b]thiophene-2-carboxamide;
(S)—N-(2,2-dimethylquinuclidin-3-yl)-6-(tetrahydro-2H-pyran-4-yl)benzo[b]thiophene-2-carboxamide;
(R)—N-(2,2-dimethylquinuclidin-3-yl)-7-fluoro-6-methoxybenzo[b]thiophene-2-carboxamide;
(S)—N-(2,2-dimethylquinuclidin-3-yl)-7-fluoro-6-methoxybenzo[b]thiophene-2-carboxamide;
(R)-7-chloro-N-(2,2-dimethylquinuclidin-3-yl)-6-methylbenzo[b]thiophene-2-carboxamide;
(S)-7-chloro-N-(2,2-dimethylquinuclidin-3-yl)-6-methylbenzo[b]thiophene-2-carboxamide;
(R)—N-(2,2-dimethylquinuclidin-3-yl)-7-fluoro-6-methylbenzo[b]thiophene-2-carboxamide;
(S)—N-(2,2-dimethylquinuclidin-3-yl)-7-fluoro-6-methylbenzo[b]thiophene-2-carboxamide;
(R)—N-(1'-azaspiro[cyclopropane-1,2'-bicyclo[2.2.2]octan]-3'-yl)benzo[b]thiophene-2-carboxamide;
(S)—N-(1'-azaspiro[cyclopropane-1,2'-bicyclo[2.2.2]octan]-3'-yl)benzo[b]thiophene-2-carboxamide;
(R)-4-chloro-N-(1'-azaspiro[cyclopropane-1,2'-bicyclo[2.2.2]octan]-3'-yl)benzamide;
(S)-4-chloro-N-(1'-azaspiro[cyclopropane-1,2'-bicyclo[2.2.2]octan]-3'-yl)benzamide;
(R)-7-chloro-N-(1'-azaspiro[cyclopropane-1,2'-bicyclo[2.2.2]octan]-3'-yl)benzo[b]thiophene-2-carboxamide;
(S)-7-chloro-N-(1'-azaspiro[cyclopropane-1,2'-bicyclo[2.2.2]octan]-3'-yl)benzo[b]thiophene-2-carboxamide;
(R)-7-fluoro-N-(1'-azaspiro[cyclopropane-1,2'-bicyclo[2.2.2]octan]-3'-yl)benzo[b]thiophene-2-carboxamide;
(S)-7-fluoro-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)benzo[b]thiophene-6-carboxamide;
(S)—N-(1'-azaspiro[cyclopropane-1,2'-bicyclo[2.2.2]octan]-3'-yl)benzo[b]thiophene-6-carboxamide;
(R)—N-(1'-azaspiro[cyclopropane-1,2'-bicyclo[2.2.2]octan]-3'-yl)benzofuran-5-carboxamide;
(S)—N-(1'-azaspiro[cyclopropane-1,2'-bicyclo[2.2.2]octan]-3'-yl)benzofuran-5-carboxamide;
(R)—N-(1'-azaspiro[cyclopropane-1,2'-bicyclo[2.2.2]octan]-3'-yl)-7-(trifluoromethyl)benzo[b]thiophene-2-carboxamide;
(S)—N-(1'-azaspiro[cyclopropane-1,2'-bicyclo[2.2.2]octan]-3'-yl)-7-(trifluoromethyl)benzo[b]thiophene-2-carboxamide;
(R)-6-fluoro-N-(1'-azaspiro[cyclopropane-1,2'-bicyclo[2.2.2]octan]-3'-yl)benzo[b]thiophene-2-carboxamide;
(S)-6-fluoro-N-(1'-azaspiro[cyclopropane-1,2'-bicyclo[2.2.2]octan]-3'-yl)benzo[b]thiophene-2-carboxamide;
(R)-6-nitro-N-(1'-azaspiro[cyclopropane-1,2'-bicyclo[2.2.2]octan]-3'-yl)benzo[b]thiophene-2-carboxamide;
(S)-6-nitro-N-(1'-azaspiro[cyclopropane-1,2'-bicyclo[2.2.2]octan]-3'-yl)benzo[b]thiophene-2-carboxamide;
(R)-6-amino-N-(1'-azaspiro[cyclopropane-1,2'-bicyclo[2.2.2]octan]-3'-yl)benzo[b]thiophene-2-carboxamide;
(S)-6-amino-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-6-(trifluoromethyl)benzo[b]thiophene-2-carboxamide;
(S)—N-(1'-azaspiro[cyclopropane-1,2'-bicyclo[2.2.2]octan]-3'-yl)-6-(trifluoromethyl)benzo[b]thiophene-2-carboxamide;
(R)-5-fluoro-N-(1'-azaspiro[cyclopropane-1,2'-bicyclo[2.2.2]octan]-3'-yl)benzo[b]thiophene-2-carboxamide;
(S)-5-fluoro-N-(1'-azaspiro[cyclopropane-1,2'-bicyclo[2.2.2]octan]-3'-yl)benzo[b]thiophene-2-carboxamide;
(R)-6-chloro-N-(1'-azaspiro[cyclopropane-1,2'-bicyclo[2.2.2]octan]-3'-yl)benzo[b]thiophene-2-carboxamide;
(S)-6-chloro-N-(1'-azaspiro[cyclopropane-1,2'-bicyclo[2.2.2]octan]-3'-yl)benzo[b]thiophene-2-carboxamide;
(R)-5-chloro-N-(1'-azaspiro[cyclopropane-1,2'-bicyclo[2.2.2]octan]-3'-yl)benzo[b]thiophene-2-carboxamide;
(S)-5-chloro-N-(1'-azaspiro[cyclopropane-1,2'-bicyclo[2.2.2]octan]-3'-yl)benzo[b]thiophene-2-carboxamide;
(R)-5,6-dichloro-N-(1'-azaspiro[cyclopropane-1,2'-bicyclo[2.2.2]octan]-3'-yl)benzo[b]thiophene-2-carboxamide;
(S)-5,6-dichloro-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)benzo[b]thiophene-2-carboxamide;
(S)-6-methyl-N-(1'-azaspiro[cyclopropane-1,2'-bicyclo[2.2.2]octan]-3'-yl)benzo[b]thiophene-2-carboxamide;
(R)-5-methyl-N-(1'-azaspiro[cyclopropane-1,2'-bicyclo[2.2.2]octan]-3'-yl)benzo[b]thiophene-2-carboxamide;
(S)-5-methyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-5-(trifluoromethyl)benzo[b]thiophene-2-carboxamide;
(S)—N-(1'-azaspiro[cyclopropane-1,2'-bicyclo[2.2.2]octan]-3'-yl)-5-(trifluoromethyl)benzo[b]thiophene-2-carboxamide;
(R)-6-cyclopropyl-N-(1'-azaspiro[cyclopropane-1,2'-bicyclo[2.2.2]octan]-3'-yl)benzo[b]thiophene-2-carboxamide;
(S)-6-cyclopropyl-N-(1'-azaspiro[cyclopropane-1,2'-bicyclo[2.2.2]octan]-3'-yl)benzo[b]thiophene-2-carboxamide;
(R)-5-cyclopropyl-N-(1'-azaspiro[cyclopropane-1,2'-bicyclo[2.2.2]octan]-3'-yl)benzo[b]thiophene-2-carboxamide;
(S)-5-cyclopropyl-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)benzo[b]thiophene-2-carboxamide;
(S)-6-methoxy-N-(1'-azaspiro[cyclopropane-1,2'-bicyclo[2.2.2]octan]-3'-yl)benzo[b]thiophene-2-carboxamide;
(R)-5-methoxy-N-(1'-azaspiro[cyclopropane-1,2'-bicyclo[2.2.2]octan]-3'-yl)benzo[b]thiophene-2-carboxamide;
(S)-5-methoxy-N-(1'-azaspiro[cyclopropane-1,2'-bicyclo[2.2.2]octan]-3'-yl)benzo[b]thiophene-2-carboxamide;

(R)—N-(1'-azaspiro[cyclopropane-1,2'-bicyclo[2.2.2]octan]-3'-yl)furo[2,3-c]pyridine-5-carboxamide;
(S)—N-(1'-azaspiro[cyclopropane-1,2'-bicyclo[2.2.2]octan]-3'-yl)furo[2,3-c]pyridine-5-carboxamide;
(R)—N-(1'-azaspiro[cyclopropane-1,2'-bicyclo[2.2.2]octan]-3'-yl)-2,3-dihydro-[1,4]dioxino[2,3-c]pyridine-7-carboxamide;
(S)—N-(1'-azaspiro[cyclopropane-1,2'-bicyclo[2.2.2]octan]-3'-yl)-2,3-dihydro-[1,4]dioxino[2,3-c]pyridine-7-carboxamide;
(R)-3-methyl-N-(1'-azaspiro[cyclopropane-1,2'-bicyclo[2.2.2]octan]-3'-yl)benzo[b]thiophene-5-carboxamide;
(S)-3-methyl-N-(1'-azaspiro[cyclopropane-1,2'-bicyclo[2.2.2]octan]-3'-yl)benzo[b]thiophene-5-carboxamide;
(R)-3-methyl-N-(1'-azaspiro[cyclopropane-1,2'-bicyclo[2.2.2]octan]-3'-yl)benzo[b]thiophene-6-carboxamide;
(S)-3-methyl-N-(1'-azaspiro[cyclopropane-1,2'-bicyclo[2.2.2]octan]-3'-yl)benzo[b]thiophene-6-carboxamide;
(R)—N-(1'-azaspiro[cyclopropane-1,2'-bicyclo[2.2.2]octan]-3'-yl)-1H-indole-6-carboxamide;
(S)—N-(1'-azaspiro[cyclopropane-1,2'-bicyclo[2.2.2]octan]-3'-yl)-1H-indole-6-carboxamide;
(R)—N-(1'-azaspiro[cyclopropane-1,2'-bicyclo[2.2.2]octan]-3'-yl)pyrazolo[1,5-b]pyridazine-3-carboxamide;
(S)—N-(1'-azaspiro[cyclopropane-1,2'-bicyclo[2.2.2]octan]-3'-yl)pyrazolo[1,5-b]pyridazine-3-carboxamide;
(R)—N-(1'-azaspiro[cyclopropane-1,2'-bicyclo[2.2.2]octan]-3'-yl)thieno[2,3-b]pyridine-2-carboxamide;
(S)—N-(1'-azaspiro[cyclopropane-1,2'-bicyclo[2.2.2]octan]-3'-yl)thieno[2,3-b]pyridine-2-carboxamide;
(R)—N-(1'-azaspiro[cyclopropane-1,2'-bicyclo[2.2.2]octan]-3'-yl)benzo[d]thiazole-2-carboxamide;
(S)—N-(1'-azaspiro[cyclopropane-1,2'-bicyclo[2.2.2]octan]-3'-yl)benzo[d]thiazole-2-carboxamide;
(R)—N-(1'-azaspiro[cyclopropane-1,2'-bicyclo[2.2.2]octan]-3'-yl)benzo[b]thiophene-5-carboxamide;
(S)—N-(1'-azaspiro[cyclopropane-1,2'-bicyclo[2.2.2]octan]-3'-yl)benzo[b]thiophene-5-carboxamide;
(R)—N-(1'-azaspiro[cyclopropane-1,2'-bicyclo[2.2.2]octan]-3'-yl)benzofuran-6-carboxamide;
(S)—N-(1'-azaspiro[cyclopropane-1,2'-bicyclo[2.2.2]octan]-3'-yl)benzofuran-6-carboxamide;
(R)-2-methyl-N-(1'-azaspiro[cyclopropane-1,2'-bicyclo[2.2.2]octan]-3'-yl)benzo[d]oxazole-5-carboxamide;
(S)-2-methyl-N-(1'-azaspiro[cyclopropane-1,2'-bicyclo[2.2.2]octan]-3'-yl)benzo[d]oxazole-5-carboxamide;
(R)-2-methyl-N-(1'-azaspiro[cyclopropane-1,2'-bicyclo[2.2.2]octan]-3'-yl)benzo[d]oxazole-6-carboxamide;
(S)-2-methyl-N-(1'-azaspiro[cyclopropane-1,2'-bicyclo[2.2.2]octan]-3'-yl)benzo[d]oxazole-6-carboxamide;
(R)-2-methyl-N-(1'-azaspiro[cyclopropane-1,2'-bicyclo[2.2.2]octan]-3'-yl)benzo[d]thiazole-5-carboxamide;
(S)-2-methyl-N-(1'-azaspiro[cyclopropane-1,2'-bicyclo[2.2.2]octan]-3'-yl)benzo[d]thiazole-5-carboxamide;
(R)-2-methyl-N-(1'-azaspiro[cyclopropane-1,2'-bicyclo[2.2.2]octan]-3'-yl)benzo[d]thiazole-6-carboxamide;
(S)-2-methyl-N-(1'-azaspiro[cyclopropane-1,2'-bicyclo[2.2.2]octan]-3'-yl)benzo[d]thiazole-6-carboxamide;
(R)—N-(1'-azaspiro[cyclopropane-1,2'-bicyclo[2.2.2]octan]-3'-yl)furo[2,3-b]pyridine-5-carboxamide;
(S)—N-(1'-azaspiro[cyclopropane-1,2'-bicyclo[2.2.2]octan]-3'-yl)furo[2,3-b]pyridine-5-carboxamide;
(R)—N-(1'-azaspiro[cyclopropane-1,2'-bicyclo[2.2.2]octan]-3'-yl)furo[3,2-b]pyridine-5-carboxamide;
(S)—N-(1'-azaspiro[cyclopropane-1,2'-bicyclo[2.2.2]octan]-3'-yl)furo[3,2-b]pyridine-5-carboxamide;
(R)-2-methyl-N-(1'-azaspiro[cyclopropane-1,2'-bicyclo[2.2.2]octan]-3'-yl)benzofuran-5-carboxamide;
(S)-2-methyl-N-(1'-azaspiro[cyclopropane-1,2'-bicyclo[2.2.2]octan]-3'-yl)benzofuran-5-carboxamide;
(R)-2-chloro-N-(1'-azaspiro[cyclopropane-1,2'-bicyclo[2.2.2]octan]-3'-yl)benzofuran-5-carboxamide;
(S)-2-chloro-N-(1'-azaspiro[cyclopropane-1,2'-bicyclo[2.2.2]octan]-3'-yl)benzofuran-5-carboxamide;
(R)-3-methyl-N-(1'-azaspiro[cyclopropane-1,2'-bicyclo[2.2.2]octan]-3'-yl)benzofuran-5-carboxamide;
(S)-3-methyl-N-(1'-azaspiro[cyclopropane-1,2'-bicyclo[2.2.2]octan]-3'-yl)benzofuran-5-carboxamide;
(R)-3-chloro-N-(1'-azaspiro[cyclopropane-1,2'-bicyclo[2.2.2]octan]-3'-yl)benzofuran-5-carboxamide;
(S)-3-chloro-N-(1'-azaspiro[cyclopropane-1,2'-bicyclo[2.2.2]octan]-3'-yl)benzofuran-5-carboxamide;
(R)-1-methyl-N-(1'-azaspiro[cyclopropane-1,2'-bicyclo[2.2.2]octan]-3'-yl)-1H-benzo[d]imidazole-5-carboxamide;
(S)-1-methyl-N-(1'-azaspiro[cyclopropane-1,2'-bicyclo[2.2.2]octan]-3'-yl)-1H-benzo[d]imidazole-5-carboxamide;
(R)-1-methyl-N-(1'-azaspiro[cyclopropane-1,2'-bicyclo[2.2.2]octan]-3'-yl)-1H-benzo[d]imidazole-6-carboxamide;
(S)-1-methyl-N-(1'-azaspiro[cyclopropane-1,2'-bicyclo[2.2.2]octan]-3'-yl)-1H-benzo[d]imidazole-6-carboxamide;
(R)—N-(1'-azaspiro[cyclopropane-1,2'-bicyclo[2.2.2]octan]-3'-yl)thieno[2,3-c]pyridine-5-carboxamide;
(S)—N-(1'-azaspiro[cyclopropane-1,2'-bicyclo[2.2.2]octan]-3'-yl)thieno[2,3-c]pyridine-5-carboxamide;
(R)—N-(1'-azaspiro[cyclopropane-1,2'-bicyclo[2.2.2]octan]-3'-yl)-6-(1H-1,2,3-triazol-1-yl)benzo[b]thiophene-2-carboxamide;
(S)—N-(1'-azaspiro[cyclopropane-1,2'-bicyclo[2.2.2]octan]-3'-yl)-6-(1H-1,2,3-triazol-1-yl)benzo[b]thiophene-2-carboxamide;
(R)-6-morpholino-N-(1'-azaspiro[cyclopropane-1,2'-bicyclo[2.2.2]octan]-3'-yl)benzo[b]thiophene-2-carboxamide;
(S)-6-morpholino-N-(1'-azaspiro[cyclopropane-1,2'-bicyclo[2.2.2]octan]-3'-yl)benzo[b]thiophene-2-carboxamide;
(R)-6-(4,4-difluoropiperidin-1-yl)-N-(1'-azaspiro[cyclopropane-1,2'-bicyclo[2.2.2]octan]-3'-yl)benzo[b]thiophene-2-carboxamide;
(S)-6-(4,4-difluoropiperidin-1-yl)-N-(1'-azaspiro[cyclopropane-1,2'-bicyclo[2.2.2]octan]-3'-yl)benzo[b]thiophene-2-carboxamide;
(R)-6-bromo-N-(1'-azaspiro[cyclopropane-1,2'-bicyclo[2.2.2]octan]-3'-yl)benzo[b]thiophene-2-carboxamide;
(S)-6-bromo-N-(1'-azaspiro[cyclopropane-1,2'-bicyclo[2.2.2]octan]-3'-yl)benzo[b]thiophene-2-carboxamide;
(R)-6-isopropoxy-N-(1'-azaspiro[cyclopropane-1,2'-bicyclo[2.2.2]octan]-3'-yl)benzo[b]thiophene-2-carboxamide;
(S)-6-isopropoxy-N-(1'-azaspiro[cyclopropane-1,2'-bicyclo[2.2.2]octan]-3'-yl)benzo[b]thiophene-2-carboxamide;
(R)-6-(methylsulfonyl)-N-(1'-azaspiro[cyclopropane-1,2'-bicyclo[2.2.2]octan]-3'-yl)benzo[b]thiophene-2-carboxamide;
(S)-6-(methylsulfonyl)-N-(1'-azaspiro[cyclopropane-1,2'-bicyclo[2.2.2]octan]-3'-yl)benzo[b]thiophene-2-carboxamide;
(R)-6-cyano-N-(1'-azaspiro[cyclopropane-1,2'-bicyclo[2.2.2]octan]-3'-yl)benzo[b]thiophene-2-carboxamide;
(S)-6-cyano-N-(1'-azaspiro[cyclopropane-1,2'-bicyclo[2.2.2]octan]-3'-yl)benzo[b]thiophene-2-carboxamide;

(R)-N-(1'-azaspiro[cyclopropane-1,2'-bicyclo[2.2.2]octan]-3'-yl)-6-(tetrahydro-2H-pyran-4-yl)benzo[b]thiophene-2-carboxamide;
(S)-N-(1'-azaspiro[cyclopropane-1,2'-bicyclo[2.2.2]octan]-3'-yl)-6-(tetrahydro-2H-pyran-4-yl)benzo[b]thiophene-2-carboxamide;
(R)-7-fluoro-6-methyl-N-(1'-azaspiro[cyclopropane-1,2'-bicyclo[2.2.2]octan]-3'-yl)benzo[b]thiophene-2-carboxamide;
(S)-7-fluoro-6-methyl-N-(1'-azaspiro[cyclopropane-1,2'-bicyclo[2.2.2]octan]-3'-yl)benzo[b]thiophene-2-carboxamide;
(R)-N-(1'-azaspiro[cyclopropane-1,2'-bicyclo[2.2.2]octan]-3'-yl)-2,3-dihydrobenzo[b][1,4]dioxine-6-carboxamide; and
(S)-N-(1'-azaspiro[cyclopropane-1,2'-bicyclo[2.2.2]octan]-3'-yl)-2,3-dihydrobenzo[b][1,4]dioxine-6-carboxamide.

In certain embodiments, specific examples of the amide compound represented by Formula (I) may include, collectively or individually, the single enantiomers listed below, and pharmaceutically acceptable salts thereof:
(R)-2-amino-N-(2,2-dimethylquinuclidin-3-yl)thieno[2,3-d]pyrimidine-6-carboxamide;
(S)-2-amino-N-(2,2-dimethylquinuclidin-3-yl)thieno[2,3-d]pyrimidine-6-carboxamide;
(R)-6,7-dichloro-N-(2,2-dimethylquinuclidin-3-yl)benzo[b]thiophene-2-carboxamide;
(S)-6,7-dichloro-N-(2,2-dimethylquinuclidin-3-yl)benzo[b]thiophene-2-carboxamide;
(R)-6-chloro-N-(2,2-dimethylquinuclidin-3-yl)-7-fluorobenzo[b]thiophene-2-carboxamide;
(S)-6-chloro-N-(2,2-dimethylquinuclidin-3-yl)-7-fluorobenzo[b]thiophene-2-carboxamide;
(R)-6-chloro-N-(2,2-dimethylquinuclidin-3-yl)-7-(trifluoromethyl)benzo[b]thiophene-2-carboxamide;
(S)-6-chloro-N-(2,2-dimethylquinuclidin-3-yl)-7-(trifluoromethyl)benzo[b]thiophene-2-carboxamide;
(R)-7-chloro-N-(2,2-dimethylquinuclidin-3-yl)-6-methoxybenzo[b]thiophene-2-carboxamide;
(S)-7-chloro-N-(2,2-dimethylquinuclidin-3-yl)-6-methoxybenzo[b]thiophene-2-carboxamide;
(R)-N-(2,2-dimethylquinuclidin-3-yl)-6-methyl-7-(trifluoromethyl)benzo[b]thiophene-2-carboxamide;
(S)-N-(2,2-dimethylquinuclidin-3-yl)-6-methyl-7-(trifluoromethyl)benzo[b]thiophene-2-carboxamide;
(R)-7-chloro-N-(2,2-dimethylquinuclidin-3-yl)-6-fluorobenzo[b]thiophene-2-carboxamide;
(S)-7-chloro-N-(2,2-dimethylquinuclidin-3-yl)-6-fluorobenzo[b]thiophene-2-carboxamide;
(R)-7-cyano-N-(2,2-dimethylquinuclidin-3-yl)benzo[b]thiophene-2-carboxamide;
(S)-7-cyano-N-(2,2-dimethylquinuclidin-3-yl)benzo[b]thiophene-2-carboxamide;
(R)-N-(2,2-dimethylquinuclidin-3-yl)-7-methoxybenzo[b]thiophene-2-carboxamide;
(S)-N-(2,2-dimethylquinuclidin-3-yl)-7-methoxybenzo[b]thiophene-2-carboxamide;
(R)-N-(2,2-dimethylquinuclidin-3-yl)-6,7-difluorobenzo[b]thiophene-2-carboxamide;
(S)-N-(2,2-dimethylquinuclidin-3-yl)-6,7-difluorobenzo[b]thiophene-2-carboxamide;
(R)-7-cyclopropyl-N-(2,2-dimethylquinuclidin-3-yl)benzo[b]thiophene-2-carboxamide;
(S)-7-cyclopropyl-N-(2,2-dimethylquinuclidin-3-yl)benzo[b]thiophene-2-carboxamide;
(R)-N-(2,2-dimethylquinuclidin-3-yl)-7-isopropylbenzo[b]thiophene-2-carboxamide;
(S)-N-(2,2-dimethylquinuclidin-3-yl)-7-isopropylbenzo[b]thiophene-2-carboxamide;
(R)-N-(2,2-dimethylquinuclidin-3-yl)-7-(trifluoromethoxy)benzo[b]thiophene-2-carboxamide;
(S)-N-(2,2-dimethylquinuclidin-3-yl)-7-(trifluoromethoxy)benzo[b]thiophene-2-carboxamide;
(R)-N-(2,2-dimethylquinuclidin-3-yl)-7-(tetrahydro-2H-pyran-4-yl)benzo[b]thiophene-2-carboxamide;
(S)-N-(2,2-dimethylquinuclidin-3-yl)-7-(tetrahydro-2H-pyran-4-yl)benzo[b]thiophene-2-carboxamide;
(R)-N-(2,2-dimethylquinuclidin-3-yl)-1H-indole-2-carboxamide;
(S)-N-(2,2-dimethylquinuclidin-3-yl)-1H-indole-2-carboxamide;
(R)-6-chloro-N-(2,2-dimethylquinuclidin-3-yl)-5-fluorobenzo[b]thiophene-2-carboxamide;
(S)-6-chloro-N-(2,2-dimethylquinuclidin-3-yl)-5-fluorobenzo[b]thiophene-2-carboxamide;
(R)-N-(2,2-dimethylquinuclidin-3-yl)-5-fluoro-6-methoxybenzo[b]thiophene-2-carboxamide;
(S)-N-(2,2-dimethylquinuclidin-3-yl)-5-fluoro-6-methoxybenzo[b]thiophene-2-carboxamide;
(R)-6-chloro-N-(2,2-dimethylquinuclidin-3-yl)-5,7-difluorobenzo[b]thiophene-2-carboxamide;
(S)-6-chloro-N-(2,2-dimethylquinuclidin-3-yl)-5,7-difluorobenzo[b]thiophene-2-carboxamide;
(R)-N-(2,2-dimethylquinuclidin-3-yl)-7-methylbenzo[b]thiophene-2-carboxamide;
(S)-N-(2,2-dimethylquinuclidin-3-yl)-7-methylbenzo[b]thiophene-2-carboxamide;
(R)-N-(2,2-dimethylquinuclidin-3-yl)-7-(2,2,2-trifluoroethyl)benzo[b]thiophene-2-carboxamide;
(S)-N-(2,2-dimethylquinuclidin-3-yl)-7-(2,2,2-trifluoroethyl)benzo[b]thiophene-2-carboxamide;
(R)-7-(dimethylamino)-N-(2,2-dimethylquinuclidin-3-yl)benzo[b]thiophene-2-carboxamide;
(S)-7-(dimethylamino)-N-(2,2-dimethylquinuclidin-3-yl)benzo[b]thiophene-2-carboxamide;
(R)-N-(2,2-dimethylquinuclidin-3-yl)-7-(thiazol-2-yl)benzo[b]thiophene-2-carboxamide;
(S)-N-(2,2-dimethylquinuclidin-3-yl)-7-(thiazol-2-yl)benzo[b]thiophene-2-carboxamide;
(R)-N-(2,2-dimethylquinuclidin-3-yl)isoquinoline-3-carboxamide;
(S)-N-(2,2-dimethylquinuclidin-3-yl)isoquinoline-3-carboxamide;
(R)-7-(tert-butyl)-N-(2,2-dimethylquinuclidin-3-yl)benzo[b]thiophene-2-carboxamide;
(S)-7-(tert-butyl)-N-(2,2-dimethylquinuclidin-3-yl)benzo[b]thiophene-2-carboxamide;
(R)-N-(2,2-dimethylquinuclidin-3-yl)-7-phenylbenzo[b]thiophene-2-carboxamide;
(S)-N-(2,2-dimethylquinuclidin-3-yl)-7-phenylbenzo[b]thiophene-2-carboxamide;
(R)-N-(2,2-dimethylquinuclidin-3-yl)-7-(1-methylcyclopropyl)benzo[b]thiophene-2-carboxamide;
(S)-N-(2,2-dimethylquinuclidin-3-yl)-7-(1-methylcyclopropyl)benzo[b]thiophene-2-carboxamide;
(R)-N-(2,2-dimethylquinuclidin-3-yl)-6-ethoxybenzo[b]thiophene-2-carboxamide;
(S)-N-(2,2-dimethylquinuclidin-3-yl)-6-ethoxybenzo[b]thiophene-2-carboxamide;
(R)-N-(2,2-dimethylquinuclidin-3-yl)-7-ethoxybenzo[b]thiophene-2-carboxamide;

(S)—N-(2,2-dimethylquinuclidin-3-yl)-7-ethoxybenzo[b]thiophene-2-carboxamide;
(R)—N-(2,2-dimethylquinuclidin-3-yl)-7-propoxybenzo[b]thiophene-2-carboxamide;
(S)—N-(2,2-dimethylquinuclidin-3-yl)-7-propoxybenzo[b]thiophene-2-carboxamide;
(R)-6-chloro-N-(2,2-dimethylquinuclidin-3-yl)-7-methoxybenzo[b]thiophene-2-carboxamide;
(S)-6-chloro-N-(2,2-dimethylquinuclidin-3-yl)-7-methoxybenzo[b]thiophene-2-carboxamide;
(R)—N-(2,2-dimethylquinuclidin-3-yl)-7-methoxy-6-methylbenzo[b]thiophene-2-carboxamide;
(S)—N-(2,2-dimethylquinuclidin-3-yl)-7-methoxy-6-methylbenzo[b]thiophene-2-carboxamide;
(R)—N-(2,2-dimethylquinuclidin-3-yl)-1H-indazole-3-carboxamide;
(S)—N-(2,2-dimethylquinuclidin-3-yl)-1H-indazole-3-carboxamide;
(R)-7-cyclopropyl-N-(2,2-dimethylquinuclidin-3-yl)-6-methylbenzo[b]thiophene-2-carboxamide;
(S)-7-cyclopropyl-N-(2,2-dimethylquinuclidin-3-yl)-6-methylbenzo[b]thiophene-2-carboxamide;
(R)—N-(2,2-dimethylquinuclidin-3-yl)-6-fluoro-7-methoxybenzo[b]thiophene-2-carboxamide;
(S)—N-(2,2-dimethylquinuclidin-3-yl)-6-fluoro-7-methoxybenzo[b]thiophene-2-carboxamide;
(R)-7-cyano-N-(2,2-dimethylquinuclidin-3-yl)-6-methylbenzo[b]thiophene-2-carboxamide;
(S)-7-cyano-N-(2,2-dimethylquinuclidin-3-yl)-6-methylbenzo[b]thiophene-2-carboxamide;
(R)—N-(2,2-dimethylquinuclidin-3-yl)-7-(methoxymethyl)benzo[b]thiophene-2-carboxamide;
(S)—N-(2,2-dimethylquinuclidin-3-yl)-7-(methoxymethyl)benzo[b]thiophene-2-carboxamide;
(R)—N-(2,2-dimethylquinuclidin-3-yl)-3,4-dihydro-2H-thieno[3,2-h]chromene-8-carboxamide;
(S)—N-(2,2-dimethylquinuclidin-3-yl)-3,4-dihydro-2H-thieno[3,2-h]chromene-8-carboxamide;
(R)—N-(2,2-dimethylquinuclidin-3-yl)-8,9-dihydro-7H-thieno[2,3-f]chromene-2-carboxamide;
(S)—N-(2,2-dimethylquinuclidin-3-yl)-8,9-dihydro-7H-thieno[2,3-f]chromene-2-carboxamide;
(R)—N-(2,2-dimethylquinuclidin-3-yl)-2-methylbenzo[b]thiophene-6-carboxamide;
(S)—N-(2,2-dimethylquinuclidin-3-yl)-2-methylbenzo[b]thiophene-6-carboxamide;
(R)-2-chloro-N-(2,2-dimethylquinuclidin-3-yl)benzo[b]thiophene-6-carboxamide;
(S)-2-chloro-N-(2,2-dimethylquinuclidin-3-yl)benzo[b]thiophene-6-carboxamide;
(R)-6-chloro-N-(2,2-dimethylquinuclidin-3-yl)-7-methylbenzo[b]thiophene-2-carboxamide;
(S)-6-chloro-N-(2,2-dimethylquinuclidin-3-yl)-7-methylbenzo[b]thiophene-2-carboxamide;
(R)-2-amino-N-(1'-azaspiro[cyclopropane-1,2'-bicyclo[2.2.2]octan]-3'-yl)thieno[2,3-d]pyrimidine-6-carboxamide;
(S)-2-amino-N-(1'-azaspiro[cyclopropane-1,2'-bicyclo[2.2.2]octan]-3'-yl)thieno[2,3-d]pyrimidine-6-carboxamide;
(R)-6,7-dichloro-N-(1'-azaspiro[cyclopropane-1,2'-bicyclo[2.2.2]octan]-3'-yl)benzo[b]thiophene-2-carboxamide;
(S)-6,7-dichloro-N-(1'-azaspiro[cyclopropane-1,2'-bicyclo[2.2.2]octan]-3'-yl)benzo[b]thiophene-2-carboxamide;
(R)-6-chloro-7-fluoro-N-(1'-azaspiro[cyclopropane-1,2'-bicyclo[2.2.2]octan]-3'-yl)benzo[b]thiophene-2-carboxamide;
(S)-6-chloro-7-fluoro-N-(1'-azaspiro[cyclopropane-1,2'-bicyclo[2.2.2]octan]-3'-yl)benzo[b]thiophene-2-carboxamide;
(R)-6-chloro-N-(1'-azaspiro[cyclopropane-1,2'-bicyclo[2.2.2]octan]-3'-yl)-7-(trifluoromethyl)benzo[b]thiophene-2-carboxamide;
(S)-6-chloro-N-(1'-azaspiro[cyclopropane-1,2'-bicyclo[2.2.2]octan]-3'-yl)-7-(trifluoromethyl)benzo[b]thiophene-2-carboxamide;
(R)-6-fluoro-N-(1'-azaspiro[cyclopropane-1,2'-bicyclo[2.2.2]octan]-3'-yl)-7-(trifluoromethyl)benzo[b]thiophene-2-carboxamide;
(S)-6-fluoro-N-(1'-azaspiro[cyclopropane-1,2'-bicyclo[2.2.2]octan]-3'-yl)-7-(trifluoromethyl)benzo[b]thiophene-2-carboxamide;
(R)-7-chloro-6-methoxy-N-(1'-azaspiro[cyclopropane-1,2'-bicyclo[2.2.2]octan]-3'-yl)benzo[b]thiophene-2-carboxamide;
(S)-7-chloro-6-methoxy-N-(1'-azaspiro[cyclopropane-1,2'-bicyclo[2.2.2]octan]-3'-yl)benzo[b]thiophene-2-carboxamide;
(R)-7-fluoro-6-methoxy-N-(1'-azaspiro[cyclopropane-1,2'-bicyclo[2.2.2]octan]-3'-yl)benzo[b]thiophene-2-carboxamide;
(S)-7-fluoro-6-methoxy-N-(1'-azaspiro[cyclopropane-1,2'-bicyclo[2.2.2]octan]-3'-yl)benzo[b]thiophene-2-carboxamide;
(R)-7-chloro-6-methyl-N-(1'-azaspiro[cyclopropane-1,2'-bicyclo[2.2.2]octan]-3'-yl)benzo[b]thiophene-2-carboxamide;
(S)-7-chloro-6-methyl-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)-7-(trifluoromethyl)benzo[b]thiophene-2-carboxamide;
(S)-6-methyl-N-(1'-azaspiro[cyclopropane-1,2'-bicyclo[2.2.2]octan]-3'-yl)-7-(trifluoromethyl)benzo[b]thiophene-2-carboxamide;
(R)-7-chloro-6-fluoro-N-(1'-azaspiro[cyclopropane-1,2'-bicyclo[2.2.2]octan]-3'-yl)benzo[b]thiophene-2-carboxamide;
(S)-7-chloro-6-fluoro-N-(1'-azaspiro[cyclopropane-1,2'-bicyclo[2.2.2]octan]-3'-yl)benzo[b]thiophene-2-carboxamide;
(R)-6-cyclopropyl-7-fluoro-N-(1'-azaspiro[cyclopropane-1,2'-bicyclo[2.2.2]octan]-3'-yl)benzo[b]thiophene-2-carboxamide;
(S)-6-cyclopropyl-7-fluoro-N-(1'-azaspiro[cyclopropane-1,2'-bicyclo[2.2.2]octan]-3'-yl)benzo[b]thiophene-2-carboxamide;
(R)-7-cyano-N-(1'-azaspiro[cyclopropane-1,2'-bicyclo[2.2.2]octan]-3'-yl)benzo[b]thiophene-2-carboxamide;
(S)-7-cyano-N-(1'-azaspiro[cyclopropane-1,2'-bicyclo[2.2.2]octan]-3'-yl)benzo[b]thiophene-2-carboxamide;
(R)-7-methoxy-N-(1'-azaspiro[cyclopropane-1,2'-bicyclo[2.2.2]octan]-3'-yl)benzo[b]thiophene-2-carboxamide;
(S)-7-methoxy-N-(1'-azaspiro[cyclopropane-1,2'-bicyclo[2.2.2]octan]-3'-yl)benzo[b]thiophene-2-carboxamide;
(R)-6,7-difluoro-N-(1'-azaspiro[cyclopropane-1,2'-bicyclo[2.2.2]octan]-3'-yl)benzo[b]thiophene-2-carboxamide;
(S)-6,7-difluoro-N-(1'-azaspiro[cyclopropane-1,2'-bicyclo[2.2.2]octan]-3'-yl)benzo[b]thiophene-2-carboxamide;
(R)-6-chloro-N-(1'-azaspiro[cyclopropane-1,2'-bicyclo[2.2.2]octan]-3'-yl)benzofuran-2-carboxamide;
(S)-6-chloro-N-(1'-azaspiro[cyclopropane-1,2'-bicyclo[2.2.2]octan]-3'-yl)benzofuran-2-carboxamide;

(R)-7-chloro-N-(1'-azaspiro[cyclopropane-1,2'-bicyclo[2.2.2]octan]-3'-yl)benzofuran-2-carboxamide;
(S)-7-chloro-N-(1'-azaspiro[cyclopropane-1,2'-bicyclo[2.2.2]octan]-3'-yl)benzofuran-2-carboxamide;
(R)-7-cyclopropyl-N-(1'-azaspiro[cyclopropane-1,2'-bicyclo[2.2.2]octan]-3'-yl)benzo[b]thiophene-2-carboxamide;
(S)-7-cyclopropyl-N-(1'-azaspiro[cyclopropane-1,2'-bicyclo[2.2.2]octan]-3'-yl)benzo[b]thiophene-2-carboxamide;
(R)-7-isopropyl-N-(1'-azaspiro[cyclopropane-1,2'-bicyclo[2.2.2]octan]-3'-yl)benzo[b]thiophene-2-carboxamide;
(S)-7-isopropyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(trifluoromethoxy)benzo[b]thiophene-2-carboxamide;
(S)—N-(1'-azaspiro[cyclopropane-1,2'-bicyclo[2.2.2]octan]-3'-yl)-7-(trifluoromethoxy)benzo[b]thiophene-2-carboxamide;
(R)—N-(1'-azaspiro[cyclopropane-1,2'-bicyclo[2.2.2]octan]-3'-yl)-7-(tetrahydro-2H-pyran-4-yl)benzo[b]thiophene-2-carboxamide;
(S)—N-(1'-azaspiro[cyclopropane-1,2'-bicyclo[2.2.2]octan]-3'-yl)-7-(tetrahydro-2H-pyran-4-yl)benzo[b]thiophene-2-carboxamide;
(R)—N-(1'-azaspiro[cyclopropane-1,2'-bicyclo[2.2.2]octan]-3'-yl)benzo[d]oxazole-2-carboxamide;
(S)—N-(1'-azaspiro[cyclopropane-1,2'-bicyclo[2.2.2]octan]-3'-yl)benzo[d]oxazole-2-carboxamide;
(R)—N-(1'-azaspiro[cyclopropane-1,2'-bicyclo[2.2.2]octan]-3'-yl)-1H-indole-2-carboxamide;
(S)—N-(1'-azaspiro[cyclopropane-1,2'-bicyclo[2.2.2]octan]-3'-yl)-1H-indole-2-carboxamide;
(R)—N-(1'-azaspiro[cyclopropane-1,2'-bicyclo[2.2.2]octan]-3'-yl)thieno[2,3-c]pyridine-2-carboxamide;
(S)—N-(1'-azaspiro[cyclopropane-1,2'-bicyclo[2.2.2]octan]-3'-yl)thieno[2,3-c]pyridine-2-carboxamide;
(R)-6-chloro-5-fluoro-N-(1'-azaspiro[cyclopropane-1,2'-bicyclo[2.2.2]octan]-3'-yl)benzo[b]thiophene-2-carboxamide;
(S)-6-chloro-5-fluoro-N-(1'-azaspiro[cyclopropane-1,2'-bicyclo[2.2.2]octan]-3'-yl)benzo[b]thiophene-2-carboxamide;
(R)-5-fluoro-6-methoxy-N-(1'-azaspiro[cyclopropane-1,2'-bicyclo[2.2.2]octan]-3'-yl)benzo[b]thiophene-2-carboxamide;
(S)-5-fluoro-6-methoxy-N-(1'-azaspiro[cyclopropane-1,2'-bicyclo[2.2.2]octan]-3'-yl)benzo[b]thiophene-2-carboxamide;
(R)-5,6-difluoro-N-(1'-azaspiro[cyclopropane-1,2'-bicyclo[2.2.2]octan]-3'-yl)benzo[b]thiophene-2-carboxamide;
(S)-5,6-difluoro-N-(1'-azaspiro[cyclopropane-1,2'-bicyclo[2.2.2]octan]-3'-yl)benzo[b]thiophene-2-carboxamide;
(R)-6-chloro-5,7-difluoro-N-(1'-azaspiro[cyclopropane-1,2'-bicyclo[2.2.2]octan]-3'-yl)benzo[b]thiophene-2-carboxamide;
(S)-6-chloro-5,7-difluoro-N-(1'-azaspiro[cyclopropane-1,2'-bicyclo[2.2.2]octan]-3'-yl)benzo[b]thiophene-2-carboxamide;
(R)-7-methyl-N-(1'-azaspiro[cyclopropane-1,2'-bicyclo[2.2.2]octan]-3'-yl)benzo[b]thiophene-2-carboxamide;
(S)-7-methyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(2,2,2-trifluoroethyl)benzo[b]thiophene-2-carboxamide;
(S)—N-(1'-azaspiro[cyclopropane-1,2'-bicyclo[2.2.2]octan]-3'-yl)-7-(2,2,2-trifluoroethyl)benzo[b]thiophene-2-carboxamide;
(R)-7-(dimethylamino)-N-(1'-azaspiro[cyclopropane-1,2'-bicyclo[2.2.2]octan]-3'-yl)benzo[b]thiophene-2-carboxamide;
(S)-7-(dimethylamino)-N-(1'-azaspiro[cyclopropane-1,2'-bicyclo[2.2.2]octan]-3'-yl)benzo[b]thiophene-2-carboxamide;
(R)-7-(methylsulfonyl)-N-(1'-azaspiro[cyclopropane-1,2'-bicyclo[2.2.2]octan]-3'-yl)benzo[b]thiophene-2-carboxamide;
(S)-7-(methylsulfonyl)-N-(1'-azaspiro[cyclopropane-1,2'-bicyclo[2.2.2]octan]-3'-yl)benzo[b]thiophene-2-carboxamide;
(R)-7-morpholino-N-(1'-azaspiro[cyclopropane-1,2'-bicyclo[2.2.2]octan]-3'-yl)benzo[b]thiophene-2-carboxamide;
(S)-7-morpholino-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(thiazol-2-yl)benzo[b]thiophene-2-carboxamide;
(S)—N-(1'-azaspiro[cyclopropane-1,2'-bicyclo[2.2.2]octan]-3'-yl)-7-(thiazol-2-yl)benzo[b]thiophene-2-carboxamide;
(R)—N-(1'-azaspiro[cyclopropane-1,2'-bicyclo[2.2.2]octan]-3'-yl)isoquinoline-3-carboxamide;
(S)—N-(1'-azaspiro[cyclopropane-1,2'-bicyclo[2.2.2]octan]-3'-yl)isoquinoline-3-carboxamide;
(R)-2-cyclopropyl-N-(1'-azaspiro[cyclopropane-1,2'-bicyclo[2.2.2]octan]-3'-yl)benzofuran-5-carboxamide;
(S)-2-cyclopropyl-N-(1'-azaspiro[cyclopropane-1,2'-bicyclo[2.2.2]octan]-3'-yl)benzofuran-5-carboxamide;
(R)-7-(tert-butyl)-N-(1'-azaspiro[cyclopropane-1,2'-bicyclo[2.2.2]octan]-3'-yl)benzo[b]thiophene-2-carboxamide;
(S)-7-(tert-butyl)-N-(1'-azaspiro[cyclopropane-1,2'-bicyclo[2.2.2]octan]-3'-yl)benzo[b]thiophene-2-carboxamide;
(R)-7-(2-hydroxypropan-2-yl)-N-(1'-azaspiro[cyclopropane-1,2'-bicyclo[2.2.2]octan]-3'-yl)benzo[b]thiophene-2-carboxamide;
(S)-7-(2-hydroxypropan-2-yl)-N-(1'-azaspiro[cyclopropane-1,2'-bicyclo[2.2.2]octan]-3'-yl)benzo[b]thiophene-2-carboxamide;
(R)-7-phenyl-N-(1'-azaspiro[cyclopropane-1,2'-bicyclo[2.2.2]octan]-3'-yl)benzo[b]thiophene-2-carboxamide;
(S)-7-phenyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(1-(trifluoromethyl)cyclopropyl)benzo[b]thiophene-2-carboxamide;
(S)—N-(1'-azaspiro[cyclopropane-1,2'-bicyclo[2.2.2]octan]-3'-yl)-7-(1-(trifluoromethyl)cyclopropyl)benzo[b]thiophene-2-carboxamide;
(R)-7-(1-methylcyclopropyl)-N-(1'-azaspiro[cyclopropane-1,2'-bicyclo[2.2.2]octan]-3'-yl)benzo[b]thiophene-2-carboxamide;
(S)-7-(1-methylcyclopropyl)-N-(1'-azaspiro[cyclopropane-1,2'-bicyclo[2.2.2]octan]-3'-yl)benzo[b]thiophene-2-carboxamide;
(R)-6-ethoxy-N-(1'-azaspiro[cyclopropane-1,2'-bicyclo[2.2.2]octan]-3'-yl)benzo[b]thiophene-2-carboxamide;
(S)-6-ethoxy-N-(1'-azaspiro[cyclopropane-1,2'-bicyclo[2.2.2]octan]-3'-yl)benzo[b]thiophene-2-carboxamide;
(R)-7-ethoxy-N-(1'-azaspiro[cyclopropane-1,2'-bicyclo[2.2.2]octan]-3'-yl)benzo[b]thiophene-2-carboxamide;
(S)-7-ethoxy-N-(1'-azaspiro[cyclopropane-1,2'-bicyclo[2.2.2]octan]-3'-yl)benzo[b]thiophene-2-carboxamide;

(R)-7-propoxy-N-(1'-azaspiro[cyclopropane-1,2'-bicyclo[2.2.2]octan]-3'-yl)benzo[b]thiophene-2-carboxamide;
(S)-7-propoxy-N-(1'-azaspiro[cyclopropane-1,2'-bicyclo[2.2.2]octan]-3'-yl)benzo[b]thiophene-2-carboxamide;
(R)-6-chloro-7-methoxy-N-(1'-azaspiro[cyclopropane-1,2'-bicyclo[2.2.2]octan]-3'-yl)benzo[b]thiophene-2-carboxamide;
(S)-6-chloro-7-methoxy-N-(1'-azaspiro[cyclopropane-1,2'-bicyclo[2.2.2]octan]-3'-yl)benzo[b]thiophene-2-carboxamide;
(R)-7-methoxy-6-methyl-N-(1'-azaspiro[cyclopropane-1,2'-bicyclo[2.2.2]octan]-3'-yl)benzo[b]thiophene-2-carboxamide;
(S)-7-methoxy-6-methyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-1H-indazole-3-carboxamide;
(S)—N-(1'-azaspiro[cyclopropane-1,2'-bicyclo[2.2.2]octan]-3'-yl)-1H-indazole-3-carboxamide;
(R)-1-methyl-N-(1'-azaspiro[cyclopropane-1,2'-bicyclo[2.2.2]octan]-3'-yl)-1H-indole-6-carboxamide;
(S)-1-methyl-N-(1'-azaspiro[cyclopropane-1,2'-bicyclo[2.2.2]octan]-3'-yl)-1H-indole-6-carboxamide;
(R)-7-cyclopropyl-6-methyl-N-(1'-azaspiro[cyclopropane-1,2'-bicyclo[2.2.2]octan]-3'-yl)benzo[b]thiophene-2-carboxamide;
(S)-7-cyclopropyl-6-methyl-N-(1'-azaspiro[cyclopropane-1,2'-bicyclo[2.2.2]octan]-3'-yl)benzo[b]thiophene-2-carboxamide;
(R)-6-fluoro-7-methoxy-N-(1'-azaspiro[cyclopropane-1,2'-bicyclo[2.2.2]octan]-3'-yl)benzo[b]thiophene-2-carboxamide;
(S)-6-fluoro-7-methoxy-N-(1'-azaspiro[cyclopropane-1,2'-bicyclo[2.2.2]octan]-3'-yl)benzo[b]thiophene-2-carboxamide;
(R)-7-cyano-6-methyl-N-(1'-azaspiro[cyclopropane-1,2'-bicyclo[2.2.2]octan]-3'-yl)benzo[b]thiophene-2-carboxamide;
(S)-7-cyano-6-methyl-N-(1'-azaspiro[cyclopropane-1,2'-bicyclo[2.2.2]octan]-3'-yl)benzo[b]thiophene-2-carboxamide;
(R)-7-(methoxymethyl)-N-(1'-azaspiro[cyclopropane-1,2'-bicyclo[2.2.2]octan]-3'-yl)benzo[b]thiophene-2-carboxamide;
(S)-7-(methoxymethyl)-N-(1'-azaspiro[cyclopropane-1,2'-bicyclo[2.2.2]octan]-3'-yl)benzo[b]thiophene-2-carboxamide;
(R)-6-(methoxymethyl)-N-(1'-azaspiro[cyclopropane-1,2'-bicyclo[2.2.2]octan]-3'-yl)benzo[b]thiophene-2-carboxamide;
(S)-6-(methoxymethyl)-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-3,4-dihydro-2H-thieno[3,2-h]chromene-8-carboxamide;
(S)—N-(1'-azaspiro[cyclopropane-1,2'-bicyclo[2.2.2]octan]-3'-yl)-3,4-dihydro-2H-thieno[3,2-h]chromene-8-carboxamide;
(R)-2-methyl-N-(1'-azaspiro[cyclopropane-1,2'-bicyclo[2.2.2]octan]-3'-yl)benzo[b]thiophene-6-carboxamide;
(S)-2-methyl-N-(1'-azaspiro[cyclopropane-1,2'-bicyclo[2.2.2]octan]-3'-yl)benzo[b]thiophene-6-carboxamide;
(R)-2-chloro-N-(1'-azaspiro[cyclopropane-1,2'-bicyclo[2.2.2]octan]-3'-yl)benzo[b]thiophene-6-carboxamide;
(S)-2-chloro-N-(1'-azaspiro[cyclopropane-1,2'-bicyclo[2.2.2]octan]-3'-yl)benzo[b]thiophene-6-carboxamide;
(R)—N-(1'-azaspiro[cyclopropane-1,2'-bicyclo[2.2.2]octan]-3'-yl)-8,9-dihydro-7H-thieno[2,3-f]chromene-2-carboxamide;
(S)—N-(1'-azaspiro[cyclopropane-1,2'-bicyclo[2.2.2]octan]-3'-yl)-8,9-dihydro-7H-thieno[2,3-f]chromene-2-carboxamide;
(R)-6-chloro-7-methyl-N-(1'-azaspiro[cyclopropane-1,2'-bicyclo[2.2.2]octan]-3'-yl)benzo[b]thiophene-2-carboxamide;
(S)-6-chloro-7-methyl-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-1-methyl-1H-benzo[d]imidazole-6-carboxamide;
(S)—N-(2,2-dimethylquinuclidin-3-yl)-1-methyl-1H-benzo[d]imidazole-6-carboxamide;
(R)-6-(tert-butyl)-N-(2,2-dimethylquinuclidin-3-yl)benzo[b]thiophene-2-carboxamide;
(S)-6-(tert-butyl)-N-(2,2-dimethylquinuclidin-3-yl)benzo[b]thiophene-2-carboxamide;
(R)—N-(2,2-dimethylquinuclidin-3-yl)-6-(1H-1,2,3-triazol-1-yl)benzo[b]thiophene-2-carboxamide;
(S)—N-(2,2-dimethylquinuclidin-3-yl)-6-(1H-1,2,3-triazol-1-yl)benzo[b]thiophene-2-carboxamide;
(R)—N-(2,2-dimethylquinuclidin-3-yl)-6-(trifluoromethoxy)benzo[b]thiophene-2-carboxamide;
(S)—N-(2,2-dimethylquinuclidin-3-yl)-6-(trifluoromethoxy)benzo[b]thiophene-2-carboxamide;
(R)—N-(2,2-dimethylquinuclidin-3-yl)-6-(oxetan-3-yl)benzo[b]thiophene-2-carboxamide;
(S)—N-(2,2-dimethylquinuclidin-3-yl)-6-(oxetan-3-yl)benzo[b]thiophene-2-carboxamide;
(R)—N-(2,2-dimethylquinuclidin-3-yl)-6-fluoro-7-(trifluoromethyl)benzo[b]thiophene-2-carboxamide;
(S)—N-(2,2-dimethylquinuclidin-3-yl)-6-fluoro-7-(trifluoromethyl)benzo[b]thiophene-2-carboxamide;
(R)—N-(2,2-dimethylquinuclidin-3-yl)-6-methoxy-7-(trifluoromethyl)benzo[b]thiophene-2-carboxamide;
(S)—N-(2,2-dimethylquinuclidin-3-yl)-6-methoxy-7-(trifluoromethyl)benzo[b]thiophene-2-carboxamide;
(R)-6-cyclopropyl-N-(2,2-dimethylquinuclidin-3-yl)-7-fluorobenzo[b]thiophene-2-carboxamide;
(S)-6-cyclopropyl-N-(2,2-dimethylquinuclidin-3-yl)-7-fluorobenzo[b]thiophene-2-carboxamide;
(R)-7-chloro-6-cyclopropyl-N-(2,2-dimethylquinuclidin-3-yl)benzo[b]thiophene-2-carboxamide;
(S)-7-chloro-6-cyclopropyl-N-(2,2-dimethylquinuclidin-3-yl)benzo[b]thiophene-2-carboxamide;
(R)—N-(2,2-dimethylquinuclidin-3-yl)-2,3-dihydrobenzo[b][1,4]dioxine-6-carboxamide;
(S)—N-(2,2-dimethylquinuclidin-3-yl)-2,3-dihydrobenzo[b][1,4]dioxine-6-carboxamide;
(R)-6-chloro-N-(2,2-dimethylquinuclidin-3-yl)benzofuran-2-carboxamide;
(S)-6-chloro-N-(2,2-dimethylquinuclidin-3-yl)benzofuran-2-carboxamide;
(R)-7-chloro-N-(2,2-dimethylquinuclidin-3-yl)benzofuran-2-carboxamide;
(S)-7-chloro-N-(2,2-dimethylquinuclidin-3-yl)benzofuran-2-carboxamide;
(R)—N-(2,2-dimethylquinuclidin-3-yl)benzo[d]oxazole-2-carboxamide;
(S)—N-(2,2-dimethylquinuclidin-3-yl)benzo[d]oxazole-2-carboxamide;

(R)—N-(2,2-dimethylquinuclidin-3-yl)-1H-benzo[d]imidazole-2-carboxamide;
(S)—N-(2,2-dimethylquinuclidin-3-yl)-1H-benzo[d]imidazole-2-carboxamide;
(R)—N-(2,2-dimethylquinuclidin-3-yl)-1-methyl-H-benzo[d]imidazole-2-carboxamide;
(S)—N-(2,2-dimethylquinuclidin-3-yl)-1-methyl-H-benzo[d]imidazole-2-carboxamide;
(R)—N-(2,2-dimethylquinuclidin-3-yl)-1-methyl-1H-indole-2-carboxamide;
(S)—N-(2,2-dimethylquinuclidin-3-yl)-1-methyl-1H-indole-2-carboxamide;
(R)—N-(2,2-dimethylquinuclidin-3-yl)thieno[2,3-c]pyridine-2-carboxamide;
(S)—N-(2,2-dimethylquinuclidin-3-yl)thieno[2,3-c]pyridine-2-carboxamide;
(R)-3,4-dichloro-N-(2,2-dimethylquinuclidin-3-yl)benzamide;
(S)-3,4-dichloro-N-(2,2-dimethylquinuclidin-3-yl)benzamide;
(R)—N-(2,2-dimethylquinuclidin-3-yl)-4-methoxy-3-methylbenzamide;
(S)—N-(2,2-dimethylquinuclidin-3-yl)-4-methoxy-3-methylbenzamide;
(R)—N-(2,2-dimethylquinuclidin-3-yl)imidazo[1,2-a]pyrazine-6-carboxamide;
(S)—N-(2,2-dimethylquinuclidin-3-yl)imidazo[1,2-a]pyrazine-6-carboxamide;
(R)—N-(2,2-dimethylquinuclidin-3-yl)-5,6-difluorobenzo[b]thiophene-2-carboxamide;
(S)—N-(2,2-dimethylquinuclidin-3-yl)-5,6-difluorobenzo[b]thiophene-2-carboxamide;
(R)—N-(2,2-dimethylquinuclidin-3-yl)-7-(methylsulfonyl)benzo[b]thiophene-2-carboxamide;
(S)—N-(2,2-dimethylquinuclidin-3-yl)-7-(methylsulfonyl)benzo[b]thiophene-2-carboxamide;
(R)—N-(2,2-dimethylquinuclidin-3-yl)-7-morpholinobenzo[b]thiophene-2-carboxamide;
(S)—N-(2,2-dimethylquinuclidin-3-yl)-7-morpholinobenzo[b]thiophene-2-carboxamide;
(R)—N-(2,2-dimethylquinuclidin-3-yl)quinoline-3-carboxamide;
(S)—N-(2,2-dimethylquinuclidin-3-yl)quinoline-3-carboxamide;
(R)—N-(2,2-dimethylquinuclidin-3-yl)quinoline-7-carboxamide;
(S)—N-(2,2-dimethylquinuclidin-3-yl)quinoline-7-carboxamide;
(R)—N-(2,2-dimethylquinuclidin-3-yl)quinoline-6-carboxamide;
(S)—N-(2,2-dimethylquinuclidin-3-yl)quinoline-6-carboxamide;
(R)-2-cyclopropyl-N-(2,2-dimethylquinuclidin-3-yl)benzofuran-5-carboxamide;
(S)-2-cyclopropyl-N-(2,2-dimethylquinuclidin-3-yl)benzofuran-5-carboxamide;
(R)—N-(2,2-dimethylquinuclidin-3-yl)-7-(2-hydroxypropan-2-yl)benzo[b]thiophene-2-carboxamide;
(S)—N-(2,2-dimethylquinuclidin-3-yl)-7-(2-hydroxypropan-2-yl)benzo[b]thiophene-2-carboxamide;
(R)—N-(2,2-dimethylquinuclidin-3-yl)-7-(1-(trifluoromethyl)cyclopropyl)benzo[b]thiophene-2-carboxamide;
(S)—N-(2,2-dimethylquinuclidin-3-yl)-7-(1-(trifluoromethyl)cyclopropyl)benzo[b]thiophene-2-carboxamide;
(R)—N-(2,2-dimethylquinuclidin-3-yl)-1H-indole-5-carboxamide;
(S)—N-(2,2-dimethylquinuclidin-3-yl)-1H-indole-5-carboxamide;
(R)-6-cyclopropyl-N-(2,2-dimethylquinuclidin-3-yl)-7-methoxybenzo[b]thiophene-2-carboxamide;
(S)-6-cyclopropyl-N-(2,2-dimethylquinuclidin-3-yl)-7-methoxybenzo[b]thiophene-2-carboxamide;
(R)—N-(2,2-dimethylquinuclidin-3-yl)benzo[d]isoxazole-5-carboxamide;
(S)—N-(2,2-dimethylquinuclidin-3-yl)benzo[d]isoxazole-5-carboxamide;
(R)—N-(2,2-dimethylquinuclidin-3-yl)benzo[d]isoxazole-6-carboxamide;
(S)—N-(2,2-dimethylquinuclidin-3-yl)benzo[d]isoxazole-6-carboxamide;
(R)—N-(2,2-dimethylquinuclidin-3-yl)-2,2-difluorobenzo[d][1,3]dioxole-5-carboxamide;
(S)—N-(2,2-dimethylquinuclidin-3-yl)-2,2-difluorobenzo[d][1,3]dioxole-5-carboxamide;
(R)—N-(2,2-dimethylquinuclidin-3-yl)-1-methyl-1H-indazole-3-carboxamide;
(S)—N-(2,2-dimethylquinuclidin-3-yl)-1-methyl-1H-indazole-3-carboxamide;
(R)—N-(2,2-dimethylquinuclidin-3-yl)benzo[d]isoxazole-3-carboxamide;
(S)—N-(2,2-dimethylquinuclidin-3-yl)benzo[d]isoxazole-3-carboxamide;
(R)—N-(2,2-dimethylquinuclidin-3-yl)-1-methyl-1H-indole-5-carboxamide;
(S)—N-(2,2-dimethylquinuclidin-3-yl)-1-methyl-1H-indole-5-carboxamide;
(R)—N-(2,2-dimethylquinuclidin-3-yl)-1-methyl-1H-indole-6-carboxamide;
(S)—N-(2,2-dimethylquinuclidin-3-yl)-1-methyl-1H-indole-6-carboxamide;
(R)-6-(dimethylamino)-N-(2,2-dimethylquinuclidin-3-yl)benzo[b]thiophene-2-carboxamide;
(S)-6-(dimethylamino)-N-(2,2-dimethylquinuclidin-3-yl)benzo[b]thiophene-2-carboxamide;
(R)—N-(2,2-dimethylquinuclidin-3-yl)-6-(methoxymethyl)benzo[b]thiophene-2-carboxamide;
(S)—N-(2,2-dimethylquinuclidin-3-yl)-6-(methoxymethyl)benzo[b]thiophene-2-carboxamide;
(R)—N-(2,2-dimethylquinuclidin-3-yl)-4,5,6,7-tetrahydrobenzo[b]thiophene-2-carboxamide;
(S)—N-(2,2-dimethylquinuclidin-3-yl)-4,5,6,7-tetrahydrobenzo[b]thiophene-2-carboxamide;
(R)-6-(tert-butyl)-N-(1'-azaspiro[cyclopropane-1,2'-bicyclo[2.2.2]octan]-3'-yl)benzo[b]thiophene-2-carboxamide;
(S)-6-(tert-butyl)-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-6-(trifluoromethoxy)benzo[b]thiophene-2-carboxamide;
(S)—N-(1'-azaspiro[cyclopropane-1,2'-bicyclo[2.2.2]octan]-3'-yl)-6-(trifluoromethoxy)benzo[b]thiophene-2-carboxamide;
(R)-6-(oxetan-3-yl)-N-(1'-azaspiro[cyclopropane-1,2'-bicyclo[2.2.2]octan]-3'-yl)benzo[b]thiophene-2-carboxamide;
(S)-6-(oxetan-3-yl)-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)-7-(trifluoromethyl)benzo[b]thiophene-2-carboxamide;
(S)-6-methoxy-N-(1'-azaspiro[cyclopropane-1,2'-bicyclo[2.2.2]octan]-3'-yl)-7-(trifluoromethyl)benzo[b]thiophene-2-carboxamide;

(R)-7-chloro-6-cyclopropyl-N-(1'-azaspiro[cyclopropane-1,2'-bicyclo[2.2.2]octan]-3'-yl)benzo[b]thiophene-2-carboxamide;
(S)-7-chloro-6-cyclopropyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-1H-benzo[d]imidazole-2-carboxamide;
(S)—N-(1'-azaspiro[cyclopropane-1,2'-bicyclo[2.2.2]octan]-3'-yl)-1H-benzo[d]imidazole-2-carboxamide;
(R)-1-methyl-N-(1'-azaspiro[cyclopropane-1,2'-bicyclo[2.2.2]octan]-3'-yl)-1H-benzo[d]imidazole-2-carboxamide;
(S)-1-methyl-N-(1'-azaspiro[cyclopropane-1,2'-bicyclo[2.2.2]octan]-3'-yl)-1H-benzo[d]imidazole-2-carboxamide;
(R)-1-methyl-N-(1'-azaspiro[cyclopropane-1,2'-bicyclo[2.2.2]octan]-3'-yl)-1H-indole-2-carboxamide;
(S)-1-methyl-N-(1'-azaspiro[cyclopropane-1,2'-bicyclo[2.2.2]octan]-3'-yl)-1H-indole-2-carboxamide;
(R)-3,4-dichloro-N-(1'-azaspiro[cyclopropane-1,2'-bicyclo[2.2.2]octan]-3'-yl)benzamide;
(S)-3,4-dichloro-N-(1'-azaspiro[cyclopropane-1,2'-bicyclo[2.2.2]octan]-3'-yl)benzamide;
(R)-4-methoxy-3-methyl-N-(1'-azaspiro[cyclopropane-1,2'-bicyclo[2.2.2]octan]-3'-yl)benzamide;
(S)-4-methoxy-3-methyl-N-(1'-azaspiro[cyclopropane-1,2'-bicyclo[2.2.2]octan]-3'-yl)benzamide;
(R)—N-(1'-azaspiro[cyclopropane-1,2'-bicyclo[2.2.2]octan]-3'-yl)imidazo[1,2-a]pyrazine-6-carboxamide;
(S)—N-(1'-azaspiro[cyclopropane-1,2'-bicyclo[2.2.2]octan]-3'-yl)imidazo[1,2-a]pyrazine-6-carboxamide;
(R)—N-(1'-azaspiro[cyclopropane-1,2'-bicyclo[2.2.2]octan]-3'-yl)quinoline-3-carboxamide;
(S)—N-(1'-azaspiro[cyclopropane-1,2'-bicyclo[2.2.2]octan]-3'-yl)quinoline-3-carboxamide;
(R)—N-(1'-azaspiro[cyclopropane-1,2'-bicyclo[2.2.2]octan]-3'-yl)quinoline-7-carboxamide;
(S)—N-(1'-azaspiro[cyclopropane-1,2'-bicyclo[2.2.2]octan]-3'-yl)quinoline-7-carboxamide;
(R)—N-(1'-azaspiro[cyclopropane-1,2'-bicyclo[2.2.2]octan]-3'-yl)quinoline-6-carboxamide;
(S)—N-(1'-azaspiro[cyclopropane-1,2'-bicyclo[2.2.2]octan]-3'-yl)quinoline-6-carboxamide;
(R)—N-(1'-azaspiro[cyclopropane-1,2'-bicyclo[2.2.2]octan]-3'-yl)-1H-indole-5-carboxamide;
(S)—N-(1'-azaspiro[cyclopropane-1,2'-bicyclo[2.2.2]octan]-3'-yl)-1H-indole-5-carboxamide;
(R)-6-cyclopropyl-7-methoxy-N-(1'-azaspiro[cyclopropane-1,2'-bicyclo[2.2.2]octan]-3'-yl)benzo[b]thiophene-2-carboxamide;
(S)-6-cyclopropyl-7-methoxy-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)benzo[d]isoxazole-5-carboxamide;
(S)—N-(1'-azaspiro[cyclopropane-1,2'-bicyclo[2.2.2]octan]-3'-yl)benzo[d]isoxazole-5-carboxamide;
(R)—N-(1'-azaspiro[cyclopropane-1,2'-bicyclo[2.2.2]octan]-3'-yl)benzo[d]isoxazole-6-carboxamide;
(S)—N-(1'-azaspiro[cyclopropane-1,2'-bicyclo[2.2.2]octan]-3'-yl)benzo[d]isoxazole-6-carboxamide;
(R)-2,2-difluoro-N-(1'-azaspiro[cyclopropane-1,2'-bicyclo[2.2.2]octan]-3'-yl)benzo[d][1,3]dioxole-5-carboxamide;
(S)-2,2-difluoro-N-(1'-azaspiro[cyclopropane-1,2'-bicyclo[2.2.2]octan]-3'-yl)benzo[d][1,3]dioxole-5-carboxamide;
(R)-1-methyl-N-(1'-azaspiro[cyclopropane-1,2'-bicyclo[2.2.2]octan]-3'-yl)-1H-indazole-3-carboxamide;
(S)-1-methyl-N-(1'-azaspiro[cyclopropane-1,2'-bicyclo[2.2.2]octan]-3'-yl)-1H-indazole-3-carboxamide;
(R)—N-(1'-azaspiro[cyclopropane-1,2'-bicyclo[2.2.2]octan]-3'-yl)benzo[d]isoxazole-3-carboxamide;
(S)—N-(1'-azaspiro[cyclopropane-1,2'-bicyclo[2.2.2]octan]-3'-yl)benzo[d]isoxazole-3-carboxamide;
(R)-1-methyl-N-(1'-azaspiro[cyclopropane-1,2'-bicyclo[2.2.2]octan]-3'-yl)-1H-indole-5-carboxamide;
(S)-1-methyl-N-(1'-azaspiro[cyclopropane-1,2'-bicyclo[2.2.2]octan]-3'-yl)-1H-indole-5-carboxamide;
(R)-6-(dimethylamino)-N-(1'-azaspiro[cyclopropane-1,2'-bicyclo[2.2.2]octan]-3'-yl)benzo[b]thiophene-2-carboxamide;
(S)-6-(dimethylamino)-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-4,5,6,7-tetrahydrobenzo[b]thiophene-2-carboxamide;
(S)—N-(1'-azaspiro[cyclopropane-1,2'-bicyclo[2.2.2]octan]-3'-yl)-4,5,6,7-tetrahydrobenzo[b]thiophene-2-carboxamide.
(R)—N-(2,2-dimethylquinuclidin-3-yl)-7-(oxetan-3-yl)benzo[b]thiophene-2-carboxamide;
(S)—N-(2,2-dimethylquinuclidin-3-yl)-7-(oxetan-3-yl)benzo[b]thiophene-2-carboxamide;
(R)-6-cyclopropoxy-N-(2,2-dimethylquinuclidin-3-yl)benzo[b]thiophene-2-carboxamide;
(S)-6-cyclopropoxy-N-(2,2-dimethylquinuclidin-3-yl)benzo[b]thiophene-2-carboxamide;
(R)-7-(oxetan-3-yl)-N-(1'-azaspiro[cyclopropane-1,2'-bicyclo[2.2.2]octan]-3'-yl)benzo[b]thiophene-2-carboxamide;
(S)-7-(oxetan-3-yl)-N-(1'-azaspiro[cyclopropane-1,2'-bicyclo[2.2.2]octan]-3'-yl)benzo[b]thiophene-2-carboxamide;
(R)-6-cyclopropoxy-N-(1'-azaspiro[cyclopropane-1,2'-bicyclo[2.2.2]octan]-3'-yl)benzo[b]thiophene-2-carboxamide; and
(S)-6-cyclopropoxy-N-(1'-azaspiro[cyclopropane-1,2'-bicyclo[2.2.2]octan]-3'-yl)benzo[b]thiophene-2-carboxamide.

In certain embodiments, specific examples of the amide compound represented by Formula (I) may include, collectively or individually, the single enantiomers listed below, and pharmaceutically acceptable salts thereof:

(R)-7-cyclobutyl-N-(2,2-dimethylquinuclidin-3-yl)benzo[b]thiophene-2-carboxamide;
(S)-7-cyclobutyl-N-(2,2-dimethylquinuclidin-3-yl)benzo[b]thiophene-2-carboxamide;
(R)-7-cyclobutyl-N-(1'-azaspiro[cyclopropane-1,2'-bicyclo[2.2.2]octan]-3'-yl)benzo[b]thiophene-2-carboxamide;
(S)-7-cyclobutyl-N-(1'-azaspiro[cyclopropane-1,2'-bicyclo[2.2.2]octan]-3'-yl)benzo[b]thiophene-2-carboxamide;
(R)-7-cyclopropyl-N-(2,2-dimethylquinuclidin-3-yl)-6-methoxybenzo[b]thiophene-2-carboxamide;
(S)-7-cyclopropyl-N-(2,2-dimethylquinuclidin-3-yl)-6-methoxybenzo[b]thiophene-2-carboxamide;
(R)-7-cyclopropyl-6-methoxy-N-(1'-azaspiro[cyclopropane-1,2'-bicyclo[2.2.2]octan]-3'-yl)benzo[b]thiophene-2-carboxamide;
(S)-7-cyclopropyl-6-methoxy-N-(1'-azaspiro[cyclopropane-1,2'-bicyclo[2.2.2]octan]-3'-yl)benzo[b]thiophene-2-carboxamide;
(R)-7-cyclopropoxy-N-(2,2-dimethylquinuclidin-3-yl)benzo[b]thiophene-2-carboxamide;
(S)-7-cyclopropoxy-N-(2,2-dimethylquinuclidin-3-yl)benzo[b]thiophene-2-carboxamide;

(R)-7-cyclopropoxy-N-(1'-azaspiro[cyclopropane-1,2'-bicyclo[2.2.2]octan]-3'-yl)benzo[b]thiophene-2-carboxamide;
(S)-7-cyclopropoxy-N-(1'-azaspiro[cyclopropane-1,2'-bicyclo[2.2.2]octan]-3'-yl)benzo[b]thiophene-2-carboxamide;
(R)-6-cyclopropoxy-N-(1'-azaspiro[cyclopropane-1,2'-bicyclo[2.2.2]octan]-3'-yl)benzo[b]thiophene-2-carboxamide;
(S)-6-cyclopropoxy-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-7-(2,2,2-trifluoroethoxy)benzo[b]thiophene-2-carboxamide;
(S)—N-(2,2-dimethylquinuclidin-3-yl)-7-(2,2,2-trifluoroethoxy)benzo[b]thiophene-2-carboxamide;
(R)—N-(1'-azaspiro[cyclopropane-1,2'-bicyclo[2.2.2]octan]-3'-yl)-7-(2,2,2-trifluoroethoxy)benzo[b]thiophene-2-carboxamide;
(S)—N-(1'-azaspiro[cyclopropane-1,2'-bicyclo[2.2.2]octan]-3'-yl)-7-(2,2,2-trifluoroethoxy)benzo[b]thiophene-2-carboxamide;
(R)—N-(2,2-dimethylquinuclidin-3-yl)-6-fluoro-7-methylbenzo[b]thiophene-2-carboxamide;
(S)—N-(2,2-dimethylquinuclidin-3-yl)-6-fluoro-7-methylbenzo[b]thiophene-2-carboxamide;
(R)-6-fluoro-7-methyl-N-(1'-azaspiro[cyclopropane-1,2'-bicyclo[2.2.2]octan]-3'-yl)benzo[b]thiophene-2-carboxamide;
(S)-6-fluoro-7-methyl-N-(1'-azaspiro[cyclopropane-1,2'-bicyclo[2.2.2]octan]-3'-yl)benzo[b]thiophene-2-carboxamide;
(R)-7-chloro-5-fluoro-N-(1'-azaspiro[cyclopropane-1,2'-bicyclo[2.2.2]octan]-3'-yl)benzo[b]thiophene-2-carboxamide;
(S)-7-chloro-5-fluoro-N-(1'-azaspiro[cyclopropane-1,2'-bicyclo[2.2.2]octan]-3'-yl)benzo[b]thiophene-2-carboxamide;
(R)-4-chloro-N-(1'-azaspiro[cyclopropane-1,2'-bicyclo[2.2.2]octan]-3'-yl)benzo[b]thiophene-2-carboxamide;
(S)-4-chloro-N-(1'-azaspiro[cyclopropane-1,2'-bicyclo[2.2.2]octan]-3'-yl)benzo[b]thiophene-2-carboxamide;
(R)-6-chloro-7-cyclopropyl-N-(1'-azaspiro[cyclopropane-1,2'-bicyclo[2.2.2]octan]-3'-yl)benzo[b]thiophene-2-carboxamide;
(S)-6-chloro-7-cyclopropyl-N-(1'-azaspiro[cyclopropane-1,2'-bicyclo[2.2.2]octan]-3'-yl)benzo[b]thiophene-2-carboxamide;
(R)-7-chloro-N-(2,2-dimethylquinuclidin-3-yl)-5-fluorobenzo[b]thiophene-2-carboxamide;
(S)-7-chloro-N-(2,2-dimethylquinuclidin-3-yl)-5-fluorobenzo[b]thiophene-2-carboxamide;
(R)-6-fluoro-N-(1'-azaspiro[cyclopropane-1,2'-bicyclo[2.2.2]octan]-3'-yl)-7-(trifluoromethoxy)benzo[b]thiophene-2-carboxamide;
(S)-6-fluoro-N-(1'-azaspiro[cyclopropane-1,2'-bicyclo[2.2.2]octan]-3'-yl)-7-(trifluoromethoxy)benzo[b]thiophene-2-carboxamide;
(R)—N-(2,2-dimethylquinuclidin-3-yl)-6-fluoro-7-(trifluoromethoxy)benzo[b]thiophene-2-carboxamide;
(S)—N-(2,2-dimethylquinuclidin-3-yl)-6-fluoro-7-(trifluoromethoxy)benzo[b]thiophene-2-carboxamide;
(R)—N-(2,2-dimethylquinuclidin-3-yl)-6-methyl-7-(thiazol-2-yl)benzo[b]thiophene-2-carboxamide;
(S)—N-(2,2-dimethylquinuclidin-3-yl)-6-methyl-7-(thiazol-2-yl)benzo[b]thiophene-2-carboxamide;
(R)-6-methyl-N-(1'-azaspiro[cyclopropane-1,2'-bicyclo[2.2.2]octan]-3'-yl)-7-(thiazol-2-yl)benzo[b]thiophene-2-carboxamide;
(S)-6-methyl-N-(1'-azaspiro[cyclopropane-1,2'-bicyclo[2.2.2]octan]-3'-yl)-7-(thiazol-2-yl)benzo[b]thiophene-2-carboxamide;
(R)-7-cyano-N-(2,2-dimethylquinuclidin-3-yl)-6-fluorobenzo[b]thiophene-2-carboxamide;
(S)-7-cyano-N-(2,2-dimethylquinuclidin-3-yl)-6-fluorobenzo[b]thiophene-2-carboxamide;
(R)-6-chloro-7-cyclopropyl-N-(2,2-dimethylquinuclidin-3-yl)benzo[b]thiophene-2-carboxamide;
(S)-6-chloro-7-cyclopropyl-N-(2,2-dimethylquinuclidin-3-yl)benzo[b]thiophene-2-carboxamide;
(R)-6-chloro-7-cyano-N-(2,2-dimethylquinuclidin-3-yl)benzo[b]thiophene-2-carboxamide;
(S)-6-chloro-7-cyano-N-(2,2-dimethylquinuclidin-3-yl)benzo[b]thiophene-2-carboxamide;
(R)-7-(tert-butoxy)-N-(2,2-dimethylquinuclidin-3-yl)benzo[b]thiophene-2-carboxamide;
(S)-7-(tert-butoxy)-N-(2,2-dimethylquinuclidin-3-yl)benzo[b]thiophene-2-carboxamide;
(R)-7-(tert-butoxy)-N-(1'-azaspiro[cyclopropane-1,2'-bicyclo[2.2.2]octan]-3'-yl)benzo[b]thiophene-2-carboxamide;
(S)-7-(tert-butoxy)-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-2,3-dihydro-1H-thieno[2',3':3,4]benzo[1,2-b][1,4]oxazine-8-carboxamide;
(S)—N-(2,2-dimethylquinuclidin-3-yl)-2,3-dihydro-1H-thieno[2',3':3,4]benzo[1,2-b][1,4]oxazine-8-carboxamide;
(R)—N-(2,2-dimethylquinuclidin-3-yl)-1-methyl-2,3-dihydro-1H-thieno[2',3':3,4]benzo[1,2-b][1,4]oxazine-8-carboxamide;
(S)—N-(2,2-dimethylquinuclidin-3-yl)-1-methyl-2,3-dihydro-1H-thieno[2',3':3,4]benzo[1,2-b][1,4]oxazine-8-carboxamide;
(R)—N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
(S)—N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
(R)-1-methyl-N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
(S)-1-methyl-N-(1'-azaspiro[cyclopropane-1,2'-bicyclo[2.2.2]octan]-3'-yl)-2,3-dihydro-1H-thieno[2',3':3,4]benzo[1,2-b][1,4]oxazine-8-carboxamide;
(R)-2-cyclopropyl-N-(2,2-dimethylquinuclidin-3-yl)benzo[b]thiophene-6-carboxamide;
(S)-2-cyclopropyl-N-(2,2-dimethylquinuclidin-3-yl)benzo[b]thiophene-6-carboxamide;
(R)-2-cyclopropyl-N-(1'-azaspiro[cyclopropane-1,2'-bicyclo[2.2.2]octan]-3'-yl)benzo[b]thiophene-6-carboxamide;
(S)-2-cyclopropyl-N-(1'-azaspiro[cyclopropane-1,2'-bicyclo[2.2.2]octan]-3'-yl)benzo[b]thiophene-6-carboxamide;
(R)-7-(difluoromethyl)-N-(2,2-dimethylquinuclidin-3-yl)benzo[b]thiophene-2-carboxamide;
(S)-7-(difluoromethyl)-N-(2,2-dimethylquinuclidin-3-yl)benzo[b]thiophene-2-carboxamide;
(R)-7-(difluoromethyl)-N-(1'-azaspiro[cyclopropane-1,2'-bicyclo[2.2.2]octan]-3'-yl)benzo[b]thiophene-2-carboxamide;
(S)-7-(difluoromethyl)-N-(1'-azaspiro[cyclopropane-1,2'-bicyclo[2.2.2]octan]-3'-yl)benzo[b]thiophene-2-carboxamide;
(R)-7-(oxetan-3-yl)-N-(1'-azaspiro[cyclopropane-1,2'-bicyclo[2.2.2]octan]-3'-yl)benzo[b]thiophene-2-carboxamide;

(S)-7-(oxetan-3-yl)-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-7-(oxetan-3-yl)benzo[b]thiophene-2-carboxamide;
(S)—N-(2,2-dimethylquinuclidin-3-yl)-7-(oxetan-3-yl)benzo[b]thiophene-2-carboxamide;
(R)-6-chloro-N-(2,2-dimethylquinuclidin-3-yl)-7-isopropoxybenzo[b]thiophene-2-carboxamide;
(S)-6-chloro-N-(2,2-dimethylquinuclidin-3-yl)-7-isopropoxybenzo[b]thiophene-2-carboxamide;
(R)-7-cyclobutoxy-N-(2,2-dimethylquinuclidin-3-yl)benzo[b]thiophene-2-carboxamide;
(S)-7-cyclobutoxy-N-(2,2-dimethylquinuclidin-3-yl)benzo[b]thiophene-2-carboxamide;
(R)-6-chloro-N-(2,2-dimethylquinuclidin-3-yl)-7-ethoxybenzo[b]thiophene-2-carboxamide;
(S)-6-chloro-N-(2,2-dimethylquinuclidin-3-yl)-7-ethoxybenzo[b]thiophene-2-carboxamide;
(R)-6-chloro-7-cyano-N-(1'-azaspiro[cyclopropane-1,2'-bicyclo[2.2.2]octan]-3'-yl)benzo[b]thiophene-2-carboxamide;
(S)-6-chloro-7-cyano-N-(1'-azaspiro[cyclopropane-1,2'-bicyclo[2.2.2]octan]-3'-yl)benzo[b]thiophene-2-carboxamide;
(R)-7-cyano-6-fluoro-N-(1'-azaspiro[cyclopropane-1,2'-bicyclo[2.2.2]octan]-3'-yl)benzo[b]thiophene-2-carboxamide;
(S)-7-cyano-6-fluoro-N-(1'-azaspiro[cyclopropane-1,2'-bicyclo[2.2.2]octan]-3'-yl)benzo[b]thiophene-2-carboxamide;
(R)-6-chloro-7-isopropoxy-N-(1'-azaspiro[cyclopropane-1,2'-bicyclo[2.2.2]octan]-3'-yl)benzo[b]thiophene-2-carboxamide;
(S)-6-chloro-7-isopropoxy-N-(1'-azaspiro[cyclopropane-1,2'-bicyclo[2.2.2]octan]-3'-yl)benzo[b]thiophene-2-carboxamide;
(R)-6-chloro-7-ethoxy-N-(1'-azaspiro[cyclopropane-1,2'-bicyclo[2.2.2]octan]-3'-yl)benzo[b]thiophene-2-carboxamide;
(S)-6-chloro-7-ethoxy-N-(1'-azaspiro[cyclopropane-1,2'-bicyclo[2.2.2]octan]-3'-yl)benzo[b]thiophene-2-carboxamide;
(R)-7-cyclobutoxy-N-(1'-azaspiro[cyclopropane-1,2'-bicyclo[2.2.2]octan]-3'-yl)benzo[b]thiophene-2-carboxamide;
(S)-7-cyclobutoxy-N-(1'-azaspiro[cyclopropane-1,2'-bicyclo[2.2.2]octan]-3'-yl)benzo[b]thiophene-2-carboxamide;
(R)-6,7-dimethyl-N-(1'-azaspiro[cyclopropane-1,2'-bicyclo[2.2.2]octan]-3'-yl)benzo[b]thiophene-2-carboxamide;
(S)-6,7-dimethyl-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-7-ethoxy-6-fluorobenzo[b]thiophene-2-carboxamide;
(S)—N-(2,2-dimethylquinuclidin-3-yl)-7-ethoxy-6-fluorobenzo[b]thiophene-2-carboxamide;
(R)-7-isopropoxy-6-methyl-N-(1'-azaspiro[cyclopropane-1,2'-bicyclo[2.2.2]octan]-3'-yl)benzo[b]thiophene-2-carboxamide;
(S)-7-isopropoxy-6-methyl-N-(1'-azaspiro[cyclopropane-1,2'-bicyclo[2.2.2]octan]-3'-yl)benzo[b]thiophene-2-carboxamide;
(R)-7-ethoxy-6-fluoro-N-(1'-azaspiro[cyclopropane-1,2'-bicyclo[2.2.2]octan]-3'-yl)benzo[b]thiophene-2-carboxamide;
(S)-7-ethoxy-6-fluoro-N-(1'-azaspiro[cyclopropane-1,2'-bicyclo[2.2.2]octan]-3'-yl)benzo[b]thiophene-2-carboxamide;
(R)-7-cyclopropyl-N-(2,2-dimethylquinuclidin-3-yl)-6-fluorobenzo[b]thiophene-2-carboxamide;
(S)-7-cyclopropyl-N-(2,2-dimethylquinuclidin-3-yl)-6-fluorobenzo[b]thiophene-2-carboxamide;
(R)-7-cyclopropyl-6-fluoro-N-(1'-azaspiro[cyclopropane-1,2'-bicyclo[2.2.2]octan]-3'-yl)benzo[b]thiophene-2-carboxamide;
(S)-7-cyclopropyl-6-fluoro-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-7-isopropoxy-6-methylbenzo[b]thiophene-2-carboxamide;
(S)—N-(2,2-dimethylquinuclidin-3-yl)-7-isopropoxy-6-methylbenzo[b]thiophene-2-carboxamide;
(R)—N-(2,2-dimethylquinuclidin-3-yl)-7-ethoxy-6-methylbenzo[b]thiophene-2-carboxamide;
(S)—N-(2,2-dimethylquinuclidin-3-yl)-7-ethoxy-6-methylbenzo[b]thiophene-2-carboxamide;
(R)-7-ethoxy-6-methyl-N-(1'-azaspiro[cyclopropane-1,2'-bicyclo[2.2.2]octan]-3'-yl)benzo[b]thiophene-2-carboxamide;
(S)-7-ethoxy-6-methyl-N-(1'-azaspiro[cyclopropane-1,2'-bicyclo[2.2.2]octan]-3'-yl)benzo[b]thiophene-2-carboxamide;
(R)—N-(2,2-dimethylquinuclidin-3-yl)-6,7-dimethylbenzo[b]thiophene-2-carboxamide;
(S)—N-(2,2-dimethylquinuclidin-3-yl)-6,7-dimethylbenzo[b]thiophene-2-carboxamide;
(R)—N-(2,2-dimethylquinuclidin-3-yl)-5-fluoro-6-methylbenzo[b]thiophene-2-carboxamide;
(S)—N-(2,2-dimethylquinuclidin-3-yl)-5-fluoro-6-methylbenzo[b]thiophene-2-carboxamide;
(R)-5-fluoro-6-methyl-N-(1'-azaspiro[cyclopropane-1,2'-bicyclo[2.2.2]octan]-3'-yl)benzo[b]thiophene-2-carboxamide;
(S)-5-fluoro-6-methyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)thieno[3,2-c]pyridine-6-carboxamide;
(S)—N-(1'-azaspiro[cyclopropane-1,2'-bicyclo[2.2.2]octan]-3'-yl)thieno[3,2-c]pyridine-6-carboxamide;
(R)—N-(2,2-dimethylquinuclidin-3-yl)thieno[3,2-c]pyridine-6-carboxamide;
(S)—N-(2,2-dimethylquinuclidin-3-yl)thieno[3,2-c]pyridine-6-carboxamide;
(R)—N-(2,2-dimethylquinuclidin-3-yl)-2,3-dihydrothieno[3,2-g]benzofuran-7-carboxamide;
(S)—N-(2,2-dimethylquinuclidin-3-yl)-2,3-dihydrothieno[3,2-g]benzofuran-7-carboxamide;
(R)—N-(1'-azaspiro[cyclopropane-1,2'-bicyclo[2.2.2]octan]-3'-yl)-2,3-dihydrothieno[3,2-g]benzofuran-7-carboxamide;
(S)—N-(1'-azaspiro[cyclopropane-1,2'-bicyclo[2.2.2]octan]-3'-yl)-2,3-dihydrothieno[3,2-g]benzofuran-7-carboxamide;
(R)—N-(2,2-dimethylquinuclidin-3-yl)-5,7-difluorobenzo[b]thiophene-2-carboxamide;
(S)—N-(2,2-dimethylquinuclidin-3-yl)-5,7-difluorobenzo[b]thiophene-2-carboxamide;
(R)-5,7-difluoro-N-(1'-azaspiro[cyclopropane-1,2'-bicyclo[2.2.2]octan]-3'-yl)benzo[b]thiophene-2-carboxamide;
(S)-5,7-difluoro-N-(1'-azaspiro[cyclopropane-1,2'-bicyclo[2.2.2]octan]-3'-yl)benzo[b]thiophene-2-carboxamide;
(R)-7-chloro-N-(2,2-dimethylquinuclidin-3-yl)pyrrolo[1,2-c]pyrimidine-3-carboxamide;

(S)-7-chloro-N-(2,2-dimethylquinuclidin-3-yl)pyrrolo[1,2-c]pyrimidine-3-carboxamide;
(R)-7-chloro-N-(1'-azaspiro[cyclopropane-1,2'-bicyclo[2.2.2]octan]-3'-yl)pyrrolo[1,2-c]pyrimidine-3-carboxamide;
(S)-7-chloro-N-(1'-azaspiro[cyclopropane-1,2'-bicyclo[2.2.2]octan]-3'-yl)pyrrolo[1,2-c]pyrimidine-3-carboxamide;
(R)—N-(2,2-dimethylquinuclidin-3-yl)pyrrolo[1,2-c]pyrimidine-3-carboxamide;
(S)—N-(2,2-dimethylquinuclidin-3-yl)pyrrolo[1,2-c]pyrimidine-3-carboxamide;
(R)—N-(2,2-dimethylquinuclidin-3-yl)-6-fluoro-7-(2,2,2-trifluoroethoxy)benzo[b]thiophene-2-carboxamide;
(S)—N-(2,2-dimethylquinuclidin-3-yl)-6-fluoro-7-(2,2,2-trifluoroethoxy)benzo[b]thiophene-2-carboxamide;
(R)-6-fluoro-N-(1'-azaspiro[cyclopropane-1,2'-bicyclo[2.2.2]octan]-3'-yl)-7-(2,2,2-trifluoroethoxy)benzo[b]thiophene-2-carboxamide;
(S)-6-fluoro-N-(1'-azaspiro[cyclopropane-1,2'-bicyclo[2.2.2]octan]-3'-yl)-7-(2,2,2-trifluoroethoxy)benzo[b]thiophene-2-carboxamide;
(R)-6-cyclopropyl-N-(2,2-dimethylquinuclidin-3-yl)-5-fluorobenzo[b]thiophene-2-carboxamide;
(S)-6-cyclopropyl-N-(2,2-dimethylquinuclidin-3-yl)-5-fluorobenzo[b]thiophene-2-carboxamide;
(R)—N-(2,2-dimethylquinuclidin-3-yl)-3,4-dihydro-2H-thieno[3',2':5,6]benzo[1,2-b][1,4]oxazine-8-carboxamide;
(S)—N-(2,2-dimethylquinuclidin-3-yl)-3,4-dihydro-2H-thieno[3',2': 5,6]benzo[1,2-b][1,4]oxazine-8-carboxamide;
(R)—N-(2,2-dimethylquinuclidin-3-yl)-4-methyl-3,4-dihydro-2H-thieno[3',2':5,6]benzo[1,2-b][1,4]oxazine-8-carboxamide;
(S)—N-(2,2-dimethylquinuclidin-3-yl)-4-methyl-3,4-dihydro-2H-thieno[3',2': 5,6]benzo[1,2-b][1,4]oxazine-8-carboxamide;
(R)-6-chloro-N-(2,2-dimethylquinuclidin-3-yl)-7-(2,2,2-trifluoroethyl)benzo[b]thiophene-2-carboxamide;
(S)-6-chloro-N-(2,2-dimethylquinuclidin-3-yl)-7-(2,2,2-trifluoroethyl)benzo[b]thiophene-2-carboxamide;
(R)—N-(2,2-dimethylquinuclidin-3-yl)-6-methyl-7-(2,2,2-trifluoroethyl)benzo[b]thiophene-2-carboxamide;
(S)—N-(2,2-dimethylquinuclidin-3-yl)-6-methyl-7-(2,2,2-trifluoroethyl)benzo[b]thiophene-2-carboxamide;
(R)—N-(2,2-dimethylquinuclidin-3-yl)-2,2-difluorothieno[2',3':3,4]benzo[1,2-d][1,3]dioxole-7-carboxamide;
(S)—N-(2,2-dimethylquinuclidin-3-yl)-2,2-difluorothieno[2',3':3,4]benzo[1,2-d][1,3]dioxole-7-carboxamide;
(R)—N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
(S)—N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
(R)-4-methyl-N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
(S)-4-methyl-N-(1'-azaspiro[cyclopropane-1,2'-bicyclo[2.2.2]octan]-3'-yl)-3,4-dihydro-2H-thieno[3',2':5,6]benzo[1,2-b][1,4]oxazine-8-carboxamide;
(R)-6-chloro-N-(1'-azaspiro[cyclopropane-1,2'-bicyclo[2.2.2]octan]-3'-yl)-7-(2,2,2-trifluoroethyl)benzo[b]thiophene-2-carboxamide;
(S)-6-chloro-N-(1'-azaspiro[cyclopropane-1,2'-bicyclo[2.2.2]octan]-3'-yl)-7-(2,2,2-trifluoroethyl)benzo[b]thiophene-2-carboxamide;
(R)-6-methyl-N-(1'-azaspiro[cyclopropane-1,2'-bicyclo[2.2.2]octan]-3'-yl)-7-(2,2,2-trifluoroethyl)benzo[b]thiophene-2-carboxamide;
(S)-6-methyl-N-(1'-azaspiro[cyclopropane-1,2'-bicyclo[2.2.2]octan]-3'-yl)-7-(2,2,2-trifluoroethyl)benzo[b]thiophene-2-carboxamide;
(R)-2,2-difluoro-N-(1'-azaspiro[cyclopropane-1,2'-bicyclo[2.2.2]octan]-3'-yl)thieno[2',3':3,4]benzo[1,2-d][1,3]dioxole-7-carboxamide;
(S)-2,2-difluoro-N-(1'-azaspiro[cyclopropane-1,2'-bicyclo[2.2.2]octan]-3'-yl)thieno[2',3':3,4]benzo[1,2-d][1,3]dioxole-7-carboxamide;
(R)—N-(1'-azaspiro[cyclopropane-1,2'-bicyclo[2.2.2]octan]-3'-yl)-7,8-dihydrothieno[2,3-e]benzofuran-2-carboxamide;
(S)—N-(1'-azaspiro[cyclopropane-1,2'-bicyclo[2.2.2]octan]-3'-yl)-7,8-dihydrothieno[2,3-e]benzofuran-2-carboxamide;
(R)-6-fluoro-N-(1'-azaspiro[cyclopropane-1,2'-bicyclo[2.2.2]octan]-3'-yl)-7-(thiazol-2-yl)benzo[b]thiophene-2-carboxamide;
(S)-6-fluoro-N-(1'-azaspiro[cyclopropane-1,2'-bicyclo[2.2.2]octan]-3'-yl)-7-(thiazol-2-yl)benzo[b]thiophene-2-carboxamide;
(R)-6-chloro-N-(1'-azaspiro[cyclopropane-1,2'-bicyclo[2.2.2]octan]-3'-yl)-7-(thiazol-2-yl)benzo[b]thiophene-2-carboxamide;
(S)-6-chloro-N-(1'-azaspiro[cyclopropane-1,2'-bicyclo[2.2.2]octan]-3'-yl)-7-(thiazol-2-yl)benzo[b]thiophene-2-carboxamide;
(R)—N-(2,2-dimethylquinuclidin-3-yl)-7,8-dihydrothieno[2,3-e]benzofuran-2-carboxamide;
(S)—N-(2,2-dimethylquinuclidin-3-yl)-7,8-dihydrothieno[2,3-e]benzofuran-2-carboxamide;
(R)—N-(2,2-dimethylquinuclidin-3-yl)-6-fluoro-7-(thiazol-2-yl)benzo[b]thiophene-2-carboxamide;
(S)—N-(2,2-dimethylquinuclidin-3-yl)-6-fluoro-7-(thiazol-2-yl)benzo[b]thiophene-2-carboxamide;
(R)-6-chloro-N-(2,2-dimethylquinuclidin-3-yl)-7-(thiazol-2-yl)benzo[b]thiophene-2-carboxamide;
(S)-6-chloro-N-(2,2-dimethylquinuclidin-3-yl)-7-(thiazol-2-yl)benzo[b]thiophene-2-carboxamide;
(R)-5,7-difluoro-6-methyl-N-(1'-azaspiro[cyclopropane-1,2'-bicyclo[2.2.2]octan]-3'-yl)benzo[b]thiophene-2-carboxamide;
(S)-5,7-difluoro-6-methyl-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)-7-(trifluoromethoxy)benzo[b]thiophene-2-carboxamide;
(S)-6-methoxy-N-(1'-azaspiro[cyclopropane-1,2'-bicyclo[2.2.2]octan]-3'-yl)-7-(trifluoromethoxy)benzo[b]thiophene-2-carboxamide;
(R)-7-cyclopropyl-5-fluoro-N-(1'-azaspiro[cyclopropane-1,2'-bicyclo[2.2.2]octan]-3'-yl)benzo[b]thiophene-2-carboxamide;
(S)-7-cyclopropyl-5-fluoro-N-(1'-azaspiro[cyclopropane-1,2'-bicyclo[2.2.2]octan]-3'-yl)benzo[b]thiophene-2-carboxamide;
(R)-6-cyclopropyl-5-fluoro-N-(1'-azaspiro[cyclopropane-1,2'-bicyclo[2.2.2]octan]-3'-yl)benzo[b]thiophene-2-carboxamide;

(S)-6-cyclopropyl-5-fluoro-N-(1'-azaspiro[cyclopropane-1,2'-bicyclo[2.2.2]octan]-3'-yl)benzo[b]thiophene-2-carboxamide;
(R)-7-chloro-5-fluoro-6-methyl-N-(1'-azaspiro[cyclopropane-1,2'-bicyclo[2.2.2]octan]-3'-yl)benzo[b]thiophene-2-carboxamide;
(S)-7-chloro-5-fluoro-6-methyl-N-(1'-azaspiro[cyclopropane-1,2'-bicyclo[2.2.2]octan]-3'-yl)benzo[b]thiophene-2-carboxamide;
(R)-4-fluoro-N-(1'-azaspiro[cyclopropane-1,2'-bicyclo[2.2.2]octan]-3'-yl)furo[2,3-c]pyridine-5-carboxamide;
(S)-4-fluoro-N-(1'-azaspiro[cyclopropane-1,2'-bicyclo[2.2.2]octan]-3'-yl)furo[2,3-c]pyridine-5-carboxamide;
(R)-3-fluoro-N-(1'-azaspiro[cyclopropane-1,2'-bicyclo[2.2.2]octan]-3'-yl)furo[2,3-c]pyridine-5-carboxamide;
(S)-3-fluoro-N-(1'-azaspiro[cyclopropane-1,2'-bicyclo[2.2.2]octan]-3'-yl)furo[2,3-c]pyridine-5-carboxamide;
(R)-2-fluoro-N-(1'-azaspiro[cyclopropane-1,2'-bicyclo[2.2.2]octan]-3'-yl)furo[2,3-c]pyridine-5-carboxamide;
(S)-2-fluoro-N-(1'-azaspiro[cyclopropane-1,2'-bicyclo[2.2.2]octan]-3'-yl)furo[2,3-c]pyridine-5-carboxamide;
(R)-4-methyl-N-(1'-azaspiro[cyclopropane-1,2'-bicyclo[2.2.2]octan]-3'-yl)furo[2,3-c]pyridine-5-carboxamide;
(S)-4-methyl-N-(1'-azaspiro[cyclopropane-1,2'-bicyclo[2.2.2]octan]-3'-yl)furo[2,3-c]pyridine-5-carboxamide;
(R)-7-methyl-N-(1'-azaspiro[cyclopropane-1,2'-bicyclo[2.2.2]octan]-3'-yl)furo[2,3-c]pyridine-5-carboxamide;
(S)-7-methyl-N-(1'-azaspiro[cyclopropane-1,2'-bicyclo[2.2.2]octan]-3'-yl)furo[2,3-c]pyridine-5-carboxamide;
(R)—N-(2,2-dimethylquinuclidin-3-yl)-5,7-difluoro-6-methylbenzo[b]thiophene-2-carboxamide;
(S)—N-(2,2-dimethylquinuclidin-3-yl)-5,7-difluoro-6-methylbenzo[b]thiophene-2-carboxamide;
(R)—N-(2,2-dimethylquinuclidin-3-yl)-6-methoxy-7-(trifluoromethoxy)benzo[b]thiophene-2-carboxamide;
(S)—N-(2,2-dimethylquinuclidin-3-yl)-6-methoxy-7-(trifluoromethoxy)benzo[b]thiophene-2-carboxamide;
(R)-7-cyclopropyl-N-(2,2-dimethylquinuclidin-3-yl)-5-fluorobenzo[b]thiophene-2-carboxamide;
(S)-7-cyclopropyl-N-(2,2-dimethylquinuclidin-3-yl)-5-fluorobenzo[b]thiophene-2-carboxamide;
(R)-7-chloro-N-(2,2-dimethylquinuclidin-3-yl)-5-fluoro-6-methylbenzo[b]thiophene-2-carboxamide;
(S)-7-chloro-N-(2,2-dimethylquinuclidin-3-yl)-5-fluoro-6-methylbenzo[b]thiophene-2-carboxamide;
(R)—N-(2,2-dimethylquinuclidin-3-yl)-4-fluorofuro[2,3-c]pyridine-5-carboxamide;
(S)—N-(2,2-dimethylquinuclidin-3-yl)-4-fluorofuro[2,3-c]pyridine-5-carboxamide;
(R)—N-(2,2-dimethylquinuclidin-3-yl)-3-fluorofuro[2,3-c]pyridine-5-carboxamide;
(S)—N-(2,2-dimethylquinuclidin-3-yl)-3-fluorofuro[2,3-c]pyridine-5-carboxamide;
(R)—N-(2,2-dimethylquinuclidin-3-yl)-2-fluorofuro[2,3-c]pyridine-5-carboxamide;
(S)—N-(2,2-dimethylquinuclidin-3-yl)-2-fluorofuro[2,3-c]pyridine-5-carboxamide;
(R)—N-(2,2-dimethylquinuclidin-3-yl)-4-methylfuro[2,3-c]pyridine-5-carboxamide;
(S)—N-(2,2-dimethylquinuclidin-3-yl)-4-methylfuro[2,3-c]pyridine-5-carboxamide;
(R)—N-(2,2-dimethylquinuclidin-3-yl)-7-methylfuro[2,3-c]pyridine-5-carboxamide;
(S)—N-(2,2-dimethylquinuclidin-3-yl)-7-methylfuro[2,3-c]pyridine-5-carboxamide;
(R)-7-(1-fluorocyclopropyl)-N-(1'-azaspiro[cyclopropane-1,2'-bicyclo[2.2.2]octan]-3'-yl)benzo[b]thiophene-2-carboxamide;
(S)-7-(1-fluorocyclopropyl)-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-6,8-dihydrothieno[2,3-e]isobenzofuran-2-carboxamide;
(S)—N-(1'-azaspiro[cyclopropane-1,2'-bicyclo[2.2.2]octan]-3'-yl)-6,8-dihydrothieno[2,3-e]isobenzofuran-2-carboxamide;
(R)-7-cyclopropoxy-6-fluoro-N-(1'-azaspiro[cyclopropane-1,2'-bicyclo[2.2.2]octan]-3'-yl)benzo[b]thiophene-2-carboxamide;
(S)-7-cyclopropoxy-6-fluoro-N-(1'-azaspiro[cyclopropane-1,2'-bicyclo[2.2.2]octan]-3'-yl)benzo[b]thiophene-2-carboxamide;
(R)-7-cyclopropoxy-6-methyl-N-(1'-azaspiro[cyclopropane-1,2'-bicyclo[2.2.2]octan]-3'-yl)benzo[b]thiophene-2-carboxamide;
(S)-7-cyclopropoxy-6-methyl-N-(1'-azaspiro[cyclopropane-1,2'-bicyclo[2.2.2]octan]-3'-yl)benzo[b]thiophene-2-carboxamide;
(R)-6-chloro-7-cyclopropoxy-N-(1'-azaspiro[cyclopropane-1,2'-bicyclo[2.2.2]octan]-3'-yl)benzo[b]thiophene-2-carboxamide;
(S)-6-chloro-7-cyclopropoxy-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)-7-(2,2,2-trifluoroethoxy)benzo[b]thiophene-2-carboxamide;
(S)-6-methyl-N-(1'-azaspiro[cyclopropane-1,2'-bicyclo[2.2.2]octan]-3'-yl)-7-(2,2,2-trifluoroethoxy)benzo[b]thiophene-2-carboxamide;
(R)-5,6-difluoro-7-methyl-N-(1'-azaspiro[cyclopropane-1,2'-bicyclo[2.2.2]octan]-3'-yl)benzo[b]thiophene-2-carboxamide;
(S)-5,6-difluoro-7-methyl-N-(1'-azaspiro[cyclopropane-1,2'-bicyclo[2.2.2]octan]-3'-yl)benzo[b]thiophene-2-carboxamide;
(R)-3-methyl-N-(1'-azaspiro[cyclopropane-1,2'-bicyclo[2.2.2]octan]-3'-yl)furo[2,3-c]pyridine-5-carboxamide;
(S)-3-methyl-N-(1'-azaspiro[cyclopropane-1,2'-bicyclo[2.2.2]octan]-3'-yl)furo[2,3-c]pyridine-5-carboxamide;
(R)-3-chloro-N-(1'-azaspiro[cyclopropane-1,2'-bicyclo[2.2.2]octan]-3'-yl)furo[2,3-c]pyridine-5-carboxamide;
(S)-3-chloro-N-(1'-azaspiro[cyclopropane-1,2'-bicyclo[2.2.2]octan]-3'-yl)furo[2,3-c]pyridine-5-carboxamide;
(R)—N-(1'-azaspiro[cyclopropane-1,2'-bicyclo[2.2.2]octan]-3'-yl)pyrrolo[1,2-a]pyrazine-3-carboxamide;
(S)—N-(1'-azaspiro[cyclopropane-1,2'-bicyclo[2.2.2]octan]-3'-yl)pyrrolo[1,2-a]pyrazine-3-carboxamide;
(R)—N-(1'-azaspiro[cyclopropane-1,2'-bicyclo[2.2.2]octan]-3'-yl)pyrrolo[1,2-c]pyrimidine-3-carboxamide;
(S)—N-(1'-azaspiro[cyclopropane-1,2'-bicyclo[2.2.2]octan]-3'-yl)pyrrolo[1,2-c]pyrimidine-3-carboxamide;
(R)—N-(1'-azaspiro[cyclopropane-1,2'-bicyclo[2.2.2]octan]-3'-yl)indolizine-6-carboxamide;
(S)—N-(1'-azaspiro[cyclopropane-1,2'-bicyclo[2.2.2]octan]-3'-yl)indolizine-6-carboxamide;
(R)-6-methyl-N-(1'-azaspiro[cyclopropane-1,2'-bicyclo[2.2.2]octan]-3'-yl)pyrrolo[1,2-a]pyrazine-3-carboxamide;

(S)-6-methyl-N-(1'-azaspiro[cyclopropane-1,2'-bicyclo[2.2.2]octan]-3'-yl)pyrrolo[1,2-a]pyrazine-3-carboxamide;
(R)—N-(1'-azaspiro[cyclopropane-1,2'-bicyclo[2.2.2]octan]-3'-yl)-1H-pyrrolo[3,2-c]pyridine-6-carboxamide;
(S)—N-(1'-azaspiro[cyclopropane-1,2'-bicyclo[2.2.2]octan]-3'-yl)-1H-pyrrolo[3,2-c]pyridine-6-carboxamide;
(R)—N-(2,2-dimethylquinuclidin-3-yl)-7-(1-fluorocyclopropyl)benzo[b]thiophene-2-carboxamide;
(S)—N-(2,2-dimethylquinuclidin-3-yl)-7-(1-fluorocyclopropyl)benzo[b]thiophene-2-carboxamide;
(R)—N-(2,2-dimethylquinuclidin-3-yl)-6,8-dihydrothieno[2,3-e]isobenzofuran-2-carboxamide;
(S)—N-(2,2-dimethylquinuclidin-3-yl)-6,8-dihydrothieno[2,3-e]isobenzofuran-2-carboxamide;
(R)-7-cyclopropoxy-N-(2,2-dimethylquinuclidin-3-yl)-6-fluorobenzo[b]thiophene-2-carboxamide;
(S)-7-cyclopropoxy-N-(2,2-dimethylquinuclidin-3-yl)-6-fluorobenzo[b]thiophene-2-carboxamide;
(R)-7-cyclopropoxy-N-(2,2-dimethylquinuclidin-3-yl)-6-methylbenzo[b]thiophene-2-carboxamide;
(S)-7-cyclopropoxy-N-(2,2-dimethylquinuclidin-3-yl)-6-methylbenzo[b]thiophene-2-carboxamide;
(R)-6-chloro-7-cyclopropoxy-N-(2,2-dimethylquinuclidin-3-yl)benzo[b]thiophene-2-carboxamide;
(S)-6-chloro-7-cyclopropoxy-N-(2,2-dimethylquinuclidin-3-yl)benzo[b]thiophene-2-carboxamide;
(R)—N-(2,2-dimethylquinuclidin-3-yl)-6-methyl-7-(2,2,2-trifluoroethoxy)benzo[b]thiophene-2-carboxamide;
(S)—N-(2,2-dimethylquinuclidin-3-yl)-6-methyl-7-(2,2,2-trifluoroethoxy)benzo[b]thiophene-2-carboxamide;
(R)—N-(2,2-dimethylquinuclidin-3-yl)-5,6-difluoro-7-methylbenzo[b]thiophene-2-carboxamide;
(S)—N-(2,2-dimethylquinuclidin-3-yl)-5,6-difluoro-7-methylbenzo[b]thiophene-2-carboxamide;
(R)—N-(2,2-dimethylquinuclidin-3-yl)-3-methylfuro[2,3-c]pyridine-5-carboxamide;
(S)—N-(2,2-dimethylquinuclidin-3-yl)-3-methylfuro[2,3-c]pyridine-5-carboxamide;
(R)-3-chloro-N-(2,2-dimethylquinuclidin-3-yl)furo[2,3-c]pyridine-5-carboxamide;
(S)-3-chloro-N-(2,2-dimethylquinuclidin-3-yl)furo[2,3-c]pyridine-5-carboxamide;
(R)—N-(2,2-dimethylquinuclidin-3-yl)pyrrolo[1,2-a]pyrazine-3-carboxamide;
(S)—N-(2,2-dimethylquinuclidin-3-yl)pyrrolo[1,2-a]pyrazine-3-carboxamide;
(R)—N-(2,2-dimethylquinuclidin-3-yl)indolizine-6-carboxamide;
(S)—N-(2,2-dimethylquinuclidin-3-yl)indolizine-6-carboxamide;
(R)—N-(2,2-dimethylquinuclidin-3-yl)-6-methylpyrrolo[1,2-a]pyrazine-3-carboxamide;
(S)—N-(2,2-dimethylquinuclidin-3-yl)-6-methylpyrrolo[1,2-a]pyrazine-3-carboxamide;
(R)—N-(2,2-dimethylquinuclidin-3-yl)-1H-pyrrolo[3,2-c]pyridine-6-carboxamide; and
(S)—N-(2,2-dimethylquinuclidin-3-yl)-1H-pyrrolo[3,2-c]pyridine-6-carboxamide;

In certain embodiments, specific examples of the amide compound represented by Formula (I) may include, collectively or individually, the single enantiomers listed below, and pharmaceutically acceptable salts thereof:
(R)—N-(2,2-dimethylquinuclidin-3-yl)benzo[b]thiophene-2-carboxamide;
(R)—N-(2,2-dimethylquinuclidin-3-yl)-7-fluoro-benzo[b]thiophene-2-carboxamide;
(R)—N-(2,2-dimethylquinuclidin-3-yl)benzofuran-5-carboxamide;
(R)-6-chloro-N-(2,2-dimethylquinuclidin-3-yl)benzo[b]thiophene-2-carboxamide;
(R)—N-(2,2-dimethylquinuclidin-3-yl)furo[2,3-c]pyridine-5-carboxamide;
(R)-7-chloro-N-(2,2-dimethylquinuclidin-3-yl)-6-methylbenzo[b]thiophene-2-carboxamide;
(R)—N-(2,2-dimethylquinuclidin-3-yl)-7-fluoro-6-methylbenzo[b]thiophene-2-carboxamide;
(R)—N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)benzo[b]thiophene-6-carboxamide;
(R)—N-(1'-azaspiro[cyclopropane-1,2'-bicyclo[2.2.2]octan]-3'-yl)benzofuran-5-carboxamide;
(R)-6-chloro-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)benzo[b]thiophene-2-carboxamide;
(R)-6-cyclopropyl-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)furo[2,3-c]pyridine-5-carboxamide;
(R)—N-(1'-azaspiro[cyclopropane-1,2'-bicyclo[2.2.2]octan]-3'-yl)-1H-indole-6-carboxamide;
(R)-2-chloro-N-(1'-azaspiro[cyclopropane-1,2'-bicyclo[2.2.2]octan]-3'-yl)benzofuran-5-carboxamide;
(R)-6-bromo-N-(1'-azaspiro[cyclopropane-1,2'-bicyclo[2.2.2]octan]-3'-yl)benzo[b]thiophene-2-carboxamide;
(R)-7-fluoro-6-methyl-N-(1'-azaspiro[cyclopropane-1,2'-bicyclo[2.2.2]octan]-3'-yl)benzo[b]thiophene-2-carboxamide;
(R)-6,7-dichloro-N-(1'-azaspiro[cyclopropane-1,2'-bicyclo[2.2.2]octan]-3'-yl)benzo[b]thiophene-2-carboxamide;
(R)-6-chloro-7-fluoro-N-(1'-azaspiro[cyclopropane-1,2'-bicyclo[2.2.2]octan]-3'-yl)benzo[b]thiophene-2-carboxamide;
(R)-7-cyano-N-(1'-azaspiro[cyclopropane-1,2'-bicyclo[2.2.2]octan]-3'-yl)benzo[b]thiophene-2-carboxamide;
(R)-7-cyclopropyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(trifluoromethoxy)benzo[b]thiophene-2-carboxamide;
(R)-5-fluoro-6-methoxy-N-(1'-azaspiro[cyclopropane-1,2'-bicyclo[2.2.2]octan]-3'-yl)benzo[b]thiophene-2-carboxamide;
(R)-7-ethoxy-N-(1'-azaspiro[cyclopropane-1,2'-bicyclo[2.2.2]octan]-3'-yl)benzo[b]thiophene-2-carboxamide; and
(R)-2-chloro-N-(1'-azaspiro[cyclopropane-1,2'-bicyclo[2.2.2]octan]-3'-yl)benzo[b]thiophene-6-carboxamide.

In certain embodiments, the amide compound represented by Formula (I), (II), or (III), may comprise the W representing the moiety represented by the ring system M-IV, wherein M-IV represents a moiety represented by ring system M-IV-1:

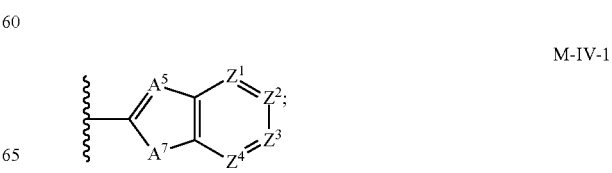

M-IV-1 wherein $Z^1$, $Z^2$, $Z^3$, and $Z^4$ independently represent $CR^4$; $A^5$ represents $CR^{15}$; and $A^7$ represents S; and may include, collectively or individually, the single enantiomers listed below, and pharmaceutically acceptable salts thereof:
(R)—N-(2,2-dimethylquinuclidin-3-yl)benzo[b]thiophene-2-carboxamide;
(R)—N-(2,2-dimethylquinuclidin-3-yl)-7-fluoro-benzo[b]thiophene-2-carboxamide;
(R)-6-chloro-N-(2,2-dimethylquinuclidin-3-yl)benzo[b]thiophene-2-carboxamide;
(R)-7-chloro-N-(2,2-dimethylquinuclidin-3-yl)-6-methylbenzo[b]thiophene-2-carboxamide;
(R)—N-(2,2-dimethylquinuclidin-3-yl)-7-fluoro-6-methylbenzo[b]thiophene-2-carboxamide;
(R)—N-(1'-azaspiro[cyclopropane-1,2'-bicyclo[2.2.2]octan]-3'-yl)benzo[b]thiophene-2-carboxamide;
(R)-6-chloro-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)benzo[b]thiophene-2-carboxamide;
(R)-6-cyclopropyl-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)benzo[b]thiophene-2-carboxamide;
(R)-6-bromo-N-(1'-azaspiro[cyclopropane-1,2'-bicyclo[2.2.2]octan]-3'-yl)benzo[b]thiophene-2-carboxamide;
(R)-7-fluoro-6-methyl-N-(1'-azaspiro[cyclopropane-1,2'-bicyclo[2.2.2]octan]-3'-yl)benzo[b]thiophene-2-carboxamide;
(R)-6,7-dichloro-N-(1'-azaspiro[cyclopropane-1,2'-bicyclo[2.2.2]octan]-3'-yl)benzo[b]thiophene-2-carboxamide;
(R)-6-chloro-7-fluoro-N-(1'-azaspiro[cyclopropane-1,2'-bicyclo[2.2.2]octan]-3'-yl)benzo[b]thiophene-2-carboxamide;
(R)-7-cyano-N-(1'-azaspiro[cyclopropane-1,2'-bicyclo[2.2.2]octan]-3'-yl)benzo[b]thiophene-2-carboxamide;
(R)-7-cyclopropyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(trifluoromethoxy)benzo[b]thiophene-2-carboxamide;
(R)-5-fluoro-6-methoxy-N-(1'-azaspiro[cyclopropane-1,2'-bicyclo[2.2.2]octan]-3'-yl)benzo[b]thiophene-2-carboxamide; and
(R)-7-ethoxy-N-(1'-azaspiro[cyclopropane-1,2'-bicyclo[2.2.2]octan]-3'-yl)benzo[b]thiophene-2-carboxamide.

In certain embodiments, the amide compound represented by Formula (I), (II), or (III), may comprise the W representing the moiety represented by the ring system M-II, wherein M-II represents a moiety represented by ring system M-II-1:

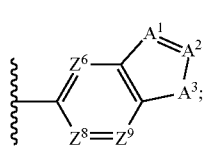

M-II-1 wherein $A^1$ and $A^2$ independently represent $CR^{11}$; $A^3$ represents O; and $Z^6$, $Z^8$, and $Z^9$ independently represent $CR^7$; and may include, collectively or individually, the single enantiomers listed below, and pharmaceutically acceptable salts thereof:
(R)—N-(2,2-dimethylquinuclidin-3-yl)benzofuran-5-carboxamide;
(R)—N-(1'-azaspiro[cyclopropane-1,2'-bicyclo[2.2.2]octan]-3'-yl)benzofuran-5-carboxamide; and
(R)-2-chloro-N-(1'-azaspiro[cyclopropane-1,2'-bicyclo[2.2.2]octan]-3'-yl)benzofuran-5-carboxamide.

In certain embodiments, the amide compound represented by Formula (I), (II), or (III), may comprise the W representing the moiety represented by the ring system M-II, wherein M-II represents a moiety represented by ring system M-II-6:

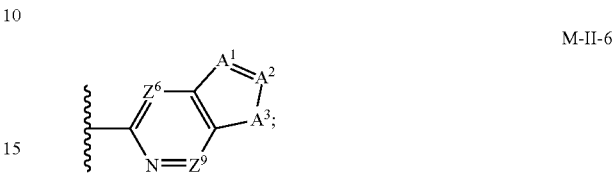

M-II-6 wherein $A^1$ and $A^2$ independently represent $CR^{11}$; $A^3$ represents O; and $Z^6$ and $Z^9$ independently represent $CR^7$; and may include, collectively or individually, the single enantiomers listed below, and pharmaceutically acceptable salts thereof:
(R)—N-(2,2-dimethylquinuclidin-3-yl)furo[2,3-c]pyridine-5-carboxamide; and
(R)—N-(1'-azaspiro[cyclopropane-1,2'-bicyclo[2.2.2]octan]-3'-yl)furo[2,3-c]pyridine-5-carboxamide.

In certain embodiments, the amide compound represented by Formula (I), (II), or (III), may comprise the W representing the moiety represented by the ring system M-II, wherein M-II represents a moiety represented by ring system M-II-2:

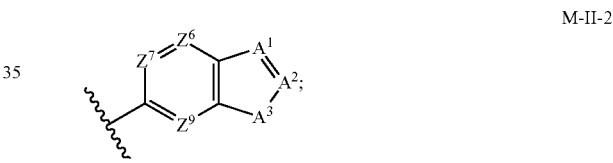

M-II-2 wherein $A^1$ and $A^2$ independently represent $CR^{11}$; $A^3$ represents $NR^{10}$; and $Z^6$, $Z^7$, and $Z^9$ independently represent $CR^7$; and may include, collectively or individually, the single enantiomer listed below, and pharmaceutically acceptable salts thereof:
(R)—N-(1'-azaspiro[cyclopropane-1,2'-bicyclo[2.2.2]octan]-3'-yl)-1H-indole-6-carboxamide.

In certain embodiments, the amide compound represented by Formula (I), (II), or (III), may comprise the W representing the moiety represented by the ring system M-II, wherein M-II represents a moiety represented by ring system M-II-2:

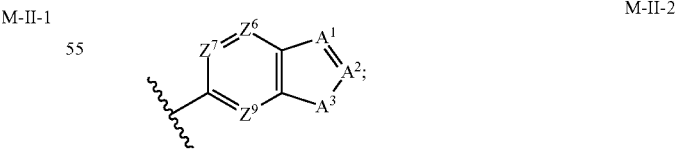

M-II-2 wherein $A^1$ and $A^2$ independently represent $CR^{11}$; $A^3$ represents S; and $Z^6$, $Z^7$, and $Z^9$ independently represent $CR^7$; and may include, collectively or individually, the single enantiomer listed below, and pharmaceutically acceptable salts thereof:
(R)—N-(1'-azaspiro[cyclopropane-1,2'-bicyclo[2.2.2]octan]-3'-yl)benzo[b]thiophene-6-carboxamide; and (R)-2-chloro-N-(1'-azaspiro[cyclopropane-1,2'-bicyclo [2.2.2]octan]-3'-yl)benzo[b]thiophene-6-carboxamide.

As used herein, the term "treating" (or "treat" or "treatment"), unless otherwise specified, includes the generally accepted meaning which encompasses improving, modifying, decreasing, prohibiting, preventing, restraining, minimizing, slowing, halting, stopping, curing, and/or reversing a symptom associated with a disease and/or a disease. Treatment may include both therapeutic and prophylactic administration. For example, treatment of a cognitive impairment, in a patient diagnosed as having a cognitive impairment, may include, but is not limited to, curing the cognitive impairment, preventing the deterioration of one or more symptoms associated with the cognitive impairment; improving cognition in a patient suffering from the cognitive impairment, slowing the progression of the cognitive impairment and/or modifying the cognitive impairment.

As used herein, the term "effective dose" (or "dose"), unless otherwise specified, is understood to include a therapeutically acceptable dose, a therapeutically acceptable amount, a therapeutically effective dose, a therapeutically effective amount, a pharmaceutically acceptable dose, a pharmaceutically acceptable amount, a pharmaceutically effective dose, or a pharmaceutically effective amount.

As used herein, the term "cognitive impairment," unless otherwise specified, includes at least one of the following: Limited Cognitive Impairment (LCI), Mild Cognitive Impairment (MCI), Alzheimer's disease (or dementia of an Alzheimer's-type) or a particular stage of Alzheimer's disease, inclusive of pre-Alzheimer's disease, early Alzheimer's disease, mild Alzheimer's disease, moderate Alzheimer's disease, severe Alzheimer's disease, pre-Alzheimer's-to-mild Alzheimer's disease, mild-to-moderate Alzheimer's disease, moderate-to-severe Alzheimer's disease, schizophrenia (for example, paranoid type schizophrenia, disorganized type schizophrenia, catatonic type schizophrenia, undifferentiated type schizophrenia), schizophreniform disorder, schizoaffective disorder, delusional disorder, positive symptoms of schizophrenia, negative symptoms of schizophrenia, or schizophrenia with dementia.

Alzheimer's disease may include, unless otherwise specified, any of the sub-diagnostic categories used to characterize the type or degree of cognitive impairment in a patient for treatment purposes. A commonly referenced diagnostic scale for characterizing the degree of cognitive impairment for a patient with Alzheimer's disease includes the 3-stage Alzheimer Disease Model. The 3-stages consist of: mild stage (also referred to as "early Alzheimer's disease" or "mild Alzheimer's disease" or "early stage Alzheimer's disease" or "mild dementia of an Alzheimer's-type"), moderate stage (also referred to as "middle Alzheimer's disease" or "moderate Alzheimer's disease" or "middle stage Alzheimer's disease" or "moderate dementia of an Alzheimer's-type"), and severe stage (also referred to as "late Alzheimer's disease" or "severe Alzheimer's disease" or "late stage Alzheimer's disease" or "severe dementia of an Alzheimer's-type"). For patients with a condition that has not progressed to the point of mild stage Alzheimer's disease, they may be diagnosed as having pre-Alzheimer's disease. It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. Another useful diagnostic scale that is used in characterizing the degree of cognitive impairment for a patient having Alzheimer's disease is the Seven Stage Alzheimer's Disease Model (sometimes known as the "Seven Stage Global Deterioration Scale" or the "Reisberg Scale"). This diagnostic scale divides the progression of the cognitive disorder associated with Alzheimer's disease as follows: Stage 1-no Alzheimer's disease (generally characterized by absence of impairment, no impairment, or normal function), Stage 2-pre-Alzheimer's disease (generally characterized by minimal impairment, normal forgetfulness, or very mild cognitive decline), Stage 3-early-stage Alzheimer's disease (generally characterized by a noticeable cognitive decline, early confusional/mild cognitive impairment, or mild cognitive decline), Stage 4-early-stage/mild Alzheimer's disease (also referred to as late confusional/ mild Alzheimer's, and generally characterized by moderate cognitive decline), Stage 5-middle-stage/moderate Alzheimer's (also referred to as early dementia/moderate Alzheimer's disease and generally characterized by moderately severe cognitive decline), Stage 6-middle dementia/moderately severe Alzheimer's disease (also referred to as middle-stage/moderate to late-stage/severe Alzheimer's disease and generally characterized by severe cognitive decline), and Stage 7-late-stage/severe Alzheimer's disease (also referred to as severe dementia or failure-to-thrive, and generally characterized by very severe cognitive decline). It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. As used herein, unless otherwise specified, Alzheimer's disease includes all of the above named diagnostic categories or disease characterizations. It is also not uncommon for a physician to categorize any one or more of the above noted states of Alzheimer's disease as being probable, for example, probable mild-to-moderate Alzheimer's disease or probable severe Alzheimer's disease, when their diagnosis does not include, for example a physical biopsy or other definitive analysis.

Mild Cognitive Impairment (MCI) is considered by some to be an intermediate stage between normal aging and the onset of Alzheimer's disease. For example, MCI may be characterized by persistent forgetfulness, but may lack some or many of the more debilitating symptoms of Alzheimer's disease. Another set of criteria that may characterize a patient as having mild cognitive impairment suitable for treatment includes a patient that meets the following: 1) memory complaints corroborated by an informant, 2) objective memory impairment for age and education, 3) normal general cognitive function, 4) intact activities of daily living, and 5) the patient does not meet criteria for dementia. In general, a patient characterized as having mild cognitive impairment may not yet have a clinical cognitive deficit. Mild cognitive impairment may also be distinguished from senile dementia in that mild cognitive impairment involves a more persistent and troublesome problem of memory loss for the age of the patient. On the clinical diagnostic scale, mild cognitive impairment is followed, in increased severity, by Alzheimer's disease.

Limited Cognitive Impairment (LCI) describes a cognitive impairment (i.e., symptoms or conditions), which precedes mild cognitive impairment on a clinical diagnostic scale, and includes any chronic or temporary impairment in cognition, learning or memory that prevents or reduces the ability of a patient from achieving their individual potential in these areas. For example, LCIs may include minor impairments to memory associated with focus and concentration (e.g., accuracy and speed of learning and recalling information), working memory (e.g., used in decision making and problem solving), cognition, focus, mental quickness, and mental clarity.

The term "stereoisomer" refers to a molecule capable of existing in more than one spatial atomic arrangement for a given atomic connectivity (e.g., enantiomers, meso compounds, and diastereomers). As used herein, the term "stereoisomer" means either or both enantiomers and diastereomers.

The amide compounds of the present invention represented by Formula (I), Formula (II), or Formula (III), or a pharmaceutically acceptable salt thereof, may contain one or more stereogenic centers. Accordingly, compounds of this invention can exist as either individual stereoisomers or mixtures of two or more stereoisomers. A compound of the present invention will include both mixtures (e.g., racemic mixtures) and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present.

The amide compounds of the present invention represented by Formula (I), Formula (II), or Formula (III), or a pharmaceutically acceptable salt thereof, may contain one or more tautomeric forms. Accordingly, compounds of this invention can exist as either individual tautomers or mixtures of tautomeric forms. A compound of the present invention will include both mixtures (e.g., mixtures of tautomeric forms) and also individual respective tautomers that are substantially free from another possible tautomer.

The amide compounds of the present invention represented by Formula (I), Formula (II), or Formula (III), or a pharmaceutically acceptable salt thereof, may contain one or more geometric isomers. Accordingly, compounds of this invention can exist as either geometric isomers or mixtures of geometric isomers. A compound of the present invention will include both mixtures (e.g., mixtures of geometric isomers) and also individual respective geometric isomers that are substantially free from another possible geometric isomer.

The term "haloalkyl" refers to an alkyl group having from 1 to 5 halogen substituents independently selected from —F, —Cl, —Br, and —I. For example, a haloalkyl may represent a —$CF_3$ group, a —$CCl_3$ group, a —$CH_2CF_3$ group, or a —$CF_2CF_3$ group.

The term "heteroaryl" refers to an aromatic ring system comprising at least one or more hetero-ring atoms, such as two, three, four, or five hetero-ring atoms, independently selected from N, O, and S. Suitable heteroaryl groups may include a single ring, for example, thienyl, pyridyl, thiazolyl, pyrazinyl, pyrimidyl, imidazolyl, furanyl, isothiazolyl, pyrazolyl, triazolyl, tetrazolyl, isoxazolyl, oxazolyl, pyrrolyl, pyridazinyl, triazinyl, oxadiazolyl, and furazanyl. Suitable heteroaryl groups may include a fused ring system, for example, a six-six fused ring system, a six-five fused ring system, or a five-six fused ring system, such as benzothienyl, quinolyl, benzofuranyl, benzothiazolyl, benzisothiazolyl, benzisoxazolyl, benzimidazolyl, indolyl, benzoxazolyl, isoquinolinyl, cinnolinyl, indazolyl, indolizinyl, phthalazinyl, isoindolyl, purinyl, benzofurazanyl, benzothiophenyl, benzothiazolyl, quinazolinyl, quinoxalinyl, naphthridinyl, and furopyridinyl.

Suitable "heterocycloalkyl" groups include those having at least one or more hetero-ring atoms, such as two or three hetero-ring atoms, independently selected from —O—, —S—, —$S(O)_2$—, —N(H)—, and —N($CH_2$)$_m$$R^{18}$. Suitable heterocycloalkyl groups may include, for example, tetrahydrofurano, tetrahydropyrano, morpholino, pyrrolidino, piperidino, piperazino, azetidino, azetidinono, oxindolo, oxetano, dihydroimidazolo, and pyrrolidinono.

The pharmaceutically acceptable salt of the amide compounds represented by Formula (I), Formula (II), or Formula (III), according to the present invention may be acid addition salts with inorganic or organic acids. Specific examples of these salts include acid addition salts with, for instance, mineral acids such as hydrochloric acid, hydrobromic acid, hydriodic acid, sulfuric acid, nitric acid or phosphoric acid; organic acids, for example carboxylic acids or sulfonic acids, such as formic acid, acetic acid, propionic acid, oxalic acid, malonic acid, succinic acid, fumaric acid, maleic acid, lactic acid, malic acid, tartaric acid, citric acid, benzoic acid, p-toluenesulfonic acid, benzenesulfonic acid, naphthalenedisulfonic acid, isethionic acid, glucuronic acid, gluconic acid, methanesulfonic acid or ethanesulfonic acid; or acidic amino acids such as aspartic acid or glutamic acid.

In certain embodiments, a pharmaceutical composition may comprise an amide compound represented by Formula (I), Formula (II), or Formula (III), or a pharmaceutically acceptable salt thereof, and at least one pharmaceutically acceptable carrier, excipient or diluent.

In certain embodiments, the amide compounds represented by Formula (I), Formula (II), or Formula (III), or a pharmaceutically acceptable salt thereof, are suitable for use as medicaments for the treatment and/or prophylaxis of diseases in humans and/or animals.

In certain embodiments, the invention relates to a method comprising administering to a patient in need thereof an effective dose of an amide compound represented by Formula (I), Formula (II), or Formula (III), or a pharmaceutically acceptable salt thereof, or administering to the patient a pharmaceutical composition comprising the amide compound represented by Formula (I), Formula (II), or Formula (III), or a pharmaceutically acceptable salt thereof, and at least one pharmaceutically acceptable carrier, excipient or diluent.

In certain embodiments, the amide compounds represented by Formula (I), Formula (II), or Formula (III), or a pharmaceutically acceptable salt thereof, act as ligands, in particular as α7-nAChR agonists.

In certain embodiments, a method of treating a patient in need thereof, comprising administering an amide compound represented by Formula (I), Formula (II), or Formula (III), or a pharmaceutically acceptable salt thereof. In certain embodiments, a method of treating a patient in need thereof, comprising administering a pharmaceutical composition comprising an amide compound represented by Formula (I), Formula (II), or Formula (III), or a pharmaceutically acceptable salt thereof. For example, the patient may suffer from a cognitive impairment or suffers from one or more symptoms associated with a cognitive impairment, such as Limited Cognitive Impairment (LCI), Mild Cognitive Impairment (MCI), Alzheimer's disease, dementia of an Alzheimer's-type, schizophrenia, schizophreniform disorder, schizoaffective disorder, delusional disorder, positive symptoms of schizophrenia, negative symptoms of schizophrenia, or schizophrenia with dementia.

In certain embodiments, the amide compounds represented by Formula (I), Formula (II), or Formula (III), or a pharmaceutically acceptable salt thereof, can, because of their pharmacological properties, be employed alone or in combination with other active ingredients for the treatment and/or prevention of cognitive impairments, for example, Alzheimer's disease or schizophrenia. Because of their selective effect as α7-nAChR agonists, the amide compounds represented by Formula (I), Formula (II), or Formula (III), or a pharmaceutically acceptable salt thereof, are particularly suitable for improving cognition, providing procognitive effects, improving perception, improving concentration, improving learning or memory, improving one or more aspects of cognition, e.g., one or more of: executive function, memory (e.g., working memory), social cognition, visual learning, verbal learning and speed of processing, especially after or associated with cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic brain syndrome, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, dyskinesias associated with dopamine agonist therapy in Parkinson's Disease, progressive nuclear palsy, dementia with corticobasal degeneration, amyotrophic lateral sclerosis (ALS), Huntington's disease, multiple sclerosis, thalamic degeneration, Creutzfeldt-Jakob dementia, HIV dementia, schizophrenia (e.g., paranoid type, disorganized type, catatonic type, and undifferentiated type), schizophreniform disorder, schizoaffective disorder, delusional disorder, positive symptoms of schizophrenia, negative symptoms of schizophrenia, schizophrenia with dementia, Korsakoff's psychosis, depression, anxiety, mood and affective disorders, traumatic brain injury, withdrawal symptoms associated with smoking cessation and dependent drug cessation, Gilles de la Tourette's Syndrome, age-related macular degeneration, glaucoma, neurodegeneration associated with glaucoma, treatment (including amelioration, prevention or delay of progression) of sleep disorders (e.g., narcolepsy, excessive daytime sleepiness, nocturnal sleep disruption and/or cataplexy), treatment (including amelioration, prevention or delay) of progression of fatigue, or use for facilitation of emergence from general anesthesia.

In certain embodiments, the amide compounds represented by Formula (I), Formula (II), or Formula (III), or a pharmaceutically acceptable salt thereof, can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

In certain embodiments, the invention relates to a method comprising administering to a patient in need thereof, such as a patient suffering from, or diagnosed as having, a cognitive impairment or having one or more symptoms associated with a cognitive impairment, an effective dose of an amide compound represented by Formula (I), Formula (II), or Formula (III), or a pharmaceutically acceptable salt thereof, or administering to the patient a pharmaceutical composition comprising the amide compound represented by Formula (I), Formula (II), or Formula (III), or a pharmaceutically acceptable salt thereof, and at least one pharmaceutically acceptable carrier, excipient or diluent. For example, the method may treat and/or improve the one or more symptoms associated with a cognitive impairment and/or the cognitive impairment.

A certain embodiment of the present invention provides a method of improving one or more cognitive symptoms, improving one or more behavioral symptoms, or both, associated with a cognitive impairment, comprising: administering to a patient in need thereof an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent.

In a certain embodiment of the present invention, the method provides a pro-cognitive effect in a patient suffering from, or diagnosed as having, a cognitive disease or dementia, comprising: administering to a patient in need thereof an effective dose of an amide compound represented by Formula (I), Formula (II), or Formula (III), or a pharmaceutically acceptable salt thereof, or administering to the patient a pharmaceutical composition comprising an effective dose of the amide compound represented by Formula (I), Formula (II), or Formula (III), or a pharmaceutically acceptable salt thereof, and at least one pharmaceutically acceptable carrier, excipient or diluent; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

A certain embodiment of the present invention provides a method of treating a patient with a cognitive disease, comprising: administering to the patient a daily dose of a pharmaceutical composition comprising an amide compound represented by Formula (I), Formula (II), or Formula (III), or a pharmaceutically acceptable salt thereof, and at least one pharmaceutically acceptable carrier, excipient or diluent.

In a certain embodiment of the present invention, the method provides a pro-cognitive effect in a patient suffering from, or diagnosed as having, schizophrenia, for example, paranoid type schizophrenia, disorganized type schizophrenia, catatonic type schizophrenia, undifferentiated type schizophrenia, schizophreniform disorder, schizoaffective disorder, delusional disorder, positive symptoms of schizophrenia, negative symptoms of schizophrenia, or schizophrenia with dementia, comprising: administering to a patient in need thereof an effective dose of an amide compound represented by Formula (I), Formula (II), or Formula (III), or a pharmaceutically acceptable salt thereof, or administering to a patient in need thereof, a pharmaceutical composition comprising an effective dose of an amide compound represented by Formula (I), Formula (II), or Formula (III), or a pharmaceutically acceptable salt thereof, and at least one pharmaceutically acceptable carrier, excipient or diluents; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

In an embodiment of the present invention, any one of the above-noted embodiments, includes wherein the daily dose is an initial daily dose.

In a certain embodiment of the present invention provides a method of improving cognition of a patient in need thereof, comprising: administering to the patient an amide compound represented by Formula (I), Formula (II), or Formula (III), or a pharmaceutically acceptable salt thereof, or administering to the patient a pharmaceutical composition comprising an effective dose of an amide compound represented by Formula (I), Formula (II), or Formula (III), or a pharmaceutically acceptable salt thereof, and at least one pharmaceutically acceptable carrier, excipient or diluents.

In a certain embodiment of the present invention provides a method of treating or improving one or more symptoms associated with a cognitive disease and/or a cognitive impairment in a patient in need thereof, comprising: administering to the patient an effective dose of an amide compound represented by Formula (I), Formula (II), or Formula (III), or a pharmaceutically acceptable salt thereof, or administering to the patient a pharmaceutical composition comprising the amide compound represented by Formula (I), Formula (II), or Formula (III), or a pharmaceutically acceptable salt thereof, and at least one pharmaceutically acceptable carrier, excipient or diluent.

In an embodiment of the present invention, any one of the above-noted embodiments, wherein the method specifically includes treating a symptom associated with a cognitive disease.

In an embodiment of the present invention, any one of the above-noted embodiments, wherein the method specifically includes improving a symptom associated with a cognitive disease.

In an embodiment of the present invention, any one of the above-noted embodiments, wherein the method specifically includes preventing progression of a cognitive disease.

In an embodiment of the present invention, any one of the above-noted embodiments, wherein the patient has been diagnosed as having a cognitive disease.

In an embodiment of the present invention, any one of the above-noted embodiments, wherein the patient has been diagnosed as having Alzheimer's disease.

In an embodiment of the present invention, any one of the above-noted embodiments, wherein the method specifically includes treating a symptom associated with Alzheimer's disease.

In an embodiment of the present invention, any one of the above-noted embodiments, wherein the method specifically includes improving a symptom associated with Alzheimer's disease.

In an embodiment of the present invention, any one of the above-noted embodiments, wherein the method specifically includes preventing progression of Alzheimer's disease.

In an embodiment of the present invention, any one of the above-noted embodiments, wherein the patient has been diagnosed as having mild-to-moderate Alzheimer's disease.

In an embodiment of the present invention, any one of the above-noted embodiments, wherein the method specifically includes treating a symptom associated with schizophrenia.

In an embodiment of the present invention, any one of the above-noted embodiments, wherein the method specifically includes improving a symptom associated with schizophrenia.

In an embodiment of the present invention, any one of the above-noted embodiments, wherein the method specifically includes preventing progression of schizophrenia.

In an embodiment of the present invention, any one of the above-noted embodiments, wherein the patient has been diagnosed as having schizophrenia.

In an embodiment of the present invention, any one of the above-noted embodiments, wherein the method specifically includes treating a symptom associated with positive symptoms of schizophrenia.

In an embodiment of the present invention, any one of the above-noted embodiments, wherein the method specifically includes improving a symptom associated with positive symptoms of schizophrenia.

In an embodiment of the present invention, any one of the above-noted embodiments, wherein the method specifically includes preventing progression of positive symptoms of schizophrenia.

In an embodiment of the present invention, any one of the above-noted embodiments, wherein the method specifically includes the patient has been diagnosed as having positive symptoms of schizophrenia.

In an embodiment of the present invention, any one of the above-noted embodiments, wherein the method specifically includes treating a symptom associated with negative symptoms of schizophrenia.

In an embodiment of the present invention, any one of the above-noted embodiments, wherein the method specifically includes improving a symptom associated with negative symptoms of schizophrenia.

In an embodiment of the present invention, any one of the above-noted embodiments, wherein the method specifically includes preventing progression of negative symptoms of schizophrenia.

In an embodiment of the present invention, any one of the above-noted embodiments, wherein the method specifically includes the patient has been diagnosed as having negative symptoms of schizophrenia.

In an embodiment of the present invention, any one of the above-noted embodiments, wherein the method specifically includes treating a symptom associated with schizophrenia with dementia.

In an embodiment of the present invention, any one of the above-noted embodiments, wherein the method specifically includes improving a symptom associated with schizophrenia with dementia.

In an embodiment of the present invention, any one of the above-noted embodiments, wherein the method specifically includes preventing progression of schizophrenia with dementia.

In an embodiment of the present invention, any one of the above-noted embodiments, wherein the method specifically includes the patient has been diagnosed as having schizophrenia with dementia.

In an embodiment of the present invention, any one of the above-noted embodiments, wherein the method specifically includes the patient has been diagnosed as having a disease associated with chronic inflammation, including atherosclerosis, rheumatoid arthritis and inflammatory bowel diseases.

In an embodiment of the present invention, any one of the above-noted embodiments, wherein the pharmaceutical composition is in the form of a tablet.

Pharmaceutical Compositions

In certain embodiments, the invention also includes pharmaceutical preparations which, besides inert, nontoxic, pharmaceutically suitable excipients, adjuvants and carriers, contain one or more amide compounds represented by Formula (I), Formula (II), or Formula (III), or a pharmaceutically acceptable salt thereof, or consist of one or more amide compounds represented by Formula (I), Formula (II), or Formula (III), or a pharmaceutically acceptable salt thereof, and processes for producing these preparations.

An amide compound represented by Formula (I), Formula (II), or Formula (III), or a pharmaceutically acceptable salt thereof, may be formulated for administration in solid or liquid form. For example, an amide compound represented by Formula (I), Formula (II), or Formula (III), or a pharmaceutically acceptable salt thereof, may be formulated for administration in a capsule, a tablet, or a powder form. For example, an amide compound represented by Formula (I), Formula (II), or Formula (III), or a pharmaceutically acceptable salt thereof, may be formulated alone or as part of a pharmaceutical composition, suitable for oral administration, such as in a capsule or tablet, intravenous administration, parenteral administration, topical administration, or transdermal administration, such as in a patch, to a patient in need thereof.

An amide compound represented by Formula (I), Formula (II), or Formula (III), or a pharmaceutically acceptable salt thereof, may be administered as a pharmaceutical composition, for example, in the presence of carriers, adjuvants, excipients, diluents, fillers, buffers, stabilizers, preservatives, lubricants, and the like, for example, administered as a pharmaceutical composition (e.g., formulation) comprising at least an amide compound represented by Formula (I), Formula (II), or Formula (III), or a pharmaceutically acceptable salt thereof, together with one or more pharmaceutically acceptable carriers, adjuvants, excipients, diluents, or other materials well known to those skilled in the art. As used herein, the term "pharmaceutically acceptable", unless otherwise specified, includes the generally accepted meaning which encompasses combinations, compounds, materials, compositions, and/or dosage forms which are, within the scope of sound medical judgment, suitable for consumption by humans without excessive toxicity, irritation, allergic response, or other problem or complication, commensurate with a reasonable benefit/risk ratio.

Suitable pharmaceutically acceptable carriers, adjuvants, excipients, and diluents, can include, but are not limited to, lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The formulations can additionally include, but are not limited to, pharmaceutically acceptable lubricating agents, glidants, wetting agents, emulsifying and suspending agents, preserving agents, sweetening agents, and/or flavoring agents. The pharmaceutical compositions of the present invention may be formulated so as to provide quick release, immediate release, sustained release, or delayed release of an amide compound represented by Formula (I), Formula (II), or Formula (III), or a pharmaceutically acceptable salt thereof, after administration to the patient by employing procedures well-known in the art.

Another embodiment of the invention further comprises methods of making Pharmaceutical Composition, comprising admixing at least an amide compound represented by Formula (I), Formula (II), or Formula (III), or a pharmaceutically acceptable salt thereof, together with one or more pharmaceutically acceptable carriers, excipients, buffers, adjuvants, stabilizers, or other materials.

In certain embodiments, the amide compounds represented by Formula (I), Formula (II), or Formula (III), or a pharmaceutically acceptable salt thereof, are to be present in these preparations in a concentration of from 0.1 to 99.5% by weight, preferably from 0.5 to 95% by weight, of the complete mixture. Besides the amide compounds represented by Formula (I), Formula (II), or Formula (III), or a pharmaceutically acceptable salt thereof, the pharmaceutical preparations may also contain other active pharmaceutical ingredients.

In certain embodiments, the novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the entire mixture, i.e., in amounts which are sufficient to reach the stated dose range.

In certain embodiments, the formulations are produced, for example, by extending the active ingredients with solvents and/or excipients, where appropriate with use of emulsifiers and/or dispersants, it being possible for example when water is used as diluent where appropriate to use organic solvents as auxiliary solvents.

In certain embodiments, administration may take place in a conventional way, for example, orally, transdermally or parenterally, especially perlingually or intravenously. In certain embodiments, administration may also take place by inhalation through the mouth or nose, for example, with the aid of a spray, or topically via the skin.

In certain embodiments, the amide compounds represented by Formula (I), Formula (II), or Formula (III), or a pharmaceutically acceptable salt thereof, may be administered in amounts of about 0.01 to 10 mg/kg, on oral administration, for example, about 0.05 to 5 mg/kg, of body weight to achieve effective results.

EXAMPLES

Analytical instrument model:

TABLE 1

| LCMS | Shimadzu UFLC MS: LCMS-2020 |
| --- | --- |
| | Agilent Technologies 1200 series MS: |
| | Agilent Technologies 6110 |
| | Agilent Technologies 1200 series MS: |
| | LC/MSD VL |

TABLE 1-continued

| | |
|---|---|
| NMR | BRUKER AVANCE III/400 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

LCMS:

LCMS Conditions A ("LCMS (A)"): Instrument: Shimadzu LCMS 2020; Mobile phase A: 4 L H2O\1.5 mL TFA, Mobile phase B: 4 L ACN\0.75 mL TFA; Method name: 10-80AB_4MIN_2W; Flow Rate: 0.8 mL/min.; Gradient: 10%-80%; Column: Boston Green ODS 2.1*30 mm, 3 μm; Column temperature: 50° C.; Wavelength: 220 nm & 254 nm.

LCMS Conditions B ("LCMS (B)"): Instrument: Agilent 1200 Series; Mobile phase A: 4 L H2O\1.5 ml TFA, Mobile phase B: 4 L ACN\0.75 mL TFA; Method name: 5-95AB_R_2W; Flow Rate: 1.5 mL/min.; Gradient: 5%-95%; Column: Chromolith@Flash RP-18e 25-2 mm; Column temperature: 50° C.; Wavelength: 220 nm & 254 nm.

LCMS Conditions C ("LCMS (C)"): Instrument: Agilent 1200 Series; Mobile phase A: 4 L H2O\2 mL NH3H2O; Mobile phase B: Acetonitrile; Method name: 5-95CD_4.5MIN_2W; Flow Rate: 0.8 mL/min.; Gradient: 5%-95%; Column: Chromolith@Flash RP-18e 25-2 mm; Column temperature 50° C.; Wavelength: 220 nm & 254 nm.

LCMS Conditions D ("LCMS (D)"): Instrument: Agilent 1200 Series; Mobile phase A: 4 L H2O\1.5 mL TFA, Mobile phase B: 4 L ACN\0.75 mL TFA; Method name: 5-95AB_R_4MIN_2W; Flow Rate: 0.8 mL/min.; Gradient: 5%-95%; Column: Chromolith@Flash RP-18e 25-2 mm; Column temperature: 50° C.; Wavelength: 220 nm & 254 nm.

LCMS Conditions E ("LCMS (E)"): Instrument: Agilent 1200 Series; Mobile phase A: 4 L H2O\1.5 ml TFA, Mobile phase B: 4 L ACN\0.75 mL TFA; Method name: 5-95AB_R; Flow Rate: 1.5 mL/min.; Gradient: 5%-95%; Column: Chromolith@Flash RP-18e 25-2 mm; Column temperature: 50° C.; Wavelength: 220 nm & 254 nm.

LCMS Conditions F ("LCMS (F)"): Instrument: Agilent 1200 Series; Mobile phase A: 4 L H2O\2 ml NH3H2O, Mobile phase B: Acetonitrile; Method name: 5-95CD_2MIN_2W; Flow Rate: 1.2 mL/min.; Gradient: 5%-95%; Column: XBridge Shield RP-18 2.1*50 mm, 5 μm; Column temperature: 30° C.; Wavelength: 220 nm & 254 nm.

LCMS Conditions G ("LCMS (G)"): Instrument: Agilent 1200 Series; Mobile phase A: 4 L H2O\2 mL NH3H2O, Mobile phase B: Acetonitrile; Method name: 10-80CD_4MIN_2W; Flow Rate: 0.8 mL/min.; Gradient: 10%-80%; Column: XBridge C-18 2.1*50 mm, 5 m; Column temperature: 40° C.; Wavelength: 220 nm & 254 nm.

LCMS Conditions H ("LCMS (H)"): Instrument: Agilent 1200 Series; Mobile phase A: 4 L H2O\1.5 mL TFA, Mobile phase B: 4 L ACN\0.75 mL TFA; Method name: 10-80AB_4MIN_2W; Flow Rate: 0.8 mL/min.; Gradient: 10%-80%; Column: Xtimate C-18, 2.1*30 mm, 3 μm; Column temperature: 50° C.; Wavelength: 220 nm & 254 nm.

LCMS Conditions I ("LCMS (I)"): Instrument: Agilent 1200 Series; Mobile phase A: 4 L H2O\2 mL NH3H2O, Mobile phase B: Acetonitrile; Method name: 0-60CD_4.5MIN_2W; Flow Rate: 0.8 ml/min.; Gradient: 0%-60%; Column: XBridge Shield RP-18 2.1*50 mm, 5 μm; Column temperature 50° C.; Wavelength: 220 nm & 254 nm.

LCMS Conditions J ("LCMS (J)"): Instrument: Agilent 1200 Series; Mobile phase A: 4 L H2O\2 mL NH3H2O, Mobile phase B: Acetonitrile; Method name: 10-80CD_2MIN_POS_2W; Flow Rate: 1.2 ml/min.; Gradient: 10%-80%; Column: Xbridge C-18 2.1*50 mm, 5 μm; Column temperature: 40° C.; Wavelength: 220 nm & 254 nm.

LCMS Conditions K ("LCMS (K)"): Instrument: Shimadzu LCMS 2020; Mobile phase A: 4 L H2O\1.5 mL TFA, Mobile phase B: 4 L ACN\0.75 mL TFA; Method name: 0-30AB_2MIN_2W; Flow Rate: 1.2 mL/min.; Gradient: 0%-30%; Column: Chromolith@Flash RP-18E 25-2 mm; Column temperature: 50° C.; Wavelength: 220 nm & 254 nm.

LCMS Conditions L ("LCMS (L)"): Instrument: Shimadzu LCMS 2020; Mobile phase A: 4 L H2O\1.5 mL TFA, Mobile phase B: 4 L ACN\0.75 mL TFA; Method name: 0-30AB_4MIN_2W; Flow Rate: 0.8 mL/min.; Gradient: 0%-30%; Column: Chromolith@Flash RP-18E 25-2 mm; Column temperature: 50° C.; Wavelength: 220 nm & 254 nm.

LCMS Conditions M ("LCMS (M)"): Instrument: Shimadzu LCMS 2020; Mobile phase A: 4 L H2O\1.5 mL TFA, Mobile phase B: 4 L ACN\0.75 mL TFA; Method name: 0-60AB_2MIN_2W; Flow Rate: 1.2 mL/min.; Gradient: 0%-60%; Column: Chromolith@Flash RP-18E 25-2 mm; Column temperature: 50° C.; Wavelength: 220 nm & 254 nm.

LCMS Conditions N ("LCMS (N)"): Instrument: Shimadzu LCMS 2020; Mobile phase A: 4 L H2O\1.5 mL TFA, Mobile phase B: 4 L ACN\0.75 mL TFA; Method name: 0-60AB_4MIN_2W; Flow Rate: 0.8 mL/min.; Gradient: 0%-60%; Column: Chromolith@Flash RP-18E 25-2 mm; Column temperature: 50° C.; Wavelength: 220 nm & 254 nm.

LCMS Conditions O ("LCMS(O)"): Instrument: Agilent 1200 Series LCMS; Mobile phase A: 4 L H2O\2 mL NH3H2O, Mobile phase B: CAN; Method name: 0-30CD_2MIN_POS_2W; Flow Rate: 1.0 mL/min.; Gradient: 0%-30%; Column: Xbridge C18 2.1*50 mm, 5 um; Column temperature: 40° C.; Wavelength: 220 nm & 254 nm.

LCMS Conditions P ("LCMS (P)"): Instrument: Agilent 1200 Series LCMS; Mobile phase A: 4 L H2O\2 mL NH3H2O, Mobile phase B: CAN; Method name: 0-60CD_2MIN_POS_2W; Flow Rate: 1.0 mL/min.; Gradient: 0%-60%; Column: Xbridge C18 2.1*50 mm, 5 um; Column temperature: 40° C.; Wavelength: 220 nm & 254 nm.

LCMS Conditions Q ("LCMS (Q)"): Instrument: Agilent 1200 Series LCMS; Mobile phase A: 4 L H2O\2 mL NH3H2O, Mobile phase B: CAN; Method name: 0-60CD_4MIN_2W; Flow Rate: 0.8 mL/min.; Gradient: 0%-60%; Column: Xbridge C18 2.1*50 mm, 5 um; Column temperature: 40° C.; Wavelength: 220 nm & 254 nm.

LCMS Conditions R ("LCMS (R)"): Instrument: Agilent 1200 Series LCMS; Mobile phase A: 4 L H2O\1.5 mL TFA, Mobile phase B: 4 L ACN\0.75 mL TFA; Method name: 10-80AB_2MIN_2W; Flow Rate: 1.2 mL/min.; Gradient: 10%-80%; Column: Xtimate C18, 2.1*30 mm, 3 um; Column temperature: 50° C.; Wavelength: 220 nm & 254 nm.

LCMS Conditions S ("LCMS (S)"): Instrument: Agilent 1200 Series LCMS; Mobile phase A: 4 L H2O\2 mL NH3H2O, Mobile phase B: CAN; Method name:

30-90CD_4MIN_POS_2W; Flow Rate: 0.8 mL/min.; Gradient: 30%-90%; Column: Xbridge C18 2.1*50 mm, 5 um; Column temperature: 40° C.; Wavelength: 220 nm & 254 nm.

LCMS Conditions T ("LCMS (T)"): Instrument: Agilent 1200 Series LCMS; Mobile phase A: 4 L H2O\1.5 mL TFA, Mobile phase B: 4 L ACN\0.75 mL TFA; Method name: 5-95AB_15MIN_YMC; Flow Rate: 1.0 mL/min.; Gradient: 5%-95%; Column: YMC-Pack ODS-A 5 μm 150*4.6 mm; Column temperature: 50° C.; Wavelength: 220 nm & 254 nm.

LCMS Conditions U ("LCMS (U)"): Instrument: Agilent 1200 Series LCMS; Mobile phase A: 4 L H2O\1.5 mL TFA, Mobile phase B: 4 L ACN\0.75 mL TFA; Method name: 0-30AB_2MIN_2W; Flow Rate: 1.2 mL/min.; Gradient: 0%-30%; Column: Chromolith@Flash RP-18E 25-2 mm; Column temperature: 50° C.; Wavelength: 220 nm & 254 nm.

LCMS Conditions V ("LCMS (V)"): Instrument: Agilent 1200 Series LCMS; Mobile phase A: 4 L H2O\1.5 mL TFA, Mobile phase B: 4 L ACN\0.75 mL TFA; Method name: 0-30AB_4MIN_2W; Flow Rate: 0.8 mL/min.; Gradient: 0%-30%; Column: Chromolith@Flash RP-18E 25-2 mm; Column temperature: 50° C.; Wavelength: 220 nm & 254 nm.

LCMS Conditions W ("LCMS (W)"): Instrument: Agilent 1200 Series LCMS; Mobile phase A: 4 L H2O\1.5 mL TFA, Mobile phase B: 4 L ACN\0.75 mL TFA; Method name: 0-60AB_2MIN_2W; Flow Rate: 1.2 mL/min.; Gradient: 0%-60%; Column: Chromolith@Flash RP-18E 25-2 mm; Column temperature: 50° C.; Wavelength: 220 nm & 254 nm.

LCMS Conditions X ("LCMS (X)"): Instrument: Agilent 1200 Series LCMS; Mobile phase A: 4 L H2O\1.5 mL TFA, Mobile phase B: 4 L ACN\0.75 mL TFA; Method name: 0-60AB_4MIN_2W; Flow Rate: 0.8 mL/min.; Gradient: 0%-60%; Column: Chromolith@Flash RP-18E 25-2 mm; Column temperature: 50° C.; Wavelength: 220 nm & 254 nm.

LCMS Conditions Y ("LCMS (Y)"): Instrument: Shimadzu LCMS 2020; Mobile phase A: 4 L H2O\1.5 ml TFA, Mobile phase B: 4 L ACN\0.75 mL TFA; Method name: 5-95AB_R_2W; Flow Rate: 1.5 mL/min.; Gradient: 5%-95%; Column: Chromolith@Flash RP-18e 25-2 mm; Column temperature: 50° C.; Wavelength: 220 nm & 254 nm.

LCMS Conditions Z ("LCMS (Z)"): Instrument: Shimadzu LCMS 2020; Mobile phase A: 4 L H2O\1.5 mL TFA, Mobile phase B: 4 L ACN\0.75 mL TFA; Method name: 5-95AB_R_4MIN_2W; Flow Rate: 0.8 mL/min.; Gradient: 5%-95%; Column: Chromolith@Flash RP-18e 25-2 mm; Column temperature: 50° C.; Wavelength: 220 nm & 254 nm.

LCMS Conditions AA ("LCMS (AA)"): Instrument: Agilent 1200 Series LCMS; Mobile phase A: 4 L H2O\2 mL NH3.H2O, Mobile phase B: ACN; Method name: 10-80CD_2MIN_NEG; Flow Rate: 1.2 mL/min.; Gradient: 10%-80%; Column: Xbridge C18 2.1*50 mm, 5 μm; Column temperature: 40° C.; Wavelength: 220 nm & 254 nm.

LCMS Conditions BB ("LCMS (BB)"): Instrument: Agilent 1200 Series LCMS; Mobile phase A: 4 L H2O\1.5 mL TFA, Mobile phase B: 4 L ACN\0.75 mL TFA; Method name: 0-60AB_R_2W; Flow Rate: 1.5 mL/min.; Gradient: 0%-60%; Column: Chromolith@Flash RP-18E 25-2 mm; Column temperature: 50° C.; Wavelength: 220 nm & 254 nm.

LCMS Conditions CC ("LCMS (CC)"): Instrument: Agilent 1200 Series LCMS; Mobile phase A: 4 L H2O\1.5 mL TFA, Mobile phase B: 4 L ACN\0.75 mL TFA; Method name: 0-30AB_R_2W; Flow Rate: 1.5 mL/min.; Gradient: 0%-30%; Column: Chromolith@Flash RP-18E 25-2 mm; Column temperature: 50° C.; Wavelength: 220 nm & 254 nm.

LCMS Conditions DD ("LCMS (DD)"): Instrument: Agilent 1200 Series LCMS; Mobile phase A: 4 L H2O\1.5 mL TFA, Mobile phase B: 4 L ACN\0.75 mL TFA; Method name: 10-80AB_R_2W; Flow Rate: 1.5 mL/min.; Gradient: 10%-80%; Column: Chromolith@Flash RP-18E 25-2 mm; Column temperature: 50° C.; Wavelength: 220 nm & 254 nm.

LCMS Conditions EE ("LCMS (EE)"): Instrument: Agilent 1200 Series; Mobile phase A: 1 L H2O\0.375 mL TFA, Mobile phase B: 4 L ACN\0.75 mL TFA; Method name: WUXIAB00; Flow Rate: 0.6-1.0 mL/min; Gradient: 0%-80%-100%; Column: Agilent 5 TC-C18 50-2.1 mm; Column temperature: 50° C.; Wavelength: 220 nm & 254 nm.

LCMS Conditions FF ("LCMS (FF)"): Instrument: Agilent 1200 Series; Mobile phase A: 1 L H2O\0.375 mL TFA, Mobile phase B: 4 L ACN\0.75 mL TFA; Method name: WUXIAB01; Flow Rate: 0.8-1.0 mL/min; Gradient: 1%-90%-100%; Column: Agilent 5 TC-C18 50-2.1 mm; Column temperature: 50° C.; Wavelength: 220 nm & 254 nm.

LCMS Conditions GG ("LCMS (GG)"): Instrument: Agilent 1200 Series; Mobile phase A: 1 L H2O\0.375 mL TFA, Mobile phase B: 4 L ACN\0.75 mL TFA; Method name: WUXIAB10; Flow Rate: 0.8-1.0 mL/min; Gradient: 10%-100%; Column: Agilent 5 TC-C18 50-2.1 mm; Column temperature: 50° C.; Wavelength: 220 nm & 254 nm.

GCMS:

GCMS Conditions Instrument: SHIMADZU GCMS-QP2010 Ultra; Carrier gas: He; Column Flow: 1.5 mL/min; Injector: 250° C.; Split Ratio: 100:1; Column: HP-5MS 15 m*0.25 mm*0.25 um; FILM From: 40° C. (holding 3 min) to 250° C. (holding 3 min) at the rate of 25° C./min.

cSFC Analytical:

cSFC Analytical Conditions: Flow rate: 3 mL/min; Wavelength: 220 nm; and Column temperature: 35° C., were used for each of the specified conditions below:

cSFC Analytical Conditions A ("cSFC analytical (A)"): Column: Chiralpak OD-3 100×4.6 mm I.D., 3 um; Mobile phase: ethanol (0.05% diethylamine ("DEA") in $CO_2$ from 5% to 40%.

cSFC Analytical Conditions B ("cSFC analytical (B)"): Column: Chiralpak OD-3 100×4.6 mm I.D., 3 um; Mobile phase: methanol (0.05% DEA) in $CO_2$ from 5% to 40%.

cSFC Analytical Conditions C ("cSFC analytical (C)"): Column: Chiralpak OD-3 100×4.6 mm I.D., 3 um; Mobile phase: 40% ethanol (0.05% DEA) in $CO_2$.

cSFC Analytical Conditions D ("cSFC analytical (D)"): Column: Chiralpak AY-3 100×4.6 mm I.D., 3 um; Mobile phase: ethanol (0.05% DEA) in $CO_2$ from 5% to 40%.

cSFC Analytical Conditions E ("cSFC analytical (E)"): Column: Chiralpak OJ-3 100×4.6 mm I.D., 3 um; Mobile phase: ethanol (0.05% DEA) in $CO_2$ from 5% to 40%.

cSFC Analytical Conditions F ("cSFC analytical (F)"): Column: Chiralpak OJ-3 100×4.6 mm I.D., 3 um; Mobile phase: methanol (0.05% DEA) in $CO_2$ from 5% to 40%.

cSFC Analytical Conditions G ("cSFC analytical (G)"): Column: Chiralpak AD-3 100×4.6 mm I.D., 3 um; Mobile phase: ethanol (0.05% DEA) in $CO_2$ from 5% to 40%.

cSFC Analytical Conditions H ("cSFC analytical (H)"): Column: Chiralpak AD-3 100×4.6 mm I.D., 3 um; Mobile phase: methanol (0.05% DEA) in $CO_2$ from 5% to 40%.

For each final compound prepared below that indicates the presence of a salt associated with the final compound (i.e., a salt complex), the specific molar equivalence of salt included in the final compound, unless specified, was not determined.

Example 1A: quinuclidin(N-borane)-3-one (A-101)

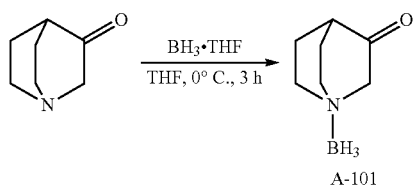

To a mixture of quinuclidin-3-one (0.20 kg, 1.6 mol) in tetrahydrofuran (1 L) at 0° C. was added dropwise 1 M borane in tetrahydrofuran (1.8 L, 1.8 mol). The mixture was stirred at 0° C. for 3 hours. On completion, the solution was quenched by methanol, evaporated and purified by silica gel chromatography (petroleum ether:ethyl acetate=10:1) to give compound A-101 (0.19 kg, 86% yield) as a white solid.

Example 2A:
2,2-dimethylquinuclidin(N-borane)-3-one (A-102)

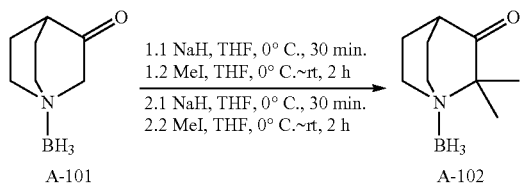

To a mixture of compound A-101 (20 g, 0.14 mol) in tetrahydrofuran (200 mL) at 0° C. was added sodium hydride (8.6 g, 60%, 0.22 mol) in portions. The reaction was stirred for 30 minutes. Iodomethane (31 g, 0.22 mol) in tetrahydrofuran (30 mL) was added dropwise to the mixture at 0° C., and the reaction was stirred at room temperature for 2 hours, and then cooled to 0° C. Sodium hydride (8.6 g, 60%, 0.22 mol) was added in portions, and stirring was continued for 30 minutes. Iodomethane (31 g, 0.22 mol) in tetrahydrofuran (30 mL) was again added dropwise to the mixture at 0° C., and the reaction was stirred at room temperature for another 2 hours. On completion, the reaction was quenched with saturated ammonium chloride aqueous solution and concentrated in vacuo. The residue was purified by silica gel chromatography (petroleum ether:ethyl acetate=10:1) to give compound A-102 (14 g, 58% yield) as a white solid.

Example 3A: 2,2-dimethylquinuclidin-3-one oxime (A-103)

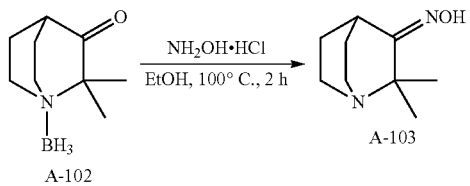

To a mixture of compound A-102 (0.50 g, 3.0 mmol) in anhydrous ethanol (2 mL) was added hydroxylamine hydrochloride (0.21 g, 3.0 mmol) at room temperature. The mixture was stirred at 100° C. for 2 hours. On completion, the solution was cooled to room temperature, resulting in formation of a precipitate. The precipitation was collected by filtration to give compound A-103 (0.48 g, 96% yield) as a white solid. LCMS (K): tR=1.093 min., (ES$^+$) m/z (M+H)$^+$= 169.1.

Example 4A:
(+/−)-2,2-dimethylquinuclidin-3-amine (rac-A-104)

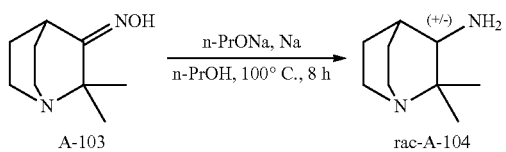

To a mixture of compound A-103 (0.60 g, 2.9 mmol) in n-propyl alcohol (6 mL) was added sodium n-propoxide (67 mg, 2.9 mmol sodium in 1 mL n-propyl alcohol) at room temperature. The solution was heated to 100° C., and sodium (0.67 g, 29 mmol) was added in portions. The mixture was stirred at this temperature for 8 hours. On completion, the mixture was poured into water (1 mL), concentrated in vacuo, diluted with dichloromethane and filtered. The resulting filtrate was concentrated in vacuo to give rac-A-104 (0.40 g, 89% yield) as a yellow oil. LCMS (K): tR=0.988 min., (ES$^+$) m/z (M+H)=155.1.

Example 5A: 2,2-dimethylquinuclidin-3-one (A-105)

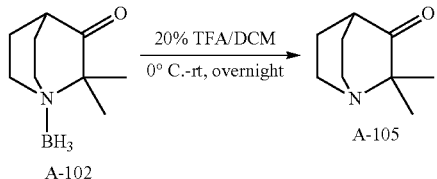

To a solution of 20% trifluoroacetic acid/dichloromethane (150 mL, v/v) at 0° C. was added portionwise compound A-102 (45 g, 0.27 mol). The mixture was stirred at room temperature overnight. On completion, the pH was adjusted to 8 by addition of saturated aqueous potassium carbonate solution at 0° C. The mixture was extracted with dichloromethane (2×200 mL). The combined organic layers were dried with sodium sulfate and concentrated in vacuo to give compound A-105 (40 g, 98% yield) as a white solid. $^1$H-NMR (CD$_3$OD, 400 MHz): 3.37-3.36 (m, 2H), 2.98-2.97 (m, 2H), 2.39-2.38 (m, 1H), 2.10-2.09 (m, 4H), 1.34 (s, 6H).

Example 6A: (R)—N-(2,2-dimethylquinuclidin-3-ylidene)-1-phenylethanamine ((R)-A-106)

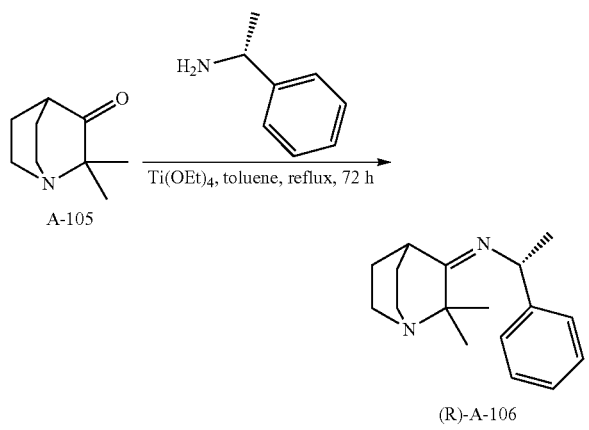

To a solution of compound A-105 (7.2 g, 47 mmol) and (R)-1-phenylethanamine (6.8 g, 56 mmol) in toluene (140 ml) was added titanium tetraethoxide (32 g, 0.14 mol), and the mixture was heated at reflux for 72 hours. On completion, the mixture was cooled to room temperature and poured into saturated aqueous potassium carbonate solution (500 mL). Ethyl acetate (500 mL) was added, and the mixture was stirred vigorously for 10 minutes and filtered over celite. The layers were separated, and the water layer was extracted with ethyl acetate (3×500 mL). The combined organic layers were dried with sodium sulfate and concentrated in vacuo to give compound (R)-A-106 (13 g, crude, 52% purity by LCMS) as a yellow oil. The material was used for the next step without further purification. LCMS (J): tR=1.337, (ES$^+$) m/z (M+H)$^+$=257.1.

Example 7A: (R)-2,2-dimethyl-N—((R)-1-phenylethyl)quinuclidin-3-amine ((R,R)-A-107)

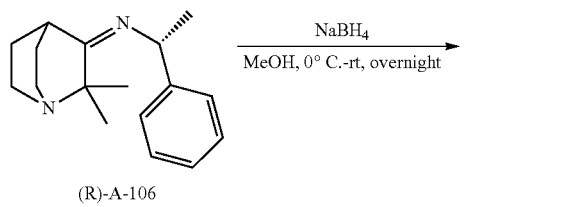

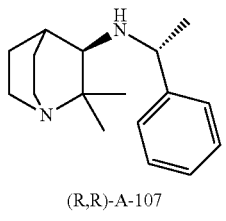

To a solution of compound (R)-A-106 (13 g, 26 mmol, 52% purity) in methanol (130 mL) at 0° C. was added sodium borohydride (5.0 g, 0.13 mol). The mixture was stirred for 30 minutes at 0° C., then allowed to warm to room temperature and stirred overnight. On completion, the reaction was poured into saturated aqueous potassium carbonate (500 mL), and the mixture was extracted with ethyl acetate (2×500 mL). The combined organic layers were dried over sodium sulfate and concentrated in vacuo to give 11 g of a clear oil. The crude product was purified by silica gel chromatography (petroleum ether:ethyl acetate=5:1) to give compound (R,R)-A-107 (7.3 g, 58% yield for two steps) as a clear oil. $^1$H-NMR (CD$_3$OD, 400 MHz): δ 7.34-7.26 (m, 4H), 7.22-7.18 (m, 1H), 3.78-3.73 (m, 1H), 3.35-3.18 (m, 1H), 3.06-3.01 (m, 1H), 2.61-2.53 (m, 2H), 2.32 (s, 1H), 1.81-1.78 (m, 1H), 1.63-1.54 (m, 2H), 1.44-1.42 (m, 1H), 1.41 (s, 3H), 1.31 (d, J=6.8 Hz, 3H), 1.30-1.26 (m, 1H), 1.21 (s, 3H).

Example 8A: (R)-2,2-dimethylquinuclidin-3-amine ((R)-A-104)

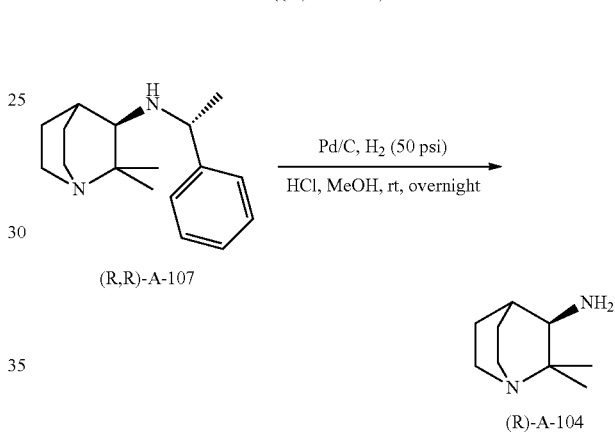

To a solution of compound (R,R)-A-107 (5.3 g, 21 mmol) in methanol (100 mL) was added 10% palladium/carbon, 50% wet (1.5 g) under nitrogen. The suspension was degassed in vacuo and purged with hydrogen several times. The resulting mixture was stirred at room temperature overnight under hydrogen (50 psi). On completion, the reaction mixture was filtered, and the filtrate was concentrated in vacuo to give compound (R)-A-104 (3.0 g, 93% yield) as a white semi-solid. $^1$H-NMR (CD$_3$OD, 400 MHz): 3.28-3.24 (m, 2H), 2.79-2.73 (m, 3H), 1.92-1.90 (m, 1H), 1.76-1.73 (m, 3H), 1.45-1.44 (m, 1H), 1.31 (s, 3H), 1.29 (s, 3H).

Example 9A: (S)—N-(2,2-dimethylquinuclidin-3-ylidene)-1-phenylethanamine ((S)-A-106)

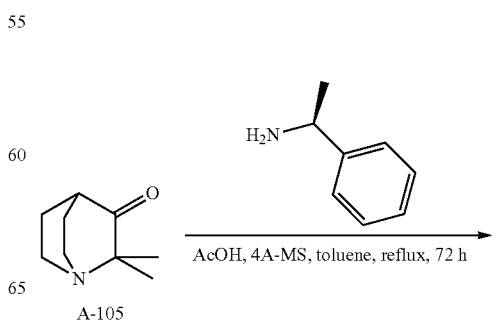

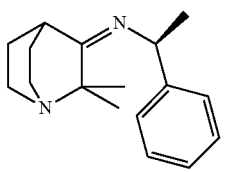

(S)-A-106

To a solution of compound A-105 (4.1 g, 27 mmol) and (S)-1-phenylethanamine (3.9 g, 32 mmol) in toluene (40 mL) were added acetic acid (1.6 g, 27 mmol) and 4A-molecular sieve (1.0 g). The mixture was heated at reflux for 72 hours. On completion, the mixture was cooled to room temperature and concentrated in vacuo to give compound (S)-A-106 (8.5 g, crude) as a yellow oil. LCMS showed 38% purity. This material was used for the next step directly without further purification. LCMS (J): tR=1.228, (ES$^+$) m/z (M+H)$^+$=257.2.

Example 10A: (S)-2,2-dimethyl-N—((S)-1-phenylethyl)quinuclidin-3-amine ((S,S)-A-107)

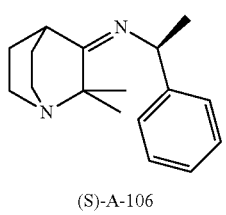

(S)-A-106

NaBH$_4$
———————————→
MeOH, 0° C.-rt, overnight

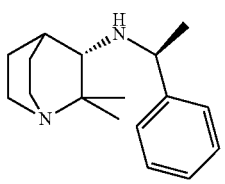

(S,S)-A-107

To a solution of compound (S)-A-106 (8.5 g, 13 mmol, 38% purity) in methanol (80 mL) at 0° C. was added sodium borohydride (2.4 g, 63 mmol). The reaction was stirred for 30 minutes at 0° C., then allowed to warm to room temperature and stirred overnight. On completion, the mixture was poured into saturated aqueous potassium carbonate (100 mL) and extracted with ethyl acetate (2×100 mL). The combined organic layers were dried over sodium sulfate and concentrated in vacuo to give 8.0 g of a clear oil. The crude product was purified by silica gel chromatography (petroleum ether:ethyl acetate=5:1) to give compound (S,S)-A-107 (1.8 g, 26% yield for two steps) as a clear oil. $^1$H-NMR (CD$_3$OD, 400 MHz): δ 7.34-7.28 (m, 4H), 7.22-7.19 (m, 1H), 3.78-3.73 (m, 1H), 3.27-3.21 (m, 1H), 3.08-3.04 (m, 1H), 2.65-2.58 (m, 2H), 2.34 (s, 1H), 1.84-1.82 (m, 1H), 1.65-1.56 (m, 2H), 1.45-1.43 (m, 1H), 1.36 (s, 3H), 1.31 (d, J=6.8 Hz, 3H), 1.23 (s, 3H), 1.15-1.14 (m, 1H).

Example 11A: (S)-2,2-dimethylquinuclidin-3-amine ((S)-A-104)

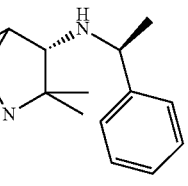

(S,S)-A-107

Pd/C, H$_2$ (50 psi)
———————————→
HCl, MeOH, rt, overnight

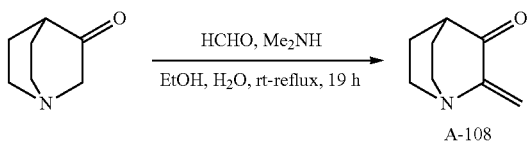

(S)-A-104

To a solution of compound (S,S)-A-107 (1.8 g, 7.0 mmol) in methanol (40 mL) was added 10% palladium/carbon, 50% wet (0.4 g) under nitrogen. The suspension was degassed in vacuo and purged with hydrogen several times. The resulting mixture was stirred under hydrogen (50 psi) at room temperature overnight. On completion, the reaction mixture was filtered, and the filtrate was concentrated in vacuo to give compound (S)-A-104 (1.0 g, 93% yield) as a white semi-solid. $^1$H-NMR (CD$_3$OD, 400 MHz): 3.44-3.36 (m, 2H), 3.03-2.93 (m, 2H), 2.90 (s, 1H), 2.07-2.02 (m, 1H), 1.92-1.85 (m, 3H), 1.65-1.58 (m, 1H), 1.43 (s, 3H), 1.39 (s, 3H).

Example 12A: 2-methylenequinuclidin-3-one (A-108)

To a mixture of quinuclidin-3-one (30 g, 0.24 mol) in ethanol/water (0.65 L, 2.5:1) was added dimethylamine (49 g, 0.36 mol) in one portion, followed by formaldehyde (28 g, 0.36 mol) in one portion at room temperature. After stirring at room temperature for 10 min, the reaction mixture was heated to reflux for 3 hours, and then stirred at 70° C. for 16 hours. TLC showed the starting material was consumed completely. The reaction mixture was cooled to room temperature and concentrated in vacuo. The residue was purified by distillation to give compound A-108 (14 g, 43% yield) as yellow oil. GCMS: tR=5.629, (EI$^+$) m/z (M)=137.2.

Example 13A: 1'-azaspiro[cyclopropane-1,2'-bicyclo[2.2.2]octan]-3'-one (A-109)

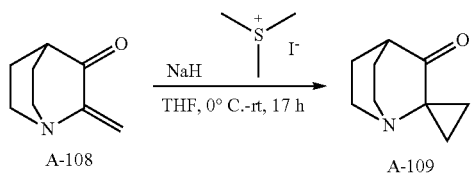

To a solution of trimethylsulfoxonium iodide (42 g, 0.19 mol) in anhydrous tetrahydrofuran (500 mL) at 0° C. was added sodium hydride (7.6 g, 0.19 mol). The reaction mixture was stirred at 0° C. for 1 hour, and compound A-108 (20 g, 0.15 mol) was added dropwise. The mixture was allowed to warm to room temperature and stirred for 16 hours. GCMS showed the reaction was completed. The reaction was quenched with saturated aqueous ammonium chloride solution and filtered. The filtrate was concentrated in vacuo, diluted with dichloromethane (200 mL) and water (200 mL) and extracted with dichloromethane (3×600 mL). The combined organic layers were washed with brine (2×400 mL), dried over anhydrous sodium sulfate, filtered and concentrated in vacuo. The residue was purified by aluminum oxide column chromatography [petroleum ether: ethyl acetate=5:1] to give compound A-109 (4.8 g, 22% yield) as a white solid. GCMS: tR=7.253, (EI$^+$) m/z (M+H)$^+$= 151.1, $^1$H-NMR (CDCl$_3$, 400 MHz): δ 3.09-3.03 (m, 4H), 2.56-2.55 (m, 1H), 2.05-2.00 (m, 4H), 1.40-1.39 (m, 2H), 1.14-1.12 (m, 2H).

Example 14A: 1'-azaspiro[cyclopropane-1,2'-bicyclo[2.2.2]octan]-3'-one oxime hydrochloride (A-110)

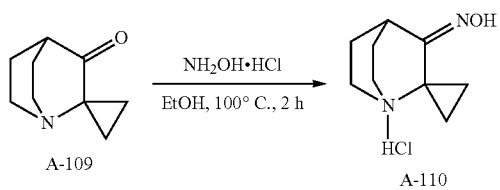

To a mixture of compound A-109 (1.0 g, 6.6 mmol) in anhydrous ethanol (5 mL) was added hydroxylamine hydrochloride (0.48 g, 7.0 mmol) at room temperature. The mixture was stirred at 100° C. for 2 hours. On completion, the solution was cooled to room temperature, resulting in formation of a precipitate. The precipitation was collected by filtration to give compound A-110 (0.80 g, 60% yield) as a white solid.

Example 15A: (+/−)-1'-azaspiro[cyclopropane-1,2'-bicyclo[2.2.2]octan]-3'-amine (rac-A-111)

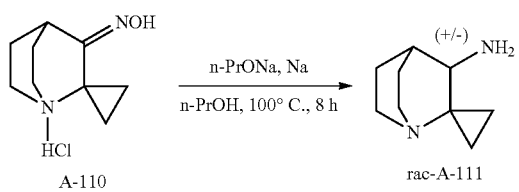

To a mixture of compound A-110 (1.0 g, 4.9 mmol) in n-propyl alcohol (10 mL) was added sodium propoxide (0.40 g, 4.9 mmol sodium in 2 mL n-propyl alcohol) at room temperature. The solution was heated to 100° C., and sodium (1.1 g, 49 mmol) was added in portions. The mixture was stirred at this temperature for 8 hours. On completion, the mixture was poured into water (2 mL), concentrated in vacuo, diluted with dichloromethane and filtered. The resulting filtrate was concentrated in vacuo to give rac-A-111 (0.50 g, 67% yield) as a yellow oil.

Example 16A: (R)-1-phenyl-N-(1'-azaspiro[cyclopropane-1,2'-bicyclo[2.2.2]octan]-3'-ylidene)ethanamine ((R)-A-112)

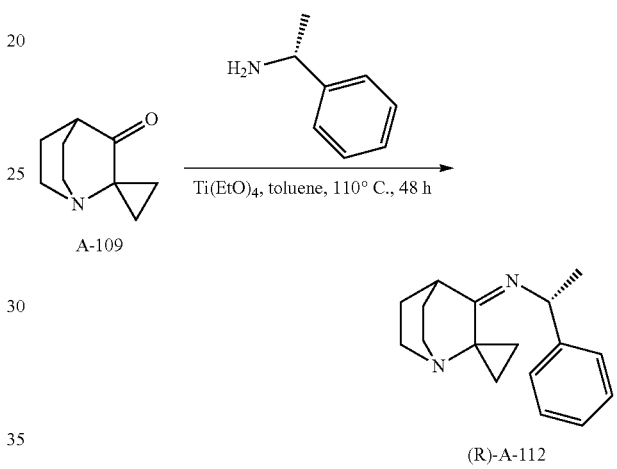

To a solution of compound A-109 (2.0 g, 13 mmol) in anhydrous toluene (30 mL) was added (R)-1-phenylethanamine (1.6 g, 13 mmol) and ethyl titanate (9.1 g, 40 mmol). The resulting mixture was stirred at 110° C. for 48 hours. On completion, the reaction was quenched with saturated aqueous potassium carbonate (100 mL) and extracted with ethyl acetate (3×100 mL). The combined organic layers were washed with brine, dried over sodium sulfate and concentrated in vacuo to give compound (R)-A-112 (3.2 g, crude) as a yellow oil, which was used for next step without further purification. LCMS (J): tR=1.594, (ES$^+$) m/z (M+H)$^+$= 255.1.

Example 17A: (R)—N—((R)-1-phenylethyl)-1'-azaspiro[cyclopropane-1,2'-bicyclo[2.2.2]octan]-3'-amine ((R,R)-A-113)

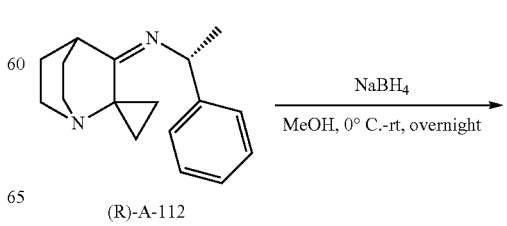

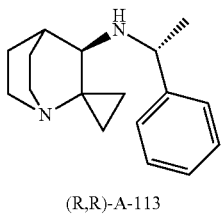

(R,R)-A-113

To a mixture of compound (R)-A-112 (3.2 g, 13 mmol) in anhydrous methanol (30 mL) was added sodium borohydride (1.0 g, 25 mmol) slowly at 0° C. The resulting mixture was stirred at room temperature overnight. On completion, the reaction was quenched with water (10 mL) and extracted with ethyl acetate (3×30 mL). The combined organic layers were washed with brine, dried over sodium sulfate, concentrated in vacuo and purified by silica gel chromatography [dichloromethane:methanol=5:1] to give compound (R,R)-A-113 (1.1 g, 41% yield for two steps) as a yellow oil. $^1$H-NMR (CD$_3$OD, 400 MHz): 7.34-7.28 (m, 4H), 7.24-7.22 (m, 1H), 3.66-3.63 (m, 1H), 3.01-2.89 (m, 1H), 2.74-2.73 (m, 1H), 2.72-2.65 (m, 3H), 1.90-1.79 (m, 2H), 1.70-1.65 (m, 1H), 1.55-1.51 (m, 1H), 1.37-1.35 (m, 1H), 1.29 (d, J=6.4 Hz, 3H), 1.12-1.07 (m, 1H), 0.85-0.80 (m, 1H), 0.59-0.47 (m, 2H).

Example 18A: (R)-1'-azaspiro[cyclopropane-1,2'-bicyclo[2.2.2]octan]-3'-amine ((R)-A-111)

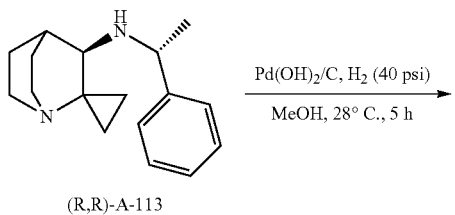

(R,R)-A-113

(R)-A-111

To a mixture of compound (R,R)-A-113 (1.4 g, 5.5 mmol) in anhydrous methanol (15 mL) was added 10% palladium hydroxide/carbon, 50% wet (600 mg) under nitrogen. The suspension was degassed in vacuo and purged with hydrogen several times. The resulting mixture was stirred under hydrogen (40 psi) at 28° C. for 5 hours. On completion, the reaction mixture was filtered, and the filtrate was concentrated in vacuo to give compound (R)-A-111 (0.75 g, 90% yield) as a light yellow oil. $^1$H-NMR (CD$_3$OD, 400 MHz): 3.04-2.94 (m, 2H), 2.82-2.76 (m, 3H), 1.92-1.84 (m, 2H), 1.79-1.70 (m, 2H), 1.46-1.43 (m, 1H), 1.00-0.95 (m, 1H), 0.82-0.77 (m, 1H), 0.58-0.49 (m, 2H).

Example 19A: (S)-1-phenyl-N-(1'-azaspiro[cyclopropane-1,2'-bicyclo[2.2.2]octan]-3'-ylidene)ethanamine ((S)-A-112)

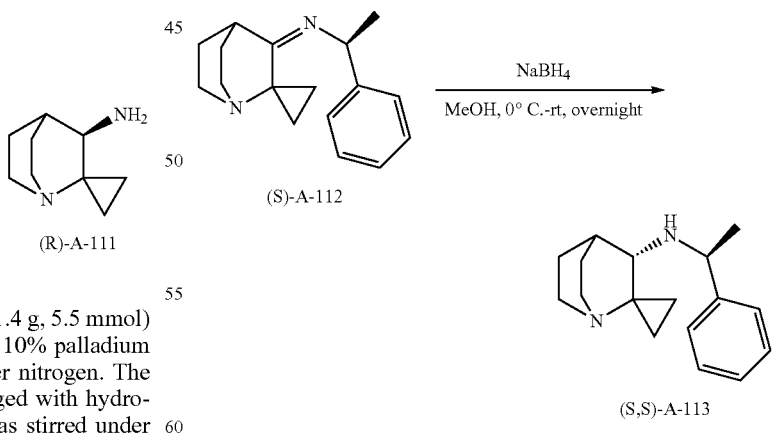

To a solution of compound A-109 (2.0 g, 13 mmol) in anhydrous toluene (30 mL) was added (S)-1-phenylethanamine (1.6 g, 13 mmol) and ethyl titanate (9.1 g, 40 mmol). The resulting mixture was stirred at 110° C. for 48 hours. On completion, the reaction was quenched with saturated aqueous potassium carbonate (100 mL) and extracted with ethyl acetate (5×30 mL). The combined organic layers were washed with brine, dried over sodium sulfate and concentrated in vacuo to give compound (S)-A-112 (2.3 g, crude) as a yellow oil, which was used for the next step without further purification. LCMS (J): tR=1.295, (ES$^+$) m/z (M+H)$^+$=255.1.

Example 20A: (S)—N—((S)-1-phenylethyl)-1'-azaspiro[cyclopropane-1,2'-bicyclo[2.2.2]octan]-3'-amine ((S,S)-A-113)

To a mixture of compound (S)-A-112 (2.3 g, crude) in anhydrous methanol (25 mL) was added sodium borohydride (1.0 g, 25 mmol) slowly at 0° C. The resulting mixture was stirred at room temperature overnight. On completion, the reaction was quenched by water (8 mL) and extracted with ethyl acetate (3×25 mL). The combined organic layers were concentrated in vacuo and purified by silica gel chromatography [dichloromethane:methanol=5:1] to give compound (S,S)-A-113 (1.0 g, 37%) yield for two steps) as a yellow oil. $^1$H-NMR (CD$_3$OD, 400 MHz): 7.32-7.25 (m, 4H), 7.22-7.18 (m, 1H), 3.64-3.58 (m, 1H), 3.02-2.99 (m, 1H), 2.89-2.86 (m, 1H), 2.76-2.64 (m, 3H), 1.85-1.76 (m, 2H), 1.67-1.65 (m, 1H), 1.52-1.50 (m, 1H), 1.34-1.32 (m, 1H), 1.26 (d, J=6.4 Hz, 3H), 1.08-1.04 (m, 1H), 0.82-0.78 (m, 1H), 0.56-0.46 (m, 2H).

Example 21A: (S)-1'-azaspiro[cyclopropane-1,2'-bicyclo[2.2.2]octan]-3'-amine ((S)-A-111)

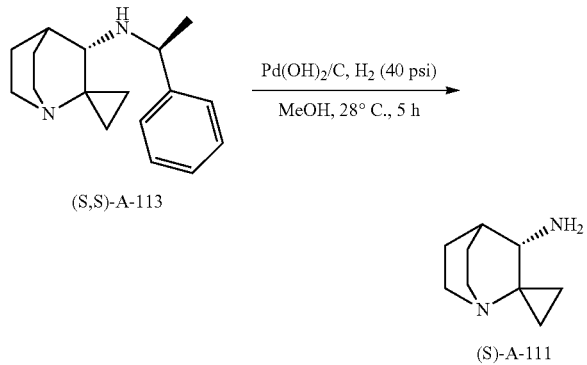

To a mixture of compound (S,S)-A-113 (1.0 g, 3.9 mmol) in anhydrous methanol (10 mL) was added 10% palladium hydroxide/carbon, 50% wet (400 mg) under nitrogen. The suspension was degassed in vacuo and purged with hydrogen several times. The mixture was stirred under hydrogen (40 psi) at 28° C. for 5 hours. On completion, the reaction mixture was filtered, and the filtrate was concentrated in vacuo to give compound (S)-A-111 (0.55 g, 92% yield) as a light yellow oil. $^1$H-NMR (CD$_3$OD, 400 MHz): 3.04-2.94 (m, 2H), 2.82-2.75 (m, 3H), 1.97-1.84 (m, 2H), 1.79-1.74 (m, 2H), 1.47-1.43 (m, 1H), 1.00-0.95 (m, 1H), 0.81-0.76 (m, 1H), 0.58-0.49 (m, 2H).

Example 1B: methyl 6-chlorobenzo[b]thiophene-2-carboxylate (B-101)

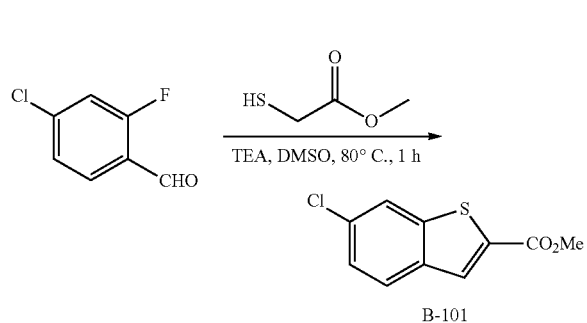

To a mixture of 4-chloro-2-fluorobenzaldehyde (50 g, 0.32 mol) and methyl 2-mercaptoacetate (40 g, 0.38 mol) in dimethylsulfoxide (500 mL) was added triethylamine (96 g, 0.95 mol) at room temperature. The mixture was stirred at 80° C. for 1 hour. On completion, the reaction mixture was cooled to room temperature and poured into ice water (4 L), resulting in formation of a solid. The mixture was stirred for half an hour, and the solid was collected by filtration, washed with water and dried in vacuo to give compound B-101 (80 g, crude) as a yellow solid. LCMS: (ES$^+$) m/z (M+H)$^+$=227.0.

Example 2B; 6-chlorobenzo[b]thiophene-2-carboxylic acid (B-102)

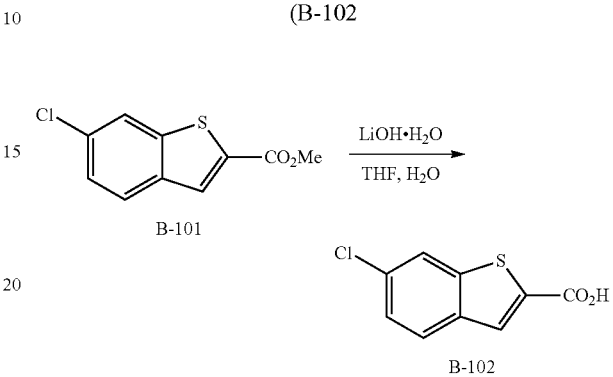

To a solution of compound B-101 (10 g, 44 mmol) in tetrahydrofuran (200 mL) and water (10 mL) was added lithium hydroxide monohydrate (5.6 g, 0.13 mol). The reaction mixture was stirred at room temperature overnight. On completion, the reaction mixture was concentrated in vacuo to remove tetrahydrofuran and poured into water (400 mL). The pH was adjusted to 3 with 4M hydrochloric acid, resulting in formation of a solid. The solid was collected by filtration, washed with water and dried in vacuo to give compound B-102 (5.6 g, 60% yield) as a white solid. LCMS: (ES$^+$) m/z (M+H)$^+$=212.9.

Example 3B: methyl 5-chlorobenzo[b]thiophene-2-carboxylate (B-103)

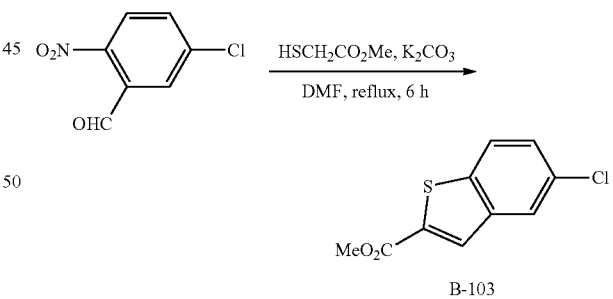

To a mixture of 5-chloro-2-nitrobenzaldehyde (10 g, 54 mmol) in anhydrous dimethyl formamide (100 mL) was added methyl 2-mercaptoacetate (5.7 g, 45 mmol) and K$_2$CO$_3$ (19 g, 135 mmol). The mixture was stirred at reflux for 6 hours. On completion, the reaction mixture was cooled to room temperature and poured into ice water (500 mL), resulting in formation of a solid. The mixture was stirred for 30 minutes, and the solid was collected by filtration, washed with water and dried in vacuo to give compound B-103 (4 g, 31% yield) as a white solid. LCMS: (ES$^+$) m/z (M+H)$^+$=227.0.

Example 4B: 5-chlorobenzo[b]thiophene-2-carboxylic acid (B-104)

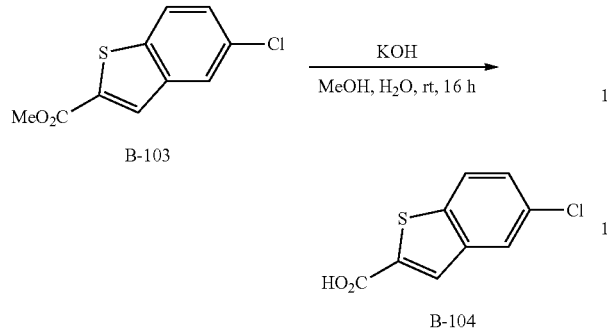

To a mixture of compound B-103 (4.0 g, 18 mmol) in methanol (80 mL) and water (40 mL) was added potassium hydroxide (2.0 g, 2.9 mmol). The mixture was stirred at room temperature for 16 hours. On completion, the reaction mixture was concentrated in vacuo to remove methanol and poured into water (400 mL). The pH was adjusted to 3 with 4M hydrochloric acid, resulting in formation of a solid. The solid was collected by filtration, washed with water and dried in vacuo to give compound B-104 (3.5 g, 93% yield) as a white solid.

Example 5B: 4,5-dichloro-2-nitrobenzaldehyde (B-105)

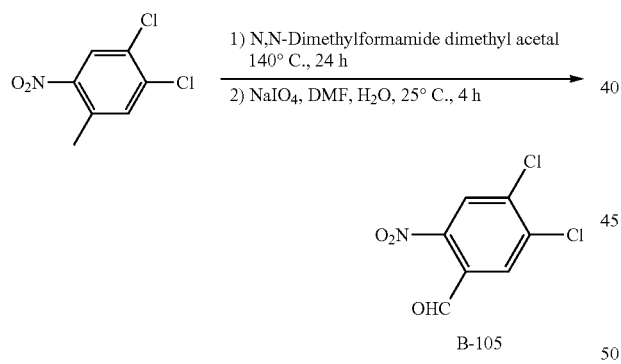

A solution of 4,5-dichloro-2-nitrotoluene (8.0 g, 39 mmol) in N,N-dimethylformamide dimethyl acetal (15 mL, 0.12 mol) was heated at reflux at 140° C. for 24 hours. The reaction mixture was then cooled to room temperature and added dropwise to a solution of sodium periodate (25 g, 0.12 mol) in N,N-dimethylformamide (50 mL) and water (75 mL). The reaction mixture was stirred at room temperature for 4 hours, and then filtered to remove solids. The filtrate was extracted with toluene (2×15 mL), and the combined organic layers were washed with water (2×30 mL) and brine (10 mL) and concentrated in vacuo. The residue was purified by silica gel chromatography [petroleum ether:ethyl acetate=10:1] to give compound B-105 (1.8 g, 21% yield) as a white solid. $^1$H-NMR (CDCl$_3$, 400 MHz): δ 10.42 (s, 1H), 8.29 (s, 1H), 8.07 (s, 1H).

Example 6B: methyl 5,6-dichlorobenzo[b]thiophene-2-carboxylate (B-106)

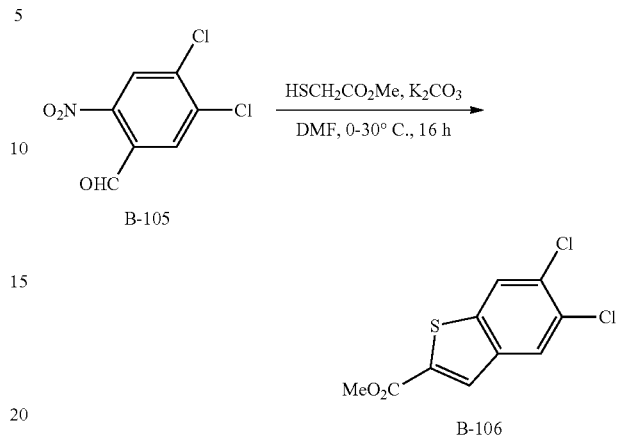

A solution of compound B-105 (1.6 g, 7.1 mmol) and potassium carbonate (2.0 g, 14 mmol) in N,N-dimethylformamide (20 mL) was stirred at 0° C. for 30 min. Methyl 2-sulfanylacetate (0.90 g, 8.5 mmol) was added slowly, and the reaction was stirred at 0° C. for 30 min and at 30° C. for 15 hours. On completion, the reaction was quenched with water (10 mL) and extracted with dichloromethane (3×20 mL). The combined organic layers were washed with brine, dried over sodium sulfate and concentrated in vacuo. The residue was purified by silica gel chromatography [petroleum ether:ethyl acetate=30:1] to give compound B-106 (1.5 g, 81% yield) as a light yellow solid.

Example 7B: methyl 5,6-dichlorobenzo[b]thiophene-2-carboxylate (B-107)

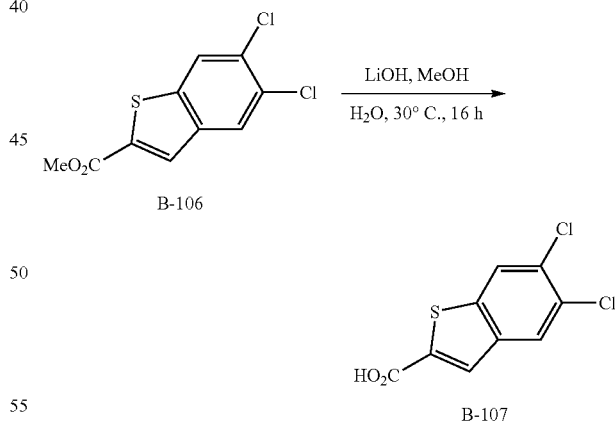

To a solution of compound B-106 (0.50 g, 1.9 mmol) in methanol (15 mL) and water (5 mL) was added lithium hydroxide (0.14 g, 5.7 mmol). The resulting mixture was stirred at 30° C. for 16 hours. On completion, the reaction solution was concentrated in vacuo to remove methanol. The pH was adjusted to 6 with concentrated hydrochloric acid, resulting in formation of a solid. The solid was collected by filtration and dried in vacuo to give compound B-107 (0.40 g, 85% yield) as a white solid. LCMS: (ES$^+$) m/z (M+H)$^+$ =200.9.

Example 8B: ethyl 5-methylbenzo[b]thiophene-2-carboxylate (B-108)

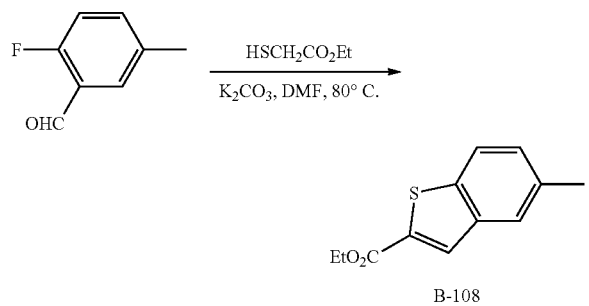

A mixture of 2-fluoro-5-methylbenzaldehyde (2.0 g, 14 mmol), ethyl 2-mercaptoacetate (1.8 g, 17 mmol) and potassium carbonate (4.0 g, 29 mmol) in N,N-dimethylformamide (30 mL) was stirred at 80° C. for 4 hours. On completion, the mixture was poured into ice-water, resulting in formation of a solid. The mixture was stirred for 30 min., and the solid was collected by filtration, washed with water and dried in vacuo to give compound B-108 (2.2 g, 74% yield) as a yellow solid.

Example 9B: 5-methylbenzo[b]thiophene-2-carboxylic acid (B-109)

To a solution of compound B-108 (0.20 g, 1.0 mmol) in tetrahydrofuran/methanol/water (1:1:1, 15 mL) was added lithium hydroxide hydrate (0.12 g, 2.9 mmol). The mixture was stirred at 25° C. for 3 hours. On completion, the reaction mixture was concentrated in vacuo to remove tetrahydrofuran and methanol and poured into water (10 mL). The pH was adjusted to 3 with 4M hydrochloric acid, resulting in formation of a solid. The solid was collected by filtration, washed with water and dried in vacuo to give compound B-109 (0.10 g, 54% yield) as a yellow solid. LCMS: (ES$^+$) m/z (M+H)$^+$=193.1.

Example 10B: methyl 6-bromobenzo[b]thiophene-2-carboxylate (B-110)

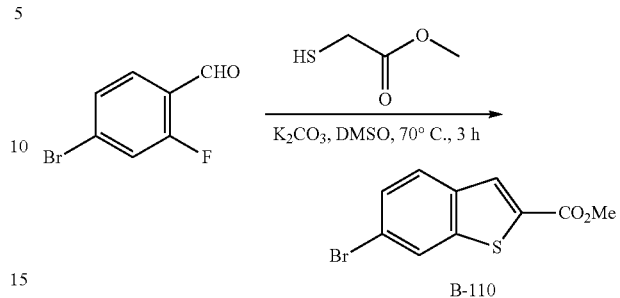

To a solution of 4-bromo-2-fluorobenzaldehyde (10 g, 49 mmol) and methyl 2-mercaptoacetate (7.8 g, 74 mmol) in dimethylsulfoxide (100 mL) was added potassium carbonate (13 g, 99 mmol) portionwise at room temperature. The resulting mixture was stirred at 70° C. for 3 hours. On completion, the mixture was poured into ice-water, resulting in formation of a solid. The mixture was stirred for 30 min., and the solid was collected by filtration, washed with water and dried in vacuo. The residue was purified by silica gel chromatography [petroleum ether:ethyl acetate=7:1] to give compound B-110 (8.1 g, 61% yield) as a white solid.

Example 11B: methyl 6-cyclopropylbenzo[b]thiophene-2-carboxylate (B-111)

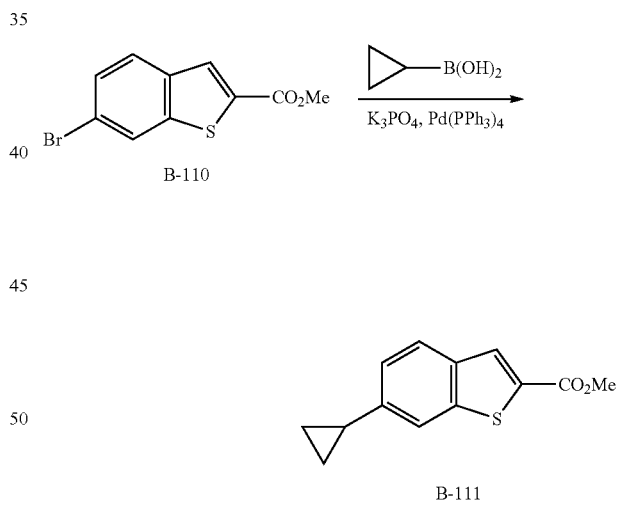

To a solution of compound B-110 (2.7 g, 10 mmol) and cyclopropylboronic acid (0.73 g, 10 mmol) in anhydrous toluene (50 mL) under N$_2$ was added tetrakis(triphenylphosphine)palladium(0) (0.54 g, 0.47 mmol), followed by a solution of potassium phosphate (3.2 g, 15 mmol) in water (5 mL). The solution was stirred at room temperature for 0.5 hour before being heated to reflux for 7 hours. On completion, the mixture was cooled to room temperature and filtered. The filtrate was concentrated and purified by silica gel chromatography [petroleum ether:ethyl acetate=60:1] to give compound B-111 (1.8 g, 70% yield) as a white solid. LCMS: (ES$^+$) m/z (M+H)$^+$=233.0.

Example 12B: 6-cyclopropylbenzo[b]thiophene-2-carboxylic acid (B-112)

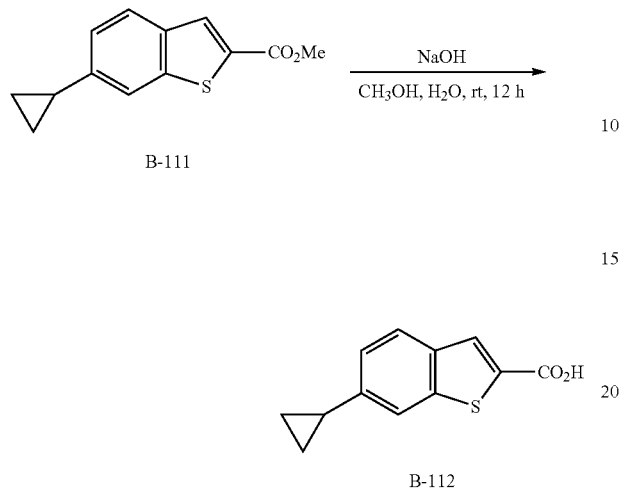

To a solution of compound B-111 (0.52 g, 2.2 mmol) in methanol/water (1:1, 10 mL) was added sodium hydroxide (0.18 g, 4.4 mmol). The mixture was stirred at room temperature for 12 hours. On completion, the reaction mixture was concentrated in vacuo to remove tetrahydrofuran and poured into water (20 mL). The pH was adjusted to 3 with 4M hydrochloric acid, and the mixture was extracted with dichloromethane (20 mL×3). The combined organic layers were washed with water and brine, dried over anhydrous sodium sulfate and concentrated in vacuo to give compound B-112 (0.38 g, 78% yield) as a white solid.

Example 13B: methyl 5-bromobenzo[b]thiophene-2-carboxylate (B-113)

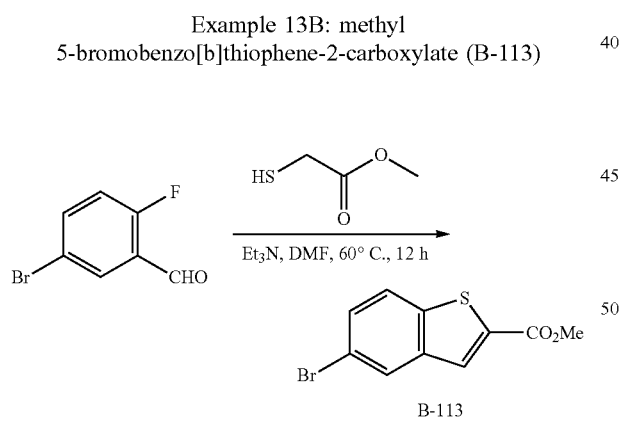

To a solution of 5-bromo-2-fluorobenzaldehyde (6.0 g, 30 mmol) and methyl 2-mercaptoacetate (3.8 g, 35 mmol) in N,N-dimethyl formamide (50 mL) was added triethylamine (8.97 g, 89 mmol) portionwise at room temperature. The resulting mixture was stirred at 60° C. for 12 hours. On completion, the mixture was poured into ice-water resulting in formation of a solid. The mixture was stirred for 30 min., and the solid was collected by filtration, washed with water and dried in vacuo. The residue was purified by silica gel chromatography [petroleum ether:ethyl acetate=7:1] to give compound B-113 (5.5 g, 69% yield) as a white solid.

Example 14B: methyl 5-cyclopropylbenzo[b]thiophene-2-carboxylate (B-114)

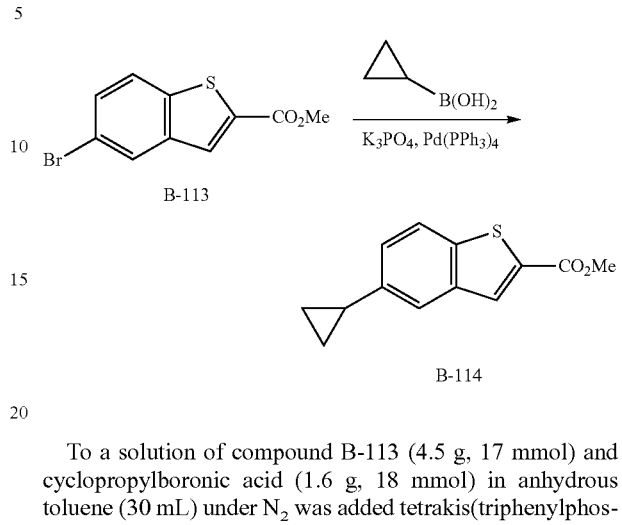

To a solution of compound B-113 (4.5 g, 17 mmol) and cyclopropylboronic acid (1.6 g, 18 mmol) in anhydrous toluene (30 mL) under $N_2$ was added tetrakis(triphenylphosphine)palladium(0) (0.98 g, 0.83 mmol), followed by a solution of potassium phosphate (5.3 g, 25 mmol) in water (10 mL). The resulting solution was stirred at room temperature for 0.5 hour before being heated to reflux for 12 hours. On completion, the mixture was cooled to room temperature and filtered. The resulting filtrate was concentrated and purified by silica gel chromatography [petroleum ether:ethyl acetate=40:1-15:1] to give compound B-114 (2.8 g, 73% yield) as a white solid. LCMS: (ES$^+$) m/z (M+H)$^+$ =233.0.

Example 15B: 5-cyclopropylbenzo[b]thiophene-2-carboxylic acid (B-115)

To a solution of compound B-114 (0.80 g, 3.4 mmol) in water (20 mL) was added lithium hydroxide hydrate (0.43 g, 10 mmol), the result mixture was stirred at room temperature for 4 hours. On completion, the reaction mixture was concentrated in vacuo to remove tetrahydrofuran and was then poured into water (20 mL). The pH was adjusted to 3 with 4M hydrochloric acid, and the mixture was extracted with dichloromethane (60 mL×3). The combined organic layers were washed with water and brine, dried over anhydrous sodium sulfate and concentrated in vacuo to give compound B-115 (0.70 g, 92% yield) as a white solid.

Example 16B: methyl 6-cyanobenzo[b]thiophene-2-carboxylate (B-116)

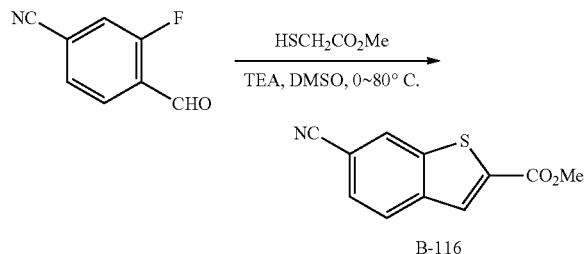

To a solution of 3-fluoro-4-formylbenzonitrile (3.6 g, 24 mmol) and triethylamine (4.8 g, 48 mmol) in dimethylsulfoxide (40 mL) was added methyl 2-mercaptoacetate (3.1 g, 29 mmol) at 0° C. The reaction was stirred at 80° C. overnight. On completion, the solution was poured into ice water, and the resulting mixture was filtered. The filtrate was concentrated in vacuo to give compound B-116 (4.0 g, 77% yield) as a yellow solid.

Example 17B: 6-cyanobenzo[b]thiophene-2-carboxylic acid (B-117)

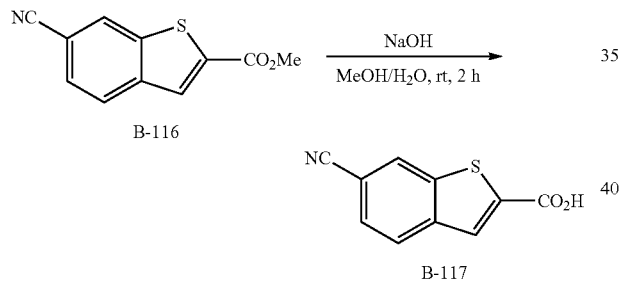

To a solution of B-116 (4.0 g, 18 mmol) in methanol (20 mL) and water (20 mL) was added sodium hydroxide (1.5 g, 37 mmol) at room temperature. The mixture was stirred for 2 hours. On completion, the solution was concentrated to remove most of the methanol, and then the pH was adjusted to 4-5, resulting in formation of a solid. The solid was collected by filtration and dried to give compound B-117 (3.4 g, 91% yield) as a brown solid.

Example 18B: (3-bromophenyl)(2,2-dimethoxypropyl)sulfane (B-118)

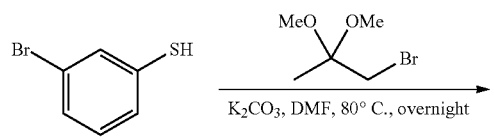

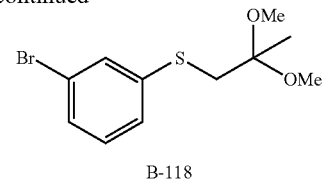

To a mixture of 3-bromobenzenethiol (8.7 g, 46 mmol) and 1-bromo-2,2-dimethoxypropane (8.4 g, 46 mmol) in N,N-dimethylformamide (50 mL) was added potassium carbonate (9.5 g, 69 mmol) at room temperature. The mixture was stirred at 80° C. overnight. On completion, the reaction mixture was quenched with water and extracted with ethyl acetate (3×100 mL). The combined organic layers were washed with water and brine, dried over anhydrous sodium sulfate and concentrated in vacuo to give crude compound B-118 (13 g, 97% yield) as colorless oil.

Example 19B: 6-bromo-3-methylbenzo[b]thiophene & 4-bromo-3-methylbenzo[b]thiophene (B-119 & B-120)

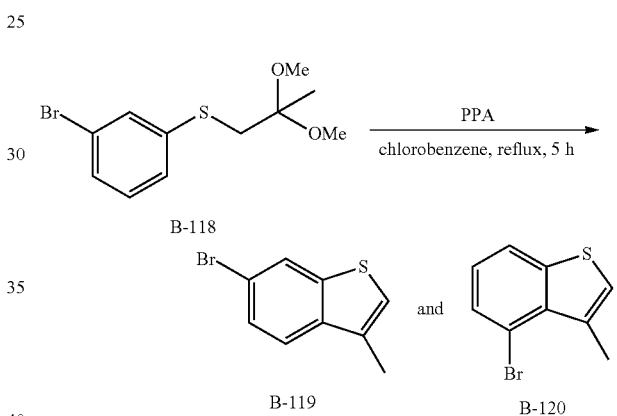

To a mixture of polyphosphoric acid (130 g) in chlorobenzene (100 mL) at reflux was added dropwise a solution of B-118 (13 g, 45 mmol) in chlorobenzene (130 mL). The mixture was stirred at reflux for 5 hours. On completion, the reaction mixture was cooled to room temperature and quenched with water (200 mL). The resulting mixture was extracted with dichloromethane (3×200 mL). The combined organic layers were washed with water and brine, dried over anhydrous sodium sulfate and concentrated in vacuo. The residue was purified by silica gel chromatography [petroleum ether:ethyl acetate=1:0] to give compound B-119 & B-120 (8.0 g, 79% yield) as a colorless oil.

Example 20B: methyl 3-methylbenzo[b]thiophene-6-carboxylate & methyl 3-methylbenzo[b]thiophene-4-carboxylate (B-121)

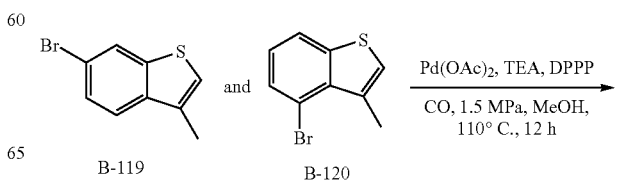

-continued

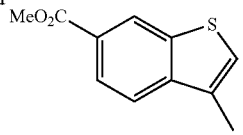

B-121

To a mixture of compound B-119 & B-120 (0.50 g, 2.2 mmol), 1,3-bis(diphenylphosphino)propane (0.45 g, 1.1 mmol) and palladium acetate (0.12 g, 0.55 mmol) in methanol (10 mL) was added triethylamine (0.67 g, 6.6 mmol) at room temperature. The resulting mixture was stirred overnight in a 50 mL autoclave at 110° C. under carbon monoxide (1.5 MPa). On completion, the mixture was cooled to room temperature and filtered. The filtrate was poured into water and extracted with ethyl acetate (3×40 mL). The combined organic layers were washed with water and brine, dried over anhydrous sodium sulfate and concentrated in vacuo. The residue was purified by silica gel chromatography [petroleum ether:ethyl acetate=1:0] to give compound B-121 (0.20 g, 44% yield) as a yellow solid. LCMS (B): tR=0.856, (ES$^+$) m/z (M)$^+$=207.1.

Example 21B: thieno[2,3-c]pyridine-5-carboxylic acid (B-122)

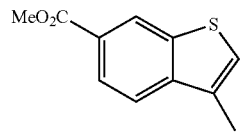

B-121

LiOH·H$_2$O
────────→
THF, MeOH, H$_2$O

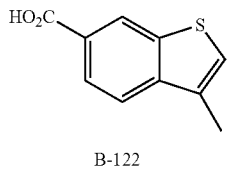

B-122

To a solution of compound B-121 (0.18 g, 0.87 mmol) in tetrahydrofuran (5 mL), methanol (5 mL) and water (5 mL) was added lithium hydroxide monohydrate (73 mg, 1.8 mmol). The reaction mixture was stirred at room temperature overnight. On completion, the reaction mixture was concentrated in vacuo to remove tetrahydrofuran and poured into water (50 mL). The pH was adjusted to 3 with 4M hydrochloric acid, resulting in formation of a solid. The solid was collected by filtration, washed with water and dried in vacuo to give compound B-122 (0.16 g, 95% yield) as a white solid.

Example 22B: methyl 2,3-dihydro-[1,4]dioxino[2,3-c]pyridine-7-carboxylate (B-123)

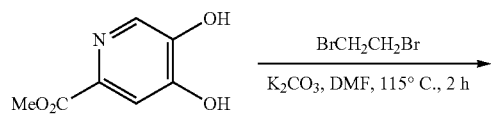

-continued

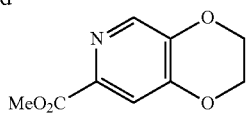

B-123

To a mixture of methyl 4,5-dihydroxypicolinate (1.0 g, 5.9 mmol) in N,N-dimethylformamide (70 mL) was added potassium carbonate (8.2 g, 59 mmol) and 1,2-dibromoethane (2.4 g, 13 mmol). The mixture was stirred at 115° C. for 2 hours. On completion, the mixture was diluted with ethyl acetate and washed with water three times. The organic layer was concentrated in vacuo to give compound B-123 (0.80 g, 69% yield) as a yellow solid.

Example 23B: 2,3-dihydro-[1,4]dioxino[2,3-c]pyridine-7-carboxylic acid (B-124)

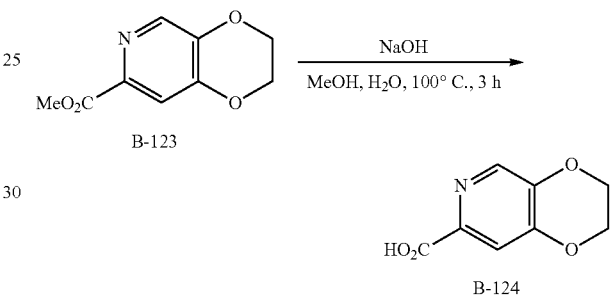

To a mixture of compound B-123 (0.80 g, 4.1 mmol) in methanol (40 mL) and water (40 mL) was added sodium hydroxide (1.6 g, 41 mmol). The mixture was stirred at 100° C. for 3 hours. On completion, the mixture was adjusted to pH=5.0 with 1 M hydrochloric acid, evaporated to removed methanol and extracted with dichloromethane three times. The organic layer was concentrated in vacuo to give compound B-124 (0.70 g, 94% yield) as a yellow solid: LCMS (A): tR=0.168 min., 182.0 m/z (M+1).

Example 24B: 1-((4-bromophenyl)thio)propan-2-one (B-125)

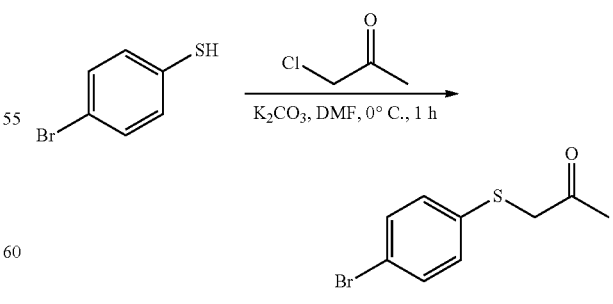

To a mixture of 4-bromobenzenethiol (20 g, 0.11 mol) in N,N-dimethylformamide (150 mL) was added 1-chloropropan-2-one (9.9 g, 0.11 mol) and potassium carbonate (29 g, 0.21 mol) at 0° C. The mixture was stirred at this temperature for 1 hour. On completion, the reaction was diluted with ethyl acetate and washed four times with water. The organic layer was dried over anhydrous sodium sulfate and concentrated in vacuo to give compound B-125 (25 g, crude) as a yellow oil which was used for the next step without another purification: LCMS (B): tR=0.828 min., 246.9 m/z (M+1).

Example 25B: 5-bromo-3-methylbenzo[b]thiophene (B-126)

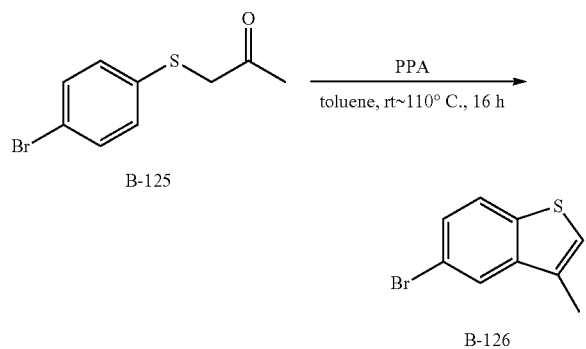

To a mixture of compound B-125 (25 g, 0.10 mol) in toluene (400 mL) was added polyphosphoric acid (0.15 kg) at room temperature. The mixture was stirred at 110° C. for 16 hours. On completion, the reaction was poured into saturated aqueous sodium bicarbonate solution and extracted with ethyl acetate three times. The combined organic layers were dried over anhydrous sodium sulfate and concentrated in vacuo. The residue was purified by silica gel chromatography (petroleum ether: ethyl acetate=10:1) to give compound B-126 (16 g, 69% yield) as a yellow oil.

Example 26B:
3-methylbenzo[b]thiophene-5-carboxylic acid (B-127)

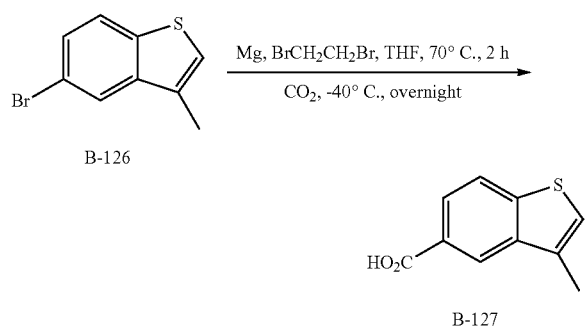

To a mixture of compound B-126 (2.0 g, 8.8 mmol) in tetrahydrofuran (20 mL) was added magnesium (0.32 g, 13 mmol) and 1,2-dibromoethane (0.17 g, 0.88 mmol) at room temperature. The mixture was stirred at 70° C. for 2 hours, and then the reaction was stirred at −40° C. under carbon dioxide gas overnight. On completion, the reaction was poured into water and washed with ethyl acetate. The pH of the aqueous phase was adjusted to 5.0 with 1 M hydrochloric acid, resulting in formation of a sold. The solid was collected by filtration and dried in vacuo to give compound B-127 (0.5 g, 30% yield) as a white solid: LCMS (B): tR=0.764 min., 193.1 m/z (M+1).

Example 27B: benzofuran-6-carboxylic acid (B-128)

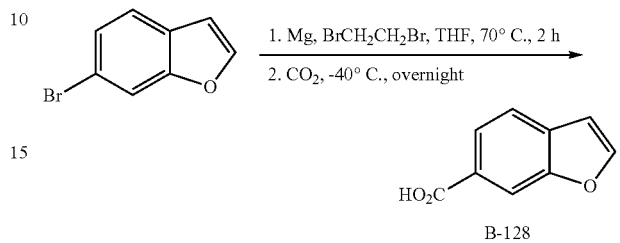

To a mixture of 6-bromobenzofuran (1.0 g, 5.1 mmol) in tetrahydrofuran (15 mL) was added magnesium (0.19 g, 7.6 mmol) and 1,2-dibromoethane (95 mg, 0.51 mmol). The mixture was stirred at 70° C. for 2 hours, and then the reaction was stirred at −40° C. under carbon dioxide gas overnight. On completion, the mixture was poured into water and washed with ethyl acetate. The aqueous phase was adjusted to pH=5.0 with hydrochloric acid, resulting in formation of a solid. The solid was collected by filtration and dried in vacuo to give compound B-128 (0.20 g, 24% yield) as a yellow solid.

Example 28B:
2-methylbenzo[d]oxazole-5-carboxylic acid (B-129)

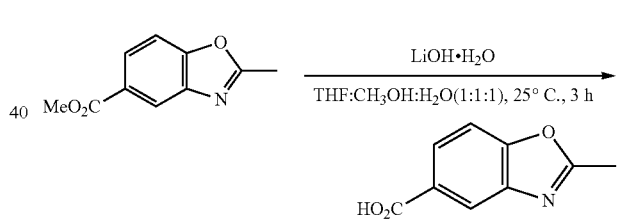

To a solution of methyl 2-methylbenzo[d]oxazole-5-carboxylate (0.50 g, 2.6 mmol) in tetrahydrofuran/methanol/water (1:1:1, 15 mL) was added lithium hydroxide hydrate (0.22 g, 5.2 mmol). The resulting mixture was stirred at 25° C. for 3 hours. On completion, the mixture was acidified by hydrochloric acid, resulting in formation of a solid. The solid was collected by filtration, washed with water and dried in vacuo. The residue was purified by silica gel chromatography [petroleum ether:ethyl acetate=1:1] to give compound B-129 (0.30 g, 65% yield) as a white solid.

Example 29B:
2-methylbenzo[d]oxazole-6-carboxylic acid (B-130)

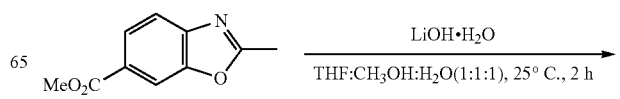

-continued

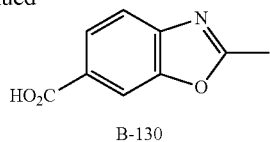

B-130

To a solution of methyl 2-methylbenzo[d]oxazole-6-carboxylate (2.0 g, 10 mmol) in tetrahydrofuran/methanol/water (1:1:1, 15 mL) was added lithium hydroxide hydrate (0.88 g, 21 mmol). The resulting mixture was stirred at 25° C. for 2 hours. On completion, the mixture was acidified with hydrochloric acid, resulting in formation of a solid. The solid was collected by filtration, washed with water and dried in vacuo to give compound B-130 (1.2 g, 65% yield) as a white solid.

Example 30B: ethyl 5-iodo-6-oxo-1,6-dihydropyridine-3-carboxylate (B-131)

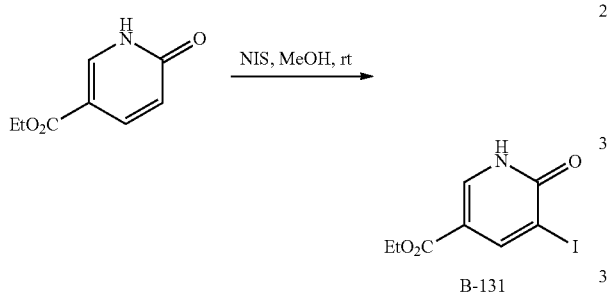

To a solution of ethyl 6-oxo-1,6-dihydropyridine-3-carboxylate (2.0 g, 12 mmol) in methanol (20 mL) was added N-iodosuccinimide (4.1 g, 18 mmol). The reaction was stirred at room temperature overnight. On completion, the solution was concentrated, and the residue was purified by silica gel chromatography [petroleum ether:ethyl acetate=15:1] to give compound B-131 (3.0 g, 85% yield) as a brown solid.

Example 31B: ethyl 6-oxo-5-vinyl-1,6-dihydropyridine-3-carboxylate (B-132)

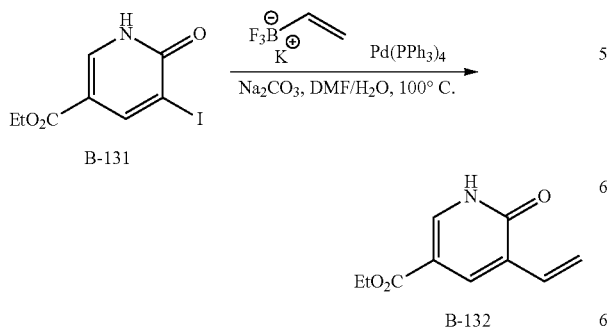

To a mixture of B-131 (2.8 g, 9.6 mmol), potassium trifluoro(vinyl)borate (1.3 g, 9.7 mmol), sodium carbonate (1.3 g, 12 mmol) in N,N-dimethyl formamide (30 mL) and water (6 mL) was added tetrakis(triphenylphosphine) palladium (0) (1.1 g, 0.96 mmol) at room temperature. The suspension was degassed under vacuum and purged with nitrogen several times, then stirred at 100° C. for 16 hours. On completion, the mixture was diluted with water (30 mL) and extracted with ethyl acetate (3×40 mL). The combined organic layers ware washed with brine, dried over anhydrous sodium sulfate and concentrated in vacuo. The residue was purified by silica gel column chromatography [petroleum ether:ethyl acetate=10:1] to give compound B-132 (0.75 g, 41% yield) as a yellow oil.

Example 32B: ethyl 3-hydroxy-2,3-dihydrofuro[2,3-b]pyridine-5-carboxylate (B-133)

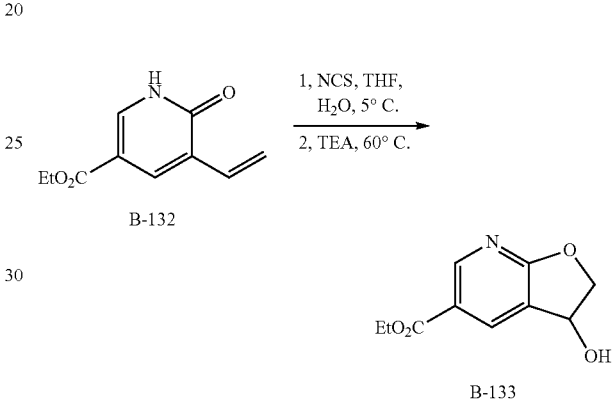

A solution of B-132 (0.45 g, 2.3 mmol) and N-chlorosuccinimide (0.31 g, 2.3 mmol) in tetrahydrofuran (4 mL) and water (4 mL) was stirred at 5° C. for 4 hours. Triethylamine (0.70 g, 6.9 mmol) was added to the mixture, and the reaction was stirred at 60° C. for another 4 hours. On completion, the mixture was extracted with ethyl acetate (3×10 mL). The combined organic layers ware washed with brine, dried over anhydrous sodium sulfate and concentrated in vacuo. The residue was purified by silica gel column chromatography [petroleum ether:ethyl acetate=5:1] to give compound B-133 (0.38 g, 78% yield) as a brown oil.

Example 33B: ethyl furo[2,3-b]pyridine-5-carboxylate (B-134)

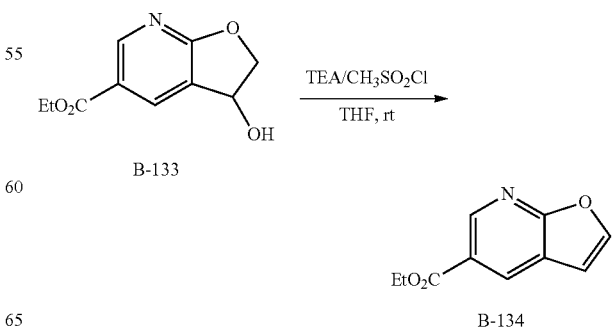

To a solution of B-133 (0.38 g, 1.8 mmol) and triethylamine (0.27 g, 2.7 mmol) in tetrahydrofuran (5 mL) was added methanesulfonyl chloride (0.31 g, 2.7 mmol) at room temperature. The mixture was stirred at room temperature for 3 hours. On completion, the reaction was quenched with water (5 mL) and extracted with ethyl acetate (3×10 mL). The combined organic layers ware washed with brine, dried over anhydrous sodium sulfate and concentrated in vacuo. The residue was purified by silica gel column chromatography [petroleum ether:ethyl acetate=10:1] to give compound B-134 (0.22 g, 64% yield) as a white solid. LCMS (B): tR=0.693, (ES$^+$) m/z (M+H)$^+$=192.1.

Example 34B: furo[2,3-b]pyridine-5-carboxylic acid (B-135)

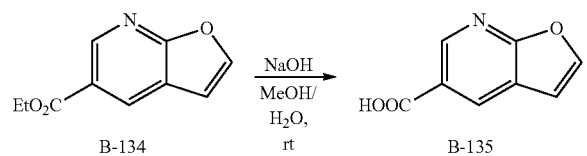

To a solution of B-134 (0.22 g, 1.2 mmol) in methanol (3 mL) and water (3 mL) was added sodium hydroxide (96 mg, 2.4 mmol) at room temperature. The mixture was stirred at room temperature for 3 hours. On completion, the solution was concentrated to remove methanol, and the pH was adjusted to 4-5, resulting in formation of a solid. The solid was collected by filtration and dried in vacuo to give compound B-135 (0.15 g, 77% yield) as a white solid.

Example 35B: 4-oxidofuro[3,2-b]pyridin-4-ium (B-136)

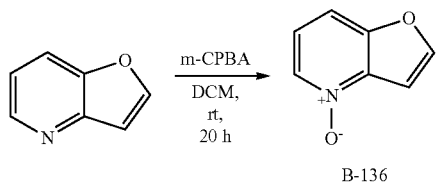 [SMILES: c1cnc2ccoc2c1 ; [O-][n+]1cccc2occc21]

To a solution of furo[3,2-b]pyridine (1.0 g, 8.5 mmol) in dichloromethane (10 mL) was added metachloroperbenzoic acid (2.5 g, 14 mmol). The mixture was stirred at room temperature for 20 hours. On completion, the reaction mixture was quenched with 1 M aqueous potassium hydroxide (50 ml). The mixture was concentrated in vacuo, and the residue was poured into dichloromethane (10 mL). The mixture was filtered, and the filtrate was concentrated to give compound B-136 (1.0 g, 87% yield) as yellow oil: LCMS (C): tR=1.070 min., (ES$^+$) m/z (M+H)$^+$=136.0.

Example 36B: furo[3,2-b]pyridine-5-carbonitrile (B-137)

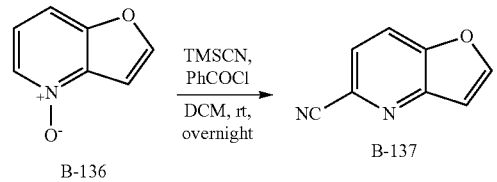 [SMILES: [O-][n+]1cccc2occc21 ; N#Cc1ccc2occc2n1]

To a solution of compound B-136 (1 g, 7.4 mmol) in dichloromethane (5 ml) was added a solution of trimethylsilyl cyanide (8 g, 81 mmol) in dichloromethane (35 ml). Then a solution of benzoyl chloride (11 g, 78 mmol) in dichloromethane (40 ml) was added dropwise. After vigorous stirring at room temperature overnight, the solvent was evaporation. The residue was purified by silica gel chromatography (petroleum ether:ethyl acetate=2:1) to give compound B-137 (730 mg, 68% yield) as light yellow solid: LCMS (A): tR=0.507 min., (ES$^+$) m/z (M+H)$^+$=145.0.

Example 37B: furo[3,2-b]pyridine-5-carboxylic acid (B-138)

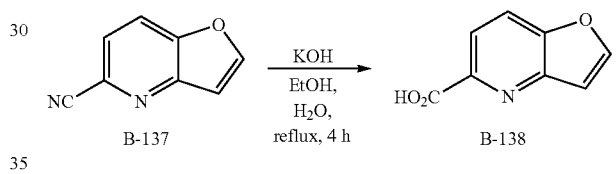

To a solution of compound B-137 (450 mg, 3 mmol) in ethanol (10 mL) and water (2.5 mL) was added potassium hydroxide (1.2 g, 20 mmol). The mixture was heated at reflux for 4 hours. After evaporation to remove ethanol, the mixture was washed with ethyl acetate. The aqueous phase was adjusted to pH 5~6 with 1N hydrochloric acid and extracted with DCM (15 mL×3). The combined organic layers were washed with water and brine, dried over anhydrous sodium sulfate and concentrated in vacuo to give crude compound B-138 (254 mg, 50% yield): $^1$H-NMR (CD$_3$OD, 400 MHz): δ 8.22 (d, J=4.4 Hz, 1H), δ 8.17 (d, J=8.4 Hz, 1H), 8.07 (d, J=8.4 Hz, 2H), 7.12 (d, J=1.6 Hz, 1H).

Example 38B: benzofuran-5-carboxylic acid (B-139)

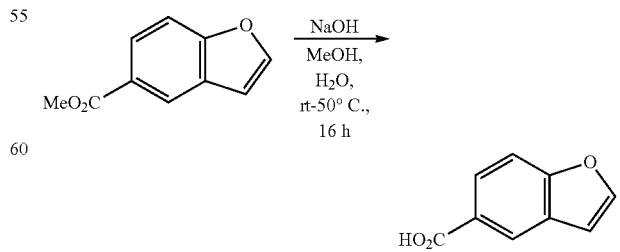

To a mixture of methyl benzofuran-5-carboxylate (1.0 g, 5.7 mmol) in methanol (10 mL) and water (1 mL) was added sodium hydroxide (0.45 g, 11 mmol). The mixture was stirred at room temperature for 16 hours. On completion, the mixture was adjusted to pH=5-6 with 4 M hydrochloric acid, resulting in formation of a solid. The solid was collected by filtration and dried in vacuo to give compound B-139 (0.61 g, 65% yield) as a white solid.

Example 39B: 2-chlorobenzofuran-5-carboxylic acid (B-140)

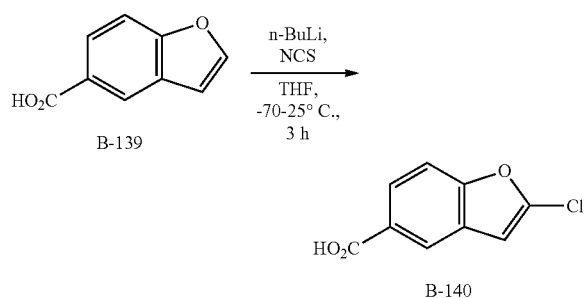

To a solution of compound B-139 (0.70 g, 4.3 mmol) in tetrahydrofuran (10 mL) at −70° C. was added n-butyl lithium (4.3 ml, 11 mmol, 2.5M in n-hexane) portionwise over half an hour. Then N-chlorosuccinimide (1.7 g, 13 mmol) was added portionwise, and the solution was stirred for another half an hour. The mixture was allowed to warmed to room temperature and stirred for another 2 hours. The reaction was quenched with saturated aqueous ammonium chloride solution (3 mL) at 0° C. and concentrated to remove tetrahydrofuran. The pH was adjusted to 4 with 1 M hydrochloric acid, resulting in formation of a solid. The solid was collected by filtration and dried in vacuo to give crude compound B-140 (500 mg, crude) as a white solid. $^1$H-NMR (DMSO-$d_6$, 400 MHz): δ 8.21 (s, 1H), 7.94 (d, J=8.8 Hz, 1H), 7.65 (d, J=8.4 Hz, 1H), 7.14 (s, 1H).

Example 40B: methyl 4-(allyloxy)-3-iodobenzoate (B-141)

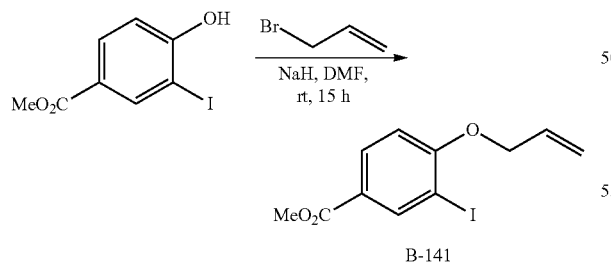

To a solution of methyl 4-hydroxy-3-iodobenzoate (21 g, 76 mmol) and 3-bromoprop-1-ene (14 g, 0.11 mol) in anhydrous N,N-dimethylformamide (200 mL) under nitrogen was added sodium hydride (4.5 g, 0.11 mol, 60%) portionwise. The resulting mixture was stirred at room temperature for 15 hours. On completion, the reaction was diluted with water (100 mL) and extracted with ethyl acetate (3×200 mL). The combined organic layers were washed with brine, dried over anhydrous sodium sulfate, and concentrated in vacuo. The residue was purified by silica gel chromatography [petroleum ether:ethyl acetate=20:1] to give compound B-141 (25 g, 90% yield) as a tan solid. LCMS (B): tR=0.916, (ES$^+$) m/z (M+H)$^+$=319.0.

Example 41B: methyl 3-methylbenzofuran-5-carboxylate (B-142)

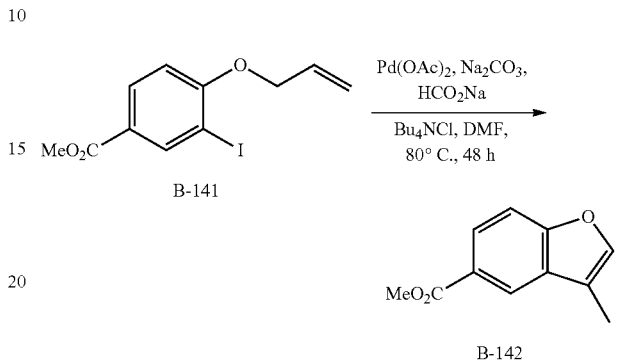

To a solution of compound B-141 (2.0 g, 6.3 mmol) in anhydrous N,N-dimethylformamide (20 mL) under nitrogen was added palladium acetate (70 mg, 0.31 mmol), sodium carbonate (1.7 g, 16 mmol), sodium formate (0.43 g, 6.3 mmol) and tetrabutylammonium chloride (1.7 g, 6.3 mmol). The resulting mixture was stirred at 80° C. for 48 hours. On completion, the reaction mixture was filtered, and the filtrate was diluted with water (20 mL) and extracted with ethyl acetate (3×20 mL). The combined organic layers were washed with brine, dried over anhydrous sodium sulfate, and concentrated in vacuo. The residue was purified by silica gel chromatography [petroleum ether:ethyl acetate=20:1] to give compound B-142 (0.5 g, 45% yield) as a white solid. LCMS (B): tR=0.842, (ES$^+$) m/z (M+H)$^+$=191.1.

Example 42B: 3-methylbenzofuran-5-carboxylic acid (B-143)

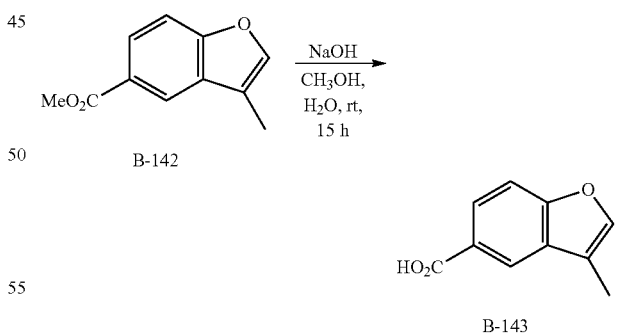

To a solution of compound B-142 (0.55 g, 2.9 mmol) in methanol/water (10:1, 11 mL) was added sodium hydroxide (0.23 g, 5.8 mmol). The resulting mixture was stirred at room temperature for 15 hours. On completion, the volatiles were removed in vacuo. The residue was diluted with water (10 mL), and washed with ethyl acetate (10 mL). The aqueous solution was adjusted to pH 5 with 2 M hydrochloric acid, resulting in formation of a solid. The solid was collected by filtration and dried in vacuo to give compound B-143 (0.47 g, 96% yield) as a white solid. LCMS (B): tR=0.708, (ES+) m/z (M+H)+=177.1. ¹H-NMR (CD₃Cl, 400 MHz): δ 8.38 (s, 1H), 8.12-8.10 (dd, J₁=8.8 Hz, J₂=4.0 Hz, 1H), 7.52 (t, J=8.0 Hz, 2H), 2.31 (s, 3H).

Example 43B: methyl 2,3-dichloro-2,3-dihydrobenzofuran-5-carboxylate (B-144)

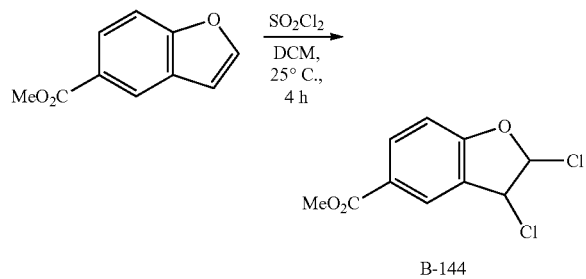

A mixture of methyl benzofuran-5-carboxylate (1.0 g, 5.7 mmol) and SO₂C₂ (3.0 g, 22.7 mmol) in dichloromethane (10 mL) was stirred at 25° C. for 4 hours. TLC showed a new spot formed. On completion, the reaction was concentrated, and the residue was purified by silica gel chromatography [petroleum ether:ethyl acetate=10:1] to give compound B-144 (0.42 g, 30% yield) as an oil.

Example 44B: methyl 3-chlorobenzofuran-5-carboxylate (B-145)

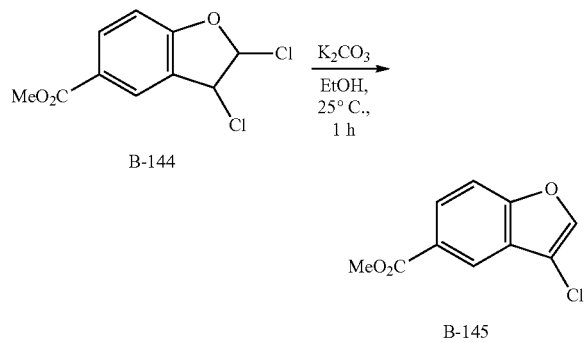

A mixture of compound B-144 (0.42 g, 1.7 mmol) and potassium carbonate (0.71 g, 5.1 mmol) in ethanol (40 mL) was stirred at 25° C. for 1 hour. On completion, the mixture was filtered, and the filtrate was concentrated to give the crude compound B-145 (0.35 g, 97% yield) as a white solid.

Example 45B: 3-chlorobenzofuran-5-carboxylic acid (B-146)

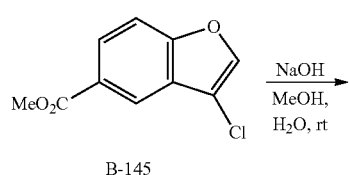

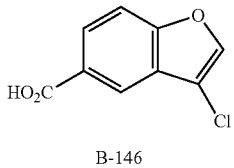

A mixture of compound B-145 (0.35 g, 1.7 mmol) and sodium hydroxide (0.14 g, 3.4 mmol) in methanol (10 mL) and water (5 mL) was stirred at room temperature for 12 hours. On completion, the reaction mixture was concentrated in vacuo to remove methanol. The residue was poured into water, and the pH was adjusted to 3, resulting in formation of a solid. The solid was collected by filtration and dried in vacuo to give compound B-146 (0.26 g, 80% yield).

Example 46B: methyl thieno[2,3-c]pyridine-5-carboxylate (B-147)

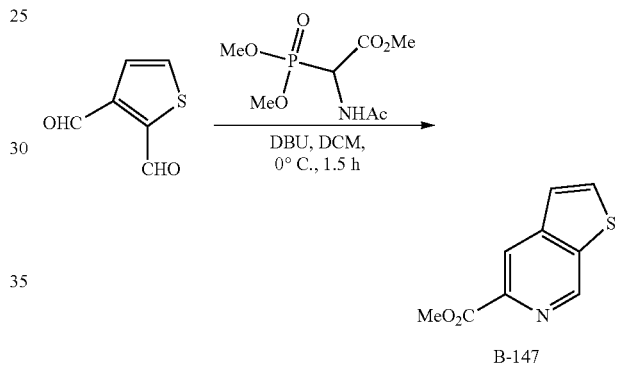

To a mixture of thiophene-2,3-dicarbaldehyde (2.0 g, 14 mmol) and methyl 2-acetamido-2-(dimethoxyphosphoryl)acetate (3.4 g, 14 mmol) in dichloromethane (20 mL) at 0° C. was added dropwise 1,8-diazabicyclo[5.4.0]undec-7-ene (2.4 g, 16 mmol). The mixture was stirred at 0° C. for 1.5 hours. On completion, the reaction mixture was quenched with water and extracted with dichloromethane (3×50 mL). The combined organic layers were washed with water and brine, dried over anhydrous sodium sulfate and concentrated in vacuo. The residue was purified by silica gel chromatography [petroleum ether:ethyl acetate=10:1] to give compound B-147 (1.5 g, 54% yield) as a white solid.

Example 47B: thieno[2,3-c]pyridine-5-carboxylic acid (B-148)

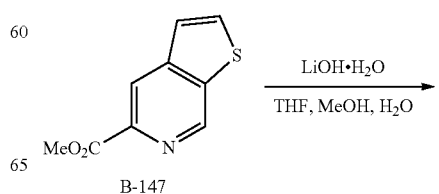

-continued

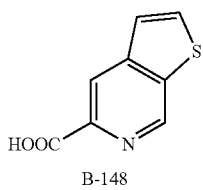

B-148

To a solution of compound B-147 (0.50 g, 2.6 mmol) in tetrahydrofuran (5 mL), methanol (5 mL) and water (5 mL) was added lithium hydroxide monohydrate (0.22 g, 5.2 mmol). The reaction mixture was stirred at room temperature overnight. On completion, the reaction mixture was concentrated in vacuo to remove tetrahydrofuran and poured into water (400 mL). The pH was adjusted to 5 with 4M hydrochloric acid, resulting in formation of a solid. The solid was collected by filtration, washed with water and dried in vacuo to give compound B-148 (0.50 g, crude) as a yellow solid.

Example 48B: methyl 6-morpholinobenzo[b]thiophene-2-carboxylate (B-149)

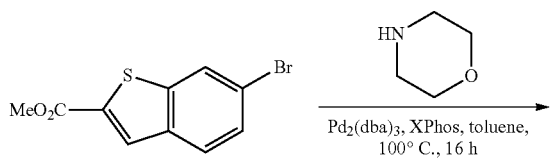

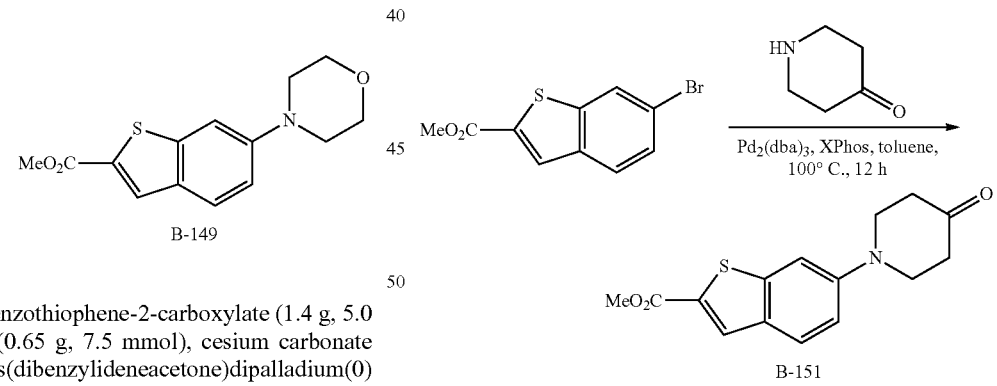

Methyl 6-bromobenzothiophene-2-carboxylate (1.4 g, 5.0 mmol), morpholine (0.65 g, 7.5 mmol), cesium carbonate (3.3 g, 10 mmol), tris(dibenzylideneacetone)dipalladium(0) (0.46 g, 0.50 mmol) and 2-dicyclohexylphosphino-2',4',6'-triisopropylbiphenyl (0.24 g, 0.50 mmol) in toluene (30 mL) was de-gassed and then heated to 100° C. for 16 hours under nitrogen. On completion, the reaction mixture was poured into water (40 mL) and extracted with ethyl acetate (30 mL×3). The organic phase was washed with brine (30 mL), dried with anhydrous sodium sulfate and concentrated in vacuo. The residue was purified by silica gel column chromatography [petroleum ether:ethyl acetate=5:1] to afford the compound B-149 (0.95 g, crude) as a yellow solid. $^1$H-NMR (CDCl$_3$, 400 MHz): 7.95 (s, 1H), 7.74 (d, J=8.8 Hz, 1H), 7.24 (d, J=2.0 Hz, 1H), 7.08 (d, J=8.8, 2.4 Hz, 1H), 3.93 (s, 3H), 3.90 (t, J=4.8 Hz, 4H), 3.27 (t, J=4.8 Hz, 4H).

Example 49B: 6-morpholinobenzo[b]thiophene-2-carboxylic acid (B-150)

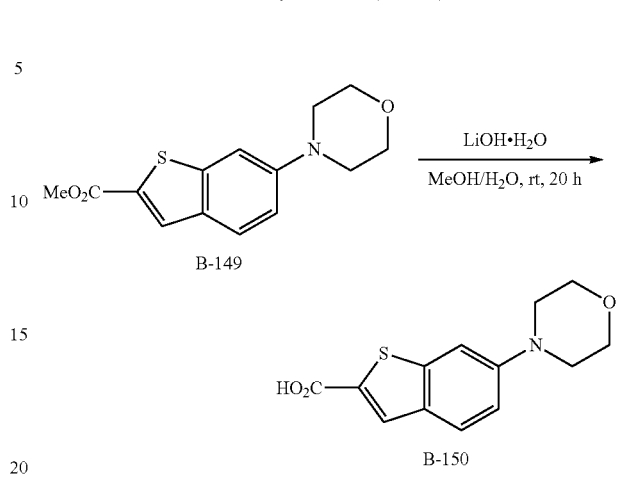

A mixture of compound B-149 (0.50 g, 1.8 mmol) and lithium hydroxide (0.42 g, 10 mmol) in methanol (10 mL) and water (5 mL) was stirred at 25° C. for 20 hours. On completion, the mixture was concentrated in vacuo and poured into water (20 mL). The aqueous phase was washed with ethyl acetate (20 mL×2), acidified and extracted with ethyl acetate (20 mL×3). The combined organic phases were washed with brine (40 mL×2), dried with anhydrous sodium sulfate, filtered and concentrated in vacuo to give compound B-150 (0.36 g, 75% yield) as faint yellow solid. $^1$H-NMR (CD$_3$OD, 400 MHz): 8.06-8.00 (m, 3H), 7.54 (d, J=9.2, 2.0 Hz, 1H), 4.04 (t, J=4.4 Hz, 4H), 3.27 (t, J=4.4 Hz, 4H).

Example 50B: methyl 6-(4-oxopiperidin-1-yl)benzo[b]thiophene-2-carboxylate (B-151)

A mixture of methyl 6-bromobenzothiophene-2-carboxylate (1.4 g, 5.0 mmol), piperidin-4-one (0.75 g, 7.5 mmol), cesium carbonate (3.3 g, 10 mmol), tris(dibenzylideneacetone)dipalladium(0) (0.46 g, 0.50 mmol) and 2-dicyclohexylphosphino-2',4',6'-triisopropylbiphenyl (0.24 g, 0.50 mmol) in toluene (30 mL) was de-gassed and then heated to 100° C. for 12 hours under nitrogen. On completion, the reaction mixture was poured into water (40 mL) and extracted with ethyl acetate (30 mL×3). The combined organic phase was washed with brine (30 mL), dried with anhydrous sodium sulfate and concentrated in vacuo. The residue was purified by silica gel column chromatography

Example 51B: methyl 6-(4,4-difluoropiperidin-1-yl)benzo[b]thiophene-2-carboxylate (B-152)

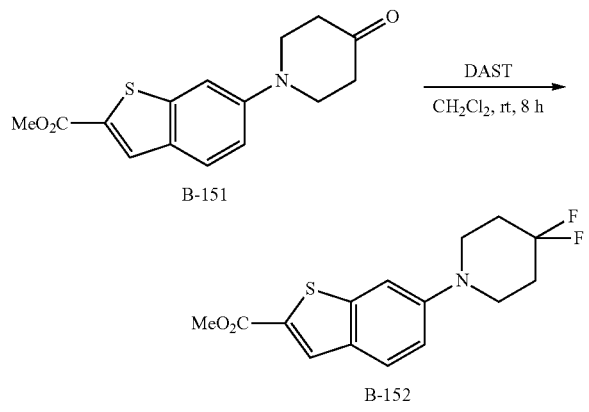

A mixture of compound B-151 (0.30 g, 1.0 mmol) and diethylaminosulfur trifluoride (0.50 g, 3.1 mmol) in dichloromethane (10 mL) was stirred at room temperature for 8 hours. On completion, the mixture was added into saturated sodium bicarbonate solution (10 mL) at 0° C. The aqueous phase was extracted with dichloromethane (20 mL×3). The organic phases were combined and washed with brine (20 mL×2), dried with anhydrous sodium sulfate, filtered and concentrated in vacuo. The residue was purified by prep-HPLC [Instrument: GX-B; Column: YMC-pack ODS-AQ C18 150×30 mm, particle size: 5 μm; Mobile phase: 50-80% acetonitrile in H$_2$O (add 0.5% TFA, v/v)] to give compound B-152 (0.16 g, 49% yield) as a yellow solid. $^1$H-NMR (CD$_3$OD, 400 MHz): 7.95 (s, 1H), 7.78 (d, J=8.8 Hz, 1H), 7.43 (d, J=1.6 Hz, 1H), 7.21 (d, J=8.8, 2.0 Hz, 1H), 3.90 (s, 3H), 3.49 (t, J=5.6 Hz, 4H), 2.16-2.06 (m, 4H).

Example 52B: 6-(4,4-difluoropiperidin-1-yl)benzo[b]thiophene-2-carboxylic acid (B-153)

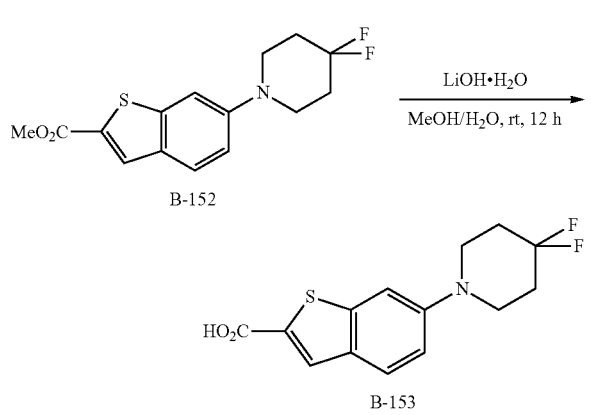

A mixture of compound B-152 (0.16 g, 0.51 mmol) and lithium hydroxide (0.11 g, 2.6 mmol) in methanol (1 mL) and water (0.5 mL) was stirred at room temperature for 12 hours. On completion, the mixture was concentrated in vacuo and poured into water (10 mL). The aqueous phase was washed with ethyl acetate (10 mL×2), acidified and extracted with ethyl acetate (10 mL×3). The combined organic phase was washed with brine (20 mL×2), dried with anhydrous sodium sulfate, filtered and concentrated in vacuo to give compound B-153 (0.11 g, 74% yield) as a yellow solid. $^1$H-NMR (CD$_3$OD, 400 MHz): 7.90 (s, 1H), 7.77 (d, J=8.8 Hz, 1H), 7.43 (s, 1H), 7.20 (d, J=9.2, 2.0 Hz, 1H), 3.48 (t, J=5.6 Hz, 4H), 2.16-2.06 (m, 4H).

Example 53B: 2-fluoro-4-isopropoxybenzaldehyde (B-154)

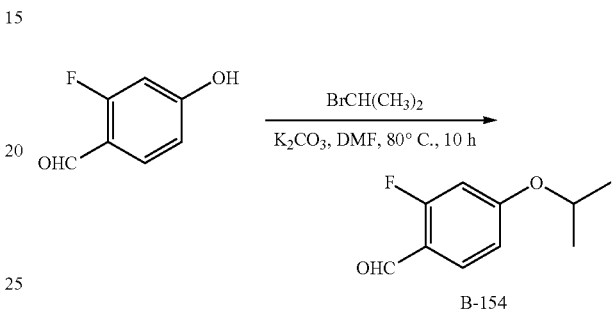

To a mixture of 2-fluoro-4-hydroxy-benzaldehyde (2.0 g, 14 mmol) and potassium carbonate (3.9 g, 29 mmol) in N,N-dimethylformamide (20 mL) at 25° C. under nitrogen was added 2-bromopropane (2.0 g, 16 mmol). The mixture was heated to 80° C. for 10 hours. On completion, the mixture was concentrated in vacuo, poured into water (20 mL) and extracted with ethyl acetate (20 mL×3). The combined organic phases were washed with brine (10 mL×5), dried with anhydrous sodium sulfate and concentrated in vacuo. The residue was purified by column chromatography [petroleum ether:ethyl acetate=10:1] to afford compound B-154 (1.6 g, crude) as a colorless liquid. $^1$H-NMR (CD$_3$OD, 400 MHz): 10.11 (s, 1H), 7.86-7.77 (m, 1H), 6.88-6.64 (m, 2H), 4.79-4.64 (m, 1H), 1.37 (d, J=6.0 Hz, 4H).

Example 54B: methyl 6-isopropoxybenzo[b]thiophene-2-carboxylate (B-155)

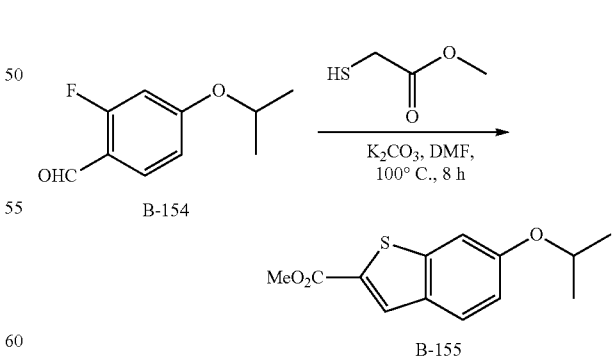

To a solution of compound B-154 (1.0 g, 5.5 mmol) in N,N-dimethylformamide (10 mL) was added potassium carbonate (2.3 g, 16 mmol) and methyl 2-mercaptoacetate (1.2 g, 11 mmol). The mixture was stirred at 100° C. for 8 hours. On completion, the mixture was diluted with water (60 mL) and extracted with ethyl acetate 270 mL (90 mL×3). The combined organic layers were washed with brine 120 mL (20 mL×6), dried with anhydrous sodium sulfate, filtered and concentrated in vacuo to give compound B-155 (1.9 g, crude) as black brown liquid, which was used directly without further purification. LCMS (B): tR=0.946 min., (ES$^+$) m/z (M+H)$^+$=251.0.

Example 55B: 6-isopropoxybenzo[b]thiophene-2-carboxylic acid (B-156)

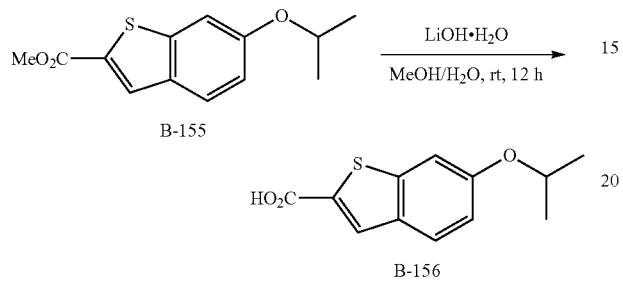

A mixture of compound B-155 (1.96 g, 7.8 mmol) and lithium hydroxide (1.6 g, 39 mmol) in methanol (10 mL) and water (5 mL) was stirred at 80° C. for 2.5 hours under nitrogen. On completion, the mixture was concentrated and poured into water (60 mL). The aqueous phase was washed with ethyl acetate (20 mL×3), acidified and extracted with ethyl acetate (70 mL×3). The combined organic phases were washed with brine (50 mL×3), dried with anhydrous sodium sulfate, filtered and concentrated in vacuo to give compound B-156 (1.0 g, 54% yield) as a red solid. $^1$H-NMR (CD$_3$OD, 400 MHz): 7.94 (s, 1H), 7.80-7.76 (m, 1H), 7.41-7.39 (m, 1H), 7.00-6.98 (m, 1H), 4.74-4.67 (m, 1H), 1.35 (d, J=4.4 Hz, 4H).

Example 56B: methyl 6-(methylsulfonyl)benzo[b]thiophene-2-carboxylate (B-157)

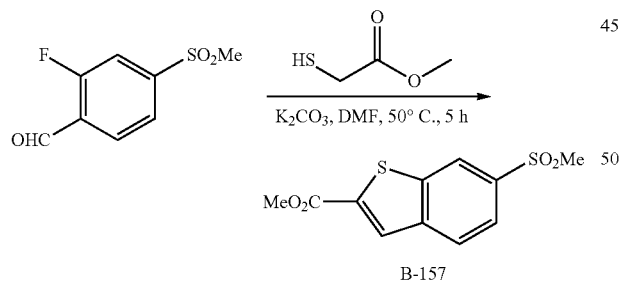

To a mixture of 2-fluoro-4-(methylsulfonyl)benzaldehyde (0.50 g, 2.5 mmol) in N,N-dimethylformamide (10 mL) was added methyl 2-mercaptoacetate (0.26 g, 2.5 mmol) and potassium carbonate (0.41 g, 3.0 mmol). The mixture was stirred at 50° C. for 5 hours. On completion, the mixture was poured into water and extracted with ethyl acetate. The organic layer was dried over anhydrous sodium sulfate and concentrated in vacuo. The residue was purified by silica gel chromatography [petroleum ether:ethyl acetate=10:1] to give compound B-157 (0.62 g, 93% yield) as a yellow solid. LCMS (A): tR=0.709 min., (ES$^+$) m/z (M+H)$^+$=271.0.

Example 57B: 6-(methylsulfonyl)benzo[b]thiophene-2-carboxylic acid (B-158)

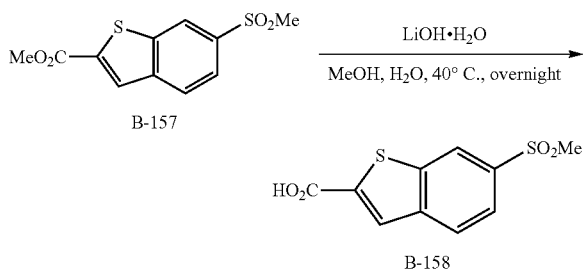

To a mixture of compound B-157 (0.62 g, 2.3 mmol) in methanol (4 mL) and water (2 mL) was added lithium hydroxide monohydrate (0.19 g, 4.6 mmol). The mixture was stirred at 40° C. overnight. On completion, the mixture was concentrated to remove methanol, diluted with water and adjusted to pH to 3.0 with 1 M hydrochloric acid, resulting in formation of a solid. The solid was collected by filtration and dried in vacuo to give compound B-158 (0.52 g, 89% yield) as a yellow solid.

Example 58B: methyl 6-nitrobenzothiophene-2-carboxylate (B-159)

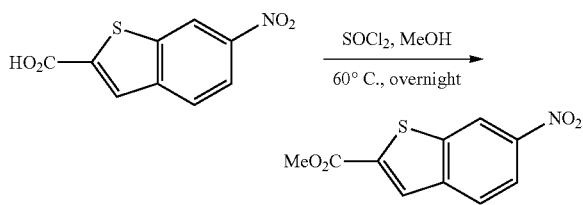

To a solution of 6-nitrobenzothiophene-2-carboxylic acid (0.98 g, 4.4 mmol) in methanol (10 mL) at 0° C. was added thionyl chloride (0.78 g, 6.6 mmol). The mixture was stirred at 60° C. overnight. On completion, the reaction mixture was evaporated to give compound B-159 (1.1 g, 97% yield) as a yellow solid, which was used for next step without further purification.

Example 59B: methyl 6-aminobenzothiophene-2-carboxylate (B-160)

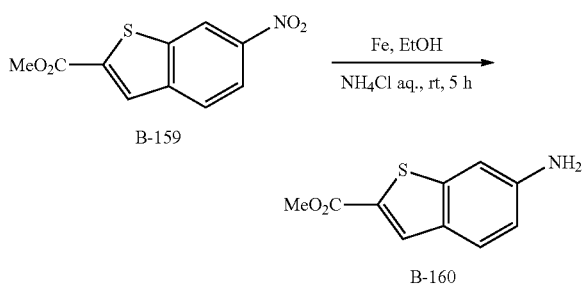

To a solution of compound B-159 (1.1 g, 4.6 mmol) in ethanol (4 mL) and saturated NH₄Cl aqueous (2 mL) under nitrogen was added iron powder (1.3 g, 23 mmol). The reaction was stirred at room temperature for 5 hours. On completion, the mixture was concentrated, and the product was purified by silica gel chromatography [petroleum ether:ethyl acetate=6:1] to give compound B-160 (0.65 g, 87% yield) as a pale yellow solid.

Example 60B: methyl 6-azidobenzothiophene-2-carboxylate (B-161)

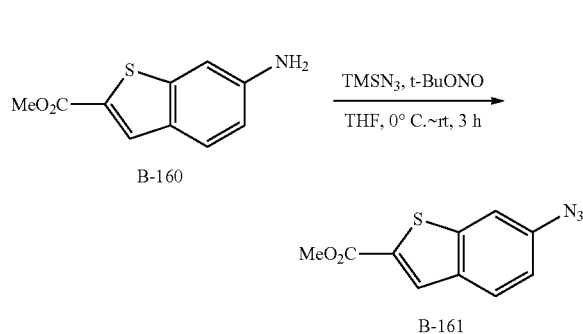

To a solution of compound B-160 (0.65 g, 3 mmol) in tetrahydrofuran (2 mL) at 0° C. was added dropwise tert-butyl nitrite (1.8 g, 17 mmol). The mixture was stirred for 5 minutes. Azidotrimethylsilane (0.82 g, 7.1 mmol) was then added dropwise. The mixture stirred at 0° C. for 30 minutes and at room temperature for 2.5 hours. On completion, the reaction mixture was concentrated, and the product was purified by silica gel chromatography [petroleum ether:ethyl acetate=20:1] to give compound B-161 (0.45 g, 62% yield) as a pale yellow solid.

Example 61B: methyl 6-(4-trimethylsilyltriazol-1-yl)benzothiophene-2-carboxylate (B-162)

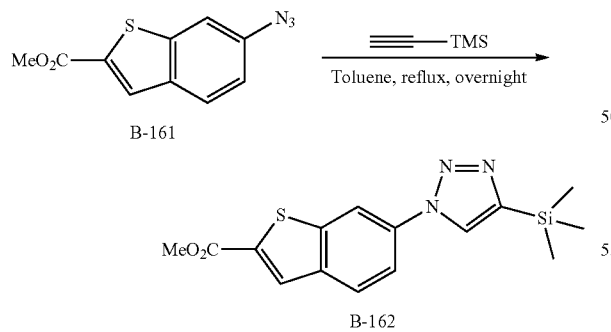

To a solution of compound B-161 (0.38 g, 1.6 mmol) in toluene (10 mL) under nitrogen was added ethynyltrimethylsilane (0.18 g, 1.8 mmol). The reaction mixture was stirred at reflux overnight. On completion, the mixture was concentrated, and the residue was purified by silica gel chromatography [petroleum ether:ethyl acetate=5:1] to give compound B-162 (0.25 g, 45% yield) as light yellow solid.

Example 62B: methyl 6-(triazol-1-yl)benzothiophene-2-carboxylate (B-163)

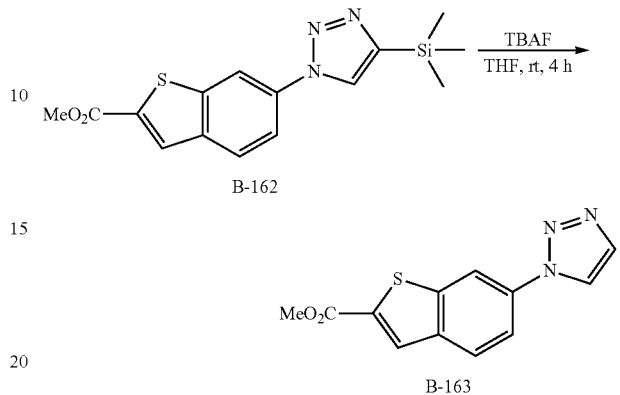

To a solution of compound B-162 (0.25 g, 0.74 mmol) in tetrahydrofuran (2 mL) was added tetrabutylammonium fluoride (0.29 g, 1.1 mmol). The reaction mixture was stirred at room temperature for 4 hours. On completion, the reaction mixture was concentrated, and the residue was purified by recrystallization from ethanol to give compound B-163 (0.19 g, 97% yield) as a yellow solid.

Example 63B: 6-(triazol-1-yl)benzothiophene-2-carboxylic acid (B-164)

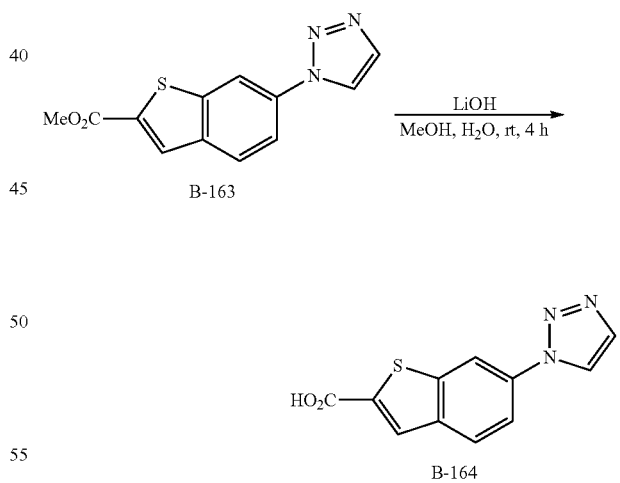

To a solution of compound B-163 (0.19 g, 0.72 mmol) in methanol (5 mL) and water (2 mL) was added LiOH.H₂O (37 mg, 0.89 mmol). The mixture was stirred at room temperature for 4 hours. After evaporation of methanol, the aqueous phase was adjusted to pH 5~6 with 1N hydrochloric acid, resulting in formation of a solid. The solid was collected by filtration and dried in vacuo to give compound B-164 (0.17 g, 97% yield) as a white solid: LCMS (E): tR=1.003 min., (ES⁺) m/z (M+H)⁺=246.0.

Example 64B: methyl 6-(3,6-dihydro-2H-pyran-4-yl)benzo[b]thiophene-2-carboxylate (B-165)

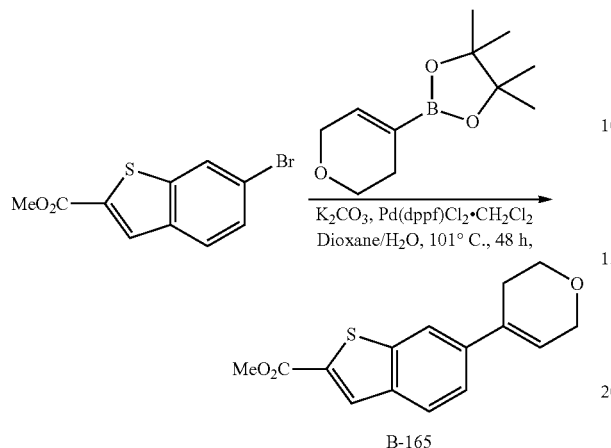

To a solution of methyl 6-bromobenzothiophene-2-carboxylate (1.0 g, 3.7 mmol) in dioxane (30 mL) and H₂O (6 mL) under nitrogen was added K₂CO₃ (1.5 g, 11 mmol), Pd(dppf)Cl₂CH₂Cl₂ (301 mg, 0.37 mmol) and 2-(3,6-dihydro-2H-pyran-4-yl)-4,4,5,5-tetramethyl-1,3,2-dioxaborolane (930 mg, 4.4 mmol). The mixture was stirred at 101° C. for 48 hours. On completion, the reaction mixture was evaporated and purified by silica gel chromatography (petroleum ether:ethyl acetate=16:1) to give compound B-165 (300 mg, 60% yield) as a white solid. ¹H-NMR (CDCl₃, 400 MHz): δ 8.04 (s, 1H), 7.83 (d, J=8.4 Hz, 2H), 7.51-7.48 (m, 1H), 6.28 (d, J=1.6 Hz, 1H), 4.38-4.36 (m, 2H), 3.99-3.96 (m, 2H), 3.95 (s, 3H), 2.62-2.59 (m, 2H).

Example 65B: methyl 6-(tetrahydro-2H-pyran-4-yl)benzo[b]thiophene-2-carboxylate (B-166)

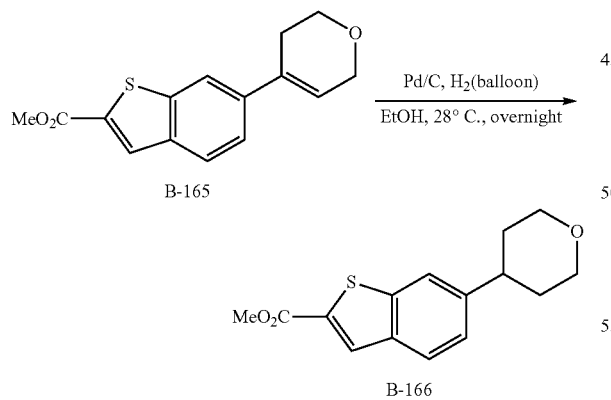

To a solution of compound B-165 (300 mg, 1.1 mmol) in ethanol (8 mL) under nitrogen was added palladium/carbon (5%, 100 mg). The suspension was degassed in vacuo and purged with hydrogen several times. The mixture was stirred under hydrogen (balloon) at 28° C. overnight. On completion, the reaction mixture was filtered, and the filtrate was concentrated to give compound B-166 (300 mg, 99% yield) as a white solid. ¹H-NMR (CDCl₃, 400 MHz): δ 8.03 (s, 1H), 7.82 (d, J=8 Hz, 2H), 7.71 (s, 1H), 7.29 (m, 1H), 4.14-4.10 (m, 2H), 3.95 (s, 3H), 3.60-3.54 (m, 2H), 2.90 (s, 1H), 2.91-2.85 (m, 4H).

Example 66B: 6-(tetrahydro-2H-pyran-4-yl)benzo[b]thiophene-2-carboxylic acid (B-167)

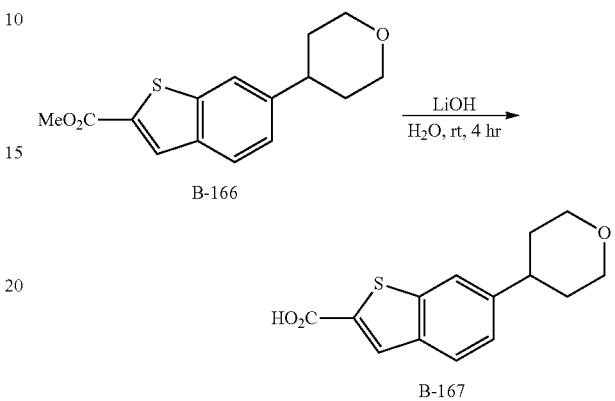

To compound B-166 (0.3 g, 1.1 mmol) in methanol (8 mL) and water (4 mL) was added lithium hydroxide hydrate (78 mg, 1.87 mmol). The reaction was stirred at room temperature for 4 hours. On completion, the reaction mixture was adjusted to pH 5~6 with 4 N hydrochloric acid, resulting in formation of a solid. The solid was collected by filtration and dried in vacuo to give compound B-167 (260 mg, 92%) as a white solid. ¹H-NMR (CDCl₃, 400 MHz): δ 7.99 (s 1H), 7.86 (d, J=8.4 Hz, 2H), 7.79 (s, 1H), 7.36-7.33 (m, 1H), 4.08-4.04 (m, 2H), 3.71-3.54 (m, 2H), 3.00-2.70 (m, 1H), 1.81-1.82 (m, 4H).

Example 67B: 2,3-difluoro-4-methoxybenzaldehyde (B-168)

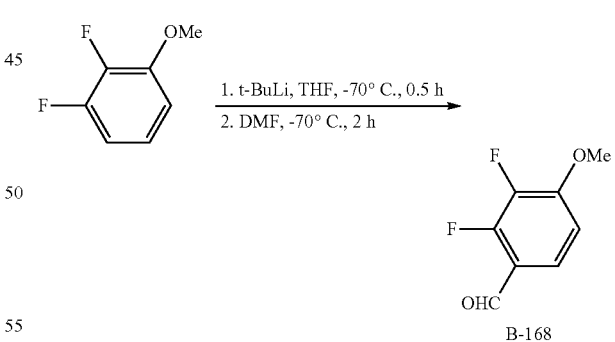

To a mixture of 1,2-difluoro-3-methoxybenzene (3.0 g, 21 mmol) in anhydrous tetrahydrofuran (40 mL) at −70° C. under nitrogen was added dropwise tert-butyllithium (19 mL, 25 mmol, 1.3 M in n-pentane). The mixture was stirred at this temperature for 30 minutes, then N,N-dimethylformamide (6.1 g, 83 mmol) was added dropwise at −70° C. The reaction was stirred at −70° C. for another 2 hours. On completion, the mixture was poured into water and extracted with ethyl acetate. The organic layer was dried over anhydrous sodium sulfate and concentrated in vacuo to give compound B-168 (4.0 g, crude) as a yellow solid. LCMS (B): tR=0.661 min., (ES⁺) m/z (M+H)⁺=173.1.

Example 68B: methyl 7-fluoro-6-methoxybenzo[b]thiophene-2-carboxylate (B-169)

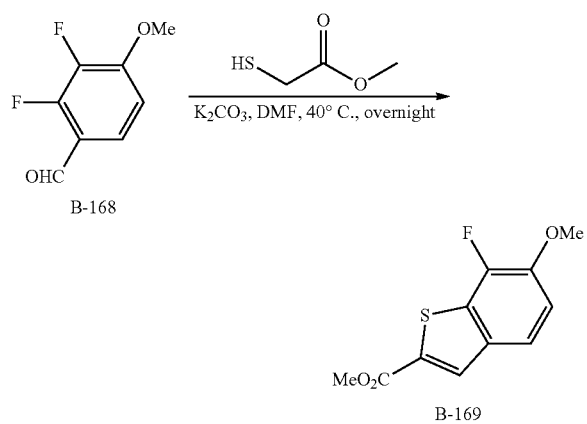

To a mixture of compound B-168 (4.0 g, 23 mmol) in N,N-dimethylformamide (60 mL) was added methyl 2-mercaptoacetate (2.5 g, 23 mmol) and potassium carbonate (3.9 g, 28 mmol). The mixture was stirred at 40° C. overnight. On completion, the mixture was poured into water and extracted with ethyl acetate. The organic layer was dried over anhydrous sodium sulfate and concentrated in vacuo. The residue was purified by silica gel chromatography [petroleum ether: ethyl acetate=10:1] to give compound B-169 (4.0 g, 72% yield) as a white solid. LCMS (B): tR=0.869 min., (ES⁺) m/z (M+H)⁺=241.0.

Example 69B: 7-fluoro-6-methoxybenzo[b]thiophene-2-carboxylic acid (B-170)

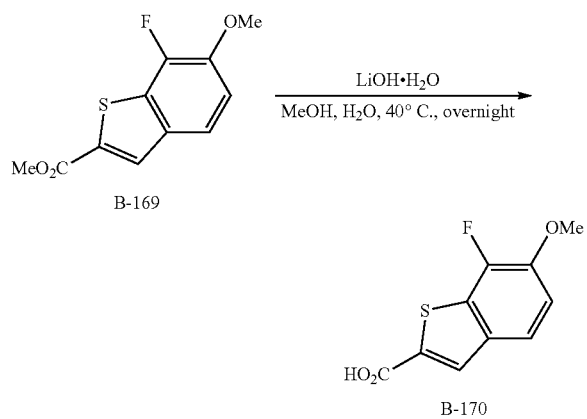

To a mixture of compound B-169 (2.5 g, 10 mmol) in methanol (14 mL) and water (7 mL) was added lithium hydroxide monohydrate (0.87 g, 21 mmol). The mixture was stirred at 40° C. overnight. On completion, the mixture was concentrated to remove methanol, diluted with water and adjusted to pH 3 with 1 M hydrochloric acid, resulting in formation of a solid. The solid was collected by filtration and dried in vacuo to give compound B-170 (2.0 g, 85% yield) as a white solid. LCMS (B): tR=0.739 min., (ES⁺) m/z (M+H)⁺=227.1.

Example 70B: 3-chloro-2-fluoro-4-methylbenzaldehyde (B-171)

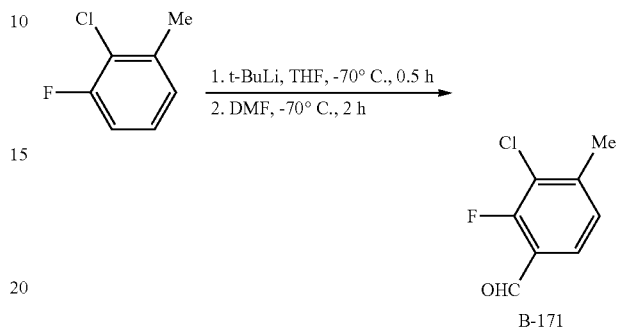

To a mixture of 2-chloro-1-fluoro-3-methylbenzene (1.0 g, 6.9 mmol) in anhydrous tetrahydrofuran (15 mL) at −70° C. under nitrogen was added dropwise tert-butyllithium (6.4 mL, 8.3 mmol, 1.3 M in n-pentane). The mixture was stirred at this temperature for 30 minutes, and then N,N-dimethylformamide (2.0 g, 28 mmol) was added dropwise at −70° C. The reaction was stirred at −70° C. for another 2 hours. On completion, the mixture was poured into water and extracted with ethyl acetate. The organic layer was dried over anhydrous sodium sulfate and concentrated in vacuo to give compound B-171 (1.5 g, crude) as a yellow solid. LCMS (B): tR=0.797 min., (ES⁺) m/z (M+H)⁺=173.1.

Example 71B: methyl 7-chloro-6-methylbenzo[b]thiophene-2-carboxylate (B-172)

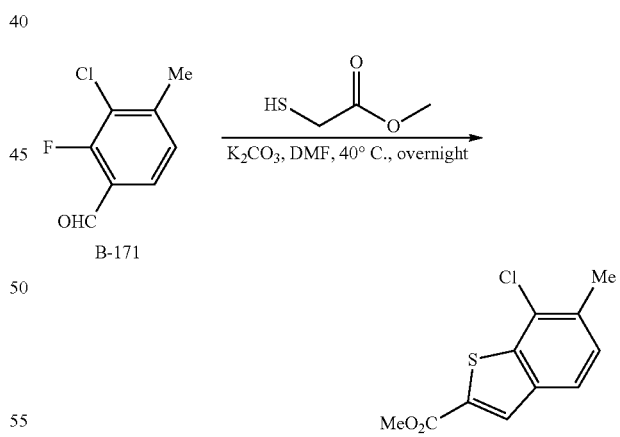

To a solution of compound B-171 (1.5 g, 8.7 mmol) in N,N-dimethylformamide (15 mL) was added methyl 2-mercaptoacetate (0.92 g, 8.7 mmol) and potassium carbonate (1.4 g, 10 mmol). The mixture was stirred at 40° C. overnight. On completion, the mixture was poured into water and extracted with ethyl acetate. The organic layer was dried over anhydrous sodium sulfate and concentrated in vacuo. The residue was purified by silica gel chromatography [petroleum ether:ethyl acetate=10:1] to give compound B-172 (1.2 g, 57% yield) as a white solid. LCMS (B): tR=0.953 min., (ES⁺) m/z (M+H)⁺=241.0.

Example 72B: 7-chloro-6-methylbenzo[b]thiophene-2-carboxylic acid (B-173)

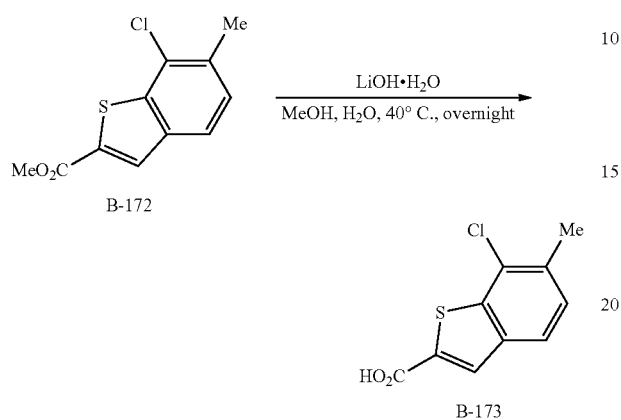

To a mixture of compound B-172 (0.6 g, 2.5 mmol) in methanol (14 mL) and water (7 mL) was added lithium hydroxide monohydrate (0.21 g, 5.0 mmol). The mixture was stirred at 40° C. overnight. On completion, the mixture was concentrated to remove methanol, diluted with water and adjusted to pH=3 with 1 M hydrochloric acid, resulting in formation of a solid. The solid was collected by filtration and dried in vacuo to give compound B-173 (0.50 g, 89% yield) as a white solid. LCMS (A): tR=0.842 min., (ES⁺) m/z (M+H)⁺=227.0.

Example 73B: methyl 7-fluoro-6-methylbenzo[b]thiophene-2-carboxylate (B-174)

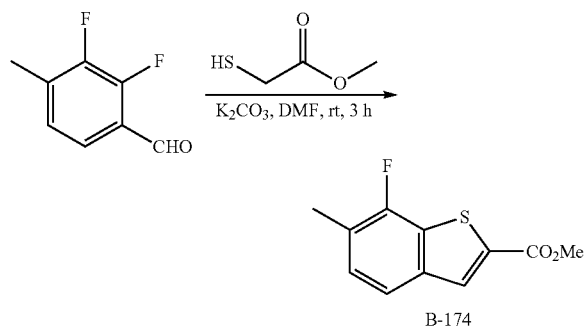

To a mixture of 2,3-difluoro-4-methylbenzaldehyde (1 g, 6.4 mmol) in N,N-dimethylformamide (40 mL) was added methyl 2-mercaptoacetate (0.68 g, 6.4 mmol) and potassium carbonate (1.06 g, 7.68 mmol). The mixture was stirred at room temperature for 3 hours. On completion, the mixture was poured into water and extracted with ethyl acetate. The organic layer was dried over anhydrous sodium sulfate and concentrated in vacuo to give compound B-174 (0.85 g, 59% yield) as a white solid. LCMS (B): tR=0.918 min., (ES⁺) m/z (M+H)⁺=225.1.

Example 74B: 7-fluoro-6-methylbenzo[b]thiophene-2-carboxylic acid (B-175)

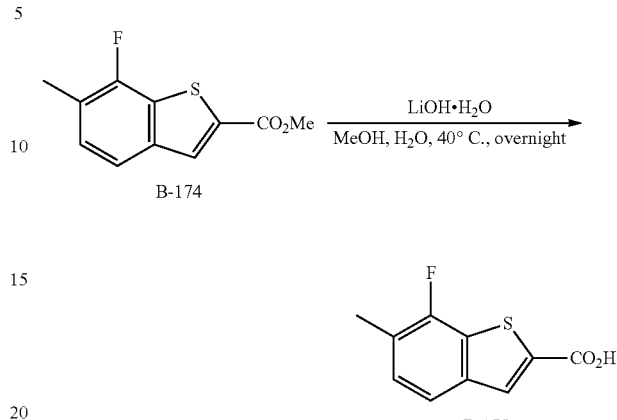

To a mixture of compound B-174 (0.45 g, 2.0 mmol) in methanol (8 mL) and water (4 mL) was added lithium hydroxide monohydrate (0.13 g, 3.0 mmol). The mixture was stirred at 40° C. overnight. On completion, the mixture was concentrated to remove methanol, diluted with water, and adjusted to pH=3 with 1 M hydrochloric acid, resulting in formation of a solid. The solid was collected by filtration and dried in vacuo to give compound B-175 (0.35 g, 83% yield) as a white solid.

Example 75B: methyl 2-((2-methoxy-2-oxoethyl)thio)thieno[2,3-d]pyrimidine-6-carboxylate (B-176)

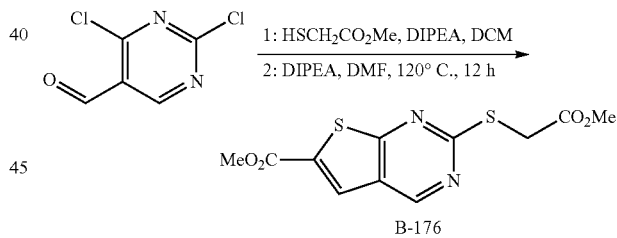

To a solution of 2,4-dichloropyrimidine-5-carbaldehyde (0.22 g, 1.2 mmol) in dichloromethane (30 mL) under nitrogen was added diisopropylethylamine (0.16 g, 1.2 mmol). Then a solution of methyl 2-sulfanylacetate (0.26 g, 2.5 mmol) in dichloromethane (15 mL) was added dropwise over 10 min. The resulting solution was stirred at room temperature for 2 hours. On completion, the mixture was diluted with water (20 mL) and extracted with dichloromethane (3×20 mL). The combined organic layers were washed with brine, dried over anhydrous sodium sulfate and concentrated in vacuo. The residue was dissolved in N,N-dimethylformamide (40 mL), and diisopropylethylamine (0.16 g, 1.2 mmol) was added. The resulting solution was heated to 120° C. for 1.5 hours. On completion, the mixture was concentrated, and the residue was purified by silica gel chromatography [petroleum ether:ethyl acetate=5:1] to give compound B-176 (0.12 g, 32% yield) as a white solid.

Example 76B: methyl 2-((2-methoxy-2-oxoethyl)sulfonyl)thieno[2,3-d]pyrimidine-6-carboxylate (B-177)

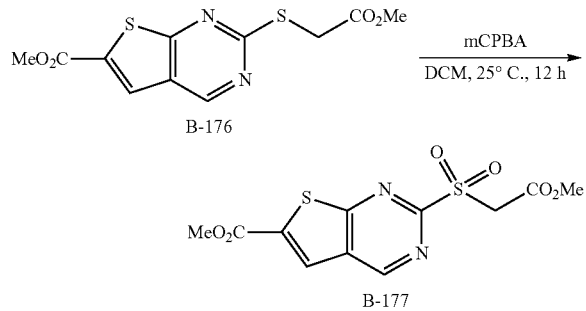

To a solution of compound B-176 (0.60 g, 2.0 mmol) in dichloromethane (40 mL) was added m-chloroperoxybenzoic acid (1.0 g, 6.0 mmol). The resulting mixture was stirred at 25° C. for 12 hours. On completion, the mixture was quenched with sodium thiosulfate, washed with water and concentrated. The residue was purified by silica gel chromatography [petroleum ether:ethyl acetate=2:1] to give compound B-177 (0.36 g, 54% yield) as a white solid.

Example 77B: methyl 2-aminothieno[2,3-d]pyrimidine-6-carboxylate (B-178)

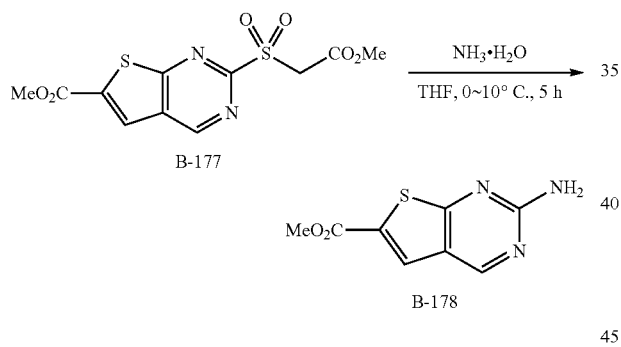

To a solution of compound B-177 (0.30 g, 0.91 mmol) in tetrahydrofuran (20 mL) at 0° C. was added aqueous ammonia (9.1 g, 0.26 mol) dropwise. The mixture was stirred at 10° C. for 5 hours, then diluted with water (20 mL) and extracted with ethyl acetate (3×20 mL). The combined organic layers were washed with brine, dried over anhydrous sodium sulfate, filtered and concentrated. The residue was purified by silica gel chromatography [petroleum ether:ethyl acetate=0:1] to give compound B-178 (0.12 g, 63% yield) as a yellow solid.

Example 78B: 2-aminothieno[2,3-d]pyrimidine-6-carboxylic acid (B-179)

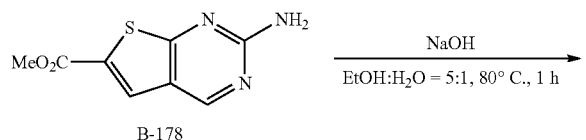

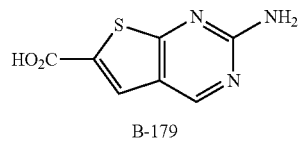

To a solution of compound B-178 (60 mg, 0.29 mmol) in ethanol (5 mL) and water (1 mL) was added sodium hydroxide (57 mg, 1.4 mmol). The mixture was stirred at 80° C. for 1 h, then concentrated to remove ethanol, diluted with water, acidified to pH 1 with hydrochloric acid and extracted with ethyl acetate (3×20 mL). The combined organic layers were washed with brine, dried over anhydrous sodium sulfate and concentrated in vacuo to give compound B-179 (60 mg, crude) as a yellow solid.

Example 79B: (3,4-dichloro-2-fluorophenyl)methanediol and 3,4-dichloro-2-fluoro-benzaldehyde (B-180)

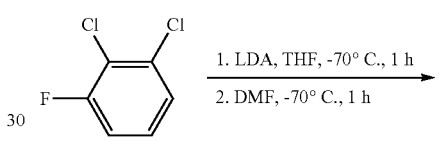

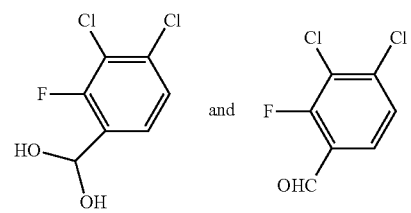

To a mixture of 1,2-dichloro-3-fluorobenzene (0.5 g, 3.0 mmol) in anhydrous tetrahydrofuran (10 mL) at −70° C. under nitrogen was added dropwise 2 M lithium diisopropylamide (2.0 M in tetrahydrofuran/n-heptane solution, 2.3 mL, 4.6 mmol). The mixture was stirred at −70° C. for 1 hour, and N,N-dimethylformamide (0.3 g, 3.6 mmol) was added dropwise. The reaction was stirred at −70° C. for another 1 hour. On completion, then quenched with saturated ammonium chloride solution (70 mL) at 0° C. and extracted with ethyl acetate (3×70 mL). The combined organic layers were washed with brine (6×15 mL), dried with anhydrous sodium sulfate, filtered and concentrated under reduced pressure. The residue was purified by silica gel chromatography [petroleum ether:ethyl acetate=20:1] to give compound mixture B-180 (335 mg, 5:1 ratio of hydrate to aldehyde by NMR) as a yellow solid. $^1$H-NMR (CD$_3$OD, 400 MHz): δ 10.23 (s, 1H), 7.76-7.77 (m, 1H), 7.53 (t, J=8.0 Hz, 6H), 7.36 (d, J=8.4 Hz, 5H), 5.73 (s, 5H).

Example 80B: methyl 6,7-dichlorobenzo[b]thiophene-2-carboxylate (B-181)

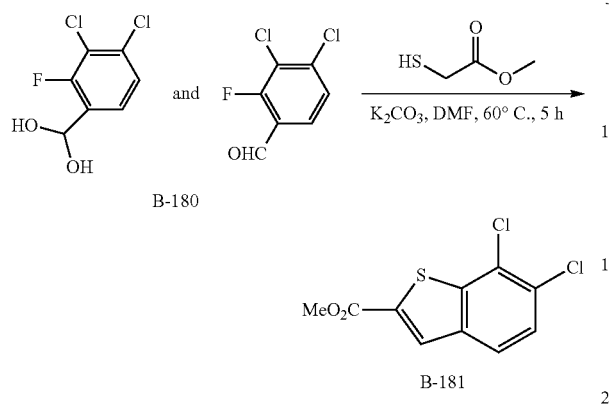

To a solution of compound mixture B-180 (0.3 g, 1.4 mmol) in N,N-dimethylformamide (3 mL) was added potassium carbonate (0.4 g, 4.3 mmol) and methyl 2-mercaptoacetate (0.3 g, 2.8 mmol). The mixture was stirred at 60° C. for 5 hours, then diluted with water (40 mL) and extracted with ethyl acetate (3×40 mL). The combined organic layers were washed with saturated brine (6×5 mL), dried with anhydrous sodium sulfate, filtered and concentrated in vacuo. The residue was purified by silica gel chromatography [petroleum ether:ethyl acetate=10:1] to give compound B-181 (0.3 g, crude) as a white solid. $^1$H-NMR (CD$_3$OD, 400 MHz): δ 8.13 (s, 1H), 7.88 (d, J=8.4 Hz, 1H), 7.59 (d, J=8.8 Hz, 1H), 3.95 (s, 3H).

Example 81B: 6,7-dichlorobenzo[b]thiophene-2-carboxylic acid (B-182)

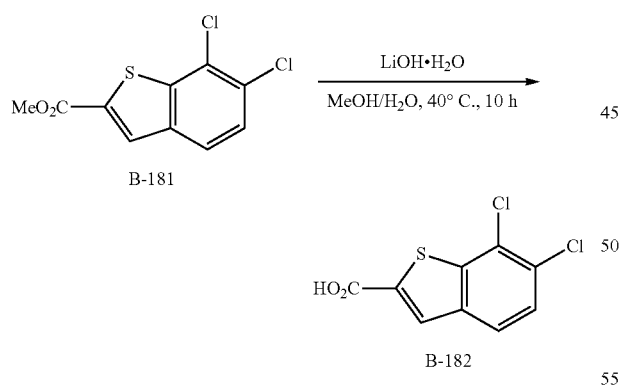

A mixture of compound B-181 (0.3 g, 1.1 mmol) and lithium hydroxide monohydrate (0.24 g, 2.8 mmol) in methanol (5 mL) and water (2.5 mL) was stirred at 40° C. for 10 hours. The mixture was concentrated in vacuo, and the residue was added into water (50 mL). The aqueous phase was washed with ethyl acetate (2×10 mL), acidified to pH 2 with concentrated hydrochloric acid and extracted with ethyl acetate (3×50 mL). The combined organic layers were with brine (3×10 mL), dried with anhydrous sodium sulfate, filtered and concentrated in vacuo. The residue was washed with the n-hexane (3×2 mL) to give compound B-182 (0.23 g, 81% yield) as a white solid. $^1$H-NMR (CD$_3$OD, 400 MHz): 8.09 (s, 1H), 7.87 (d, J=7.6 Hz, 1H), 7.58 (d, J=7.2 Hz, 1H).

Example 82B: methyl 6-chloro-7-fluorobenzo[b]thiophene-2-carboxylate (B-183)

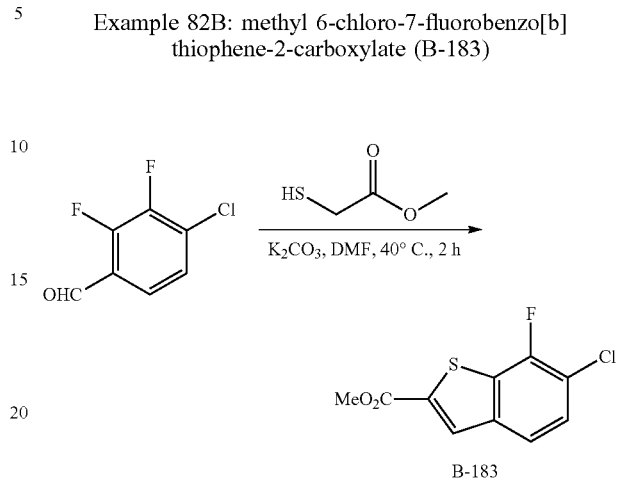

To a mixture of 4-chloro-2,3-difluorobenzaldehyde (1.0 g, 5.7 mmol) in N,N-dimethylformamide (15 mL) was added methyl 2-mercaptoacetate (0.60 g, 5.7 mmol) and potassium carbonate (1.6 g, 11 mmol). The mixture was stirred at 40° C. for 2 hours. On completion, the mixture was poured into water and extracted with ethyl acetate. The organic layer was dried over anhydrous sodium sulfate, concentrated in vacuo and purified by silica gel chromatography [petroleum ether:ethyl acetate=10:1] to give compound B-183 (1.2 g, 87% yield) as a white solid. LCMS (B): tR=0.930 min., (ES$^+$) m/z (M+H)$^+$=245.0.

Example 83B: 6-chloro-7-fluorobenzo[b]thiophene-2-carboxylic acid (B-184)

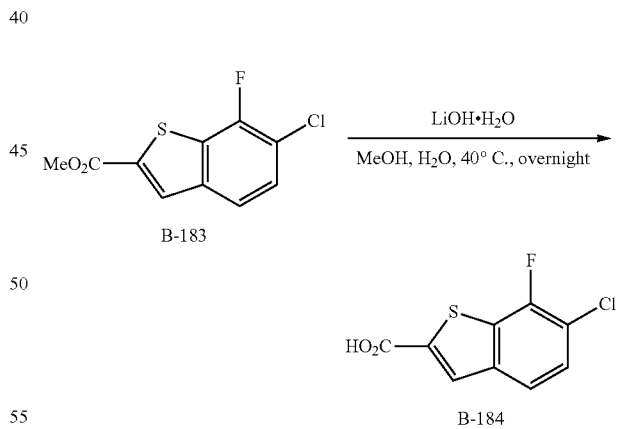

To a mixture of compound B-183 (1.2 g, 4.9 mmol) in methanol (16 mL) and water (8 mL) was added lithium hydroxide monohydrate (0.41 g, 9.8 mmol). The mixture was stirred at 40° C. overnight. On completion, the mixture was concentrated to remove methanol, diluted with water and acidified to pH 3 with 1 M hydrochloric acid, resulting in formation of a solid. The white solid was collected by filtration and dried in vacuo to give compound B-184 (0.70 g, 62% yield). LCMS (B): tR=0.829 min., (ES$^+$) m/z (M+H)$^+$=231.0.

Example 84B: (4-chloro-2-fluoro-3-(trifluoromethyl)phenyl)methanediol and 4-chloro-2-fluoro-3-(trifluoromethyl)benzaldehyde (B-185)

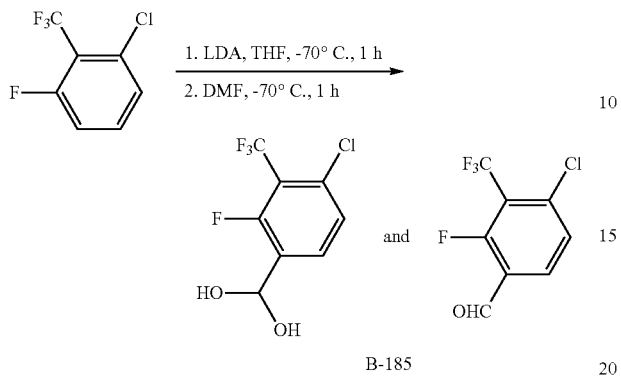

B-185

To a mixture of 1-chloro-3-fluoro-2-(trifluoromethyl)benzene (2 g, 10 mmol) in anhydrous tetrahydrofuran (40 mL) at −70° C. under nitrogen was added dropwise 2 M lithium diisopropylamide (2.0 M in tetrahydrofuran/n-heptane, 7.6 mL, 15 mmol). The mixture was stirred for 1 hour, and then N,N-dimethylformamide (0.9 g, 12 mmol) was added dropwise at −70° C. The reaction was stirred at −70° C. for another 1 hour, then quenched by addition of water (20 mL), acidified to pH 2 with concentrated hydrochloric acid at 0° C., and extracted with ethyl acetate (3×30 mL). The combined organic layers were washed with saturated brine (3×10 mL), dried with anhydrous sodium sulfate, filtered and concentrated under reduced pressure to give compound mixture B-185 (1.7 g, 11:1 ratio of hydrate:aldehyde) as a yellow solid. $^1$H-NMR (CD$_3$OD, 400 MHz): δ 10.27 (s, 1H), 8.09-8.03 (m, 1H), 7.81 (t, J=8.0 Hz, 11H), 7.60 (d, J=8.0 Hz, 1H), 7.43 (d, J=8.8 Hz, 11H), 5.75 (s, 11H).

Example 85B: methyl 6-chloro-7-(trifluoromethyl)benzo[b]thiophene-2-carboxylate (B-186)

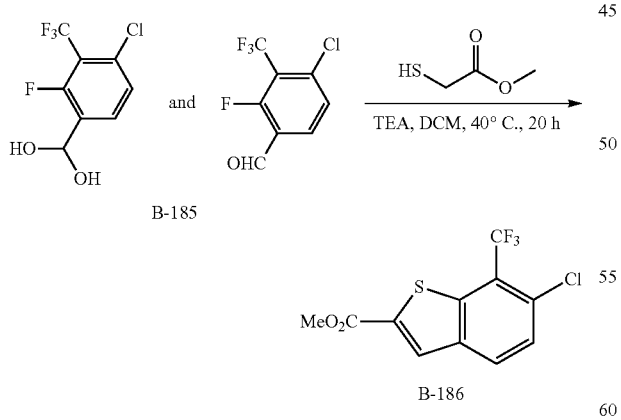

B-186

To a solution of compound mixture B-185 (0.5 g, 2 mmol) in dichloromethane (5 mL) was added triethylamine (0.3 g, 3 mmol) and methyl 2-sulfanylacetate (0.3 g, 3 mmol). The mixture was stirred at 40° C. for 20 hours, then diluted with water (40 mL) and extracted with ethyl acetate (3×40 mL). The combined organic layers were washed with brine (3×10 mL), dried with anhydrous sodium sulfate, filtered and concentrated in vacuo. The residue was purified by silica gel chromatography [petroleum ether:ethyl acetate=10:1] to give compound B-186 (0.4 g, 70% yield) as a white solid. $^1$H-NMR (CD$_3$OD, 400 MHz): δ 8.14 (d, J=6.4 Hz, 2H), 7.65 (d, J=8.4 Hz, 1H), 3.96 (s, 3H).

Example 86B: 6-chloro-7-(trifluoromethyl)benzo[b]thiophene-2-carboxylic acid (B-187)

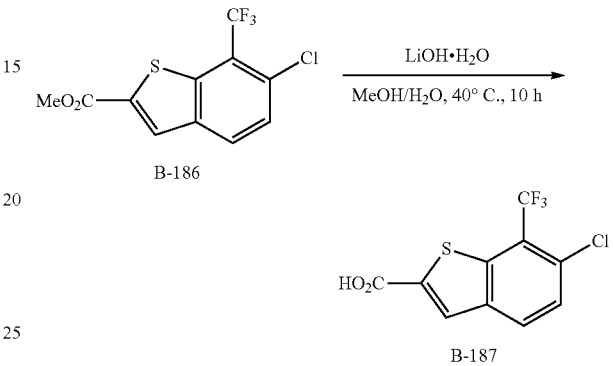

B-187

A mixture of compound B-186 (0.40 g, 1.4 mmol) and lithium hydroxide monohydrate (0.40 g, 9.5 mmol) in methanol (8 mL) and water (4 mL) was stirred at 40° C. for 10 hours. The mixture was concentrated in vacuo, diluted with water (50 mL), acidified to pH 2 with concentrated hydrochloric acid, and extracted with ethyl acetate (3×50 mL). The combined organic phase was washed with brine (3×10 mL), dried with anhydrous sodium sulfate, filtered and concentrated in vacuo to give compound B-187 (0.3 g, 81% yield) as a yellow solid. $^1$H-NMR (CD$_3$OD, 400 MHz): 8.16-8.11 (m, 2H), 7.66-7.63 (m, 1H).

Example 87B: 3-chloro-2-fluoro-4-methoxybenzaldehyde (B-188)

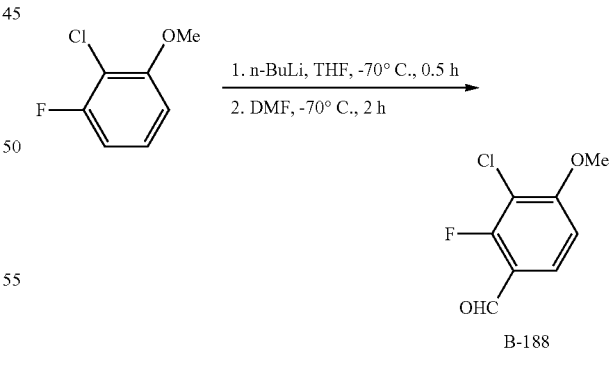

B-188

To a mixture of 2-chloro-1-fluoro-3-methoxybenzene (1.0 g, 6.2 mmol) in anhydrous tetrahydrofuran (15 mL) at −70° C. under nitrogen was added dropwise n-butyllithium (2.5 M in n-hexane, 3.7 mL, 9.3 mmol). The mixture was stirred for 30 minutes, and N,N-dimethylformamide (0.91 g, 12 mmol) was added dropwise at −70° C. The reaction was stirred at −70° C. for another 2 hours, then poured into water and extracted with ethyl acetate. The organic layer was dried over anhydrous sodium sulfate and concentrated in vacuo to give compound B-188 (1.0 g, crude) as a white solid.

Example 88B: methyl 7-chloro-6-methoxybenzo[b]thiophene-2-carboxylate (B-189)

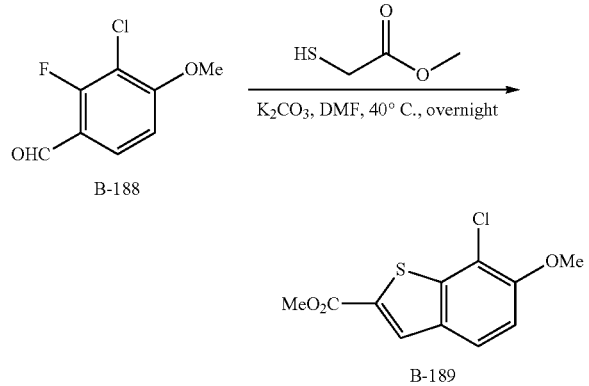

To a mixture of compound B-188 (1.0 g, 5.3 mmol) in N,N-dimethylformamide (15 mL) was added methyl 2-mercaptoacetate (0.56 g, 5.3 mmol) and potassium carbonate (1.5 g, 11 mmol). The mixture was stirred at 40° C. overnight, then poured into ice water, resulting in formation of a solid. The white solid was collected by filtration and dried in vacuo to give compound B-189 (1.1 g, 81% yield). LCMS (R): tR=1.121 min., (ES$^+$) m/z (M+H)$^+$=257.0.

Example 89B: 7-chloro-6-methoxybenzo[b]thiophene-2-carboxylic acid (B-190)

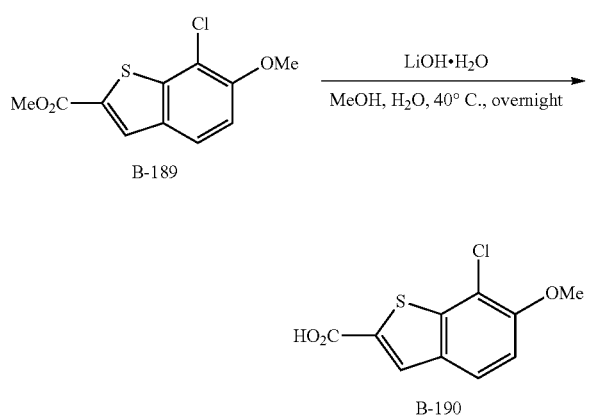 [SMILES: COC(=O)c1cc2ccc(OC)c(Cl)c2s1 ; "LiOH·H2O" ; COc1ccc2cc(C(=O)O)sc2c1Cl]

To a mixture of compound B-189 (0.60 g, 2.3 mmol) in methanol (10 mL) and water (5 mL) was added lithium hydroxide monohydrate (0.20 g, 4.7 mmol). The mixture was stirred at 40° C. overnight, then concentrated to remove methanol, diluted with water and acidified to pH 3 with 1 M hydrochloric acid, resulting in formation of a solid. The white solid was collected by filtration and dried in vacuo to give compound B-190 (0.50 g, 88% yield). LCMS (B): tR=0.765 min., (ES$^+$) m/z (M+H)$^+$=243.0.

Example 90B: 2-fluoro-4-methyl-3-(trifluoromethyl)benzaldehyde (B-191)

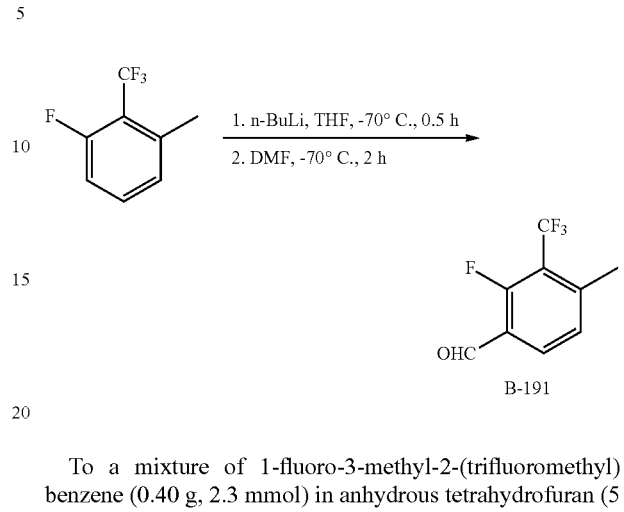

To a mixture of 1-fluoro-3-methyl-2-(trifluoromethyl)benzene (0.40 g, 2.3 mmol) in anhydrous tetrahydrofuran (5 mL) at −70° C. under nitrogen was added dropwise n-butyllithium (2.5 M in cyclohexane, 1.4 mL, 3.4 mmol). The mixture was stirred at this temperature for half an hour, and N,N-dimethylformamide (0.49 g, 6.8 mmol) was added dropwise. The reaction was stirred at −70° C. for another 2 hours, then acidified to pH 5.0 with 6 N HCl and extracted with ethyl acetate (2×20 mL). The combined organic layers were dried over anhydrous sodium sulfate and concentrated in vacuo to give compound B-191 (0.40 g, 86% yield) as yellow oil. LCMS (DD): tR=0.983 min., (ES$^+$) m/z (M+H)$^+$= 207.0.

Example 91B: methyl 6-methyl-7-(trifluoromethyl)benzo[b]thiophene-2-carboxylate (B-192)

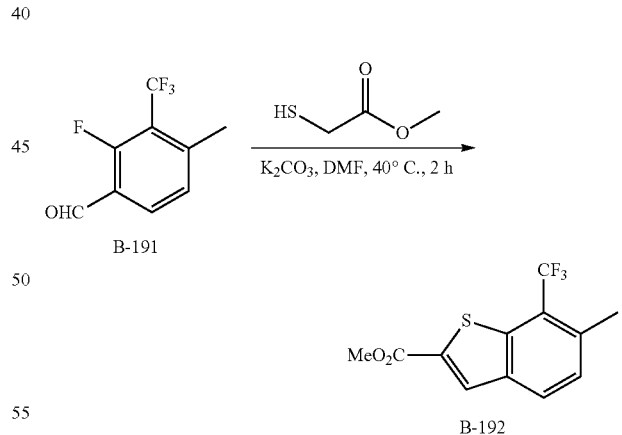

To a mixture of compound B-191 (0.38 g, 1.8 mmol) in N,N-dimethylformamide (5 mL) was added methyl 2-mercaptoacetate (0.23 g, 2.2 mmol) and potassium carbonate (0.51 g, 3.7 mmol). The mixture was stirred at 40° C. for 2 hours, then poured into water (5 mL) and extracted with ethyl acetate (2×20 mL). The organic layer was dried over anhydrous sodium sulfate and concentrated in vacuo to give compound B-192 (0.50 g, 95% yield) as a yellow solid. LCMS (DD): tR=1.157 min., (ES$^+$) m/z (M+H)$^+$=275.0.

Example 92B: 6-methyl-7-(trifluoromethyl)benzo[b]thiophene-2-carboxylic acid (B-193)

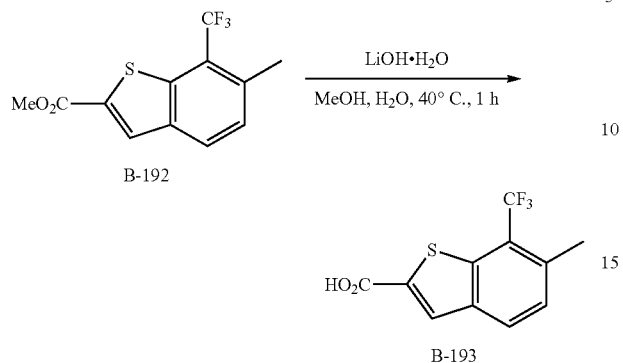

To a mixture of compound B-192 (0.48 g, 1.8 mmol) in methanol (6 mL) and water (3 mL) was added lithium hydroxide monohydrate (0.15 g, 3.5 mmol). The mixture was stirred at 40° C. for 1 hour, then concentrated to remove methanol, diluted with water and acidified to pH 3 with 1 M hydrochloric acid, resulting in formation of a solid. The white solid was collected by filtration and dried in vacuo to give compound B-193 (0.40 g, 88% yield). LCMS (DD): tR=1.009 min., (ES$^+$) m/z (M+H)$^+$=261.0.

Example 93B: methyl 7-chloro-6-fluorobenzo[b]thiophene-2-carboxylate (B-194)

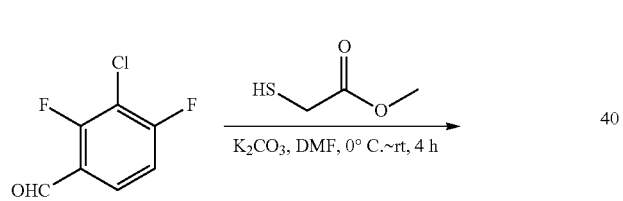

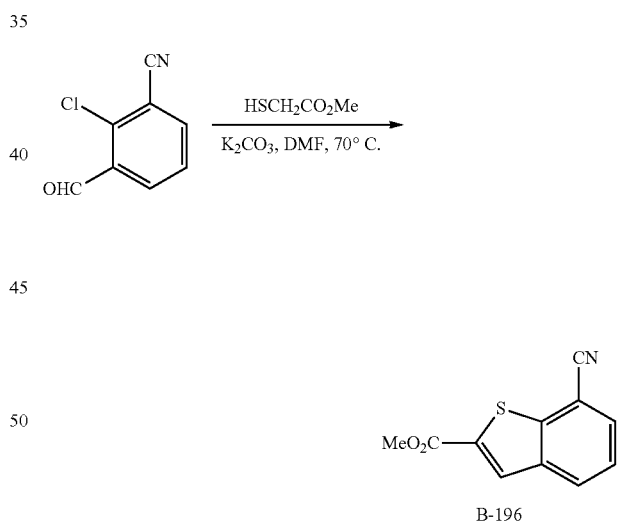

To a solution of 3-chloro-2,4-difluorobenzaldehyde (2.0 g, 11 mmol) and potassium carbonate (2.4 g, 17 mmol) in N,N-dimethylformamide (20 mL) at 0° C. was added dropwise methyl 2-mercaptoacetate (1.4 g, 14 mmol). The mixture was stirred at room temperature for 4 hours, then diluted with water (30 mL) and extracted with ethyl acetate (2×50 mL). The organic layer was concentrated in vacuo, and the residue was purified by silica gel chromatography [petroleum ether: ethyl acetate=20:1] to give compound B-194 (1.6 g, 58% yield) as a yellow solid. LCMS (B): tR=0.912 min., (ES$^+$) m/z (M+H)=245.0.

Example 94B: 7-chloro-6-fluorobenzo[b]thiophene-2-carboxylic acid (B-195)

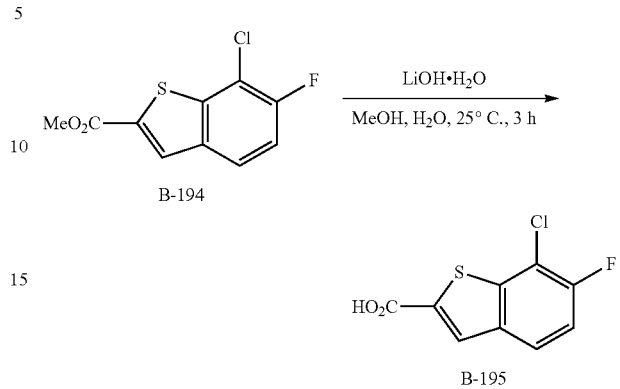

To a mixture of compound B-194 (2.5 g, 10 mmol) in methanol (10 mL) and water (10 mL) was added lithium hydroxide monohydrate (0.82 g, 20 mmol). The mixture was stirred at 25° C. for 3 hours, then concentrated to remove methanol, diluted with water and acidified to pH 3 with 1 M hydrochloric acid, resulting in formation of a solid. The yellow solid was collected by filtration and dried in vacuo to give compound B-195 (1.5 g, 64% yield).

Example 95B: methyl 7-cyanobenzo[b]thiophene-2-carboxylate (B-196)

To a solution of 2-chloro-3-formylbenzonitrile (1.2 g, 7.3 mmol) and potassium carbonate (2.0 g, 15 mmol) in N,N-dimethylformamide (15 mL) at 28° C. was added methyl 2-mercaptoacetate (1.5 g, 15 mmol). The mixture was stirred overnight at 70° C., then diluted with water (20 mL) and extracted with ethyl acetate (3×30 mL). The combined organic layers were washed with brine (2×30 mL), dried over anhydrous sodium sulfate and concentrated in vacuo. The residue was purified by silica gel column chromatography [petroleum ether:ethyl acetate=20:1] to give compound B-196 (0.98 g, 62% yield) as a yellow solid.

Example 96B: 7-cyanobenzo[b]thiophene-2-carboxylic acid (B-197)

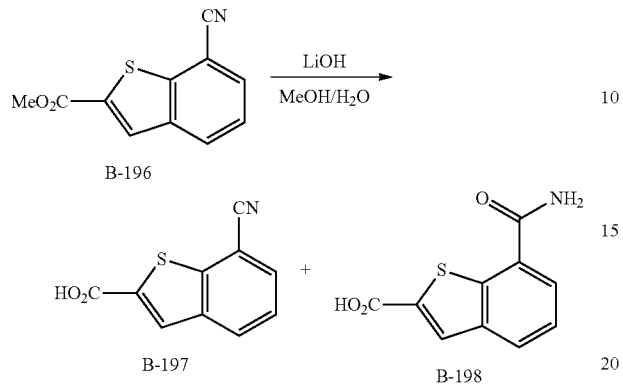

To a solution of B-196 (0.98 g, 4.5 mmol) in methanol (10 mL) and water (2 mL) was added lithium hydroxide (0.38 g, 9.0 mmol) at room temperature. The mixture was stirred for 1 hour until TLC showed the reaction was complete. The solution was concentrated to remove most of methanol and acidified to pH 4~5, resulting in formation of a solid. The solid was collected by filtration and dried in vacuo to give compound B-197 as a mixture with compound B-198 (0.75 g) as a white solid.

Example 97B: methyl 7-methoxybenzo[b]thiophene-2-carboxylate (B-199)

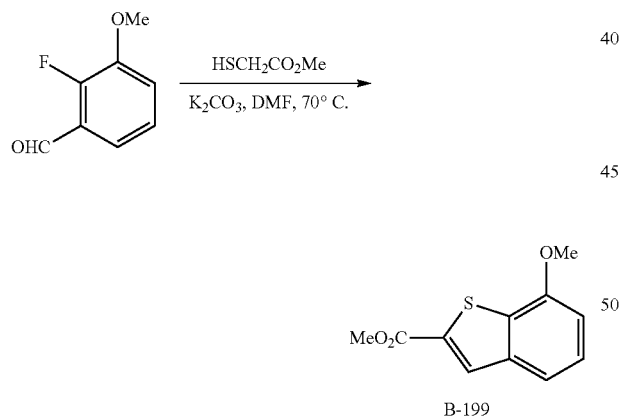

To a solution of 2-fluoro-3-methoxybenzaldehyde (2.0 g, 13 mmol) and potassium carbonate (3.6 g, 26 mmol) in N,N-dimethylformamide (20 mL) at 28° C. was added methyl 2-mercaptoacetate (1.7 g, 11 mmol). The mixture was stirred at 70° C. overnight, then diluted with water (20 mL) and extracted with ethyl acetate (3×30 mL). The combined organic layers were washed with brine (2×30 mL), dried over anhydrous sodium sulfate and concentrated in vacuo. The residue was then purified by silica gel column chromatography [petroleum ether:ethyl acetate=20:1] to give compound B-199 (2.5 g, 89% yield) as a white solid.

Example 98B: 7-methoxybenzo[b]thiophene-2-carboxylic acid (B-200)

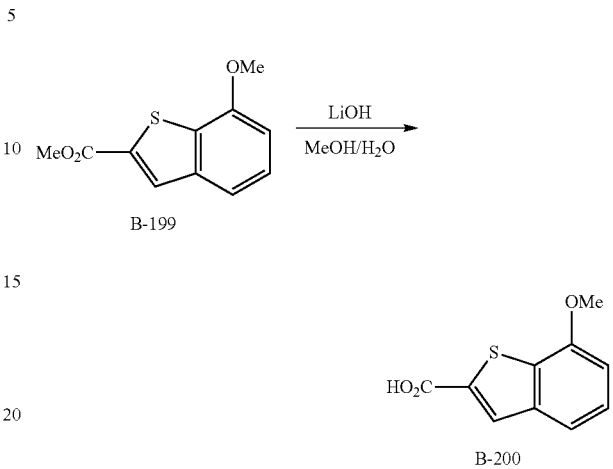

To a solution of B-199 (1.0 g, 4.5 mmol) in methanol (10 mL) and water (2 mL) at room temperature was added lithium hydroxide (0.38 g, 9.0 mmol). The mixture was stirred for 2 hours, then concentrated to remove most of methanol and acidified to pH 4~5, resulting in formation of a solid. The white solid was collected by filtration and dried in vacuo to give compound B-200 (0.85 g, 91% yield). 1H-NMR (CD3OD, 400 MHz): δ 8.04 (s, 1H), 7.53 (d, J=8.0 Hz, 1H), 7.40 (t, J=8.0 Hz, 1H), 7.01 (d, J=8.0 Hz, 1H), 4.03 (s, 3H).

Example 99B: methyl 2-((2,3-difluoro-6-formylphenyl)thio)acetate (B-201)

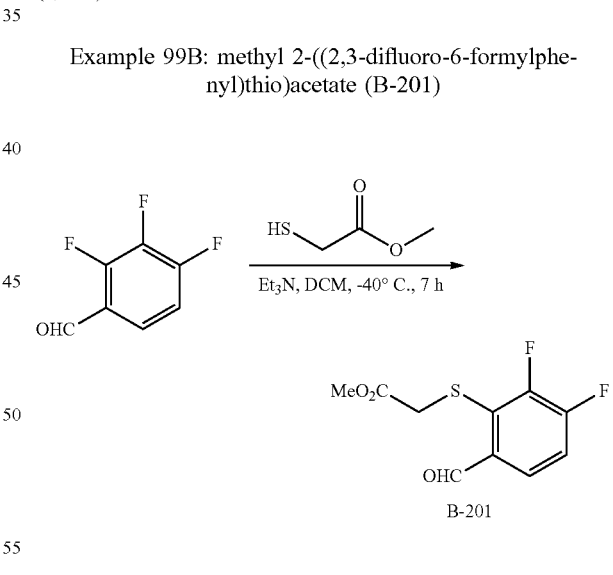

To a solution of 2,3,4-trifluorobenzaldehyde (1.00 g, 6.25 mmol) and methyl 2-sulfanylacetate (663 mg, 6.25 mmol) in dichloromethane (15 mL) at −40° C. was added triethylamine (632 mg, 6.25 mmol). The reaction was stirred at this temperature for 7 hours, then poured into water and extracted with ethyl acetate. The organic layer was dried over anhydrous sodium sulfate and concentrated in vacuo. The residue was purified by column chromatography [petroleum ether:ethyl acetate=10:1] to give compound B-201 (0.25 g, 17% yield) as white as a white solid. LCMS (B): tR=0.735 min., (ES$^+$) m/z (M+H)$^+$=246.0.

Example 100B: methyl 67-difluorobenzo[b]thiophene-2-carboxylate (B-202)

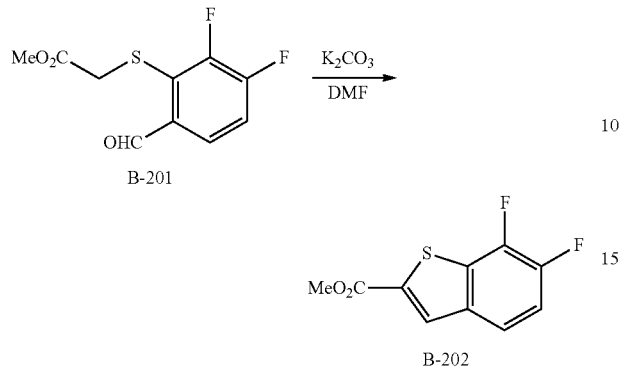

A mixture of compound B-201 (100 mg, 0.41 mmol) and potassium carbonate (56 mg, 0.41 mmol) in N,N-dimethylformamide (5.0 mL) was stirred at 50° C. for 16 hrs. On completion, the mixture was poured into water and extracted with ethyl acetate. The organic layer was dried over anhydrous sodium sulfate concentrated in vacuo and purified by column chromatography [petroleum ether:ethyl acetate=10:1] to give compound B-202 (88 mg, 95% yield) as a white solid. LCMS (B): tR=0.871 min., (ES+) m/z (M+H)+= 228.0.

Example 101B: 6,7-difluorobenzo[b]thiophene-2-carboxylic acid (B-203)

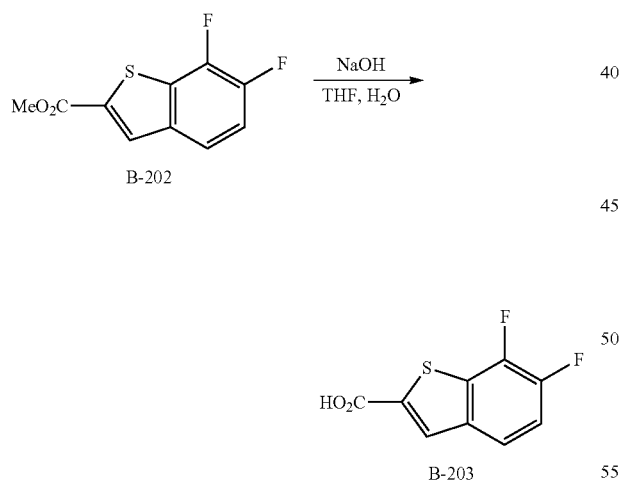

To a solution of compound B-202 (88 mg, 0.39 mmol) in tetrahydrofuran (15 mL) at 25° C. was added sodium hydroxide (23 mg, 0.57 mmol) and water (6.0 mL). The mixture was stirred at room temperature for 4 hrs, then concentrated to remove tetrahydrofuran and acidified to pH 3 with 0.2 N hydrochloric acid, resulting in formation of a solid. The white solid was collected by filtration and dried in vacuo to give compound B-203 (76 mg, 92% yield). $^1$H-NMR (CD$_3$OD, 400 MHz): δ 8.10 (d, J=4, 1H), 7.80-7.77 (dd, J$_1$=4, J$_2$=8.8, 1H), 7.45-7.38 (m, 1H).

Example 102B: methyl 7-cyclopropylbenzo[b]thiophene-2-carboxylate (B-204)

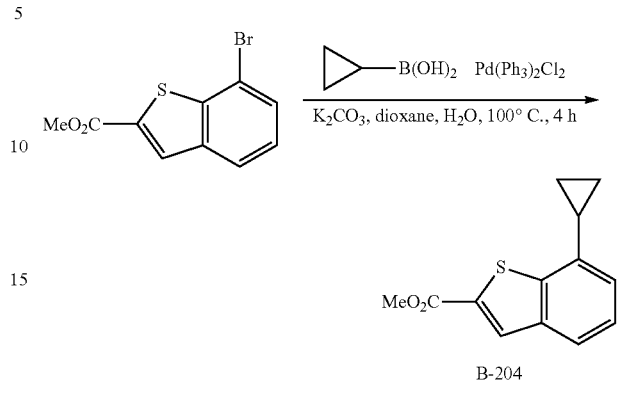

A mixture of methyl 7-bromobenzo[b]thiophene-2-carboxylate (1.0 g, 3.7 mmol), cyclopropylboronic acid (0.38 g, 4.4 mmol), bis(triphenylphosphine)palladium(II) dichloride (0.26 g, 0.37 mmol) and potassium carbonate (1.5 g, 11 mmol) in dioxane (15 mL) and water (3 ml) was stirred at 100° C. under nitrogen for 4 hours. On completion, the solution was diluted with water (20 mL) and extracted with ethyl acetate (2×40 mL). The combined organic layers were concentrated in vacuo to give compound B-204 (0.70 g, crude) as a yellow solid, used for the next step without further purification.

Example 103B: 7-cyclopropylbenzo[b]thiophene-2-carboxylic acid (B-205)

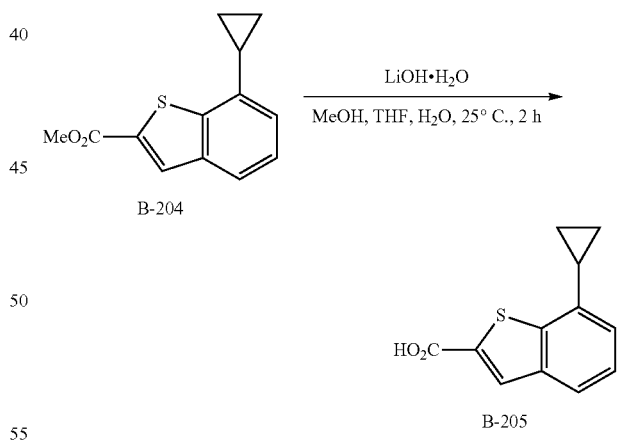

To a mixture of compound B-204 (1.0 g, 4.3 mmol) in methanol (5 mL), tetrahydrofuran (5 mL) and water (5 mL) was added lithium hydroxide monohydrate (0.55 g, 13 mmol). The mixture was stirred at 25° C. for 2 h, then concentrated to remove methanol, diluted with water and acidified to pH 3 with 1 M hydrochloric acid, resulting in formation of a solid. The yellow solid was collected by filtration and dried in vacuo to give compound B-205 (0.70 g, 75% yield). LCMS (B): tR=0.817 min., (ES$^+$) m/z (M+H)$^+$=219.1.

Example 104B: methyl 7-(prop-1-en-2-yl)benzo[b]thiophene-2-carboxylate (B-206)

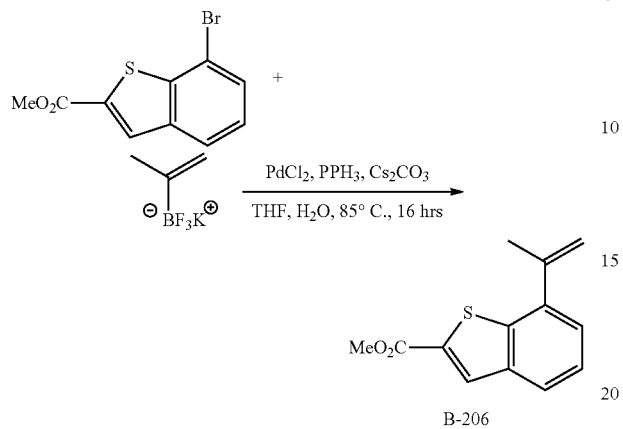

A solution of potassium vinyltrifluoroborate (0.33 g, 2.2 mmol), palladium chloride (6.5 mg, 37 umol), triphenylphosphine (29 mg, 0.11 mmol), cesium carbonate (1.8 g, 5.5 mmol) and methyl 7-bromobenzo[b]thiophene-2-carboxylate (0.50 g, 1.8 mmol) in tetrahydrofuran (9 mL) and water (1 mL) was stirred under nitrogen at 85° C. for 16 hours. On completion, the mixture was cooled to room temperature, diluted with water (10 mL) and extracted with dichloromethane (3×10 mL). The combined organic layers were washed with water (10 mL) and brine (10 mL) and concentrated in vacuo. The residue was purified by silica gel column chromatography [petroleum ether:ethyl acetate=100:1] to give compound B-206 (0.30 g, 70% yield) as an oil. LCMS (B): (ES$^+$) m/z (M+H)$^+$=233.0, tR=0.997.

Example 105B: methyl 7-(prop-1-en-2-yl)benzo[b]thiophene-2-carboxylate (B-207)

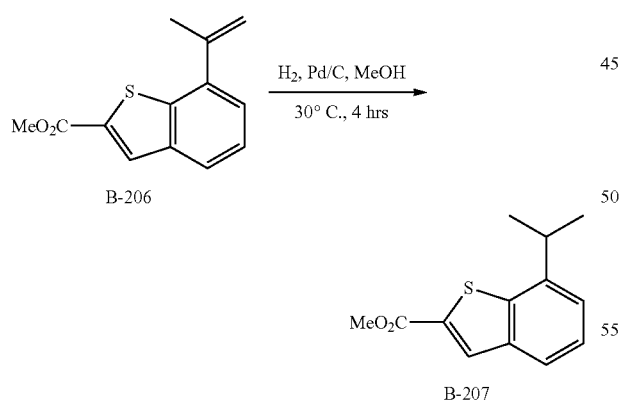

To a solution of compound B-206 (0.30 m, 1.3 mmol) in methanol (10 mL) under nitrogen was added wet 10% palladium/carbon (30 mg). The suspension was degassed under vacuum and purged with hydrogen several times. The mixture was stirred under balloon hydrogen at 30° C. for 4 hours until TLC showed the starting material was consumed completely. The reaction mixture was filtered, and the filtrate was concentrated in vacuo and purified by prep-HPLC-HCl [Instrument: GX-E; Column: Phenomenex Synergi C18 250*21.2 mm, particle size: 4 μm; Mobile phase: 58-88% acetonitrile in H$_2$O (add 0.5% HCl, v/v)] to give compound B-207 (0.25 g, 83% yield) as a yellow solid. $^1$H-NMR (CD$_3$OD, 400 MHz): δ 8.12 (s, 1H), 7.81-7.78 (m, 1H), 7.46-7.40 (m, 2H), 3.29-3.19 (m, 1H), 1.43-1.42 (d, J=7.2 Hz, 6H).

Example 106B: 7-isopropylbenzo[b]thiophene-2-carboxylic acid (B-208)

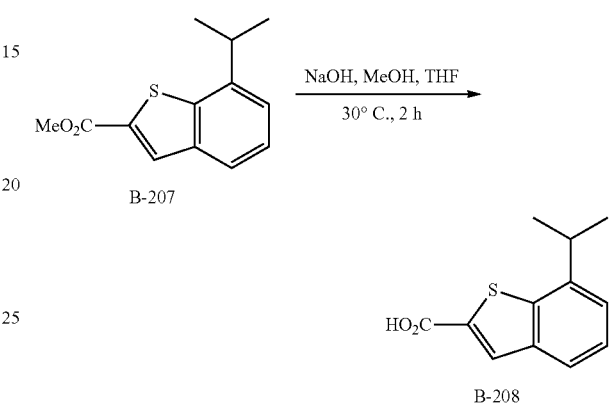

To a solution of compound B-207 (0.25 g, 1.1 mmol) in methanol (2 mL) and tetrahydrofuran (12 mL) was added aqueous sodium hydroxide (1 M, 1.6 mL, 1.6 mmol). The resulting mixture was stirred at 30° C. for 2 hours, then partially concentrated and acidified to pH-6 with concentrated hydrochloric acid, resulting in formation of a solid. The white solid was collected by filtration and dried in vacuo to give compound B-208 (0.20 g, 85% yield). LCMS (AA): (ES$^+$) m/z (M+H)$^+$=219.1, tR=0.21.

Example 107B: methyl 7-(trifluoromethoxy)benzo[b]thiophene-2-carboxylate (B-209)

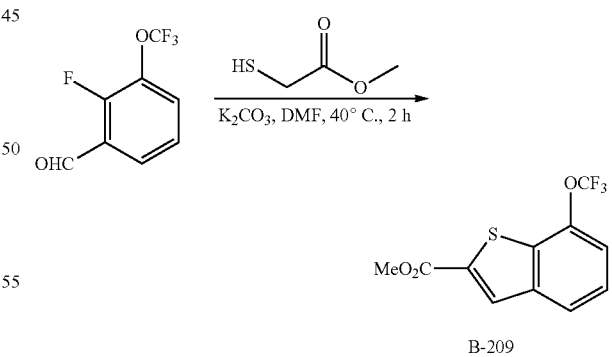

To a mixture of 2-fluoro-3-(trifluoromethoxy)benzaldehyde (0.5 g, 2.4 mmol) in N,N-dimethylformamide (5 mL) was added methyl 2-mercaptoacetate (0.28 g, 2.6 mmol) and potassium carbonate (0.66 g, 4.8 mmol). The mixture was stirred at 40° C. for 2 hours, then poured into water and extracted with ethyl acetate. The organic layer was dried over anhydrous sodium sulfate and concentrated in vacuo to give compound B-209 (0.6 g, 90% yield) as a white solid.

¹H-NMR (CD₃OD, 400 MHz): δ 8.17 (s, 1H), 7.95 (d, J=8.0 Hz, 1H), 7.53 (t, J=8.0 Hz, 1H), 7.46 (d, J=7.6 Hz, 1H), 3.96 (s, 3H).

Example 108B: 7-(trifluoromethoxy)benzo[b]thiophene-2-carboxylic acid (B-210)

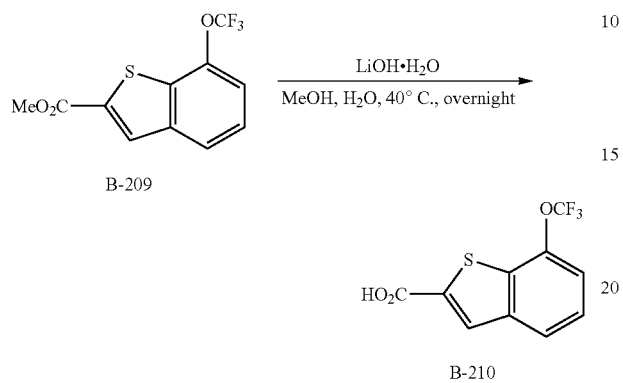

To a mixture of compound B-209 (0.6 g, 2.3 mmol) in methanol (8 mL) and water (4 mL) was added lithium hydroxide monohydrate (0.14 g, 3.4 mmol). The mixture was stirred at 40° C. overnight, then concentrated to remove methanol, diluted with water and acidified to pH to 2 with 1 M hydrochloric acid, resulting in formation of a solid. The white solid was collected by filtration and dried in vacuo to give compound B-210 (0.48 g, 84% yield) as a white solid. ¹H-NMR (CD₃OD, 400 MHz): δ 8.13 (s, 1H), 7.95 (d, J=10.4 Hz, 1H), 7.53 (t, J=10.4 Hz, 1H), 7.45 (d, J=10.8 Hz, 1H).

Example 109B: methyl 7-(3,6-dihydro-2H-pyran-4-yl)benzo[b]thiophene-2-carboxylate (B-211)

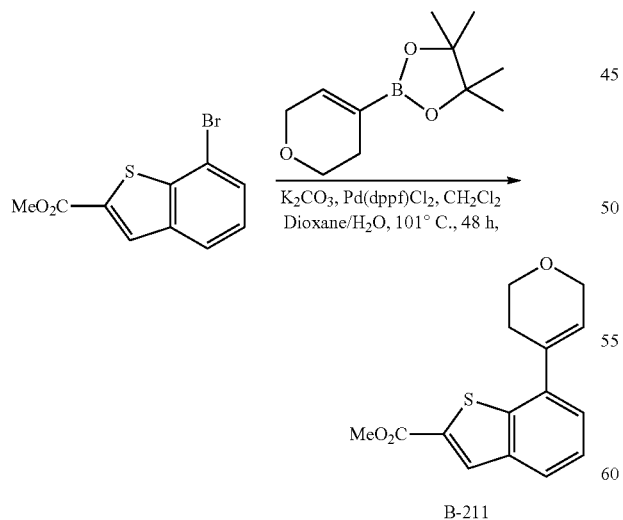

To a solution of methyl 7-(3,6-dihydro-2H-pyran-4-yl)benzo[b]thiophene-2-carboxylate (1.0 g, 3.7 mmol) in dioxane (30 mL) and water (6 mL) under nitrogen was added K₂CO₃ (1.5 g, 11 mmol), Pd(dppf)Cl₂·CH₂Cl₂ (301 mg, 0.37 mmol) and 2-(3,6-dihydro-2H-pyran-4-yl)-4,4,5,5-tetramethyl-1,3,2-dioxaborolane (930 mg, 4.4 mmol). The mixture was stirred at 101° C. for 48 hours. On completion, the reaction mixture was concentrated and purified by silica gel chromatography [petroleum ether:ethyl acetate=16:1] to give compound B-211 (300 mg, 60% yield) as a white solid. ¹H-NMR (CD₃OD, 400 MHz): δ 8.12 (s, 1H), 7.86 (dd, J₁=8.0 Hz, J₂=1.6 Hz 1H), 7.48-7.42 (m, 2H), 6.35-6.34 (m, 1H), 4.39-4.36 (m, 2H), 4.00-3.97 (m, 2H), 3.93 (s, 3H), 2.62-2.59 (m, 2H).

Example 110B: methyl 7-(tetrahydro-2H-pyran-4-yl)benzo[b]thiophene-2-carboxylate (B-212)

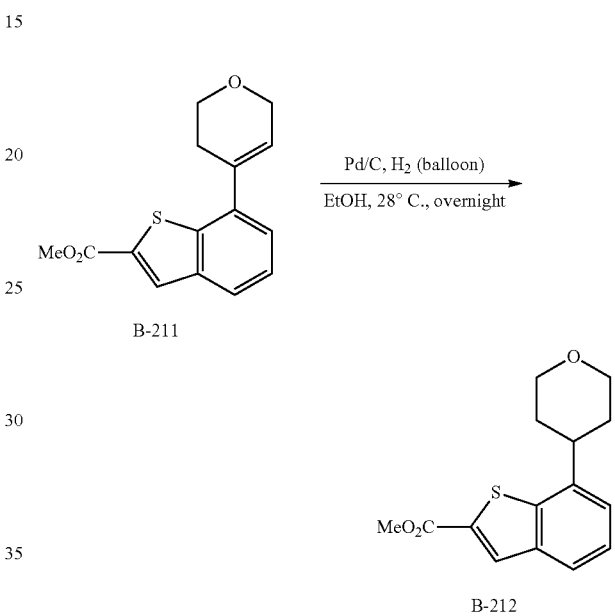

To a solution of compound B-211 (300 mg, 1.1 mmol) in ethanol (8 mL) under nitrogen was added Pd/C (10%, 100 mg). The suspension was degassed under vacuo and purged with hydrogen several times. The mixture was stirred under balloon hydrogen at 28° C. overnight. On completion, the reaction mixture was filtered, and the filtrate was concentrated to give compound B-212 (300 mg, 99% yield) as a white solid. ¹H-NMR (CD₃OD, 400 MHz): δ 8.12 (s, 1H), 7.80 (dd, J₁=8.0 Hz, J₂=1.2 Hz, 1H), 7.47-7.40 (m, 2H), 4.12-4.08 (m, 2H), 3.94 (s, 3H), 3.72-3.63 (m, 2H), 3.15-3.10 (m, 1H), 1.99-1.91 (m, 4H).

Example 111B: 7-(tetrahydro-2H-pyran-4-yl)benzo[b]thiophene-2-carboxylic acid (B-213)

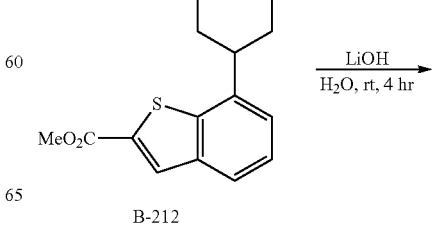

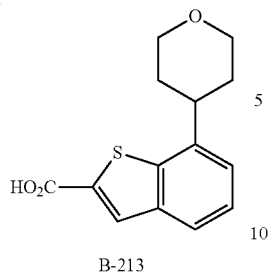

B-213

To compound B-212 (300 mg, 1.1 mmol) in methanol (8 mL) and water (4 mL) was added lithium hydroxide monohydrate (78 mg, 1.87 mmol). The mixture was stirred at room temperature for 4 hours, then acidified to pH 5~6, resulting in formation of a solid. The white solid was collected by filtration and dried in vacuo to give compound B-213 (260 mg, 92%). $^1$H-NMR (CD$_3$OD, 400 MHz): δ 8.08 (s, 1H), 7.80 (dd, J$_1$=8.0 Hz, J$_2$=1.2 Hz, 1H), 7.48-7.39 (m, 2H), 4.11 (d, J=12 Hz, 2H), 3.70-3.63 (m, 2H), 3.17-3.10 (m, 1H), 2.03-1.95 (m, 4H).

Example 112B: methyl 6-chloro-5-fluorobenzo[b]thiophene-2-carboxylate (B-214)

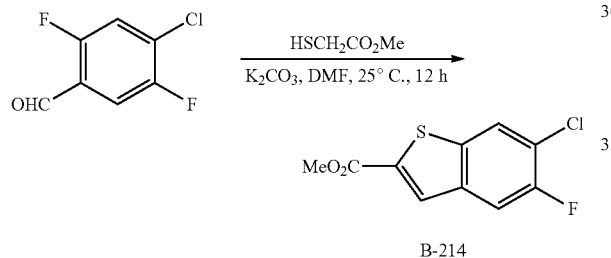

B-214

A mixture of 4-chloro-2,5-difluorobenzaldehyde (1.0 g, 5.7 mmol), ethyl 2-mercaptoacetate (0.7 g, 6.8 mmol) and potassium carbonate (1.6 g, 11 mmol) in N,N-dimethylformamide (20 mL) was stirred at 25° C. for 24 hours. On completion, the mixture was diluted with water (50 mL) and extracted with EtOAc (3×30 mL). The combined organic layers were washed with brine, dried with anhydrous sodium sulfate, filtered and concentrated to dryness. The residue was purified by silica gel chromatography [petroleum ether:ethyl acetate=3:1] to give compound B-214 (0.7 g, 50% yield) as a white solid. LCMS (C): tR=1.072 min., 244.9 m/z (M+1); $^1$H-NMR (CDCl$_3$, 400 MHz): δ 7.97 (s, 1H), δ 7.91-7.90 (d, J=6.4 Hz, 1H), 7.63-7.61 (d, J=8.8 Hz, 1H), 3.96 (s, 3H).

Example 113B: 6-chloro-5-fluorobenzo[b]thiophene-2-carboxylic acid (B-215)

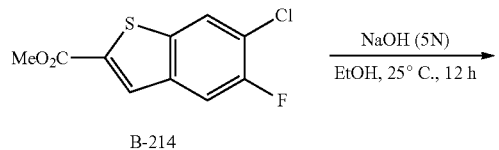

B-214

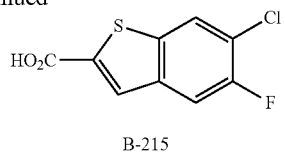

B-215

To a solution of compound B-214 (0.7 g, 3.0 mmol) in ethanol (15 mL) was added an aqueous solution of sodium hydroxide (5 N, 1.8 mL, 9 mmol). The reaction was stirred at 25° C. for 12 hours. On completion, the volatiles were removed in vacuo. The residue was dissolved in water, washed with ethyl acetate (2×20 mL) and acidified to pH 3 with 6 N hydrochloric acid (6 N), resulting in formation of a solid. The white solid was collected by filtration and dried in vacuo to give compound B-215 (0.6 g, 91% yield) as a white solid. LCMS (C): tR=1.211 min., 228.9 m/z (M-1); $^1$H-NMR (DMSO-d6, 400 MHz): δ 8.42-8.41 (d, J=6.8 Hz, 1H), 8.07 (s, 1H), 8.05-8.03 (d, J=10 Hz, 1H).

Example 114B: 5-fluoro-6-methoxybenzo[b]thiophene-2-carboxylic acid (B-216

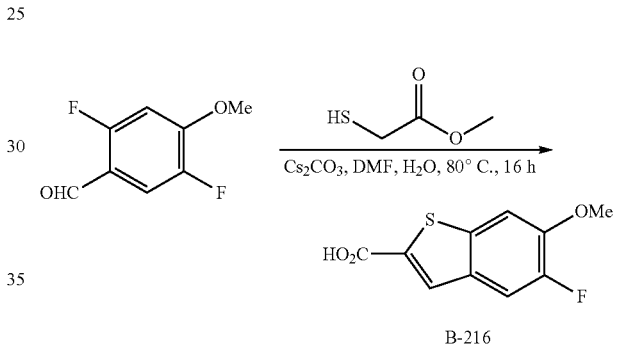

B-216

To a mixture of 2,5-difluoro-4-methoxybenzaldehyde (0.20 g, 1.2 mmol) and methyl 2-mercaptoacetate (0.15 g, 1.4 mmol) in N,N-dimethylformamide (10 mL) was added cesium carbonate (1.1 g, 3.5 mmol). The mixture was stirred at 80° C. for 16 hours. On completion, water (1.0 mL) was added to the reaction mixture, and stirring was continued at 80° C. for half an hour. The solution was cooled to room temperature and poured into ice water (10 mL), resulting in formation of a solid. After stirring for half an hour, the white solid was collected by filtration, washed with water and dried in vacuo to give compound B-216 (231 mg, 89% yield). LCMS (B): (ES$^+$) m/z (M+H)$^+$=227.1, tR=0.719.

Example 115B: (3-chloro-2,4-difluorophenyl)(4-methoxybenzyl)sulfane (B-217)

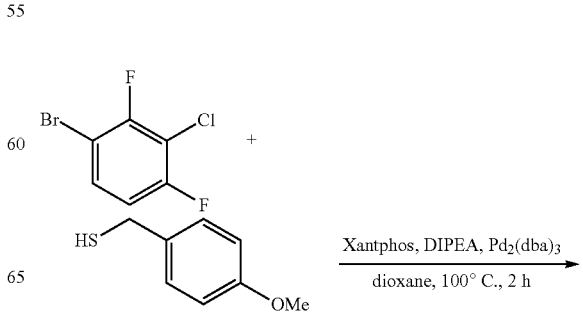

-continued

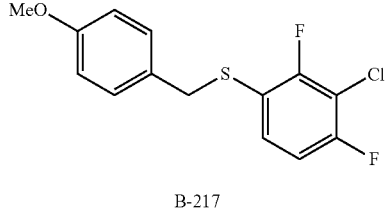

B-217

To a mixture of 1-bromo-3-chloro-2,4-difluoro-benzene (8.0 g, 35 mmol), (4-methoxyphenyl) methanethiol (5.4 g, 35 mmol) and N,N-diisopropylethylamine (9.1 g, 70 mmol) in dioxane (100 mL) at room temperature under nitrogen were added 4,5-bis(diphenylphosphino)-9,9-dimethyxanthene (1.0 g, 1.8 mmol) and tris(dibenzylideneacetone)dipalladium(0) (0.97 g, 1.1 mmol). The reaction mixture was stirred at 100° C. for 2 hours, then filtered, concentrated in vacuo and purified by silica gel chromatography [petroleum ether:ethyl acetate=20:1] to give compound B-217 (9.0 g, 85% yield) as a white solid. $^1$H-NMR (CDCl$_3$, 400 MHz): δ 7.17-7.13 (m, 3H), 6.89-6.87 (m, 1H), 6.83-6.81 (d, J=8.4 Hz, 2H), 4.03 (s, 2H), 3.80 (s, 3H).

Example 116B: 3-chloro-2,4-difluorobenzenethiol (B-218)

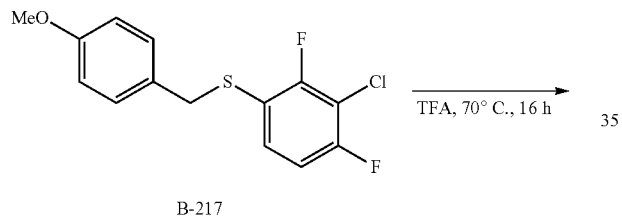

B-217

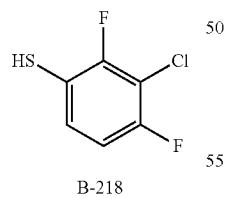

B-218

A solution of compound B-217 (3.0 g, 10 mmol) in trifluoroacetic acid (10 mL) was stirred at 70° C. for 16 hours. On completion, the reaction mixture was quenched with aqueous sodium bicarbonate to pH 7-8 and extracted with ethyl acetate (3×50 mL). The combined organic layers were washed with brine, dried over anhydrous sodium sulfate and concentrated in vacuo to give compound B-218 (2.0 g, crude) as a yellow oil. TLC [petroleum ether:ethyl acetate=10:1]: Rf=0.57.

Example 117B: (3-chloro-2,4-difluorophenyl)(2,2-dimethoxyethyl)sulfane (B-219)

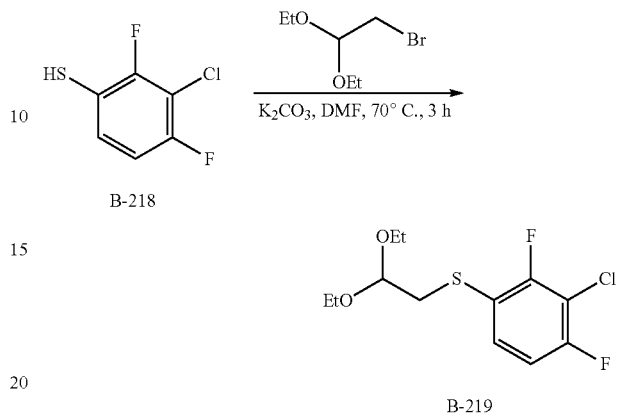

B-218

B-219

A mixture of compound B-218 (1.5 g, 8.31 mmol), 2-bromo-1,1-diethoxy-ethane (1.8 g, 9.14 mmol) and potassium carbonate (1.7 g, 12 mmol) in N,N-dimethylformamide (15 mL) was stirred at 70° C. for 3 hours. On completion, the mixture was poured into water (20 mL) and extracted with ethyl acetate (2×20 mL). The combined organic layers were washed with brine, dried with anhydrous sodium sulfate, filtered and concentrated in vacuo to give compound B-219 (2.0 g, crude) as a yellow oil. [petroleum ether:ethyl acetate=8:1]: Rf=0.70.

Example 118B: 6-chloro-5,7-difluorobenzo[b]thiophene (B-220)

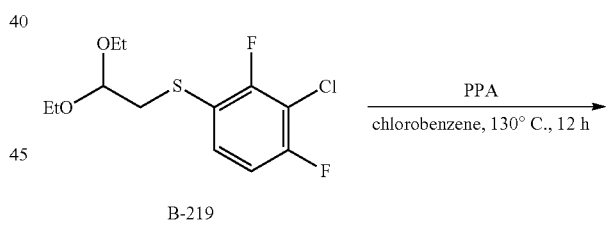

B-219

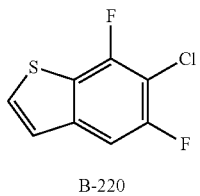

B-220

A solution of compound B-219 (1.5 g, 5.6 mmol) and polyphosphoric acid (10 g, 74 mmol) in chlorobenzene (50 mL) was stirred at 130° C. for 12 hours. On completion, the mixture was poured into water (20 mL) and extracted with ethyl acetate (3×20 mL). The combined organic layers were washed with brine (2×20 mL), dried over anhydrous sodium sulfate, filtered and concentrated in vacuo to afford compound B-220 (0.20 g, 18% yield) as a yellow oil. $^1$H-NMR (CDCl$_3$, 400 MHz): δ 7.59-7.57 (d, J=7.2 Hz, 1H), 7.45-7.42 (m, 1H), 7.34-7.31 (m, 1H).

Example 119B: 6-chloro-5,7-difluorobenzo[b]thiophene-2-carboxylic acid (B-221)

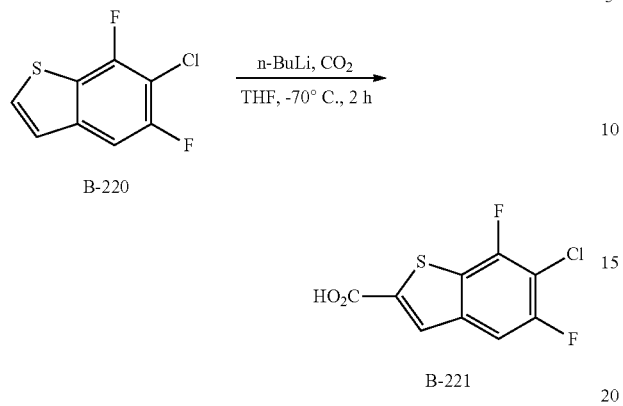

To a solution of compound B-220 (0.15 g, 0.73 mmol) in anhydrous tetrahydrofuran (20 mL) at −70° C. was added dropwise n-butyllithium (0.35 mL, 2.5 N in hexane, 0.88 mmol). The reaction was stirred at −70° C. for 1 hour and then under carbon dioxide at −70° C. for 1 hour. On completion, the mixture was quenched with saturated ammonium chloride solution (20 mL) at 0° C. and extracted with ethyl acetate (2×20 mL). The combined organic layers were washed with brine, dried with anhydrous sodium sulfate and concentrated in vacuo. The residue was purified by prep-HPLC [Instrument: GX-E; Column: Agella Venusil ASB C18 150×30 mm, particle size: 5 μm; Mobile phase: 19-49% acetonitrile in H$_2$O (add 0.05% TFA, v/v)] to give compound B-221 (80 mg, 44% yield) as a yellow solid. LCMS (M): tR=1.165 min., (ES$^+$) m/z (M+H)$^+$=249.0.

Example 120B: methyl 7-methylbenzo[b]thiophene-2-carboxylate (B-222)

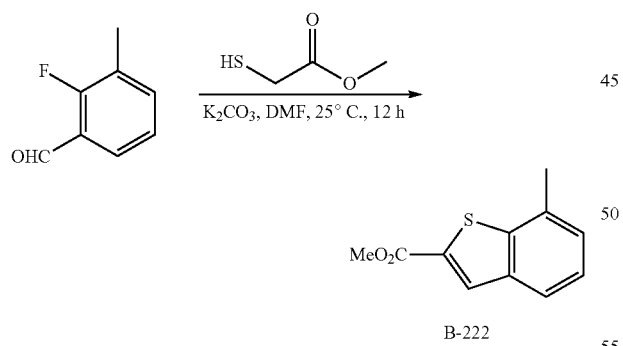

To a mixture of 2-fluoro-3-methylbenzaldehyde (1.0 g, 7.2 mmol) in N,N-dimethylformamide (10 mL) was added methyl 2-mercaptoacetate (1.5 g, 14.5 mmol) and potassium carbonate (2.0 g, 14.5 mmol). The mixture was stirred at 25° C. for 12 hours. On completion, the mixture was poured into water and extracted with ethyl acetate (3×20 mL). The combined organic layers were dried over anhydrous sodium sulfate, concentrated in vacuo and purified by silica gel chromatography [petroleum ether:ethyl acetate=10:1] to give compound B-222 (180 mg, 11% yield) as a white solid. LCMS (B): tR=0.872 min., (ES$^+$) m/z (M+H)$^+$=207.1.

Example 121B: 7-methylbenzo[b]thiophene-2-carboxylic acid (B-223)

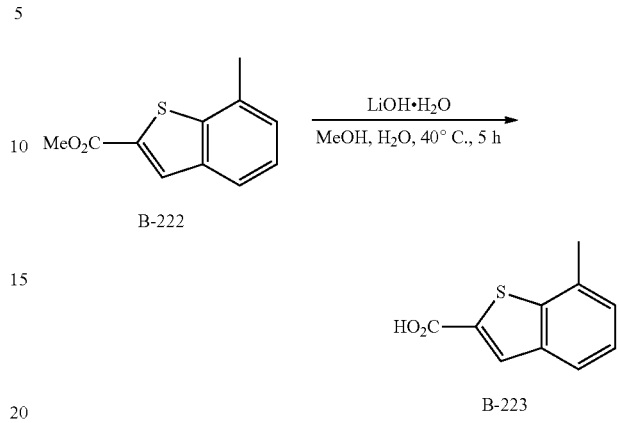

To a mixture of compound B-222 (150 mg, 4.9 mmol) in methanol (6 mL) and water (3 mL) was added lithium hydroxide monohydrate (46 mg, 1.1 mmol). The mixture was stirred at 40° C. for 5, then concentrated to remove methanol, diluted with water and acidified to pH 3 with 1 M hydrochloric acid, resulting in formation of a solid. The white solid was collected by filtration and dried in vacuo to give compound B-223 (125 mg, 87% yield). $^1$H-NMR (DMSO-d6, 400 MHz): δ 8.15 (s, 1H), 7.86 (d, J=7.6 Hz, 1H), 7.43-7.35 (m, 2H), 2.53 (s, 3H).

Example 122B: methyl 7-(4,4,5,5-tetramethyl-1,3,2-dioxaborolan-2-yl)benzo[b]thiophene-2-carboxylate (B-224)

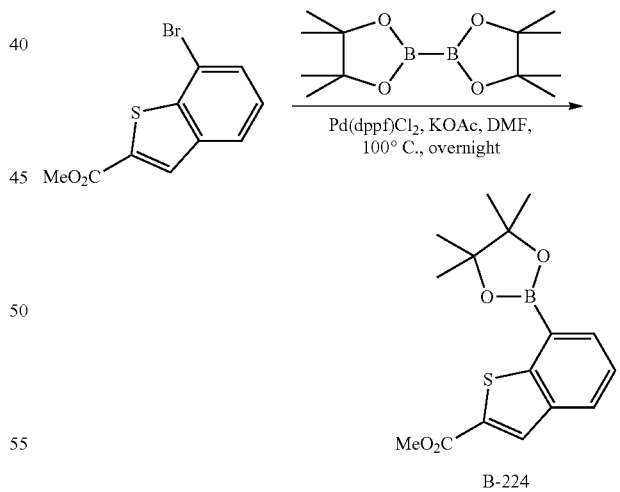

To a mixture of methyl 7-bromobenzo[b]thiophene-2-carboxylate (1.0 g, 3.7 mmol) in N,N-dimethylformamide (10 mL) under nitrogen was added 4,4,4',4',5,5,5',5'-octamethyl-2,2'-bi(1,3,2-dioxaborolane) (1.9 g, 7.4 mmol), [1,1'-bis(diphenylphosphino)ferrocene]dichloropalladium (0.27 g, 0.37 mmol) and potassium acetate (1.1 g, 11 mmol). The mixture was stirred at 100° C. overnight. On completion, the mixture was poured into water (20 mL) and extracted with ethyl acetate (2×50 mL). The combined organic layers were dried over anhydrous sodium sulfate and concentrated in vacuo. The residue was purified by silica gel chromatography [petroleum ether:ethyl acetate=20:1] to give compound B-224 (1.0 g, 55% yield) as a white solid. LCMS (DD): tR=1.182 min., (ES$^+$) m/z (M+H)$^+$=319.1.

Example 123B: methyl 7-(2,2,2-trifluoroethyl)benzo[b]thiophene-2-carboxylate (B-225)

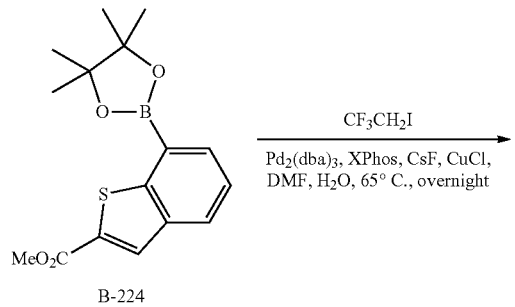

To a mixture of compound B-224 (1.0 g, 3.1 mmol) and 1,1,1-trifluoro-2-iodoethane (1.3 g, 6.3 mmol) in N,N-dimethylformamide (10 mL) and water (1 mL) under nitrogen was added tris(dibenzylideneacetone)dipalladium (86 mg, 94 µmol), 2-(dicyclohexylphosphino)-2',4',6'-triisopropylbiphenyl (0.15 g, 0.31 mmol), cesium fluoride (1.4 g, 9.4 mmol) and cuprous chloride (0.31 g, 3.1 mmol). The mixture was stirred at 65° C. overnight. On completion, the mixture was poured into water (10 mL) and extracted with ethyl acetate (2×20 mL). The combined organic layers were dried over anhydrous sodium sulfate and concentrated in vacuo. The residue was purified by silica gel chromatography [petroleum ether:ethyl acetate=10:1] to give compound B-225 (0.22 g, 26% yield) as a white solid.

Example 124B: 7-(2,2,2-trifluoroethyl)benzo[b]thiophene-2-carboxylic acid (B-226)

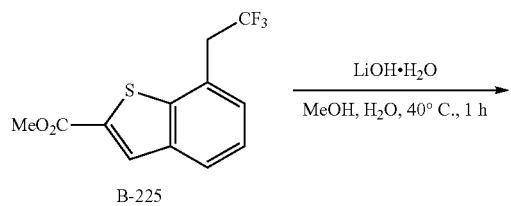

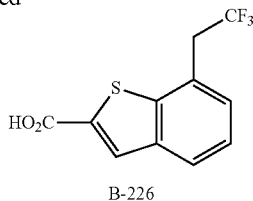

To a mixture of compound B-225 (0.22 g, 0.80 mmol) in methanol (3 mL) and water (1.5 mL) was added lithium hydroxide monohydrate (67 mg, 1.6 mmol). The mixture was stirred at 40° C. for 1 hour, then concentrated to remove methanol, diluted with water and acidified to pH 3 with 1 M hydrochloric acid, resulting in formation of a solid. The yellow solid was collected by filtration and dried in vacuo to give compound B-226 (0.15 g, 72% yield). LCMS (DD): tR=0.912 min., (ES$^+$) m/z (M+H)$^+$=261.0.

Example 125B: methyl 7-(dimethylamino)benzo[b]thiophene-2-carboxylate (B-227)

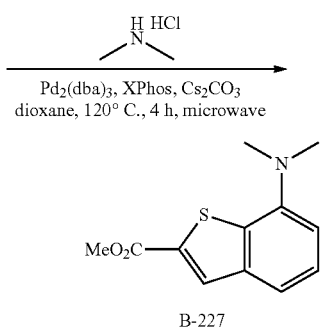

Methyl 7-bromobenzothiophene-2-carboxylate (600 mg, 2.2 mmol), cesium carbonate (2.2 g, 6.6 mmol), tris(dibenzylideneacetone)dipalladium(0) (405 mg, 0.44 mmol), 2-(dicyclohexylphosphino)-2',4',6'-triisopropylbiphenyl (421 mg, 0.88 mmol), and N-methylmethanamine hydrochloride (1.1 g, 13 mmol) in dioxane (10 mL) were placed in a microwave reaction vessel. The mixture was degassed by bubbling nitrogen through it for 6 min. The reaction was heated by microwave irradiation at 120° C. for 4 hours. On completion, the solvent was evaporated. The residue was purified by silica gel column chromatography [petroleum ether] to give compound B-227 (1.0 g, crude) as a green solid.

Example 126B: 7-(dimethylamino)benzo[b]thiophene-2-carboxylic acid (B-228)

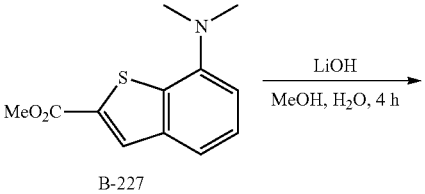

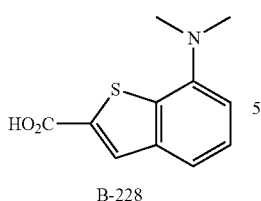

B-228

To compound B-227 (900 mg, crude) in methanol (8 mL) and water (4 mL) was added lithium hydroxide monohydrate (160 mg, 3.8 mmol). The reaction was stirred at room temperature for 4 hours, then acidified to pH 5~6, resulting in formation of a solid. The green solid was collected by filtration and dried to give compound B-228 (400 mg, 67%), which was used for the next step without further purification. LCMS (N): tR=1.909 min., (ES$^+$) m/z (M+H)$^+$=222.0.

Example 127B: methyl 7-(thiazol-2-yl)benzo[b]thiophene-2-carboxylate (B-229)

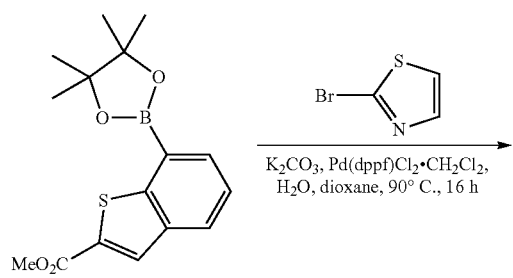

To a solution of methyl 7-(4,4,5,5-tetramethyl-1,3,2-dioxaborolan-2-yl)benzothiophene-2-carboxylate (500 mg, 1.6 mmol) in water (4.5 mL) and dioxane (45.00 mL) was added 2-bromothiazole (387 mg, 2.4 mmol), potassium carbonate (1.2 g, 8.6 mmol), and [1,1'-bis(diphenylphosphino)ferrocene]dichloropalladium(ii) (257 mg, 0.31 mmol). The vessel was flushed with argon and stirred at 90° C. for 16 h. On completion, the reaction mixture was concentrated under reduced pressure and purified by silica gel column chromatography [petroleum ether:ethyl acetate=20:1] to give compound B-229 (280 mg, 65%) as a white solid. $^1$H-NMR (CD$_3$OD, 400 MHz): 8.17 (s, 1H), 8.09-8.03 (m, 3H), 7.67 (d, J=3.2 Hz, 1H), 7.59-7.57 (m, 1H), 3.96 (s, 3H).

Example 128B: 7-(thiazol-2-yl)benzo[b]thiophene-2-carboxylic acid (B-230)

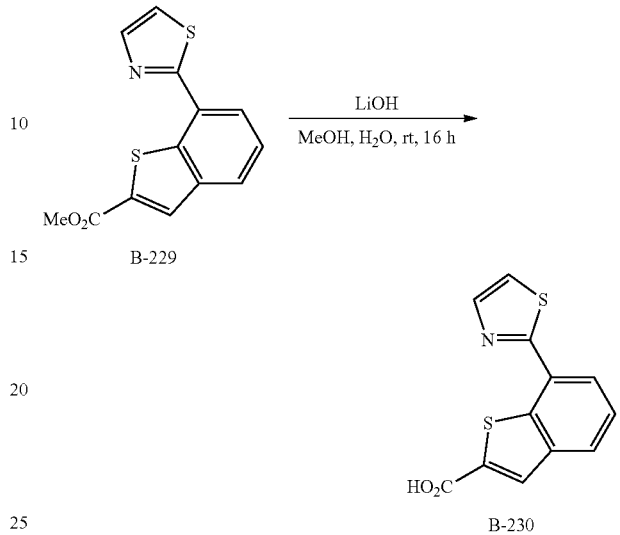

To a solution of compound B-229 (290 mg, 1.1 mmol) in methanol (8 mL) and H$_2$O (4 mL) was added lithium hydroxide monohydrate (44 mg, 1.1 mmol). The reaction was stirred at room temperature for 16 hours, then concentrated to remove methanol and acidified to pH 5~6, resulting in formation of a solid. The white solid was collected by filtration and dried to give compound B-230 (230 mg, 83%). $^1$H-NMR (CD$_3$OD, 400 MHz): 8.14 (s, 1H), 8.09-8.04 (m, 3H), 7.67 (d, J=4 Hz, 1H), 7.59-7.55 (m, 1H).

Example 129B: (2-(tert-butyl)phenyl)(2,2-dimethoxyethyl)sulfane (B-231)

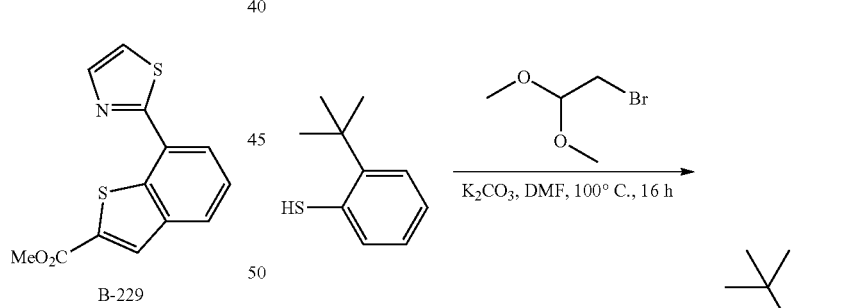

To a solution of 2-(tert-butyl)benzenethiol (1.5 g, 9.0 mmol) and 2-bromo-1,1-dimethoxy-ethane (1.7 g, 9.9 mmol) in N,N-dimethylformamide (8.0 mL) was added potassium carbonate (1.9 g, 14 mmol). The mixture was heated to 100° C. for 16 hours, then diluted with water (30 mL) and extracted with tert-butyl methyl ether (3×40 mL). The combined organic phases were washed with brine (2×25 mL), dried over anhydrous sodium sulfate and concentrated in vacuo to give compound B-231 (2.2 g, crude) as a yellow oil. ¹H-NMR (CD₃OD, 400 MHz): δ 7.50-7.47 (m, 1H), 7.42-7.39 (m, 1H), 7.20-7.14 (m, 1H), 3.39 (s, 1H), 3.18-3.19 (m, 2H), 1.55 (s, 9H).

Example 130B: 7-(tert-butyl)benzo[b]thiophene (B-232)

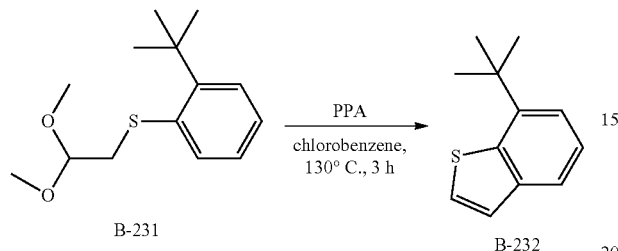

To a solution of polyphosphoric acid (16 g, 63 mmol, 8.0 eq) in chlorobenzene (15 mL) at 100° C. was added compound B-231 (2.0 g, 7.9 mmol). The reaction was heated at 130° C. for 3 hours, then concentrated under vacuum, diluted with water (30 mL), and extracted with tert-butyl methyl ether (3×40 mL). The combined organic phases were washed with brine (2×25 mL) and concentrated to give compound B-232 (0.5 g, crude) as a yellow oil. 1H-NMR (CD₃OD, 400 MHz): δ 7.78-7.74 (m, 2H), 7.48 (d, J=5.6 Hz, 1H), 7.37-7.30 (m, 2H).

Example 131B: 7-(tert-butyl)benzo[b]thiophene-2-carboxylic acid (B-233)

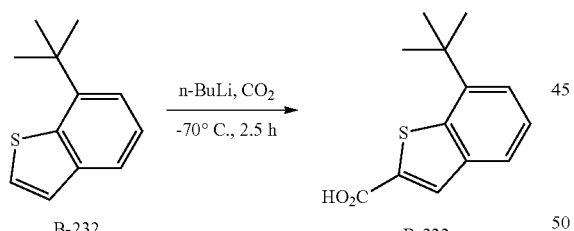

To a solution of compound B-232 (0.50 g, 2.6 mmol) in anhydrous tetrahydrofuran (2.0 mL) at −70° C. was added n-butyllithium (2.5 M in cyclohexane, 1.6 mL). The reaction was stirred for 0.5 h at −70° C. Then carbon dioxide was bubbled through the reaction for about 0.5 hour, and stirring was continued at −70° C. for another 1.5 h until TLC analysis showed the reaction was complete. The reaction was quenched slowly with 0.02 N hydrochloric acid (10 ml) and extracted with ethyl acetate (3×25 mL). The combined organic phases were concentrated to give compound B-233 (0.3 g, crude) as a gray solid.

Example 132B: methyl 7-phenylbenzo[b]thiophene-2-carboxylate (B-234)

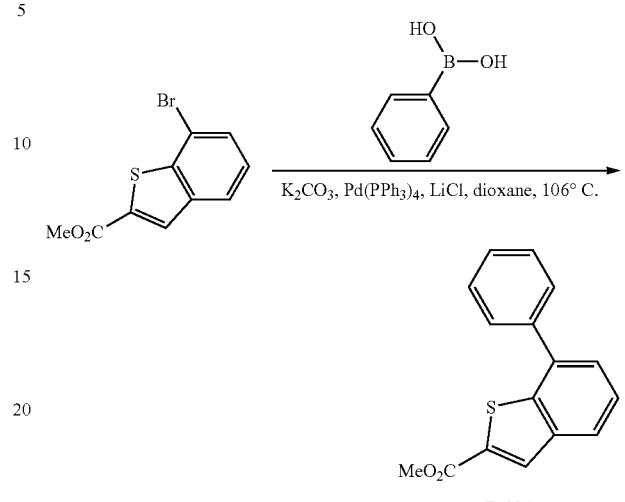

To a solution of methyl 7-bromobenzo[b]thiophene-2-carboxylate (1.2 g, 4.4 mmol) in dioxane (15 mL) at room temperature under nitrogen was added potassium carbonate (1.2 g, 8.8 mmol), phenylboronic acid (0.64 g, 5.3 mmol), tetrakis(triphenylphosphine)palladium(0) (0.50 g, 0.44 mmol) and lithium chloride (0.53 g, 8.8 mmol). The mixture was stirred at 106° C. for 7 hours, then diluted with water (30 mL) and extracted with ethyl acetate (3×50 mL). The combined organic layers were washed with brine (2×50 mL), dried over anhydrous sodium sulfate and concentrated in vacuo. The residue was purified by silica gel column chromatography [petroleum ether:ethyl acetate=40:1] to give compound B-234 (0.48 g, 40% yield) as a yellow solid.

Example 133B: 7-phenylbenzo[b]thiophene-2-carboxylic acid (B-235)

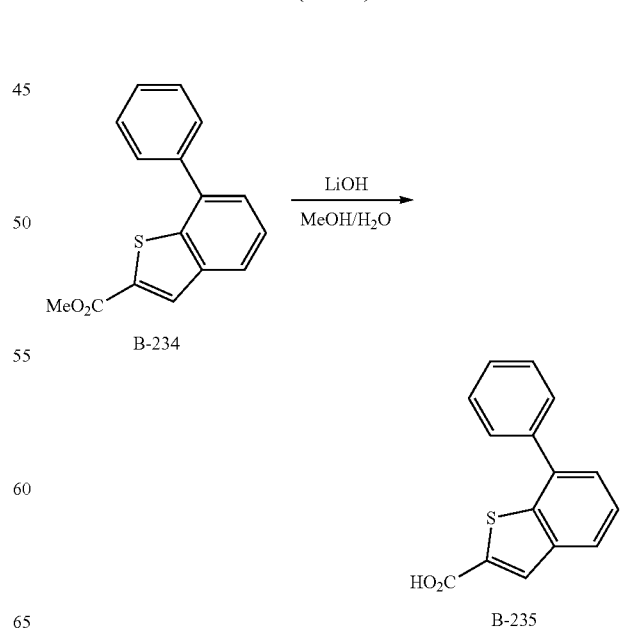

To a solution of compound B-234 (0.48 g, 1.8 mmol) in methanol (10 mL) and water (5 mL) was added lithium hydroxide monohydrate (0.15 g, 3.6 mmol). The mixture was stirred at room temperature for 1 hour, then concentrated to remove most of the methanol and acidified to pH 4~5, resulting in the formation a solid. The white solid was collected by filtration and dried in vacuo to give compound B-235 (0.36 g, 79% yield). 1H-NMR (CD$_3$OD, 400 MHz): δ 8.10 (s, 1H), 7.93 (d, J=7.2 Hz, 1H), 7.73 (d, J=7.2 Hz, 2H), 7.56-7.44 (m, 5H).

Example 134B: methyl 7-(1-methylcyclopropyl)benzo[b]thiophene-2-carboxylate (B-236)

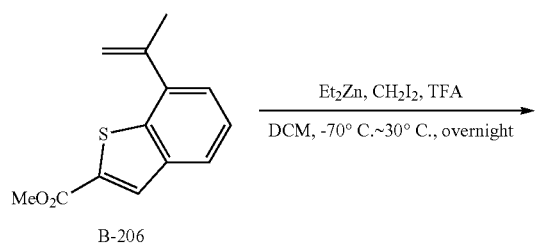

To a solution of diethylzinc (40 mL, 1.0 mol/L in toluene, 40 mmol) in anhydrous dichlormethane (20 mL) at –70° C. under nitrogen was added dropwise a solution of diiodomethane (11 g, 40 mmol), maintaining the temperature below –70° C. for the duration of the addition. The reaction mixture was warmed to –15° C. and stirred for 30 min. Then trifluoroacetic acid (4.5 g, 40 mmol) was added dropwise to the mixture, and stirring was continued at –15° C. for another 0.5 hour. Then compound B-206 (0.77 g, 3.3 mmol) was added. The reaction mixture was stirred at 30° C. for 7 hours, then quenched dropwise at 0° C. with saturate aqueous ammonium chloride (40 mL) and extracted with ethyl acetate (3×50 mL). The combined organic layers were washed with brine (2×50 mL), dried over anhydrous sodium sulfate and concentrated in vacuo. The residue was purified by silica gel column chromatography [petroleum ether:ethyl acetate=40:1] to give compound B-236 (0.42 g, 51% yield) as a yellow oil. GCMS: tR=8.328 min., 246.1 m/z (M).

Example 135B: 7-(1-methylcyclopropyl)benzo[b]thiophene-2-carboxylic acid (B-237)

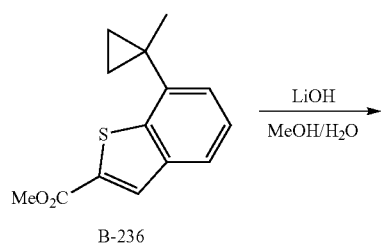

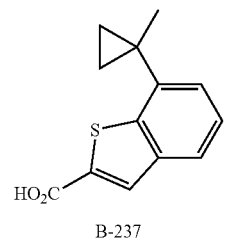

To a solution of B-236 (0.42 g, 1.8 mmol) in methanol (10 mL) and water (5 mL) was added lithium hydroxide monohydrate (0.15 g, 3.6 mmol). The mixture was stirred at 25° C. for 1 hour, then concentrated to remove methanol, diluted with water and acidified to pH 4-5 with 1 M hydrochloric acid, resulting in precipitation of a solid. The solid was collected by filtration and dried in vacuo to give compound B-237 (0.32 g, 81% yield) as a white solid. 1H-NMR (CDCl$_3$, 400 MHz): δ 8.22 (s, 1H), 7.79 (d, J=7.6 Hz, 1H), 7.47 (d, J=7.2 Hz, 1H), 7.39 (t, J=8.0 Hz, 1H), 1.50 (s, 3H), 0.99-0.98 (m, 2H), 0.88-0.86 (m, 2H).

Example 136B: 4-ethoxy-2-fluorobenzaldehyde (B-238)

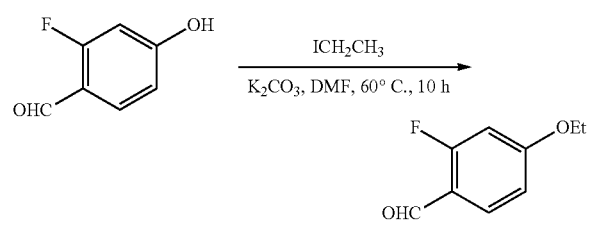

To a mixture of 2-fluoro-4-hydroxy-benzaldehyde (1.0 g, 7.1 mmol) and potassium carbonate (2.0 g, 14 mmol) in N,N-dimethylformamide (10 mL) at 25° C. under nitrogen was added iodoethane (1.1 g, 7.1 mmol). The mixture was stirred at 60° C. for 10 hours, concentrated in vacuo, diluted with ethyl acetate (200 mL), washed with saturated sodium bicarbonate solution (3×50 mL) and brine (3×50 mL), dried with anhydrous sodium sulfate and concentrated in vacuo to give compound B-238 (1.0 g, 83% yield) as a red solid. $^1$H-NMR (CD$_3$OD, 400 MHz): 10.09 (s, 1H), 7.76-7.67 (m, 1H), 6.83-6.74 (m, 2H), 4.11 (t, J=6.8 Hz, 2H), 1.40 (t, J=7.0 Hz, 3H).

Example 137B: methyl 6-ethoxybenzo[b]thiophene-2-carboxylate (B-239)

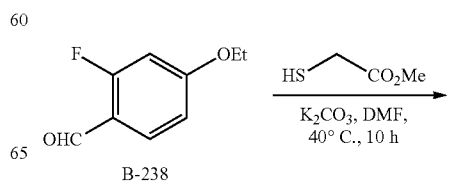

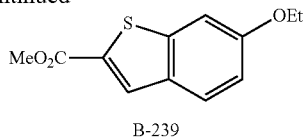

B-239

To a solution of compound B-238 (0.5 g, 3 mmol) in N,N-dimethylformamide (5 mL) was added potassium carbonate (0.8 g, 6 mmol) and methyl 2-mercaptoacetate (0.6 g, 6 mmol). The mixture was stirred at 40° C. for 10 hours, then diluted with ethyl acetate (250 mL), washed with brine 120 (4×30 mL), dried with anhydrous sodium sulfate, filtered and concentrated in vacuo to give compound B-239 (0.58 g, 83% yield) as a yellow solid. $^1$H-NMR (CD$_3$OD, 400 MHz): 7.97 (s, 1H), 7.77 (d, J=8.4 Hz, 1H), 7.40 (s, 1H), 7.02 (d, J=8.8 Hz, 1H), 4.10 (q, J=2.8 Hz, 2H), 3.89 (s, 3H), 1.14 (t, J=6.8 Hz, 3H).

Example 138B:
6-ethoxybenzo[b]thiophene-2-carboxylic acid
(B-240)

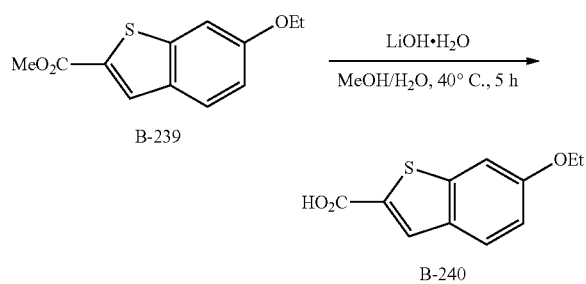

A mixture of compound B-239 (0.5 g, 2.1 mmol) and lithium hydroxide monohydrate (0.62 g, 15 mmol) in methanol (5 mL) and water (2.5 mL) was stirred at 40° C. for 5 hours. The mixture was concentrated in vacuo, added to water (50 mL), washed with ethyl acetate (3×10 mL), acidified and extracted with ethyl acetate (3×50 mL). The combined organic phases were washed with brine (3×10 mL), dried with anhydrous sodium sulfate, filtered and concentrated in vacuo to give compound B-240 (0.36 g, 76% yield) as a yellow solid. $^1$H-NMR (CD$_3$OD, 400 MHz): 7.92 (s, 1H), 7.75 (d, J=8.8 Hz, 1H), 7.38 (d, J=2.0 Hz, 1H), 6.99 (dd, J=8.8, 2.0, Hz, 1H), 4.10 (q, J=7.2 Hz, 2H), 1.40 (t, J=7.0 Hz, 3H).

Example 139B: 1-ethoxy-2-fluorobenzene (B-241)

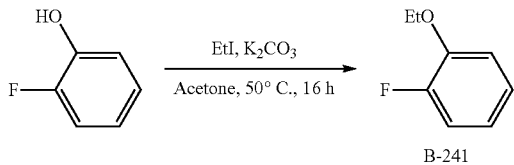

A mixture of 2-fluorophenol (5.0 g, 45 mmol), iodoethane (11 g, 71 mmol) and finely powdered potassium carbonate (12 g, 89 mmol) was stirred in acetone (5.0 mL) at 50° C. for 16 h. On completion, the mixture was filtered over a pad of silica gel, washing with methyl tert-butyl ether. The solution was carefully concentrated (due to volatility of product) to give compound B-241 (6.0 g, 96%) as a colorless liquid.

Example 140B: 3-ethoxy-2-fluorobenzaldehyde
(B-242)

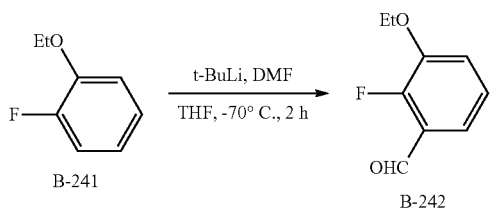

To a solution of compound B-241 (6.0 g, 44 mmol) in tetrahydrofuran (30 mL) at −70° C. was added dropwise tert-butyllithium (41 mL, 1.3 M). The mixture was stirred for 30 min, and then N, N-dimethyl formamide (6.8 g, 88 mmol) was added, and stirring was continued for an additional 30 min. The cold bath was removed, and the reaction mixture was stirred at 15° C. for 1 hour. On completion, the reaction was quenched with water (20 ml) and extracted with ethyl acetate (3×20 mL). The combined organic phases were dried over sodium sulfate, filtered and concentrated in vacuo to give compound B-242 (7.0 g, 94%) as colorless liquid. LCMS (Y): tR=0.770 min., (ES$^+$) m/z (M+H)$^+$= 169.1.

Example 141B:
7-ethoxybenzo[b]thiophene-2-carboxylic acid
(B-243)

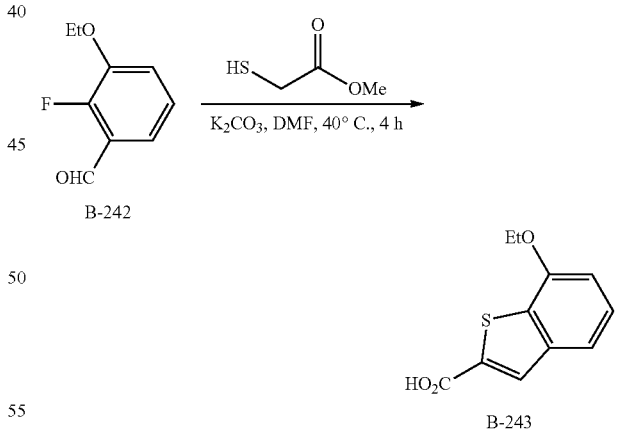

To a solution of compound B-242 (7.0 g, 43 mmol) in dimethyl formamide (70 mL) was added methyl 2-mercaptoacetate (5.5 g, 51 mmol) and potassium carbonate (12 g, 86 mmol). The reaction mixture was stirred at 40° C. for 4 hours, then quenched with water (15 mL), washed with ethyl acetate (3×10 mL), acidified with 4 N HCl and extracted with ethyl acetate (3×10 mL). The combined organic phases were dried over sodium sulfate, filtered and concentrated in vacuo to give compound B-243 (9.0 g, 95% yield) as a light yellow solid. $^1$H-NMR (CD$_3$OD, 400 MHz): δ 8.01 (s, 1H), 7.49 (d, J=8.0 Hz, 1H), 7.37-7.33 (m, 1H), 6.96 (d, J=8.0 Hz, 1H), 4.25 (dd, J₁=8.4 Hz, J₂=2.0 Hz, 2H), 1.50-1.17 (m, 3H).

Example 142B: 1-fluoro-2-isopropoxybenzene (B-244)

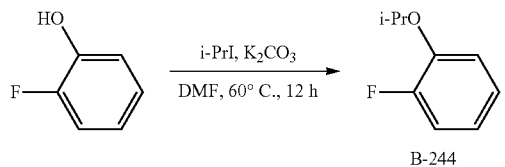

A mixture of 2-fluorophenol (1.0 g, 8.9 mmol), 2-iodopropane (3.0 g, 17.8 mmol) and finely powdered potassium carbonate (4.9 g, 35.7 mmol) was stirred in N,N-dimethylformamide (10.0 mL) at 60° C. for 12 h. On completion, the mixture was filtered over a pad of silica gel, washing with methyl tert-butyl ether. The solution was carefully concentrated (due to volatility of product) to give compound B-244 (1.4 g, 58%) as a yellow oil. ¹H-NMR (CDCl₃, 400 MHz): δ 7.29-7.01 (m, 3H), 6.92-6.91 (m, 1H), 4.59-4.53 (m, 1H), 1.40-1.33 (m, 6H).

Example 143B: 2-fluoro-3-isopropoxybenzaldehyde (B-245)

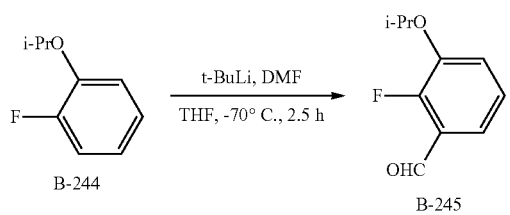

To a solution of compound B-244 (2.0 g, 13 mmol) in tetrahydrofuran (20 mL) at −70° C. was added dropwise tert-butyllithium (20.0 mL, 1.3 M). The reaction was stirred for 30 mins., and then N,N-dimethylformamide (1.9 g, 25.9 mmol) was added, and stirring was continued for an additional 2 h. On completion, the reaction was quenched with water (5 ml) and extracted with ethyl acetate (3×30 mL). The combined organic phases were dried over sodium sulfate and concentrated to give compound B-245 (2.4 g, 50%) as a yellow oil. LCMS (B): tR=0.700 min., (ES⁺) m/z (M+H)⁺= 183.2.

Example 144B: 7-isopropoxybenzo[b]thiophene-2-carboxylic acid (B-246)

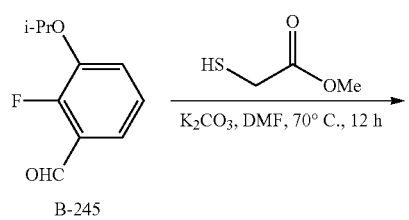

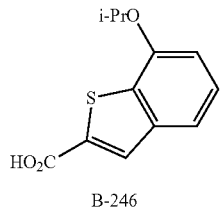

To a solution of compound B-245 (2.5 g, 13.7 mmol) in N,N-dimethylformamide (25 mL) was added methyl 2-mercaptoacetate (2.9 g, 27.4 mmol) and potassium carbonate (3.8 g, 27.4 mmol). The reaction mixture was stirred at 70° C. for 12 hours, then quenched with water (20 mL), washed with ethyl acetate (3×20 mL) and acidified to pH 3 with 1 M hydrochloric acid, resulting in formation of a solid. The white solid was collected by filtration and dried in vacuo to give compound B-246 (700 mg, 21% yield). ¹H-NMR (CDCl₃, 400 MHz): δ 8.17 (s, 1H), 7.52 (d, J=8.0 Hz, 1H), 7.38 (t, J=8.0 Hz, 1H), 6.93 (d, J=7.6 Hz, 1H), 4.80-4.77 (m, 1H), 1.48-1.46 (m, 6H).

Example 145B: methyl 6-chloro-7-methoxybenzo[b]thiophene-2-carboxylate (B-247)

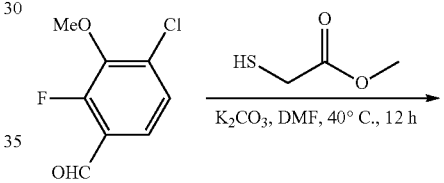

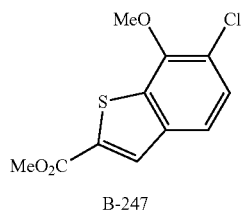

To a mixture of 4-chloro-2-fluoro-3-methoxybenzaldehyde (0.5 g, 2.65 mmol) in N,N-dimethylformamide (5.0 mL) was added methyl 2-mercaptoacetate (0.56 g, 5.30 mmol) and potassium carbonate (0.73 g, 5.30 mmol). The mixture was stirred at 40° C. for 12 hours. On completion, the mixture was poured into water and extracted with ethyl acetate. The organic layer was dried over anhydrous sodium sulfate and concentrated in vacuo. The residue was purified by silica gel chromatography [petroleum ether:ethyl acetate=10:1] to give compound B-247 (230 mg, 33% yield) as a white solid. LCMS (B): tR=0.820 min., (ES⁺) m/z (M+H)⁺=257.1.

Example 146B: 6-chloro-7-methoxybenzo[b]thiophene-2-carboxylic acid (B-248)

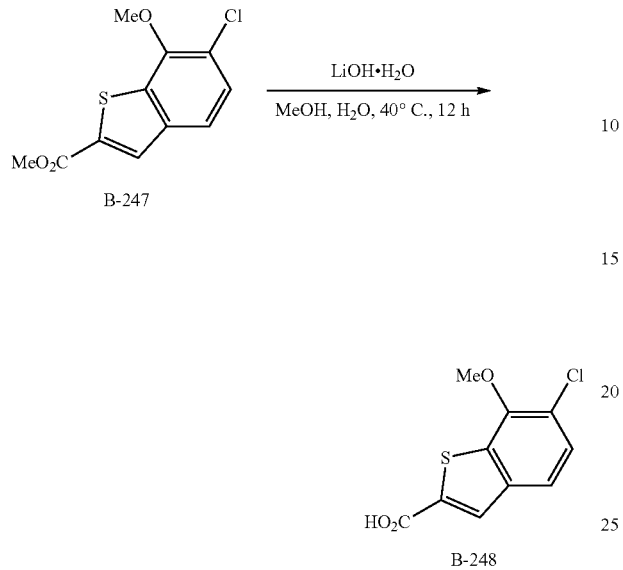

To a mixture of compound B-247 (230 mg, 0.90 mmol) in methanol (6 mL) and water (3 mL) was added lithium hydroxide monohydrate (56 mg, 1.3 mmol). The mixture was stirred at 40° C. for 12 hours, then concentrated o remove methanol, diluted with water and acidified to pH 3 with 1 M hydrochloric acid, resulting in formation of a solid. The white solid was collected by filtration and dried in vacuo to give compound B-248 (200 mg, 91% yield). $^1$H-NMR (DMSO-d6, 400 MHz): δ 13.71 (s, 1H), 8.16 (s, 1H), 7.80 (d, J=8.4 Hz, 1H), 7.57 (d, J=8.8 Hz, 1H), 4.00 (s, 3H).

Example 147B: 4-bromo-2-fluoro-3-methoxybenzaldehyde (B-249)

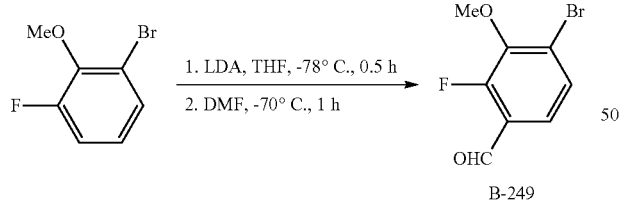

To a mixture of 1-bromo-3-fluoro-2-methoxybenzene (5.0 g, 25 mmol) in anhydrous tetrahydrofuran (50 mL) at −78° C. under nitrogen was added dropwise lithium diisopropylamide (2.0 M in n-heptane, 18 mL, 37 mmol). The mixture was stirred at this temperature for half an hour, then N,N-dimethylformamide (5.4 g, 73 mmol) was added dropwise, and stirring was continued at −78° C. for another 1 hour. On completion, the mixture was poured into water (50 mL) and extracted with ethyl acetate (2×80 mL). The combined organic layers were dried over anhydrous sodium sulfate and concentrated in vacuo to give compound B-249 (5.5 g, crude) as yellow oil.

Example 148B: methyl 6-bromo-7-methoxybenzo[b]thiophene-2-carboxylate (B-250)

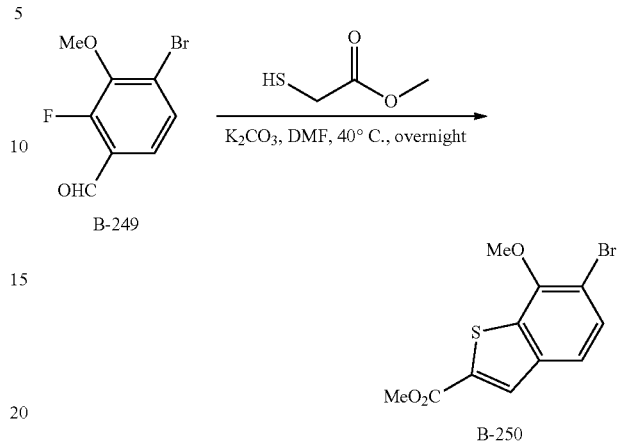

To a mixture of compound B-249 (5.5 g, crude) in N,N-dimethylformamide (55 mL) was added methyl 2-mercaptoacetate (3.0 g, 28 mmol) and potassium carbonate (6.5 g, 47 mmol). The mixture was stirred at 40° C. overnight, then poured into water (20 mL) and extracted with ethyl acetate (2×50 mL). The combined organic layers were dried over anhydrous sodium sulfate and concentrated in vacuo. The residue was purified by silica gel chromatography [petroleum ether:ethyl acetate=20:1] to give compound B-250 (3.2 g, 45% yield) as a white solid. LCMS (R): tR=0.900 min., (ES$^+$) m/z (M+H)$^+$=302.9.

Example 149B: 7-methoxy-6-methylbenzo[b]thiophene-2-carboxylic acid (B-251)

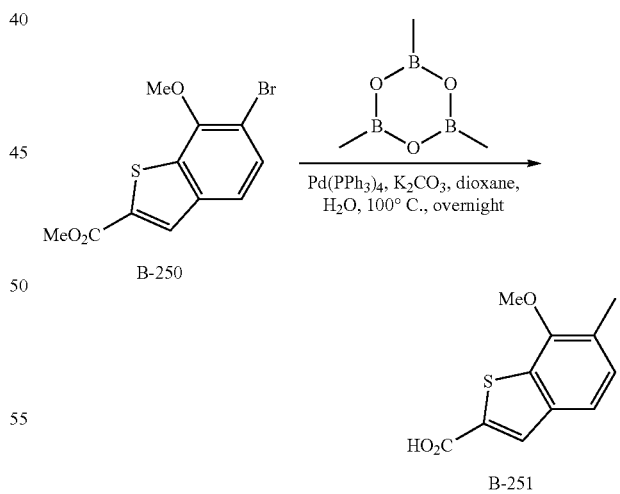

To a mixture of methyl compound B-250 (1.0 g, 3.3 mmol) in dioxane (20 mL) and water (4 mL) under nitrogen was added 2,4,6-trimethyl-1,3,5,2,4,6-trioxatriborinane (1.3 g, 10 mmol), tetrakis(triphenylphosphine)palladium (0.38 g, 0.33 mmol) and potassium carbonate (0.92 g, 6.6 mmol). The mixture was stirred at 100° C. overnight, then concentrated in vacuo to remove dioxane, poured into water (20 mL) and extracted with ethyl acetate (2×50 mL). The combined organic layers were dried over anhydrous sodium sulfate and concentrated in vacuo. The residue was purified by prep-HPLC [Instrument: GX-E; Column: Phenomenex Synergi C18 150×30 mm, particle size: 4 μm; Mobile phase: 33-63% acetonitrile in H₂O (add 0.05% HCl, v/v)] to give compound B-251 (0.20 g, 27% yield) as a white solid. LCMS (B): tR=0.764 min., (ES⁺) m/z (M+H)⁺=223.1.

Example 150B: 3-bromo-2-fluoro-4-methylbenzaldehyde (B-252)

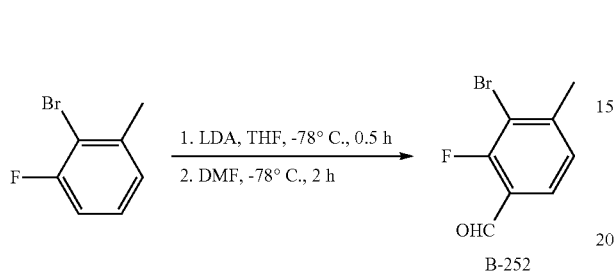

To a mixture of 2-bromo-1-fluoro-3-methylbenzene (3.0 g, 16 mmol) in anhydrous tetrahydrofuran (30 mL) at −78° C. under nitrogen was added dropwise lithium diisopropylamide (2.0 M in n-heptane solution, 12 mL, 24 mmol). The mixture was stirred at this temperature for 0.5 hour, then N,N-dimethylformamide (3.5 g, 48 mmol) was added dropwise at −78° C. The reaction mixture was stirred at −78° C. for another 2 hours. On completion, the mixture was poured into water (20 mL) and extracted with ethyl acetate (2×30 mL). The combined organic layers were dried over anhydrous sodium sulfate and concentrated in vacuo. The residue was purified by silica gel chromatography [petroleum ether: ethyl acetate=20:1] to give compound B-252 (2.1 g, 62% yield) as a white solid. TLC [Petroleum ether: Ethyl acetate=10:1]: Rf=0.4.

Example 151B: methyl 7-bromo-6-methylbenzo[b]thiophene-2-carboxylate (B-253)

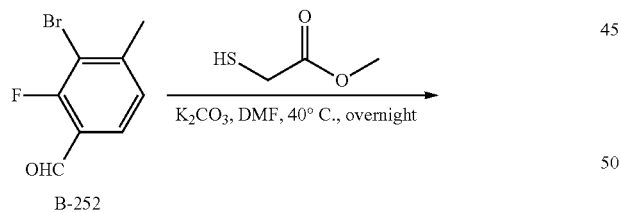

To a mixture of compound B-252 (2.1 g, 9.8 mmol) in N,N-dimethylformamide (30 mL) was added methyl 2-mercaptoacetate (1.4 g, 13 mmol) and potassium carbonate (2.7 g, 20 mmol). The mixture was stirred at 40° C. overnight. On completion, the mixture was poured into water (20 mL), extracted with ethyl acetate (2×40 mL). The combined organic layers were dried over anhydrous sodium sulfate and concentrated in vacuo to give compound B-253 (2.4 g, 92% purity, 79% yield) as a white solid. LCMS (B): tR=1.052 min., (ES⁺) m/z (M+H)⁺=287.0.

Example 152B: methyl 7-cyclopropyl-6-methylbenzo[b]thiophene-2-carboxylate (B-254)

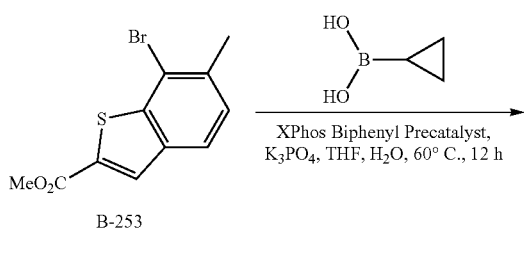

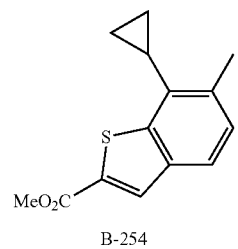

To a mixture of compound B-253 (0.60 g, 2.1 mmol) in tetrahydrofuran (15 mL) and water (5 mL) under nitrogen was added cyclopropylboronic acid (0.90 g, 11 mmol), potassium phosphate (0.89 g, 4.2 mmol) and [2-(2-aminophenyl)phenyl]-chloro-palladium; dicyclohexyl-[3-(2,4,6-triisopropylphenyl)phenyl]phosphane (83 mg, 0.11 mmol). The mixture was stirred at 60° C. for 12 hours, then diluted with water (15 mL) and extracted with ethyl acetate (2×30 mL). The organic layer was dried over anhydrous sodium sulfate and concentrated in vacuo. The residue was purified by silica gel chromatography [petroleum ether:ethyl acetate=50:1] to give compound B-254 (0.43 g, 83% purity, 69% yield) as a yellow solid. LCMS (B): tR=0.935 min., (ES⁺) m/z (M+H)⁺=247.1.

Example 153B: 7-cyclopropyl-6-methylbenzo[b]thiophene-2-carboxylic acid (B-255)

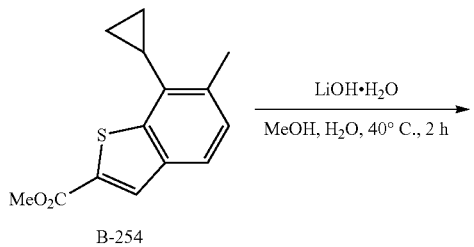

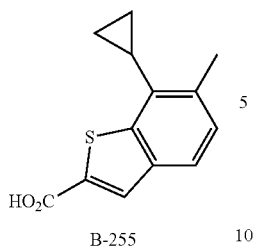

B-255

To a mixture of compound B-254 (0.43 g, 1.8 mmol) in methanol (8 mL) and water (4 mL) was added lithium hydroxide monohydrate (0.15 g, 3.5 mmol). The mixture was stirred at 40° C. for 2 hours, then concentrated to remove methanol, diluted with water, acidified to pH 3 with 6 M hydrochloric acid and extracted with ethyl acetate (2×20 mL). The combined organic layers were dried over anhydrous sodium sulfate and concentrated in vacuo to give compound B-255 (0.39 g, 81% purity, 78% yield) as a white solid. LCMS (B): tR=0.815 min., (ES$^+$) m/z (M+H)$^+$=233.1.

Example 154B: 1,3-difluoro-2-methoxy-benzene (B-256)

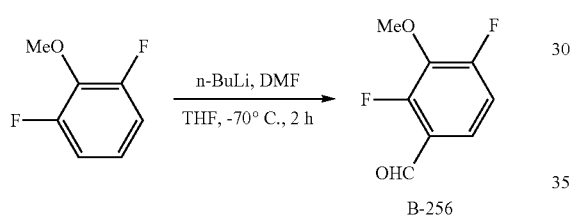

B-256

To a solution of 1,3-difluoro-2-methoxy-benzene (3.0 g, 20.8 mmol) in tetrahydrofuran (30 mL) at −70° C. was added dropwise n-butyl lithium (1.6 g, 25.0 mmol). The reaction was stirred for 30 mins. Then N,N-dimethylformamide (4.6 g, 63 mmol) was added, and stirring was continued for another 30 minute. The cold bath was removed, and the reaction mixture was stirred at 15° C. for 1 hour. On completion, the mixture was extracted with ethyl acetate (2×15 mL). The aqueous phase was acidified with 4 M hydrochloric acid and extracted with ethyl acetate (3×10 mL). The organic phases were combined, dried over sodium sulfate and evaporated in vacuo to give compound B-256 (3.0 g, 84% yield) as a light yellow liquid. LCMS (B): tR=0.624 min., 173.1 m/z (M+1).

Example 155B: methyl 6-fluoro-7-methoxybenzo[b]thiophene-2-carboxylate (B-257)

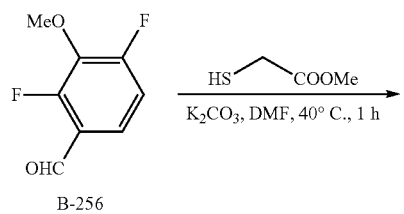

B-256

To a solution of compound B-256 (3.0 g, 17.4 mmol) in N,N-dimethylformamide (30 mL) was added methyl 2-mercaptoacetate (1.8 g, 17.4 mmol) and potassium carbonate (4.8 g, 34.9 mmol). The mixture was stirred at 15° C. for 2 hours, then poured in to water (30 mL) and extracted with ethyl acetate (3×10 mL). The combined organic phases were washed with brine (2×10 mL), dried over sodium sulfate and concentrated in vacuo to give compound B-257 (2.1 g, 50% yield) as a light yellow solid. LCMS (B): tR=0.882 min., 241.0 m/z (M+1).

Example 156B: 6-fluoro-7-methoxybenzo[b]thiophene-2-carboxylic acid (B-258)

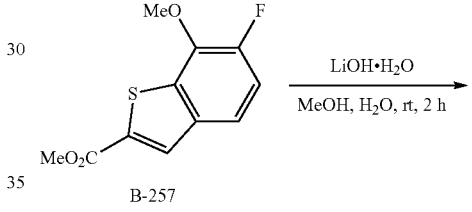

B-257

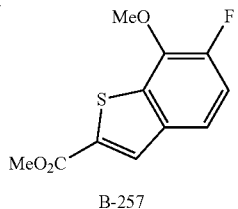

B-258

To a solution of B-257 (2.1 g, 8.7 mmol) in methanol (20 mL) and water (10 mL) was added lithium hydroxide hydrate (367 mg, 8.7 mmol). The mixture was stirred at 25° C. for 2 hours, then concentrated to remove methanol, diluted with water, and acidified to pH 3 with 1 M hydrochloric acid and extracted with ethyl acetate (2×10 mL). The combined organic layers were washed with brine, dried over sodium sulfate and concentrated in vacuo to give B-258 (900 mg, 46% yield) as a white solid. $^1$H-NMR (CD$_3$OD, 400 MHz): δ 8.01 (s, 1H), 7.54 (dd, J$_1$=8.4 Hz, J$_2$=4.0 Hz, 1H), 7.26 (dd, J$_1$=12 Hz, J$_2$=8.4 Hz, 1H), 4.12 (d, J=2.4 Hz, 3H).

Example 157B: methyl 7-cyano-6-methylbenzo[b]thiophene-2-carboxylate (B-259)

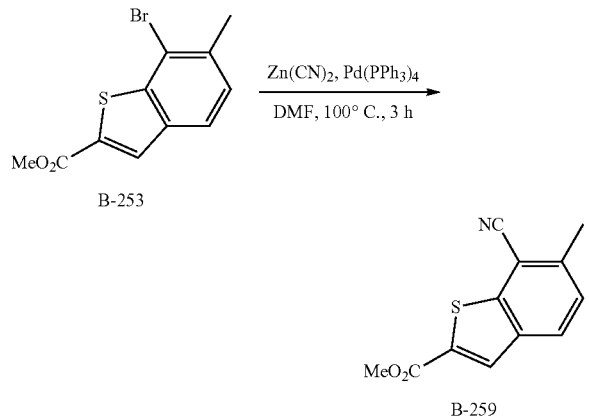

To a mixture of compound B-253 (0.50 g, 1.8 mmol) in N,N-dimethylformamide (20 mL) under nitrogen was added zinc cyanide (0.41 g, 3.5 mmol) and tetrakis(triphenylphosphine)palladium (0.20 g, 0.18 mmol). The mixture was stirred at 100° C. for 3 hours, then diluted with water (20 mL) and extracted with ethyl acetate (2×30 mL). The combined organic layers were dried over anhydrous sodium sulfate and concentrated in vacuo. The residue was purified by silica gel chromatography [petroleum ether:ethyl acetate=20:1] to give compound B-259 (0.15 g, 96% purity, 36% yield) as a white solid. LCMS (B): tR=0.846 min., (ES$^+$) m/z (M+H)$^+$=232.0.

Example 158B: 7-cyano-6-methylbenzo[b]thiophene-2-carboxylic acid (B-260)

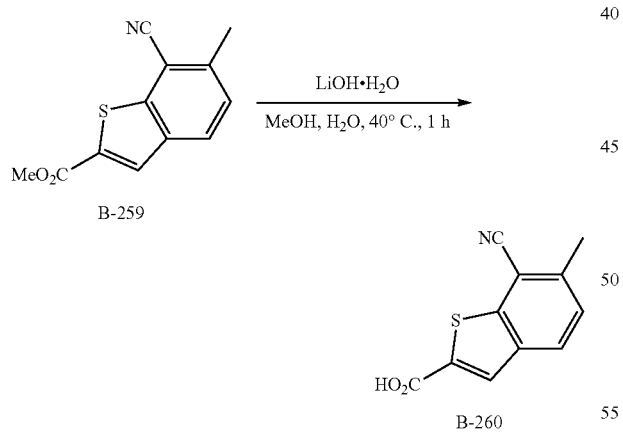

To a mixture of compound B-259 (0.15 g, 0.65 mmol) in methanol (2 mL) and water (1 mL) was added lithium hydroxide monohydrate (54 g, 1.3 mmol). The mixture was stirred at 40° C. for 1 hour, then concentrated to remove methanol, diluted with water, acidified to pH 3 with 6 M hydrochloric acid and extracted with ethyl acetate (2×5 mL). The combined organic layers were dried over anhydrous sodium sulfate and concentrated in vacuo to give compound B-260 (0.14 g, 98% purity, 93% yield) as a white solid. LCMS (B): tR=0.724 min., (ES$^+$) m/z (M+H)$^+$=218.0.

Example 159B: 1-bromo-2-fluoro-3-(methoxymethyl)benzene (B-261)

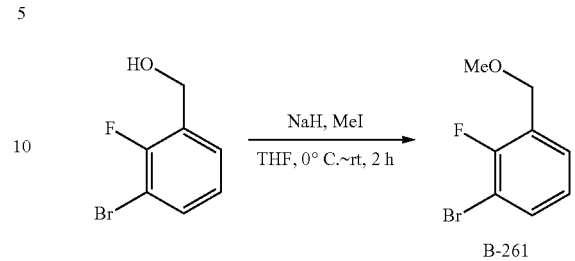

To a solution of (3-bromo-2-fluorophenyl)methanol (5.0 g, 24 mmol) in tetrahydrofuran (50 mL) at 0° C. under nitrogen was added sodium hydride (1.9 g, 49 mmol, 60% w/w) in portions. The mixture was stirred at 0° C. for 30 minutes, and iodomethane (17 g, 72 mmol) was added to the mixture. The reaction mixture was stirred at room temperature for 1.5 h, then quenched with ice-water (50 mL), stirred for 30 min. and extracted with ethyl acetate (3×50 mL). The combined organic layers were washed with brine (2×50 mL), dried over anhydrous sodium sulfate, concentrated in vacuo and purified by silica gel column chromatography [petroleum ether:ethyl acetate=15:1] to give compound B-261 (5.2 g, 94% yield) as a yellow oil.

Example 160B: 2-fluoro-3-(methoxymethyl)benzaldehyde (B-262)

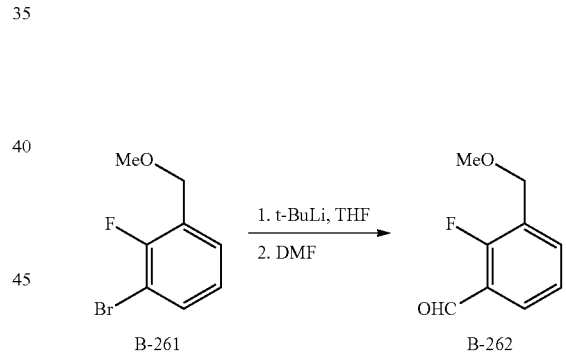

To a solution of compound B-261 (3.0 g, 14 mmol) in tetrahydrofuran (30 mL) at −78° C. was added n-butyllithium (2.5 mol/L, 3.8 mL, 15 mmol). The reaction mixture was stirred at this temperature for 30 min., and N,N-dimethylformamide (2.0 g, 28 mmol) was added. The reaction was allowed to warm from −78° C. to 0° C. over 1 hour, then quenched with saturated aqueous ammonium chloride (30 mL) and extracted with ethyl acetate (3×50 mL). The combined organic phases were concentrated, and the residue was purified by silica gel chromatography [petroleum ether:ethyl acetate=20:1] to give compound B-262 (1.6 g, 69% yield) as a yellow oil. $^1$H-NMR (CDCl$_3$, 400 MHz): δ 7.50 (t, J=7.2 Hz, 1H), 7.38 (t, J=6.8 Hz, 1H), 7.05 (t, J=7.6 Hz, 1H).

Example 161B: methyl 7-(methoxymethyl)benzo[b]thiophene-2-carboxylate (B-263)

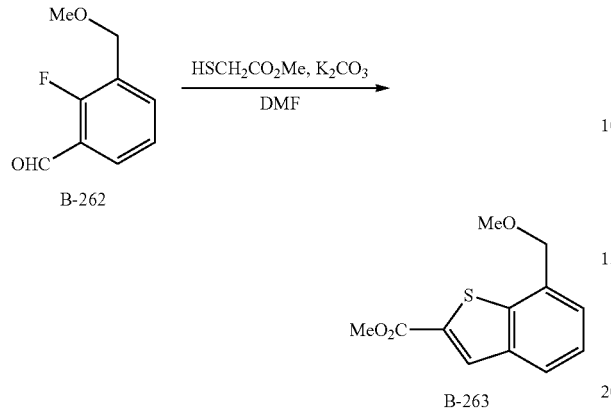

To a solution of compound B-262 (1.6 g, 9.5 mmol) in N,N-dimethylformamide (20 mL) under nitrogen was added potassium carbonate (2.6 g, 19 mmol) and methyl 2-mercaptoacetate (1.5 g, 14 mmol). The resulting mixture was stirred at 50° C. for 5 hours. On completion, the mixture was diluted with water (20 mL) and extracted with ethyl acetate (3×20 mL). The combined organic layers were washed with brine, dried over anhydrous sodium sulfate, filtered and concentrated in vacuum. The residue was purified by silica gel chromatography [petroleum ether:ethyl acetate=30:1] to give compound B-263 (1.8 g, 80% yield) as a yellow oil. $^1$H-NMR (CDCl$_3$, 400 MHz): δ 8.02 (s, 1H), 7.79-7.74 (m, 1H), 7.34-7.32 (m, 2H), 4.67 (s, 2H), 3.88 (s, 3H), 3.38 (s, 3H).

Example 162B: 7-(methoxymethyl)benzo[b]thiophene-2-carboxylic acid (B-264)

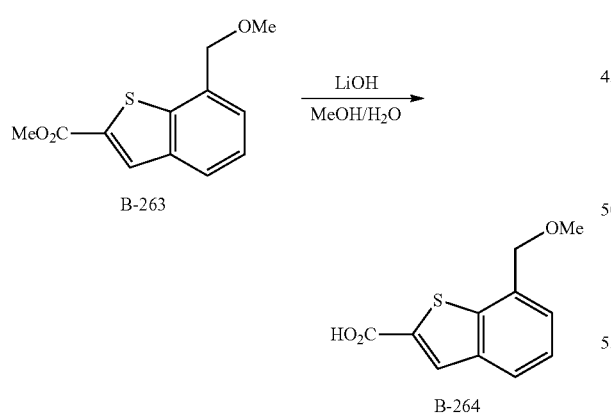

To a solution of B-263 (1.8 g, 7.6 mmol) in methanol (10 mL) and water (5 mL) was added lithium hydroxide monohydrate (0.36 g, 15 mmol). The mixture was stirred at 25° C. for 1 hour, then concentrated to remove methanol, diluted with water, and acidified to pH 4-5 with 1 M hydrochloric acid, resulting in precipitation of a solid. The solid was collected by filtration and dried in vacuo to give compound B-264 (1.7 g, 71% yield) as a white solid. $^1$H-NMR (CDCl$_3$, 400 MHz): δ 7.50 (s, 1H), 7.89-7.87 (dd, J$_1$=7.2 Hz, J$_2$=2.0 Hz, 1H), 7.47-7.42 (m, 2H), 4.78 (s, 2H), 3.49 (s, 3H).

Example 163B: 8-fluorochroman (B-265)

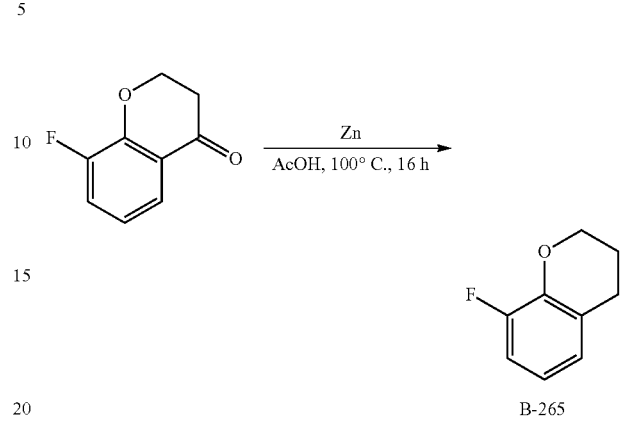

To a mixture of zinc powder (30 g, 0.45 mol) in acetic acid (10 mL) at room temperature was added slowly a solution of 8-fluorochroman-4-one (3.0 g, 18 mmol) in acetic acid (10 mL). The reaction mixture was stirred at 100° C. for 16 hours, then diluted with ethyl acetate (100 mL) and filtered. The filtrate was concentrated in vacuo and purified by silica gel chromatography [petroleum ether:ethyl acetate=50:1] to give compound B-265 (2.1 g, 67% yield) as a yellow oil. $^1$H-NMR (CDCl$_3$, 400 MHz): δ 6.94-6.89 (m, 1H), 6.84-6.82 (m, 1H), 6.79-6.76 (m, 1H), 4.30-4.27 (t, J=5.2 Hz, 2H), 2.85-2.81 (t, J=6.4 Hz, 2H), 2.12-2.04 (m, 2H).

Example 164B: 8-fluorochroman-7-carbaldehyde (B-266)

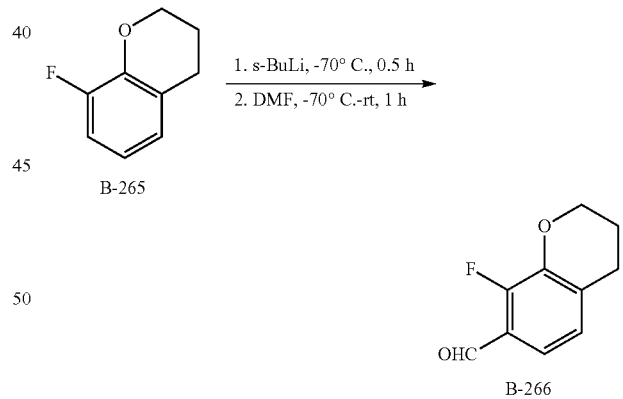

To a mixture of compound B-265 (1.0 g, 6.6 mmol) in anhydrous tetrahydrofuran (50 mL) at −70° C. under nitrogen was added dropwise sec-butyllithium (1.3 M in n-hexane solution, 10 mL, 13 mmol). The mixture was stirred at −70° C. for 0.5 hour, and then N,N-dimethylformamide (2.4 g, 33 mmol) was added dropwise. The reaction was allowed to warm from −70° C. to room temperature over 1 hour, then quenched at 0° C. with saturated ammonium chloride solution (150 mL) and extracted with ethyl acetate (3×150 mL). The combined organic layers were washed with brine (100 mL), dried with anhydrous sodium sulfate, filtered and concentrated under in vacuo. The residue was purified by silica gel chromatography [petroleum ether:ethyl acetate=20:1] to give compound B-266 (701 mg, 59% yield) as a yellow oil. $^{1}$H-NMR (CDCl$_{3}$, 400 MHz): δ 10.33 (s, 1H), 7.32-7.28 (m, 1H), 6.94-6.92 (d, J=8.0 Hz, 1H), 4.33-4.26 (m, 2H), 2.89-2.86 (t, J=6.4 Hz, 2H), 2.11-2.06 (m, 2H).

Example 165B: methyl 3,4-dihydro-2H-thieno[3,2-h]chromene-8-carboxylate (B-267)

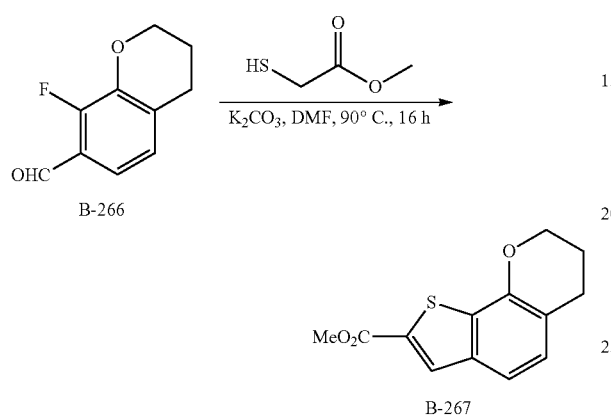

To a solution of compound B-266 (0.60 g, 3.3 mmol) in N,N-dimethylformamide (20 mL) was added potassium carbonate (0.92 g, 6.7 mmol) and methyl 2-mercaptoacetate (0.42 g, 4.0 mmol). The mixture was stirred at 90° C. for 16 hours, then quenched with water (100 mL) and extracted with ethyl acetate (3×100 mL). The combined organic layers were washed with brine (100 mL), dried with anhydrous sodium sulfate, filtered and concentrated in vacuo to give compound B-267 (0.70 g, crude) as a yellow solid. LCMS (M): tR=1.132 min., (ES$^{+}$) m/z (M+H)$^{+}$=248.9.

Example 166B: 3,4-dihydro-2H-thieno[3,2-h]chromene-8-carboxylic acid (B-268)

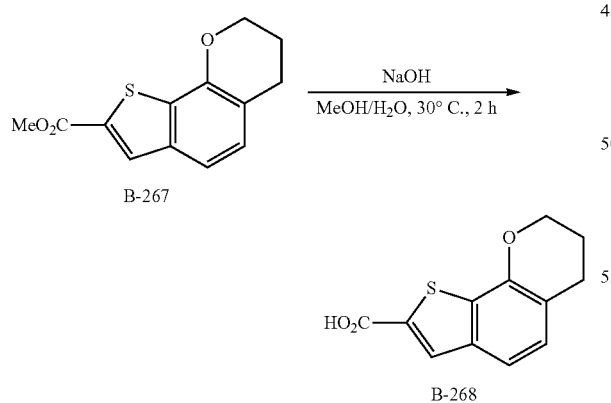

To a mixture of compound B-267 (0.60 g, 2.4 mmol) in methanol (20 mL) and water (4 mL) was added sodium hydroxide (0.20 g, 4.8 mmol). The mixture was stirred at 30° C. for 2 hours, then concentrated to remove methanol, diluted with water, and acidified to pH 2 with 1 M hydrochloric acid, resulting in precipitation of a solid. The solid was collected by filtration and dried in vacuo to give compound B-268 (0.50 g, 88% yield) as a yellow solid. $^{1}$H-NMR (CD$_{3}$OD, 400 MHz): δ 7.97 (s, 1H), 7.41-7.39 (d, J=8.0 Hz, 1H), 7.17-7.13 (d, J=8.0 Hz, 1H), 4.38-4.36 (t, J=5.2 Hz, 2H), 2.93-2.90 (t, J=6.4 Hz, 2H), 2.15-2.09 (m, 2H).

Example 167B: 5-fluorochroman (B-269)

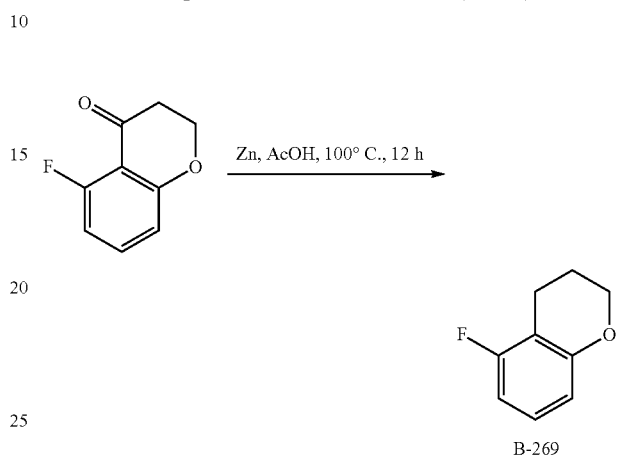

To a mixture of zinc (9.8 g, 0.15 mol) in acetic acid (20 mL) was added a solution of 5-fluorochroman-4-one (1.0 g, 6.0 mmol) in acetic acid (20 mL). The mixture was stirred at 100° C. for 12 hours, then filtered (washing with ethyl acetate) and concentrated in vacuo. The residue was purified by silica gel column chromatography [petroleum ether:ethyl acetate=1:0] to give compound B-269 (0.50 g, 55% yield) as a yellow solid. GCMS: tR=6.634 min., (ES$^{+}$) m/z (M)$^{+}$=152.1.

Example 168B: 5-fluorochroman-6-carbaldehyde (B-270)

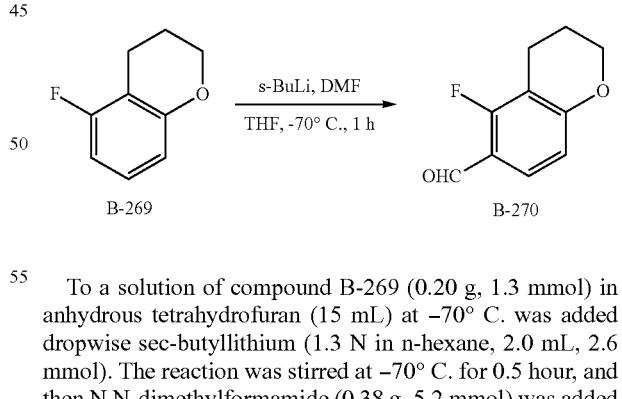

To a solution of compound B-269 (0.20 g, 1.3 mmol) in anhydrous tetrahydrofuran (15 mL) at −70° C. was added dropwise sec-butyllithium (1.3 N in n-hexane, 2.0 mL, 2.6 mmol). The reaction was stirred at −70° C. for 0.5 hour, and then N,N-dimethylformamide (0.38 g, 5.2 mmol) was added dropwise. The reaction was stirred at −70° C. for 0.5 hour, then quenched with saturated aqueous ammonium chloride (20 ml) and extracted with ethyl acetate (2×20 mL). The combined organic layers were washed with brine, dried with anhydrous sodium sulfate and concentrated in vacuo to give compound B-270 (0.20 g, crude) as a yellow solid. LCMS (B): tR=0.699 min., (ES$^{+}$) m/z (M+H)$^{+}$=181.2.

Example 169B: methyl 8,9-dihydro-7H-thieno[2,3-f]chromene-2-carboxylate (B-271)

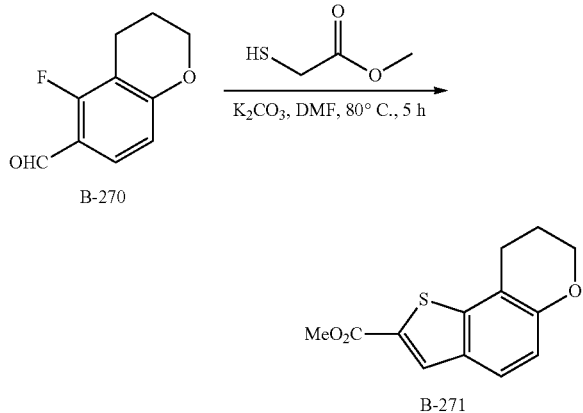

A mixture of compound B-270 (0.30 g, 1.7 mmol), potassium carbonate (0.46 g, 3.3 mmol) and methyl 2-mercaptoacetate (0.21 g, 2.0 mmol) in N,N-dimethylformamide (15 mL) was stirred at 80° C. for 5 hours. On completion, the mixture was poured into water (20 ml) and extracted with ethyl acetate (2×20 mL). The combined organic layers were washed with brine, dried with anhydrous sodium sulfate and concentrated in vacuo to give compound B-271 (0.25 g, crude) as a yellow solid. LCMS (B): tR=0.759 min., (ES$^+$) m/z (M+H)$^+$=249.1.

Example 170B: 8,9-dihydro-7H-thieno[2,3-f]chromene-2-carboxylic acid (B-272)

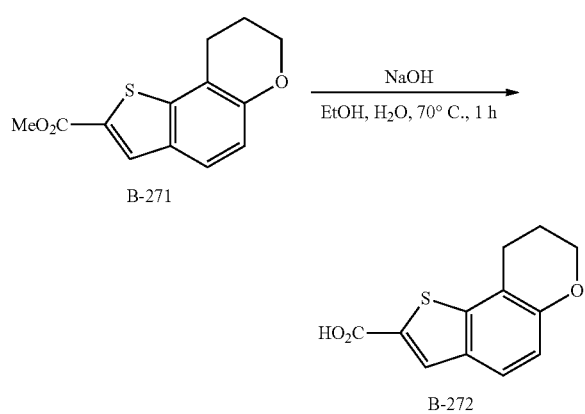

To a mixture of compound B-271 (0.12 g, 0.48 mmol) in ethanol (5.0 mL) and water (1.0 mL) was added sodium hydroxide (97 mg, 2.4 mmol). The mixture was stirred at 70° C. for 1 hour, then concentrated to remove methanol, diluted with water, and acidified to pH 1 with 1 M hydrochloric acid, resulting in precipitation of a solid. The solid was collected by filtration and dried in vacuo to give compound B-272 (0.10 g, crude). TLC [dichloromethane:methanol=10:1]: Rf=0.04.

Example 171B: 6-bromo-2-methylbenzo[b]thiophene (B-273)

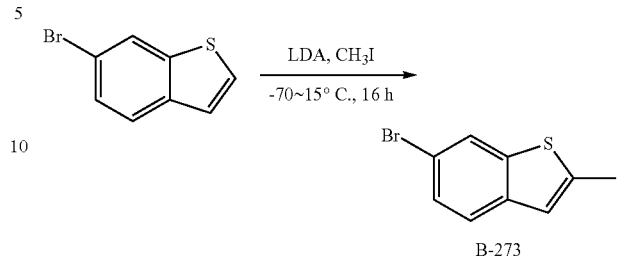

To a solution of 6-bromobenzothiophene (3.0 g, 14 mmol) in THF (10 mL) was added lithium diisopropylamide (2 M in tetrahydrofuran/n-heptane, 8.4 mL 17 mmol). The mixture was stirred at −70° C. for 30 min, and then iodomethane (17.98 g, 126.71 mmol) was added dropwise. The mixture was stirred at 15° C. for 15.5 hours, then quenched at −70° C. with saturated aqueous ammonium chloride (2 mL), diluted with water (10 mL) and extracted with ethyl acetate (3×80 mL). The combined organic phases were concentrated in vacuo. The residue was purified by silica gel chromatography [petroleum ether:ethyl acetate=1:0] to give compound B-273 (1.60 g, 50% yield). $^1$H-NMR (CD$_3$OD, 400 MHz): δ 7.94 (s, 1H), 7.42-7.39 (m, 1H), 7.20-7.14 (m, 1H), 3.39 (s, 1H), 3.18-3.19 (m, 2H), 1.55 (s, 9H).

Example 172B: methyl 2-methylbenzo[b]thiophene-6-carboxylate (B-274)

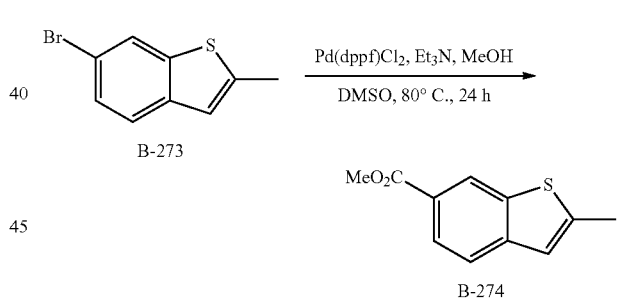

To a solution of compound B-273 (600 mg, 2.6 mmol) in dimethylsulfoxide (10 mL) was added [1,1′-bis(diphenylphosphino)ferrocene]dichloropalladium(II) (193 mg, 0.26 mmol), triethylamine (801 mg, 7.9 mmol) and methanol (254 mg, 7.9 mmol). The mixture was stirred at 80° C. under CO atmosphere (100 psi) for 24 hours until TLC analysis showed the reaction was complete. The mixture was added to water (30 mL) and extracted with methyl tert-butyl ether (3×40 mL). The combined organic phases were washed with water (2×40 mL), dried over sodium sulfate, filtered and concentrated in vacuo. The residue was purified by silica gel chromatography [petroleum ether:ethyl acetate=20:1] to give compound B-274 (0.30 g, 55% yield) as a white solid. TLC [petroleum ether:ethyl acetate=20:1]: Rf=0.4; $^1$H-NMR (CD$_3$OD, 400 MHz): δ 8.33 (s, 1H), 7.82 (d, J=8.4 Hz, 1H), 7.61 (d, J=8.4 Hz, 1H), 7.01 (s, 1H), 4.77 (s, 2H), 3.82 (s, 3H), 2.52 (s, 3H).

Example 173B: 2-methylbenzo[b]thiophene-6-carboxylic acid (B-275)

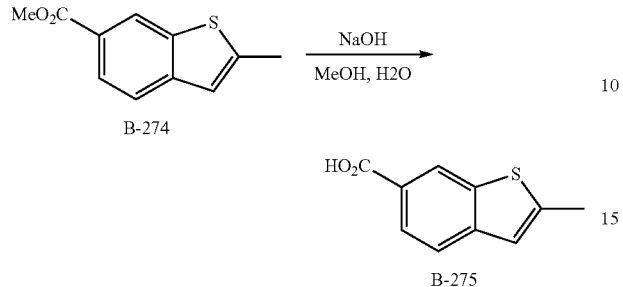

To a solution of compound B-274 (200 mg, 0.91 mmol) in methanol (10 mL) and water (1.0 mL) was added sodium hydroxide (91 mg, 2.3 mmol). The mixture was stirred at 15° C. for 1 hour, then concentrated to remove methanol, diluted with water, acidified to pH 3 with 5 M hydrochloric acid and extracted with ethyl acetate (3×30 mL). The combined organic phases were washed with brine (3×30 mL) and concentrated to give compound B-275 (0.15 g, 86% yield) as a white solid. TLC [petroleum ether:ethyl acetate=1:1]: Rf=0.4.

Example 174B: ethyl benzo[b]thiophene-6-carboxylate (B-276)

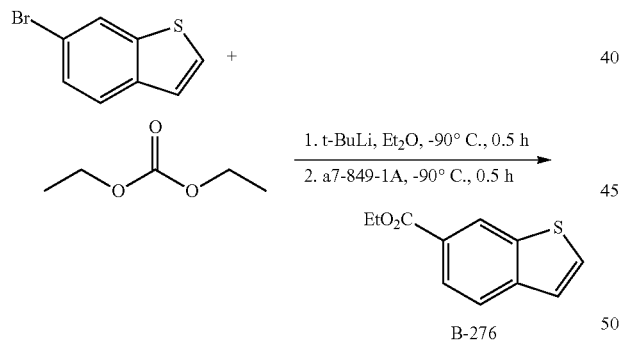

To a mixture of 6-bromobenzo[b]thiophene (5.0 g, 23 mmol) in diethyl ether (50 mL) at −90° C. under nitrogen was added dropwise tert-butyllithium (1.3 M in pentane solution, 27 mL, 35 mmol). The mixture was stirred at −90° C. for 0.5 hour, and diethyl carbonate (4.1 g, 35 mmol) was added dropwise. The reaction was stirred at −90° C. for another 0.5 hour, then quenched at 0° C. with saturated aqueous ammonium chloride (20 mL) and extracted with ethyl acetate (2×30 mL). The combined organic layers were washed with brine (3×20 mL), dried with anhydrous sodium sulfate, filtered and concentrated in vacuo. The residue was purified by silica gel chromatography [petroleum ether:ethyl acetate=50:1] to give compound B-276 (1.0 g) as a yellow oil. LCMS (B): tR=0.863 min., (ES$^+$) m/z (M+H)$^+$=207.1.

Example 175B ethyl 2-chlorobenzo[b]thiophene-6-carboxylate (B-277)

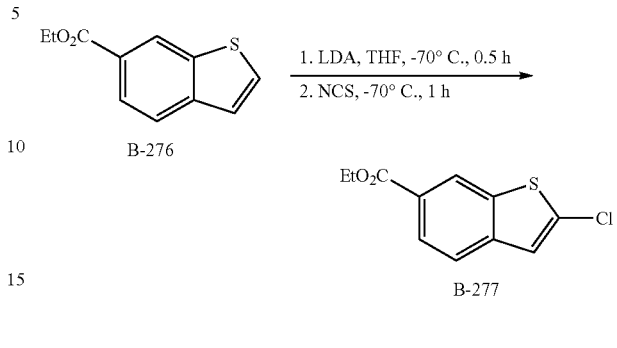

To a mixture of compound B-276 (0.40 g, 1.93 mmol) in anhydrous tetrahydrofuran (10 mL) at −70° C. under nitrogen was added dropwise lithium diisopropylamide (2.0 M in tetrahydrofuran/n-heptane, 1.2 mL, 2.4 mmol). The mixture was stirred for 0.5 hour, and then 1-chloropyrrolidine-2,5-dione (0.31 g, 2.3 mmol) was added dropwise at −70° C. The reaction was stirred at −70° C. for another 1 hour, then quenched with water (10 mL), acidified to pH 4 with 2 N hydrochloric acid at 0° C., and extracted with ethyl acetate (3×30 mL). The combined organic layers were washed with brine (3×10 mL), dried with anhydrous sodium sulfate, filtered and concentrated in vacuo to give a 1:1 mixture (350 mg) of starting material compound B-276 and product compound B-277 as a white solid. LCMS (B): tR=0.864 min., (ES$^+$) m/z (M+H)$^+$=207.0; tR=0.950 min., (ES$^+$) m/z (M+H)$^+$=241.0.

Example 176B: 2-chlorobenzo[b]thiophene-6-carboxylic acid (B-278)

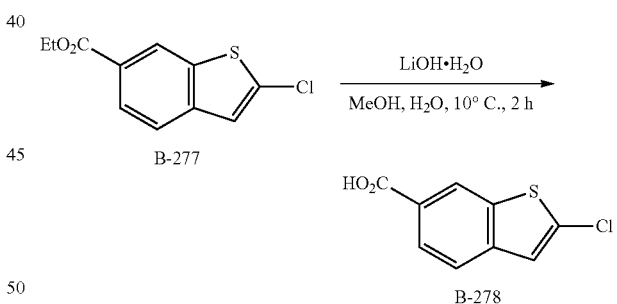

To a mixture of compound B-277 (0.35 g, 0.64 mmol, 45% purity) in methanol (5 mL) and water (5 mL) was added sodium hydroxide (80 mg, 1.9 mmol). The mixture was stirred at 10° C. for 2 hour, then concentrated to remove methanol, diluted with water, acidified to pH 2 with 1 M hydrochloric acid, and extracted with ethyl acetate (2×20 mL). The combined organic phase was washed with brine (3×10 mL), dried with anhydrous sodium sulfate, filtered, concentrated in vacuo and purified by prep-HPLC [Instrument: GX-E; Column: Phenomenex Synergi C18 150×30 mm, particle size: 4 μm; Mobile phase: 40-65% acetonitrile in H$_2$O (add 0.05% HCl, v/v)] to give compound B-278 (70 mg, 51% yield) as a white solid. $^1$H-NMR (DMSO, 400 MHz): 8.59 (s, 1H), 7.95 (d, J=8.4 Hz, 1H), 7.88 (d, J=8.4 Hz, 1H), 7.65 (s, 1H).

Example 177B: 4-chloro-2-fluoro-3-methylbenzaldehyde (B-279)

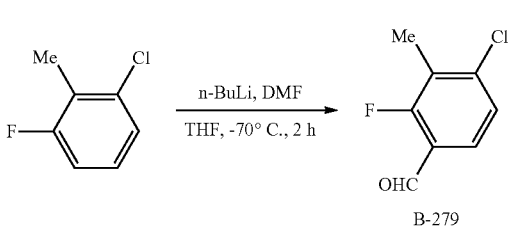

To a solution of 1-chloro-3-fluoro-2-methylbenzene (3.5 g, 24 mmol) in anhydrous tetrahydrofuran (50 mL) at −70° C. was added dropwise n-butyllithium (2.5 M in n-hexane, 19 mL, 48 mmol). The reaction was stirred at −70° C. for 0.5 hour, and then N,N-dimethylformamide (7.1 g, 97 mmol) was added dropwise. The reaction was stirred at −70° C. for 0.5 hour, then quenched with saturated aqueous ammonium chloride (20 mL) and extracted with ethyl acetate (2×20 mL). The combined organic layers were washed with brine, dried with anhydrous sodium sulfate and concentrated in vacuo. The residue was purified by silica gel chromatography [petroleum ether:ethyl acetate=10:1] to give compound B-279 (0.40 g, 10% yield) as a yellow solid. TLC [petroleum ether: ethyl acetate=10:1]: Rf=0.19.

Example 178B: methyl 6-chloro-7-methylbenzo[b]thiophene-2-carboxylate (B-280)

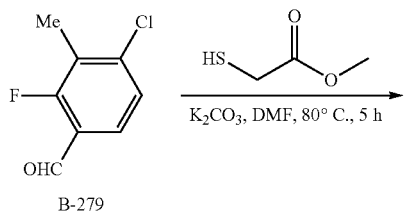

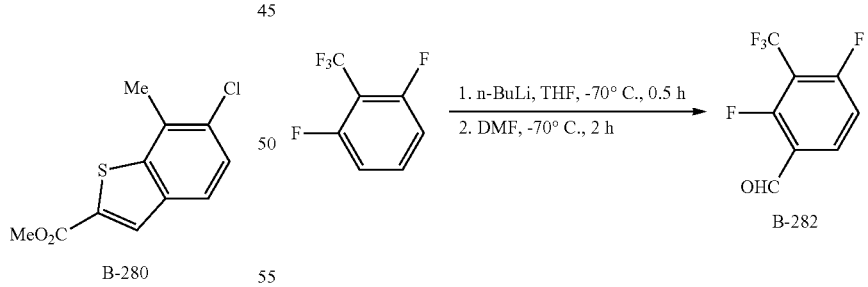

A mixture of compound B-279 (0.36 g, 2.1 mmol), potassium carbonate (0.58 g, 4.2 mmol) and methyl 2-mercaptoacetate (0.27 g, 2.5 mmol) in N,N-dimethylformamide (15 mL) was stirred at 80° C. for 5 hours. On completion, the mixture was poured into water (20 ml) and extracted with ethyl acetate (2×20 mL). The combined organic layers were washed with brine, dried with anhydrous sodium sulfate and concentrated in vacuo to give compound B-280 (0.40 g, crude) as a yellow solid. LCMS (B): tR=0.944 min., (ES$^+$) m/z (M+H)$^+$=241.0.

Example 179B: 6-chloro-7-methylbenzo[b]thiophene-2-carboxylic acid (B-281)

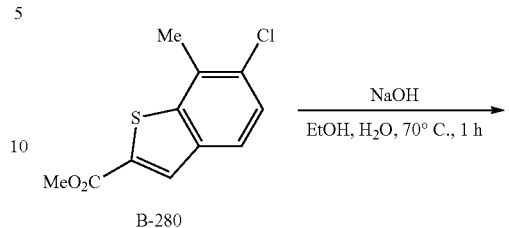

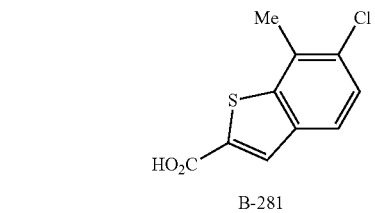

To a mixture of compound B-280 (0.40 g, 1.7 mmol) in ethanol (10 mL) and water (2.0 mL) was added sodium hydroxide (0.33 g, 8.3 mmol). The mixture was stirred at 80° C. for 1 hour, then concentrated to remove methanol, diluted with water, and acidified to pH 1 with 1 M hydrochloric acid, resulting in precipitation of a solid. The solid was collected by filtration and dried in vacuo to give compound B-281 (0.35 g, 93% yield) as a white solid. TLC [petroleum ether:ethyl acetate=10:1]: Rf=0.04.

Example 180B: 2,4-difluoro-3-(trifluoromethyl)benzaldehyde (B-282)

To a mixture of 1,3-difluoro-2-(trifluoromethyl)benzene (2.0 g, 11 mmol) in anhydrous tetrahydrofuran (30 mL) at −70° C. under nitrogen was added dropwise n-butyllithium (2.5 M in cyclohexane, 5.3 mL, 13 mmol). The mixture was stirred for 30 minutes, and N,N-dimethylformamide (1.6 g, 22 mmol) was added dropwise at −70° C. The reaction was stirred at −70° C. for another 2 hours, then acidified pH to 5.0 with 6 N hydrochloric acid, then diluted with water (10 mL) and extracted with ethyl acetate (2×20 mL). The combined organic layers were dried over anhydrous sodium sulfate and concentrated in vacuo to give compound B-282 (1.5 g, 65% yield) as a yellow oil.

Example 181B: methyl 2-((3-fluoro-6-formyl-2-(trifluoromethyl)phenyl)thio)acetate (B-283)

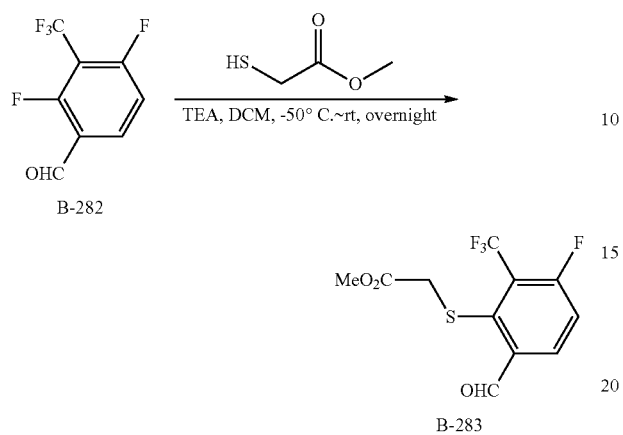

To a mixture of compound B-282 (1.0 g, 4.8 mmol) and triethylamine (0.48 g, 4.8 mmol) in dichloromethane (15 mL) at −50° C. was added dropwise methyl 2-mercaptoacetate (0.51 g, 4.8 mmol). The mixture was stirred at room temperature overnight. On completion, the mixture was concentrated in vacuo to give compound B-283 (1.0 g, crude) as a yellow solid, which was used in the next step without further purification.

Example 182B: methyl 6-fluoro-7-(trifluoromethyl)benzo[b]thiophene-2-carboxylate (B-284)

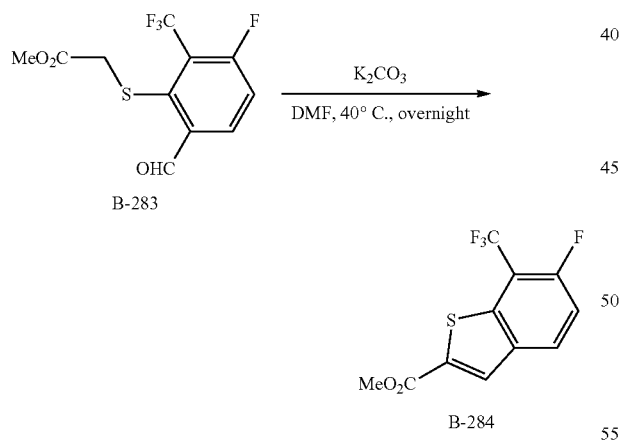

To a mixture of compound B-283 (2.0 g, 6.8 mmol) in N,N-dimethylformamide (20 mL) was added potassium carbonate (1.9 g, 14 mmol). The mixture was stirred at 40° C. overnight. On completion, the mixture was poured into water (20 mL) and extracted with ethyl acetate (2×40 mL). The organic layer was dried over anhydrous sodium sulfate and concentrated in vacuo. The residue was purified by silica gel chromatography [petroleum ether:ethyl acetate=20:1] to give compound B-284 (0.5 g, 25% yield) as a yellow solid. LCMS (R): tR=1.172 min., (ES$^+$) m/z (M+H)$^+$=279.0.

Example 183B: 6-fluoro-7-(trifluoromethyl)benzo[b]thiophene-2-carboxylic acid (B-285)

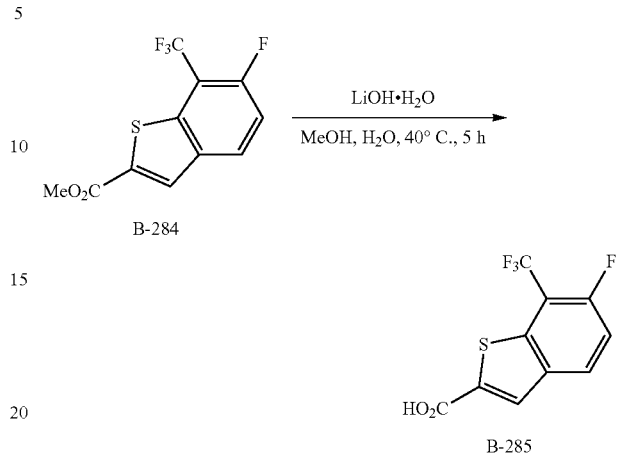

To a mixture of compound B-284 (0.40 g, 1.4 mmol) in methanol (4 mL) and water (2 mL) was added lithium hydroxide monohydrate (0.12 g, 2.9 mmol). The mixture was stirred at 40° C. for 5 hours, then concentrated to remove methanol, diluted with water and acidified to pH 3 with 1 M hydrochloric acid, resulting in formation of a solid. The solid was collected by filtration and dried in vacuo to give compound B-285 (0.25 g, 66% yield) as a yellow solid. LCMS (R): tR=1.044 min., (ES$^+$) m/z (M+H)$^+$=265.0.

Example 184B: methyl 6-bromo-7-fluorobenzo[b]thiophene-2-carboxylate (B-286)

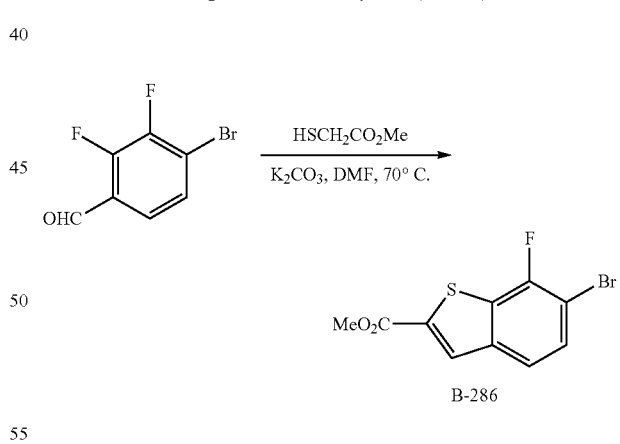

To a solution of 4-bromo-2,3-difluorobenzaldehyde (2.0 g, 9.1 mmol) and potassium carbonate (2.5 g, 18 mmol) in N,N-dimethylformamide (20 mL) at 28° C. was added methyl 2-mercaptoacetate (1.2 g, 11 mmol). The mixture was stirred at 70° C. overnight, then diluted with water (20 mL) and extracted with ethyl acetate (3×30 mL). The combined organic layers were washed with brine (2×30 mL), dried over anhydrous sodium sulfate and concentrated in vacuo. The residue was purified by silica gel column chromatography [petroleum ether:ethyl acetate=20:1] to give compound B-286 (2.2 g, 85% yield) as a white solid.

Example 185B: methyl 6-cyclopropyl-7-fluorobenzo[b]thiophene-2-carboxylate (B-287)

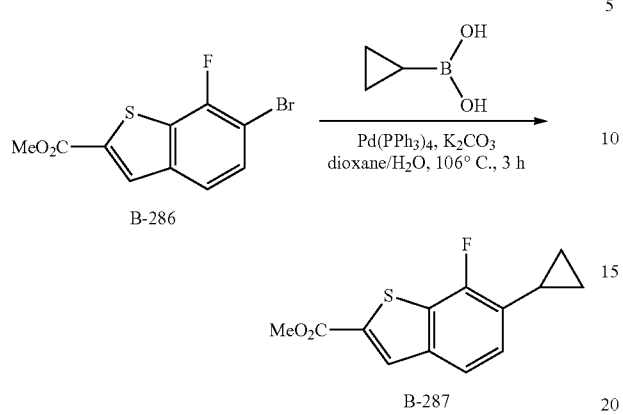

To a solution of B-286 (1.2 g, 4.2 mmol) in dioxane (10 mL) and water (2 mL) under nitrogen at room temperature was added potassium carbonate (1.2 g, 8.4 mmol), cyclopropylboronic acid (0.72 g, 8.4 mmol) and Pd(PPh$_3$)$_4$ (0.23 g, 0.21 mmol). The mixture was stirred at 106° C. for 3 hours, then diluted with water (5 mL) and extracted with ethyl acetate (3×20 mL). The combined organic layers were washed with brine (2×20 mL), dried over anhydrous sodium sulfate and concentrated in vacuo. The residue was purified by silica gel column chromatography [petroleum ether:ethyl acetate=20:1] to give compound B-287 (0.80 g, 76% yield) as a white solid.

Example 186B: 6-cyclopropyl-7-fluorobenzo[b]thiophene-2-carboxylic acid (B-288)

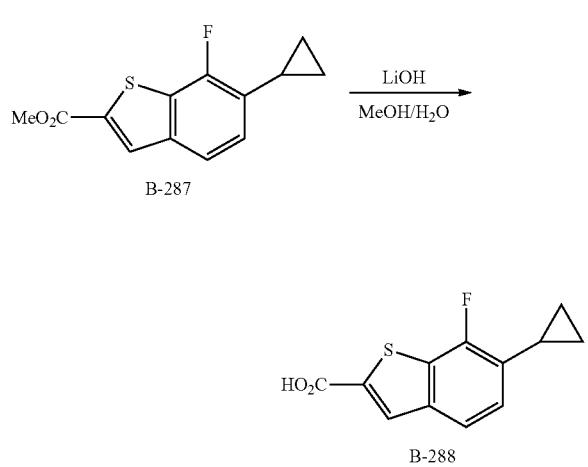

To a solution of B-287 (0.80 g, 3.2 mmol) in methanol (10 mL) and water (2 mL) was added lithium hydroxide (0.27 g, 6.4 mmol) at room temperature. The mixture was stirred for 2 hours, then concentrated to remove most of the methanol, and acidified to pH 4~5, resulting in formation of a solid. The solid was collected by filtration dried to give compound B-288 (0.65 g, 86% yield) as a brown solid.

Example 187B: ethyl 6-chlorobenzofuran-2-carboxylate (B-289)

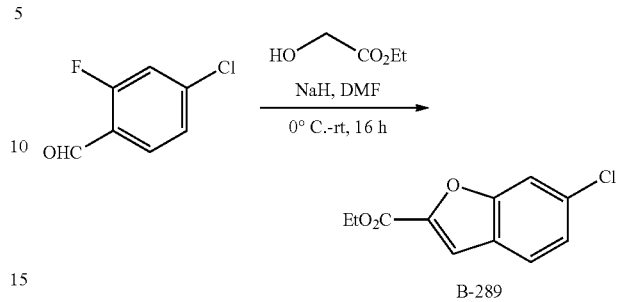

To a mixture of ethyl 2-hydroxyacetate (0.66 g, 6.3 mmol) in N,N-dimethylformamide (10 mL) at 0° C. was added sodium hydride (0.30 g, 7.6 mmol) in portions, followed by 4-chloro-2-fluoro-benzaldehyde (1.0 g, 6.3 mmol) in portions. The resulting mixture was stirred at 0° C. for 2 hr, then allowed to warm to 25° C. and stirred for 14 hr. On completion, the mixture was quenched at 0° C. dropwise with saturated aqueous ammonium chloride (15 ml) and extracted with ethyl acetate (2×40 mL). The combined organic layers were dried over anhydrous sodium sulfate and concentrated in vacuo. The residue was purified by silica gel column chromatography [petroleum ether] to give compound B-289 as a mixture with compound B-290 (0.30 g, crude) as a yellow solid

Example 188B: 6-chlorobenzofuran-2-carboxylic acid (B-290)

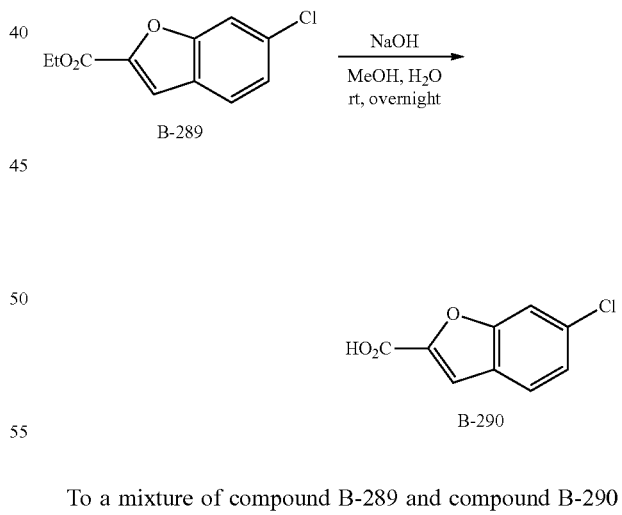

To a mixture of compound B-289 and compound B-290 (0.40 g, 1.8 mmol) in methanol (10 mL) and water (1 mL) was added sodium hydroxide (143 mg, 3.7 mmol). The mixture was stirred at 25° C. overnight, then concentrated to remove methanol, diluted with water, and acidified to pH 3 with 1 M hydrochloric acid, resulting in formation of a solid. The white solid was collected by filtration and dried in vacuo to give compound B-290 (0.15 g, 43% yield). $^1$H-NMR (CD$_3$OD, 400 MHz): δ 7.93 (s, 1H), 7.81 (d, J=8.5 Hz, 1H), 7.67 (s, 1H), 7.41 (dd, J, =8.3 Hz, J$_2$=1.8 Hz, 1H).

Example 189B: ethyl 7-chlorobenzofuran-2-carboxylate (B-291)

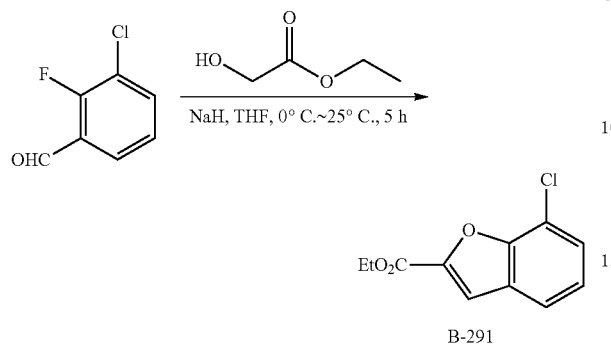

To a solution of ethyl 2-hydroxyacetate (1.6 g, 15 mmol) in tetrahydrofuran (25 mL) at 0° C. was added sodium hydride (0.61 g, 15 mmol). The reaction was stirred for 0.5 hour, and 3-chloro-2-fluorobenzaldehyde (2.0 g, 13 mmol) was added. The mixture was stirred at 25° C. for 4.5 hours, then quenched with water (5 mL) and extracted with ethyl acetate (2×40 mL). The combined organic layers were concentrated in vacuo and purified by silica gel chromatography [petroleum ether:ethyl acetate=15:1] to give compound B-291 (0.80 g, 28% yield) as a yellow solid. LCMS (J): tR=1.551 min., (ES) m/z (M+H)$^+$=225.0.

Example 190B: 7-chlorobenzofuran-2-carboxylic acid (B-292)

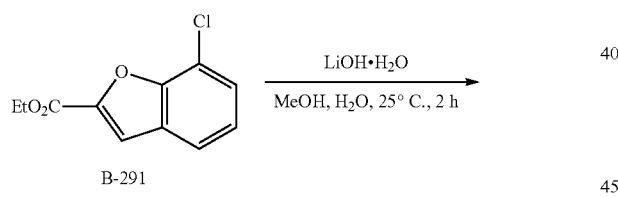

To a mixture of compound B-291 (1.24 g, 5.5 mmol) in methanol (7 mL) and water (7 mL) was added lithium hydroxide monohydrate (0.46 g, 11 mmol). The mixture was stirred at 25° C. for 2 h, then concentrated to remove methanol, diluted with water and acidified to pH 3 with 1 M hydrochloric acid, resulting in formation of a solid. The white solid was collected by filtration and dried in vacuo to give compound B-292 (0.50 g, 46% yield). $^1$H-NMR (DMSO-d6, 400 MHz): δ 7.79-7.77 (m, 2H), 7.62 (d, J=7.6 Hz, 1H), 7.37 (t, J=7.6 Hz, 1H).

Example 191B: (2,2-diethoxyethyl)(3,4-difluorophenyl)sulfane (B-293)

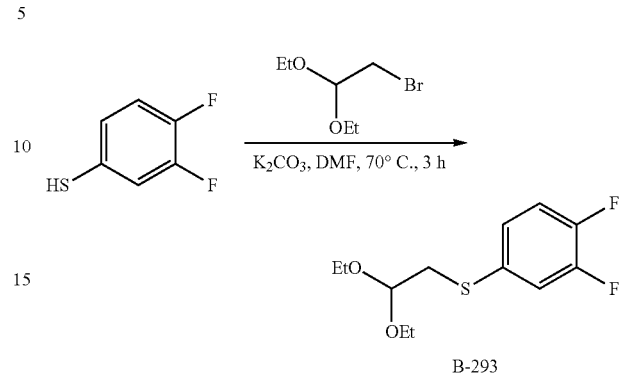

A solution of 3,4-difluorobenzenethiol (3.0 g, 21 mmol), 2-bromo-1,1-diethoxy-ethane (4.5 g, 23 mmol) and potassium carbonate (4.3 g, 31 mmol) in N,N-dimethylformamide (50 mL) was stirred at 70° C. for 3 hours. On completion, the mixture was poured into water (40 mL) and extracted with ethyl acetate (3×40 mL). The combined organic layers were washed with water and brine, dried over anhydrous sodium sulfate and concentrated in vacuo to give compound B-293 (5.0 g, crude) as a yellow solid.

Example 192B: 5,6-difluorobenzo[b]thiophene (B-294)

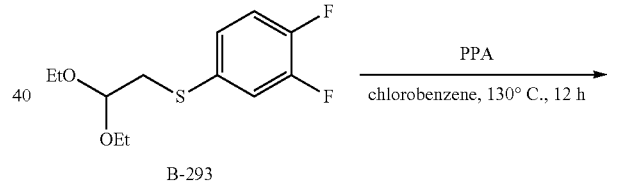

A solution of compound B-293 (7.0 g, 28 mmol) and polyphosphoric acid (15 g) in chlorobenzene (100 mL) was stirred at 130° C. for 12 hours. On completion, the mixture was poured into water (40 mL) and extracted with ethyl acetate (3×40 mL). The combined organic layers were washed with water and brine, dried over anhydrous sodium sulfate and concentrated in vacuo. The residue was purified by silica gel chromatography [petroleum ether:ethyl acetate=1:0] to give compound B-294 (2.6 g, 57% yield) as a yellow solid.

Example 193B: 5,6-difluorobenzo[b]thiophene-2-carboxylic acid (B-295)

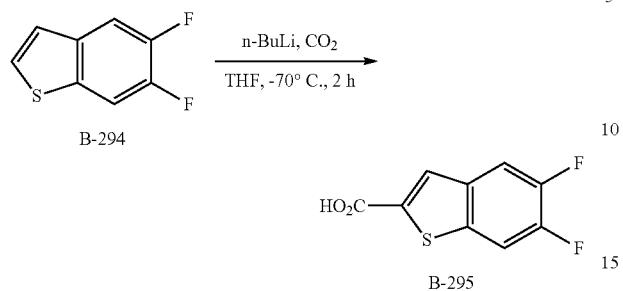

To a solution of compound B-294 (1.0 g, 5.9 mmol) in anhydrous tetrahydrofuran (30 mL) was added n-butyllithium (2.6 mL, 2.5 N in hexane, 6.5 mmol) dropwise at −70° C. The reaction was stirred at −70° C. for 1 hour. The atmosphere was replaced with carbon dioxide, and the reaction was stirred for an additional 1 hour at −70° C. On completion, the mixture was quenched with saturated ammonium chloride solution (2.6 mL) at 0° C. and extracted with ethyl acetate (3×50 mL). The combined organic layers were washed with water and brine, dried over anhydrous sodium sulfate and concentrated in vacuo. The residue was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give compound B-295 (0.24 g, 19% yield) as a white solid.

Example 194B: methyl 7-(methylsulfonyl)benzo[b]thiophene-2-carboxylate (B-296)

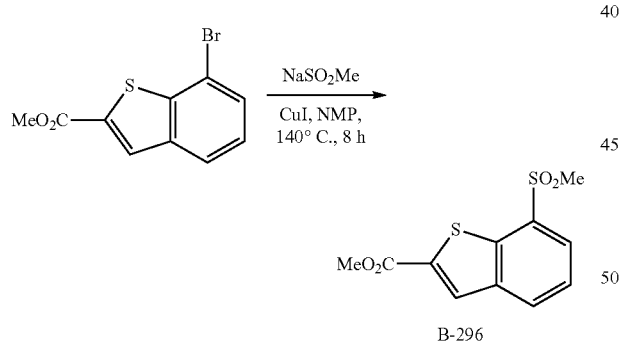

A mixture of methyl 7-bromobenzo[b]thiophene-2-carboxylate (1.0 g, 3.7 mmol), sodium methanesulfinate (1.7 g, 17 mmol) and copper iodide (3.2 g, 17 mmol) in N-methyl-2-pyrrolidone (25 mL) was de-gassed and then heated to 140° C. for 8 hours under nitrogen. The mixture was diluted with ethyl acetate (500 mL), filtered, washed with brine (6×50 mL), dried with anhydrous sodium sulfate and concentrated in vacuo. The residue was purified by column chromatography [petroleum ether:ethyl acetate=5:1 to 10:1] to afford compound B-296 (0.42 g, 42% yield) as a yellow solid. $^1$H-NMR (CD$_3$OD, 400 MHz): 8.28 (d, J=8.0 Hz, 1H), 8.24 (s, 1H), 8.10 (d, J=8.0 Hz, 1H), 7.69 (t, J=8.0 Hz, 1H), 3.95 (s, 3H), 3.20 (s, 3H).

Example 195B: 7-(methylsulfonyl)benzo[b]thiophene-2-carboxylic acid (B-297)

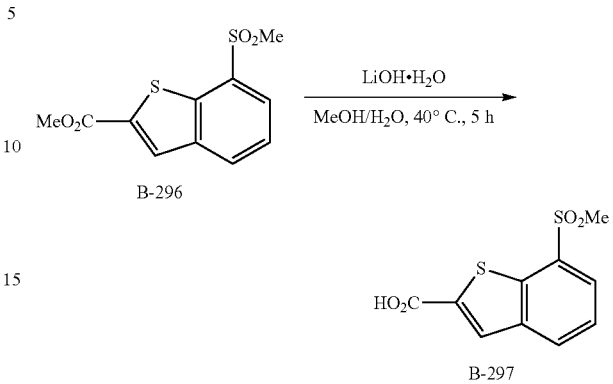

A mixture of compound B-296 (0.40 g, 1.5 mmol) and lithium hydroxide monohydrate (0.43 g, 10 mmol) in methanol (4 mL) and water (2 mL) was stirred at 40° C. for 5 hours. On completion, the mixture was concentrated in vacuo, added to water (50 mL), washed with ethyl acetate (3×10 mL), acidified and extracted with ethyl acetate (3×50 mL). The combined organic phases were washed with brine (3×10 mL), dried with anhydrous sodium sulfate, filtered and concentrated in vacuo to give compound B-297 (0.34 g, 90% yield) as a yellow solid. $^1$H-NMR (CD$_3$OD, 400 MHz): 8.27 (d, J=8.0 Hz, 1H), 8.20 (s, 1H), 8.09 (d, J=7.2 Hz, 1H), 7.68 (t, J=8.0 Hz, 1H), 3.19 (s, 3H).

Example 196B: methyl 7-morpholinobenzo[b]thiophene-2-carboxylate (B-298)

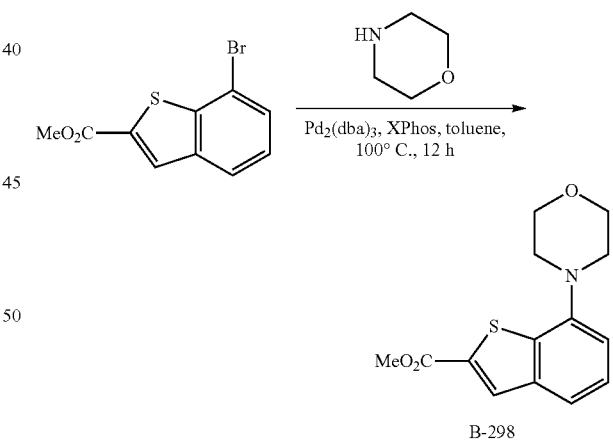

Methyl 7-bromobenzo[b]thiophene-2-carboxylate (1.0 g, 3.7 mmol), morpholine (0.32 g, 3.7 mmol), cesium carbonate (2.4 g, 7.4 mmol), tris(dibenzylideneacetone)dipalladium(0) (0.34 g, 0.37 mmol) and 2-dicyclohexylphosphino-2',4',6'-triisopropylbiphenyl (0.18 g, 0.37 mmol) in toluene (50 mL) was de-gassed and heated to 100° C. for 12 hours under nitrogen. The reaction mixture was poured into water (40 mL) and extracted with ethyl acetate (120 mL). The organic phase was washed with brine (3×20 mL), dried with anhydrous sodium sulfate, concentrated in vacuo and purified by column chromatography [petroleum ether:ethyl acetate=10:1] to afford the compound B-298 (0.95 g, crude) as a yellow gum. LCMS (B): tR=0.838 min., (ES⁺) m/z (M+H)⁺=278.1

Example 197B: 7-morpholinobenzo[b]thiophene-2-carboxylic acid (B-299)

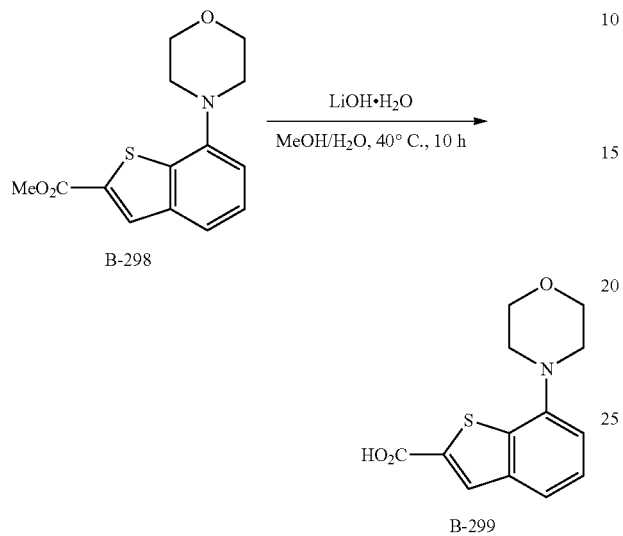

A mixture of compound B-298 (0.95 g, 2.8 mmol) and lithium hydroxide monohydrate (0.81 g, 19 mmol) in methanol (10 mL) and water (5 mL) was stirred at 40° C. for 10 hours. The mixture was concentrated in vacuo, added into water (50 mL), washed with ethyl acetate (3×10 mL), acidified and extracted with ethyl acetate (3×50 mL). The combined organic layers were washed with brine (3×15 mL), dried with anhydrous sodium sulfate, filtered and concentrated in vacuo to give compound B-299 (0.63 g, 86% yield) as a yellow solid. ¹H-NMR (CD₃OD, 400 MHz): 8.02 (s, 1H), 7.60 (d, J=8.4 Hz, 1H), 7.37 (t, J=8.0 Hz, 1H), 7.10 (d, J=8.0 Hz, 1H), 3.89 (t, J=4.8 Hz, 4H), 3.17 (t, J=4.8 Hz, 4H).

Example 198B: methyl 2-cyclopropylbenzofuran-5-carboxylate (B-300)

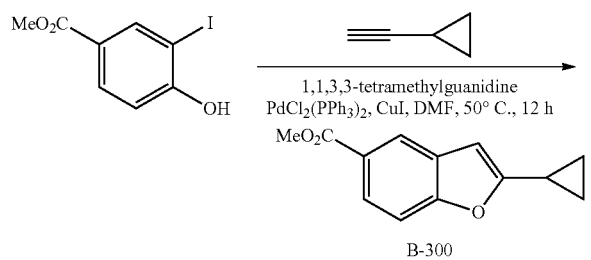

A solution of methyl 4-hydroxy-3-iodobenzoate (4.2 g, 15 mmol), ethynylcyclopropane (1.0 g, 15 mmol), 1,1,3,3-tetramethylguanidine (17 g, 0.15 mol), bis(triphenylphosphine)palladium(II)chloride (1.05 g, 1.5 mol) and copper iodide (0.29 g, 1.5 mmol) in N,N-dimethylformamide (40 mL) was stirred at 50° C. for 12 hours. On completion, the reaction mixture was quenched with 50 mL of water and extracted with dichloromethane (3×50 mL). The combined organic phases were washed with brine, dried over anhydrous sodium sulfate, concentrated in vacuo and purified by silica gel chromatography [petroleum ether:ethyl acetate=8:1] to give compound B-300 (2.0 g, 61% yield) as a yellow solid.

Example 199B: 2-cyclopropylbenzofuran-5-carboxylic acid (B-301)

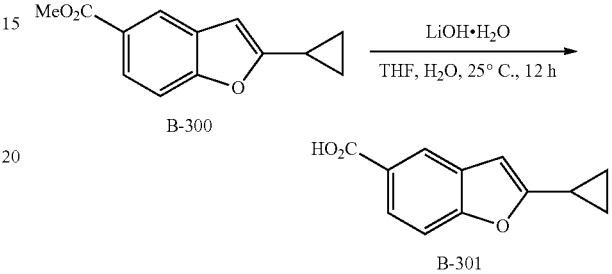

To a solution of compound B-300 (0.50 g, 2.3 mmol) in THF (15 mL) was added lithium hydroxide monohydrate (0.29 g, 6.9 mmol) in water (5.0 mL). The resulting solution was stirred at room temperature for 12 hours, then acidified with 2.0 M aqueous hydrochloric acid and extracted with ethyl acetate (3×20 mL). The combined organic extracts were washed with brine, dried over anhydrous sodium sulfate and concentrated in vacuo to give compound B-301 (0.16 g, 34% yield) as a yellow solid.

Example 200B: 2-(benzo[b]thiophen-7-yl)propan-2-ol (B-302)

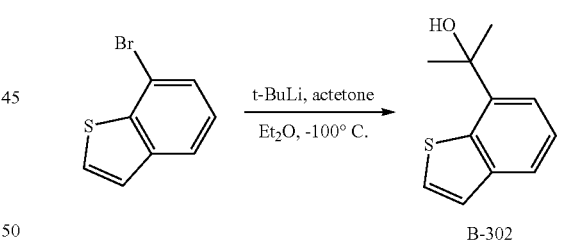

To a solution of 7-bromobenzo[b]thiophene (5.0 g, 24 mmol) in diethyl ether (50 mL) at −100° C. under nitrogen was added dropwise t-BuLi (1.3 mol/L, 55 mL). The mixture was stirred at −100° C. for 15 min, and dry acetone (3.6 g, 48 mmol) was added dropwise at −100° C. The mixture was stirred at −100° C. for 2 hours. TLC showed the reaction was complete and the formation of two products (about 1:1). The reaction mixture was quenched with saturated aqueous ammonium chloride (20 mL) dropwise at 0° C., and then extracted with ethyl acetate (3×50 mL). The combined organic layers were washed with brine (2×50 mL), dried over anhydrous sodium sulfate, concentrated in vacuo and purified by silica gel column chromatography [petroleum ether:ethyl acetate=40:1] to give compound B-302 (0.80 g, 34% yield, the lower spot on TLC) as a yellow oil.

Example 201B: 7-(2-hydroxypropan-2-yl)benzo[b]thiophene-2-carboxylic acid (B-303)

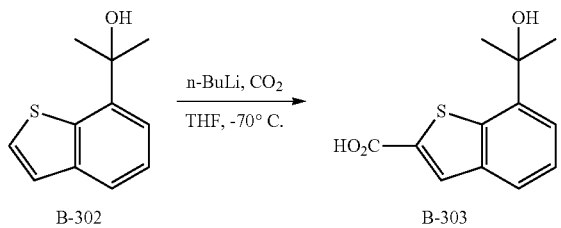

To a solution of B-302 (0.80 g, 4.2 mmol) in tetrahydrofuran (10 mL) at −70° C. under nitrogen was added n-BuLi (2.5 mol/L, 4 mL, 10 mmol) dropwise. The mixture was stirred at −70° C. for 0.5 hour. Carbon dioxide was bubbled into the mixture for 0.5 hour. On completion, the reaction mixture was quenched with saturated aqueous ammonium chloride (10 mL) dropwise at 0° C., and washed with ethyl acetate (2×20 mL). The aqueous phase was acidified to pH 4-5 with HCl (aq), then extracted with ethyl acetate (3×30 mL). The combined organic layers were washed with brine (2×30 mL), dried over anhydrous sodium sulfate and concentrated in vacuo to give compound B-303 (0.85 g, 36% yield) as a white solid. $^1$H-NMR (CDCl$_3$, 400 MHz): δ 8.20 (s, 1H), 7.85-7.83 (m, 1H), 7.44 (m, 2H), 1.79 (s, 3H).

Example 202B: methyl 7-(3,3,3-trifluoroprop-1-en-2-yl)benzo[b]thiophene-2-carboxylate (B-304)

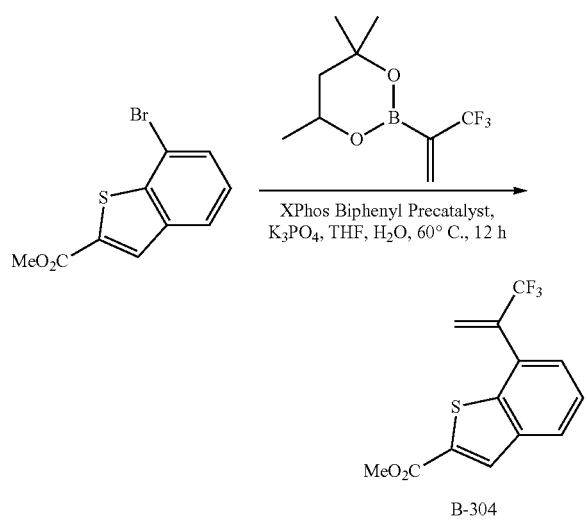

To a mixture of methyl 7-bromobenzo[b]thiophene-2-carboxylate (0.60 g, 2.2 mmol) in tetrahydrofuran (20 mL) and water (6 mL) under nitrogen was added 4,4,6-trimethyl-2-(3,3,3-trifluoroprop-1-en-2-yl)-1,3,2-dioxaborinane (0.59 g, 2.7 mmol), potassium phosphate (0.94 g, 4.4 mmol) and [2-(2-aminophenyl)phenyl]-chloro-palladium; dicyclohexyl-[3-(2,4,6-triisopropylphenyl)phenyl]phosphane (87 mg, 0.11 mmol). The mixture was stirred at 60° C. for 12 hours, then added into water (10 mL) and extracted with ethyl acetate (2×20 mL). The combined organic layers were dried over anhydrous sodium sulfate and concentrated in vacuo. The residue was purified by silica gel chromatography [petroleum ether:ethyl acetate=20:1] to give compound B-304 (0.60 g, 95% purity, 90% yield) as a yellow solid. LCMS (B): tR=0.906 min., (ES$^+$) m/z (M+H)$^+$=287.1.

Example 203B: methyl 7-(3-(trifluoromethyl)-4,5-dihydro-3H-pyrazol-3-yl)benzo[b]thiophene-2-carboxylate (B-305)

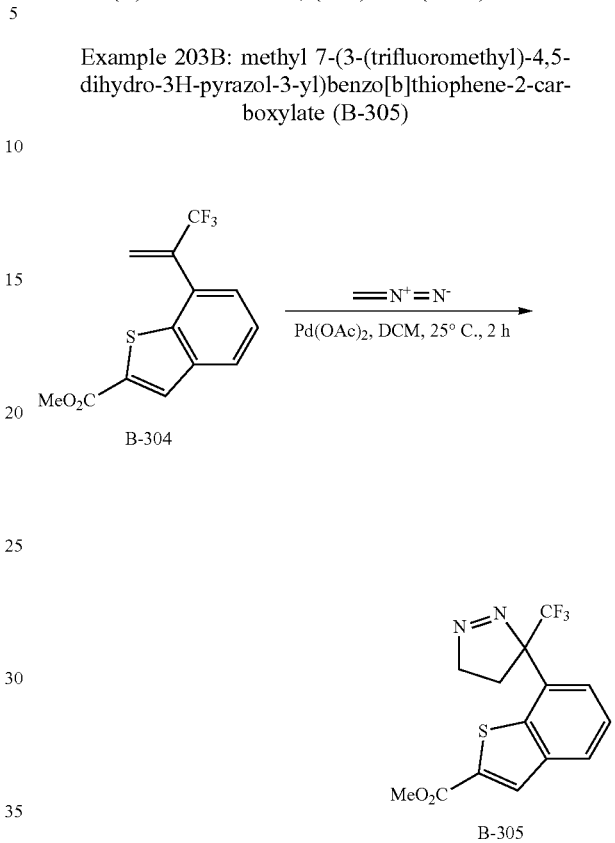

To a mixture of compound B-304 (0.60 g, 2.1 mmol) in dichloromethane (18 mL) under nitrogen was added diazomethane (0.46 M in diethyl ether, 0.14 L) and palladium acetate (47 mg, 0.21 mmol). The mixture was stirred at 25° C. for 2 hours. On completion, the mixture was added into acetic acid (3.8 g, 63 mmol), concentrated in vacuo to remove diethyl ether, diluted with water (15 mL) and extracted with ethyl acetate (2×30 mL). The combined organic layers were dried over anhydrous sodium sulfate and concentrated in vacuo to give compound B-305 (0.70 g, 82% purity, 83% yield) as a yellow solid. LCMS (B): tR=0.856 min., (ES$^+$) m/z (M+H)$^+$=329.1.

Example 204B: methyl 7-(1-(trifluoromethyl)cyclopropyl)benzo[b]thiophene-2-carboxylate (B-306)

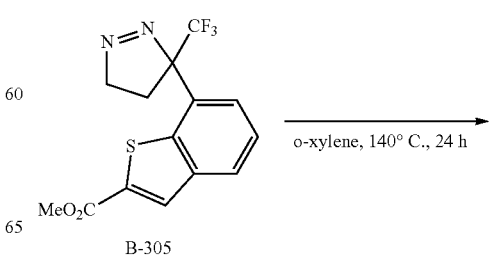

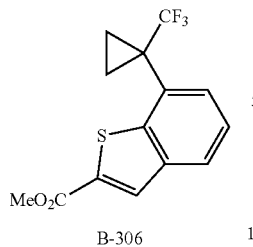

B-306

A mixture of compound B-305 (0.70 g, 2.1 mmol) in o-xylene (50 mL) was stirred at 140° C. for 24 hours. On completion, the mixture was concentrated in vacuo. The residue was purified by silica gel chromatography [petroleum ether:ethyl acetate=20:1] to give compound B-306 (0.24 g, 85% purity, 32% yield) as a white solid. LCMS (B): tR=0.920 min., (ES⁺) m/z (M+H)⁺=301.1.

Example 205B: 7-(1-(trifluoromethyl)cyclopropyl) benzo[b]thiophene-2-carboxylic acid (B-307)

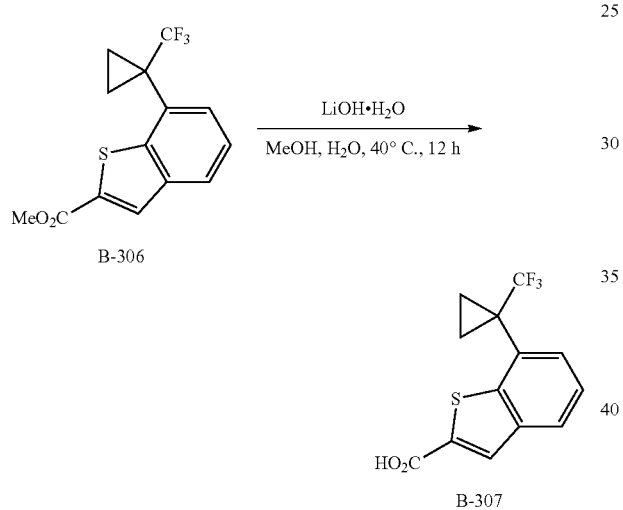

To a mixture of compound B-306 (0.40 g, 1.3 mmol) in methanol (5 mL) and water (2 mL) was added lithium hydroxide monohydrate (0.11 g, 2.7 mmol). The mixture was stirred at 40° C. for 12 hours, then concentrated to remove methanol, diluted with water, acidified to pH 3 with 6 M hydrochloric acid and extracted with ethyl acetate (2×20 mL). The combined organic layers were dried over anhydrous sodium sulfate and concentrated in vacuo to give compound B-307 (0.38 g, 90% purity, 90% yield) as a white solid. LCMS (B): tR=0.831 min., (ES⁺) m/z (M+H)⁺=287.1.

Example 206B:
1-bromo-2-fluoro-4-(methoxymethyl)benzene
(B-308)

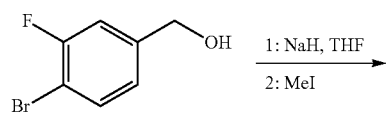

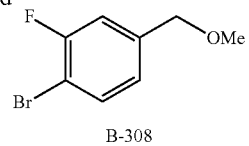

B-308

To a solution of (4-bromo-3-fluorophenyl)methanol (5.0 g, 24 mmol) in tetrahydrofuran (150 mL) at 0° C. was added sodium hydride (1.4 g, 34 mmol). The reaction was stirred at this temperature for 10 min, and then methyl iodide (4.1 g, 29 mmol) was added. The reaction was allowed to warm from 0° C. to 20° C. over 3 hours, then quenched with saturated aqueous ammonium chloride (50 mL) and extracted with ethyl acetate (3×100 mL). The combined organic layers were washed with brine, dried over anhydrous sodium sulfate and concentrated in vacuo. The residue was purified by silica gel chromatography [petroleum ether:ethyl acetate=30:1] to give compound B-308 (4.8 g, 90% yield) as an orange oil. TLC [petroleum ether:ethyl acetate=10:1]: Rf=0.5; ¹H-NMR (CDCl₃, 400 MHz): δ 7.53 (t, J=8.0 Hz, 1H), 7.14 (d, J=9.2 Hz, 1H), 7.01 (d, J=8.0 Hz, 1H), 4.43 (s, 2H), 3.42 (s, 3H).

Example 207B:
2-fluoro-4-(methoxymethyl)benzaldehyde (B-309)

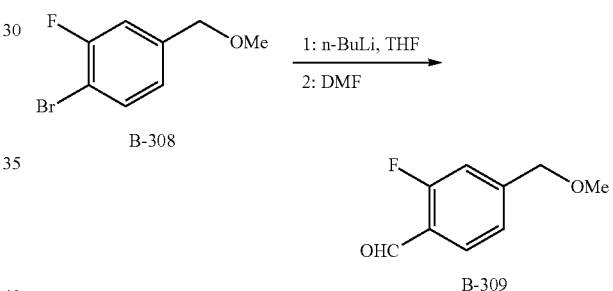

To a solution of compound B-308 (4.0 g, 18 mmol) in tetrahydrofuran (50 mL) at −78° C. was added n-butyllithium (20 mmol, 8.0 mL). The reaction was stirred at this temperature for 30 min, and then N,N-dimethylformamide (6.7 g, 91 mmol) was added. The reaction was allowed to warm from −78° C. to 0° C. over 1 hour, then quenched with saturated aqueous ammonium chloride (30 mL) and extracted with ethyl acetate (3×50 mL). The combined organic phase was concentrated and purified by silica gel chromatography [petroleum ether:ethyl acetate=20:1] to give compound B-309 (2.1 g, 68% yield) as a yellow oil. TLC [petroleum ether:ethyl acetate=10:1]: Rf=0.4; ¹H-NMR (CDCl₃, 400 MHz): δ 10.22 (s, 1H), δ 7.72 (t, J=8.0 Hz, 1H), 7.09-7.04 (m, 2H), 4.39 (s, 2H), 3.32 (s, 3H).

Example 208B: methyl 2-aminothieno[2,3-d]pyrimidine-6-carboxylate (B-310)

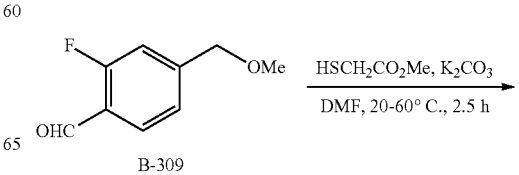

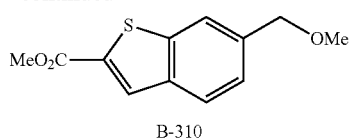

B-310

To a solution of compound B-309 (2.0 g, 12 mmol) in N,N-dimethylformamide (20 mL) under nitrogen was added potassium carbonate (3.3 g, 24 mmol) and methyl 2-mercaptoacetate (1.9 g, 18 mmol). The mixture was stirred at 60° C. for 2.5 hours, then diluted with water (20 mL) and extracted with ethyl acetate (3×20 mL). The combined organic layers were washed with brine, dried over anhydrous sodium sulfate, filtered and concentrated. The residue was purified by silica gel chromatography [petroleum ether:ethyl acetate=10:1] to give compound B-310 (1.5 g, 53% yield) as a yellow oil. LCMS (B): tR=0.792 min., (ES+) m/z (M+1)$^+$ =237.0.

Example 209B: 6-(methoxymethyl)benzo[b]thiophene-2-carboxylic acid (B-311)

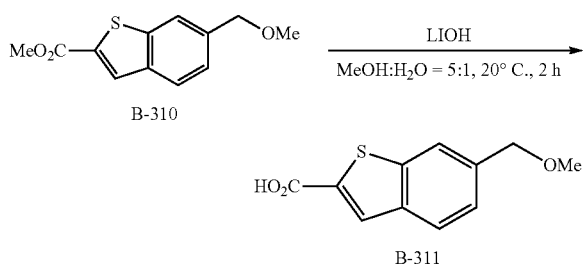

To a solution of compound B-310 (1.5 g, 6.4 mmol) in methanol (15 mL) and water (3 mL) was added lithium hydroxide (0.30 g, 13 mmol). The mixture was stirred at 25° C. for 2 hours, then concentrated to remove methanol, diluted with water, and acidified to pH 3 with 1 M hydrochloric acid, resulting in precipitation of a solid. The solid was collected by filtration and dried in vacuo to give compound B-311 (0.70 g, 50% yield) as a white solid. TLC [dichloromethane:methanol=10:1]: Rf=0.4. $^1$H-NMR (CDCl$_3$, 400 MHz): δ 8.18 (s, 1H), δ 7.92-7.90 (m, 2H), 7.42 (d, J=8 Hz, 1H), 4.64 (s, 2H), 3.47 (s, 3H).

General Procedure A:
Synthesis and Chiral Separation of Amides

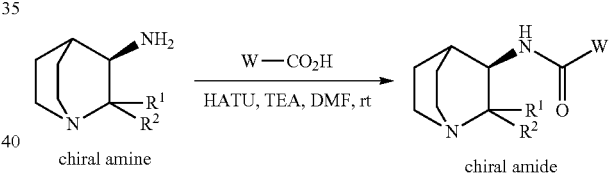

A mixture of carboxylic acid in thionyl chloride (5 mL/mmol carboxylic acid) was stirred at 60° C. for 2 hours. On completion, the solution was concentrated in vacuo to give the acid chloride, which was used directly without further purification. This material (1.1 eq) was added to a mixture of racemic amine (1 eq.) and triethylamine (2 eq.) in dichloromethane (3-5 mL/mmol racemic amine) at room temperature. The mixture was stirred at this temperature for 2 hours. On completion, the reaction was filtered, and the resulting filtrate was concentrated and purified by prep-HPLC to give racemic amide product.

Chiral Separation:
A solution of racemic amide product in 3-5 mL of methanol or ethanol was separated by cSFC (Waters SFC Prep 80, Column temperature: 35° C., back pressure: 100 bar, and wavelength: 220 nm). Each set of collected fractions was concentrated at room temperature and lyophilized. The resulting solids were dissolved in 0.2 M hydrochloric acid solution and again lyophilized to give each enantiomer of the amide product.

General Procedure B:
Synthesis of Chiral Amide Products from Chiral Amines

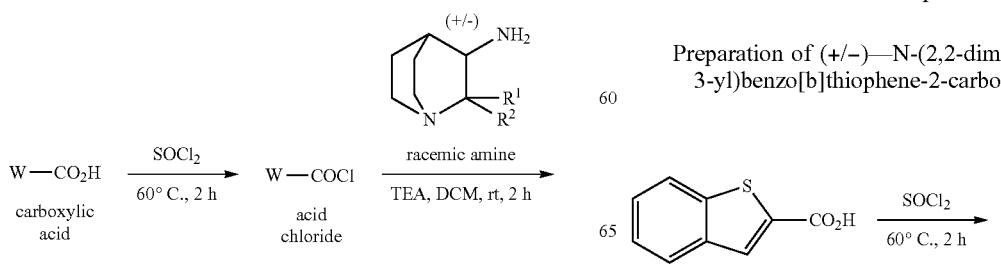

To a mixture of carboxylic acid (1 eq.) in N,N-dimethylformamide (2 mL/mmol carboxylic acid) was added 2-(3H-[1,2,3]triazolo[4,5-b]pyridin-3-yl)-1,1,3,3-tetramethylisouronium hexafluorophosphate (1.2 eq.), followed by chiral amine (1 eq.) and triethylamine (2 eq.). The mixture was stirred at room temperature for 2-12 hours. On completion, the reaction was diluted with ethyl acetate and washed 4 times with water. The organic layer was dried over anhydrous sodium sulfate and concentrated in vacuo. The residue was purified by prep-HPLC and lyophilized to give the target compound.

Example 1

Preparation of (+/−)—N-(2,2-dimethylquinuclidin-3-yl)benzo[b]thiophene-2-carboxamide (rac-1)

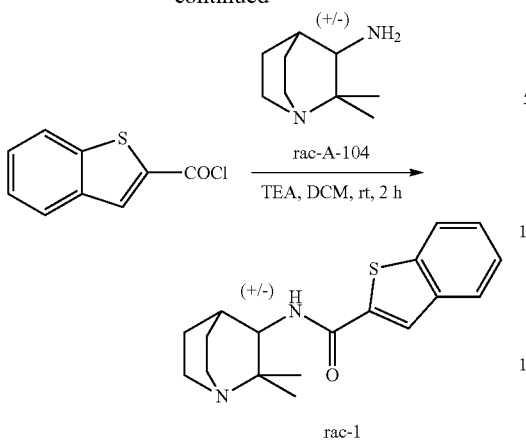

Following general procedure A, rac-1 was prepared from benzo[b]thiophene-2-carboxylic acid and rac-A-104 (0.10 g, 0.65 mmol). The product was purified by prep-HPLC [Instrument: GX-C; Column: Phenomenex Gemini C18 150× 30 mm, particle size: 5 μm; Mobile phase: 35-65% acetonitrile in H$_2$O (add 0.5% NH$_3$.H2O, v/v)] to give rac-1 (0.15 g, 73% yield) as a white solid. LCMS: (ES$^+$) m/z (M+H)$^+$=315.1.

Chiral Separation:

rac-1 (0.20 g, 0.64 mmol) in 3 mL of methanol was separated by SFC (Instrument: SFC 80; Column: Chiralpak AD-H 250×30 mm I.D., 10 μm; Mobile phase: 50% methanol (0.01% NH$_3$.H$_2$O) in CO$_2$) according to general procedure A to give:

N-(2,2-dimethylquinuclidin-3-yl)benzo[b]thiophene-2-carboxamide-enantiomer1 hydrochloride (compound 1a) (0.08 g, 40% yield) as a white solid: cSFC analytical (A) tR=2.80 min., purity: 100%; LCMS (Z): tR=1.459 min., (ES$^+$) m/z (M+H)$^+$=315.0; $^1$H-NMR (DMSO-d$_6$, 400 MHz): δ 10.50 (s, 1H), 8.61 (d, J=8.0 Hz, 1H), 8.39 (s, 1H), 8.04-8.02 (m, 1H), 7.98-7.95 (m, 1H), 7.50-7.45 (m, 2H), 4.11 (d, J=7.6 Hz, 1H), 3.50 (m, 2H), 3.22-3.11 (m, 2H), 2.43-2.42 (m, 1H), 2.10-2.02 (m, 2H), 1.92-1.87 (m, 1H), 1.73-1.67 (m, 1H), 1.62 (s, 3H), 1.40 (s, 3H); and N-(2,2-dimethylquinuclidin-3-yl)benzo[b]thiophene-2-carboxamide-enantiomer2 hydrochloride (compound 1b) (0.08 g, 40% yield) as a white solid: cSFC analytical (A) tR=3.43 min., purity: 99.72%; LCMS (Z): tR=1.439 min., (ES$^+$) m/z (M+H)$^+$=315; $^1$H-NMR (DMSO-d$_6$, 400 MHz): δ 10.43 (s, 1H), 8.61 (d, J=7.6 Hz, 1H), 8.38 (s, 1H), 8.04-8.02 (m, 1H), 7.98-7.96 (m, 1H), 7.50-7.45 (m, 2H), 4.11 (d, J=7.6 Hz, 1H), 3.50 (m, 2H), 3.22-3.12 (m, 2H), 2.43-2.42 (m, 1H), 2.11-2.02 (m, 2H), 1.93-1.87 (m, 1H), 1.73-1.67 (m, 1H), 1.62 (s, 3H), 1.40 (s, 3H).

Preparation of (R)—N-(2,2-dimethylquinuclidin-3-yl)benzo[b]thiophene-2-carboxamide hydrochloride ((R)-1)

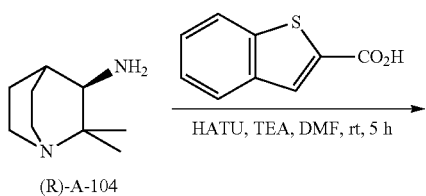

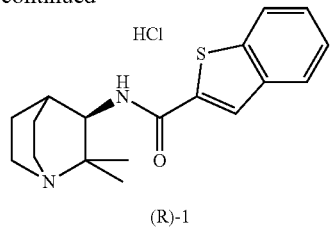

Following general procedure B, compound (R)-1 was prepared from benzo[b]thiophene-2-carboxylic acid (0.35 g, 1.9 mmol) and compound (R)-A-104 (0.30 g, 1.9 mmol), with a reaction time of 5 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(R)—N-(2,2-dimethylquinuclidin-3-yl)benzo[b]thiophene-2-carboxamide hydrochloride (compound (R)-1) (0.22 g, 36% yield) as a white solid: cSFC analytical (A) tR=2.78 min., purity: 98.60%; LCMS (Z): tR=1.496 min., 315.0 m/z (M+1); $^1$H-NMR (CD$_3$OD, 400 MHz): δ 8.16 (s, 1H), 7.94-7.92 (m, 2H), 7.49-7.42 (m, 2H), 4.26 (s, 1H), 3.76-3.67 (m, 2H), 3.38-3.33 (m, 2H), 2.43-2.41 (m, 1H), 2.29-2.27 (m, 1H), 2.18-2.10 (m, 2H), 1.97-1.94 (m, 1H), 1.75 (s, 3H), 1.50 (s, 3H).

Example 2: (+/−)-4-chloro-N-(2,2-dimethylquinuclidin-3-yl)benzamide (rac-2)

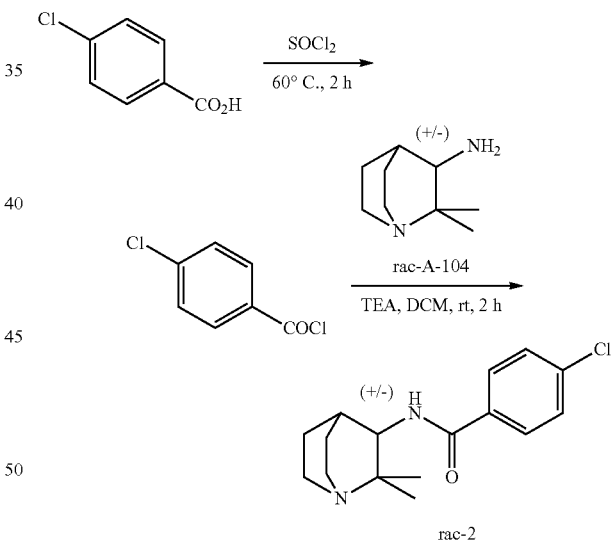

Following general procedure A, rac-2 was prepared from 4-chlorobenzoic acid and rac-A-104 (0.31 g, 1.76 mmol). The product was purified by prep-HPLC [Instrument: GX-D; Column: Boston Symmetrix C18 ODS-R 150*30 mm, particle size: 5 μm; Mobile phase: 6-36% acetonitrile in H$_2$O (add 0.5% NH$_3$.H2O, v/v)] to give rac-2 (0.5 g, 37% yield) as a yellow solid. LCMS: (ES$^+$) m/z (M+H)$^+$=293.2.

Chiral Separation:

rac-2 (0.15 g, 0.51 mmol) in 3 mL of methanol was separated by SFC (Instrument: SFC 80; Column: Chiralpak AD-H 250×25 mm I.D., 10 μm; Mobile phase: 30% methanol (0.01% NH$_3$H$_2$O) in CO$_2$) according to general procedure A to give:

4-chloro-N-(2,2-dimethylquinuclidin-3-yl)benzamide-enantiomer1 hydrochloride (compound 2a) (0.05 g, 33% yield) as yellow solid: cSFC analytical (B) tR: 2.02 min., purity: 99.83%; LCMS (Y): tR: 0.603 min., (ES$^+$) m/z (M+H)$^+$=293.0; $^1$H-NMR (CD$_3$OD, 400 MHz): δ 7.84 (d, J=8.4 Hz, 2H), 7.51 (d, J=8.4 Hz, 2H), 4.23 (s, 1H), 3.75-3.63 (m, 2H), 3.36-3.34 (m, 1H), 3.28-3.26 (m, 1H), 2.35-2.24 (m, 1H), 2.23-2.21 (m, 1H), 2.16-2.06 (m, 2H), 1.94-1.88 (m, 1H), 1.75 (s, 3H), 1.46 (s, 3H); and 4-chloro-N-(2,2-dimethylquinuclidin-3-yl)benzamide-enantiomer2 hydrochloride (compound 2b) (0.051 g, 33% yield) as yellow solid: cSFC analytical (B) tR: 2.40 min., purity: 99.84%; LCMS (Y): tR: 0.592 min., (ES$^+$) m/z (M+H)$^+$=293.0; $^1$H-NMR (CD$_3$OD, 400 MHz): δ 7.84 (d, J=8.4 Hz, 2H), 7.51 (d, J=8.4 Hz, 2H), 4.23 (s, 1H), 3.72-3.67 (m, 2H), 3.36-3.34 (m, 1H), 3.28-3.26 (m, 1H), 2.38-2.33 (m, 1H), 2.24-2.23 (m, 1H), 2.19-2.09 (m, 2H), 1.94-1.88 (m, 1H), 1.75 (s, 3H), 1.46 (s, 3H).

Example 3

Preparation of (R)-7-chloro-N-(2,2-dimethylquinuclidin-3-yl)benzo[b]thiophene-2-carboxamide hydrochloride ((R)-3)

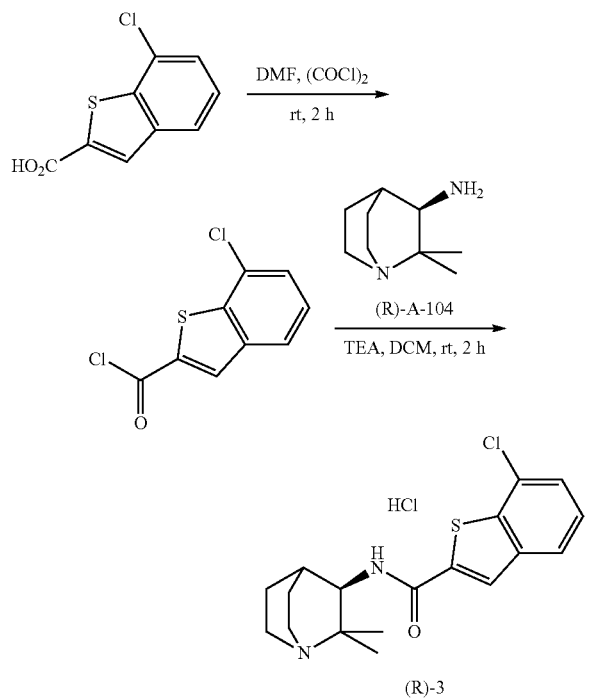

To a mixture of 7-chlorobenzo[b]thiophene-2-carboxylic acid (70 mg, 0.33 mmol) in oxalyl chloride (2 mL) was added N,N-dimethylformamide (2 drops). The mixture was stirred at room temperature for 2 hours. On completion, the solution was concentrated in vacuo to give the acid chloride, which was used directly without further purification. This material (1.0 eq.) was added to a mixture of compound (R)-A-104 (50 mg, 0.32 mmol) and triethylamine (66 mg, 0.65 mmol) in dichloromethane (2 mL) at room temperature. The mixture was stirred at this temperature for 2 hours. On completion, the reaction was filtered, and the resulting filtrate was concentrated and purified by prep-HPLC [Instrument: GX-E; Column: Agella Venusil ASB C18 150×21.2 mm, particle size: 5 μm; Mobile phase: 19-49% acetonitrile in H$_2$O (add 0.5% HCl, v/v)] to give:

(R)-7-chloro-N-(2,2-dimethylquinuclidin-3-yl)benzo[b]thiophene-2-carboxamide hydrochloride (compound (R)-3) (53.9 mg, 43% yield) as white solid: cSFC analytical (A) tR=3.04 min., purity: 98.99%; LCMS (A): tR=1.642 min., (ES$^+$) m/z (M+H)$^+$=349.1; $^1$H-NMR (CD$_3$OD, 400 MHz): δ 8.22 (s, 1H), 7.89 (d, J=8.0 Hz, 1H), 7.52-7.44 (m, 2H), 4.26 (s, 1H), 3.73-3.69 (m, 2H), 3.38-3.31 (m, 2H), 2.45-2.37 (m, 1H), 2.28-2.27 (m, 1H), 2.18-2.06 (m, 2H), 1.97-1.91 (m, 1H), 1.75 (m, 3H), 1.49 (m, 3H);

Preparation of (S)-7-chloro-N-(2,2-dimethylquinuclidin-3-yl)benzo[b]thiophene-2-carboxamide hydrochloride ((S)-3)

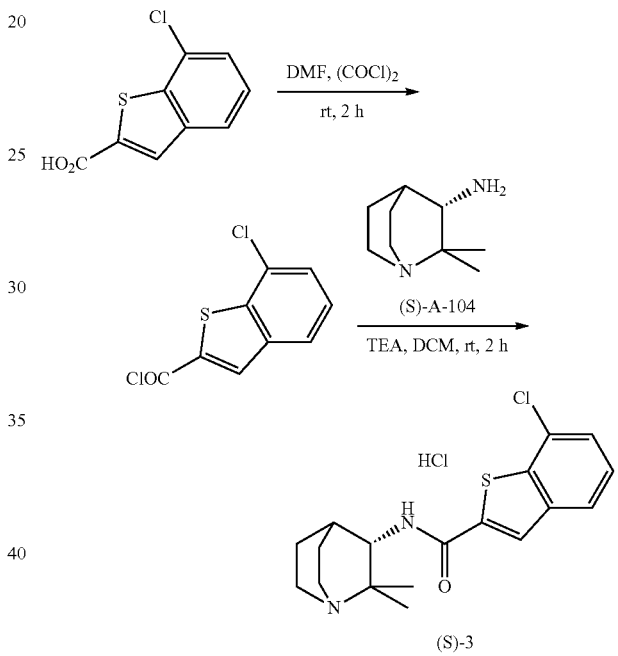

To a mixture of 7-chlorobenzo[b]thiophene-2-carboxylic acid (70 mg, 0.33 mmol) in oxalyl chloride (2 mL) was added N,N-dimethylformamide (2 drops). The mixture was stirred at room temperature for 2 hours. On completion, the solution was concentrated in vacuo to give the acid chloride, which was used directly without further purification. This material (1.0 eq.) was added to a mixture of compound (S)-A-104 (50 mg, 0.32 mmol) and triethylamine (66 mg, 0.65 mmol) in dichloromethane (2 mL) at room temperature. The mixture was stirred at this temperature for 2 hours. On completion, the reaction was filtered, and the resulting filtrate was concentrated and purified by prep-HPLC [Instrument: GX-E; Column: Agella Venusil ASB C18 150×21.2 mm, particle size: 5 μm; Mobile phase: 19-49% acetonitrile in H$_2$O (add 0.5% HCl, v/v)] to give:

(S)-7-chloro-N-(2,2-dimethylquinuclidin-3-yl)benzo[b]thiophene-2-carboxamide hydrochloride (compound (S)-3) (35 mg, 31% yield) as white solid: cSFC analytical (A) tR=4.40 min., purity: 97.85%; LCMS (B): tR=0.699 min., (ES$^+$) m/z (M+H)$^+$=349.1; $^1$H-NMR (CD$_3$OD, 400 MHz): δ 8.24 (s, 1H), 7.89 (d, J=8.0 Hz, 1H), 7.52-7.44 (m, 2H), 4.26 (s, 1H), 3.76-3.66 (m, 2H), 3.38-3.33 (m, 2H), 2.46-2.43 (m, 1H), 2.28-2.27 (m, 1H), 2.17-2.10 (m, 2H), 1.97-1.91 (m, 1H), 1.76 (m, 3H), 1.51 (m, 3H);

Example 4

Preparation of (R)—N-(2,2-dimethylquinuclidin-3-yl)-7-fluoro-benzo[b]thiophene-2-carboxamide hydrochloride ((R)-4)

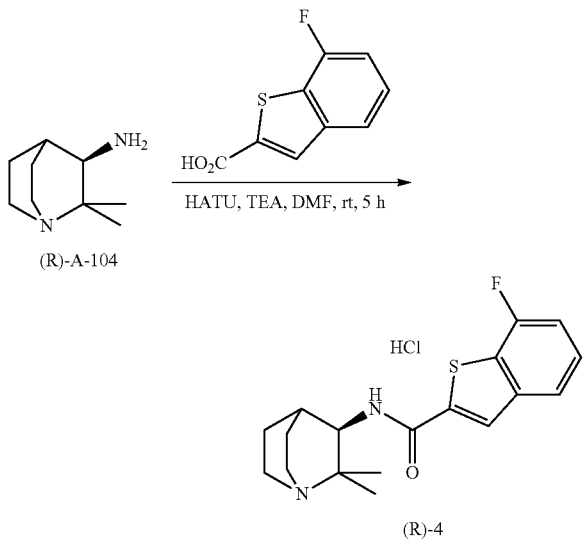

Following general procedure B, Compound (R)-4 was prepared from 7-fluorobenzo[b]thiophene-2-carboxylic acid (76 mg, 0.39 mmol) and compound (R)-A-104 (0.30 g, 1.9 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(R)—N-(2,2-dimethylquinuclidin-3-yl)-7-fluoro-benzo[b]thiophene-2-carboxamide hydrochloride (compound (R)-4) (37 mg, 31% yield) as a white solid: cSFC analytical (A) tR=2.71 min., purity: 100%; LCMS (A): tR=1.509 min., (ES$^+$) m/z (M+H)$^+$=333.1; $^1$H-NMR (CD$_3$OD, 400 MHz): δ 8.20 (d, J=3.6 Hz, 1H), 7.76 (d, J=8.0 Hz, 1H), 7.26-7.20 (m, 2H), 4.26 (s, 1H), 3.76-3.65 (m, 2H), 3.38-3.32 (m, 2H), 2.45-2.40 (m, 1H), 2.29-2.27 (m, 1H), 2.18-2.10 (m, 2H), 1.98-1.91 (m, 1H), 1.75 (s, 3H), 1.50 (s, 3H).

Preparation of (S)—N-(2,2-dimethylquinuclidin-3-yl)-7-fluoro-benzo[b]thiophene-2-carboxamide hydrochloride ((S)-4)

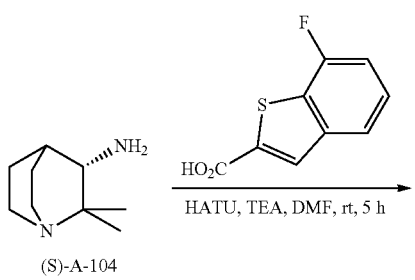

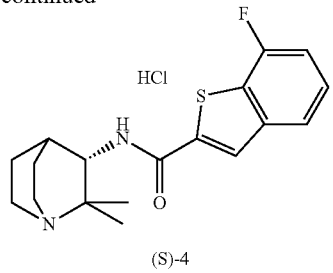

Following general procedure B, Compound (S)-4 was prepared from 7-fluorobenzo[b]thiophene-2-carboxylic acid (76 mg, 0.39 mmol) and compound (S)-A-104 (0.50 g, 0.32 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(S)—N-(2,2-dimethylquinuclidin-3-yl)-7-fluoro-benzo[b]thiophene-2-carboxamide hydrochloride (compound (S)-4) (31 mg, 29% yield) as a white solid: cSFC analytical (A) tR=3.54 min., purity: 100%; LCMS (B): tR=0.694 min., (ES$^+$) m/z (M+H)$^+$=333.1; $^1$H-NMR (CD$_3$OD, 400 MHz): δ 8.22 (d, J=3.2 Hz, 1H), 7.77 (d, J=7.6 Hz, 1H), 7.49-7.44 (m, 2H), 4.26 (s, 1H), 3.76-3.67 (m, 2H), 3.38-3.35 (m, 2H), 2.43-2.42 (m, 1H), 2.29-2.28 (m, 1H), 2.18-2.10 (m, 2H), 1.98-1.91 (m, 1H), 1.75 (s, 3H), 1.50 (s, 3H).

Example 5

Preparation of (R)—N-(2,2-dimethylquinuclidin-3-yl)benzo[b]thiophene-6-carboxamide hydrochloride ((R)-5)

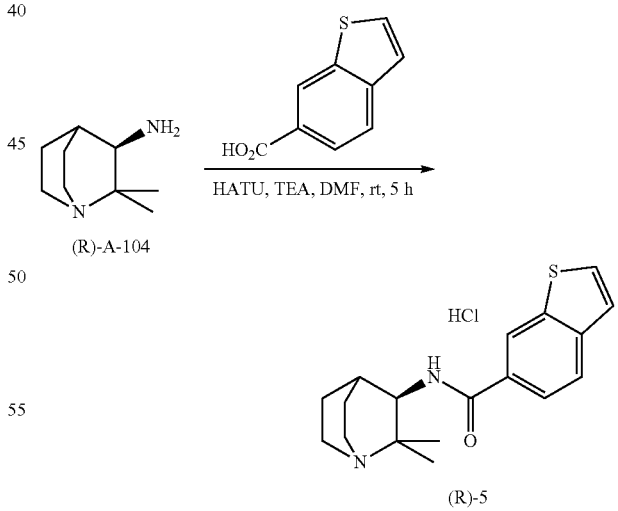

Following general procedure B, Compound (R)-5 was prepared from benzo[b]thiophene-6-carboxylic acid (57 mg, 0.32 mmol) and compound (R)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give:

(R)—N-(2,2-dimethylquinuclidin-3-yl)benzo[b]thiophene-6-carboxamide hydrochloride (compound (R)-5) (53 mg, 46% yield) as a white solid: cSFC analytical (A) tR=2.96 min., purity: 95.55%; LCMS (A): tR=1.153 min., 315.1 m/z (M+1); $^1$H-NMR (CD$_3$OD, 400 MHz): δ 8.46 (s, 1H), 7.95 (d, J=8.4 Hz, 1H), 7.85 (dd, J$_1$=8.4 Hz, J$_2$=1.6 Hz, 1H), 7.80 (d, J=5.6 Hz, 1H), 7.47 (d, J=6 Hz, 1H), 4.29 (s, 1H), 3.76-3.65 (m, 2H), 3.37-3.33 (m, 2H), 2.43-2.38 (m, 1H), 2.28-2.26 (m, 1H), 2.19-2.09 (m, 2H), 1.95-1.89 (m, 1H), 1.77 (s, 3H), 1.49 (s, 3H).

Preparation of (S)—N-(2,2-dimethylquinuclidin-3-yl)benzo[b]thiophene-6-carboxamide hydrochloride ((S)-5)

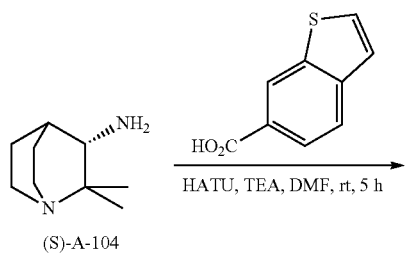

Following general procedure B, Compound (S)-5 was prepared from benzo[b]thiophene-6-carboxylic acid (57 mg, 0.32 mmol) and compound (S)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give:

(S)—N-(2,2-dimethylquinuclidin-3-yl)benzo[b]thiophene-6-carboxamide hydrochloride (compound (S)-5) (32 mg, 31% yield) as a white solid: cSFC analytical (A) tR=3.92 min., purity: 97.22%; LCMS (B): tR=0.569 min., 315.1 m/z (M+1); $^1$H-NMR (CD$_3$OD, 400 MHz): δ 8.46 (s, 1H), 7.95 (d, J=8.8 Hz, 1H), 7.84 (dd, J$_1$=8.0 Hz, J$_2$=1.2 Hz, 1H), 7.80 (d, J=5.6 Hz, 1H), 7.47 (d, J=5.6 Hz, 1H), 4.29 (s, 1H), 3.76-3.65 (m, 2H), 3.37-3.35 (m, 2H), 2.42-2.39 (m, 1H), 2.28-2.27 (m, 1H), 2.19-2.10 (m, 2H), 1.96-1.89 (m, 1H), 1.78 (s, 3H), 1.50 (s, 3H).

Example 6

Preparation of (R)—N-(2,2-dimethylquinuclidin-3-yl)benzofuran-5-carboxamide hydrochloride ((R)-6)

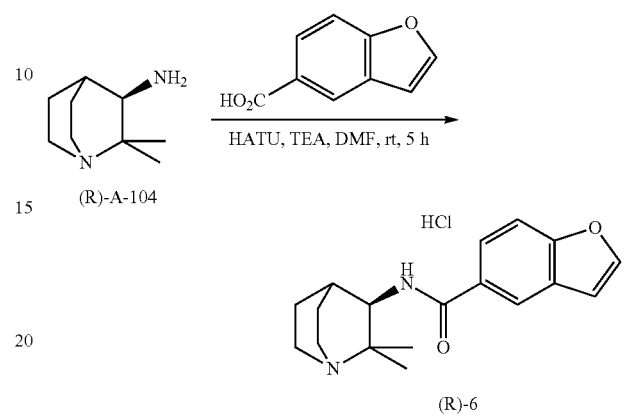

Following general procedure B, Compound (R)-6 was prepared from benzofuran-5-carboxylic acid (52 mg, 0.32 mmol) and compound (R)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 21-51% acetonitrile in H$_2$O (add 0.5% HCl, v/v)] to give:

(R)—N-(2,2-dimethylquinuclidin-3-yl)benzofuran-5-carboxamide hydrochloride (compound (R)-6) (57 mg, 52% yield) as a white solid: cSFC analytical (A) tR=2.45 min., purity: 98.53%; LCMS (A): tR=0.566 min., 299.1 m/z (M+1); $^1$H-NMR (CD$_3$OD, 400 MHz): δ 8.17 (d, J=1.2 Hz, 1H), 7.87 (d, J=2.0 Hz, 1H), 7.82 (dd, J$_1$=8.8 Hz, J$_2$=1.0 Hz, 1H), 7.60 (d, J=8.4 Hz, 1H), 6.96 (d, J=1.6 Hz, 1H), 4.27 (s, 1H), 3.76-3.65 (m, 2H), 3.37-3.34 (m, 2H), 2.41-2.39 (m, 1H), 2.38-2.36 (m, 1H), 2.26-2.09 (m, 2H), 1.96-1.89 (m, 1H), 1.77 (s, 3H), 1.49 (s, 3H).

Preparation of (S)—N-(2,2-dimethylquinuclidin-3-yl)benzofuran-5-carboxamide hydrochloride ((S)-6)

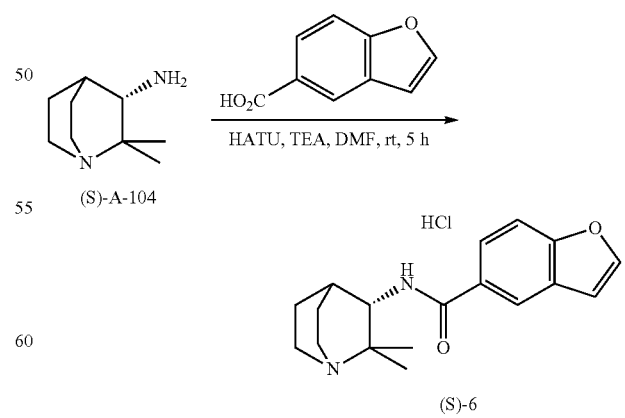

Following general procedure B, Compound (S)-6 was prepared from benzofuran-5-carboxylic acid (52 mg, 0.32 mmol) and compound (S)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 21-51% acetonitrile in H$_2$O (add 0.5% HCl, v/v)] to give:

(S)—N-(2,2-dimethylquinuclidin-3-yl)benzofuran-5-carboxamide hydrochloride (compound (S)-6) (35 mg, 36% yield) as a white solid: cSFC analytical (A) tR=2.97 min., purity: 98.28%; LCMS (B): tR=0.156 min., 299.2 m/z (M+1); $^1$H-NMR (CD$_3$OD, 400 MHz): δ 8.18 (d, J=1.6 Hz, 1H), 7.88 (d, J=2.4 Hz, 1H), 7.82 (dd, J$_1$=8.8 Hz, J$_2$=2.0 Hz, 1H), 7.61 (d, J=8.4 Hz, 1H), 6.97 (d, J=1.6 Hz, 1H), 4.28 (s, 1H), 3.76-3.67 (m, 2H), 3.38-3.33 (m, 2H), 2.41-2.39 (m, 1H), 2.28-2.26 (m, 1H), 2.19-2.10 (m, 2H), 1.96-1.89 (m, 1H), 1.77 (s, 3H), 1.50 (s, 3H).

Example 7

Preparation of (R)—N-(2,2-dimethylquinuclidin-3-yl)-7-(trifluoromethyl)benzo[b]thiophene-2-carboxamide ((R)-7)

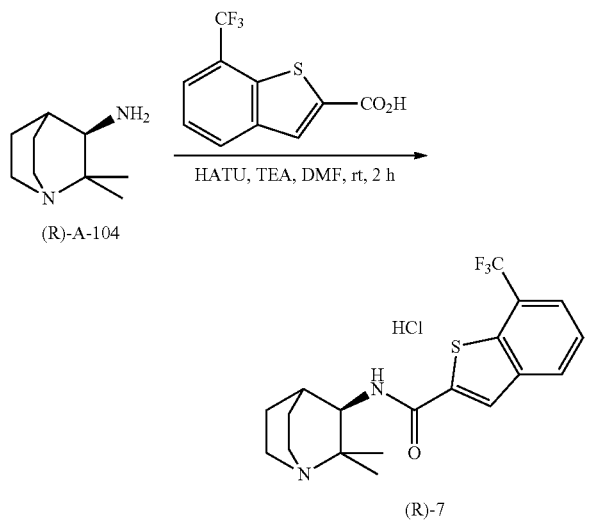

Following general procedure B, Compound (R)-7 was prepared from 7-(trifluoromethyl)benzo[b]thiophene-2-carboxylic acid (80 mg, 1.9 mmol) and compound (R)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(R)—N-(2,2-dimethylquinuclidin-3-yl)-7-(trifluoromethyl)benzo[b]thiophene-2-carboxamide hydrochloride (compound (R)-7) (39 mg, 31% yield) as a white solid: cSFC analytical (A) tR=2.49 min., purity: 98.99%; LCMS (T): tR=2.323 min., 383.1 m/z (M+1); $^1$H-NMR (CD$_3$OD, 400 MHz): 8.30 (s, 1H), 8.22 (d, J=8.4 Hz, 1H), 7.85 (d, J=7.6 Hz, 1H), 7.67-7.63 (t, J=7.2 Hz, 1H), 4.30 (s, 1H), 3.75-3.69 (m, 2H), 3.40-3.36 (m, 2H), 2.45 (m, 1H), 2.31 (m, 1H), 2.20-2.13 (m, 2H), 2.00-1.94 (m, 1H), 1.78 (s, 3H), 1.53 (s, 3H).

Preparation of (S)—N-(2,2-dimethylquinuclidin-3-yl)-7-(trifluoromethyl)benzo[b]thiophene-2-carboxamide ((S)-7)

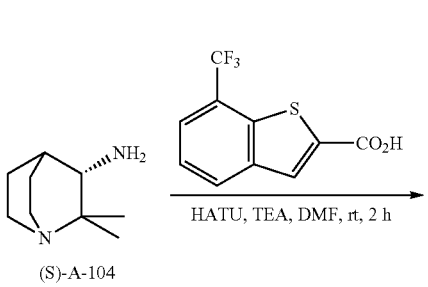

Following general procedure B, Compound (S)-7 was prepared from 7-(trifluoromethyl)benzo[b]thiophene-2-carboxylic acid (80 mg, 1.9 mmol) and compound (S)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(S)—N-(2,2-dimethylquinuclidin-3-yl)-7-(trifluoromethyl)benzo[b]thiophene-2-carboxamide hydrochloride (compound (S)-7) (46 mg, 37% yield) as a white solid: cSFC analytical (A) tR=3.31 min., purity: 98.39%; LCMS (G): tR=2.772 min., 383.1 m/z (M+1); $^1$H-NMR (CD$_3$OD, 400 MHz): δ 8.28 (s, 1H), 8.21 (d, J=8.4 Hz, 1H), 7.86 (d, J=7.6 Hz, 1H), 7.67-7.63 (t, J=8.0 Hz, 1H), 4.29 (s, 1H), 3.79-3.69 (m, 2H), 3.40-3.37 (m, 2H), 2.47-2.43 (m, 1H), 2.32-2.31 (m, 1H), 2.21-1.94 (m, 3H), 1.78 (s, 3H), 1.52 (s, 3H).

Example 8

Preparation of (R)—N-(2,2-dimethylquinuclidin-3-yl)-6-fluorobenzo[b]thiophene-2-carboxamide hydrochloride ((R)-8)

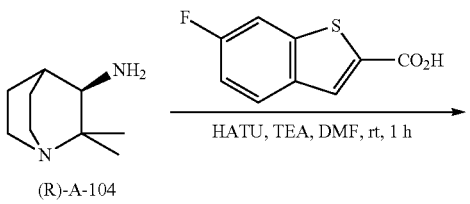

-continued

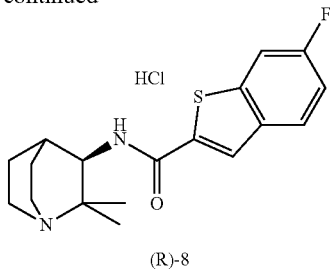

(R)-8

Following general procedure B, Compound (R)-8 was prepared from 6-fluorobenzo[b]thiophene-2-carboxylic acid (76 mg, 0.39 mmol) and compound (R)-A-104 (50 mg, 0.32 mmol), with a reaction time of 1 hour. The product was purified by prep-HPLC [Instrument: GX-E; Column: Agella Venusil ASB C18 150×21.2 mm, particle size: 5 μm; Mobile phase: 18-48% acetonitrile in H₂O (add 0.5% HCl, v/v)] to give:

(R)—N-(2,2-dimethylquinuclidin-3-yl)-6-fluorobenzo[b]thiophene-2-carboxamide hydrochloride (compound (R)-8) (30 mg, 25% yield) as a white solid: cSFC analytical (A) tR=2.66 min., purity: 98.54%; LCMS (B): tR=0.648 min., 333.2 m/z (M+1); ¹H-NMR (CD₃OD, 400 MHz): δ 8.15 (s, 1H), 7.95 (dd, J=8.8 Hz, 1H), 7.73 (dd, J=8.8 Hz, 1H), 7.26 (td, J=9.2 Hz, 1H), 4.27 (s, 1H), 3.78-3.68 (m, 2H), 3.39-3.30 (m, 2H), 2.46-2.43 (m, 1H), 2.30-2.29 (m, 1H), 2.20-2.12 (m, 2H), 1.99-1.93 (m, 1H), 1.76 (s, 3H), 1.50 (s, 3H).

Preparation of (S)—N-(2,2-dimethylquinuclidin-3-yl)-6-fluorobenzo[b]thiophene-2-carboxamide hydrochloride ((S)-8)

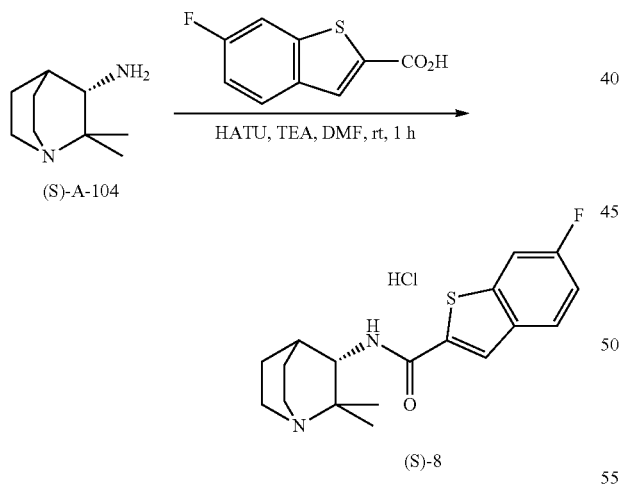

(S)-8

Following general procedure B, Compound (S)-8 was prepared from 6-fluorobenzo[b]thiophene-2-carboxylic acid (76 mg, 0.39 mmol) and compound (S)-A-104 (50 mg, 0.32 mmol), with a reaction time of 1 hour. The product was purified by prep-HPLC [Instrument: GX-E; Column: Agella Venusil ASB C18 150×21.2 mm, particle size: 5 μm; Mobile phase: 26-56% acetonitrile in H₂O (add 0.5% HCl, v/v)] to give:

(S)—N-(2,2-dimethylquinuclidin-3-yl)-6-fluorobenzo[b]thiophene-2-carboxamide hydrochloride (compound (S)-8) (60 mg, 50% yield) as a white solid: cSFC analytical (A) tR=3.38 min., purity: 98.22%; LCMS (A): tR=1.422 min., 333.1 m/z (M+1); ¹H-NMR (CD₃OD, 400 MHz): δ 8.14 (s, 1H), 7.95 (dd, J=8.8 Hz, 1H), 7.73 (dd, J=8.8 Hz, 1H), 7.27 (td, J=9.2 Hz, 1H), 4.27 (s, 1H), 3.77-3.68 (m, 2H), 3.39-3.33 (m, 2H), 2.43-2.42 (m, 1H), 2.30-2.29 (m, 1H), 2.20-2.12 (m, 2H), 1.99-1.93 (m, 1H), 1.76 (s, 3H), 1.50 (s, 3H).

Example 9

Preparation of (R)-6-cyano-N-(2,2-dimethylquinuclidin-3-yl)benzo[b]thiophene-2-carboxamide hydrochloride ((R)-9)

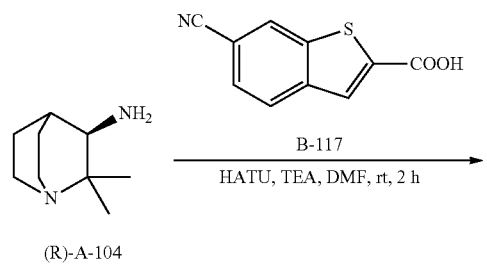

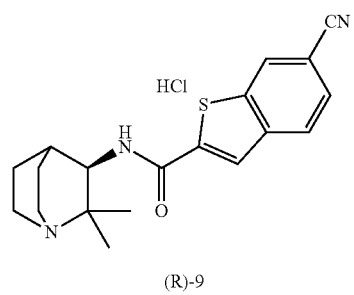

(R)-9

Following general procedure B, Compound (R)-9 was prepared from compound B-117 (66 mg, 0.32 mmol) and compound (R)-A-104 (50 mg, 0.32 mmol), with a reaction time of 2 hours. The product was purified by prep-HPLC [Instrument: GX-E; Column: Agella Venusil ASB C18 150× 30 mm, particle size: 5 μm; Mobile phase: 27-57% acetonitrile in H₂O (add 0.5% HCl, v/v)] to give:

(R)-6-cyano-N-(2,2-dimethylquinuclidin-3-yl)benzo[b]thiophene-2-carboxamide hydrochloride (compound (R)-9) (31 mg, 28% yield) as a yellow solid: cSFC analytical (A) tR=3.07 min., purity: 98.89%; LCMS (T): tR=1.977 min., 340.5 m/z (M+1); ¹H-NMR (CD₃OD, 400 MHz): δ 8.45 (s, 1H), 8.27 (s, 1H), 8.10 (d, J=8.4 Hz, 2H), 7.73 (d, J=8.0 Hz, 1H), 4.28 (s, 1H), 3.78-3.69 (m, 2H), 3.40-3.37 (m, 2H), 2.48-2.43 (m, 1H), 2.31-2.20 (m, 1H), 2.19-2.13 (m, 2H), 2.08-1.94 (m, 1H), 1.77 (s, 3H), 1.52 (s, 3H).

Preparation of (S)-6-cyano-N-(2,2-dimethylquinuclidin-3-yl)benzo[b]thiophene-2-carboxamide hydrochloride ((S)-9)

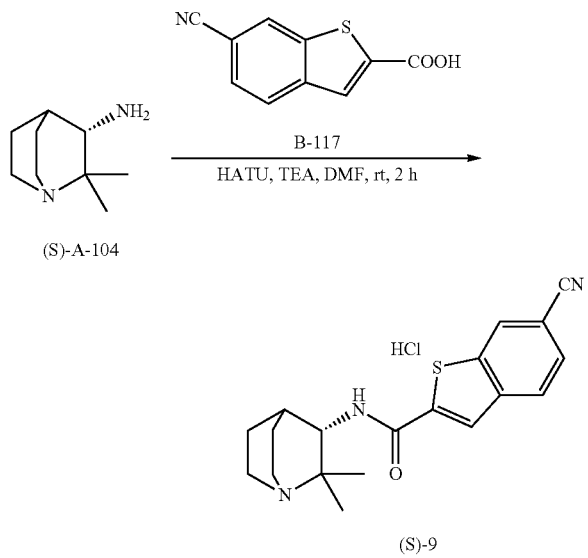

Following general procedure B, Compound (S)-9 was prepared from compound B-117 (66 mg, 0.32 mmol) and compound (S)-A-104 (50 mg, 0.32 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in $H_2O$ (add 0.5% HCl, v/v)] to give:

(S)-6-cyano-N-(2,2-dimethylquinuclidin-3-yl)benzo[b]thiophene-2-carboxamide hydrochloride (compound (S)-9) (20 mg, 18% yield) as a yellow solid: cSFC analytical (A) tR=4.30 min., purity: 97.74%; LCMS (R): tR=0.781 min., 340.5 m/z (M+1); $^1$H-NMR (DMSO-$d_6$, 400 MHz): δ 10.49 (s, 1H), 8.82 (d, J=7.6 Hz, 1H), 8.68 (s, 1H), 8.53 (s, 2H), 8.16 (d, J=8.0 Hz, 1H), 7.83 (d, J=8.0 Hz, 1H), 4.12 (d, J=7.2 Hz, 1H), 3.18 (m, 3H), 2.34 (m, 2H), 2.11-2.02 (m, 2H), 1.91 (m, 1H), 1.71 (m, 1H), 1.62 (s, 3H), 1.41 (s, 3H).

Example 10

Preparation of (R)—N-(2,2-dimethylquinuclidin-3-yl)-6-(trifluoromethyl)benzo[b]thiophene-2-carboxamide ((R)-10)

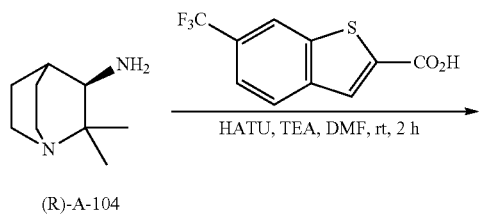

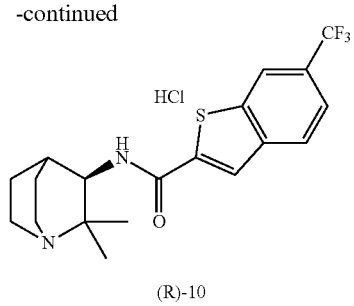

Following general procedure B, Compound (R)-10 was prepared from 6-(trifluoromethyl)benzo[b]thiophene-2-carboxylic acid (80 mg, 1.9 mmol) and compound (R)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in $H_2O$ (add 0.5% HCl, v/v)] to give:

(R)—N-(2,2-dimethylquinuclidin-3-yl)-6-(trifluoromethyl)benzo[b]thiophene-2-carboxamide hydrochloride (compound (R)-10) (32 mg, 26% yield) as a white solid: cSFC analytical (A) tR=2.44 min., purity: 98.49%; LCMS (T): tR=2.345 min., 383.1 m/z (M+1); $^1$H-NMR (CD$_3$OD, 400 MHz): 8.37 (s, 1H), 8.26 (s, 1H), 8.13 (d, J=8.8 Hz, 1H), 7.72 (d, J=8.4 Hz, 1H), 4.29 (s, 1H), 3.79-3.68 (m, 2H), 3.40-3.36 (m, 2H), 2.47-2.44 (m, 1H), 2.31-2.21 (m, 1H), 2.20-2.13 (m, 2H), 2.12-1.94 (m, 1H), 1.76 (s, 3H), 1.52 (s, 3H).

Preparation of (S)—N-(2,2-dimethylquinuclidin-3-yl)-6-(trifluoromethyl)benzo[b]thiophene-2-carboxamide ((S)-10)

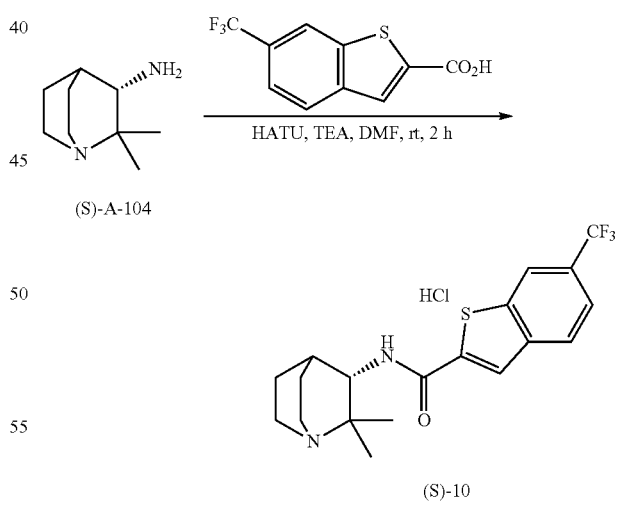

Following general procedure B, Compound (S)-10 was prepared from 6-(trifluoromethyl)benzo[b]thiophene-2-carboxylic acid (80 mg, 1.9 mmol) and compound (S)-A-104 (50 mg, 0.32 mmol), with a reaction time of 5 hours. The product was purified by prep-HPLC [Instrument: GX-E; Column: Agella Venusil ASB C18 150×21.2 mm, particle size: 5 μm; Mobile phase: 15-45% acetonitrile in $H_2O$ (add 0.5% HCl, v/v)] to give:

(S)—N-(2,2-dimethylquinuclidin-3-yl)-6-(trifluoromethyl)benzo[b]thiophene-2-carboxamide hydrochloride (compound (S)-10) (41 mg, 33% yield) as a white solid: cSFC analytical (A) tR=3.52 min., purity: 97.90%; LCMS (G): tR=2.850 min., 383.1 m/z (M+1); $^1$H-NMR (CD$_3$OD, 400 MHz): 8.37 (s, 1H), 8.27 (s, 1H), 8.13 (d, J=8.4 Hz, 1H), 7.72 (d, J=8.4 Hz, 1H), 4.29 (s, 1H), 3.78-3.69 (m, 2H), 3.40-3.36 (m, 2H), 2.48-2.44 (m, 1H), 2.31-2.21 (m, 1H), 2.20-2.13 (m, 2H), 2.12-1.94 (m, 1H), 1.77 (s, 3H), 1.52 (s, 3H).

Example 11

Preparation of (R)—N-(2,2-dimethylquinuclidin-3-yl)-5-fluorobenzo[b]thiophene-2-carboxamide hydrochloride ((R)-11)

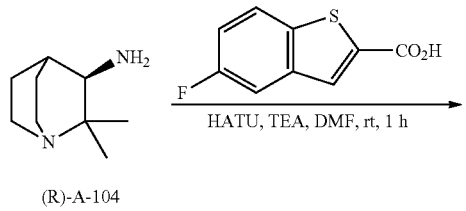

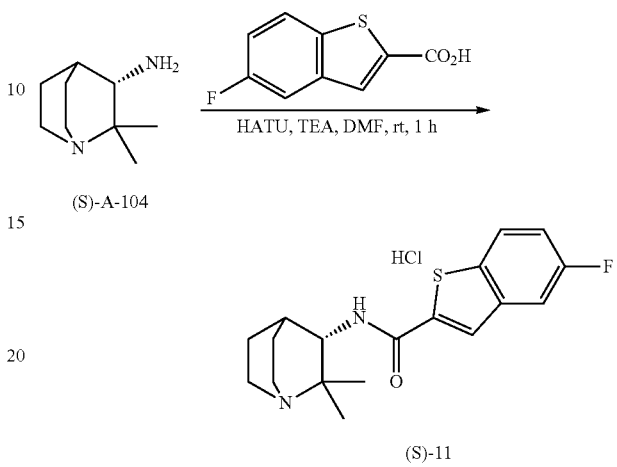

Following general procedure B, Compound (R)-11 was prepared from 5-fluorobenzo[b]thiophene-2-carboxylic acid (76 mg, 0.39 mmol) and compound (R)-A-104 (50 mg, 0.32 mmol), with a reaction time of 1 hour. The product was purified by prep-HPLC [Instrument: GX-E; Column: Agella Venusil ASB C18 150×21.2 mm, particle size: 5 μm; Mobile phase: 18-48% acetonitrile in H$_2$O (add 0.5% HCl, v/v)] to give:

(R)—N-(2,2-dimethylquinuclidin-3-yl)-5-fluorobenzo[b]thiophene-2-carboxamide hydrochloride (compound (R)-11) (60 mg, 50% yield) as a white solid: cSFC analytical (A) tR=2.62 min., purity: 98.90%; LCMS (B): tR=0.644 min., 333.2 m/z (M+1); $^1$H-NMR (CD$_3$OD, 400 MHz): δ 8.47 (d, 1H), 8.12 (s, 1H), 7.96 (dd, J=8.8 Hz, 1H), 7.65 (dd, J=9.2 Hz, 1H), 7.30 (td, J=9.2 Hz, 1H), 4.27 (s, 1H), 3.75-3.68 (m, 2H), 3.38-3.30 (m, 2H), 2.44-2.42 (m, 1H), 2.30-2.29 (m, 1H), 2.20-2.12 (m, 2H), 1.99-1.93 (m, 1H), 1.77 (s, 3H), 1.51 (s, 3H).

Preparation of (S)—N-(2,2-dimethylquinuclidin-3-yl)-5-fluorobenzo[b]thiophene-2-carboxamide hydrochloride ((S)-11)

Following general procedure B, Compound (S)-11 was prepared from 5-fluorobenzo[b]thiophene-2-carboxylic acid (76 mg, 0.39 mmol) and compound (S)-A-104 (50 mg, 0.32 mmol), with a reaction time of 1 hours. The product was purified by prep-HPLC [Instrument: GX-E; Column: Agella Venusil ASB C18 150×21.2 mm, particle size: 5 μm; Mobile phase: 26-56% acetonitrile in H$_2$O (add 0.5% HCl, v/v)] to give:

(S)—N-(2,2-dimethylquinuclidin-3-yl)-5-fluorobenzo[b]thiophene-2-carboxamide hydrochloride (compound (S)-11) (70 mg, 58% yield) as a white solid: cSFC analytical (A) tR=3.08 min., purity: 97.88%; LCMS (B): tR=0.695 min., 333.2 m/z (M+1); $^1$H-NMR (CD$_3$OD, 400 MHz): δ 8.48 (d, 1H), 8.12 (s, 1H), 7.96 (dd, J=8.8 Hz, 1H), 7.65 (dd, J=9.2 Hz, 1H), 7.30 (td, J=8.8 Hz, 1H), 4.27 (s, 1H), 3.78-3.68 (m, 2H), 3.40-3.32 (m, 2H), 2.44-2.42 (m, 1H), 2.30-2.29 (m, 1H), 2.20-2.12 (m, 2H), 1.99-1.93 (m, 1H), 1.77 (s, 3H), 1.51 (s, 3H).

Example 12

Preparation of (R)-6-chloro-N-(2,2-dimethylquinuclidin-3-yl)benzo[b]thiophene-2-carboxamide hydrochloride ((R)-12)

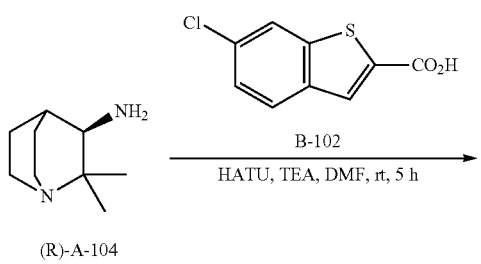

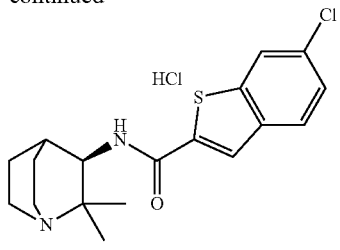

(R)-12

Following general procedure B, Compound (R)-12 was prepared from compound B-102 (66 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150× 21.2 mm, particle size: 5 μm; Mobile phase: 25-55% acetonitrile in $H_2O$ (add 0.5% HCl, v/v)] to give:

(R)-6-chloro-N-(2,2-dimethylquinuclidin-3-yl)benzo[b]thiophene-2-carboxamide hydrochloride (compound (R)-12) (45 mg, 45% yield) as a white solid: cSFC analytical (A) tR=3.01 min., purity: 99.84%; LCMS (B): tR=0.705 min., 349.1 m/z (M+1); $^1$H-NMR (CD$_3$OD, 400 MHz): δ 8.13 (s, 1H), δ 8.01 (d, J=4 Hz, 1H), 7.90 (d, J=8 Hz, 1H), 7.45 (dd, J$_1$=8 Hz, J$_2$=4 Hz, 1H), 4.25 (s, 1H), 3.72-3.69 (m, 2H), 3.37-3.35 (m, 2H), 2.41-2.40 (m, 1H), 2.28-2.26 (m, 1H), 2.17-2.10 (m, 2H), 1.97-1.94 (m, 1H), 1.74 (s, 3H), 1.48 (s, 3H).

Preparation of (S)-6-chloro-N-(2,2-dimethylquinuclidin-3-yl)benzo[b]thiophene-2-carboxamide hydrochloride ((S)-12)

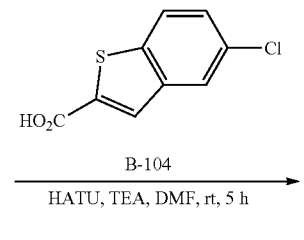

Following general procedure B, Compound (S)-12 was prepared from compound B-102 (66 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150× 30 mm, particle size: 5 μm; Mobile phase: 29-59% acetonitrile in $H_2O$ (add 0.5% HCl, v/v)] to give:

(S)-6-chloro-N-(2,2-dimethylquinuclidin-3-yl)benzo[b]thiophene-2-carboxamide hydrochloride (compound (S)-12) (46 mg, 46% yield) as a white solid: cSFC analytical (A) tR=3.78 min., purity: 98.88%; LCMS (R): tR=0.890 min., 348.1 m/z (M+1); $^1$H-NMR (CD$_3$OD, 400 MHz): δ 8.15 (s, 1H), 8.00 (s, 1H), 7.90 (d, J=8 Hz, 1H), 7.44 (dd, J=4 Hz, J=8 Hz, 1H), 4.25 (s, 1H), 3.75-3.66 (m, 2H), 3.34-3.31 (m, 2H), 2.42-2.41 (m, 1H), 2.28-2.27 (m, 1H), 2.17-2.10 (m, 2H), 1.97-1.94 (m, 1H), 1.74 (s, 3H), 1.49 (s, 3H).

Example 13

Preparation of (R)-5-chloro-N-(2,2-dimethylquinuclidin-3-yl)benzo[b]thiophene-2-carboxamide hydrochloride ((R)-13)

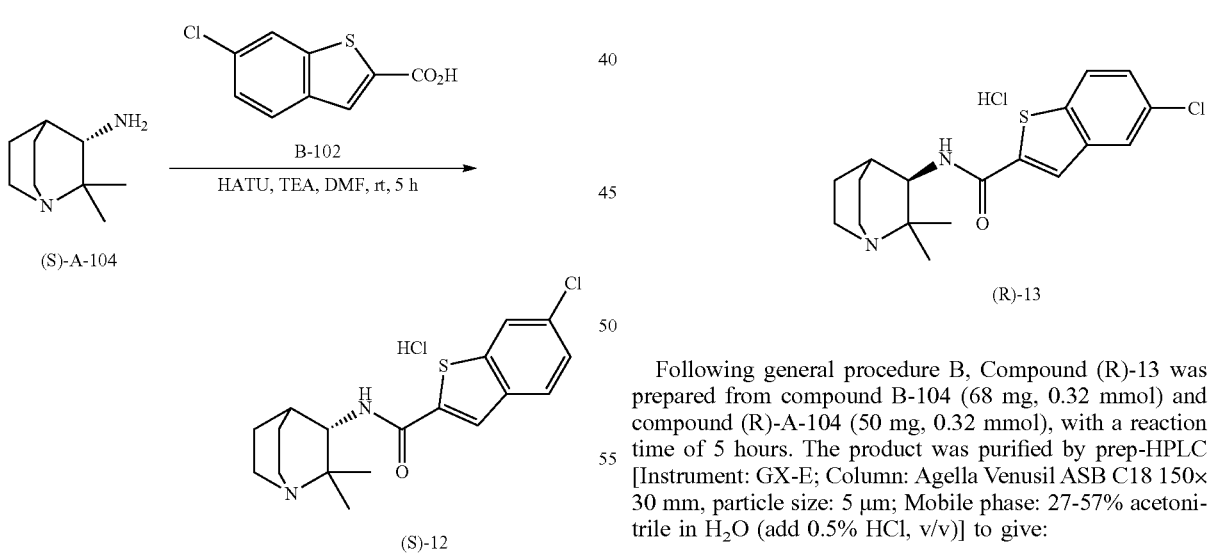

Following general procedure B, Compound (R)-13 was prepared from compound B-104 (68 mg, 0.32 mmol) and compound (R)-A-104 (50 mg, 0.32 mmol), with a reaction time of 5 hours. The product was purified by prep-HPLC [Instrument: GX-E; Column: Agella Venusil ASB C18 150× 30 mm, particle size: 5 μm; Mobile phase: 27-57% acetonitrile in $H_2O$ (add 0.5% HCl, v/v)] to give:

(R)-5-chloro-N-(2,2-dimethylquinuclidin-3-yl)benzo[b]thiophene-2-carboxamide hydrochloride (compound (R)-13) (59 mg, 47% yield) as a white solid: cSFC analytical (A) tR=2.98 min., purity: 97.23%; LCMS (A): tR=1.629 min., 349.1 m/z (M+1); $^1$H-NMR (CD$_3$OD, 400 MHz): δ 8.09 (s, 1H), 7.95-7.91 (m, 2H), 7.45 (dd, J$_1$=8.8 Hz, J$_2$=1.2 Hz, 1H), 4.25 (s, 1H), 3.75-3.66 (m, 2H), 3.37-3.32 (m, 2H), 2.44-2.41 (m, 1H), 2.28-2.26 (m, 1H), 2.17-2.10 (m, 2H), 1.97-1.91 (m, 1H), 1.74 (s, 3H), 1.49 (s, 3H).

233

Preparation of (S)-5-chloro-N-(2,2-dimethylquinuclidin-3-yl)benzo[b]thiophene-2-carboxamide hydrochloride ((S)-13)

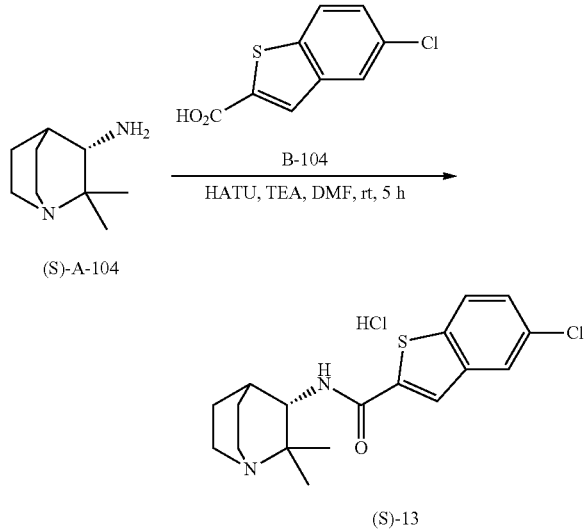

(S)-A-104

(S)-13

Following general procedure B, Compound (S)-13 was prepared compound B-104 (68 mg, 0.32 mmol) and compound (S)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(S)-5-chloro-N-(2,2-dimethylquinuclidin-3-yl)benzo[b]thiophene-2-carboxamide hydrochloride (compound (S)-13) (33 mg, 29% yield) as a white solid: cSFC analytical (A) tR=3.59 min., purity: 98.95%; LCMS (B): tR=0.720 min., 349.1 m/z (M+1); $^1$H-NMR (CD$_3$OD, 400 MHz): δ 8.12 (s, 1H), 7.95-7.91 (m, 2H), 7.45 (dd, J$_1$=8.8 Hz, J$_2$=2.0 Hz, 1H), 4.25 (s, 1H), 3.75-3.67 (m, 2H), 3.37-3.34 (m, 2H), 2.46-2.42 (m, 1H), 2.28-2.27 (m, 1H), 2.18-2.08 (m, 2H), 1.97-1.91 (m, 1H), 1.75 (s, 3H), 1.50 (s, 3H).

Example 14

Preparation of (R)-5,6-dichloro-N-(2,2-dimethylquinuclidin-3-yl)benzo[b]thiophene-2-carboxamide hydrochloride ((R)-14)

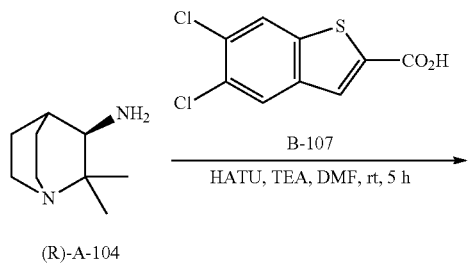

(R)-A-104

234

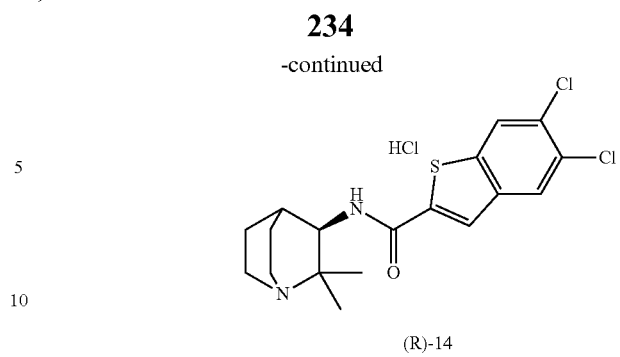

(R)-14

Following general procedure B, Compound (R)-14 was prepared from compound B-107 (77 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150× 21.2 mm, particle size: 5 μm; Mobile phase: 25-55% acetonitrile in H$_2$O (add 0.5% HCl, v/v)] to give:

(R)-5,6-dichloro-N-(2,2-dimethylquinuclidin-3-yl)benzo[b]thiophene-2-carboxamide hydrochloride (compound (R)-14) (47 mg, 43% yield) as a white solid: cSFC analytical (A) tR=3.30 min., purity: 99.85%; LCMS (B): tR=0.749 min., 382.1 m/z (M+1); $^1$H-NMR (CD$_3$OD, 400 MHz): δ 8.19 (s, 1H), δ 8.11 (s, 1H), 8.10 (s, 1H), 4.25 (s, 1H), 3.73-3.66 (m, 2H), 3.38-3.33 (m, 2H), 2.41-2.40 (m, 1H), 2.28-2.26 (m, 1H), 2.17-2.10 (m, 2H), 1.97-1.95 (m, 1H), 1.74 (s, 3H), 1.48 (s, 3H).

Preparation of (S)-5,6-dichloro-N-(2,2-dimethylquinuclidin-3-yl)benzo[b]thiophene-2-carboxamide hydrochloride ((S)-14)

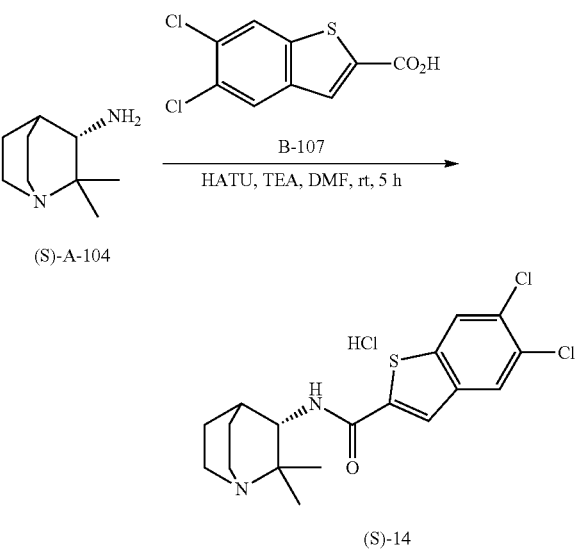

(S)-A-104

(S)-14

Following general procedure B, Compound (S)-14 was prepared from compound B-107 (77 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150× 30 mm, particle size: 5 μm; Mobile phase: 24-54% acetonitrile in H$_2$O (add 0.5% HCl, v/v)] to give:

(S)-5,6-dichloro-N-(2,2-dimethylquinuclidin-3-yl)benzo[b]thiophene-2-carboxamide hydrochloride (compound (S)-

14) (40 mg, 38% yield) as a white solid: cSFC analytical (A) tR=3.86 min., purity: 98.88%; LCMS (R): tR=0.956 min., 382.1 m/z (M+1); $^1$H-NMR (CD$_3$OD, 400 MHz): δ 8.20 (s, 1H), 8.13 (s, 1H), 8.12 (s, 1H), 4.25 (s, 1H), 3.73-3.70 (m, 2H), 3.37-3.34 (m, 2H), 2.45-2.44 (m, 1H), 2.30-2.29 (m, 1H), 2.19-2.12 (m, 2H), 1.99-1.97 (m, 1H), 1.76 (s, 3H), 1.51 (s, 3H).

Example 15

Preparation of (R)—N-(2,2-dimethylquinuclidin-3-yl)-6-methylbenzo[b]thiophene-2-carboxamide hydrochloride ((R)-15)

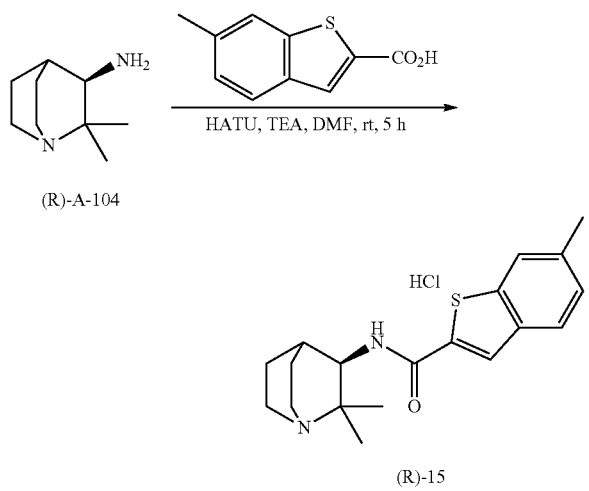

Following general procedure B, Compound (R)-15 was prepared from 6-methylbenzo[b]thiophene-2-carboxylic acid (60 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150×21.2 mm, particle size: 5 μm; Mobile phase: 26-56% acetonitrile in H$_2$O (add 0.5% HCl, v/v)] to give:

(R)—N-(2,2-dimethylquinuclidin-3-yl)-6-methylbenzo[b]thiophene-2-carboxamide hydrochloride (compound (R)-15) (43 mg, 45% yield) as a white solid: cSFC analytical (A) tR=2.98 min., purity: 99.54%; LCMS (B): tR=0.688 min., 328.2 m/z (M+1); $^1$H-NMR (CD$_3$OD, 400 MHz): δ 8.08 (s, 1H), δ 7.80 (d, J=8 Hz, 1H), 7.73 (s, 1H), 7.28 (d, J=8 Hz, 1H), 4.25 (s, 1H), 3.76-3.66 (m, 2H), 3.37-3.34 (m, 2H), 2.49 (s, 3H), 2.41-2.40 (m, 1H), 2.27-2.26 (m, 1H), 2.17-2.10 (m, 2H), 1.97-1.94 (m, 1H), 1.74 (s, 3H), 1.48 (s, 3H).

Preparation of (S)—N-(2,2-dimethylquinuclidin-3-yl)-6-methylbenzo[b]thiophene-2-carboxamide hydrochloride ((S)-15)

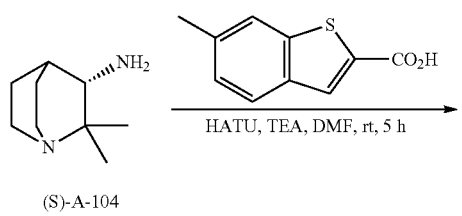

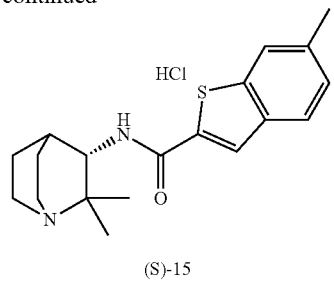

Following general procedure B, Compound (S)-15 was prepared from 6-chlorobenzo[b]thiophene-2-carboxylic acid (60 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150×30 mm, particle size: 5 μm; Mobile phase: 24-54% acetonitrile in H$_2$O (add 0.5% HCl, v/v)] to give:

(S)—N-(2,2-dimethylquinuclidin-3-yl)-6-methylbenzo[b]thiophene-2-carboxamide hydrochloride (compound (S)-15) (40 mg, 42% yield) as a white solid: cSFC analytical (A) tR=3.45 min., purity: 99.45%; LCMS (R): tR=0.861 min., 328.2 m/z (M+1); $^1$H-NMR (CD$_3$OD, 400 MHz): δ 8.09 (s, 1H), 7.80 (d, J=8 Hz, 1H), 7.73 (s, 1H), 7.28 (d, J=8 Hz, 1H), 4.25 (s, 1H), 3.73-3.69 (m, 2H), 3.37-3.34 (m, 2H), 2.49 (s, 3H), 2.41-2.40 (m, 1H), 2.27-2.26 (m, 1H), 2.17-2.10 (m, 2H), 1.97-1.90 (m, 1H), 1.74 (s, 3H), 1.49 (s, 3H).

Example 16

Preparation of (R)—N-(2,2-dimethylquinuclidin-3-yl)-5-methylbenzo[b]thiophene-2-carboxamide hydrochloride ((R)-16)

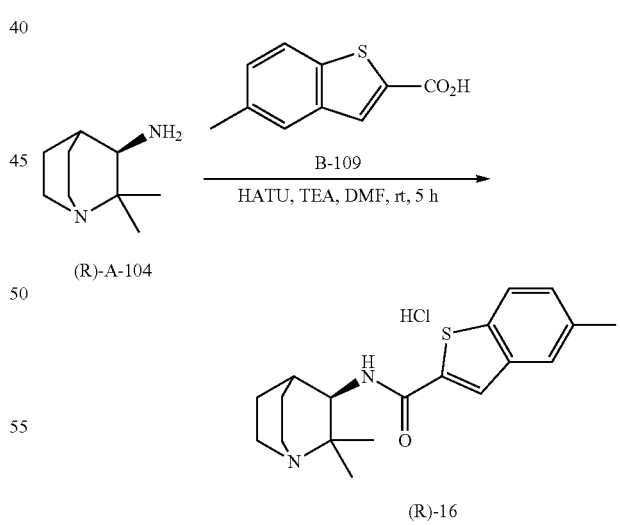

Following general procedure B, Compound (R)-16 was prepared from compound B-109 (60 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150× 21.2 mm, particle size: 5 μm; Mobile phase: 18-48% acetonitrile in H$_2$O (add 0.5% HCl, v/v)] to give:

(R)—N-(2,2-dimethylquinuclidin-3-yl)-5-methylbenzo[b]thiophene-2-carboxamide hydrochloride (compound (R)-16) (35 mg, 37% yield) as a white solid: cSFC analytical (A) tR=2.99 min., purity: 99.11%; LCMS (B): tR=0.687 min., 328.2 m/z (M+1); $^1$H-NMR (CD$_3$OD, 400 MHz): δ 8.07 (s, 1H), 7.80 (d, J=8 Hz, 1H), 7.72 (s, 1H), 7.32 (d, J=8 Hz, 1H), 4.25 (s, 1H), 3.72-3.66 (m, 2H), 3.38-3.34 (m, 2H), 2.48 (s, 3H), 2.28-2.27 (m, 1H), 2.17-2.10 (m, 2H), 1.97-1.94 (m, 1H), 1.75 (s, 3H), 1.49 (s, 3H).

Preparation of (S)—N-(2,2-dimethylquinuclidin-3-yl)-5-methylbenzo[b]thiophene-2-carboxamide hydrochloride ((S)-16)

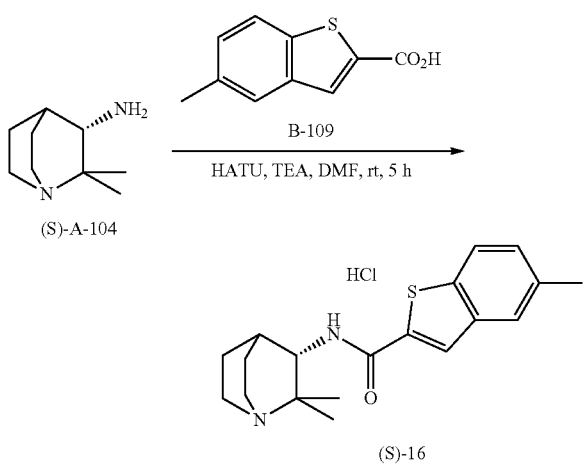

Following general procedure B, Compound (S)-16 was prepared from compound B-109 (60 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(S)—N-(2,2-dimethylquinuclidin-3-yl)-5-methylbenzo[b]thiophene-2-carboxamide hydrochloride (compound (S)-16) (31 mg, 33% yield) as a white solid: cSFC analytical (A) tR=3.68 min., purity: 99.80%; LCMS (R): tR=0.866 min., 328.2 m/z (M+1); $^1$H-NMR (CD$_3$OD, 400 MHz): δ 8.06 (s, 1H), 7.80 (d, J=8 Hz, 1H), 7.72 (s, 1H), 7.32 (d, J=8 Hz, 1H), 4.25 (s, 1H), 3.73-3.69 (m, 2H), 3.38-3.34 (m, 2H), 2.48 (s, 3H), 2.28-2.27 (m, 1H), 2.17-2.10 (m, 2H), 1.97-1.94 (m, 1H), 1.75 (s, 3H), 1.49 (s, 3H).

Example 17

Preparation of (R)—N-(2,2-dimethylquinuclidin-3-yl)-5-(trifluoromethyl)benzo[b]thiophene-2-carboxamide ((R)-17)

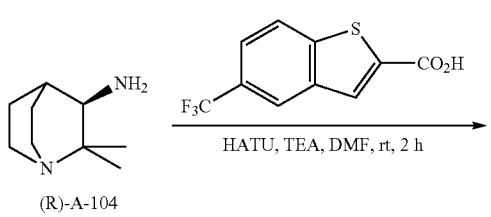

-continued

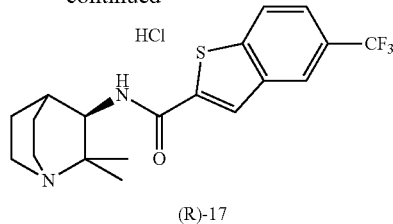

Following general procedure B, Compound (R)-17 was prepared from 5-(trifluoromethyl)benzo[b]thiophene-2-carboxylic acid (80 mg, 1.9 mmol) and compound (R)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(R)—N-(2,2-dimethylquinuclidin-3-yl)-5-(trifluoromethyl)benzo[b]thiophene-2-carboxamide hydrochloride (compound (R)-17) (58 mg, 46% yield) as a yellow solid: cSFC analytical (A) tR=2.17 min., purity: 98.14%; LCMS (T): tR=0.741 min., 383.1 m/z (M+1); $^1$H-NMR (CD$_3$OD, 400 MHz): 8.28 (s, 2H), 8.18 (d, J=8.8 Hz, 1H), 7.74 (d, J=8.0 Hz, 1H), 4.29 (s, 1H), 3.78-3.69 (m, 2H), 3.40-3.36 (m, 2H), 3.45-3.44 (m, 1H), 2.31 (m, 1H), 2.21-2.11 (m, 2H), 2.01-1.94 (m, 1H), 1.77 (s, 3H), 1.52 (s, 3H).

Preparation of (S)—N-(2,2-dimethylquinuclidin-3-yl)-5-(trifluoromethyl)benzo[b]thiophene-2-carboxamide ((S)-17)

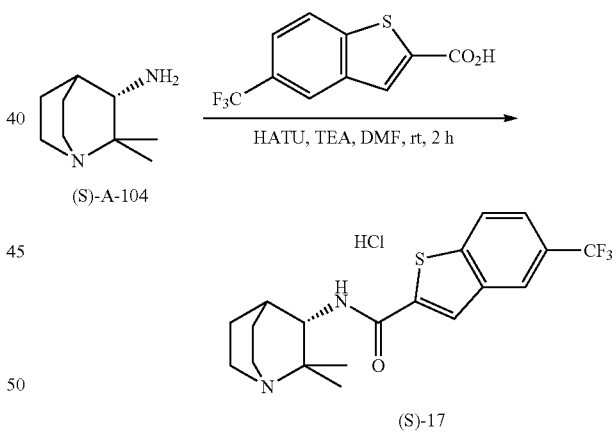

Following general procedure B, Compound (S)-17 was prepared from 5-(trifluoromethyl)benzo[b]thiophene-2-carboxylic acid (80 mg, 1.9 mmol) and compound (S)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(S)—N-(2,2-dimethylquinuclidin-3-yl)-5-(trifluoromethyl)benzo[b]thiophene-2-carboxamide hydrochloride (compound (S)-17) (32 mg, 26% yield) as a yellow solid: cSFC analytical (A) tR=2.49 min., purity: 97.08%; LCMS (B): tR=0.724 min., 383.1 m/z (M+1); $^1$H-NMR (CD$_3$OD, 400 MHz): 8.28 (s, 2H), 8.18 (d, J=8.4 Hz, 1H), 7.74 (d, J=8.8 Hz, 1H), 4.29 (s, 1H), 3.79-3.69 (m, 2H), 3.40-3.36 (m, 2H), 3.48-3.45 (m, 1H), 2.43 (m, 1H), 2.31-2.13 (m, 2H), 2.00-1.94 (m, 1H), 1.78 (s, 3H), 1.52 (s, 3H).

Example 18

Preparation of (R)-6-cyclopropyl-N-(2,2-dimethylquinuclidin-3-yl)benzo[b]thiophene-2-carboxamide hydrochloride ((R)-18)

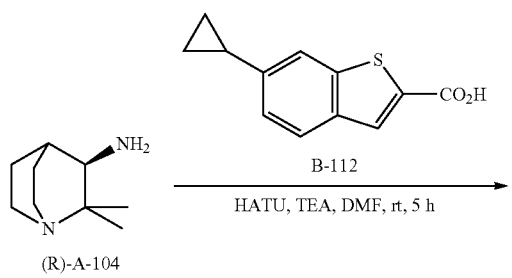

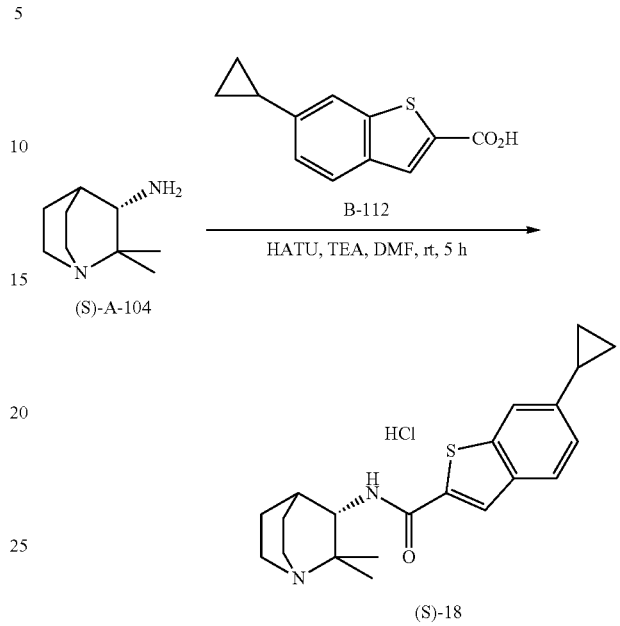

Following general procedure B, Compound (R)-18 was prepared from compound B-112 (68 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150× 21.2 mm, particle size: 5 μm; Mobile phase: 26-56% acetonitrile in H$_2$O (add 0.5% HCl, v/v)] to give:

(R)-6-cyclopropyl-N-(2,2-dimethylquinuclidin-3-yl)benzo[b]thiophene-2-carboxamide hydrochloride (compound (R)-18) (36 mg, 36% yield) as a white solid: cSFC analytical (A) tR=3.19 min., purity: 99.84%; LCMS (B): tR=0.726 min., 354.2 m/z (M+1); $^1$H-NMR (CD$_3$OD, 400 MHz): δ 8.07 (s, 1H), δ 7.78 (d, J=8 Hz, 1H), 7.63 (s, 1H), 7.17 (d, J=8 Hz, 1H), 4.24 (s, 1H), 3.73-3.66 (m, 2H), 3.37-3.34 (m, 2H), 2.41 (m, 1H), 2.27-2.26 (m, 1H), 2.16-2.06 (m, 3H), 2.05-1.94 (m, 1H), 1.74 (s, 3H), 1.48 (s, 3H), 1.07-1.03 (m, 2H), 0.81-0.78 (m, 2H).

Preparation of (S)-6-cyclopropyl-N-(2,2-dimethylquinuclidin-3-yl)benzo[b]thiophene-2-carboxamide hydrochloride ((S)-18)

Following general procedure B, Compound (S)-18 was prepared from compound B-112 (68 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150× 30 mm, particle size: 5 μm; Mobile phase: 25-55% acetonitrile in H$_2$O (add 0.5% HCl, v/v)] to give:

(S)-6-cyclopropyl-N-(2,2-dimethylquinuclidin-3-yl)benzo[b]thiophene-2-carboxamide hydrochloride (compound (S)-18) (34 mg, 34% yield) as a white solid: cSFC analytical (A) tR=3.74 min., purity: 99.91%; LCMS (R): tR=0.920 min., 354.2 m/z (M+1); $^1$H-NMR (CD$_3$OD, 400 MHz): δ 8.07 (s, 1H), δ 7.78 (d, J=8 Hz, 1H), 7.63 (s, 1H), 7.17 (dd, J$_1$=4 Hz, J$_2$=8 Hz, 1H), 4.24 (s, 1H), 3.75-3.66 (m, 2H), 3.37-3.34 (m, 2H), 2.41 (m, 1H), 2.27-2.26 (m, 1H), 2.14-2.05 (m, 3H), 2.04-1.94 (m, 1H), 1.74 (s, 3H), 1.48 (s, 3H), 1.07-1.03 (m, 2H), 0.81-0.78 (m, 2H).

Example 19

Preparation of (R)-5-cyclopropyl-N-(2,2-dimethylquinuclidin-3-yl)benzo[b]thiophene-2-carboxamide hydrochloride ((R)-19)

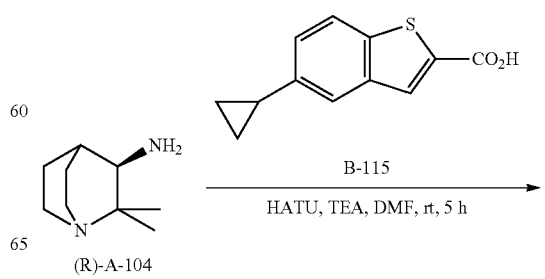

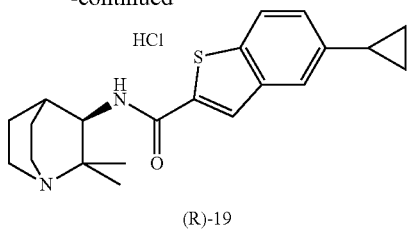

(R)-19

Following general procedure B, Compound (R)-19 was prepared from compound B-115 (68 mg, 0.31 mmol) and compound (R)-A-104 (40 mg, 0.26 mmol), with a reaction time of 5 hours. The product was purified by prep-HPLC [Instrument: GX-E; Column: Agella Venusil ASB C18 150× 21.2 mm, particle size: 5 μm; Mobile phase: 27-57% acetonitrile in H$_2$O (add 0.5% HCl, v/v)] to give:

(R)-5-cyclopropyl-N-(2,2-dimethylquinuclidin-3-yl)benzo[b]thiophene-2-carboxamide hydrochloride (compound (R)-19) (46 mg, 45% yield) as a white solid: cSFC analytical (A) tR=3.25 min., purity: 100%; LCMS (B): tR=0.728 min., 354.2 m/z (M+1); $^1$H-NMR (CD$_3$OD, 400 MHz): δ 8.05 (s, 1H), δ 7.89 (d, J=8 Hz, 1H), 7.63 (s, 1H), 7.21 (d, J$_1$=8 Hz, J$_2$=1.6 Hz, 1H), 4.25 (s, 1H), 3.70-3.69 (m, 2H), 3.35 (m, 2H), 2.41 (m, 1H), 2.28-2.27 (m, 1H), 2.14-2.06 (m, 3H), 2.05-1.94 (m, 1H), 1.74 (s, 3H), 1.49 (s, 3H), 1.04-1.01 (m, 2H), 0.77-0.74 (m, 2H).

Preparation of (S)-5-cyclopropyl-N-(2,2-dimethylquinuclidin-3-yl)benzo[b]thiophene-2-carboxamide hydrochloride ((S)-19)

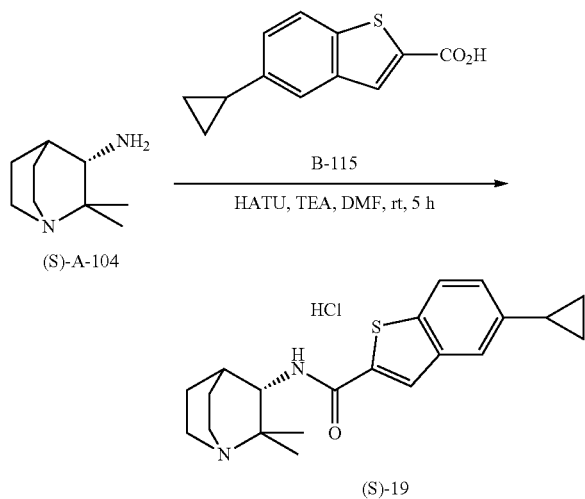

Following general procedure B, Compound (S)-19 was prepared from compound B-115 (68 mg, 0.31 mmol) and compound (S)-A-104 (40 mg, 0.26 mmol), with a reaction time of 5 hours. The product was purified by prep-HPLC [Instrument: GX-E; Column: Agella Venusil ASB C18 150× 30 mm, particle size: 5 μm; Mobile phase: 18-48% acetonitrile in H$_2$O (add 0.5% HCl, v/v)] to give:

(S)-5-cyclopropyl-N-(2,2-dimethylquinuclidin-3-yl)benzo[b]thiophene-2-carboxamide hydrochloride (compound (S)-19) (44 mg, 43% yield) as a white solid: cSFC analytical (A) tR=3.80 min., purity: 99.95%; LCMS (R): tR=0.922 min., 354.2 m/z (M+1); $^1$H-NMR (CD$_3$OD, 400 MHz): δ 8.04 (s, 1H), δ 7.89 (d, J=8 Hz, 1H), 7.63 (s, 1H), 7.21 (d, J$_1$=8 Hz, J$_2$=1.6 Hz, 1H), 4.25 (s, 1H), 3.73-3.66 (m, 2H), 3.73-3.34 (m, 2H), 2.41-2.39 (m, 1H), 2.28-2.27 (m, 1H), 2.14-2.06 (m, 3H), 2.05-1.94 (m, 1H), 1.74 (s, 3H), 1.49 (s, 3H), 1.04-1.00 (m, 2H), 0.77-0.74 (m, 2H).

Example 20

Preparation of (R)—N-(2,2-dimethylquinuclidin-3-yl)-6-methoxybenzo[b]thiophene-2-carboxamide ((R)-20)

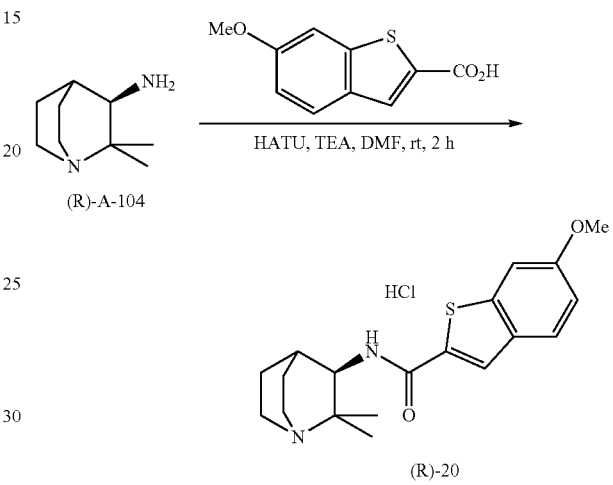

Following general procedure B, Compound (R)-20 was prepared from 6-methoxybenzo[b]thiophene-2-carboxylic acid (67 mg, 0.32 mmol) and compound (R)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H$_2$O (add 0.5% HCl, v/v)] to give:

(R)—N-(2,2-dimethylquinuclidin-3-yl)-6-methoxybenzo[b]thiophene-2-carboxamide hydrochloride (compound (R)-20) (45 mg, 41% yield) as a white solid: cSFC analytical (A) tR=2.95 min., purity: 98.73%; LCMS (T): tR=2.050 min., 345.1 m/z (M+1); $^1$H-NMR (CD$_3$OD, 400 MHz): 8.32 (d, J=7.6 Hz, 1H), 8.09 (s, 1H), 7.80 (d, J=8.8 Hz, 1H), 7.47 (s, 1H), 7.09-7.06 (dd, J$_1$=2.4 Hz, J$_2$=8.8 Hz, 1H), 4.26 (s, 1H), 3.93 (s, 3H), 3.77-3.68 (m, 2H), 3.39-3.29 (m, 2H), 2.46-2.43 (m, 1H), 2.28 (m, 1H), 2.18-2.12 (m, 2H), 1.99-1.92 (m, 1H), 1.76 (s, 3H), 1.50 (s, 3H).

Preparation of (S)—N-(2,2-dimethylquinuclidin-3-yl)-6-methoxybenzo[b]thiophene-2-carboxamide ((S)-20)

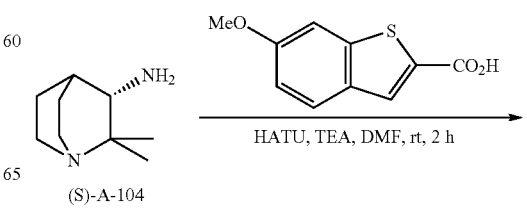

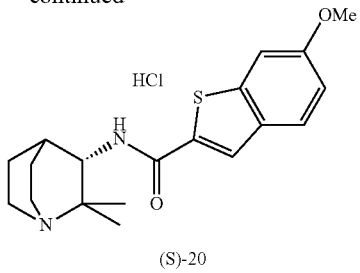

(S)-20

Following general procedure B, Compound (S)-20 was prepared from 6-methoxybenzo[b]thiophene-2-carboxylic acid (67 mg, 0.32 mmol) and compound (S)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H₂O (add 0.5% HCl, v/v)] to give:

(S)—N-(2,2-dimethylquinuclidin-3-yl)-6-methoxybenzo[b]thiophene-2-carboxamide hydrochloride (compound (S)-20) (25 mg, 23% yield) as a white solid: cSFC analytical (A) tR=3.34 min., purity: 97.60%; LCMS (B): tR=0.634 min., 345.1 m/z (M+1); ¹H-NMR (CD₃OD, 400 MHz): 8.31 (d, J=7.2 Hz, 1H), 8.08 (s, 1H), 7.80 (d, J=9.2 Hz, 1H), 7.47 (s, 1H), 7.08 (dd, J₁=8.8 Hz, J₂=2.4 Hz, 1H), 4.25 (s, 1H), 3.90 (s, 3H), 3.78-3.68 (m, 2H), 3.39-3.34 (m, 2H), 2.46-2.41 (m, 1H), 2.28 (m, 1H), 2.19-2.12 (m, 2H), 1.99-1.92 (m, 1H), 1.76 (s, 3H), 1.50 (s, 3H).

Example 21

Preparation of (R)—N-(2,2-dimethylquinuclidin-3-yl)-5-methoxybenzo[b]thiophene-2-carboxamide ((R)-21)

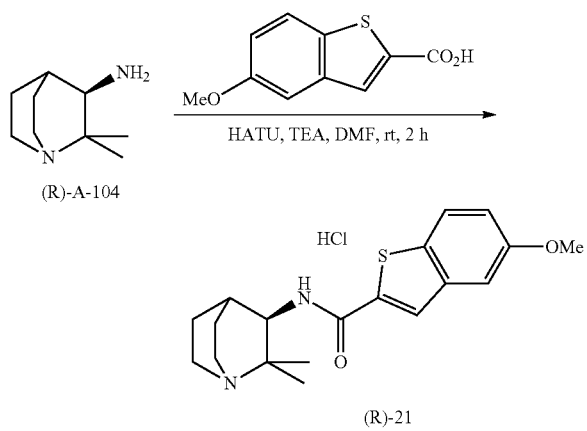

Following general procedure B, Compound (R)-21 was prepared from 5-methoxybenzo[b]thiophene-2-carboxylic acid (67 mg, 0.32 mmol) and compound (R)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H₂O (add 0.5% HCl, v/v)] to give:

(R)—N-(2,2-dimethylquinuclidin-3-yl)-5-methoxybenzo[b]thiophene-2-carboxamide hydrochloride (compound (R)-21) (22 mg, 20% yield) as a white solid: cSFC analytical (A) tR=2.98 min., purity: 94.47%; LCMS (B): tR=0.664 min., 345.1 m/z (M+1); ¹H-NMR (CD₃OD, 400 MHz): 8.42 (d, J=7.6 Hz, 1H), 8.10-8.06 (m, 1H), 7.81 (d, J=8.8 Hz, 1H), 7.42 (s, 1H), 7.16-7.13 (dd, J₁=8.8 Hz, J₂=2.0 Hz, 1H), 4.27 (s, 1H), 3.90 (s, 3H), 3.75-3.69 (m, 2H), 3.39-3.36 (m, 2H), 2.43 (m, 1H), 2.30-2.19 (m, 1H), 2.16-2.08 (m, 2H), 1.99-1.93 (m, 1H), 1.77 (s, 3H), 1.51 (s, 3H).

Preparation of (S)—N-(2,2-dimethylquinuclidin-3-yl)-5-methoxybenzo[b]thiophene-2-carboxamide ((S)-21)

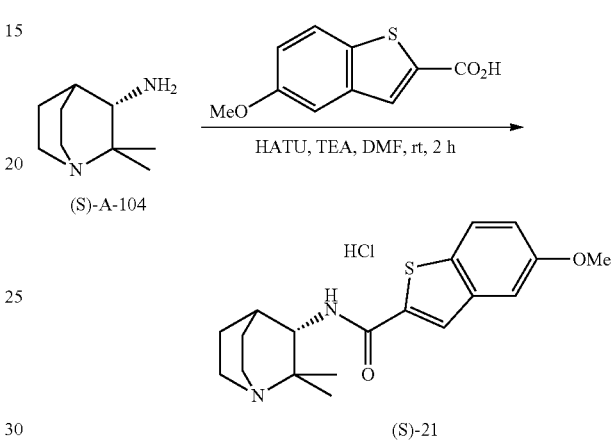

Following general procedure B, Compound (S)-21 was prepared from 5-methoxybenzo[b]thiophene-2-carboxylic acid (67 mg, 0.32 mmol) and compound (S)-A-104 (50 mg, 0.32 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H₂O (add 0.5% HCl, v/v)] to give:

(S)—N-(2,2-dimethylquinuclidin-3-yl)-5-methoxybenzo[b]thiophene-2-carboxamide hydrochloride (compound (S)-21) (19 mg, 17% yield) as a white solid: cSFC analytical (A) tR=3.40 min., purity: 97.93%; LCMS (B): tR=0.664 min., 345.1 m/z (M+1); ¹H-NMR (CD₃OD, 400 MHz): 8.42 (d, J=7.2 Hz, 1H), 8.10 (s, 1H), 7.80 (d, J=9.2 Hz, 1H), 7.42 (s, 1H), 7.14 (dd, J₁=8.8 Hz, J₂=2.4 Hz, 1H), 4.27 (d, J=6.8 Hz, 1H), 3.89 (s, 3H), 3.75-3.70 (m, 2H), 3.39-3.37 (m, 2H), 2.45 (m, 1H), 2.30-2.18 (m, 1H), 2.18-2.09 (m, 2H), 2.08-1.93 (m, 1H), 1.77 (s, 3H), 1.52 (s, 3H).

Example 22

Preparation of (R)—N-(2,2-dimethylquinuclidin-3-yl)furo[2,3-c]pyridine-5-carboxamide hydrochloride ((R)-22)

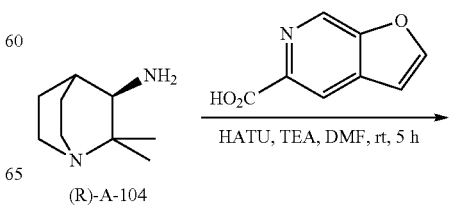

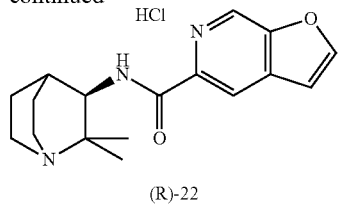

(R)-22

Following general procedure B, Compound (R)-22 was prepared from furo[2,3-c]pyridine-5-carboxylic acid (53 mg, 0.32 mmol) and compound (R)-A-104 (50 mg, 0.32 mmol), with a reaction time of 5 hours. The product was purified by prep-HPLC [Instrument: GX-B; Column: Phenomenex Synergi C18 150×30 mm, particle size: 4 μm; Mobile phase: 5-35% acetonitrile in H₂O (add 0.5% TFA, v/v)], treated with 0.2 M hydrochloric acid and lyophilized to give:

(R)—N-(2,2-dimethylquinuclidin-3-yl)furo[2,3-c]pyridine-5-carboxamide hydrochloride (compound (R)-22) (40 mg, 41% yield) as a yellow solid: cSFC analytical (H) tR=2.49 min., purity: 100%; LCMS (L): tR=2.148 min., 300.0 m/z (M+1); ¹H-NMR (CD₃OD, 400 MHz): δ 9.24 (s, 1H), 8.90 (s, 1H), 8.51 (d, J=2.0 Hz, 1H), 7.40 (d, J=1.6 Hz, 1H), 4.33 (s, 1H), 3.77-3.71 (m, 2H), 3.40-3.34 (m, 2H), 2.49-2.45 (m, 1H), 2.33-2.32 (m, 1H), 2.19-2.12 (m, 2H), 2.01-1.95 (m, 1H), 1.78 (s, 3H), 1.54 (s, 3H).

Preparation of (S)—N-(2,2-dimethylquinuclidin-3-yl)furo[2,3-c]pyridine-5-carboxamide hydrochloride ((S)-22)

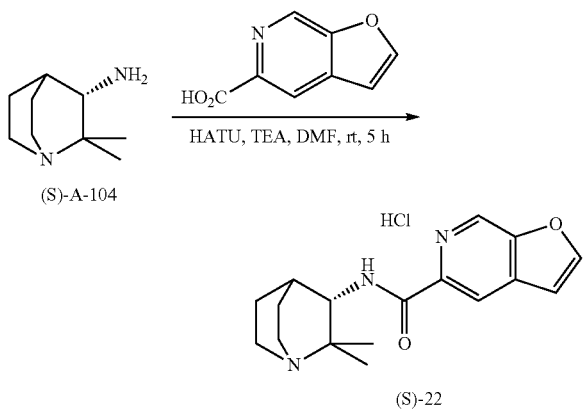

(S)-22

Following general procedure B, Compound (S)-22 was prepared from furo[2,3-c]pyridine-5-carboxylic acid (53 mg, 0.32 mmol) and compound (S)-A-104 (50 mg, 0.32 mmol), with a reaction time of 5 hours. The product was purified by prep-HPLC [Instrument: GX-B; Column: Phenomenex Synergi C18 150×30 mm, particle size: 4 μm; Mobile phase: 5-35% acetonitrile in H₂O (add 0.5% TFA, v/v)], treated with 0.2 M hydrochloric acid and lyophilized to give:

(S)—N-(2,2-dimethylquinuclidin-3-yl)furo[2,3-c]pyridine-5-carboxamide hydrochloride (compound (S)-22) (30 mg, 33% yield) as a yellow solid: cSFC analytical (H) tR=3.40 min., purity: 97.76%; LCMS (L): tR=2.116 min., 300.0 m/z (M+1); ¹H-NMR (CD₃OD, 400 MHz): δ 9.10 (s, 1H), 8.70 (s, 1H), 8.35 (d, J=2.0 Hz, 1H), 7.28 (d, J=1.6 Hz, 1H), 4.31 (s, 1H), 3.77-3.71 (m, 2H), 3.40-3.34 (m, 2H), 2.40-2.39 (m, 1H), 2.31-2.30 (m, 1H), 2.21-2.09 (m, 2H), 2.02-1.95 (m, 1H), 1.77 (s, 3H), 1.51 (s, 3H).

Example 23

Preparation of (R)—N-(2,2-dimethylquinuclidin-3-yl)-2,3-dihydro-[1,4]dioxino[2,3-c]pyridine-7-carboxamide hydrochloride ((R)-23)

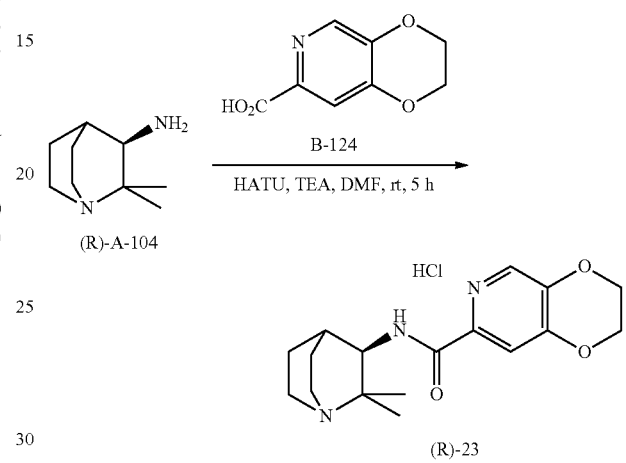

(R)-23

Following general procedure B, Compound (R)-23 was prepared from compound B-124 (59 mg, 0.32 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 10 μm; Mobile phase: 5-40% acetonitrile in H₂O (add 0.5% HCl, v/v)] to give:

(R)—N-(2,2-dimethylquinuclidin-3-yl)-2,3-dihydro-[1,4]dioxino[2,3-c]pyridine-7-carboxamide hydrochloride (compound (R)-23) (55 mg, 53% yield) as a yellow solid: cSFC analytical (H) tR=3.36 min., purity: 95.72%; LCMS (M): tR=0.929 min., 318.0 m/z (M+1); ¹H-NMR (CD₃OD, 400 MHz): δ 8.45 (s, 1H), 8.18 (s, 1H), 4.67-4.65 (m, 2H), 4.57-4.55 (m, 2H), 4.29 (s, 1H), 3.76-3.69 (m, 2H), 3.40-3.36 (m, 2H), 2.47-2.44 (m, 1H), 2.30 (m, 1H), 2.19-2.12 (m, 2H), 1.99-1.93 (m, 1H), 1.77 (s, 3H), 1.51 (s, 3H).

Preparation of (S)—N-(2,2-dimethylquinuclidin-3-yl)-2,3-dihydro-[1,4]dioxino[2,3-c]pyridine-7-carboxamide hydrochloride ((S)-23)

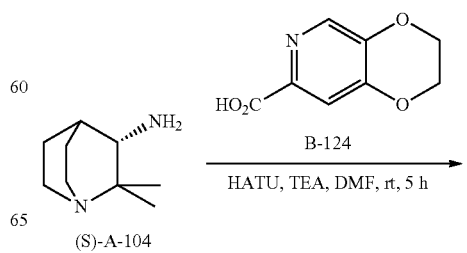

-continued

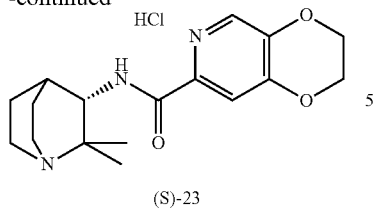

(S)-23

Following general procedure B, Compound (S)-23 was prepared from compound B-124 (47 mg, 0.26 mmol) and compound (S)-A-104 (40 mg, 0.26 mmol), with a reaction time of 5 hours. The product was purified by prep-HPLC [Instrument: GX-E; Column: Phenomenex Synergi C18 150×30 mm, particle size: 10 μm; Mobile phase: 5-40% acetonitrile in H₂O (add 0.5% HCl, v/v)] to give:

(S)—N-(2,2-dimethylquinuclidin-3-yl)-2,3-dihydro-[1,4]dioxino[2,3-c]pyridine-7-carboxamide hydrochloride (compound (S)-23) (50 mg, 61% yield) as a yellow solid: cSFC analytical (H) tR=3.67 min., purity: 98.64%; LCMS (M): tR=0.916 min., 318.0 m/z (M+1); $^1$H-NMR (CD$_3$OD, 400 MHz): δ 8.45 (s, 1H), 8.17 (s, 1H), 4.65-4.63 (m, 2H), 4.54-4.52 (m, 2H), 4.27 (s, 1H), 3.74-3.67 (m, 2H), 3.38-3.34 (m, 2H), 2.45-2.40 (m, 1H), 2.28-2.27 (m, 1H), 2.17-2.11 (m, 2H), 1.97-1.91 (m, 1H), 1.75 (s, 3H), 1.49 (s, 3H).

Example 24: (R)—N-(2,2-dimethylquinuclidin-3-yl)-3-methylbenzo[b]thiophene-5-carboxamide hydrochloride ((R)-24)

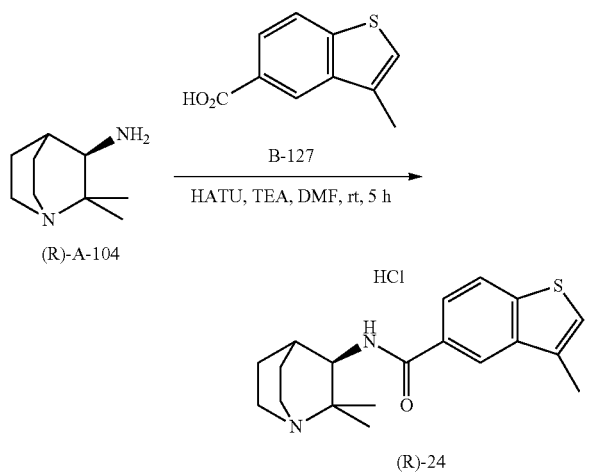

(R)-24

Following general procedure B, Compound (R)-24 was prepared from compound B-127 (62 mg, 0.32 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 10 μm; Mobile phase: 20-50% acetonitrile in H₂O (add 0.5% HCl, v/v)] to give:

(R)—N-(2,2-dimethylquinuclidin-3-yl)-3-methylbenzo[b]thiophene-5-carboxamide hydrochloride (compound (R)-24) (65 mg, 61% yield) as a white solid: cSFC analytical (B) tR=2.87 min., purity: 98.24%; LCMS (B): tR=0.658 min., 329.2 m/z (M+1); $^1$H-NMR (CD$_3$OD, 400 MHz): δ 8.28 (d, J=1.2 Hz, 1H), 7.98 (d, J=8.4 Hz, 1H), 7.83 (d, J$_1$=8.4 Hz, J$_2$=1.2 Hz, 1H), 7.33 (s, 1H), 4.30 (s, 1H), 3.77-3.67 (m, 2H), 3.38-3.34 (m, 2H), 2.52 (s, 3H), 2.52-2.41 (m, 1H), 2.40-2.29 (m, 1H), 2.19-2.11 (m, 2H), 1.97-1.90 (m, 1H), 1.79 (s, 3H), 1.51 (s, 3H).

Example 25: (R)—N-(2,2-dimethylquinuclidin-3-yl)-3-methylbenzo[b]thiophene-6-carboxamide ((R)-25)

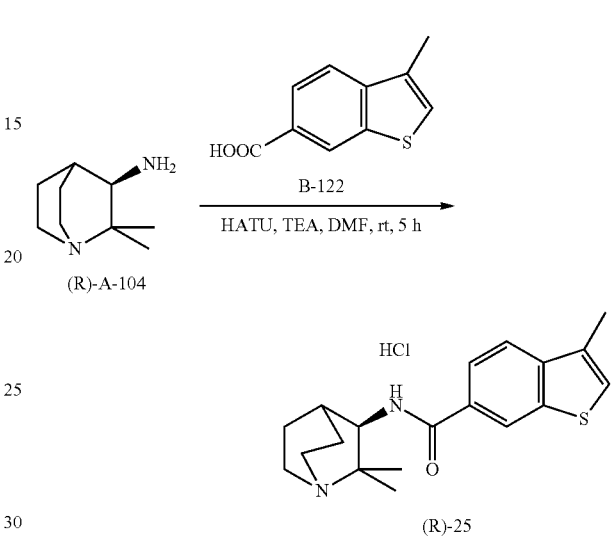

(R)-25

Following general procedure B, Compound (R)-25 was prepared from compound B-122 (69 mg, 0.36 mmol) and compound (R)-A-104 (50 mg, 0.32 mmol), with a reaction time of 5 hours. The product was purified by prep-HPLC [Instrument: GX-E; Column: Phenomenex SynergiC18 150×30 mm, particle size: 10 μm; Mobile phase: 14-44% acetonitrile in H₂O (add 0.5% HCl, v/v)] to give:

(R)—N-(2,2-dimethylquinuclidin-3-yl)-3-methylbenzo[b]thiophene-6-carboxamide hydrochloride (compound (R)-25) (30 mg, 25% yield) as a white solid: cSFC analytical (A) tR=2.96 min., purity: 97.81%; LCMS (B): tR=0.663 min., 329.1 m/z (M+1); $^1$H-NMR (DMSO, 400 MHz): δ 10.40 (s, 1H), 8.53 (s, 1H), 8.41 (d, J=8.0 Hz, 1H), 7.91-7.85 (m, 2H), 7.61 (s, 1H), 4.14 (d, J=7.2 Hz, 1H), 3.52-3.49 (m, 2H), 3.23-3.11 (m, 2H), 2.44 (s, 3H), 2.42-2.34 (m, 1H), 2.12-2.03 (m, 2H), 1.94-1.88 (m, 1H), 1.76-1.69 (m, 1H), 1.65 (s, 3H), 1.41 (s, 3H).

Example 26: (R)—N-(2,2-dimethylquinuclidin-3-yl)-H-indole-6-carboxamide ((R)-26)

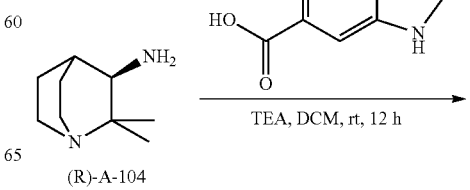

-continued

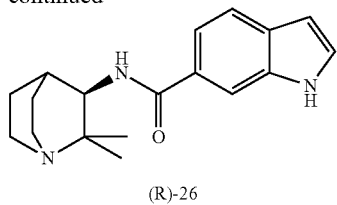

(R)-26

Following general procedure B, Compound (R)-26 was prepared from 1H-indole-6-carboxylic acid and compound (R)-A-104 (50 mg, 0.32 mmol), with a reaction time of 12 hours. The product was purified by prep-HPLC [Instrument: GX-A; Column: Phenomenex Gemini C18 150×25 mm, particle size: 10 μm; Mobile phase: 28-58% acetonitrile in H$_2$O (add 0.5% NH$_3$.H2O, v/v)]. The resulting solid was dissolved in 0.2 M hydrochloric acid solution and again lyophilized to give:

(R)—N-(2,2-dimethylquinuclidin-3-yl)-1H-indole-6-carboxamide hydrochloride (compound (R)-26) (20 mg, 21% yield) as a white solid: cSFC analytical (A) tR: 3.17 min., purity: 96%; LCMS (P): tR=1.672 min., 298.1 m/z (M+1); $^1$H-NMR (CD$_3$OD, 400 MHz): δ 7.93 (s, 1H), 7.64 (d, J=8.4 Hz, 1H), 7.51-7.49 (m, 1H), 7.42 (d, J=2.8 Hz, 1H), 6.54 (d, J=3.2 Hz, 1H), 4.07 (s, 1H), 3.39-3.35 (m, 2H), 2.84-2.82 (m, 2H), 2.07-2.05 (m, 1H), 1.96 (s, 1H), 1.88-1.83 (m, 2H), 1.58-1.56 (m, 1H), 1.50 (s, 3H), 1.33 (s, 3H).

Example 27

Preparation of (R)—N-(2,2-dimethylquinuclidin-3-yl)pyrazolo[1,5-b]pyridazine-3-carboxamide hydrochloride ((R)-27)

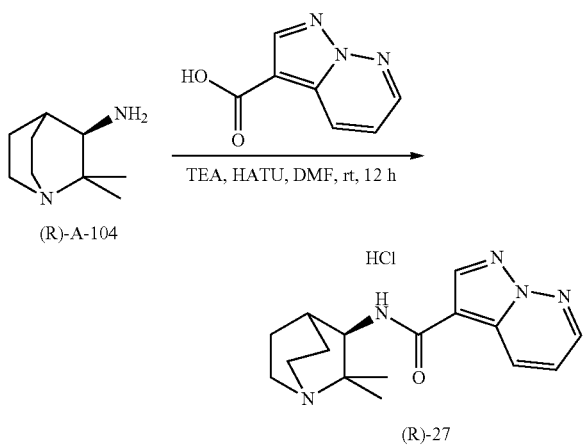

(R)-27

Following general procedure B, Compound (R)-27 was prepared from pyrazolo[1,5-b]pyridazine-3-carboxylic acid (50 mg, 0.31 mmol) and compound (R)-A-104 (47 mg, 0.31 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(R)—N-(2,2-dimethylquinuclidin-3-yl)pyrazolo[1,5-b] pyridazine-3-carboxamide hydrochloride (compound (R)-27) (30 mg, 33% yield) as a white solid: cSFC analytical (B) tR=3.40 min., purity: 99.40%; LCMS (N): tR=1.485 min., (ES$^+$) m/z (M+H)$^+$=300.1; $^1$H-NMR (CD$_3$OD, 400 MHz): δ 8.71 (s, 1H), 8.66 (dd, J$_1$=8.8 Hz, J$_2$=1.6 Hz, 1H), 8.53 (dd, J$_1$=4.4 Hz, J$_2$=2.0 Hz, 1H), 7.43-7.40 (m, 1H), 4.29 (s, 1H), 3.74-3.67 (m, 2H), 3.37-3.31 (m, 2H), 2.45-2.42 (m, 1H), 2.27-2.25 (m, 1H), 2.17-2.14 (m, 2H), 1.97-1.90 (m, 1H), 1.76 (m, 3H), 1.49 (m, 3H).

Preparation of (S)—N-(2,2-dimethylquinuclidin-3-yl)pyrazolo[1,5-b]pyridazine-3-carboxamide hydrochloride ((S)-27)

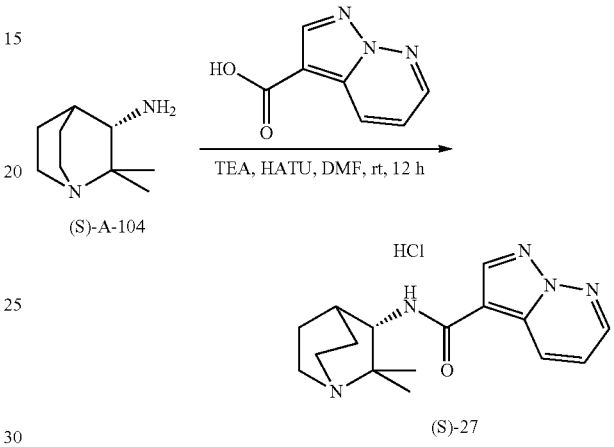

(S)-27

Following general procedure B, Compound (S)-27 was prepared from pyrazolo[1,5-b]pyridazine-3-carboxylic acid (50 mg, 0.31 mmol) and compound (S)-A-104 (47 mg, 0.20 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(S)—N-(2,2-dimethylquinuclidin-3-yl)pyrazolo[1,5-b] pyridazine-3-carboxamide hydrochloride (compound (S)-27) (44 mg, 48% yield) as a white solid: cSFC analytical (B) tR=3.14 min., purity: 99.11%; LCMS (N): tR=1.579 min., (ES$^+$) m/z (M+H)$^+$=300.1; $^1$H-NMR (CD$_3$OD, 400 MHz): δ 8.69 (s, 1H), 8.66 (dd, J$_1$=9.2 Hz, J$_2$=1.6 Hz, 1H), 8.53-8.52 (dd, J$_1$=4.4 Hz, J$_2$=1.6 Hz, 1H), 7.43-7.40 (m, 1H), 4.28 (s, 1H), 3.75-3.66 (m, 2H), 3.37-3.31 (m, 2H), 2.45-2.40 (m, 1H), 2.27-2.24 (m, 1H), 2.17-2.06 (m, 2H), 1.96-1.90 (m, 1H), 1.76 (m, 3H), 1.48 (m, 3H).

Example 28

Preparation of (R)—N-(2,2-dimethylquinuclidin-3-yl)thieno[2,3-b]pyridine-2-carboxamide hydrochloride ((R)-28)

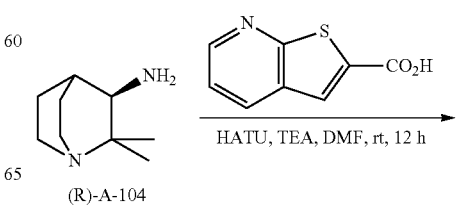

(R)-A-104

-continued

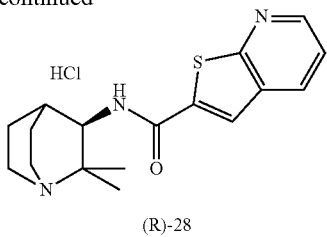

(R)-28

Following general procedure B, Compound (R)-28 was prepared from thieno[2,3-b]pyridine-2-carboxylic acid (58 mg, 0.32 mmol) and compound (R)-A-104 (50 mg, 0.32 mmol), with a reaction time of 12 hours. The product was purified by prep-HPLC [Instrument: GX-B; Column: Phenomenex Synergi C18 150×30 mm, particle size: 4 μm; Mobile phase: 4-34% acetonitrile in $H_2O$ (add 0.5% TFA, v/v)], treated with 0.2 M hydrochloric acid solution and lyophilized to give:

(R)—N-(2,2-dimethylquinuclidin-3-yl)thieno[2,3-b]pyridine-2-carboxamide hydrochloride (compound (R)-28) (45 mg, 39% yield) as a yellow solid: cSFC analytical (A) tR=3.006 min., purity: 98.57%; LCMS (X): tR=1.517 min., (ES$^+$) m/z (M+H)$^+$=316.1; $^1$H-NMR (CD$_3$OD, 400 MHz): δ 8.79 (d, J=5.2 Hz, 1H), 8.60 (d, J=8.0 Hz, 1H), 8.30 (s, 1H), 7.69 (t, d=8.4 Hz, 1H), 4.30 (s, 1H), 3.78-3.71 (m, 2H), 3.40-3.36 (m, 2H), 2.50-2.45 (m, 1H), 2.32-2.31 (m, 1H), 2.21-2.10 (m, 2H), 2.00-1.94 (m, 1H), 1.78 (s, 3H), 1.53 (s, 3H).

Preparation of (S)—N-(2,2-dimethylquinuclidin-3-yl)thieno[2,3-b]pyridine-2-carboxamide hydrochloride ((S)-28)

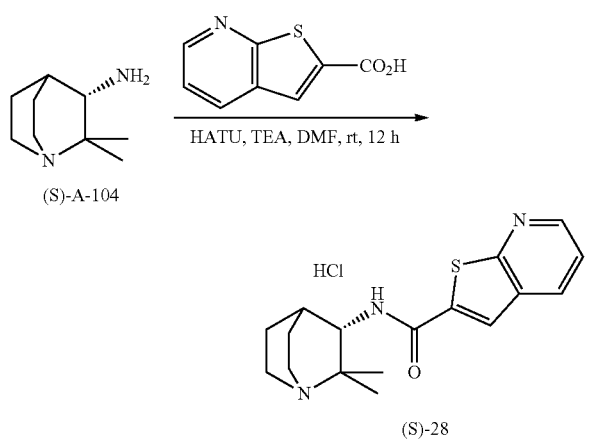

(S)-28

Following general procedure B, Compound (S)-28 was prepared from thieno[2,3-b]pyridine-2-carboxylic acid (58 mg, 0.32 mmol) and compound (S)-A-104 (50 mg, 0.32 mmol), with a reaction time of 12 hours. The product was purified by prep-HPLC [Instrument: GX-B; Column: Phenomenex Synergi C18 150×30 mm, particle size: 4 μm; Mobile phase: 4-34% acetonitrile in $H_2O$ (add 0.5% TFA, v/v)], treated with 0.2 M hydrochloric acid solution and lyophilized to give:

(S)—N-(2,2-dimethylquinuclidin-3-yl)thieno[2,3-b]pyridine-2-carboxamide hydrochloride (compound (S)-28) (36 mg, 32% yield) as a yellow solid: cSFC analytical (A) tR=3.684 min., purity: 98.05%; LCMS (X): tR=1.523 min., (ES$^+$) m/z (M+H)$^+$=316.1; $^1$H-NMR (CD$_3$OD, 400 MHz): δ 8.78 (d, J=4.8 Hz, 1H), 8.58 (d, J=8.0 Hz, 1H), 8.29 (s, 1H), 7.68 (t, d=8.4 Hz, 1H), 4.30 (s, 1H), 3.78-3.70 (m, 2H), 3.40-3.36 (m, 2H), 2.50-2.45 (m, 1H), 2.32-2.31 (m, 1H), 2.21-2.10 (m, 2H), 2.00-1.94 (m, 1H), 1.78 (s, 3H), 1.53 (s, 3H).

Example 29

Preparation of (R)—N-(2,2-dimethylquinuclidin-3-yl)benzo[d]thiazole-2-carboxamide hydrochloride ((R)-29)

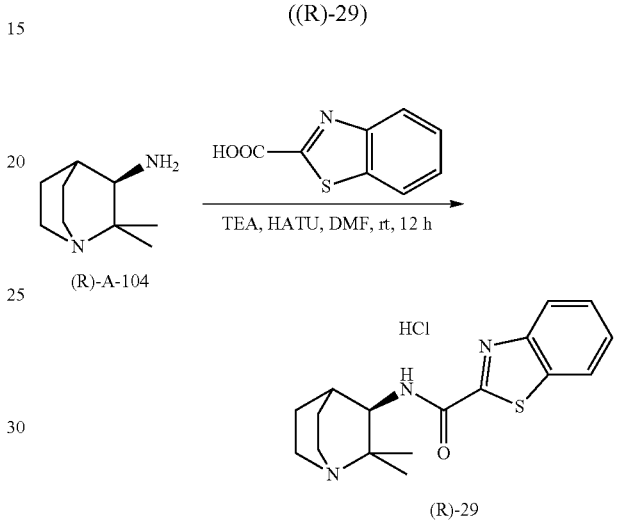

(R)-29

Following general procedure B, Compound (R)-29 was prepared from benzo[d]thiazole-2-carboxylic acid (58 mg, 0.33 mmol) and (R)-A-104 (50 mg, 0.33 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in $H_2O$ (add 0.5% HCl, v/v)] to give:

(R)—N-(2,2-dimethylquinuclidin-3-yl)benzo[d]thiazole-2-carboxamide hydrochloride (compound (R)-29) (40 mg, 39% yield) as a white solid: cSFC analytical (D) tR=2.93 min., purity: 99.32%; LCMS (X): tR=1.793 min., (ES$^+$) m/z (M+H)$^+$=316.1; $^1$H-NMR (CD$_3$OD, 400 MHz): δ 8.17-8.10 (m, 2H), 7.65-7.56 (m, 2H), 4.30 (m, 1H), 3.72-3.69 (m, 2H), 3.39-3.33 (m, 2H), 2.40-2.39 (m, 1H), 2.31-2.20 (m, 1H), 2.18-2.08 (m, 2H), 2.00-1.94 (m, 1H), 1.76 (m, 3H), 1.52 (m, 3H).

Preparation of (S)—N-(2,2-dimethylquinuclidin-3-yl)benzo[d]thiazole-2-carboxamide hydrochloride ((S)-29)

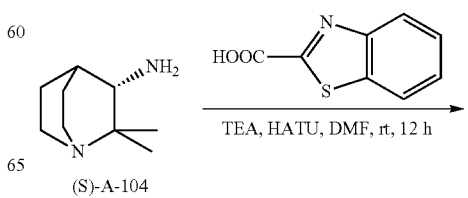

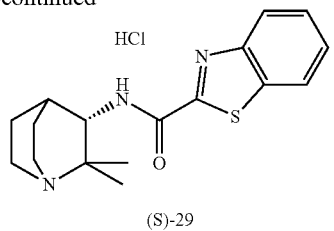

(S)-29

Following general procedure B, Compound (S)-29 was prepared from benzo[d]thiazole-2-carboxylic acid (50 mg, 0.31 mmol) and compound (S)-A-104 (47 mg, 0.20 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in $H_2O$ (add 0.5% HCl, v/v)] to give:

(S)—N-(2,2-dimethylquinuclidin-3-yl)benzo[d]thiazole-2-carboxamide hydrochloride (compound (S)-29) (44 mg, 48% yield) as a white solid: cSFC analytical (D) tR=3.38 min., purity: 98.29%; LCMS (X): tR=1.781 min., (ES$^+$) m/z (M+H)$^+$=316.1; $^1$H-NMR (CD$_3$OD, 400 MHz): δ 8.17-8.11 (m, 2H), 7.66-7.56 (m, 2H), 4.30 (m, 1H), 3.76-3.70 (m, 2H), 3.37-3.34 (m, 2H), 2.40-2.39 (m, 1H), 2.31-2.21 (m, 1H), 2.20-2.11 (m, 2H), 2.00-1.94 (m, 1H), 1.75 (m, 3H), 1.52 (m, 3H).

Example 30: (R)—N-(2,2-dimethylquinuclidin-3-yl)benzo[b]thiophene-5-carboxamide hydrochloride ((R)-30)

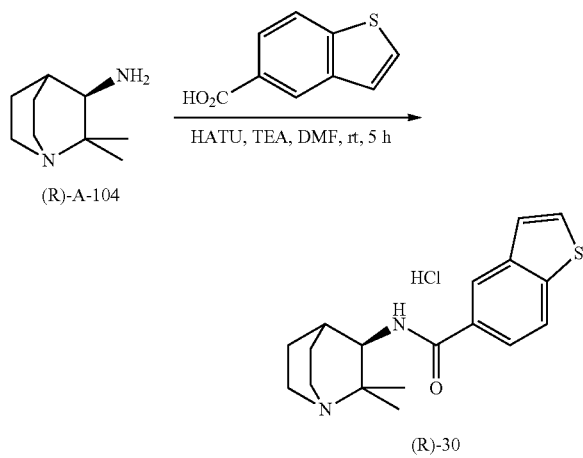

(R)-30

Following general procedure B, Compound (R)-30 was prepared from benzo[b]thiophene-5-carboxylic acid (60 mg, 0.34 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 4 μm; Mobile phase: 15-45% acetonitrile in $H_2O$ (add 0.5% HCl, v/v)] to give:

(R)—N-(2,2-dimethylquinuclidin-3-yl)benzo[b]thiophene-5-carboxamide hydrochloride (compound (R)-30) (30 mg, 28% yield) as a white solid: cSFC analytical (A) tR=2.998 min., purity: 96.86%; LCMS (J): tR=1.355 min., 315.1 m/z (M+1); $^1$H-NMR (CD$_3$OD, 400 MHz): δ 8.39 (s, 1H), 8.05 (d, J=8.8 Hz, 1H), 7.83 (d, J=8.4 Hz, 1H), 7.73 (d, J=5.2 Hz, 1H), 7.52 (d, J=5.6 Hz, 1H), 4.61 (s, 1H), 4.30 (s, 1H), 3.75-3.60 (m, 2H), 3.28-3.25 (m, 1H), 2.39 (m, 1H), 2.28 (m, 1H), 2.18-2.12 (m, 2H), 1.93 (m, 1H), 1.78 (s, 3H), 1.51 (s, 3H).

Example 31: (R)—N-(2,2-dimethylquinuclidin-3-yl)benzofuran-6-carboxamide hydrochloride ((R)-31)

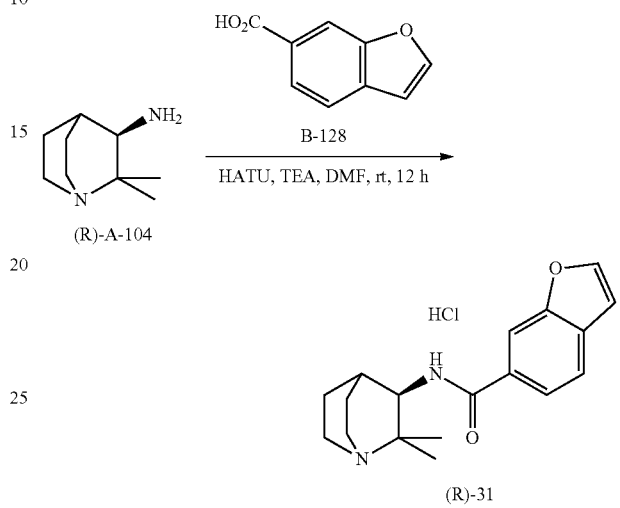

(R)-31

Following general procedure B, Compound (R)-31 was prepared from compound B-128 (53 mg, 0.32 mmol) and compound (R)-A-104 (50 mg, 0.32 mmol), with a reaction time of 12 hours. The product was purified by prep-HPLC [Instrument: GX-E; Column: Phenomenex Synergi C18 150×30 mm, particle size: 10 μm; Mobile phase: 12-42% acetonitrile in $H_2O$ (add 0.5% HCl, v/v)] to give:

(R)—N-(2,2-dimethylquinuclidin-3-yl)benzofuran-6-carboxamide hydrochloride (compound (R)-31) (46 mg, 42% yield) as a white solid: cSFC analytical (A) tR=2.52 min., purity: 97.64%; LCMS (B): tR=0.115 min., (ES$^+$) m/z (M+H)$^+$=299.2; $^1$H-NMR (CD$_3$OD, 400 MHz): δ 8.05 (s, 1H), 7.93 (d, J=2.0 Hz, 1H), 7.78-7.72 (m, 2H), 6.94 (d, J=1.2 Hz, 1H), 4.28 (s, 1H), 3.75-3.66 (m, 2H), 3.37-3.31 (m, 2H), 2.39-2.38 (m, 1H), 2.27-2.26 (m, 1H), 2.18-2.10 (m, 2H), 1.96-1.89 (m, 1H), 1.77 (s, 3H), 1.49 (s, 3H).

Example 32: (R)—N-(2,2-dimethylquinuclidin-3-yl)-2-methylbenzo[d]oxazole-5-carboxamide ((R)-32)

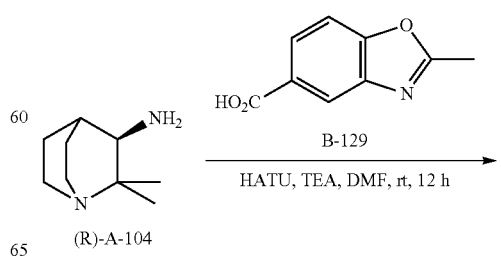

-continued

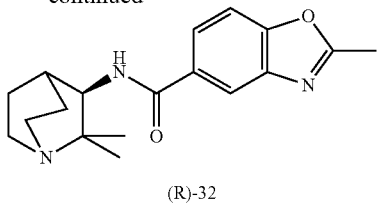

(R)-32

Following general procedure B, Compound (R-32 was prepared from compound B-129 (69 mg, 0.39 mmol) and compound (R)-A-104 (50 mg, 0.32 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H2O, v/v)] to give:

(R)—N-(2,2-dimethylquinuclidin-3-yl)-2-methylbenzo[d]oxazole-5-carboxamide (compound (R)-32) (30 mg, 30% yield) as a white solid: cSFC analytical (A) tR=2.44 min., purity: 96.08%; LCMS (J): tR=0.995 min., 314.1 m/z (M+1); $^1$H-NMR (CD$_3$OD, 400 MHz): δ 8.10 (s, 1H), 7.87-7.85 (m, 1H), 7.67 (d, J=8.8 Hz, 1H), 4.07 (s, 1H), 3.33-3.33 (m, 2H), 2.85-2.85 (m, 2H), 2.69 (s, 3H), 2.09-2.09 (m, 1H), 1.97-1.86 (m, 3H), 1.67-1.64 (m, 1H), 1.51 (s, 3H), 1.32 (s, 3H).

Example 33: (R)—N-(2,2-dimethylquinuclidin-3-yl)-2-methylbenzo[d]oxazole-6-carboxamide ((R)-33)

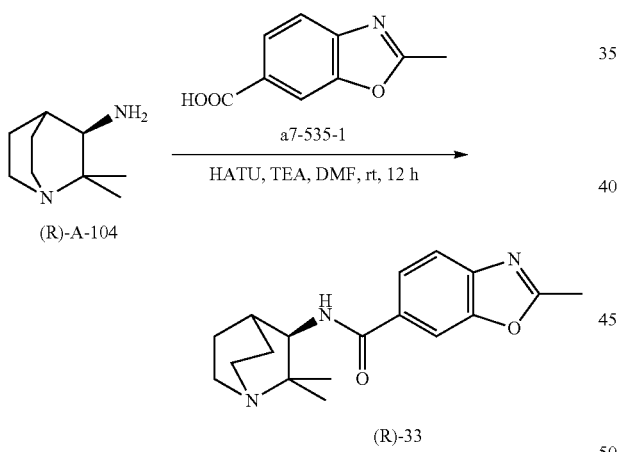

Following general procedure B, Compound (R)-33 was prepared from compound B-130 (60 mg, 0.34 mmol) and compound (R)-A-104 (52 mg, 0.34 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H2O, v/v)] to give:

(R)—N-(2,2-dimethylquinuclidin-3-yl)-2-methylbenzo[d]oxazole-6-carboxamide (compound (R)-33) (40 mg, 38% yield) as a white solid: cSFC analytical (A) tR=2.42 min., purity: 97.31%; LCMS (J): tR=0.986 min., 314.1 m/z (M+1); $^1$H-NMR (CD$_3$OD, 400 MHz): δ 8.05 (s, 1H), 7.86-7.84 (m, 1H), 7.70 (d, J=8.4 Hz, 1H), 4.03 (s, 1H), 3.33-3.33 (m, 2H), 2.81-2.75 (m, 2H), 2.70 (s, 3H), 2.02-2.02 (m, 1H), 1.91-1.91 (m, 1H), 1.82-1.80 (m, 2H), 1.53-1.50 (m, 1H), 1.46 (s, 3H), 1.29 (s, 3H).

Example 34: (R)—N-(2,2-dimethylquinuclidin-3-yl)-2-methylbenzo[d]thiazole-5-carboxamide hydrochloride ((R)-34)

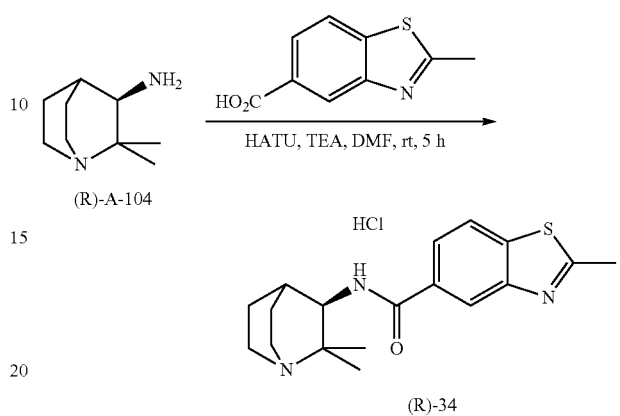

Following general procedure B, Compound (R)-34 was prepared from 2-methylbenzo[d]thiazole-5-carboxylic acid (63 mg, 0.32 mmol) and compound (R)-A-104 (50 mg, 0.32 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(R)—N-(2,2-dimethylquinuclidin-3-yl)-2-methylbenzo[d]thiazole-5-carboxamide hydrochloride (compound (R)-34) (35 mg, 33% yield) as a white solid: cSFC analytical (A) tR=2.85 min., purity: 94.01%; LCMS (K): tR=1.217 min., (ES$^+$) m/z (M+H)$^+$=330.0; $^1$H-NMR (CD$_3$OD, 400 MHz): δ 8.39 (s, 1H), 8.08 (d, J=8.4 Hz, 1H), 7.88 (d, J=8.4 Hz, 1H), 4.29 (s, 1H), 3.78-3.68 (m, 2H), 3.38-3.31 (m, 2H), 2.88 (s, 3H), 2.39-2.38 (m, 1H), 2.28-2.27 (m, 1H), 2.18-2.07 (m, 2H), 1.99-1.90 (m, 1H), 1.78 (s, 3H), 1.51 (s, 3H).

Example 35: (R)—N-(2,2-dimethylquinuclidin-3-yl)-2-methylbenzo[d]thiazole-6-carboxamide hydrochloride ((R)-35)

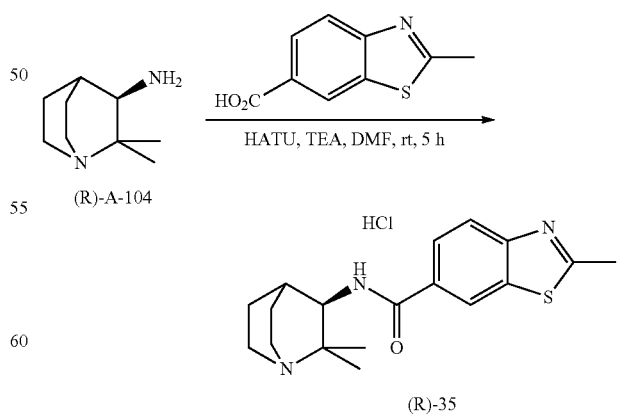

Following general procedure B, Compound (R)-35 was prepared from 2-methylbenzo[d]thiazole-6-carboxylic acid (62 mg, 0.32 mmol) and compound (R)-A-104 (50 mg, 0.32 mmol), with a reaction time of 5 hours. The product was purified by prep-HPLC [Instrument: GX-B; Column: Phenomenex Synergi C18 150×30 mm, particle size: 4 μm; Mobile phase: 8-38% acetonitrile in H₂O (add 0.5% TFA, v/v)], treated with HCl and then lyophilized to give:

(R)—N-(2,2-dimethylquinuclidin-3-yl)-2-methylbenzo[d]thiazole-6-carboxamide hydrochloride (compound (R)-35) (70 mg, 59% yield) as a white solid: cSFC analytical (A) tR=2.81 min., purity: 97.50%; LCMS (K): tR=1.192 min., (ES⁺) m/z (M+H)⁺=330.0; ¹H-NMR (CD₃OD, 400 MHz): δ 8.49 (s, 1H), 7.98 (m, 2H), 4.28 (s, 1H), 3.74-3.69 (m, 2H), 3.35-3.31 (m, 2H), 2.90 (s, 3H), 2.42-2.38 (m, 1H), 2.26-2.27 (m, 1H), 2.09-2.19 (m, 2H), 1.89-1.96 (m, 1H), 1.77 (s, 3H), 1.50 (s, 3H).

Example 36: (R)—N-(2,2-dimethylquinuclidin-3-yl)furo[2,3-b]pyridine-5-carboxamide ((R)-36)

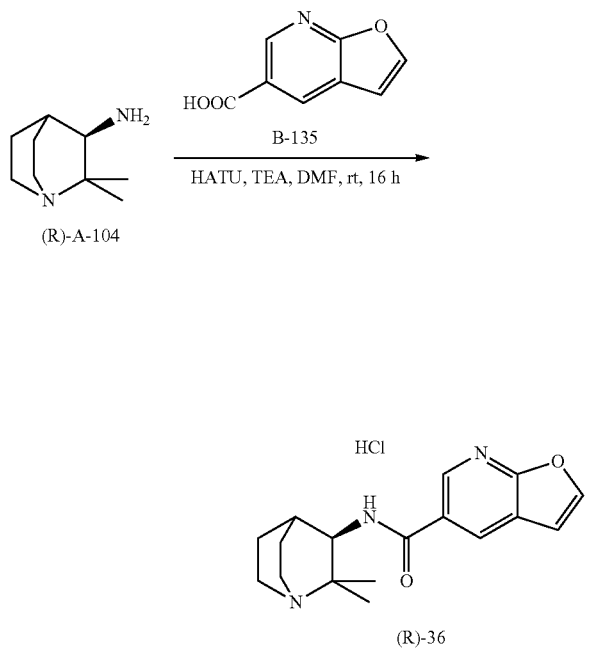

Following general procedure B, Compound (R)-36 was prepared from compound B-135 (53 mg, 0.32 mmol) and compound (R)-A-104 (50 mg, 0.32 mmol), with a reaction time of 16 hours. The product was purified by prep-HPLC [Instrument: GX-H; Column: welch Xtimate C18 150×30 mm, particle size: 5 μm; Mobile phase: 20-50% acetonitrile in H₂O (add 0.5% NH₃.H₂O, v/v)]. The resulting solid was dissolved in 0.2 M hydrochloric acid solution and again lyophilized to give:

(R)—N-(2,2-dimethylquinuclidin-3-yl)furo[2,3-b]pyridine-5-carboxamide hydrochloride (compound (R)-36) (20 mg, 19% yield) as a white solid: cSFC analytical (A) tR=2.95 min., purity: 100%; LCMS (J): tR=1.17 min., 300.1 m/z (M+1); ¹H-NMR (CD₃OD, 400 MHz): 8.73 (d, J=2 Hz, 1H), 8.52 (d, J=2 Hz, 1H), 8.02 (d, J=2.4 Hz, 1H), 7.05 (d, J=2.4 Hz, 1H), 4.08 (s, 1H), 3.40-3.34 (m, 2H), 2.88-2.78 (m, 2H), 2.06-1.97 (m, 1H), 1.96-1.91 (m, 1H), 1.88-1.83 (m, 2H), 1.58-1.50 (m, 4H), 1.32 (s, 3H).

Example 37: (R)—N-(2,2-dimethylquinuclidin-3-yl)furo[3,2-b]pyridine-5-carboxamide hydrochloride ((R)-37)

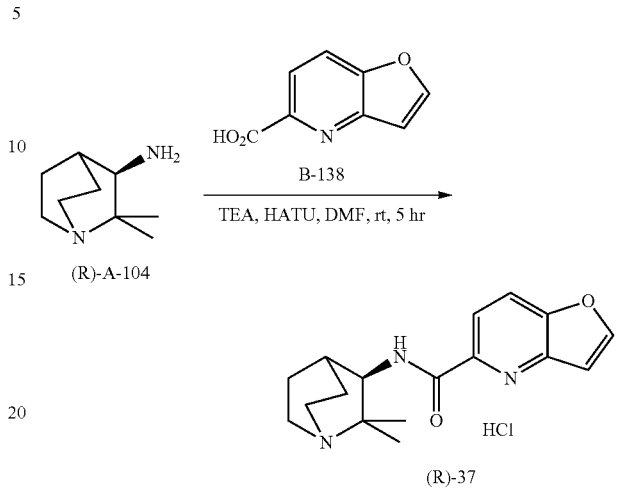

Following general procedure B, Compound (R)-37 was prepared from compound B-138 (53 mg, 0.33 mmol) and compound (R)-A-104 (50 mg, 0.33 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H₂O (add 0.5% HCl, v/v)] to give:

(R)—N-(2,2-dimethylquinuclidin-3-yl)furo[3,2-b]pyridine-5-carboxamide hydrochloride (compound (R)-37) (45 mg, 46% yield) as a white solid: cSFC analytical (A) tR=2.30 min., purity: 97.55%; LCMS (M): tR=0.918 min., (ES⁺) m/z (M+H)⁺=300.1; ¹H-NMR (CD₃OD, 400 MHz): δ 8.34 (d, J=2.4 Hz, 1H), 8.25 (s, 2H), 7.20 (d, J=2.4 Hz, 1H), 4.29 (s, 1H), 3.74-3.73 (m, 2H), 3.38-3.31 (m, 2H), 2.38-2.31 (m, 1H), 2.30-2.29 (m, 1H), 2.19-2.12 (m, 2H), 2.02-1.99 (m, 1H), 1.77 (s, 3H), 1.51 (s, 3H).

Example 38: (R)—N-(2,2-dimethylquinuclidin-3-yl)-2-methylbenzofuran-5-carboxamide hydrochloride ((R)-38)

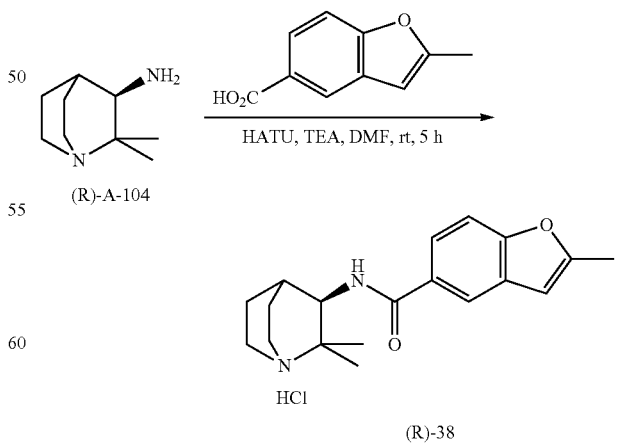

Following general procedure B, Compound (R)-38 was prepared from 2-methylbenzofuran-5-carboxylic acid (60 mg, 0.34 mmol) and compound (R)-A-104 (50 mg, 0.32 mmol), with a reaction time of 5 hours. The product was purified by prep-HPLC [Instrument: GX-B; Column: YMC-pack ODS-AQ 150×30 mm, particle size: 5 μm; Mobile phase: 25-55% acetonitrile in $H_2O$ (add 0.5% HCl, v/v)] to give:

(R)—N-(2,2-dimethylquinuclidin-3-yl)-2-methylbenzofuran-5-carboxamide hydrochloride (compound (R)-38) (20 mg, 17% yield) as a white solid: cSFC analytical (A) tR=2.46 min., purity: 98.28%; LCMS (B): tR=0.601 min., 313.2 m/z (M+1); $^1$H-NMR (DMSO-$d_6$, 400 MHz): δ 10.70 (s, 1H), 8.35 (d, J=8.0, 1H), 8.08 (s, 1H), 7.74 (q, 1H), 7.57 (d, J=8.8, 1H), 6.69 (s, 1H), 4.12 (d, J=7.2, 1H), 3.50-3.43 (m, 2H), 3.19-3.08 (m, 2H), 2.48 (s, 3H), 2.39-2.38 (m, 1H), 2.08-2.01 (m, 2H), 1.93-1.87 (m, 1H), 1.70-1.64 (m, 4H), 1.40 (s, 3H).

Example 39: (R)-2-chloro-N-(2,2-dimethylquinuclidin-3-yl)benzofuran-5-carboxamide hydrochloride ((R)-39)

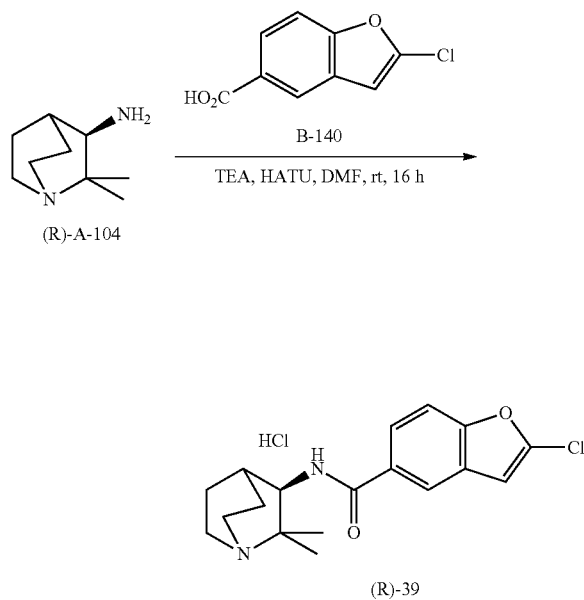

Following general procedure B, Compound (R)-39 was prepared from compound B-140 (0.11 g, 0.57 mmol) and compound (R)-A-104 (80 mg, 0.52 mmol), with a reaction time of 16 hours.

The product was purified by prep-HPLC [Instrument: GX-E; Column: Agella Venusil ASB C18 150×30 mm, particle size: 10 μm; Mobile phase: 15-45% acetonitrile in $H_2O$ (add 0.5% HCl, v/v)] to give:

(R)-2-chloro-N-(2,2-dimethylquinuclidin-3-yl)benzofuran-5-carboxamide hydrochloride (compound (R)-39) (18 mg, 10% yield) as a white solid: cSFC analytical (A) tR=2.51 min., purity: 98.66%; LCMS (S): tR=1.24 min., (ES$^+$) m/z (M+H)$^+$=333.1; $^1$H-NMR (CD$_3$OD, 400 MHz): δ 8.11 (s, 1H), 7.85 (dd, $J_1$=8.4 Hz, $J_1$=1.2 Hz 1H), 7.60 (d, $J_1$=8.8 Hz, 1H), 6.91 (s, 1H), 4.28 (s, 1H), 3.77-3.70 (m, 2H), 3.39-3.36 (m, 1H), 3.35-3.29 (m, 1H), 2.43-2.38 (m, 1H), 2.28-2.27 (m, 1H), 2.20-2.12 (m, 2H), 1.97-1.91 (m, 1H), 1.79 (s, 3H), 1.51 (s, 3H).

Example 40: (R)—N-(2,2-dimethylquinuclidin-3-yl)-3-methylbenzofuran-5-carboxamide hydrochloride ((R)-40)

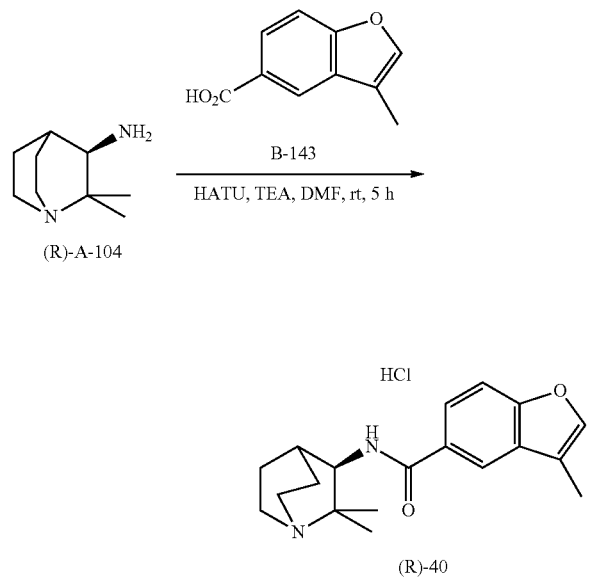

Following general procedure B, Compound (R)-40 was prepared from compound B-143 (69 mg, 0.39 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 10 μm; Mobile phase: 10-40% acetonitrile in $H_2O$ (add 0.5% HCl, v/v)] to give:

(R)—N-(2,2-dimethylquinuclidin-3-yl)-3-methylbenzofuran-5-carboxamide hydrochloride (compound (R)-40) (61 mg, 54% yield) as a yellow solid: cSFC analytical (A) tR=2.51 min., purity: 99.57%; LCMS (B): tR=0.609 min., 313.2 m/z (M+1); $^1$H-NMR (CD$_3$OD, 400 MHz): δ 8.14 (d, J=4 Hz, 1H), δ 7.83 (d, $J_1$=8 Hz, $J_2$=4 Hz, 1H), 7.65 (d, J=4 Hz, 1H), 7.54 (d, J=8 Hz, 1H), 4.28 (s, 1H), 3.73-3.70 (m, 2H), 3.35-3.34 (m, 2H), 2.41-2.40 (m, 1H), 2.32 (s, 3H), 2.31-2.28 (m, 1H), 2.18-2.11 (m, 2H), 1.97-1.90 (m, 1H), 1.78 (s, 3H), 1.50 (s, 3H).

Example 41: (R)-3-chloro-N-(2,2-dimethylquinuclidin-3-yl)benzofuran-5-carboxamide hydrochloride ((R)-41)

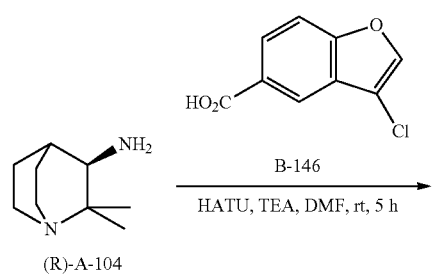

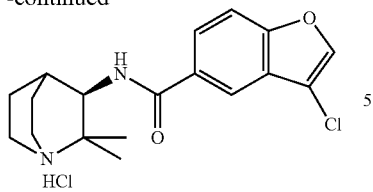

(R)-41

Following general procedure B, Compound (R)-41 was prepared from compound B-146 (66 mg, 0.34 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 4 μm; Mobile phase: 15-45% acetonitrile in $H_2O$ (add 0.5% HCl, v/v)] to give:

(R)-3-chloro-N-(2,2-dimethylquinuclidin-3-yl)benzofuran-5-carboxamide hydrochloride (compound (R)-41) (20 mg, 17% yield) as a white solid: cSFC analytical (A) tR=2.48 min., purity: 97.53%; LCMS (B): tR=0.622 min., 333.1 m/z (M+1); $^1$H-NMR (CD$_3$OD, 400 MHz): δ 8.18 (s, 1H), 8.06 (s, 1H), 7.95 (d, J=8.8, 1H), 7.67 (d, J=8.8, 1H), 4.30 (s, 1H), 3.75-3.68 (m, 2H), 3.40-3.35 (m, 2H), 2.42 (m, 1H), 2.30 (m, 1H), 2.29-2.10 (m, 2H), 1.98-1.92 (m, 1H), 1.80 (s, 3H), 1.53 (s, 3H).

Example 42: (R)—N-(2,2-dimethylquinuclidin-3-yl)-1-methyl-1H-benzo[d]imidazole-5-carboxamide hydrochloride ((R)-42)

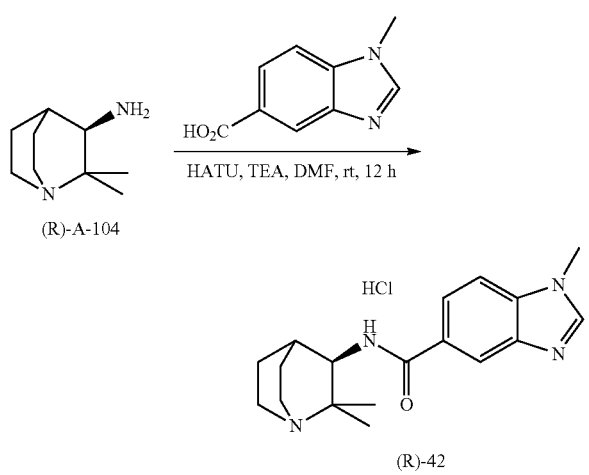

(R)-42

Following general procedure B, Compound (R)-42 was prepared from 1-methyl-1H-benzo[d]imidazole-5-carboxylic acid (64 mg, 0.34 mmol) and compound (R)-A-104 (50 mg, 0.32 mmol), with a reaction time of 12 hours. The product was purified by prep-HPLC [Instrument: GX-E; Column: Agella Venusil ASB C18 150×21.2 mm, particle size: 5 μm; Mobile phase: 15-45% acetonitrile in $H_2O$ (add 0.5% HCl, v/v)] to give:

(R)—N-(2,2-dimethylquinuclidin-3-yl)-1-methyl-1H-benzo[d]imidazole-5-carboxamide hydrochloride (compound (R)-42) (20 mg, 17% yield) as a white solid: cSFC analytical (A) tR=3.43 min., purity: 100.00%; LCMS (J): tR=0.976 min., 313.1 m/z (M+1); $^1$H-NMR (CD$_3$OD, 400 MHz): δ 9.57 (s, 1H), 8.43 (s, 1H), 8.23 (d, J=8.8, 1H), 8.08 (d, J=8.8, 1H), 4.32 (s, 1H), 4.22 (s, 3H), 3.76-3.72 (m, 2H), 2.47 (m, 1H), 2.32-2.31 (m, 1H), 2.20-2.11 (m, 2H), 2.01-1.93 (m, 1H), 1.80 (s, 3H), 1.55 (s, 3H).

Example 43: (R)—N-(2,2-dimethylquinuclidin-3-yl)thieno[2,3-c]pyridine-5-carboxamide ((R)-43)

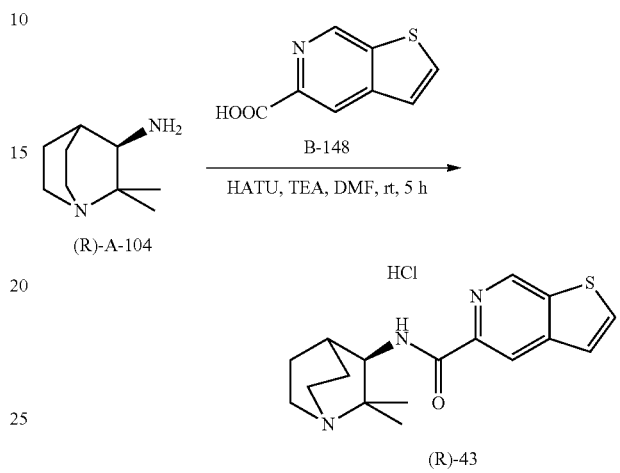

(R)-43

Following general procedure B, Compound (R)-43 was prepared from compound B-148 (70 mg, 0.39 mmol) and compound (R)-A-104 (50 mg, 0.32 mmol), with a reaction time of 5 hours. The product was purified by prep-HPLC [Instrument: GX-A; Column: Phenomenex SynergiC18 150×25 mm, particle size: 10 μm; Mobile phase: 30-60% acetonitrile in $H_2O$ (add 0.5% NH$_3$.H2O, v/v)]. The resulting solids were dissolved in 0.2 M hydrochloric acid solution and again lyophilized to give:

(R)—N-(2,2-dimethylquinuclidin-3-yl)thieno[2,3-c]pyridine-5-carboxamide hydrochloride (compound (R)-43) (35 mg, 31% yield) as a yellow solid: cSFC analytical (A) tR=2.93 min., purity: 99.60%; LCMS (B): tR=0.583 min., 316.1 m/z (M+1); $^1$H-NMR (CD$_3$OD, 400 MHz): δ 9.60 (s, 1H), 9.09 (s, 1H), 8.84 (d, J=5.2 Hz, 1H), 7.95 (d, J=5.6 Hz, 1H), 4.38 (s, 1H), 3.80-3.75 (m, 2H), 3.42-3.36 (m, 2H), 2.51-2.50 (m, 1H), 2.36-2.35 (m, 1H), 2.29-2.16 (m, 2H), 2.03-1.97 (m, 1H), 1.81 (s, 3H), 1.57 (s, 3H).

Example 44: (R)—N-(2,2-dimethylquinuclidin-3-yl)-6-morpholinobenzo[b]thiophene-2-carboxamide hydrochloride ((R)-44)

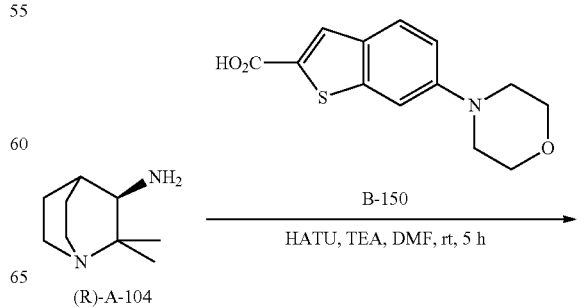

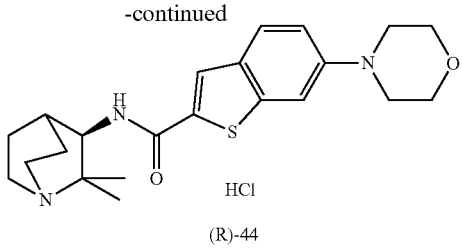

(R)-44

Following general procedure B, Compound (R)-44 was prepared from compound B-150 (85 mg, 0.33 mmol) and compound (R)-A-104 (50 mg, 0.33 mmol), with a reaction time of 5 hours. The product was purified by prep-HPLC [Instrument: GX-B; Column: YMC-pack ODS-AQ C18 150×30 mm, particle size: 5 μm; Mobile phase: 20-50% acetonitrile in $H_2O$ (add 0.5% TFA, v/v)]. The combined fractions were treated with 0.2 M hydrochloric acid and lyophilized to give:

(R)—N-(2,2-dimethylquinuclidin-3-yl)-6-morpholinobenzo[b]thiophene-2-carboxamide hydrochloride (compound (R)-44) (47 mg, 33% yield) as a white solid: cSFC analytical (A) tR=3.74 min., purity: 98.92%; LCMS (K): tR=1.328 min., (ES$^+$) m/z (M+H)$^+$=400.1; $^1$H-NMR (DMSO-d$_6$, 400 MHz): δ 10.42 (s, 1H), 8.42 (d, J=7.6 Hz, 1H), 8.22 (s, 1H), 7.78 (d, J=8.8 Hz, 1H), 7.48 (s, 1H), 7.21 (d, J=8.8 Hz, 1H), 4.08 (d, J=7.6 Hz, 1H), 3.78 (m, 4H), 3.49 (m, 2H), 3.23 (t, J=4.4 Hz, 4H), 3.16-3.14 (m, 2H), 2.41 (m, 1H), 2.07 (m, 1H), 2.01 (m, 1H), 1.92-1.86 (m, 1H), 1.72-1.66 (m, 1H), 1.61 (s, 3H), 1.39 (s, 3H).

Example 45: (R)-6-(4,4-difluoropiperidin-1-yl)-N-(2,2-dimethylquinuclidin-3-yl)benzo[b]thiophene-2-carboxamide hydrochloride ((R)-45)

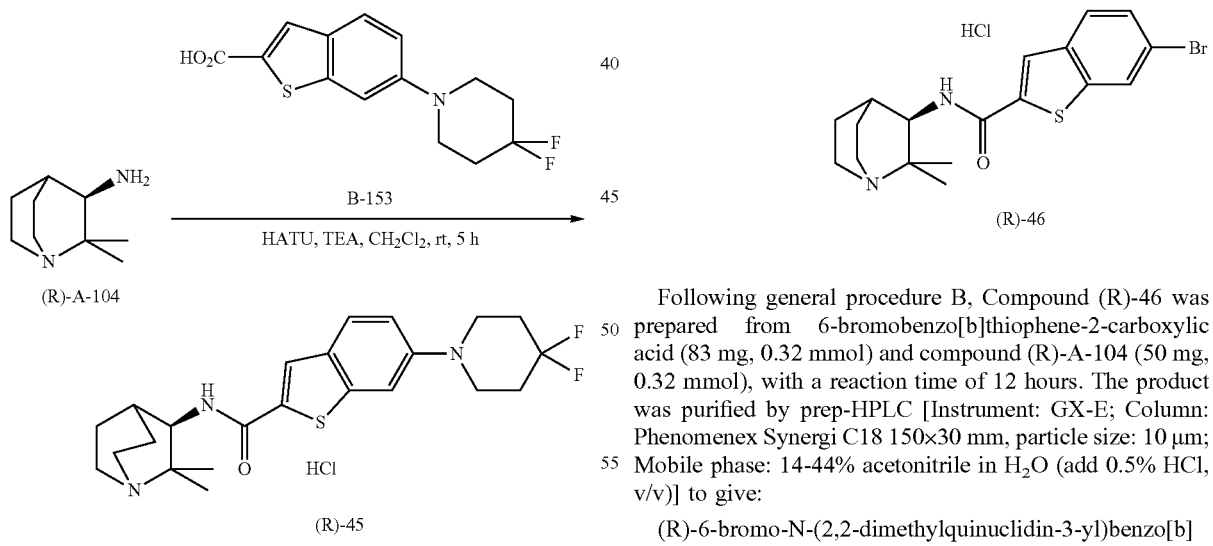

(R)-45

Following general procedure B, Compound (R)-45 was prepared from compound B-153 (70 mg, 0.24 mmol) and compound (R)-A-104 (44 mg, 0.28 mmol), with a reaction time of 5 hours. The product was purified by prep-HPLC [Instrument: GX-E; Column: Innoval C18 150×30 mm, particle size: 5 μm; Mobile phase: 9-39% acetonitrile in $H_2O$ (add 0.5% TFA, v/v)]. The solution was treated with 0.2 M hydrochloric acid solution and lyophilized to give:

(R)-6-(4,4-difluoropiperidin-1-yl)-N-(2,2-dimethylquinuclidin-3-yl)benzo[b]thiophene-2-carboxamide hydrochloride (compound (R)-45) (38 mg, 34% yield) as a yellow solid: cSFC analytical (A) tR=3.41 min., purity: 100%; LCMS (N): tR=2.761 min., (ES$^+$) m/z (M+H)$^+$=434.1; $^1$H-NMR (DMSO-d$_6$, 400 MHz): δ 10.45 (s, 1H), 8.43 (d, J=8.0 Hz, 1H), 8.23 (s, 1H), 7.77 (d, J=8.8 Hz, 1H), 7.55 (s, 1H), 7.24 (d, J=8.8 Hz, 1H), 4.08 (d, J=7.2 Hz, 1H), 3.58-3.44 (m, 6H), 3.18-3.10 (m, 2H), 2.41 (m, 1H), 2.11-1.86 (m, 7H), 1.76-1.60 (m, 4H), 1.38 (s, 3H).

Example 46: (R)-6-bromo-N-(2,2-dimethylquinuclidin-3-yl)benzo[b]thiophene-2-carboxamide hydrochloride ((R)-46)

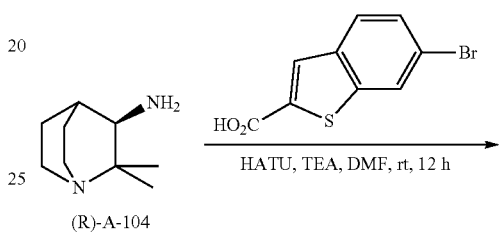

(R)-46

Following general procedure B, Compound (R)-46 was prepared from 6-bromobenzo[b]thiophene-2-carboxylic acid (83 mg, 0.32 mmol) and compound (R)-A-104 (50 mg, 0.32 mmol), with a reaction time of 12 hours. The product was purified by prep-HPLC [Instrument: GX-E; Column: Phenomenex Synergi C18 150×30 mm, particle size: 10 μm; Mobile phase: 14-44% acetonitrile in $H_2O$ (add 0.5% HCl, v/v)] to give:

(R)-6-bromo-N-(2,2-dimethylquinuclidin-3-yl)benzo[b]thiophene-2-carboxamide hydrochloride (compound (R)-46) (55 mg, 43% yield) as a white solid: cSFC analytical (A) tR=3.19 min., purity: 100%; LCMS (B): tR=0.714 min., (ES$^+$) m/z (M+H)$^+$=393.0; $^1$H-NMR (CD$_3$OD, 400 MHz): δ 8.16 (s, 1H), 8.13 (s, 1H), 7.83 (d, J=8.4 Hz, 1H), 7.58 (dd, J$_1$=8.8 Hz, J$_2$=1.6, 1H), 4.25 (s, 1H), 3.73-3.66 (m, 2H), 3.36-3.31 (m, 2H), 2.41-2.40 (m, 1H), 2.27-2.26 (m, 1H), 2.17-2.10 (m, 2H), 1.96-1.94 (m, 1H), 1.74 (s, 3H), 1.48 (s, 3H).

Example 47: (R)—N-(2,2-dimethylquinuclidin-3-yl)-6-isopropoxybenzo[b]thiophene-2-carboxamide hydrochloride ((R)-47)

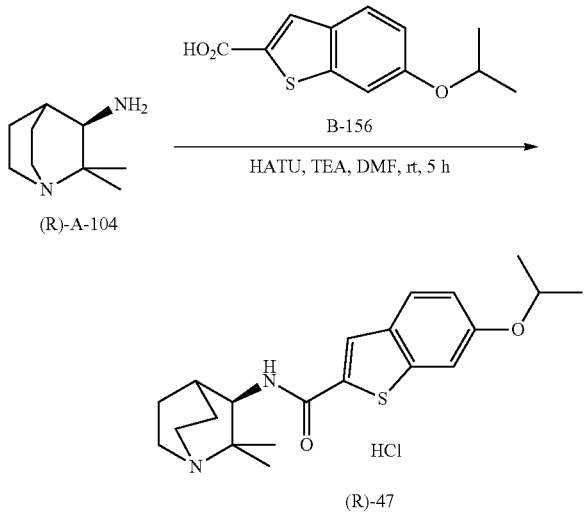

Following general procedure B, Compound (R)-47 was prepared from compound B-156 (77 mg, 0.33 mmol) and compound (R)-A-104 (50 mg, 0.33 mmol), with a reaction time of 5 hours. The product was purified by prep-HPLC [Instrument: GX-B; Column: YMC-pack ODS-AQ C18 150×30 mm, particle size: 5 µm; Mobile phase: 30-60% acetonitrile in H$_2$O (add 0.5% TFA, v/v)]. The combined fractions were treated with 0.2 M hydrochloric acid solution and lyophilized to give:

(R)—N-(2,2-dimethylquinuclidin-3-yl)-6-isopropoxybenzo[b]thiophene-2-carboxamide hydrochloride (compound (R)-47) (63 mg, 48% yield) as a yellow solid: cSFC analytical (A) tR=2.92 min., purity: 98.15%; LCMS (N): tR=2.367 min., (ES$^+$) m/z (M+H)$^+$=373.0; $^1$H-NMR (CD$_3$OD, 400 MHz): δ 8.02 (s, 1H), 7.76 (d, J=8.8 Hz, 1H), 7.42 (d, J=1.6 Hz, 1H), 7.02 (d, J=8.8, 2.0 Hz, 1H), 4.74-4.65 (m, 1H), 4.23 (s, 1H), 3.74-3.64 (m, 2H), 3.36-3.30 (m, 2H), 2.40-2.38 (m, 1H), 2.26-2.25 (m, 1H), 2.16-2.08 (m, 2H), 1.95-1.89 (m, 1H), 1.73 (s, 3H), 1.47 (s, 3H), 1.35 (d, J=6.0 Hz, 6H).

Example 48: (R)—N-(2,2-dimethylquinuclidin-3-yl)-6-(methylsulfonyl)benzo[b]thiophene-2-carboxamide hydrochloride ((R)-48)

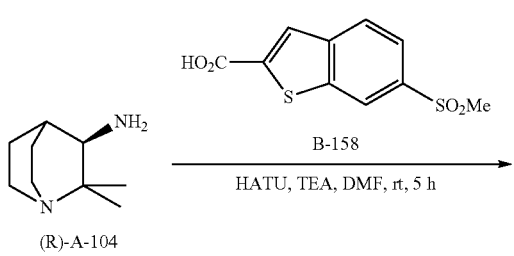

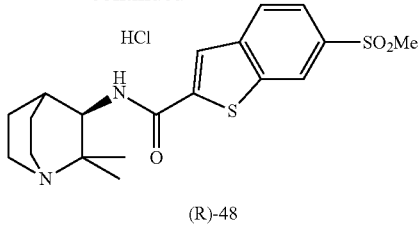

Following general procedure B, Compound (R)-48 was prepared from compound B-158 (83 mg, 0.32 mmol) and compound (R)-A-104 (50 mg, 0.32 mmol), with a reaction time of 5 hours. The product was purified by prep-HPLC [Instrument: GX-B; Column: YMC-pack ODS-AQ 150×30 mm, particle size: 5 µm; Mobile phase: 11-44% acetonitrile in H$_2$O (add 0.5% TFA, v/v)]. The combined fractions were treated with 0.2 N HCl and lyophilized to give:

(R)—N-(2,2-dimethylquinuclidin-3-yl)-6-(methylsulfonyl)benzo[b]thiophene-2-carboxamide hydrochloride (compound (R)-48) (35 mg, 25% yield) as a white solid: cSFC analytical (A) tR=3.27 min., purity: 100%; LCMS (M): tR=1.003 min., (ES$^+$) m/z (M+H)$^+$=393.0; $^1$H-NMR (CD$_3$OD, 400 MHz): δ 8.62 (s, 1H), 8.29 (s, 1H), 8.16 (d, J=8.4 Hz, 1H), 7.97 (dd, J$_1$=8.4 Hz, J$_2$=1.2 Hz, 1H), 4.27 (s, 1H), 3.74-3.68 (m, 2H), 3.38-3.31 (m, 2H), 3.20 (s, 3H), 2.43 (m, 1H), 2.30-2.29 (m, 1H), 2.18-2.08 (m, 2H), 1.98-1.92 (m, 1H), 1.76 (s, 3H), 1.51 (s, 3H).

Example 49

Preparation of (R)—N-(2,2-dimethylquinuclidin-3-yl)-6-nitrobenzo[b]thiophene-2-carboxamide ((R)-49-int)

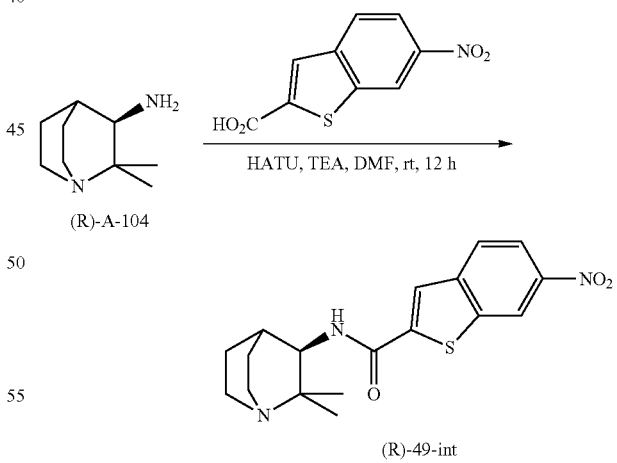

Following general procedure B, Compound (R)-49-int was prepared from 6-nitrobenzo[b]thiophene-2-carboxylic acid (72 mg, 0.32 mmol) and compound (R)-A-104 (50 mg, 0.32 mmol), with a reaction time of 12 hours. The product was purified by prep-HPLC [Instrument: GX-E; Column: Phenomenex SynergiC18 150×30 mm, particle size: 10 µm; Mobile phase: 10-40% acetonitrile in H$_2$O (add 0.5% HCl, v/v)] to give:

(R)—N-(2,2-dimethylquinuclidin-3-yl)-6-nitrobenzo[b]thiophene-2-carboxamide (compound (R)-49-int) (45 mg, 39% yield) as a white solid.

Preparation of (R)-6-amino-N-(2,2-dimethylquinuclidin-3-yl)benzo[b]thiophene-2-carboxamide hydrochloride ((R)-49)

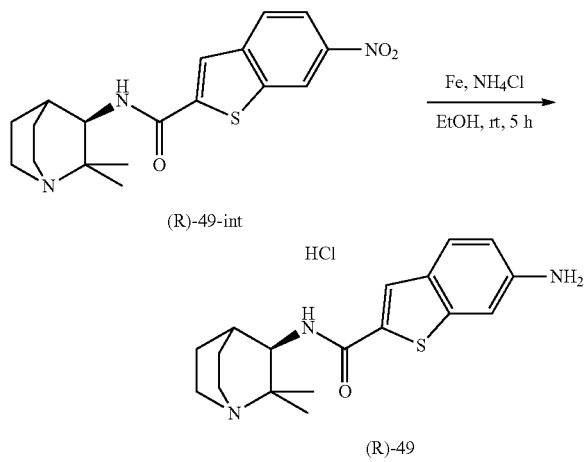

To a mixture of compound (R)-49-int (40 mg, 0.11 mmol) in EtOH (6 mL) was added iron (31 mg, 0.56 mmol) and saturated aqueous NH₄Cl (3 mL). The mixture was stirred at 25° C. for 5 hours. On completion, the mixture was filtered. The filtrate was concentrated in vacuo. The residue was purified by prep-HPLC [Instrument: GX-E; Column: Phenomenex SynergiC18 150×30 mm, particle size: 4 μm; Mobile phase: 10-40% acetonitrile in H$_2$O (add 0.5% HCl, v/v)] to give:

(R)-6-amino-N-(2,2-dimethylquinuclidin-3-yl)benzo[b]thiophene-2-carboxamide hydrochloride (compound (R)-49) (25 mg, 68% yield) as a white solid: cSFC analytical (C) tR=2.24 min., purity: 100%; LCMS (M): tR=0.812 min., (ES$^+$) m/z (M+H)$^+$=330.0; $^1$H-NMR (CD$_3$OD, 400 MHz): δ 8.22 (s, 1H), 8.04 (d, J=8.4 Hz, 1H), 7.89 (s, 1H), 7.37 (dd, J$_1$=8.4 Hz, J$_2$=1.6 Hz, 1H), 4.26 (s, 1H), 3.73-3.71 (m, 2H), 3.38-3.31 (m, 2H), 2.43 (m, 1H), 2.28-2.27 (m, 1H), 2.17-2.16 (m, 2H), 1.97-1.1 (m, 1H), 1.75 (s, 3H), 1.50 (s, 3H).

Example 50: (R)—N-(2,2-dimethylquinuclidin-3-yl)-6-(tetrahydro-2H-pyran-4-yl)benzo[b]thiophene-2-carboxamide hydrochloride ((R)-50)

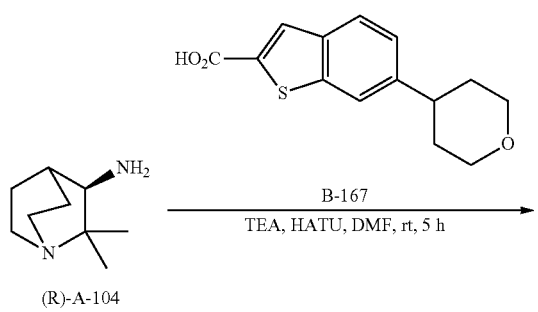

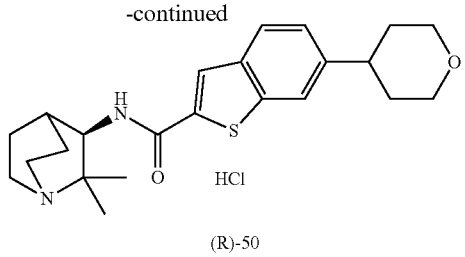

Following general procedure B, Compound (R)-50 was prepared from compound B-167 (54 mg, 0.33 mmol) and compound (R)-A-104 (50 mg, 0.33 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(R)—N-(2,2-dimethylquinuclidin-3-yl)-6-(tetrahydro-2H-pyran-4-yl)benzo[b]thiophene-2-carboxamide hydrochloride (compound (R)-50) (50 mg, 51% yield) as a white solid: cSFC analytical (A) tR=3.50 min., purity: 98.16%; LCMS (Y): tR=0.750 min., (ES$^+$) m/z (M+H)$^+$=399.1; $^1$H-NMR (CD$_3$OD, 400 MHz): δ 8.13 (s, 1H), 7.86 (d, J=8.4 Hz, 1H), 7.80 (s, 1H), 7.36-7.34 (m, 1H), 4.24 (s, 1H), 4.07-4.04 (m, 2H), 3.72-3.67 (m, 2H), 3.61-3.55 (m, 2H), 3.36-3.31 (m, 2H), 2.94-2.93 (m, 1H), 2.42-2.31 (m, 1H), 2.26-2.25 (m, 1H), 2.15-2.12 (m, 2H), 1.96-1.81 (m, 5H), 1.74 (s, 3H), 1.50 (s, 3H).

Example 51: (R)—N-(2,2-dimethylquinuclidin-3-yl)-7-fluoro-6-methoxybenzo[b]thiophene-2-carboxamide hydrochloride ((R)-51)

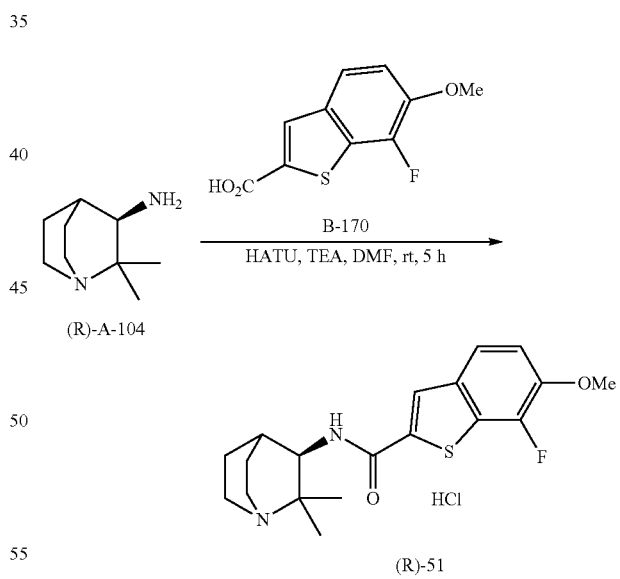

Following general procedure B, Compound (R)-51 was prepared from compound B-170 (73 mg, 0.32 mmol) and compound (R)-A-104 (50 mg, 0.32 mmol), with a reaction time of 5 hours. The product was purified by prep-HPLC [Instrument: GX-B; Column: YMC-pack ODS-AQ 150×30 mm, particle size: 5 μm; Mobile phase: 20-50% acetonitrile in H$_2$O (add 0.5% TFA, v/v)]. The combined fractions were treated with 0.2 N HCl and lyophilized to give:

(R)—N-(2,2-dimethylquinuclidin-3-yl)-7-fluoro-6-methoxybenzo[b]thiophene-2-carboxamide hydrochloride (compound (R)-51) (25 mg, 19% yield) as a white solid: cSFC analytical (A) tR=2.947 min., purity: 92.25%; LCMS (Y): tR=0.849 min., (ES+) m/z (M+H)+=363.0; $^1$H-NMR (CD$_3$OD, 400 MHz): δ 8.10 (d, J=3.2 Hz, 1H), 7.70 (d, J=8.4 Hz, 1H), 7.33 (t, J=8.0 Hz, 1H), 4.24 (s, 1H), 3.98 (s, 3H), 3.71-3.66 (m, 2H), 3.33 (m, 1H), 3.31 (m, 1H), 2.40-2.39 (m, 1H), 2.27-2.26 (m, 1H), 2.26-1.97 (m, 2H), 1.94-1.90 (m, 1H), 1.74 (m, 3H), 1.48 (s, 3H).

Example 52: (R)-7-chloro-N-(2,2-dimethylquinuclidin-3-yl)-6-methylbenzo[b]thiophene-2-carboxamide hydrochloride ((R)-52)

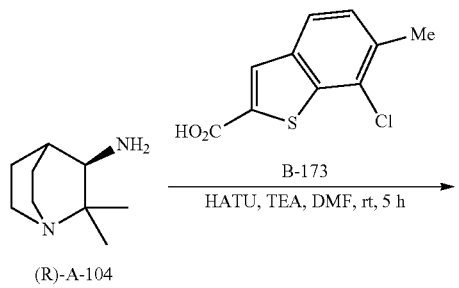

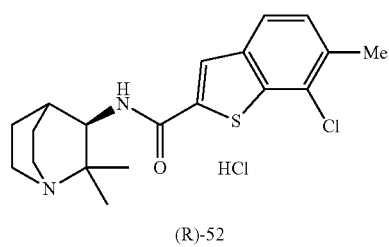

Following general procedure B, Compound (R)-52 was prepared from compound B-173 (73 mg, 0.32 mmol) and compound (R)-A-104 (50 mg, 0.32 mmol), with a reaction time of 5 hours. The product was purified by prep-HPLC [Instrument: GX-B; Column: YMC-pack ODS-AQ 150×30 mm, particle size: 5 μm; Mobile phase: 25-55% acetonitrile in H$_2$O (add 0.5% TFA, v/v)]. The combined fractions were treated with 0.2 N HCl and lyophilized to give:

(R)-7-chloro-N-(2,2-dimethylquinuclidin-3-yl)-6-methylbenzo[b]thiophene-2-carboxamide hydrochloride (compound (R)-52) (25 mg, 19% yield) as a white solid: cSFC analytical (A) tR=3.026 min., purity: 97.65%; LCMS (Y): tR=0.885 min., (ES+) m/z (M+H)+=363.0; $^1$H-NMR (CD$_3$OD, 400 MHz): δ 8.15 (s, 1H), 7.77 (d, J=8.4 Hz, 1H), 7.40 (d, J=8.0 Hz, 1H), 4.26 (s, 1H), 3.73-3.69 (m, 2H), 3.36-3.34 (m, 1H), 3.31-3.28 (m, 1H), 2.53 (s, 3H), 2.28 (m, 1H), 2.27 (m, 1H), 2.17-2.11 (m, 2H), 2.10-1.94 (m, 1H), 1.75 (s, 3H), 1.48 (s, 3H).

Example 53: (R)—N-(2,2-dimethylquinuclidin-3-yl)-7-fluoro-6-methylbenzo[b]thiophene-2-carboxamide hydrochloride ((R)-53)

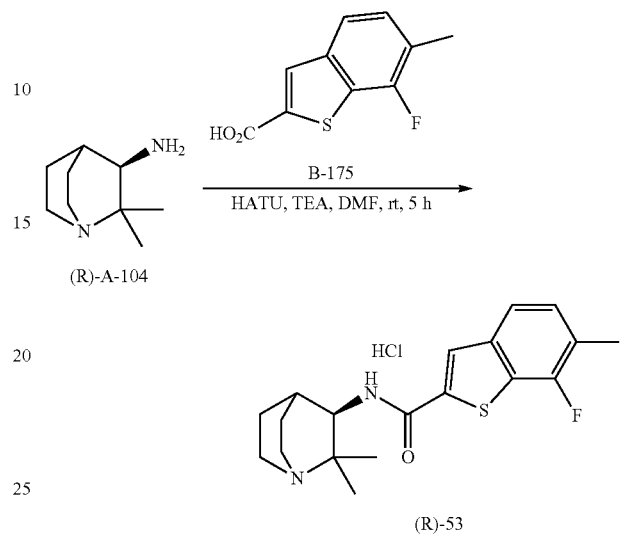

Following general procedure B, Compound (R)-53 was prepared from compound B-175 (68 mg, 0.32 mmol) and compound (R)-A-104 (50 mg, 0.32 mmol), with a reaction time of 5 hours. The product was purified by prep-HPLC [Instrument: GX-E; Column: Phenomenex Synergi C18 150×30 mm, particle size: 4 μm; Mobile phase: 19-49% acetonitrile in H$_2$O (add 0.5% HCl, v/v)] to give:

(R)—N-(2,2-dimethylquinuclidin-3-yl)-7-fluoro-6-methylbenzo[b]thiophene-2-carboxamide hydrochloride (compound (R)-53) (40 mg, 32% yield) as a white solid: cSFC analytical (A) tR=2.728 min., purity: 96.99%; LCMS (Y): tR=0.800 min., (ES+) m/z (M+H)+=347.0; $^1$H-NMR (CD$_3$OD, 400 MHz): δ 8.14 (d, J=3.6 Hz, 1H), 7.64 (d, J=8.0 Hz, 1H), 7.33 (t, J=7.6 Hz, 1H), 4.25 (s, 1H), 3.73-3.66 (m, 2H), 3.37-3.31 (m, 2H), 2.42-2.41 (m, 4H), 2.28-2.27 (m, 1H), 2.18-2.10 (m, 2H), 1.94 (m, 1H), 1.75 (s, 3H), 1.49 (s, 3H).

Example 54: (+/−)—N-(1'-azaspiro[cyclopropane-1,2'-bicyclo[2.2.2]octan]-3'-yl)benzo[b]thiophene-2-carboxamide (rac-54)

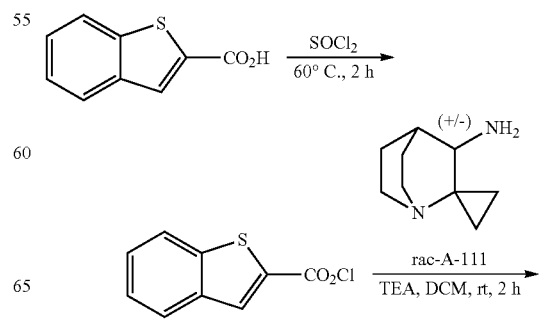

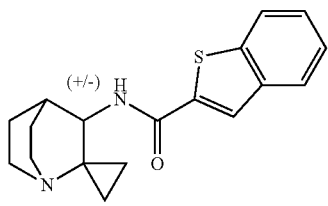

rac-54

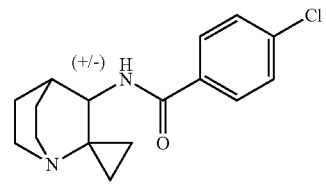

rac-55

Following general procedure A, rac-54 was prepared from benzo[b]thiophene-2-carboxylic acid and rac-A-111 (1.32 g, 8.6 mmol). The product was purified by prep-HPLC [Instrument: GX-A; Column: Phenomenex Gemini C18 150×25 mm, particle size: 10 μm; Mobile phase: 30-60% acetonitrile in H$_2$O (add 0.5% NH$_3$.H$_2$O, v/v)] to give rac-54 (1.6 g, 70% yield) as a white solid. LCMS: (ES$^+$) m/z (M+H)$^+$=313.1.

Chiral Separation:

Rac-54 (0.70 g, 0.22 mmol) in 5 mL of methanol was separated by SFC (Instrument: SFC 80; Column: OD-10 m; Mobile phase: 60% methanol (0.01% NH$_3$.H$_2$O) in CO$_2$) according to general procedure A to give:

N-(1'-azaspiro[cyclopropane-1,2'-bicyclo[2.2.2]octan]-3'-yl)benzo[b]thiophene-2-carboxamide-enantiomer1 hydrochloride (compound 54a) (0.33 g, 47% yield) as a white solid: cSFC analytical (A) tR=3.15 min., purity: 99.77%; LCMS (W): tR=0.990 min., (ES$^+$) m/z (M+H)$^+$=313.1; $^1$H-NMR (CD$_3$OD, 400 MHz): δ 8.18 (s, 1H), 7.94-7.91 (m, 2H), 7.48-7.43 (m, 2H), 4.57 (d, J=2.4 Hz, 1H), 3.74-3.58 (m, 1H), 3.57-3.42 (m, 3H), 2.44-2.43 (m, 1H), 2.35-1.95 (m, 4H), 1.40-1.18 (m, 4H); and N-(1'-azaspiro[cyclopropane-1,2'-bicyclo[2.2.2]octan]-3'-yl)benzo[b]thiophene-2-carboxamide-enantiomer2 hydrochloride (compound 54b) (0.33 g, 47% yield) as a white solid: cSFC analytical (A) tR=2.44 min., purity: 99.79%; LCMS (W): tR=0.986 min., (ES$^+$) m/z (M+H)$^+$=313.1; $^1$H-NMR (CD$_3$OD, 400 MHz): δ 8.17 (s, 1H), 7.94-7.91 (m, 2H), 7.48-7.43 (m, 2H), 4.57 (d, J=2.4 Hz, 1H), 3.74-3.57 (m, 1H), 3.56-3.42 (m, 3H), 2.45-2.43 (m, 1H), 2.35-1.98 (m, 4H), 1.40-1.18 (m, 4H).

Example 55: (+/−)-4-chloro-N-(1'-azaspiro[cyclopropane-1,2'-bicyclo[2.2.2]octan]-3'-yl)benzamide (rac-55)

Following general procedure A, rac-55 was prepared from 4-chlorobenzoic acid and rac-A-111 (0.45 g, 2.5 mmol). The product was purified by prep-HPLC [Instrument: GX-A; Column: Phenomenex Gemini C18 150×25 mm, particle size: 10 μm; Mobile phase: 30-60% acetonitrile in H$_2$O (add 0.5% NH$_3$.H2O, v/v)] to give rac-55 (0.36 g, 49% yield) as a white solid. LCMS: (ES$^+$) m/z (M+H)$^+$=291.2.

Chiral Separation:

Rac-55 (0.12 g, 0.41 mmol) in 3 mL of methanol was separated by SFC (Instrument: SFC 80; Column: OD-250× 30 mm, I.D., 10 μm; Mobile phase: 40% ethanol (0.01% NH$_3$.H$_2$O) in CO$_2$) according to general procedure A to give:

4-chloro-N-(1'-azaspiro[cyclopropane-1,2'-bicyclo[2.2.2]octan]-3'-yl)benzamide-enantiomer1 hydrochloride (compound 55a) (60 mg, 50% yield) as a white solid: cSFC analytical (A) tR: 2.39 min., purity: 98.47%; LCMS (M): tR=0.888 min., (ES$^+$) m/z (M+H)$^+$=291.0; $^1$H-NMR (DMSO-d6, 400 MHz): δ 10.16 (s, 1H), 8.55 (d, J=8.8 Hz, 1H), 7.87 (d, J=8.8 Hz, 2H), 7.57 (d, J=8.8 Hz, 2H), 4.36 (d, J=5.6 Hz, 1H), 3.52-3.28 (m, 3H), 2.25-1.74 (m, 5H), 1.31-1.26 (m, 3H), 1.03-0.97 (m, 2H); and 4-chloro-N-(1'-azaspiro[cyclopropane-1,2'-bicyclo[2.2.2]octan]-3'-yl)benzamide-enantiomer2 hydrochloride (compound 55b) (60 mg, 50% yield) as a white solid: cSFC analytical (A) tR: 1.85 min., purity: 99.15%; LCMS (M): tR=0.898 min., (ES$^+$) m/z (M+H)$^+$=291.0; $^1$H-NMR (DMSO-d6, 400 MHz): δ 10.54 (s, 1H), 8.56 (d, J=8.0 Hz, 1H), 7.88 (d, J=8.8 Hz, 2H), 7.55 (d, J=8.8 Hz, 2H), 4.35 (dd, J$_1$=8.0 Hz, J$_2$=2.8 Hz, 1H), 3.54-3.23 (m, 3H), 2.25-1.70 (m, 5H), 1.34-1.30 (m, 3H), 1.03-0.94 (m, 2H).

Example 56: (+/−)-7-chloro-N-(1'-azaspiro[cyclopropane-1,2'-bicyclo[2.2.2]octan]-3'-yl)benzo[b]thiophene-2-carboxamide (rac-56)

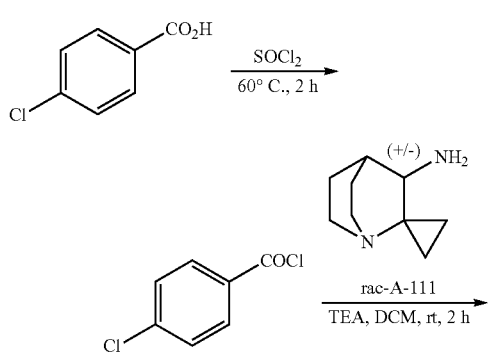

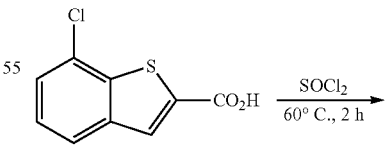

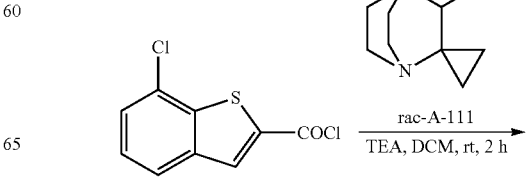

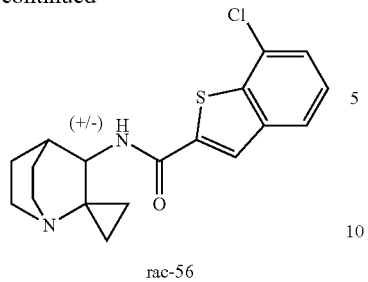

rac-56

Following general procedure A, rac-56 was prepared from 7-chlorobenzo[b]thiophene-2-carboxylic acid and rac-A-111 (0.14 g, 0.93 mmol). The product was purified by prep-HPLC [Instrument: GX-A; Column: Phenomenex Gemini C18 150×25 mm, particle size: 10 μm; Mobile phase: 45-75% acetonitrile in $H_2O$ (add 0.5% $NH_3.H_2O$, v/v)] to give rac-56 (0.15 g, 46% yield) as a white solid. LCMS: ($ES^+$) m/z $(M+H)^+=347.1$.

Chiral Separation:

Rac-56 (0.15 g, 0.43 mmol) in 5 mL of methanol was separated by SFC (Instrument: SFC 80; Column: Chiralpak OD-H 250×30 mm I.D., 10 μm; Mobile phase: 55% ethanol (0.01% $NH_3.H_2O$) in $CO_2$) according to general procedure A. The compounds were not treated with HCl but rather were isolated as the free bases:

7-chloro-N-(1'-azaspiro[cyclopropane-1,2'-bicyclo[2.2.2]octan]-3'-yl)benzo[b]thiophene-2-carboxamide-enantiomer1 (compound 56a) (62 mg, 41% yield) as a white solid: cSFC analytical (A) tR=2.59 min., purity: 100%; LCMS (G): tR=2.699 min., ($ES^+$) m/z $(M+H)^+=347.1$; $^1$H-NMR ($CD_3OD$, 400 MHz): δ 8.17 (s, 1H), 7.87 (d, J=7.6 Hz, 1H), 7.50-7.42 (m, 2H), 4.21 (d, J=1.6 Hz, 1H), 3.28-3.25 (m, 1H), 3.08-3.07 (m, 1H), 2.93-2.85 (m, 2H), 2.11 (m, 1H), 2.01-1.93 (m, 1H), 1.87-1.84 (m, 2H), 1.61-1.53 (m, 1H), 0.91-0.87 (m, 2H), 0.78-0.75 (m, 1H), 0.70-0.64 (m, 1H); and 7-chloro-N-(1'-azaspiro[cyclopropane-1,2'-bicyclo[2.2.2]octan]-3'-yl)benzo[b]thiophene-2-carboxamide-enantiomer2 (compound 56b) (62 mg, 41% yield) as a white solid: cSFC analytical (B) tR=3.71 min., purity: 99.79%; LCMS (G): tR=2.697 min., ($ES^+$) m/z $(M+H)^+=347.1$; $^1$H-NMR ($CD_3OD$, 400 MHz): δ 8.19 (s, 1H), 7.88 (d, J=7.6 Hz, 1H), 7.52-7.44 (m, 2H), 4.23 (d, J=2.0 Hz, 1H), 3.29-3.28 (m, 1H), 3.11-3.07 (m, 1H), 2.97-2.87 (m, 2H), 2.14-2.13 (m, 1H), 2.03-1.96 (m, 1H), 1.90-1.86 (m, 2H), 1.63-1.55 (m, 1H), 0.95-0.89 (m, 2H), 0.80-0.77 (m, 1H), 0.72-0.70 (m, 1H).

Example 57: (+/−)-7-fluoro-N-(1'-azaspiro[cyclopropane-1,2'-bicyclo[2.2.2]octan]-3'-yl)benzo[b]thiophene-2-carboxamide (rac-57)

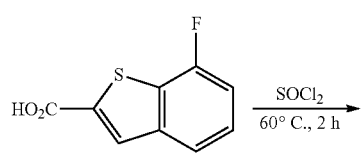

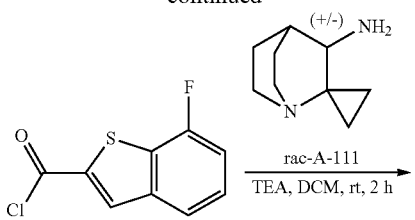

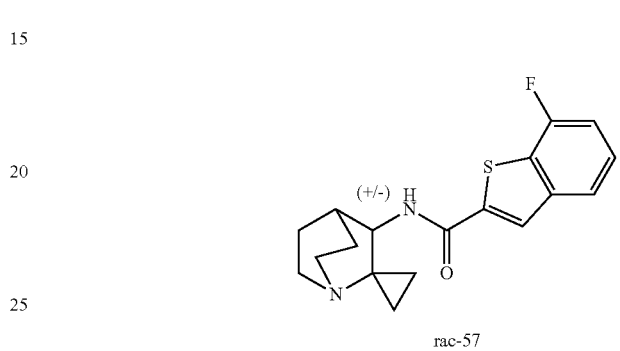

rac-57

Following general procedure A, rac-57 was prepared from benzo[b]thiophene-2-carboxylic acid and rac-A-111 (0.22 g, 1.4 mmol). The product was purified by prep-HPLC [Instrument: GX-C; Column: Phenomenex Gemini C18 150×30 mm, particle size: 5 μm; Mobile phase: 35-65% acetonitrile in $H_2O$ (add 0.5% $NH_3.H_2O$, v/v)] to give rac-57 (0.16 g, 34% yield) as a white solid. LCMS: ($ES^+$) m/z $(M+H)^+=331.0$.

Chiral Separation:

Rac-57 (0.16 g, 0.48 mmol) in 3 mL of methanol was separated by SFC (Instrument: SFC 80; Column: AD-10 m; Mobile phase: 30% methanol (0.01% $NH_3.H_2O$) in $CO_2$) according to general procedure A to give:

7-fluoro-N-(1'-azaspiro[cyclopropane-1,2'-bicyclo[2.2.2]octan]-3'-yl)benzo[b]thiophene-2-carboxamide-enantiomer1 hydrochloride (compound 57a) (0.02 g, 13% yield) as a white solid: cSFC analytical (A) tR: 2.22 min., purity: 99.96%; LCMS (N): tR: 1.994 min., ($ES^+$) m/z $(M+H)^+=331.0$; $^1$H-NMR (MeOD, 400 MHz): δ 8.27 (d, J=3.6 Hz, 1H), 7.54 (d, J=8 Hz, 1H), 7.46-7.40 (m, 1H), 7.21-7.17 (m, 1H), 4.56 (d, J=3.6 Hz, 1H), 3.79-3.72 (m, 1H), 3.56-3.54 (m, 1H), 3.49-3.40 (m, 2H), 2.43-2.42 (m, 1H), 2.38-2.33 (m, 1H), 2.20-2.13 (m, 2H), 2.02-1.94 (m, 1H), 1.45-1.39 (m, 1H), 1.35-1.34 (m, 1H), 1.26-1.24 (m, 1H), 1.18-1.15 (m, 1H); and 7-fluoro-N-(1'-azaspiro[cyclopropane-1,2'-bicyclo[2.2.2]octan]-3'-yl)benzo[b]thiophene-2-carboxamide-enantiomer2 hydrochloride (compound 57b) (0.02 g, 13% yield) as a white solid: cSFC analytical (A) tR: 3.11 min., purity: 98.46%; LCMS (N): tR: 2.101 min., ($ES^+$) m/z $(M+H)^+=331.0$; $^1$H-NMR (MeOD, 400 MHz): δ 8.23 (d, J=3.2 Hz, 1H), 7.76 (d, J=8 Hz, 1H), 7.48-7.43 (m, 1H), 7.24-7.20 (m, 1H), 4.57 (d, J=2.4 Hz, 1H), 3.76-3.71 (m, 1H), 3.58-3.57 (m, 1H), 3.49-3.42 (m, 2H), 2.46-2.44 (m, 1H), 2.38-2.33 (m, 1H), 2.23-2.17 (m, 2H), 2.00-1.95 (m, 1H), 1.39-1.36 (m, 1H), 1.29-1.27 (m, 1H), 1.26-1.24 (m, 1H), 1.21-1.19 (m, 1H).

Example 58: (+/−)—N-(1'-azaspiro[cyclopropane-1,2'-bicyclo[2.2.2]octan]-3'-yl)benzo[b]thiophene-6-carboxamide (rac-58)

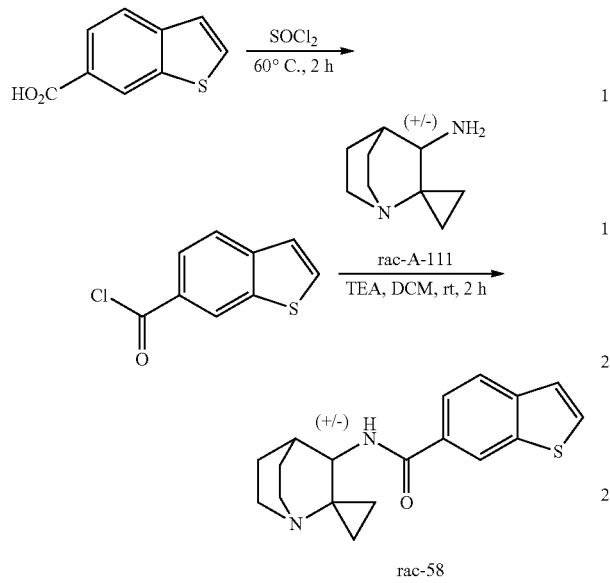

rac-58

Following general procedure A, rac-58 was prepared from benzo[b]thiophene-6-carboxylic acid and rac-A-111 (0.15 g, 0.99 mmol). The product was purified by prep-HPLC [Instrument: GX-A; Column: Phenomenex Gemini C18 150×25 mm, particle size: 10 μm; Mobile phase: 25-55% acetonitrile in $H_2O$ (add 0.5% $NH_3.H_2O$, v/v)] to give rac-58 (70 mg, 23% yield) as a white solid. LCMS: $(ES^+)$ m/z $(M+H)^+$= 313.2.

Chiral Separation:

Rac-58 (70 mg, 0.22 mmol) in 3 mL of methanol was separated by SFC (Instrument: SFC 80; Column: Chiralpak OD-H 250×30 mm I.D., 10 μm; Mobile phase: 50% ethanol (0.01% $NH_3.H_2O$) in $CO_2$) according to general procedure A. The compounds were not treated with HCl but rather were isolated as the free bases:

N-(1'-azaspiro[cyclopropane-1,2'-bicyclo[2.2.2]octan]-3'-yl)benzo[b]thiophene-6-carboxamide-enantiomer1 (compound 58a) (20 mg, 29% yield) as a white solid: cSFC analytical (A) tR=2.55 min., purity: 100%; LCMS (G): tR=2.230 min., $(ES^+)$ m/z $(M+H)^+$=313.1; $^1$H-NMR ($CD_3OD$, 400 MHz): δ 8.40 (s, 1H), 7.92 (d, J=8.4 Hz, 1H), 7.81-7.76 (m, 2H), 7.45 (d, J=5.6 Hz, 1H), 4.23 (d, J=2.0 Hz, 1H), 3.27-3.21 (m, 1H), 3.08-3.06 (m, 1H), 2.90-2.84 (m, 2H), 2.12-2.11 (m, 1H), 2.00-1.94 (m, 1H), 1.90-1.84 (m, 2H), 1.58-1.51 (m, 1H), 0.91-0.85 (m, 2H), 0.75-0.66 (m, 2H); and N-(1'-azaspiro[cyclopropane-1,2'-bicyclo[2.2.2]octan]-3'-yl)benzo[b]thiophene-6-carboxamide-enantiomer2 (compound 58b) (19 mg, 27% yield) as a white solid: cSFC analytical (A) tR=3.32 min., purity: 98.60%; LCMS (G): tR=2.225 min., $(ES^+)$ m/z $(M+H)^+$=313.1; $^1$H-NMR ($CD_3OD$, 400 MHz): δ 8.40 (s, 1H), 7.92 (d, J=8.8 Hz, 1H), 7.81-7.76 (m, 2H), 7.45 (d, J=5.6 Hz, 1H), 4.23 (d, J=1.6 Hz, 1H), 3.28-3.23 (m, 1H), 3.11-3.06 (m, 1H), 2.90-2.84 (m, 2H), 2.12-2.11 (m, 1H), 1.99-1.94 (m, 1H), 1.89-1.80 (m, 2H), 1.58-1.54 (m, 1H), 0.91-0.85 (m, 2H), 0.77-0.66 (m, 2H).

Example 59

Preparation of (+/−)—N-(1'-azaspiro[cyclopropane-1,2'-bicyclo[2.2.2]octan]-3'-yl)benzofuran-5-carboxamide (rac-59)

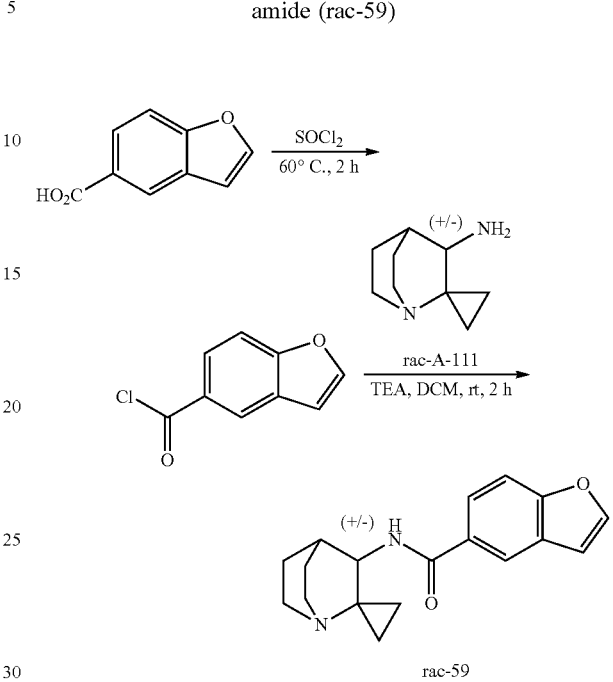

rac-59

Following general procedure A, rac-59 was prepared from benzofuran-5-carboxylic acid and rac-A-111 (0.19 g, 1.2 mmol). The product was purified by prep-HPLC [Instrument: GX-A; Column: Phenomenex Gemini C18 150×25 mm, particle size: 10 μm; Mobile phase: 22-52% acetonitrile in $H_2O$ (add 0.5% $NH_3.H_2O$, v/v)] to give rac-59 (0.10 g, 27% yield) as a white solid. LCMS: $(ES^+)$ m/z $(M+H)^+$= 297.2.

Chiral Separation:

Rac-59 (0.10 g, 0.34 mmol) in 4 mL of methanol was separated by SFC (Instrument: SFC 80; Column: Chiralpak AD-H 250×30 mm I.D., 10 μm; Mobile phase: 30% ethanol (0.01% $NH_3.H_2O$) in $CO_2$) according to general procedure A. The compounds were not treated with HCl but rather were isolated as the free bases:

N-(1'-azaspiro[cyclopropane-1,2'-bicyclo[2.2.2]octan]-3'-yl)benzofuran-5-carboxamide-enantiomer1 (compound 59a) (38 mg, 38% yield) as a white solid: cSFC analytical (G) tR=2.28 min., purity: 99.03%; LCMS (G): tR=2.010 min., $(ES^+)$ m/z $(M+H)^+$=297.2; $^1$H-NMR ($CD_3OD$, 400 MHz): δ 8.11 (s, 1H), 7.85 (d, J=1.6 Hz, 1H), 7.77 (d, J=8.8 Hz, 1H), 7.57 (d, J=8.8 Hz, 1H), 6.95 (s, 1H), 4.21 (s, 1H), 3.26-3.21 (m, 1H), 3.07-3.04 (m, 1H), 2.91-2.84 (m, 2H), 2.11-2.10 (m, 1H), 1.99-1.94 (m, 1H), 1.86-1.80 (m, 2H), 1.58-1.50 (m, 1H), 0.90-0.85 (m, 2H), 0.74-0.65 (m, 2H); and N-(1'-azaspiro[cyclopropane-1,2'-bicyclo[2.2.2]octan]-3'-yl)benzofuran-5-carboxamide-enantiomer2 (compound 59b) (37 mg, 37% yield) as a white solid: cSFC analytical (G) tR=2.55 min., purity: 97.24%; LCMS (G): tR=2.008 min., $(ES^+)$ m/z $(M+H)^+$=297.1; $^1$H-NMR ($CD_3OD$, 400 MHz): δ 8.11 (s, 1H), 7.85 (d, J=1.6 Hz, 1H), 7.77 (d, J=8.8 Hz, 1H), 7.57 (d, J=8.8 Hz, 1H), 6.95 (s, 1H), 4.21 (s, 1H), 3.26-3.21 (m, 1H), 3.07-3.04 (m, 1H), 2.91-2.84 (m, 2H), 2.11-2.10 (m, 1H), 1.96-1.94 (m, 1H), 1.86-1.80 (m, 2H), 1.58-1.50 (m, 1H), 0.90-0.85 (m, 2H), 0.74-0.65 (m, 2H).

Preparation of (R)—N-(1'-azaspiro[cyclopropane-1,2'-bicyclo[2.2.2]octan]-3'-yl)benzofuran-5-carboxamide hydrochloride ((R)-59)

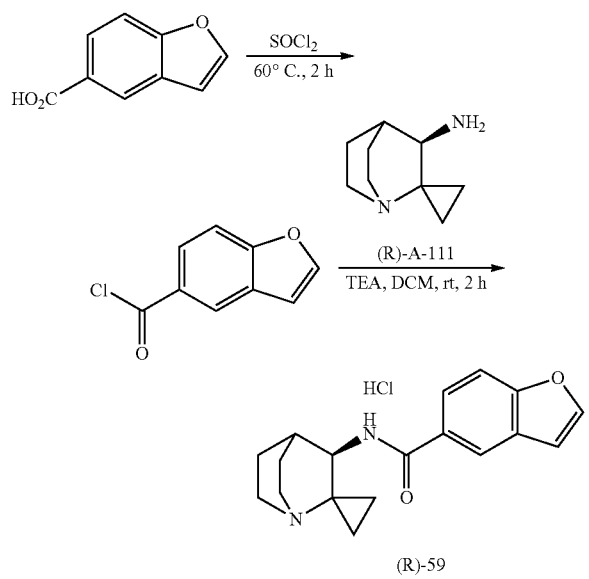

(R)-59

A mixture of benzofuran-5-carboxylic acid (0.25 g, 1.5 mmol) in thionyl chloride (3 mL) was stirred at 60° C. for 2 hours. On completion, the solution was concentrated in vacuo to give the acid chloride, which was used directly without further purification. This material (1.1 eq) was added to a mixture of compound (R)-A-111 (0.20 g, 1.3 mmol) and triethylamine (0.27 g, 2.6 mmol) in dichloromethane (5 mL) at room temperature. The mixture was stirred at this temperature for 2 hours. On completion, the reaction was filtered, and the resulting filtrate was concentrated and purified by prep-HPLC [Instrument: GX-E; Column: Phenomenex Synergi C18 150×30 mm, particle size: 4 μm; Mobile phase: 4-34% acetonitrile in H₂O (add 0.5% HCl, v/v)] to give:

(R)—N-(1'-azaspiro[cyclopropane-1,2'-bicyclo[2.2.2]octan]-3'-yl)benzofuran-5-carboxamide hydrochloride (compound (R)-59) (0.22 g, 57% yield) as white solid: cSFC analytical (A) tR=2.05 min., purity: 97.22%; LCMS (Z): tR=1.424 min., (ES$^+$) m/z (M+H)$^+$=297.0; $^1$H-NMR (CD$_3$OD, 400 MHz): δ 8.17 (d, J=1.6 Hz, 1H), 7.88 (d, J=2.0 Hz, 1H), 7.81 (dd, J$_1$=8.4 Hz, J$_2$=1.6 Hz, 1H), 7.59 (d, J=8.8 Hz, 1H), 6.96 (d, J=1.2 Hz, 1H), 4.58 (d, J=2.4 Hz, 1H), 3.70-3.68 (m, 1H), 3.57-3.56 (m, 1H), 3.46-3.42 (m, 2H), 2.46-2.44 (m, 1H), 2.32-2.31 (m, 1H), 2.22-2.18 (m, 2H), 1.99-1.98 (m, 1H), 1.42-1.39 (m, 1H), 1.30-1.20 (m, 3H).

Example 60: (+/−)—N-(1'-azaspiro[cyclopropane-1,2'-bicyclo[2.2.2]octan]-3'-yl)-7-(trifluoromethyl)benzo[b]thiophene-2-carboxamide (rac-60)

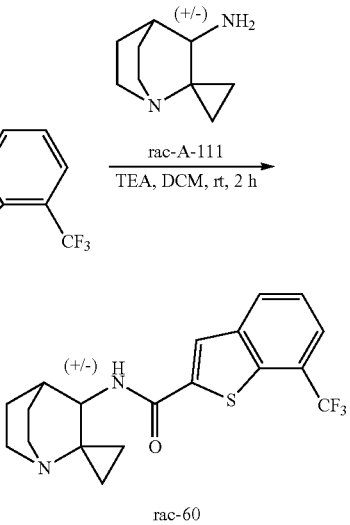

rac-60

Following general procedure A, rac-60 was prepared from 7-(trifluoromethyl)benzo[b]thiophene-2-carboxylic acid and rac-A-111 (0.10 g, 0.65 mmol). The product was purified by prep-HPLC [Instrument: GX-C; Column: Phenomenex Gemini C18 150×30 mm, particle size: 5 μm; Mobile phase: 35-65% acetonitrile in H₂O (add 0.5% NH₃.H2O, v/v)] to give rac-60 (0.18 g, 72% yield) as a white solid. LCMS: (ES$^+$) m/z (M+H)$^+$=381.4.

Chiral Separation:
Rac-60 (0.18 g, 0.47 mmol) in 3 mL of ethanol was separated by SFC (Instrument: SFC 80; Column: Chiralpak OD-H 250×25 mm I.D., 10 m; Mobile phase: 60% ethanol (0.1% NH₃H₂O) in CO₂) according to general procedure A. The compounds were not treated with HCl but rather were isolated as the free bases:

N-(1'-azaspiro[cyclopropane-1,2'-bicyclo[2.2.2]octan]-3'-yl)-7-(trifluoromethyl)benzo[b]thiophene-2-carboxamide-enantiomer1 (compound 60a) (86 mg, 48% yield) as a white solid: cSFC analytical (A) tR=2.00 min., purity: 99.80%; LCMS (J): tR=1.470 min., (ES$^+$) m/z (M+H)$^+$=381.4; $^1$H-NMR (CD$_3$OD-d$_4$, 400 MHz): δ 8.25 (s, 1H), 8.19 (d, J=7.2 Hz, 1H), 7.83 (d, J=7.2 Hz, 1H), 7.63 (t, J=7.2 Hz, 1H), 4.23 (s, 1H), 3.27 (m, 1H), 3.10-3.08 (m, 1H), 2.95-2.85 (m, 2H), 2.13 (s, 1H), 2.00-1.87 (m, 3H), 1.58 (m, 1H), 0.91 (m, 2H), 0.82-0.69 (m, 2H); and N-(1'-azaspiro[cyclopropane-1,2'-bicyclo[2.2.2]octan]-3'-yl)-7-(trifluoromethyl)benzo[b]thiophene-2-carboxamide-enantiomer2 (compound 60b) (78 mg, 43% yield) as a white solid: cSFC analytical (A) tR=3.18 min., purity: 99.89%; LCMS (J): tR=1.470 min., (ES$^+$) m/z (M+H)$^+$=381.4; $^1$H-NMR (CD$_3$OD-d$_4$, 400 MHz): δ 8.24 (s, 1H), 8.18 (d, J=8.0 Hz, 1H), 7.82 (d, J=7.6 Hz, 1H), 7.63 (t, J=7.6 Hz, 1H), 4.23 (s, 1H), 3.28-3.26 (m, 1H), 3.11-3.06 (m, 1H), 2.95-2.84 (m, 2H), 2.13 (s, 1H), 2.06-1.86 (m, 3H), 1.62-1.58 (m, 1H), 0.9-0.76 (m, 2H), 0.70-0.65 (m, 2H).

Example 61: (+/−)-6-fluoro-N-(1'-azaspiro[cyclopropane-1,2'-bicyclo[2.2.2]octan]-3'-yl)benzo[b]thiophene-2-carboxamide (rac-61)

-continued

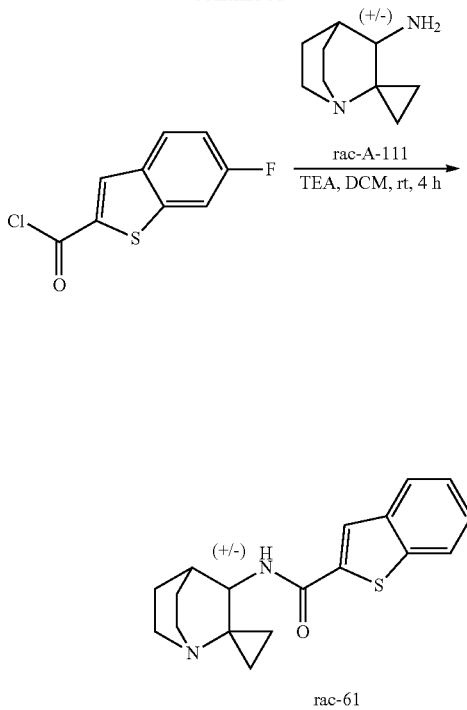

Example 62

Preparation of (+/−)-6-nitro-N-(1'-azaspiro[cyclopropane-1,2'-bicyclo[2.2.2]octan]-3'-yl)benzo[b]thiophene-2-carboxamide (rac-62-int)

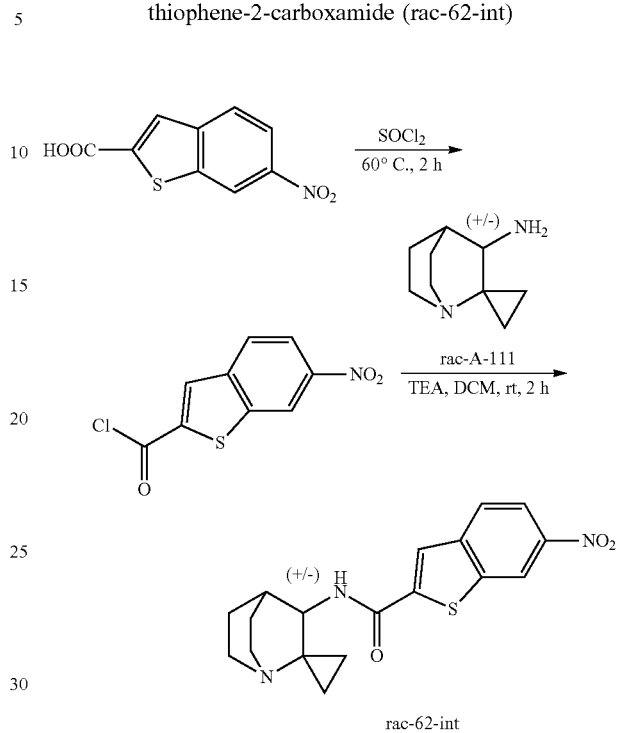

Following general procedure A, rac-61 was prepared from 6-fluorobenzo[b]thiophene-2-carboxylic acid and rac-A-111 (0.20 g, 1.3 mmol). The product was purified by prep-HPLC [Instrument: GX-A; Column: Phenomenex Gemini C18 150×25 mm, particle size: 10 μm; Mobile phase: 40-70% acetonitrile in H$_2$O (add 0.5% NH$_3$.H$_2$O, v/v)] to give rac-61 (0.16 g, 40% yield) as a green solid.

Chiral Separation:

Rac-61 (0.16 g, 0.48 mmol) in 3 mL of methanol was separated by SFC (Instrument: SFC 80; Column: Chiralpak OD-H 250×25 mm I.D., 10 μm; Mobile phase: 50% ethanol (0.01% NH$_3$.H$_2$O) in CO$_2$) according to general procedure A. The compounds were not treated with HCl but rather were isolated as the free bases:

6-fluoro-N-(1'-azaspiro[cyclopropane-1,2'-bicyclo[2.2.2]octan]-3'-yl)benzo[b]thiophene-2-carboxamide-enantiomer1 (compound 61a) (50 mg, 31% yield) as a white solid: cSFC analytical (A) tR=2.17 min., purity: 99.53%; LCMS (J): tR=1.287 min., (ES$^+$) m/z (M+H)$^+$=331.1; $^1$H-NMR (CD3OD, 400 MHz): δ 8.11 (s, 1H), 7.92 (dd, J$_1$=8.8 Hz, J$_2$=5.6 Hz, 1H), 7.70 (d, J=8.8 Hz, 1H), 7.24 (td, J=8.8 Hz, 1H), 4.22 (s, 1H), 3.28-3.26 (m, 1H), 3.10-3.08 (m, 1H), 2.95-2.89 (m, 2H), 2.12 (s, 1H), 2.03-1.94 (m, 1H), 1.89-1.85 (m, 2H), 1.62-1.55 (m, 1H), 0.94-0.88 (m, 2H), 0.78-0.76 (m, 1H), 0.75-0.68 (m, 1H); and 6-fluoro-N-(1'-azaspiro[cyclopropane-1,2'-bicyclo[2.2.2]octan]-3'-yl)benzo[b]thiophene-2-carboxamide-enantiomer2 (compound 61b) (50 mg, 31% yield) as a white solid: cSFC analytical (A) tR=3.24 min., purity: 99.79%; LCMS (J): tR=1.285 min., (ES$^+$) m/z (M+H)$^+$=331.1; $^1$H-NMR (CD3OD, 400 MHz): δ 8.11 (s, 1H), 7.93 (dd, J$_1$=8.8 Hz, J$_2$=5.2 Hz, 1H), 7.70 (dd, J=8.8 Hz, 1H), 7.24 (td, J=8.8 Hz, 1H), 4.22 (s, 1H), 3.30-3.27 (m, 1H), 3.11-3.09 (m, 1H), 2.97-2.86 (m, 2H), 2.12 (s, 1H), 2.04-1.96 (m, 1H), 1.90-1.86 (m, 2H), 1.63-1.59 (m, 1H), 0.95-0.89 (m, 2H), 0.79-0.78 (m, 1H), 0.72-0.69 (m, 1H).

Following general procedure A, rac-62-int was prepared from 6-nitrobenzo[b]thiophene-2-carboxylic acid and rac-A-111 (0.29 g, 1.9 mmol). The product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H2O, v/v)] to give rac-62-int (0.39 g, 57% yield) as a white solid. LCMS: (ES$^+$) m/z (M+H)$^+$=358.0.

Preparation of (+/−)-6-amino-N-(1'-azaspiro[cyclopropane-1,2'-bicyclo[2.2.2]octan]-3'-yl)benzo[b]thiophene-2-carboxamide (rac-62)

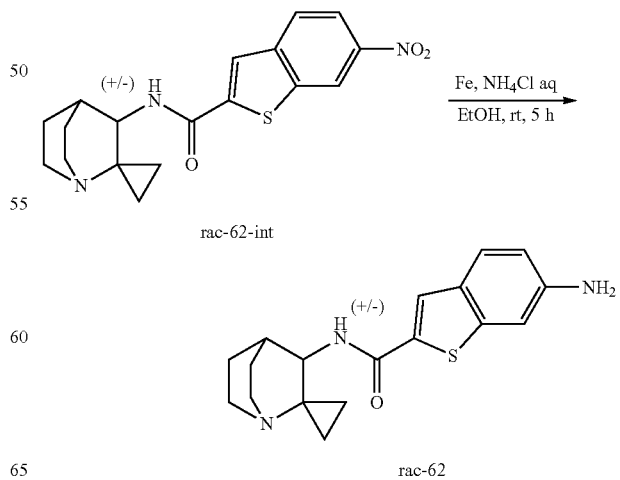

To a mixture of rac-62-int (0.39 g, 54 mmol) in ethanol (200 mL) was added iron powder (0.43 g, 7.6 mmol) and saturated aqueous ammonium chloride solution. The mixture was stirred at room temperature for 5 hours. On completion, the product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H2O, v/v)] to give rac-62 (0.10 g, 28% yield) as a white solid. LCMS: (ES$^+$) m/z (M+H)$^+$= 328.2.

Chiral Separation:

Rac-62 (0.10 g, 0.30 mmol) in 3 mL of methanol was separated by SFC (Instrument: SFC 80; Column: AD-10 m; Mobile phase: 30% methanol (0.01% NH$_3$.H$_2$O) in CO$_2$) according to general procedure A to give:

6-amino-N-(1'-azaspiro[cyclopropane-1,2'-bicyclo[2.2.2]octan]-3'-yl)benzo[b]thiophene-2-carboxamide-enantiomer1 hydrochloride (compound 62a) (20 mg, 20% yield) as a white solid: cSFC analytical (F) tR=3.15 min., purity: 99.67%; LCMS (N): tR=1.289 min., (ES$^+$) m/z (M+H)$^+$=328.0; $^1$H-NMR (CD$_3$OD, 400 MHz): δ 8.35 (s, 1H), 8.09 (d, J=8.4 Hz, 1H), 8.03 (s, 1H), 7.47 (d, J=8.4 Hz, 1H), 4.56 (s, 1H), 3.83-3.76 (m, 1H), 3.56-3.52 (m, 1H), 3.49-3.39 (m, 2H), 2.43-2.35 (m, 2H), 2.20-2.14 (m, 2H), 2.02-1.95 (m, 1H), 1.45-1.36 (m, 2H), 1.27-1.25 (m, 1H), 1.15-1.12 (m, 1H); and 6-amino-N-(1'-azaspiro[cyclopropane-1,2'-bicyclo[2.2.2]octan]-3'-yl)benzo[b]thiophene-2-carboxamide-enantiomer2 hydrochloride (compound 62b) (20 mg, 20% yield) as a white solid: cSFC analytical (F) tR=3.94 min., purity: 96.35%; LCMS (N): tR=1.279 min., (ES$^+$) m/z (M+H)$^+$=328.0; $^1$H-NMR (CD$_3$OD, 400 MHz): δ 8.29 (s, 1H), 8.11 (d, J=8.4 Hz, 1H), 8.01 (s, 1H), 7.46 (d, J=8.8 Hz, 1H), 4.57 (s, 1H), 3.78-3.74 (m, 1H), 3.58-3.49 (m, 1H), 3.47-3.41 (m, 2H), 2.46-2.43 (m, 1H), 2.36-2.30 (m, 1H), 2.23-2.16 (m, 2H), 2.01-1.98 (m, 1H), 1.42-1.38 (m, 1H), 1.31-1.24 (m, 2H), 1.20-1.17 (m, 1H).

Example 63: (+/−)—N-(1'-azaspiro[cyclopropane-1,2'-bicyclo[2.2.2]octan]-3'-yl)-6-(trifluoromethyl)benzo[b]thiophene-2-carboxamide (rac-63)

Following general procedure A, Compound rac-63 was prepared from 6-(trifluoromethyl)benzo[b]thiophene-2-carboxylic acid and rac-A-111 (0.10 g, 0.65 mmol). The product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H2O, v/v)] to give rac-63 (0.16 g, 64% yield) as a white solid.

Chiral Separation:

Racemate rac-63 (0.16 g, 0.26 mmol) in 3 mL of ethanol was separated by SFC (Instrument: SFC 80; Column: Chiralpak OD-H 250×25 mm I.D., 10 m; Mobile phase: 60% ethanol (0.1% NH$_3$.H2O) in CO$_2$) according to general procedure A. The compounds were not treated with HCl but rather were isolated as the free bases:

N-(1'-azaspiro[cyclopropane-1,2'-bicyclo[2.2.2]octan]-3'-yl)-6-(trifluoromethyl)benzo[b]thiophene-2-carboxamide-enantiomer1 (compound 63a) (62 mg, 62% yield) as a white solid: cSFC analytical (A) tR=1.95 min., purity: 99.08%; LCMS (J): tR=1.415 min., (ES$^+$) m/z (M+H)$^+$=381.4; $^1$H-NMR (CD3OD, 400 MHz): δ 8.31 (s, 1H), 8.19 (s, 1H), 8.07 (d, J=8.0 Hz, 1H), 7.67 (d, J=8.0 Hz, 1H), 4.23 (s, 1H), 3.27 (m, 1H), 3.08-3.07 (m, 1H), 2.94-2.84 (m, 2H), 2.20 (s, 1H), 2.12-1.85 (m, 3H), 1.58 (m, 1H), 0.91-0.69 (m, 4H); and N-(1'-azaspiro[cyclopropane-1,2'-bicyclo[2.2.2]octan]-3'-yl)-6-(trifluoromethyl)benzo[b]thiophene-2-carboxamide-enantiomer2 (compound 63b) (33 mg, 21% yield) as a white solid: cSFC analytical (A) tR=3.53 min., purity: 99.77%; LCMS (J): tR=1.41 min., (ES$^+$) m/z (M+H)$^+$=381.4; $^1$H-NMR (CD3OD, 400 MHz): δ 8.34 (s, 1H), 8.21 (s, 1H), 8.09 (d, J=8.4 Hz, 1H), 7.69 (d, J=8.8 Hz, 1H), 4.23 (s, 1H), 3.28-3.25 (m, 1H), 3.09-3.08 (m, 1H), 2.96-2.87 (m, 2H), 2.13 (s, 1H), 2.03-1.82 (m, 3H), 1.62-1.55 (m, 1H), 0.94-0.89 (m, 2H), 0.79-0.67 (m, 2H).

Example 64: (+/−)-5-fluoro-N-(1'-azaspiro[cyclopropane-1,2'-bicyclo[2.2.2]octan]-3'-yl)benzo[b]thiophene-2-carboxamide (rac-64)

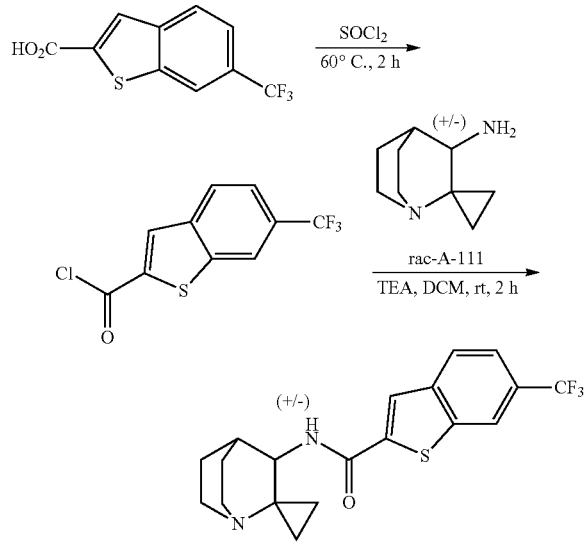

rac-63

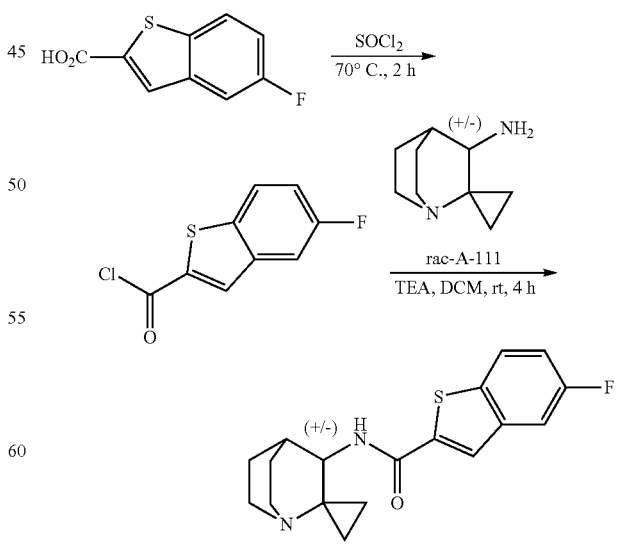

rac-64

Following general procedure A, rac-64 was prepared from 5-fluorobenzo[b]thiophene-2-carboxylic acid and rac-A-111 (0.20 g, 1.3 mmol), with a reaction time of 4 hours in the second step. The product was purified by prep-HPLC [Instrument: GX-A; Column: Phenomenex Gemini C18 150×25 mm, particle size: 10 µm; Mobile phase: 38-68% acetonitrile in H$_2$O (add 0.5% NH$_3$.H2O, v/v)] to give rac-64 (0.16 g, 40% yield) as a brown solid.

Chiral Separation:

Rac-64 (0.16 g, 0.48 mmol) in 3 mL of methanol was separated by SFC (Instrument: SFC 80; Column: Chiralpak OD-H 250×25 mm I.D., 10 µm; Mobile phase: 35% methanol (0.01% NH$_3$H$_2$O) in CO$_2$) according to general procedure A. The compounds were not treated with HCl but rather were isolated as the free bases:

5-fluoro-N-(1'-azaspiro[cyclopropane-1,2'-bicyclo[2.2.2]octan]-3'-yl)benzo[b]thiophene-2-carboxamide-enantiomer1 (compound 64a) (70 g, 44% yield) as a white solid: cSFC analytical (A) tR=2.17 min., purity: 99.74%; LCMS (J): tR=1.282 min., (ES$^+$) m/z (M+H)$^+$=331.1; $^1$H-NMR (CD3OD, 400 MHz): δ 8.08 (s, 1H), 7.94 (dd, J$_1$=8.8 Hz, J$_2$=4.8 Hz, 1H), 7.63 (dd, J=9.6 Hz, 1H), 7.27 (td, J=8.8 Hz, 1H), 4.22 (s, 1H), 3.30-3.26 (m, 1H), 3.09-3.08 (m, 1H), 2.95-2.88 (m, 2H), 2.11 (s, 1H), 2.02-1.96 (m, 1H), 1.89-1.85 (m, 2H), 1.62-1.54 (m, 1H), 0.93-0.88 (m, 2H), 0.78-0.77 (m, 1H), 0.70-0.67 (m, 1H); and 5-fluoro-N-(1'-azaspiro[cyclopropane-1,2'-bicyclo[2.2.2]octan]-3'-yl)benzo[b]thiophene-2-carboxamide-enantiomer2 (compound 64b) (80 g, 50% yield) as a white solid: cSFC analytical (A) tR=2.88 min., purity: 99.75%; LCMS (J): tR=1.282 min., (ES$^+$) m/z (M+H)$^+$=331.1; $^1$H-NMR (CD3OD, 400 MHz): δ 8.08 (s, 1H), 7.94 (dd, J$_1$=8.8 Hz, J$_2$=4.8 Hz, 1H), 7.63 (dd, J=9.2 Hz, 1H), 7.27 (td, J=9.2 Hz, 1H), 4.22 (s, 1H), 3.30-3.26 (m, 1H), 3.12-3.08 (m, 1H), 2.96-2.88 (m, 2H), 2.12 (s, 1H), 2.03-1.97 (m, 1H), 1.89-1.85 (m, 2H), 1.62-1.59 (m, 1H), 0.94-0.88 (m, 2H), 0.79-0.78 (m, 1H), 0.71-0.68 (m, 1H).

Example 65: (+/−)-6-chloro-N-(1'-azaspiro[cyclopropane-1,2'-bicyclo[2.2.2]octan]-3'-yl)benzo[b]thiophene-2-carboxamide (rac-65)

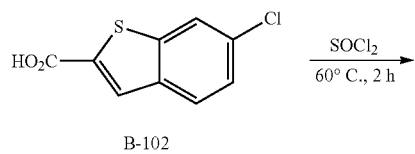

B-102

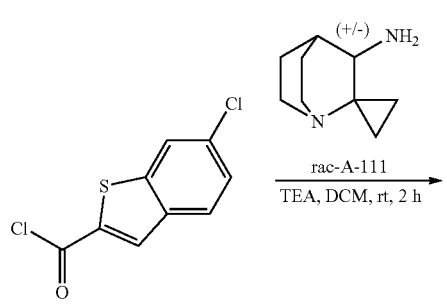

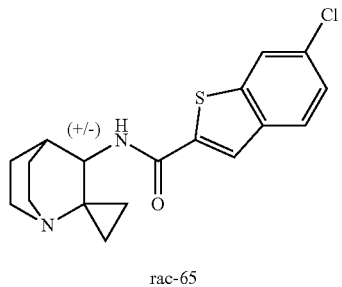

rac-65

Following general procedure A, rac-65 was prepared from compound B-102 and rac-A-111 (0.21 g, 1.4 mmol). The product was purified by prep-HPLC [Instrument: GX-A; Column: Phenomenex Gemini C18 150×25 mm, particle size: 10 µm; Mobile phase: 36-66% acetonitrile in H$_2$O (add 0.5% NH$_3$.H2O, v/v)] to give rac-65 (0.25 g, 51% yield) as a yellow solid. LCMS: (ES$^+$) m/z (M+H)$^+$=347.1.

Chiral Separation:

Rac-65 (0.25 g, 0.72 mmol) in 5 mL of ethanol was separated by SFC (Instrument: SFC 80; Column: Chiralpak OD-H 250×30 mm I.D., 10 m; Mobile phase: 60% ethanol (0.01% NH$_3$.H$_2$O) in CO$_2$) according to general procedure A to give:

6-chloro-N-(1'-azaspiro[cyclopropane-1,2'-bicyclo[2.2.2]octan]-3'-yl)benzo[b]thiophene-2-carboxamide-enantiomer1 hydrochloride (compound 65a) (0.10 g, 40% yield) as a white solid: cSFC analytical (A) tR=2.51 min., purity: 100%; LCMS (B): tR=0.700 min., (ES$^+$) m/z (M+H)$^+$=347.1; $^1$H-NMR (CD$_3$OD, 400 MHz): δ 8.14 (s, 1H), 8.02 (s, 1H), 7.92 (d, J=8.4 Hz, 1H), 7.46 (dd, J$_1$=8.4 Hz, J$_1$=1.6 Hz, 1H), 4.59 (d, J=2.4 Hz, 1H), 3.75-3.71 (m, 1H), 3.61-3.60 (m, 1H), 3.52-3.45 (m, 2H), 2.47-2.46 (m, 1H), 2.36-2.33 (m, 1H), 2.26-2.18 (m, 2H), 2.03-2.00 (m, 1H), 1.40-1.35 (m, 1H), 1.29-1.21 (m, 3H); and 6-chloro-N-(1'-azaspiro[cyclopropane-1,2'-bicyclo[2.2.2]octan]-3'-yl)benzo[b]thiophene-2-carboxamide-enantiomer2 hydrochloride (compound 65b) (0.10 g, 40% yield) as a white solid: cSFC analytical (A) tR=3.77 min., purity: 100%; LCMS (B): tR=0.696 min., (ES$^+$) m/z (M+H)$^+$=347.1; $^1$H-NMR (CD$_3$OD, 400 MHz): δ 8.17 (s, 1H), 8.01 (s, 1H), 7.921 (d, J=8.8 Hz, 1H), 7.46 (dd, J$_1$=8.4 Hz, J$_1$=1.6 Hz, 1H), 4.58 (d, J=2.0 Hz, 1H), 3.74-3.73 (m, 1H), 3.60-3.59 (m, 1H), 3.50-3.43 (m, 2H), 2.47-2.46 (m, 1H), 2.36-2.34 (m, 1H), 2.25-2.18 (m, 2H), 2.05-2.01 (m, 1H), 1.39-1.37 (m, 1H), 1.31-1.17 (m, 3H).

Example 66: (+/−)-5-chloro-N-(1'-azaspiro[cyclopropane-1,2'-bicyclo[2.2.2]octan]-3'-yl)benzo[b]thiophene-2-carboxamide (rac-66)

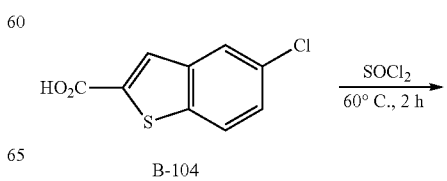

B-104

-continued

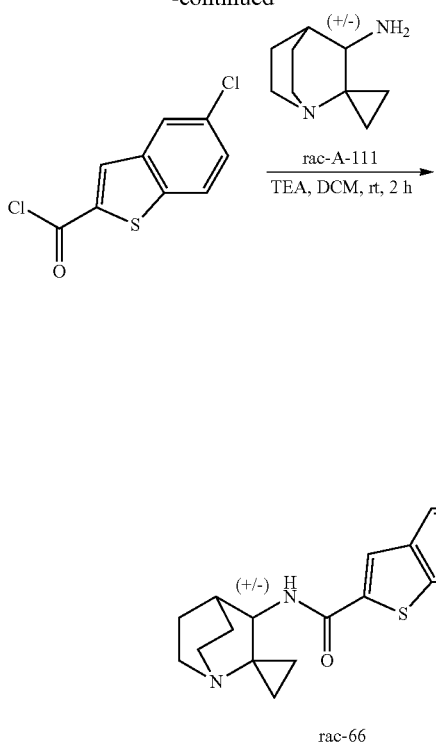

rac-66

Following general procedure A, rac-66 was prepared from compound B-104 and rac-A-111 (0.20 g, 1.3 mmol). The product was purified by prep-HPLC [Instrument: GX-C; Column: Phenomenex Gemini C18 150×30 mm, particle size: 5 μm; Mobile phase: 35-65% acetonitrile in H₂O (add 0.5% NH₃.H₂O, v/v)] to give rac-66 (0.21 g, 64% yield) as a white solid. LCMS: (ES⁺) m/z (M+H)⁺=347.0.

Chiral Separation:

Rac-66 (0.21 g, 0.58 mmol) in 3 mL of methanol was separated by SFC (Instrument: SFC 80; Column: AD-10 m; Mobile phase: 30% methanol (0.01% NH₃.H₂O) in CO₂) according to general procedure A to give:

5-chloro-N-(1'-azaspiro[cyclopropane-1,2'-bicyclo[2.2.2]octan]-3'-yl)benzo[b]thiophene-2-carboxamide-enantiomer1 hydrochloride (compound 66a) (40 mg, 19% yield) as a white solid: cSFC analytical (E) tR=2.60 min., purity: 100%; LCMS (N): tR=2.253 min., (ES⁺) m/z (M+H)⁺=346.9; ¹H-NMR (CD₃OD, 400 MHz): δ 8.09 (s, 1H), 7.94-7.91 (m, 2H), 7.45 (dd, J₁=8.8 Hz, J₂=2.0 Hz, 1H), 4.57 (d, J=1.2 Hz, 1H), 3.72-3.70 (m, 1H), 3.58-3.57 (m, 1H), 3.49-3.42 (m, 2H), 2.45-2.43 (m, 1H), 2.34-2.22 (m, 1H), 2.21-2.17 (m, 2H), 2.05-1.95 (m, 1H), 1.37-1.34 (m, 1H), 1.28-1.19 (m, 3H).

5-chloro-N-(1'-azaspiro[cyclopropane-1,2'-bicyclo[2.2.2]octan]-3'-yl)benzo[b]thiophene-2-carboxamide-enantiomer1 hydrochloride (compound 66b) (90 mg, 42% yield) as a white solid: cSFC analytical (E) tR=3.22 min., purity: 99.12%; LCMS (N): tR=2.230 min., (ES⁺) m/z (M+H)⁺=347.0; ¹H-NMR (CD₃OD, 400 MHz): δ 8.09 (s, 1H), 7.94-7.91 (m, 2H), 7.45 (dd, J₁=8.4 Hz, J₂=2.0 Hz, 1H), 4.57 (d, J=2.8 Hz, 1H), 3.72-3.70 (m, 1H), 3.58-3.57 (m, 1H), 3.50-3.40 (m, 2H), 2.46-2.43 (m, 1H), 2.34-2.33 (m, 1H), 2.21-2.16 (m, 2H), 2.00-1.95 (m, 1H), 1.38-1.34 (m, 1H), 1.30-1.15 (m, 3H).

Example 67: (+/−)-5,6-dichloro-N-(1'-azaspiro[cyclopropane-1,2'-bicyclo[2.2.2]octan]-3'-yl)benzo[b]thiophene-2-carboxamide (rac-67)

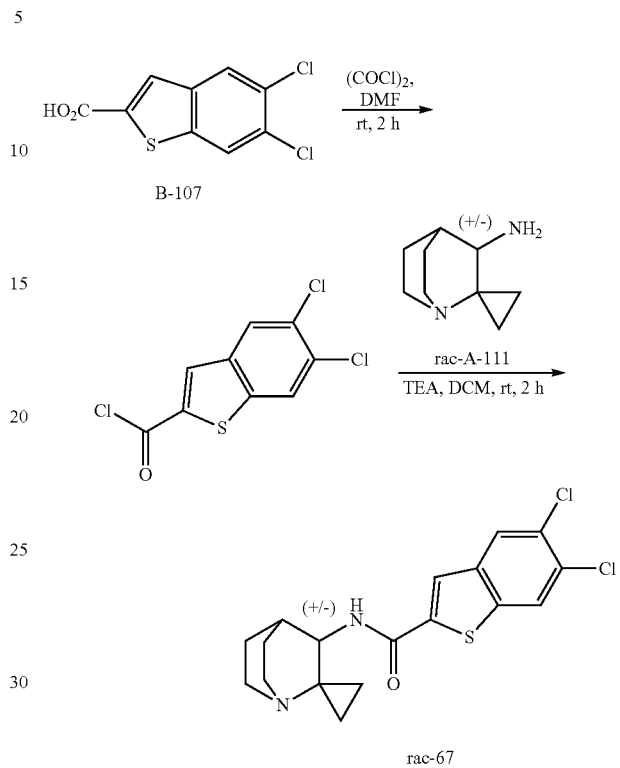

rac-67

To a solution of compound B-107 (0.18 g, 0.73 mmol) in dichloromethane (5 mL) at 0° C. was added dropwise oxalyl chloride (0.17 g, 1.3 mmol), followed by N,N-dimethylformamide (1 drop). The solution was stirred at this temperature for 1 hour. On completion, the solution was concentrated in vacuo to give the acid chloride, which was used directly without further purification to prepare rac-67 from rac-A-111 (0.10 g, 0.66 mmol) according to general procedure A. The product was purified by prep-HPLC [Instrument: GX-C; Column: Waters Xterra C18 150*30 mm, particle size: 5 μm; Mobile phase: 36-66% acetonitrile in H₂O (add 0.5% NH₃.H2O, v/v)] to give rac-67 (0.15 g, 60% yield) as a white solid. LCMS: (ES⁺) m/z (M+H)⁺=381.1.

Chiral Separation:

Rac-67 (0.15 g, 0.39 mmol) in 3 mL of methanol was separated by SFC (Instrument: SFC 80; Column: Chiralpak OD-H 250×30 mm I.D., 10 m; Mobile phase: 60% methanol (0.01% NH₃H₂O) in CO₂) according to general procedure A to give:

5,6-dichloro-N-(1'-azaspiro[cyclopropane-1,2'-bicyclo[2.2.2]octan]-3'-yl)benzo[b]thiophene-2-carboxamide-enantiomer1 hydrochloride (compound 67a) (65 mg, 43% yield) as a white solid: cSFC analytical (E) tR=2.75 min., purity: 99.83%; LCMS (B): tR=0.740 min., (ES⁺) m/z (M+H)⁺=381.1; ¹H-NMR (CD₃OD, 400 MHz): δ 8.19 (s, 1H), 8.14-8.10 (m, 2H), 4.58 (s, 1H), 3.73-3.52 (m, 1H), 3.65-3.55 (m, 1H), 3.55-3.40 (m, 2H), 2.47-2.46 (m, 1H), 2.38-2.33 (m, 1H), 2.25-2.19 (m, 2H), 2.16-2.02 (m, 1H), 1.41-1.38 (m, 1H), 1.29-1.22 (m, 3H); and 5,6-dichloro-N-(1'-azaspiro[cyclopropane-1,2'-bicyclo[2.2.2]octan]-3'-yl)benzo[b]thiophene-2-carboxamide-enantiomer2 hydrochloride (compound 67b) (0.65 mg, 43% yield) as a white solid: cSFC analytical (E) tR=3.29 min., purity: 99.85%; LCMS (B): tR=0.740 min., (ES⁺) m/z (M+H)⁺=381.1; ¹H-NMR (CD₃OD, 400 MHz): δ 8.19 (s, 1H), 8.12-8.11 (m, 2H), 4.58 (s, 1H), 3.72-3.53 (m, 1H), 3.52-3.49 (m, 1H), 3.47-3.42 (m, 2H), 2.47-2.46 (m, 1H), 2.38-2.33 (m, 1H), 2.25-2.19 (m, 2H), 2.16-2.02 (m, 1H), 1.39-1.37 (m, 1H), 1.30-1.20 (m, 3H).

Example 68: (+/−)-6-methyl-N-(1'-azaspiro[cyclopropane-1,2'-bicyclo[2.2.2]octan]-3'-yl)benzo[b]thiophene-2-carboxamide (rac-68)

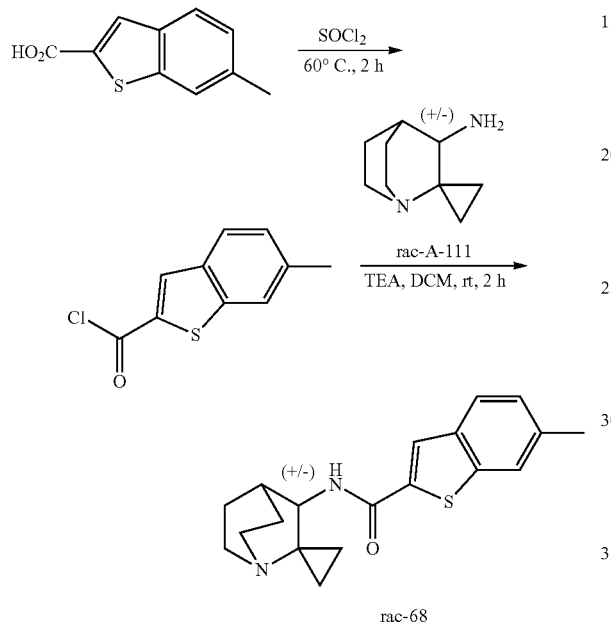

Following general procedure A, rac-68 was prepared from 6-methylbenzo[b]thiophene-2-carboxylic acid and rac-A-111 (0.10 g, 0.67 mmol). The product was purified by prep-HPLC [Instrument: GX-C; Column: Waters Xterra C18 150*30 mm, particle size: 5 μm; Mobile phase: 35-64% acetonitrile in H₂O (add 0.5% NH₃.H₂O, v/v)] to give rac-68 (0.12 g, 57% yield) as a white solid. LCMS: (ES⁺) m/z (M+H)⁺=327.0.

Chiral Separation:

Rac-68 (0.12 g, 0.37 mmol) in 3 mL of methanol was separated by SFC (Instrument: SFC 80; Column: Chiralpak AD-H 250×30 mm I.D., 10 μm; Mobile phase: 40% methanol (0.01% NH₃H₂O) in CO₂) according to general procedure A to give:

6-methyl-N-(1'-azaspiro[cyclopropane-1,2'-bicyclo[2.2.2]octan]-3'-yl)benzo[b]thiophene-2-carboxamide-enantiomer1 hydrochloride (compound 68a) (50 mg, 42% yield) as a white solid: cSFC analytical (A) tR=2.496 min., purity: 99.28%; LCMS (Z): tR=1.623 min., (ES⁺) m/z (M+H)⁺=327.0; ¹H-NMR (CD₃OD, 400 MHz): δ 8.09 (s, 1H), 7.83-7.81 (d, J=8.0 Hz, 1H), 7.74 (s, 1H), 7.31-7.29 (d, J=8.4 Hz, 1H), 4.59 (s, 1H), 3.77-3.70 (m, 1H), 3.62-3.52 (m, 1H), 3.49-3.42 (m, 2H), 2.50-2.46 (m, 4H), 2.39-2.33 (m, 1H), 2.25-2.16 (m, 2H), 2.05-1.97 (m, 1H), 1.41-1.31 (m, 1H), 1.29-1.17 (m, 3H); and 6-methyl-N-(1'-azaspiro[cyclopropane-1,2'-bicyclo[2.2.2]octan]-3'-yl)benzo[b]thiophene-2-carboxamide-enantiomer2 hydrochloride (compound 68b) (50 mg, 42% yield) as a white solid: cSFC analytical (A) tR=3.082 min., purity: 97.83%; LCMS (Z): tR=1.606 min., (ES⁺) m/z (M+H)⁺=327.0; ¹H-NMR (CD₃OD, 400 MHz): δ 8.10 (s, 1H), 7.83-7.81 (d, J=8.0 Hz, 1H), 7.74 (s, 1H), 7.31-7.29 (d, J=8.4 Hz, 1H), 4.58 (s, 1H), 3.76-3.69 (m, 1H), 3.60-3.49 (m, 1H), 3.47-3.42 (m, 2H), 2.51-2.46 (m, 4H), 2.39-2.33 (m, 1H), 2.25-2.16 (m, 2H), 2.05-2.02 (m, 1H), 1.38-1.35 (m, 1H), 1.31-1.20 (m, 3H).

Example 69: (+/−)-5-methyl-N-(1'-azaspiro[cyclopropane-1,2'-bicyclo[2.2.2]octan]-3'-yl)benzo[b]thiophene-2-carboxamide (rac-69)

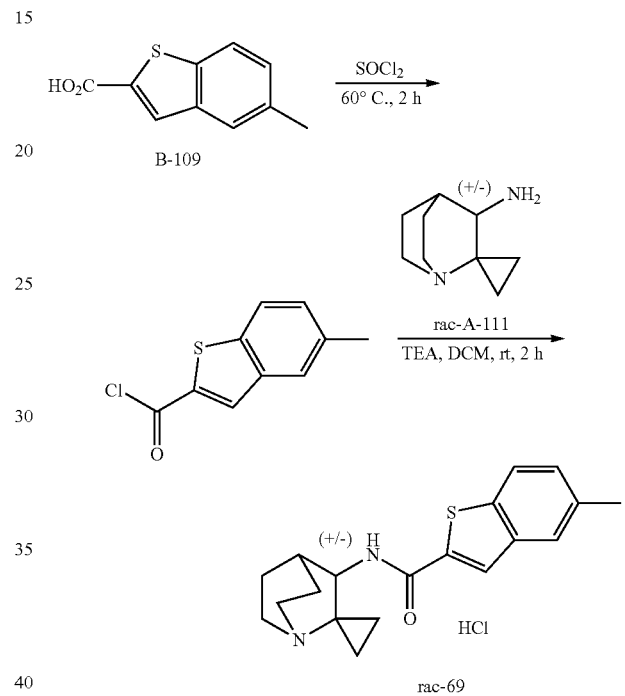

Following general procedure A, rac-69 was prepared from compound B-109 and rac-A-111 (0.24 g, 1.6 mmol). The product was purified by prep-HPLC [Instrument: GX-A; Column: Phenomenex Gemini C18 150×25 mm, particle size: 10 μm; Mobile phase: 44-74% acetonitrile in H₂O (add 0.5% NH₃.H₂O, v/v)] to give rac-69 (0.20 g, 64%) as a yellow solid. LCMS: (ES⁺) m/z (M+H)⁺=327.1.

Chiral Separation:

Rac-69 (0.20 g, 0.61 mmol) in 5 mL of methanol was separated by SFC (Instrument: SFC 80; Column: OD-250× 30 mm, I.D., 10 μm; Mobile phase: 50% methanol (0.01% NH₃.H2O) in CO₂) according to general procedure A to give:

5-methyl-N-(1'-azaspiro[cyclopropane-1,2'-bicyclo[2.2.2]octan]-3'-yl)benzo[b]thiophene-2-carboxamide-enantiomer1 hydrochloride (compound 69a) (55 mg, 28% yield) as a white solid: cSFC analytical (A) tR=2.483 min., purity: 100.00%; LCMS (B): tR=0.686 min., (ES⁺) m/z (M+H)⁺=327.1; ¹H-NMR (CD₃OD, 400 MHz): δ 8.10-8.09 (m, 1H), 7.81 (d, J=8.4 Hz, 1H), 7.74 (s, 1H), 7.33 (d, J=8.4 Hz, 1H), 4.58 (s, 1H), 3.75-3.59 (m, 1H), 3.59-3.59 (m, 1H), 3.48-3.44 (m, 2H), 2.49 (s, 3H), 2.45-2.45 (m, 1H), 2.36-2.33 (m, 1H), 2.24-2.19 (m, 2H), 2.01-2.00 (m, 1H), 1.42-1.40 (m, 1H), 1.31-1.19 (m, 3H); and 5-methyl-N-(1'-azaspiro[cyclopropane-1,2'-bicyclo[2.2.2]octan]-3'-yl)benzo[b]thiophene-2-carboxamide-enantiomer2 hydrochloride (compound 69b) (25 mg, 13% yield) as a white solid: cSFC analytical (A) tR=3.099 min., purity: 98.88%; LCMS (B): tR=0.661 min., (ES⁺) m/z (M+H)⁺=327.1; ¹H-NMR (CD₃OD, 400 MHz): δ 8.09-8.09 (m, 1H), 7.81 (d, J=8.0 Hz, 1H), 7.74 (s, 1H), 7.33 (d, J=8.0 Hz, 1H), 4.58 (s, 1H), 3.75-3.73 (m, 1H), 3.59-3.59 (m, 1H), 3.58-3.44 (m, 2H), 2.49 (s, 3H), 2.46-2.45 (m, 1H), 2.36-2.36 (m, 1H), 2.25-2.18 (m, 2H), 2.01-2.00 (m, 1H), 1.42-1.40 (m, 1H), 1.31-1.19 (m, 3H).

Example 70: (+/−)—N-(1'-azaspiro[cyclopropane-1,2'-bicyclo[2.2.2]octan]-3'-yl)-5-(trifluoromethyl)benzo[b]thiophene-2-carboxamide (rac-70)

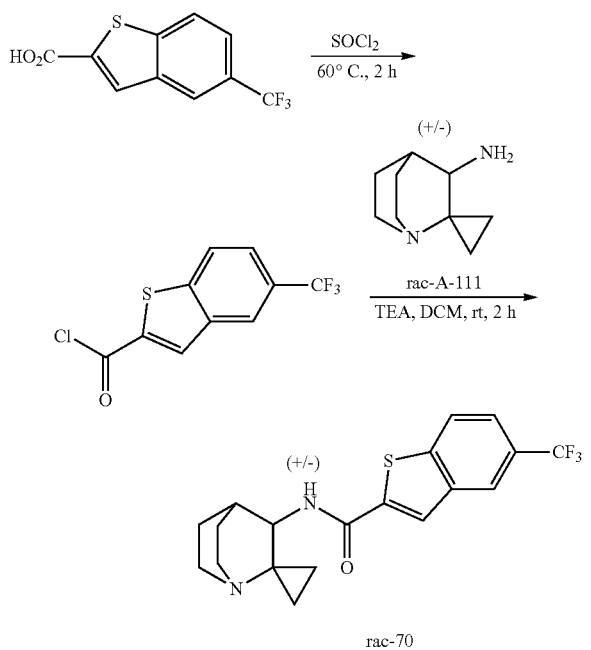

rac-70

Following general procedure A, rac-70 was prepared from 5-(trifluoromethyl)benzo[b]thiophene-2-carboxylic acid and rac-A-111 (0.10 g, 0.65 mmol). The product was purified by prep-HPLC [Instrument: GX-C; Column: Phenomenex Gemini C18 150×30 mm, particle size: 5 μm; Mobile phase: 35-65% acetonitrile in H₂O (add 0.5% NH₃.H2O, v/v)] to give rac-70 (0.18 g, 72% yield) as a white solid.

Chiral Separation:

Rac-70 (0.12 g, 0.32 mmol) in 3 mL of ethanol was separated by SFC (Instrument: SFC 80; Column: Chiralpak OD-H 250×25 mm I.D., 10 μm; Mobile phase: 40% ethanol (0.1% NH₃.H2O) in CO₂) according to general procedure A to give:

N-(1'-azaspiro[cyclopropane-1,2'-bicyclo[2.2.2]octan]-3'-yl)-5-(trifluoromethyl)benzo[b]thiophene-2-carboxamide-enantiomer1 hydrochloride (compound 70a) (54 mg, 45% yield) as a white solid: cSFC analytical (A) tR=1.87 min., purity: 100%; LCMS (J): tR=1.415 min., (ES⁺) m/z (M+H)⁺= 381.4; ¹H-NMR (CD₃OD, 400 MHz): δ 8.26 (s, 1H), 8.23 (s, 1H), 8.15 (d, J=8.4 Hz, 1H), 7.72 (d, J=8.4 Hz, 1H), 4.30 (s, 1H), 3.40-3.22 (m, 1H), 3.20-3.18 (m, 1H), 3.06-2.98 (m, 2H), 2.21-2.18 (m, 1H), 2.10-1.92 (m, 2H), 1.71-1.63 (m, 1H), 1.03-0.96 (m, 1H), 0.88-0.78 (m, 2H); and N-(1'-azaspiro[cyclopropane-1,2'-bicyclo[2.2.2]octan]-3'-yl)-5-(trifluoromethyl)benzo[b]thiophene-2-carboxamide-enantiomer2 hydrochloride (compound 70b) (60 mg, 50% yield) as a white solid: cSFC analytical (A) tR=2.59 min., purity: 100%; LCMS (J): tR=2.63 min., (ES⁺) m/z (M+H)⁺= 381.4; ¹H-NMR (CD₃OD, 400 MHz): δ 8.26 (s, 1H), 8.24 (s, 1H), 8.15 (d, J=8.4 Hz, 1H), 7.73-7.70 (d, J=8.4 Hz, 1H), 4.33 (s, 1H), 3.42-3.37 (m, 1H), 3.24-3.21 (m, 1H), 3.09-3.00 (m, 2H), 2.22-2.21 (m, 1H), 2.10-1.94 (m, 3H), 1.74-1.66 (m, 1H), 1.05-0.99 (m, 2H), 0.91-0.80 (m, 2H).

Example 71: (+/−)-6-cyclopropyl-N-(1'-azaspiro[cyclopropane-1,2'-bicyclo[2.2.2]octan]-3'-yl)benzo[b]thiophene-2-carboxamide (rac-71)

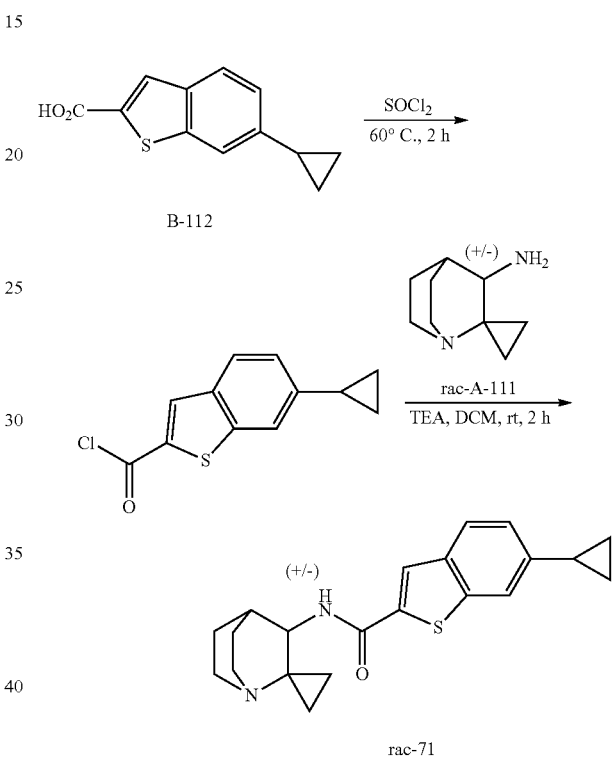

rac-71

Following general procedure A, rac-71 was prepared from compound B-112 and rac-A-111 (0.14 g, 0.89 mmol). The product was purified by prep-HPLC [Instrument: GX-A; Column: Phenomenex Gemini C18 150×25 mm, particle size: 10 μm; Mobile phase: 44-74% acetonitrile in H₂O (add 0.5% NH₃.H2O, v/v)] to give rac-71 (0.20 g, 64%) as a white solid. LCMS: (ES⁺) m/z (M+H)⁺=353.1.

Chiral Separation:

Rac-71 (0.20 g, 0.57 mmol) in 5 mL of methanol was separated by SFC (Instrument: SFC 80; Column: OD-250×30 mm, I.D., 10 m; Mobile phase: 50% methanol (0.01% NH₃.H2O) in CO₂) according to general procedure A to give:

6-cyclopropyl-N-(1'-azaspiro[cyclopropane-1,2'-bicyclo[2.2.2]octan]-3'-yl)benzo[b]thiophene-2-carboxamide-enantiomer1 hydrochloride (compound 71a) (0.10 g, 50% yield) as a white solid: cSFC analytical (B) tR=2.796 min., purity: 100.00%; LCMS (M): tR=1.111 min., (ES⁺) m/z (M+H)⁺=353.0; ¹H-NMR (CD₃OD, 400 MHz): δ 8.05 (s, 1H), 7.78 (d, J=8.4 Hz, 1H), 7.62 (s, 1H), 7.16 (d, J=8.4 Hz, 1.4 Hz, 1H), 4.57 (d, J=2.4 Hz, 1H), 3.74-3.43 (m, 4H), 2.44-2.03 (m, 6H), 1.36-1.04 (m, 6H), 0.80-0.76 (m, 2H), and 6-cyclopropyl-N-(1'-azaspiro[cyclopropane-1,2'-bicyclo[2.2.2]octan]-3'-yl)benzo[b]thiophene-2-carboxamide-enantiomer2 hydrochloride (compound 71b) (0.10 g, 50% yield) as a white solid: cSFC analytical (B) tR=3.478 min., purity: 99.43%; LCMS (M): tR=1.114 min., (ES$^+$) m/z (M+H)$^+$=353.0; $^1$H-NMR (CD$_3$OD, 400 MHz): δ 8.05 (s, 1H), 7.78 (d, J=8.4 Hz, 1H), 7.62 (s, 1H), 7.16 (d, J=8.4 Hz, 1H), 4.55 (d, J=2.4 Hz, 1H), 3.46-3.43 (m, 4H), 2.43-2.03 (m, 6H), 1.30-1.03 (m, 6H), 0.79-0.77 (m, 2H).

Example 72: (+/−)-5-cyclopropyl-N-(1'-azaspiro[cyclopropane-1,2'-bicyclo[2.2.2]octan]-3'-yl)benzo[b]thiophene-2-carboxamide (rac-72)

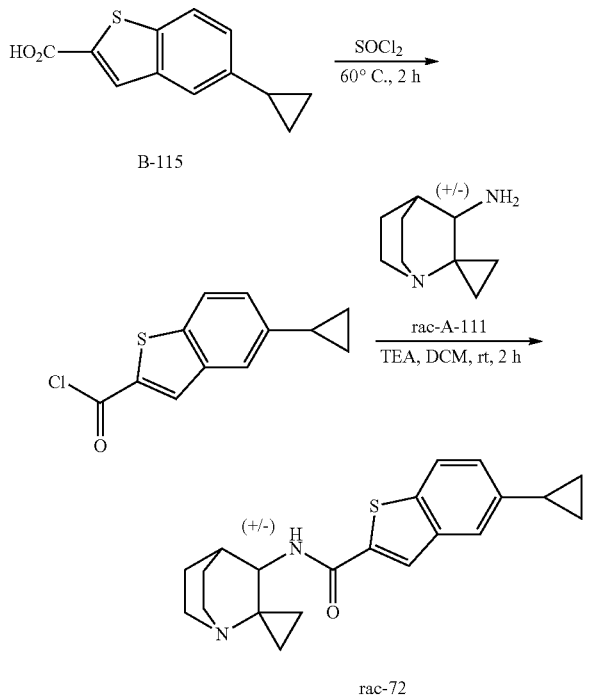

Following general procedure A, rac-72 was prepared from compound B-115 and rac-A 111 (0.14 g, 0.89 mmol). The product was purified by prep-HPLC [Instrument: GX-A; Column: Phenomenex Gemini C18 150×30 mm, particle size: 4 μm; Mobile phase: 35-65% acetonitrile in H$_2$O (add 0.5% TFA, v/v)] to give rac-72 (0.10 g, 31%) as a white solid. LCMS: (ES$^+$) m/z (M+H)$^+$=353.1.

Chiral Separation:

Rac-72 (0.10 g, 0.28 mmol) in 3 mL of methanol was separated by SFC (Instrument: SFC 80; Column: OD-250× 30 mm, I.D., 10 μm; Mobile phase: 50% methanol (0.01% NH$_3$.H2O) in CO$_2$) according to general procedure A to give:

5-cyclopropyl-N-(1'-azaspiro[cyclopropane-1,2'-bicyclo[2.2.2]octan]-3'-yl)benzo[b]thiophene-2-carboxamide-enantiomer1 hydrochloride (compound 72a) (50 mg, 50% yield) as a white solid: cSFC analytical (A) tR: 2.70 min., purity: 100.00%; LCMS (B): tR=0.728 min., (ES$^+$) m/z (M+H)$^+$=353.1; $^1$H-NMR (CD$_3$OD, 400 MHz): δ 8.08 (s, 1H), 7.80 (d, J=8.8 Hz, 1H), 7.65 (s, 1H), 7.23-7.21 (dd, J=8.8 Hz, 1.2 Hz, 1H), 4.58 (d, J=2.4 Hz, 1H), 3.73-3.44 (m, 4H), 2.46-2.07 (m, 6H), 1.39-1.03 (m, 4H), 0.78-0.76 (m, 2H); and 5-cyclopropyl-N-(1'-azaspiro[cyclopropane-1,2'-bicyclo[2.2.2]octan]-3'-yl)benzo[b]thiophene-2-carboxamide-enantiomer2 hydrochloride (compound 72b) (50 mg, 50% yield) as a white solid: cSFC analytical (A) tR: 3.32 min., purity: 99.22%; LCMS (B): tR=0.734 min., (ES$^+$) m/z (M+H)$^+$=353.1; $^1$H-NMR (CD$_3$OD, 400 MHz): δ 8.08 (d, J=9.2 Hz, 3.2 Hz, 1H), 7.80 (d, J=8.4 Hz, 1H), 7.65 (s, 1H), 7.22 (d, J=8.8 Hz, 1H), 4.58 (s, 1H), 3.74-3.41 (m, 4H), 2.45-2.07 (m, 6H), 1.29-1.03 (m, 4H), 0.78-0.76 (m, 2H).

Example 73: (+/−)-6-methoxy-N-(1'-azaspiro[cyclopropane-1,2'-bicyclo[2.2.2]octan]-3'-yl)benzo[b]thiophene-2-carboxamide (rac-73)

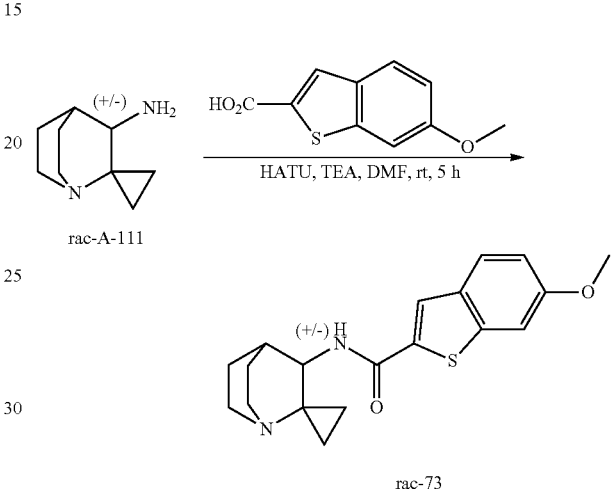

To a mixture of 6-methoxybenzo[b]thiophene-2-carboxylic acid (0.30 g, 1.4 mmol) in N, N-dimethylformamide (2.8 mL) was added 2-(3H-[1,2,3]triazolo[4,5-b]pyridin-3-yl)-1,1,3,3-tetramethylisouronium hexafluorophosphate (0.66 g, 1.7 mmol), followed by rac-A-111 (0.22 g, 1.4 mmol) and triethylamine (0.29 g, 2.8 mmol). The mixture was stirred at room temperature for 1 hour. On completion, the reaction was diluted with ethyl acetate and washed 4 times with water. The organic layer was dried over anhydrous sodium sulfate and concentrated in vacuo. The residue was purified by prep-HPLC [Instrument: GX-A; Column: Phenomenex Gemini C18 150×25 mm, particle size: 10 μm; Mobile phase: 36-66% acetonitrile in H$_2$O (add 0.5% NH$_3$.H2O, v/v)] to give racemate rac-73 (0.13 g, 26% yield) as a white solid.

Chiral Separation:

Rac-73 (0.13 g, 0.38 mmol) in 3 mL of methanol was separated by SFC (Instrument: SFC 80; Column: Chiralpak OD-H 250×25 mm I.D., 10 μm; Mobile phase: 50% ethanol (0.01% NH$_3$.H$_2$O) in CO$_2$) according to general procedure A to give:

6-methoxy-N-(1'-azaspiro[cyclopropane-1,2'-bicyclo[2.2.2]octan]-3'-yl)benzo[b]thiophene-2-carboxamide-enantiomer1 hydrochloride (compound 73a) (70 mg, 49% yield) as a white solid: cSFC analytical (A) tR=2.61 min., purity: 100%; LCMS (J): tR=1.265 min., (ES$^+$) m/z (M+H)$^+$= 343.1; $^1$H-NMR (CD$_3$OD, 400 MHz): δ 8.04 (s, 1H), 7.79 (d, J=8.8 Hz, 1H), 7.46 (s, 1H), 7.06 (dd, J=8.8 Hz, 1H), 4.34 (s, 1H), 3.90 (s, 3H), 3.44-3.42 (m, 1H), 3.28-3.25 (m, 1H), 3.12-3.04 (m, 2H), 2.23-2.22 (m, 1H), 2.15-2.10 (m, 1H), 2.00-1.97 (m, 2H), 1.73 (m, 1H), 1.08-1.01 (m, 2H), 0.95-0.86 (m, 2H); and 6-methoxy-N-(1'-azaspiro[cyclopropane-1,2'-bicyclo[2.2.2]octan]-3'-yl)benzo[b]thiophene-2-carboxamide-enantiomer2 hydrochloride (compound 73b) (70 mg, 49% yield) as a white solid: cSFC analytical (A) tR=3.26 min., purity: 99.63%; LCMS (J): tR=1.278 min., (ES+) m/z (M+H)+=343.1; 1H-NMR (CD3OD, 400 MHz): δ 8.06 (s, 1H), 7.79 (d, J=9.2 Hz, 1H), 7.46 (s, 1H), 7.06 (dd, J=8.8 Hz, 1H), 4.44 (s, 1H), 3.90 (s, 3H), 3.57-3.56 (m, 1H), 3.41-3.40 (m, 1H), 3.28-3.25 (m, 2H), 2.33-2.31 (m, 1H), 2.23-2.21 (m, 1H), 2.11-2.05 (m, 2H), 1.86-1.84 (m, 1H), 1.23-1.20 (m, 1H), 1.14-1.10 (m, 2H), 1.08-1.00 (m, 1H).

Example 74: (+/−)-5-methoxy-N-(1'-azaspiro[cyclopropane-1,2'-bicyclo[2.2.2]octan]-3'-yl)benzo[b]thiophene-2-carboxamide (rac-74)

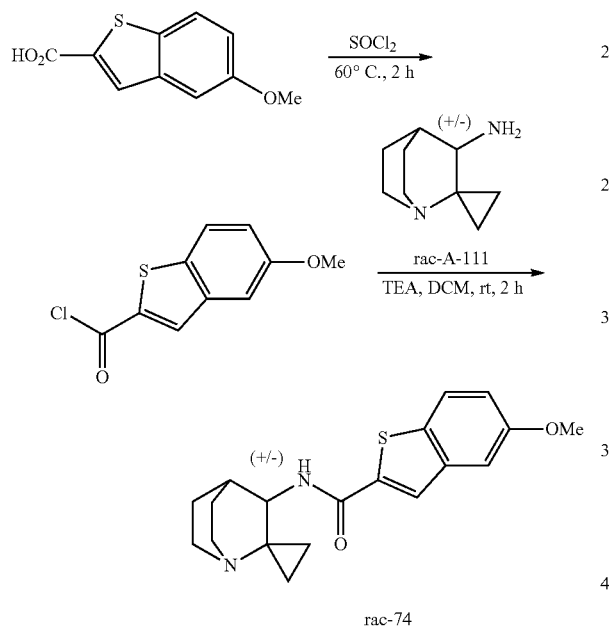

rac-74

Following general procedure A, rac-74 was prepared from 5-methoxybenzo[b]thiophene-2-carboxylic acid and rac-A-111 (0.10 g, 0.65 mmol). The product was purified by prep-HPLC [Instrument: GX-C; Column: Phenomenex Gemini C18 150×30 mm, particle size: 5 μm; Mobile phase: 35-65% acetonitrile in H2O (add 0.5% NH3.H2O, v/v)] to give rac-74 (0.12 g, 54% yield) as a white solid.

Chiral Separation:

Rac-74 (0.10 g, 0.29 mmol) in 3 mL of ethanol was separated by SFC (Instrument: SFC 80; Column: Chiralpak OD-H 250×25 mm I.D., 10 μm; Mobile phase: 45% ethanol (0.1% NH3.H2O) in CO2) according to general procedure A to give:

5-methoxy-N-(1'-azaspiro[cyclopropane-1,2'-bicyclo[2.2.2]octan]-3'-yl)benzo[b]thiophene-2-carboxamide-enantiomer1 hydrochloride (compound 74a) (80 mg, 67% yield) as a white solid: cSFC analytical (A) tR=2.56 min., purity: 99.60%; LCMS (G): tR=2.231 min., (ES+) m/z (M+H)+=343.1; 1H-NMR (CD3OD, 400 MHz): δ 8.06 (s, 1H), 7.79 (d, J=8.8 Hz, 1H), 7.40 (d, J=2.4 Hz, 1H), 7.13 (dd, J1=2.4 Hz, J2=8.8 Hz, 1H), 4.58 (s, 1H), 3.89 (s, 3H), 3.75-3.72 (m, 1H), 3.60-3.45 (m, 3H), 2.47-2.36 (m, 2H), 2.25-2.19 (m, 2H), 1.37-1.36 (m, 1H), 1.28-1.21 (m, 3H); and 5-methoxy-N-(1'-azaspiro[cyclopropane-1,2'-bicyclo[2.2.2]octan]-3'-yl)benzo[b]thiophene-2-carboxamide-enantiomer2 hydrochloride (compound 74b) (12 mg, 10% yield) as a white solid: cSFC analytical (A) tR=3.03 min., purity: 99.49%; LCMS (B): tR=0.656 min., (ES+) m/z (M+H)+=343.1; 1H-NMR (CD3OD, 400 MHz): δ 8.08 (s, 1H), 7.79 (d, J=8.8 Hz, 1H), 7.40 (d, J=2.0 Hz, 1H), 7.14 (dd, J1=2.8 Hz, J2=8.8 Hz, 1H), 4.58 (s, 1H), 3.89 (s, 3H), 3.78-3.60 (m, 1H), 3.59-3.44 (m, 3H), 2.46-2.45 (m, 1H), 2.37-2.19 (m, 3H), 2.03-2.00 (m, 1H), 1.41-1.39 (m, 1H), 1.31-1.20 (m, 3H).

Example 75

Preparation of (R)—N-(1'-azaspiro[cyclopropane-1,2'-bicyclo[2.2.2]octan]-3'-yl)furo[2,3-c]pyridine-5-carboxamide hydrochloride ((R)-75)

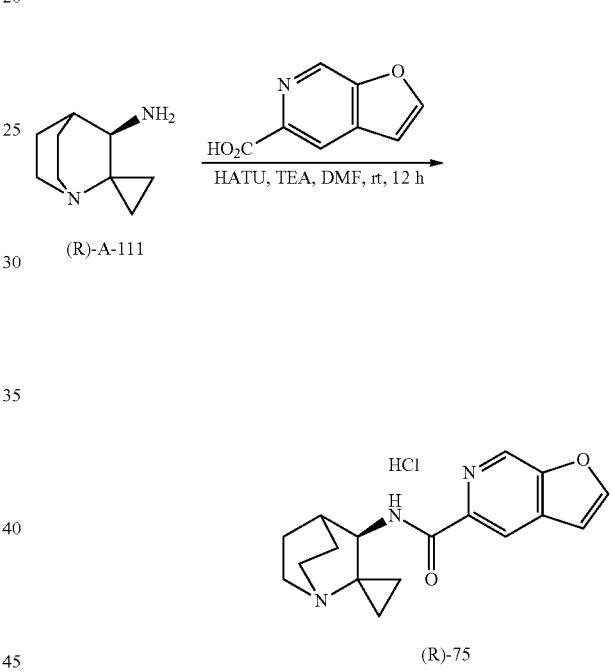

(R)-75

Following general procedure B, Compound (R)-75 was prepared from furo[2,3-c]pyridine-5-carboxylic acid (54 mg, 0.33 mmol) and compound (R)-A-111 (50 mg, 0.33 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in H2O (add 0.5% HCl, v/v)] to give:

(R)—N-(1'-azaspiro[cyclopropane-1,2'-bicyclo[2.2.2]octan]-3'-yl)furo[2,3-c]pyridine-5-carboxamide hydrochloride (compound (R)-75) (77 mg, 79% yield) as a white solid: cSFC analytical (H) tR=2.39 min., purity: 99.53%; LCMS (X): tR=1.513 min., (ES+) m/z (M+H)+=298.1; 1H-NMR (CD3OD, 400 MHz): δ 9.22 (s, 1H), 8.90 (s, 1H), 8.50 (d, J=1.6 Hz, 1H), 7.39 (d, J=1.2 Hz, 1H), 4.63 (s, 1H), 3.80-3.79 (m, 1H), 3.59-3.58 (m, 1H), 3.52-3.41 (m, 2H), 2.50-2.49 (m, 1H), 2.42-2.36 (m, 1H), 2.25-2.16 (m, 2H), 2.05-2.02 (m, 1H), 1.45-1.40 (m, 1H), 1.34-1.29 (m, 2H), 1.21-1.19 (m, 1H).

Preparation of (S)—N-(1'-azaspiro[cyclopropane-1,2'-bicyclo[2.2.2]octan]-3'-yl)furo[2,3-c]pyridine-5-carboxamide hydrochloride ((S)-75)

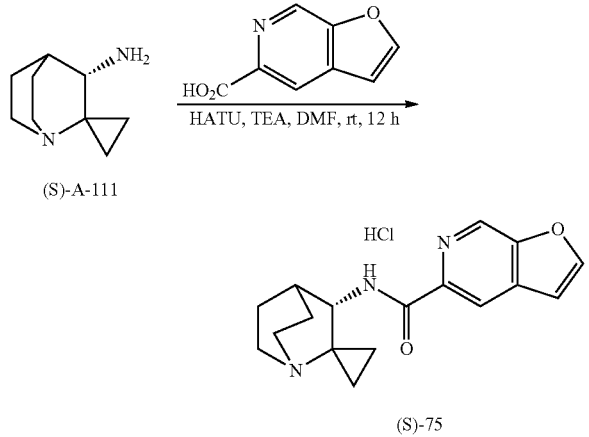

Following general procedure B, Compound 498-SBA was prepared from furo[2,3-c]pyridine-5-carboxylic acid (30 mg, 0.20 mmol) and compound (S)-A-111 (0.30 g, 0.20 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(S)—N-(1'-azaspiro[cyclopropanene-1,2'-bicyclo[2.2.2]octan]-3'-yl)furo[2,3-c]pyridine-5-carboxamide hydrochloride (compound (S)-75) (50 mg, 85% yield) as a white solid: cSFC analytical (H) tR=3.04 min., purity: 99.45%; LCMS (X): tR=1.528 min., (ES$^+$) m/z (M+H)$^+$=333.1; $^1$H-NMR (CD$_3$OD, 400 MHz): δ 9.21 (s, 1H), 8.87 (s, 1H), 8.49 (d, J=2.8 Hz, 1H), 7.38 (d, J=2.0 Hz, 1H), 4.63 (s, 1H), 3.80-3.78 (m, 1H), 3.60-3.59 (m, 1H), 3.52-3.41 (m, 2H), 2.50-2.49 (m, 1H), 2.42-2.36 (m, 1H), 2.25-2.16 (m, 2H), 2.05-2.01 (m, 1H), 1.43-1.38 (m, 1H), 1.34-1.28 (m, 2H), 1.22-1.17 (m, 1H).

Example 76

Preparation of (R)—N-(1'-azaspiro[cyclopropane-1,2'-bicyclo[2.2.2]octan]-3'-yl)-2,3-dihydro-[1,4]dioxino[2,3-c]pyridine-7-carboxamide hydrochloride ((R)-76)

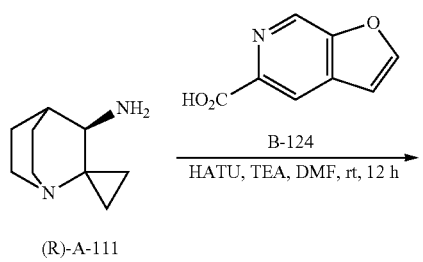

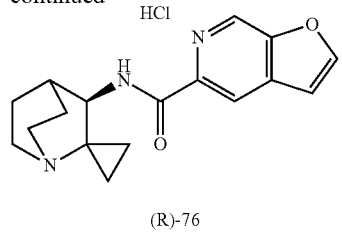

Following general procedure B, Compound (R)-76 was prepared from compound B-124 (60 mg, 0.33 mmol) and compound (R)-A-111 (50 mg, 0.33 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(R)—N-(1'-azaspiro[cyclopropane-1,2'-bicyclo[2.2.2]octan]-3'-yl)-2,3-dihydro-[1,4]dioxino[2,3-c]pyridine-7-carboxamide hydrochloride (compound (R)-76) (30 mg, 29% yield) as a white solid: cSFC analytical (G) tR=2.73 min., purity: 99.87%; LCMS (X): tR=1.464 min., (ES$^+$) m/z (M+H)$^+$=316.1; $^1$H-NMR (CD$_3$OD, 400 MHz): δ 8.42 (s, 1H), 8.17 (s, 1H), 4.64-4.63 (m, 2H), 4.62-4.60 (m, 1H), 4.54-4.52 (m, 2H), 3.78-3.70 (m, 1H), 3.57-3.56 (m, 1H), 3.49-3.39 (m, 2H), 2.46-2.43 (m, 1H), 2.32-2.29 (m, 1H), 2.22-2.16 (m, 2H), 2.00-1.94 (m, 1H), 1.43-1.37 (m, 1H), 1.31-1.24 (m, 2H), 1.17-1.16 (m, 1H).

Preparation of (S)—N-(1'-azaspiro[cyclopropane-1,2'-bicyclo[2.2.2]octan]-3'-yl)-2,3-dihydro-[1,4]dioxino[2,3-c]pyridine-7-carboxamide hydrochloride ((S)-76)

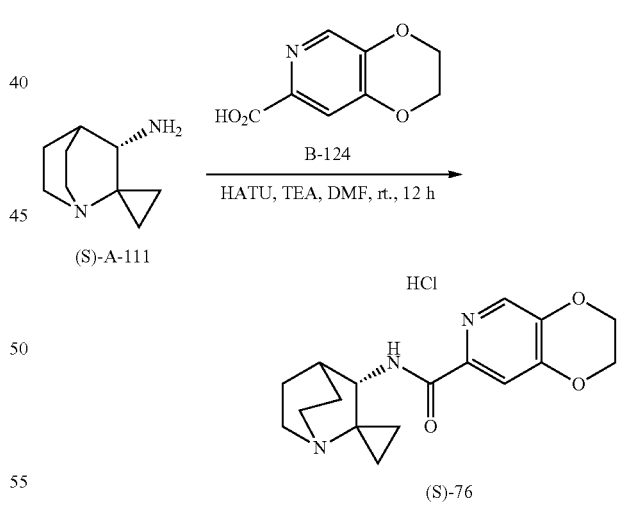

Following general procedure B, Compound (S)-76 was prepared from compound B-124 (30 mg, 0.20 mmol) and compound (S)-A-111 (0.30 g, 0.20 mmol), with a reaction time of 12 hours. The product was purified by prep-HPLC [Instrument: GX-E; Column: Agella Venusil ASB C18 150×30 mm, particle size: 5 μm; Mobile phase: 16-46% acetonitrile in H$_2$O (add 0.5% HCl, v/v)] to give:

(S)—N-(1'-azaspiro[cyclopropane-1,2'-bicyclo[2.2.2]octan]-3'-yl)-2,3-dihydro-[1,4]dioxino[2,3-c]pyridine-7-carboxamide hydrochloride (compound (S)-76) (50 mg, 85% yield) as a white solid: cSFC analytical (G) tR=2.88 min., purity: 99.21%; LCMS (X): tR=1.464 min., (ES⁺) m/z (M+H)⁺=316.1; ¹H-NMR (CD₃OD, 400 MHz): δ 8.42 (s, 1H), 8.19 (s, 1H), 4.65-4.63 (m, 2H), 4.62-4.60 (m, 1H), 4.54-4.52 (m, 2H), 3.75-3.73 (m, 1H), 3.57-3.56 (m, 1H), 3.49-3.40 (m, 2H), 2.45-2.44 (m, 1H), 2.34-2.30 (m, 1H), 2.22-2.14 (m, 2H), 2.02-1.94 (m, 1H), 1.43-1.39 (m, 1H), 1.37-1.25 (m, 2H), 1.18-1.15 (m, 1H).

Example 77: (R)-3-methyl-N-(1'-azaspiro[cyclopropane-1,2'-bicyclo[2.2.2]octan]-3'-yl)benzo[b]thiophene-5-carboxamide hydrochloride ((R)-77)

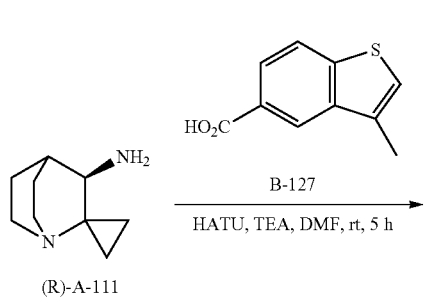

Following general procedure B, Compound (R)-77 was prepared from compound B-127 (63 mg, 0.32 mmol) and compound (R)-A-111 (50 mg, 0.32 mmol), with a reaction time of 5 hours. The product was purified by prep-HPLC [Instrument: GX-E; Column: Phenomenex Synergi C18 150×30 mm, particle size: 10 μm; Mobile phase: 20-50% acetonitrile in H₂O (add 0.5% HCl, v/v)] to give:

(R)-3-methyl-N-(1'-azaspiro[cyclopropane-1,2'-bicyclo[2.2.2]octan]-3'-yl)benzo[b]thiophene-5-carboxamide hydrochloride (compound (R)-77) (60 mg, 56% yield) as a white solid: cSFC analytical (A) tR=2.62 min., purity: 97.93%; LCMS (B): tR=0.664 min., 327.1 m/z (M+1); ¹H-NMR (CD₃OD, 400 MHz): δ 8.28 (d, J=1.2 Hz, 1H), 7.97 (d, J=8.8 Hz, 1H), 7.82 (dd, J₁=8.4 Hz, J₂=1.6 Hz, 1H), 7.33 (s, 1H), 4.63 (d, J=2.0 Hz, 1H), 3.71-3.69 (m, 1H), 3.60-3.59 (m, 1H), 3.50-3.43 (m, 2H), 2.52 (s, 3H), 2.52-2.47 (m, 1H), 2.34 (m, 1H), 2.26-2.18 (m, 2H), 2.00-1.99 (m, 1H), 1.41-1.38 (m, 1H), 1.29-1.19 (m, 3H).

Example 78: (R)-3-methyl-N-(1'-azaspiro[cyclopropane-1,2'-bicyclo[2.2.2]octan]-3'-yl)benzo[b]thiophene-6-carboxamide ((R)-78)

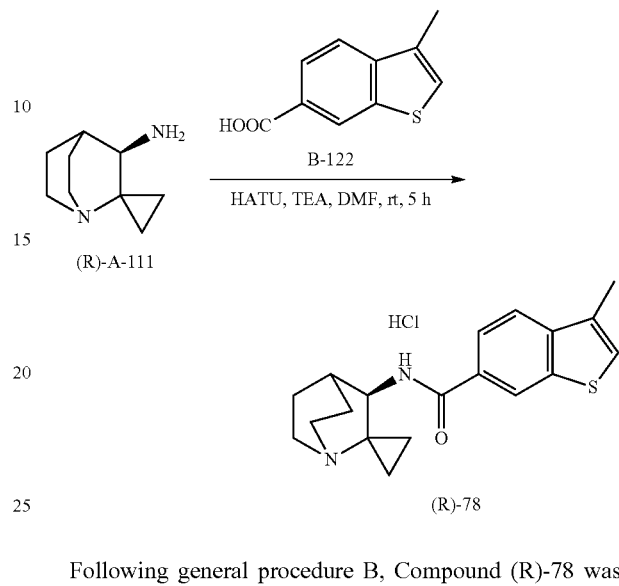

Following general procedure B, Compound (R)-78 was prepared from compound B-122 (69 mg, 0.36 mmol) and compound (R)-A-111 (50 mg, 0.33 mmol), with a reaction time of 5 hours. The product was purified by prep-HPLC [Instrument: GX-E; Column: Phenomenex SynergiC18 150×30 mm, particle size: 10 μm; Mobile phase: 20-50% acetonitrile in H₂O (add 0.5% HCl, v/v)] to give:

(R)-3-methyl-N-(1'-azaspiro[cyclopropane-1,2'-bicyclo[2.2.2]octan]-3'-yl)benzo[b]thiophene-6-carboxamide hydrochloride (compound (R)-78) (30 mg, 25% yield) as a white solid: cSFC analytical (A) tR=2.58 min., purity: 97.59%; LCMS (B): tR=0.643 min., 327.1 m/z (M+1); ¹H-NMR (CD₃OD, 400 MHz): δ 8.42 (s, 1H), 8.46 (d, J=8.0 Hz, 1H), 7.45 (s, 1H), 4.62 (d, J=2 Hz, 1H), 3.72-3.70 (m, 1H), 3.61-3.60 (m, 1H), 3.52-3.42 (m, 2H), 2.54-2.50 (m, 4H), 2.34-2.20 (m, 3H), 2.04-2.01 (m, 1H), 1.40-1.37 (m, 1H), 1.30-1.22 (m, 3H).

Example 79: (R)—N-(1'-azaspiro[cyclopropane-1,2'-bicyclo[2.2.2]octan]-3'-yl)-1H-indole-6-carboxamide ((R)-79)

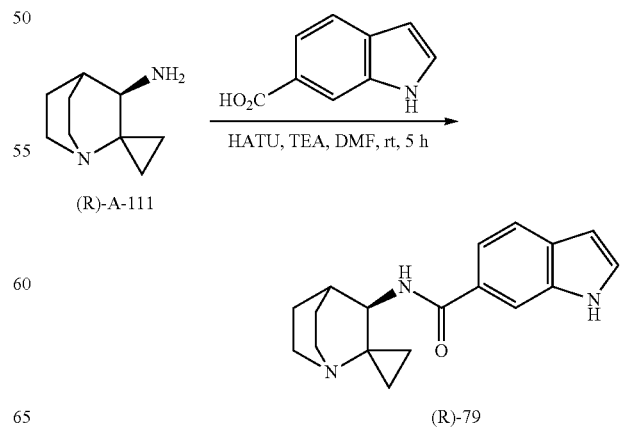

Following general procedure B, Compound (R)-79 was prepared from 1H-indole-6-carboxylic acid (53 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 150×30 mm, particle size: 10 μm; Mobile phase: 25-55% acetonitrile in H₂O (add 0.5% NH₃.H2O, v/v)] to give:

(R)—N-(1'-azaspiro[cyclopropane-1,2'-bicyclo[2.2.2]octan]-3'-yl)-1H-indole-6-carboxamide (compound (R)-79) (24 mg, 25% yield) as a white solid: cSFC analytical (A) tR=2.77 min., purity: 97.84%; LCMS (G): tR=2.234 min., (ES⁺) m/z (M+H)⁺=296.1; ¹H-NMR (CD₃OD, 400 MHz): δ 7.92 (s, 1H), 7.63 (d, J=8.4 Hz, 1H), 7.50 (dd, J=8.0, 1.2 Hz, 1H), 7.41 (d, J=2.8 Hz, 1H), 6.53 (d, J=2.8 Hz, 1H), 4.24 (d, J=1.6 Hz, 1H), 3.33-3.23 (m, 1H), 3.10-3.08 (m, 1H), 2.93-2.86 (m, 2H), 2.12 (d, J=3.2 Hz, 1H), 2.02-1.90 (m, 1H), 1.89-1.82 (m, 2H), 1.57 (m, 1H), 0.93-0.87 (m, 2H), 0.79-0.70 (m, 2H).

Example 80

Preparation of (R)—N-(1'-azaspiro[cyclopropane-1, 2'-bicyclo[2.2.2]octan]-3'-yl)pyrazolo[1,5-b] pyridazine-3-carboxamide hydrochloride ((R)-80)

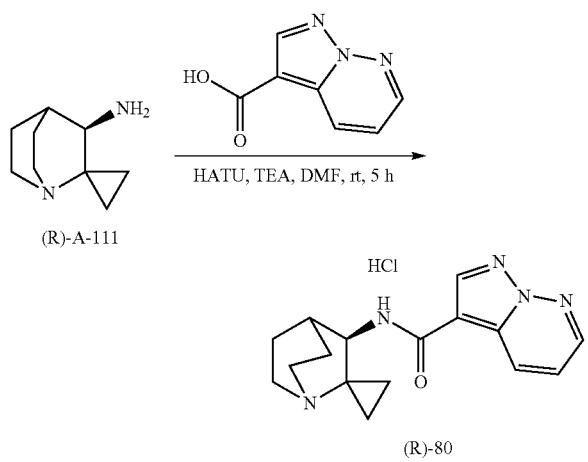

Following general procedure B, Compound (R)-80 was prepared from pyrazolo[1,5-b]pyridazine-3-carboxylic acid (53 mg, 0.33 mmol) and compound (R)-A-111 (50 mg, 0.33 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H₂O (add 0.5% HCl, v/v)] to give:

(R)—N-(1'-azaspiro[cyclopropane-1,2'-bicyclo[2.2.2]octan]-3'-yl)pyrazolo[1,5-b]pyridazine-3-carboxamide hydrochloride (compound (R)-80) (30 mg, 31% yield) as a white solid: cSFC analytical (G) tR=3.73 min., purity: 96.63%; LCMS (X): tR=1.319 min., (ES⁺) m/z (M+H)⁺=298.1; ¹H-NMR (CD₃OD, 400 MHz): δ 8.69 (s, 1H), 8.63 (dd, J₁=9.4 Hz, J₂=2.0 Hz, 1H), 8.53-8.51 (dd, J₁=4.4 Hz, J₂=2.0 Hz, 1H), 7.42-7.38 (m, 1H), 4.60 (d, J=2.4 Hz, 1H), 3.69-3.58 (m, 1H), 3.57-3.47 (m, 1H), 3.45-3.41 (m, 2H), 2.44-2.42 (m, 1H), 2.36-2.30 (m, 1H), 2.23-2.18 (m, 2H), 2.00-1.97 (m, 1H), 1.39-1.34 (m, 1H), 1.26-1.20 (m, 3H).

Preparation of (S)—N-(1'-azaspiro[cyclopropane-1, 2'-bicyclo[2.2.2]octan]-3'-yl)pyrazolo[1,5-b] pyridazine-3-carboxamide hydrochloride ((S)-80)

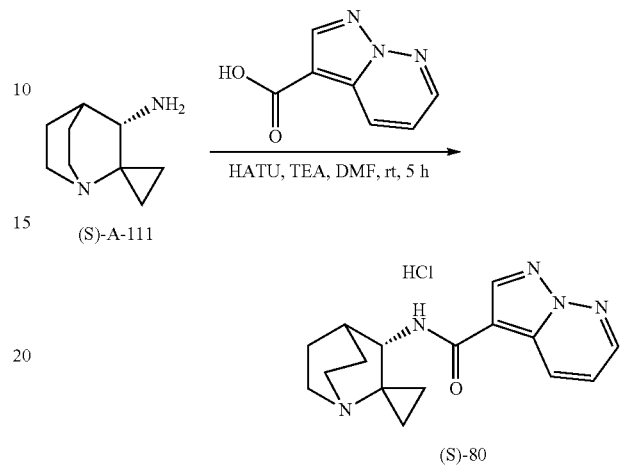

Following general procedure B, Compound (S)-80 was prepared from pyrazolo[1,5-b]pyridazine-3-carboxylic acid (50 mg, 0.31 mmol) and compound (S)-A-111 (47 mg, 0.31 mmol), with a reaction time of 5 hours. The product was purified by prep-HPLC [Instrument: GX-E; Column: Agella Venusil ASB C18 150×30 mm, particle size: 5 μm; Mobile phase: 16-46% acetonitrile in H₂O (add 0.5% HCl, v/v)] to give:

(S)—N-(1'-azaspiro[cyclopropane-1,2'-bicyclo[2.2.2]octan]-3'-yl)pyrazolo[1,5-b]pyridazine-3-carboxamide hydrochloride (compound (S)-80) (30 mg, 33% yield) as a white solid: cSFC analytical (G) tR=2.98 min., purity: 99.29%; LCMS (X): tR=1.309 min., (ES⁺) m/z (M+H)⁺=298.1; ¹H-NMR (CD₃OD, 400 MHz): δ 8.69 (s, 1H), 8.63 (dd, J=9.4 Hz, J₂=2.0 Hz, 1H), 8.52 (dd, J₁=4.4 Hz, J₂=2.0 Hz, 1H), 7.41-7.38 (m, 1H), 4.59 (d, J=2.4 Hz, 1H), 3.73-3.72 (m, 1H), 3.57-3.47 (m, 1H), 3.45-3.41 (m, 2H), 2.44-2.42 (m, 1H), 2.36-2.29 (m, 1H), 2.24-2.18 (m, 2H), 2.00-1.96 (m, 1H), 1.39-1.34 (m, 1H), 1.23-1.17 (m, 3H).

Example 81

Preparation of (R)—N-(1'-azaspiro[cyclopropane-1, 2'-bicyclo[2.2.2]octan]-3'-yl)thieno[2,3-b]pyridine-2-carboxamide hydrochloride ((R)-81)

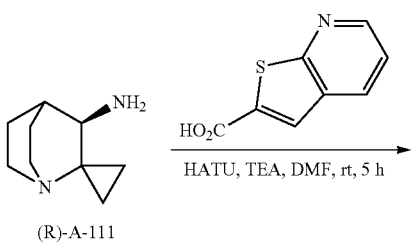

-continued

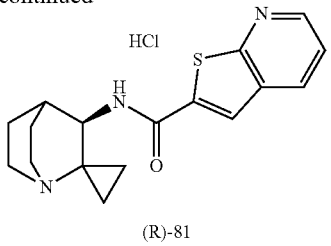

(R)-81

Following general procedure B, Compound (R)-81 was prepared from thieno[2,3-b]pyridine-2-carboxylic acid (59 mg, 0.33 mmol) and compound (R)-A-111 (50 mg, 0.33 mmol), with a reaction time of 5 hours. The product was purified by prep-HPLC [Instrument: GX-B; Column: Phenomenex Synergi C18 150×30 mm, particle size: 4 μm; Mobile phase: 8-38% acetonitrile in $H_2O$ (add 0.5% TFA, v/v)], treated with 0.2 M hydrochloric acid solution and lyophilized to give:

(R)—N-(1'-azaspiro[cyclopropane-1,2'-bicyclo[2.2.2]octan]-3'-yl)thieno[2,3-b]pyridine-2-carboxamide hydrochloride (compound (R)-81) (43 mg, 42% yield) as a yellow solid: cSFC analytical (A) tR=2.62 min., purity: 97.29%; LCMS (U): tR=1.124 min., (ES$^+$) m/z (M+H)$^+$=314.0; $^1$H-NMR (CD$_3$OD, 400 MHz): δ 8.72 (d, J=4.8, 1.2 Hz, 1H), 8.51 (d, J=8.0, 1.2 Hz, 1H), 8.25 (s, 1H), 7.62 (d, J=8.0, 4.8 Hz, 1H), 4.58 (d, J=2.0 Hz, 1H), 3.77-3.73 (m, 1H), 3.59-3.58 (m, 1H), 3.50-3.43 (m, 2H), 2.47-2.45 (m, 1H), 2.36 (m, 1H), 2.24-2.17 (m, 2H), 2.01-1.99 (m, 1H), 1.40-1.36 (m, 1H), 1.31-1.28 (m, 2H), 1.26-1.20 (m, 1H).

Preparation of (S)—N-(1'-azaspiro[cyclopropane-1,2'-bicyclo[2.2.2]octan]-3'-yl)thieno[2,3-b]pyridine-2-carboxamide hydrochloride ((S)-81)

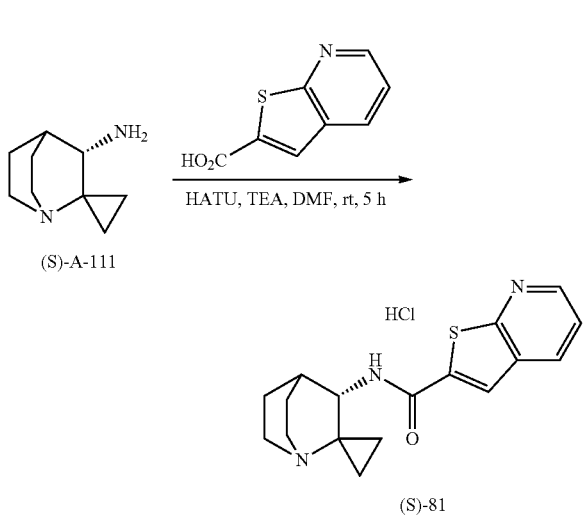

Following general procedure B, Compound (S)-81 was prepared from thieno[2,3-b]pyridine-2-carboxylic acid (47 mg, 0.26 mmol) and compound (S)-A-111 (40 mg, 0.26 mmol), with a reaction time of 5 hours. The product was purified by prep-HPLC [Instrument: GX-B; Column: Phenomenex Synergi C18 150×30 mm, particle size: 4 μm; Mobile phase: 8-38% acetonitrile in $H_2O$ (add 0.5% TFA, v/v)], treated with 0.2 M hydrochloric acid solution and lyophilized to give:

(S)—N-(1'-azaspiro[cyclopropane-1,2'-bicyclo[2.2.2]octan]-3'-yl)thieno[2,3-b]pyridine-2-carboxamide hydrochloride (compound (S)-81) (50 mg, 61% yield) as a yellow solid: cSFC analytical (A) tR=3.52 min., purity: 97.73%; LCMS (U): tR=1.127 min., (ES$^+$) m/z (M+H)$^+$=314.0; $^1$H-NMR (CD$_3$OD, 400 MHz): δ 8.85-8.84 (m, 1H), 8.75 (d, J=8.4 Hz, 1H), 8.43 (s, 1H), 7.80 (d, J=8.4, 5.2 Hz, 1H), 4.59 (d, J=2.4 Hz, 1H), 3.79-3.75 (m, 1H), 3.58-3.57 (m, 1H), 3.50-3.43 (m, 2H), 2.46-2.36 (m, 2H), 2.23-2.17 (m, 2H), 2.03-1.96 (m, 1H), 1.40-1.39 (m, 1H), 1.35-1.28 (m, 2H), 1.18-1.17 (m, 1H).

Example 82

Preparation of (R)—N-(1'-azaspiro[cyclopropane-1,2'-bicyclo[2.2.2]octan]-3'-yl)benzo[d]thiazole-2-carboxamide hydrochloride ((R)-82)

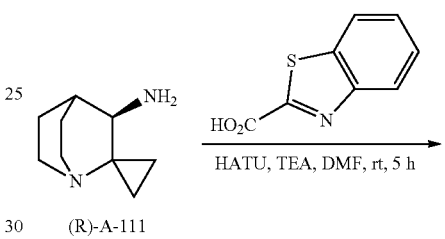

(R)-A-111

Following general procedure B, Compound (R)-82 was prepared from benzo[d]thiazole-2-carboxylic acid (59 mg, 0.33 mmol) and compound (R)-A-111 (50 mg, 0.33 mmol), with a reaction time of 5 hours. The product was purified by prep-HPLC [Instrument: GX-H; Column: YMC-pack ODS-AQ 150×30 mm, particle size: 5 μm; Mobile phase: 14-44% acetonitrile in $H_2O$ (add 0.5% TFA, v/v)], treated with 0.2 M hydrochloric acid and lyophilized to give:

(R)—N-(1'-azaspiro[cyclopropane-1,2'-bicyclo[2.2.2]octan]-3'-yl)benzo[d]thiazole-2-carboxamide hydrochloride (compound (R)-82) (58 mg, 56% yield) as a white solid: cSFC analytical (A) tR=2.10 min., purity: 97.31%; LCMS (V): tR=2.478 min., 314.1 m/z (M+1); $^1$H-NMR (CD$_3$OD, 400 MHz): δ 8.17 (d, J=8.4 Hz, 1H), 8.11 (d, J=7.6 Hz, 1H), 7.64 (t, J=7.6 Hz, 1H), 7.58 (t, J=7.6 Hz, 1H), 4.60 (d, J=2.0 Hz, 1H), 3.80-3.77 (m, 1H), 3.60-3.59 (m, 1H), 3.52-3.41 (m, 2H), 2.49-2.48 (m, 1H), 2.36 (m, 1H), 2.26-2.18 (m, 2H), 2.01-1.97 (m, 1H), 1.40-1.37 (m, 1H), 1.31-1.20 (m, 3H).

Preparation of (S)—N-(1'-azaspiro[cyclopropane-1,2'-bicyclo[2.2.2]octan]-3'-yl)benzo[d]thiazole-2-carboxamide hydrochloride ((S)-82)

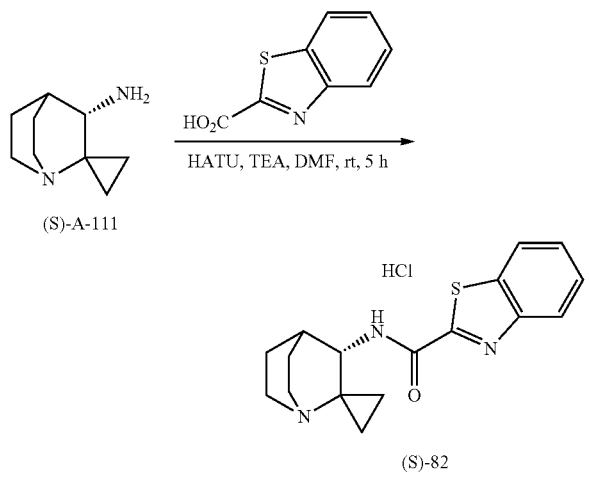

Following general procedure B, Compound (S)-82 was prepared from benzo[d]thiazole-2-carboxylic acid (47 mg, 0.26 mmol) and compound (S)-A-111 (40 mg, 0.26 mmol), with a reaction time of 5 hours. The product was purified by prep-HPLC [Instrument: GX-H; Column: YMC-pack ODS-AQ 150×30 mm, particle size: 5 μm; Mobile phase: 14-44% acetonitrile in H$_2$O (add 0.5% TFA, v/v)], treated with 0.2 M hydrochloric acid and lyophilized to give:

(S)—N-(1'-azaspiro[cyclopropane-1,2'-bicyclo[2.2.2]octan]-3'-yl)benzo[d]thiazole-2-carboxamide hydrochloride (compound (S)-82) (40 mg, 49% yield) as a white solid: cSFC analytical (A) tR=2.27 min., purity: 97.78%; LCMS (V): tR=2.469 min., 314.1 m/z (M+1); $^1$H-NMR (CD$_3$OD, 400 MHz): δ 8.17 (d, J=8.4 Hz, 1H), 8.11 (d, J=8.0 Hz, 1H), 7.64 (t, J=7.6 Hz, 1H), 7.58 (t, J=7.6 Hz, 1H), 4.60 (s, 1H), 3.78-3.74 (m, 1H), 3.60-3.59 (m, 1H), 3.52-3.44 (m, 2H), 2.49-2.48 (m, 1H), 2.36-2.34 (m, 1H), 2.25-2.14 (m, 2H), 2.01 (m, 1H), 1.40-1.35 (m, 1H), 1.34-1.20 (m, 3H).

Example 83: (R)—N-(1'-azaspiro[cyclopropane-1,2'-bicyclo[2.2.2]octan]-3'-yl)benzo[b]thiophene-5-carboxamide hydrochloride ((R)-83)

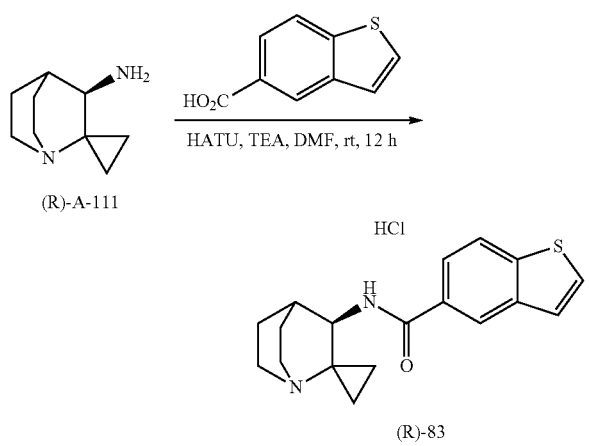

Following general procedure B, Compound (R)-83 was prepared from benzo[b]thiophene-5-carboxylic acid (64 mg, 0.36 mmol) and compound (R)-A-111 (50 mg, 0.33 mmol), with a reaction time of 12 hours. The product was purified by prep-HPLC [Instrument: GX-E; Column: Phenomenex Synergi C18 150×30 mm, particle size: 10 μm; Mobile phase: 5-35% acetonitrile in H$_2$O (add 0.5% HCl, v/v)] to give:

(R)—N-(1'-azaspiro[cyclopropane-1,2'-bicyclo[2.2.2]octan]-3'-yl)benzo[b]thiophene-5-carboxamide hydrochloride (compound (R)-83) (15 mg, 15% yield) as a white solid: cSFC analytical (B) tR=2.57 min., purity: 98.14%; LCMS (C): tR=1.267 min., (ES$^+$) m/z (M+H)$^+$=313.1; $^1$H-NMR (CD$_3$OD, 400 MHz): δ 8.38 (s, 1H), 8.04 (d, J=8.0 Hz, 1H), 7.81 (d, J=8.0 Hz, 1H), 7.73 (d, J=5.2 Hz, 1H), 7.52 (d, J=5.2 Hz, 1H), 4.62 (s, 1H), 3.72-3.68 (m, 1H), 3.60-3.51 (m, 1H), 3.50-3.33 (m, 2H), 2.49-2.48 (m, 1H), 2.38-2.17 (m, 3H), 2.01 (m, 1H), 1.42-1.38 (m, 1H), 1.30-1.20 (m, 3H).

Example 84: (R)—N-(1'-azaspiro[cyclopropane-1,2'-bicyclo[2.2.2]octan]-3'-yl)benzofuran-6-carboxamide hydrochloride ((R)-84)

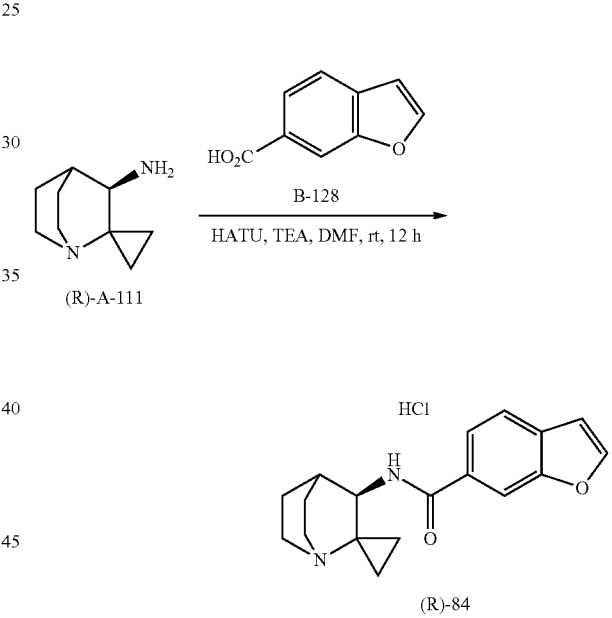

Following general procedure B, Compound (R)-84 was prepared from compound B-128 (53 mg, 0.33 mmol) and compound (R)-A-111 (50 mg, 0.33 mmol), with a reaction time of 12 hours. The product was purified by prep-HPLC [Instrument: GX-E; Column: Phenomenex Synergi C18 150×30 mm, particle size: 10 μm; Mobile phase: 3-33% acetonitrile in H$_2$O (add 0.5% HCl, v/v)] to give:

(R)—N-(1'-azaspiro[cyclopropane-1,2'-bicyclo[2.2.2]octan]-3'-yl)benzofuran-6-carboxamide hydrochloride (compound (R)-84) (45 mg, 41% yield) as a white solid: cSFC analytical (A) tR=2.11 min., purity: 97.07%; LCMS (R): tR=0.417, 297.1 m/z (M+1); $^1$H-NMR (CD$_3$OD, 400 MHz): δ 8.04 (s, 1H), 7.93 (d, J=2.4 Hz, 1H), 7.76-7.71 (m, 2H), 6.96 (d, J=1.2 Hz, 1H), 4.58 (s, 1H), 3.69-3.65 (m, 1H), 3.56-3.55 (m, 1H), 3.46-3.38 (m, 2H), 2.44 (d, J=3.2 Hz, 1H), 2.33-2.26 (m, 3H), 1.96 (s, 1H), 1.35-1.25 (m, 1H), 1.24-1.17 (m, 1H).

Example 85: (R)-2-methyl-N-(1'-azaspiro[cyclopropane-1,2'-bicyclo[2.2.2]octan]-3'-yl)benzo[d]oxazole-5-carboxamide ((R)-85)

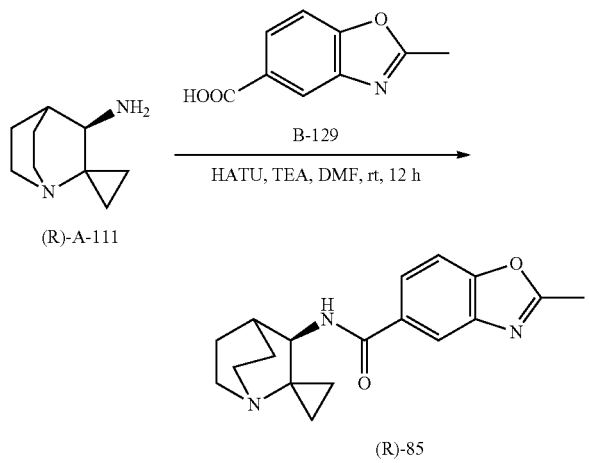

Following general procedure B, Compound (R)-85 was prepared from compound B-129 (0.069 g, 0.39 mmol) and compound (R)-A-111 (0.051 g, 0.34 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in $H_2O$ (add 0.5% $NH_3.H2O$, v/v)] to give:

(R)-2-methyl-N-(1'-azaspiro[cyclopropane-1,2'-bicyclo[2.2.2]octan]-3'-yl)benzo[d]oxazole-5-carboxamide (compound (R)-85) (0.030 g, 29% yield) as a white solid: cSFC analytical (A) tR=2.04 min., purity: 97.63%; LCMS (J): tR=0.970 min., 312.1 m/z (M+1); $^1$H-NMR ($CD_3OD$, 400 MHz): δ 8.10 (s, 1H), 7.85 (m, 1H), 7.65 (d, J=8.4 Hz, 1H), 4.23 (s, 1H), 3.27-3.23 (m, 1H), 3.09-3.07 (m, 1H), 2.92-2.85 (m, 2H), 2.69 (s, 3H), 2.12-2.12 (m, 1H), 2.00-1.85 (m, 3H), 1.56-1.56 (m, 1H), 0.91-0.87 (m, 2H), 0.76-0.68 (m, 2H).

Example 86: (R)-2-methyl-N-(1'-azaspiro[cyclopropane-1,2'-bicyclo[2.2.2]octan]-3'-yl)benzo[d]oxazole-6-carboxamide ((R)-86)

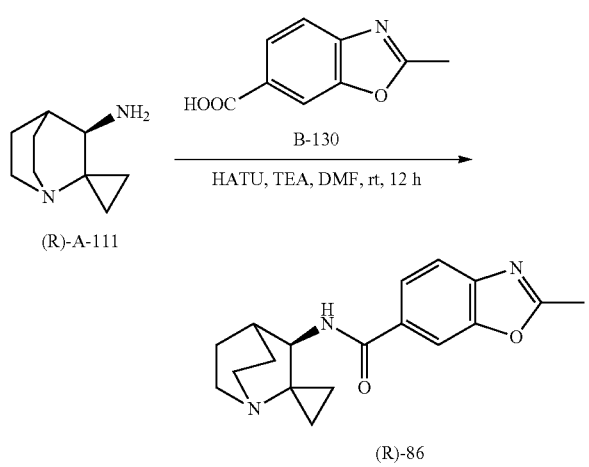

Following general procedure B, Compound (R)-86 was prepared from compound B-130 (0.060 g, 0.34 mmol) and compound (R)-A-111 (0.052 g, 0.34 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in $H_2O$ (add 0.5% $NH_3.H2O$, v/v)] to give:

(R)-2-methyl-N-(1'-azaspiro[cyclopropane-1,2'-bicyclo[2.2.2]octan]-3'-yl)benzo[d]oxazole-6-carboxamide (compound (R)-86) (0.040 g, 38% yield) as a white solid: cSFC analytical (A) tR=2.14 min., purity: 97.62%; LCMS (J): tR=0.960 min., 312.1 m/z (M+1); $^1$H-NMR ($CD_3OD$, 400 MHz): δ 8.05 (s, 1H), 7.87-7.84 (m, 1H), 7.70 (d, J=8.4 Hz, 1H), 4.24-4.23 (s, 1H), 3.25-3.23 (m, 1H), 3.09-3.09 (m, 1H), 2.92-2.83 (m, 2H), 2.70 (s, 3H), 2.13-2.12 (m, 1H), 2.00-1.85 (m, 3H), 1.57-1.57 (m, 1H), 0.91-0.87 (m, 2H), 0.76-0.68 (m, 2H).

Example 87: (R)-2-methyl-N-(1'-azaspiro[cyclopropane-1,2'-bicyclo[2.2.2]octan]-3'-yl)benzo[d]thiazole-5-carboxamide hydrochloride ((R)-87)

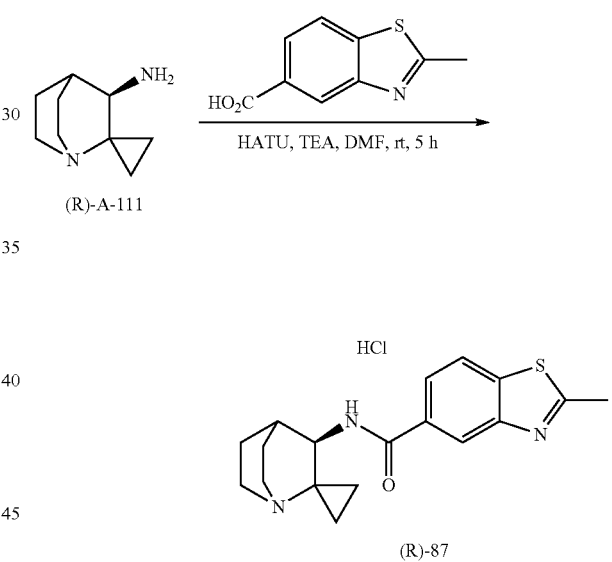

Following general procedure B, Compound (R)-87 was prepared from 2-methylbenzo[d]thiazole-5-carboxylic acid (63 mg, 0.33 mmol) and compound (R)-A-111 (50 mg, 0.33 mmol), with a reaction time of 5 hours. The product was purified by prep-HPLC [Instrument: GX-B; Column: Phenomenex Synergi C18 150×30 mm, particle size: 4 μm; Mobile phase: 8-38% acetonitrile in $H_2O$ (add 0.5% TFA, v/v)], treated with HCl and lyophilized to give:

(R)-2-methyl-N-(1'-azaspiro[cyclopropane-1,2'-bicyclo[2.2.2]octan]-3'-yl)benzo[d]thiazole-5-carboxamide hydrochloride (compound (R)-87) (50 mg, 42% yield) as a white solid: cSFC analytical (A) tR=2.34 min., purity: 97.73%; LCMS (K): tR=1.210 min., ($ES^+$) m/z $(M+H)^+$=328.0; $^1$H-NMR ($CD_3OD$, 400 MHz): δ 8.39 (s, 1H), 8.09 (d, J=8.8 Hz, 1H), 7.91 (d, J=8.0 Hz, 1H), 4.62 (s, 1H), 3.72-3.71 (m, 1H), 3.61-3.60 (m, 1H), 3.50-3.43 (m, 2H), 2.91 (s, 3H), 2.49-2.48 (m, 1H), 2.37-2.16 (m, 3H), 2.05-2.00 (m, 1H), 1.44-1.41 (m, 1H), 1.32-1.22 (m, 3H).

307

Example 88: (R)-2-methyl-N-(1'-azaspiro[cyclopropane-1,2'-bicyclo[2.2.2]octan]-3'-yl)benzo[d]thiazole-6-carboxamide hydrochloride ((R)-88)

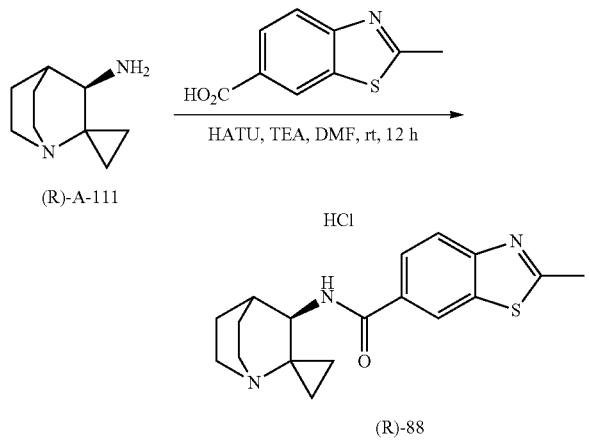

Following general procedure B, Compound (R)-88 was prepared from 2-methylbenzo[d]thiazole-6-carboxylic acid (63 mg, 0.33 mmol) and compound (R)-A-111 (50 mg, 0.33 mmol), with a reaction time of 12 hours. The product was purified by prep-HPLC [Instrument: GX-B; Column: Phenomenex Synergi C18 150×30 mm, particle size: 4 μm; Mobile phase: 8-38% acetonitrile in $H_2O$ (add 0.5% TFA, v/v)], treated with 0.2 N HCl and lyophilized to give:

(R)-2-methyl-N-(1'-azaspiro[cyclopropane-1,2'-bicyclo[2.2.2]octan]-3'-yl)benzo[d]thiazole-6-carboxamide hydrochloride (compound (R)-88) (48 mg, 40% yield) as a white solid: cSFC analytical (A) tR=2.50 min., purity: 97.89%; LCMS (K): tR=1.164 min., (ES$^+$) m/z (M+H)$^+$=328.0; $^1$H-NMR (CD$_3$OD, 400 MHz): δ8.58 (s, 1H), 8.06-7.99 (m, 2H), 4.58 (s, 1H), 3.72-3.58 (m, 1H), 3.57-3.48 (m, 1H), 3.46-3.41 (m, 2H), 2.97 (s, 3H), 2.47-2.46 (m, 1H), 2.33-2.30 (m, 1H), 2.24-2.17 (m, 2H), 2.02-1.95 (m, 1H), 1.42-1.41 (m, 1H), 1.33-1.20 (m, 3H).

Example 89: (R)—N-(1'-azaspiro[cyclopropane-1,2'-bicyclo[2.2.2]octan]-3'-yl)furo[2,3-b]pyridine-5-carboxamide ((R)-89)

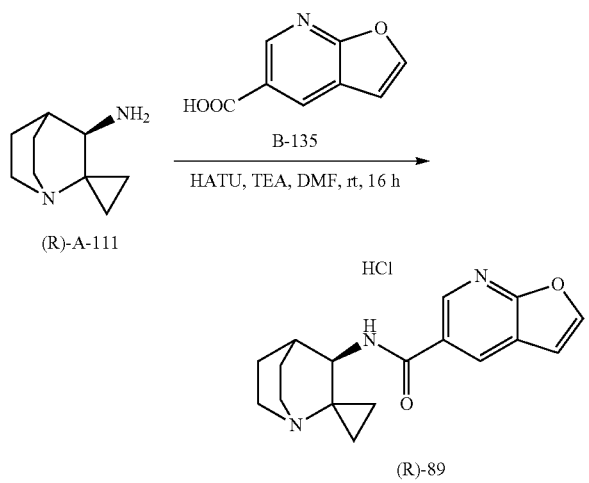

308

Following general procedure B, Compound (R)-89 was prepared from compound B-135 (54 mg, 0.33 mmol) and compound (R)-A-111 (50 mg, 0.33 mmol), with a reaction time of 16 hours. The product was purified by prep-HPLC [Instrument: GX-A; Column: Phenomenex Gemini C18 150×25 mm, particle size: 10 μm; Mobile phase: 15-45% acetonitrile in $H_2O$ (add 0.5% $NH_3.H_2O$, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)furo[2,3-b]pyridine-5-carboxamide hydrochloride (compound (R)-89) (40 mg, 38% yield) as a white solid: cSFC analytical (A) tR=2.75 min., purity: 100%; LCMS (J): tR=1.27 min., 298.1 m/z (M+1); $^1$H-NMR (CD$_3$OD, 400 MHz): 8.76 (d, J=2 Hz, 1H), 8.56 (s, 1H), 8.03 (d, J=2 Hz, 1H), 7.07 (d, J=2.4 Hz, 1H), 4.53 (s, 1H), 3.59-3.49 (m, 2H), 3.40-3.37 (m, 2H), 2.04-2.42 (m, 1H), 2.28-2.11 (m, 3H), 1.92 (m, 1H), 1.29-1.12 (m, 4H).

Example 90: (R)—N-(1'-azaspiro[cyclopropane-1,2'-bicyclo[2.2.2]octan]-3'-yl)furo[3,2-b]pyridine-5-carboxamide hydrochloride ((R)-90)

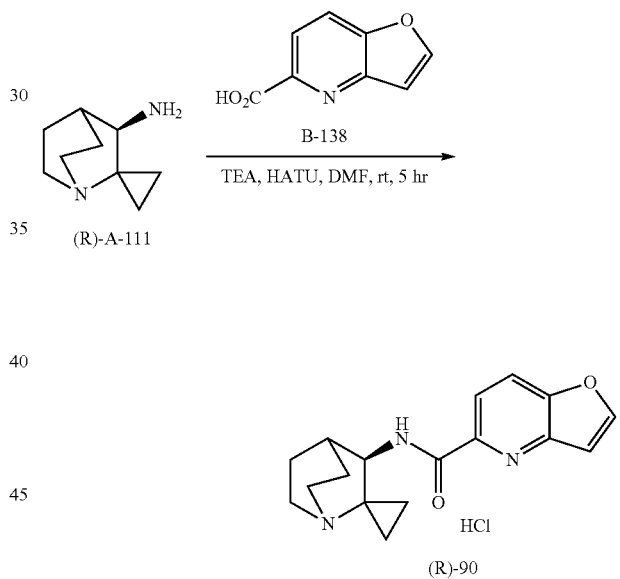

Following general procedure B, Compound (R)-90 was prepared from compound B-138 (54 mg, 0.33 mmol) and compound (R)-A-111 (50 mg, 0.33 mmol), with a reaction time of 5 hours. The product was purified by prep-HPLC [Instrument: GX-E; Column: Agella Venusil ASB C18 150× 30 mm, particle size: 5 μm; Mobile phase: 16-46% acetonitrile in $H_2O$ (add 0.5% HCl, v/v)] to give:

(R)—N-(1'-azaspiro[cyclopropane-1,2'-bicyclo[2.2.2]octan]-3'-yl)furo[3,2-b]pyridine-5-carboxamide hydrochloride (compound (R)-90) (50 mg, 51% yield) as a white solid: cSFC analytical (A) tR=1.94 min., purity: 98.64%; LCMS (M): tR=0.899 min., (ES$^+$) m/z (M+H)$^+$=298.0; $^1$H-NMR (CD$_3$OD, 400 MHz): δ 8.34 (d, J=2.4 Hz, 1H), 8.26 (m, 2H), 8.21 (d, J=2.0 Hz, 1H), 4.60 (s, 1H), 3.77-3.75 (m, 1H), 3.59-3.58 (m, 1H), 3.50-3.44 (m, 2H), 2.47-2.46 (m, 1H), 2.39-2.33 (m, 1H), 2.22-2.19 (m, 2H), 2.02-1.99 (m, 1H), 1.32-1.30 (m, 1H), 1.26-1.11 (m, 3H).

Example 91: (R)-2-methyl-N-(1'-azaspiro[cyclopropane-1,2'-bicyclo[2.2.2]octan]-3'-yl)benzofuran-5-carboxamide hydrochloride ((R)-91)

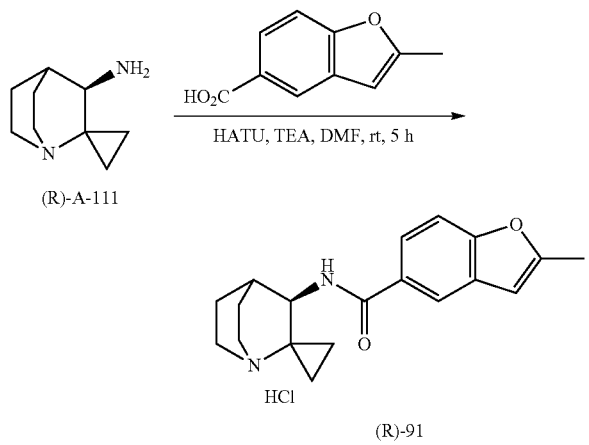

Following general procedure B, Compound (R)-91 was prepared from 2-methylbenzofuran-5-carboxylic acid (60 mg, 0.34 mmol) and compound (R)-A-111 (50 mg, 0.33 mmol), with a reaction time of 5 hours. The product was purified by prep-HPLC [Instrument: GX-B; Column: YMC-pack ODS-AQ 150×30 mm, particle size: 5 μm; Mobile phase: 18-48% acetonitrile in H$_2$O (add 0.5% HCl, v/v)] to give:

(R)-2-methyl-N-(1'-azaspiro[cyclopropane-1,2'-bicyclo[2.2.2]octan]-3'-yl)benzofuran-5-carboxamide hydrochloride (compound (R)-91) (15 mg, 13% yield) as a white solid: cSFC analytical (A) tR=2.103 min., purity: 97.71%; LCMS (B): tR=0.640 min., 311.1 m/z (M+1); $^1$H-NMR (CD$_3$OD, 400 MHz): δ 8.02 (s, 1H), 7.73 (d, J=8.4, 1H), 7.49 (d, J=8.4, 1H), 6.58 (s, 1H), 4.60 (m, 1H), 3.69-3.61 (m, 1H), 3.60-3.59 (m, 2H), 3.50-3.44 (m, 2H), 2.47-2.46 (m, 4H), 2.33-2.19 (m, 3H), 2.01-1.99 (m, 1H), 1.40-1.36 (m, 1H), 1.27-1.20 (m, 3H).

Example 92: (R)-2-chloro-N-(1'-azaspiro[cyclopropane-1,2'-bicyclo[2.2.2]octan]-3'-yl)benzofuran-5-carboxamide hydrochloride ((R)-92)

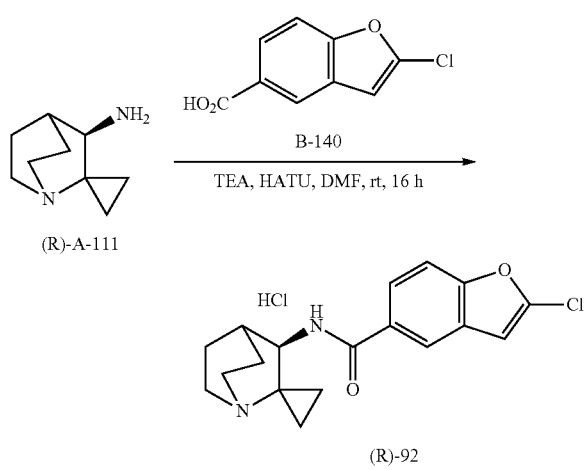

Following general procedure B, Compound (R)-92 was prepared from compound B-140 (71 mg, 0.36 mmol) and compound (R)-A-111 (50 mg, 0.33 mmol), with a reaction time of 16 hours. The product was purified by prep-HPLC [Instrument: GX-E; Column: Agella Venusil ASB C18 150×30 mm, particle size: 10 μm; Mobile phase: 15-45% acetonitrile in H$_2$O (add 0.5% HCl, v/v)] to give:

(R)-2-chloro-N-(1'-azaspiro[cyclopropane-1,2'-bicyclo[2.2.2]octan]-3'-yl)benzofuran-5-carboxamide hydrochloride (compound (R)-92) (23 mg, 21% yield) as a white solid: cSFC analytical (A) tR: 2.10 min., purity: 97.99%; LCMS (S): tR=0.89 min., (ES$^+$) m/z (M+H)$^+$=331.1; $^1$H-NMR (CD$_3$OD, 400 MHz): δ 8.10 (d, J=1.2 Hz, 1H), 7.83 (dd, J$_1$=8.8 Hz, J$_1$=1.6 Hz, 1H), 7.60 (d, J=1.6 Hz, 1H), 6.91 (s, 1H), 4.59 (d, J=2 Hz, 1H), 3.71-3.50 (m, 2H), 3.48-3.44 (m, 2H), 2.53-2.46 (m, 1H), 2.33-2.18 (m, 3H), 2.02-1.99 (m, 1H), 1.42-1.38 (m, 1H), 1.30-1.20 (m, 3H).

Example 93: (R)-3-methyl-N-(1'-azaspiro[cyclopropane-1,2'-bicyclo[2.2.2]octan]-3'-yl)benzofuran-5-carboxamide hydrochloride ((R)-93)

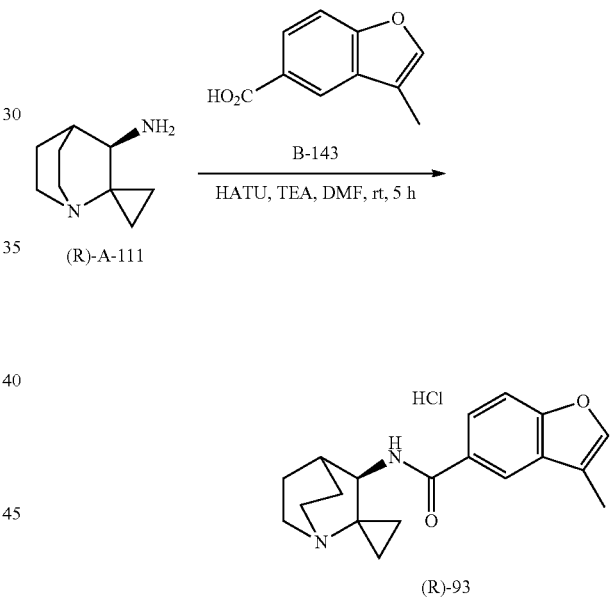

Following general procedure B, Compound (R)-93 was prepared from compound B-143 (69 mg, 0.39 mmol) and compound (R)-A-111 (50 mg, 0.33 mmol), with a reaction time of 5 hours. The product was purified by prep-HPLC [Instrument: GX-E; Column: Phenomenex Synergi C18 150×30 mm, particle size: 5 μm; Mobile phase: 10-40% acetonitrile in H$_2$O (add 0.5% HCl, v/v)] to give:

(R)-3-methyl-N-(1'-azaspiro[cyclopropane-1,2'-bicyclo[2.2.2]octan]-3'-yl)benzofuran-5-carboxamide hydrochloride (compound (R)-93) (47 mg, 41% yield) as a white solid: cSFC analytical (A) tR=2.06 min., purity: 99.42%; LCMS (B): tR=0.606 min., 311.2 m/z (M+1); $^1$H-NMR (CD$_3$OD, 400 MHz): δ 8.13 (d, J=4 Hz, 1H), δ 7.81 (dd, J$_1$=8 Hz, J$_2$=4 Hz, 1H), 7.64 (d, J=4 Hz, 1H), 7.53 (d, J=8 Hz, 1H), 4.60 (m, 1H), 3.59-3.58 (m, 1H), 3.48-3.46 (m, 1H), 3.45-3.43 (m, 1H), 2.46-2.45 (m, 1H), 2.31 (m, 4H), 2.24-2.18 (m, 1H), 2.00 (m, 1H), 1.40-1.35 (m, 1H), 1.27-1.20 (m, 1H).

Example 94: (R)-3-chloro-N-(1'-azaspiro[cyclopropane-1,2'-bicyclo[2.2.2]octan]-3'-yl)benzofuran-5-carboxamide hydrochloride ((R)-94)

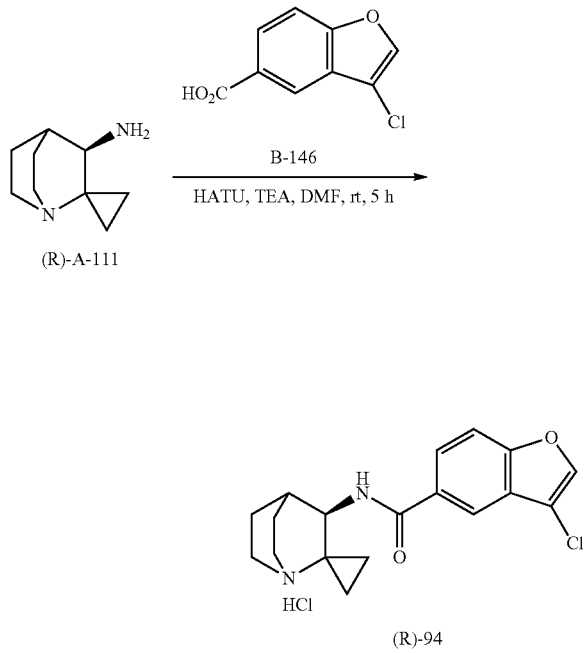

Following general procedure B, Compound (R)-94 was prepared from compound B-146 (64 mg, 0.34 mmol) and compound (R)-A-111 (50 mg, 0.33 mmol), with a reaction time of 5 hours. The product was purified by prep-HPLC [Instrument: GX-E; Column: Phenomenex Synergi C18 150×30 mm, particle size: 10 μm; Mobile phase: 10-40% acetonitrile in H₂O (add 0.5% HCl, v/v)] to give:

(R)-3-chloro-N-(1'-azaspiro[cyclopropane-1,2'-bicyclo[2.2.2]octan]-3'-yl)benzofuran-5-carboxamide hydrochloride (compound (R)-94) (20 mg, 17% yield) as a white solid: cSFC analytical (A) tR=2.09 min., purity: 97.90%; LCMS (B): tR=0.622 min., 331.1 m/z (M+1); ¹H-NMR (CD₃OD, 400 MHz): δ 8.19-8.18 (m, 1H), 8.06 (s, 1H), 7.94 (d, J=8.8, 1H), 7.67 (d, J=8.8, 1H), 3.71-3.60 (m, 2H), 3.51-3.41 (s, 2H), 2.49-2.48 (m, 1H), 2.37-2.19 (m, 3H), 2.01 (m, 1H), 1.40-1.20 (m, 5H).

Example 95: (R)-1-methyl-N-(1'-azaspiro[cyclopropane-1,2'-bicyclo[2.2.2]octan]-3'-yl)-1H-benzo[d]imidazole-5-carboxamide hydrochloride ((R)-95)

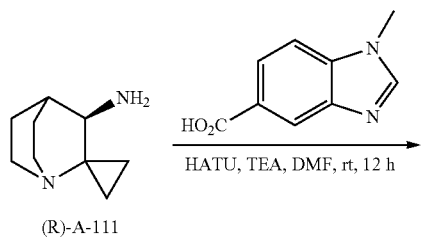

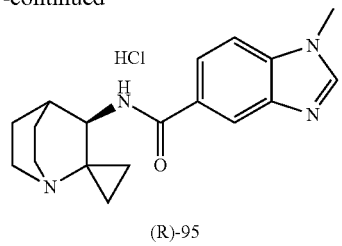

Following general procedure B, Compound (R)-95 was prepared from 1-methyl-1H-benzo[d]imidazole-5-carboxylic acid (60 mg, 0.34 mmol) and compound (R)-A-111 (52 mg, 0.34 mmol), with a reaction time of 12 hours. The product was purified by prep-HPLC [Instrument: GX-E; Column: Agella Venusil ASB C18 150×21.2 mm, particle size: 5 μm; Mobile phase: 15-45% acetonitrile in H₂O (add 0.5% HCl, v/v)] to give:

(R)-1-methyl-N-(1'-azaspiro[cyclopropane-1,2'-bicyclo[2.2.2]octan]-3'-yl)-1H-benzo[d]imidazole-5-carboxamide hydrochloride (compound (R)-95) (20 mg, 19% yield) as a white solid: cSFC analytical (A) tR=3.01 min., purity: 97.72%; LCMS (O): tR=1.726 min., 311.1 m/z (M+1); ¹H-NMR (CD₃OD, 400 MHz): δ 9.40 (s, 1H), 8.40 (s, 1H), 8.16 (d, J=8.8, 1H), 8.02 (d, J=8.8, 1H), 4.18 (s, 3H), 3.78-3.75 (m, 1H), 3.61-3.60 (m, 1H), 3.51-3.44 (m, 2H), 2.50-2.49 (m, 1H), 2.37-2.35 (m, 1H), 2.27-2.21 (m, 2H), 2.02-1.97 (m, 1H), 1.44-1.41 (m, 1H), 1.34-1.22 (m, 3H).

Example 96: (R)-1-methyl-N-(1'-azaspiro[cyclopropane-1,2'-bicyclo[2.2.2]octan]-3'-yl)-1H-benzo[d]imidazole-6-carboxamide ((R)-96)

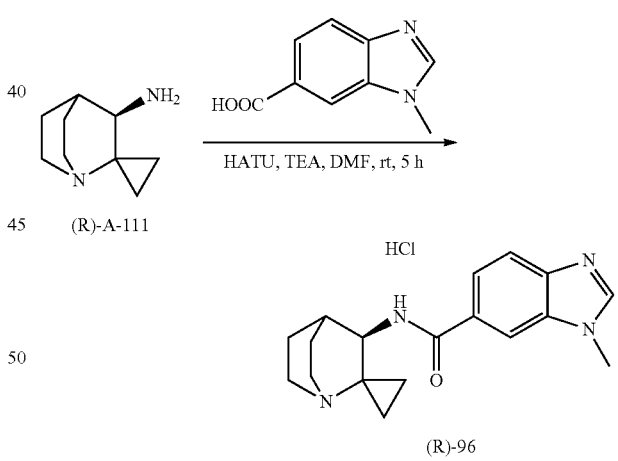

Following general procedure B, Compound (R)-96 was prepared from 1-methyl-1H-benzo[d]imidazole-6-carboxylic acid (58 mg, 0.33 mmol) and compound (R)-A-111 (50 mg, 0.33 mmol), with a reaction time of 5 hours. The product was purified by prep-HPLC [Instrument: GX-H; Column: welch Xtimate C18 150×30 mm, particle size: 5 μm; Mobile phase: 15-45% acetonitrile in H₂O (add 0.5% NH₃.H2O, v/v)]. The resulting solids were dissolved in 0.2 M hydrochloric acid solution and again lyophilized to give:

(R)-1-methyl-N-(1'-azaspiro[cyclopropane-1,2'-bicyclo[2.2.2]octan]-3'-yl)-1H-benzo[d]imidazole-6-carboxamide hydrochloride (compound (R)-96) (40 mg, 39% yield) as a white solid: cSFC analytical (A) tR=2.96 min., purity: 96.48%; LCMS (Q): tR=2.633 min., 311.1 m/z (M+1); ¹H-NMR (CD₃OD, 400 MHz): δ 9.53 (s, 1H), 8.60 (s, 1H), 8.19 (d, J=8.8 Hz, 1H), 7.97 (d, J=8.8 Hz, 1H), 4.65 (s, 1H), 4.26 (s, 1H), 3.85-3.78 (m, 1H), 3.61 (m, 1H), 3.52-3.42 (m, 2H), 2.50-2.40 (m, 2H), 2.25-2.18 (m, 2H), 2.05-2.02 (m, 1H), 1.45-1.41 (m, 1H) 1.36-1.31 (m, 2H) 1.24-1.21 (m, 1H).

Example 97: (R)—N-(1'-azaspiro[cyclopropane-1, 2'-bicyclo[2.2.2]octan]-3'-yl)thieno[2,3-c]pyridine-5-carboxamide ((R)-97)

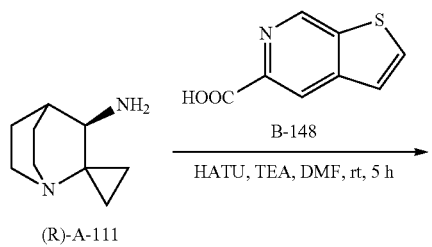

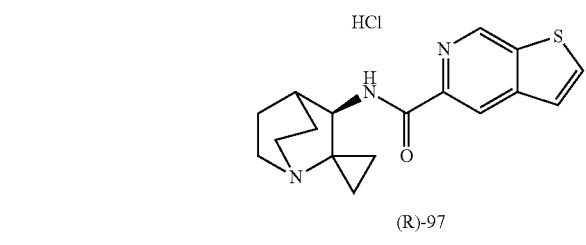

Following general procedure B, Compound (R)-97 was prepared from compound B-148 (71 mg, 0.39 mmol) and compound (R)-A-111 (50 mg, 0.33 mmol), with a reaction time of 5 hours. The product was purified by prep-HPLC [Instrument: GX-A; Column: Phenomenex SynergiC18 150×25 mm, particle size: 10 µm; Mobile phase: 27-57% acetonitrile in H₂O (add 0.5% NH₃.H2O, v/v)]. The resulting solids were dissolved in 0.2 M hydrochloric acid solution and again lyophilized to give:

(R)—N-(1'-azaspiro[cyclopropane-1,2'-bicyclo[2.2.2]octan]-3'-yl)thieno[2,3-c]pyridine-5-carboxamide hydrochloride (compound (R)-97) (40 mg, 35% yield) as a yellow solid: cSFC analytical (A) tR=2.42 min., purity: 98.60%; LCMS (J): tR=1.454 min., 314.1 m/z (M+1); ¹H-NMR (CD₃OD, 400 MHz): δ 9.46 (s, 1H), 8.87 (s, 1H), 8.43 (d, J=5.2 Hz, 1H), 7.83 (d, J=5.2 Hz, 1H), 4.66 (s, 1H), 3.82-3.80 (m, 1H), 3.62-3.54 (m, 1H), 3.52-3.44 (m, 1H), 2.40-2.29 (m, 1H), 2.28-2.21 (m, 2H), 2.19-2.05 (m, 1H), 1.43-1.41 (m, 1H) 1.33-1.29 (m, 1H) 1.26-1.23 (m, 1H).

Example 98: (R)—N-(1'-azaspiro[cyclopropane-1, 2'-bicyclo[2.2.2]octan]-3'-yl)-6-(1H-1,2,3-triazol-1-yl)benzo[b]thiophene-2-carboxamide hydrochloride ((R)-98)

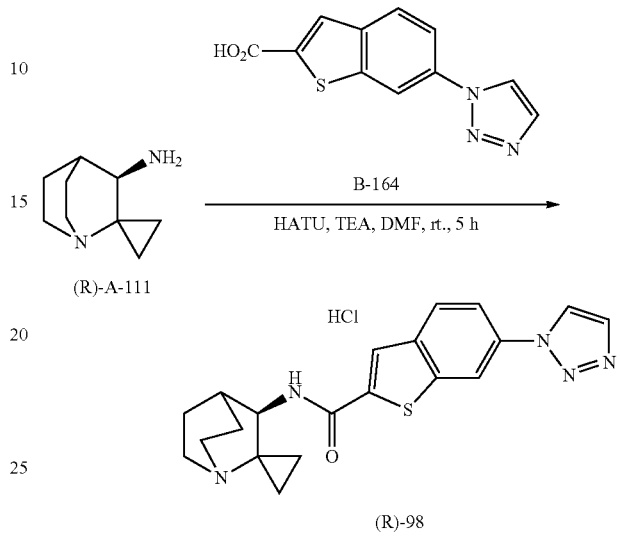

Following general procedure B, Compound (R)-98 was prepared from compound B-164 (80 mg, 0.33 mmol) and compound (R)-A-111 (50 mg, 0.33 mmol), with a reaction time of 5 hours. The product was purified by prep-HPLC [Instrument: GX-E; Column: Agella Venusil ASB C18 150× 30 mm, particle size: 5 µm; Mobile phase: 16-46% acetonitrile in H₂O (add 0.5% HCl, v/v)] to give:

(R)—N-(1'-azaspiro[cyclopropane-1,2'-bicyclo[2.2.2]octan]-3'-yl)-6-(1H-1,2,3-triazol-1-yl)benzo[b]thiophene-2-carboxamide hydrochloride (compound (R)-98) (31 mg, 25% yield) as a white solid: cSFC analytical (A) tR=3.33 min., purity: 100%; LCMS (M): tR=0.986 min., (ES⁺) m/z (M+H)⁺=380.0; ¹H-NMR (D₂O, 400 MHz): δ 8.30 (d, J=0.8 Hz, 1H), 8.00 (d, J=1.6 Hz, 1H), 7.83-7.81 (m, 2H), 7.77 (s, 1H), 7.56 (dd, J₁=8.8 Hz, J₂=2.0 Hz, 1H), 4.38 (s, 1H), 3.57-3.51 (m, 2H), 3.39-3.28 (m, 2H), 2.33-2.32 (m, 1H), 2.19-2.06 (m, 2H), 2.00-1.91 (m, 1H), 1.19-1.14 (m, 2H), 1.09-1.05 (m, 2H).

Example 99: (R)-6-morpholino-N-(1'-azaspiro[cyclopropane-1,2'-bicyclo[2.2.2]octan]-3'-yl)benzo[b]thiophene-2-carboxamide hydrochloride ((R)-99)

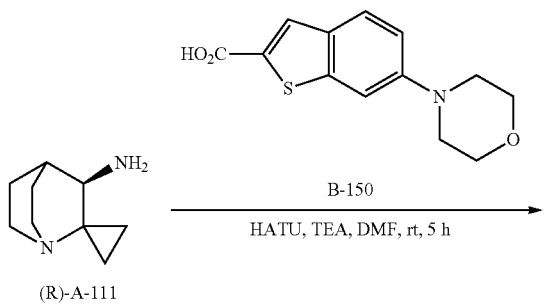

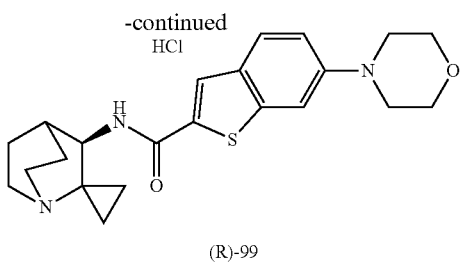

(R)-99

Following general procedure B, Compound (R)-99 was prepared from compound B-150 (86 mg, 0.33 mmol) and compound (R)-A-111 (50 mg, 0.33 mmol), with a reaction time of 5 hours. The product was purified by prep-HPLC [Instrument: GX-H; Column: Waters Xbridge C18 150×20 mm, particle size: 5 μm; Mobile phase: 52-70% acetonitrile in H$_2$O (add 0.5% NH$_3$.H2O, v/v)]. The resulting solids were dissolved in 0.2 M hydrochloric acid solution and again lyophilized to give:

(R)-6-morpholino-N-(1'-azaspiro[cyclopropane-1,2'-bicyclo[2.2.2]octan]-3'-yl)benzo[b]thiophene-2-carboxamide hydrochloride (compound (R)-99) (18 mg, 13% yield) as a white solid: cSFC analytical (A) tR=3.38 min., purity: 97.39%; LCMS (L): tR=2.827 min., (ES$^+$) m/z (M+H)$^+$=398.1; $^1$H-NMR (DMSO-d$_6$, 400 MHz): δ 10.40 (s, 1H), 8.56 (d, J=8.4 Hz, 1H), 8.18 (s, 1H), 7.78 (d, J=8.8 Hz, 1H), 7.45 (s, 1H), 7.19 (d, J=8.8 Hz, 1H), 4.35 (d, J=6.0 Hz, 1H), 3.76 (t, J=4.4 Hz, 4H), 3.60 (m, 2H), 3.35-3.22 (m, 6H), 2.25 (m, 2H), 2.00-1.97 (m, 2H), 1.75 (m, 1H), 1.36-1.23 (m, 2H), 1.04-0.96 (m, 2H).

Example 100: (R)-6-(4,4-difluoropiperidin-1-yl)-N-(1'-azaspiro[cyclopropane-1,2'-bicyclo[2.2.2]octan]-3'-yl)benzo[b]thiophene-2-carboxamide hydrochloride ((R)-100)

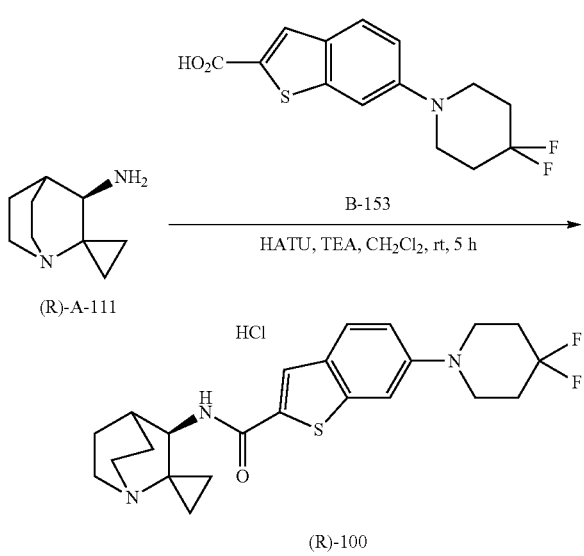

Following general procedure B, Compound (R)-100 was prepared from compound B-153 (70 mg, 0.24 mmol) and compound (R)-A-111 (43 mg, 0.28 mmol), with a reaction time of 5 hours. The product was purified by prep-HPLC [Instrument: GX-D; Column: Boston Symmetrix C18 150× 30 mm, particle size: 5 μm; Mobile phase: 25-55% acetonitrile in H$_2$O (add 0.5% FA, v/v)]. The combined fractions were treated with 0.2 M hydrochloric acid solution and lyophilized to give:

(R)-6-(4,4-difluoropiperidin-1-yl)-N-(1'-azaspiro[cyclopropane-1,2'-bicyclo[2.2.2]octan]-3'-yl)benzo[b]thiophene-2-carboxamide hydrochloride (compound (R)-100) (21 mg, 19% yield) as a yellow solid: cSFC analytical (A) tR=3.04 min., purity: 97.13%; LCMS (X): tR=2.301 min., (ES$^+$) m/z (M+H)$^+$=432.1; $^1$H-NMR (CD$_3$OD, 400 MHz): δ 8.23 (s, 1H), 8.18 (s, 1H), 8.03 (d, J=8.4 Hz, 1H), 7.66 (d, J=8.8 Hz, 1H), 4.54 (d, J=2.0 Hz, 1H), 3.81 (t, J=5.6 Hz, 4H), 3.74-3.72 (m, 1H), 3.56-3.54 (m, 1H), 3.47-3.29 (m, 2H), 2.51-2.42 (m, 5H), 2.34 (m. 1H), 2.19-2.16 (m, 2H), 2.00-1.96 (m, 1H), 1.41-1.36 (m, 1H), 1.31-1.25 (m, 2H), 1.22-1.08 (m, 1H).

Example 101: (R)-6-bromo-N-(1'-azaspiro[cyclopropane-1,2'-bicyclo[2.2.2]octan]-3'-yl)benzo[b]thiophene-2-carboxamide hydrochloride ((R)-101)

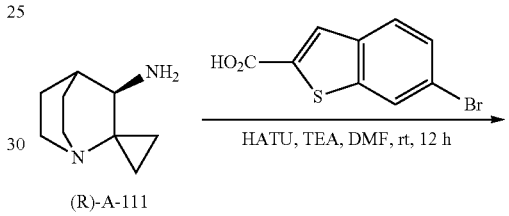

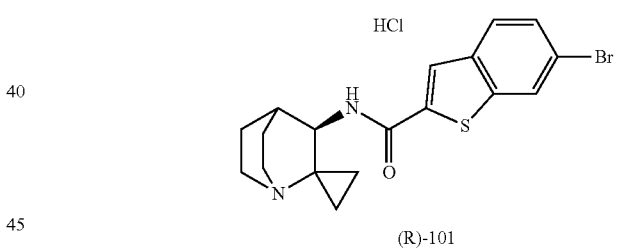

(R)-101

Following general procedure B, Compound (R)-101 was prepared from 6-bromobenzo[b]thiophene-2-carboxylic acid (84 mg, 0.33 mmol) and compound (R)-A-111 (50 mmg, 0.33 mmol), with a reaction time of 12 hours. The product was purified by prep-HPLC [Instrument: GX-E; Column: Phenomenex Synergi C18 150×30 mm, particle size: 10 μm; Mobile phase: 18-48% acetonitrile in H$_2$O (add 0.5% HCl, v/v)] to give:

(R)-6-bromo-N-(1'-azaspiro[cyclopropane-1,2'-bicyclo[2.2.2]octan]-3'-yl)benzo[b]thiophene-2-carboxamide hydrochloride (compound (R)-101) (63 mg, 45% yield) as a white solid: cSFC analytical (A) tR=2.70 min., purity: 98.09%; LCMS (Y): tR=0.797 min., (ES$^+$) m/z (M+H)$^+$=392.9; $^1$H-NMR (CD$_3$OD, 400 MHz): δ 8.15-8.14 (m, 2H), 7.84 (d, J=8.4 Hz, 1H), 7.57 (dd, J$_1$=8.4, J$_2$=1.6, 2H), 4.56 (s, 1H), 3.71-3.58 (m, 1H), 3.58-3.57 (m, 1H), 3.50-3.31 (m, 2H), 2.45-2.44 (m, 1H), 2.37-2.34 (m, 1H), 2.23-2.14 (m, 2H), 2.00-1.99 (m, 1H), 1.38-1.35 (m, 1H). 1.28-1.15 (m, 3H).

Example 102: (R)-6-isopropoxy-N-(1'-azaspiro[cyclopropane-1,2'-bicyclo[2.2.2]octan]-3'-yl)benzo[b]thiophene-2-carboxamide hydrochloride ((R)-102)

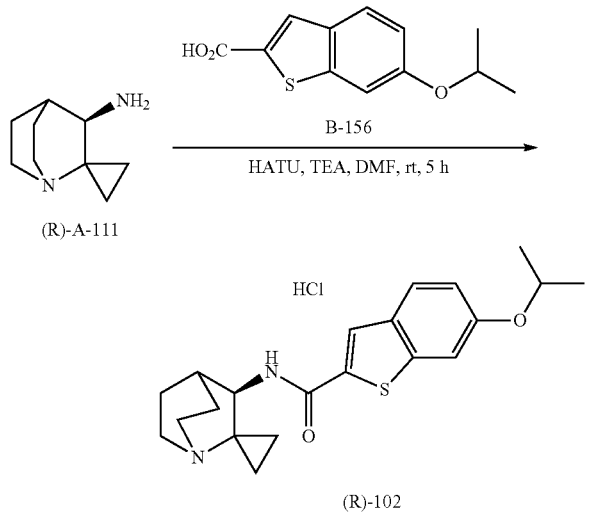

Following general procedure B, Compound (R)-102 was prepared from compound B-156 (78 mg, 0.33 mmol) and compound (R)-A-104 (50 mg, 0.33 mmol), with a reaction time of 5 hours. The product was purified by prep-HPLC [Instrument: GX-A; Column: Phenomenex Gemini C18 150×25 mm, particle size: 10 μm; Mobile phase: 40-70% acetonitrile in H$_2$O (add 0.5% NH$_3$H$_2$O, v/v)]. The resulting solids were dissolved in 0.2 M hydrochloric acid solution and again lyophilized to give:

(R)-6-isopropoxy-N-(1'-azaspiro[cyclopropane-1,2'-bicyclo[2.2.2]octan]-3'-yl)benzo[b]thiophene-2-carboxamide hydrochloride (compound (R)-102) (33 mg, 25% yield) as a white solid: cSFC analytical (A) tR=2.44 min., purity: 98.84%; LCMS (N): tR=2.381 min., (ES$^+$) m/z (M+H)$^+$ =371.0; $^1$H-NMR (CD$_3$OD, 400 MHz): δ 8.05 (d, J=2.8 Hz, 1H), 7.77 (d, J=8.8 Hz, 1H), 7.41 (s, 1H), 7.01 (dd, J=8.8, 2.0 Hz, 1H), 4.73-4.65 (m, 1H), 4.54 (s, 1H), 3.75-3.68 (m, 1H), 3.56 (m, 1H), 3.49-3.38 (m, 2H), 2.42 (s, 1H), 2.36-2.31 (m, 1H), 2.20-2.15 (m, 2H), 2.01-1.94 (m, 1H), 1.35-1.34 (m, 7H), 1.29-1.17 (m, 3H).

Example 103: (R)-6-(methylsulfonyl)-N-(1'-azaspiro[cyclopropane-1,2'-bicyclo[2.2.2]octan]-3'-yl)benzo[b]thiophene-2-carboxamide hydrochloride ((R)-103)

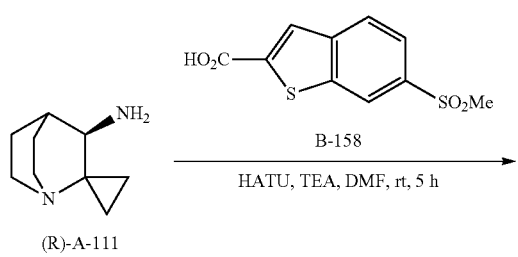

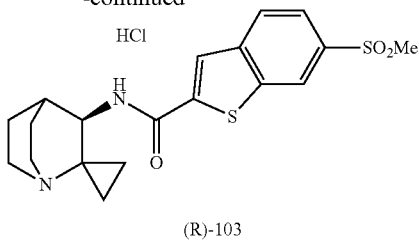

Following general procedure B, Compound (R)-103 was prepared from compound B-158 (84 mg, 0.33 mmol) and compound (R)-A-111 (50 mg, 0.33 mmol), with a reaction time of 5 hours. The product was purified by prep-HPLC [Instrument: GX-B; Column: YMC-pack ODS-AQ 150×30 mm, particle size: 5 μm; Mobile phase: 11-41% acetonitrile in H$_2$O (add 0.5% TFA, v/v)]. The combined fractions were treated with 0.2 N HCl and lyophilized to give:

(R)-6-(methylsulfonyl)-N-(1'-azaspiro[cyclopropane-1,2'-bicyclo[2.2.2]octan]-3'-yl)benzo[b]thiophene-2-carboxamide hydrochloride (compound (R)-103) (30 mg, 21% yield) as a white solid: cSFC analytical (A) tR=2.94 min., purity: 100%; LCMS (M): tR=1.016 min., (ES$^+$) m/z (M+H)= 391.0; $^1$H-NMR (CD$_3$OD, 400 MHz): δ 8.64 (s, 1H), 8.27 (s, 1H), 8.16 (d, J=8.4 Hz, 1H), 7.97 (dd, J$_1$=8.4 Hz, J$_2$=1.2 Hz, 1H), 4.59 (d, J=2.4 Hz, 1H), 3.72-3.71 (m, 1H), 3.59-3.51 (m, 1H), 3.49-3.44 (m, 2H), 3.20 (s, 3H), 2.47-2.46 (m, 1H), 2.35-2.32 (m, 1H), 2.24-2.17 (m, 2H), 2.01-2.00 (m, 1H), 1.39-1.35 (m, 1H), 1.29-1.20 (m, 3H).

Example 104: (R)-6-cyano-N-(1'-azaspiro[cyclopropane-1,2'-bicyclo[2.2.2]octan]-31-yl)benzo[b]thiophene-2-carboxamide ((R)-104)

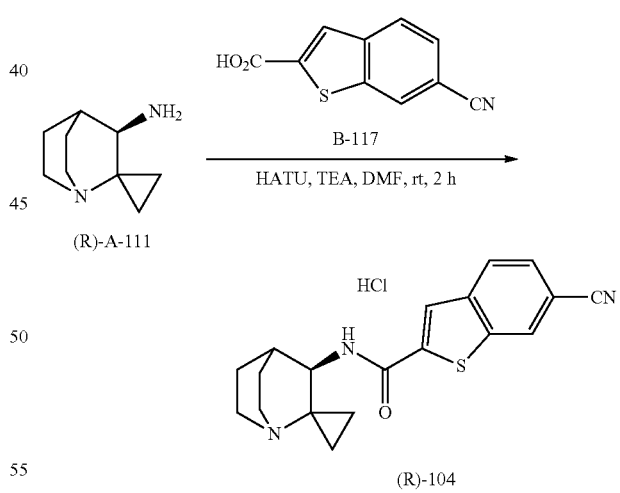

Following general procedure B, Compound (R)-104 was prepared from compound B-117 (67 mg, 0.33 mmol) and compound (R)-A-111 (50 mg, 0.33 mmol), with a reaction time of 2 hours. The product was purified by prep-HPLC [Instrument: GX-E; Column: Agella Venusil ASB C18 150× 21.2 mm, particle size: 5 μm; Mobile phase: 15-45% acetonitrile in H$_2$O (add 0.5% HCl, v/v)] to give:

(R)-6-cyano-N-(1'-azaspiro[cyclopropane-1,2'-bicyclo[2.2.2]octan]-3'-yl)benzo[b]thiophene-2-carboxamide hydrochloride (compound (R)-104) (39 mg, 35% yield) as a white solid: cSFC analytical (A) tR=2.63 min., purity: 100%; LCMS (B): tR=0.617 min., 338.1 m/z (M+1); ¹H-NMR (CD₃OD, 400 MHz): 8.42 (s, 1H), 8.29 (s, 1H), 8.09 (d, J=8.4 Hz, 1H), 7.72-7.70 (dd, J₁=1.2 Hz, J₂=8.4 Hz, 1H), 4.59 (s, 1H), 3.79-3.75 (m, 1H), 3.62-3.45 (m, 3H), 2.48-2.35 (m, 2H), 2.25-2.16 (m, 2H), 2.06-2.02 (m, 1H), 1.42-1.20 (m, 4H).

Example 105: (R)—N-(1'-azaspiro[cyclopropane-1,2'-bicyclo[2.2.2]octan]-3'-yl)-6-(tetrahydro-2H-pyran-4-yl)benzo[b]thiophene-2-carboxamide hydrochloride ((R)-105)

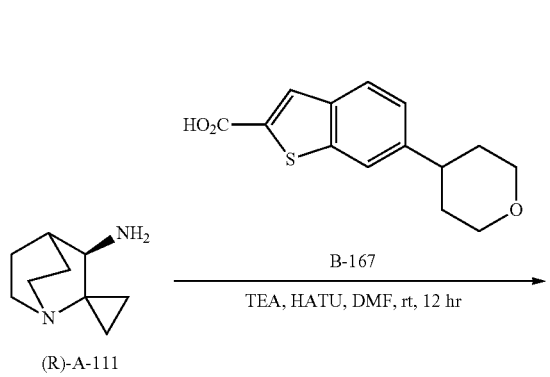

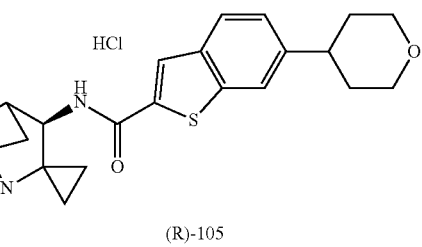

Following general procedure B, Compound (R)-105 was prepared from compound B-167 (86 mg, 0.33 mmol) and compound (R)-A-104 (50 mg, 0.33 mmol), with a reaction time of 12 hours. The product was purified by prep-HPLC [Instrument: GX-E; Column: Agella Venusil ASB C18 150× 30 mm, particle size: 5 μm; Mobile phase: 16-46% acetonitrile in H₂O (add 0.5% HCl, v/v)] to give:

(R)—N-(1'-azaspiro[cyclopropane-1,2'-bicyclo[2.2.2]octan]-3'-yl)-6-(tetrahydro-2H-pyran-4-yl)benzo[b]thiophene-2-carboxamide hydrochloride (compound (R)-105) (44 mg, 31% yield) as a white solid: cSFC analytical (A) tR: 3.04 min., purity: 97.73%; LCMS (Y): tR: 0.747 min., (ES⁺) m/z (M+H)⁺=397.1; ¹H-NMR (CD₃OD, 400 MHz): δ 8.14 (s, 1H), 7.85 (d, J=8.4 Hz, 1H), 7.78 (s, 1H), 7.36-7.33 (m, 1H), 4.54 (d, J=2.4 Hz, 1H), 4.06-4.03 (m, 2H), 3.74-3.69 (m, 1H), 3.60-3.52 (m, 3H), 3.43-3.38 (m, 2H), 2.97-2.89 (m, 1H), 2.42-2.31 (m, 2H), 2.19-2.16 (m, 2H), 1.98 (s, 1H), 1.86-1.79 (m, 4H), 1.41-1.38 (m, 1H), 1.32-1.22 (m, 2H), 1.16-1.14 (m, 1H).

Example 106: (R)-7-fluoro-6-methyl-N-(1'-azaspiro[cyclopropane-1,2'-bicyclo[2.2.2]octan]-3'-yl)benzo[b]thiophene-2-carboxamide hydrochloride ((R)-106)

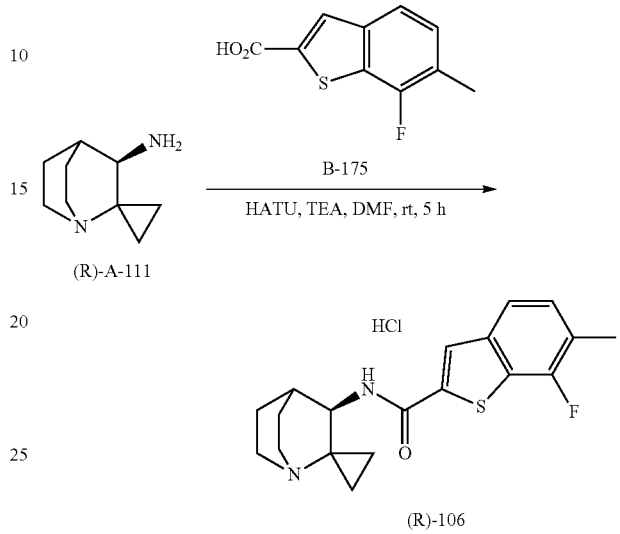

Following general procedure B, Compound (R)-106 was prepared from compound B-175 (69 mg, 0.33 mmol) and compound (R)-A-111 (50 mg, 0.33 mmol), with a reaction time of 5 hours. The product was purified by prep-HPLC [Instrument: GX-E; Column: Phenomenex Synergi C18 150×30 mm, particle size: 4 μm; Mobile phase: 19-49% acetonitrile in H₂O (add 0.5% HCl, v/v)] to give:

(R)-7-fluoro-6-methyl-N-(1'-azaspiro[cyclopropane-1,2'-bicyclo[2.2.2]octan]-3'-yl)benzo[b]thiophene-2-carboxamide hydrochloride (compound (R)-106) (85 mg, 68% yield) as a white solid: cSFC analytical (A) tR=2.273 min., purity: 96.72%; LCMS (Y): tR=0.807 min., (ES⁺) m/z (M+H)⁺= 345.0; ¹H-NMR (CD₃OD, 400 MHz): δ 8.13 (d, J=3.6 Hz, 1H), 7.64 (d, J=8.0 Hz, 1H), 7.33 (t, J=8.0 Hz, 1H), 4.57 (d, J=2 Hz, 1H), 3.71-3.70 (m, 1H), 3.59-3.50 (m, 1H), 3.48-3.43 (m, 2H), 2.42-2.41 (m, 4H), 2.34-2.32 (m, 1H), 2.23-2.18 (m, 2H), 2.00-1.99 (m, 1H), 1.38-1.33 (m, 1H), 1.27-1.20 (m, 3H).

Example 107: (R)—N-(1'-azaspiro[cyclopropane-1,2'-bicyclo[2.2.2]octan]-3'-yl)-2,3-dihydrobenzo[b][1,4]dioxine-6-carboxamide ((R)-107)

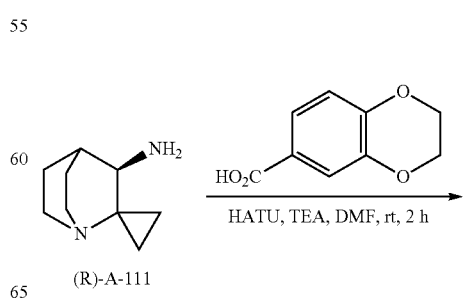

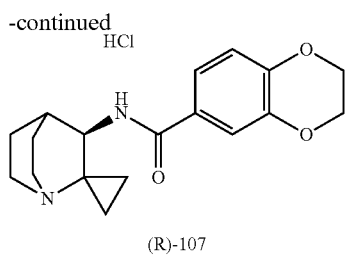

(R)-107

Following general procedure B, Compound (R)-107 was prepared from 2,3-dihydrobenzo[b][1,4]dioxine-6-carboxylic acid (36 mg, 0.33 mmol) and compound (R)-A-111 (50 mg, 0.33 mmol), with a reaction time of 2 hours. The product was purified by prep-HPLC [Instrument: GX-E; Column: Agella Venusil ASB C18 150×21.2 mm, particle size: 5 μm; Mobile phase: 15-45% acetonitrile in H₂O (add 0.5% HCl, v/v)] to give:

(R)—N-(1'-azaspiro[cyclopropane-1,2'-bicyclo[2.2.2]octan]-3'-yl)-2,3-dihydrobenzo[b][1,4]dioxine-6-carboxamide hydrochloride (compound (R)-107) (58 mg, 56% yield) as a white solid: cSFC analytical (A) tR=2.28 min., purity: 98.41%; LCMS (W): tR=0.817 min., 315.1 m/z (M+1); ¹H-NMR (CD₃OD, 400 MHz): 7.40 (s, 1H), 7.38 (s, 1H), 6.93 (d, J=8.8 Hz, 1H), 4.53 (s, 1H), 4.32-4.29 (m, 4H), 3.73-3.41 (m, 4H), 2.41-2.16 (m, 4H), 1.98-1.93 (m, 1H), 1.43-1.14 (m, 4H).

Example 108: (R)-2-amino-N-(2,2-dimethylquinuclidin-3-yl)thieno[2,3-d]pyrimidine-6-carboxamide hydrochloride ((R)-108)

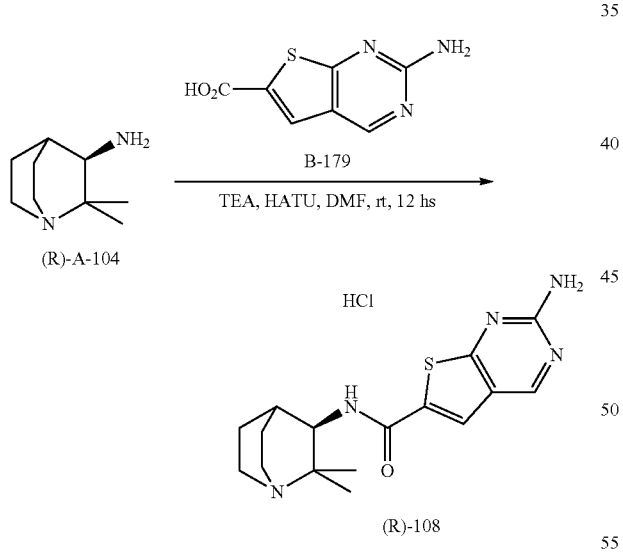

(R)-108

Following general procedure B, Compound (R)-108 was prepared from compound B-179 (60 mg, 0.31 mmol) and compound (R)-A-104 (47 mg, 0.31 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in H₂O (add 0.5% NH₃.H2O, v/v)]. The resulting solid was dissolved in 0.2 M hydrochloric acid solution and again lyophilized to give:

(R)-2-amino-N-(2,2-dimethylquinuclidin-3-yl)thieno[2,3-d]pyrimidine-6-carboxamide-hydrochloride (compound (R)-108) (50 mg, 49% yield) as a white solid: cSFC analytical (A) tR=3.42 min., purity: 99.14%; LCMS (M): tR=0.812 min., 332.0 m/z (M+1); ¹H-NMR (CD₃OD, 400 MHz): δ 9.01 (s, 1H), 8.20 (s, 1H), 4.26 (m, 1H), 3.75-3.70 (m, 2H), 3.39-3.30 (m, 2H), 2.49-2.48 (m, 1H), 2.29-2.28 (m, 1H), 2.18-2.12 (m, 2H), 1.98-1.92 (m, 1H), 1.75 (s, 3H), 1.51 (s, 3H).

Example 109: (R)-6,7-dichloro-N-(2,2-dimethylquinuclidin-3-yl)benzo[b]thiophene-2-carboxamide hydrochloride ((R)-109)

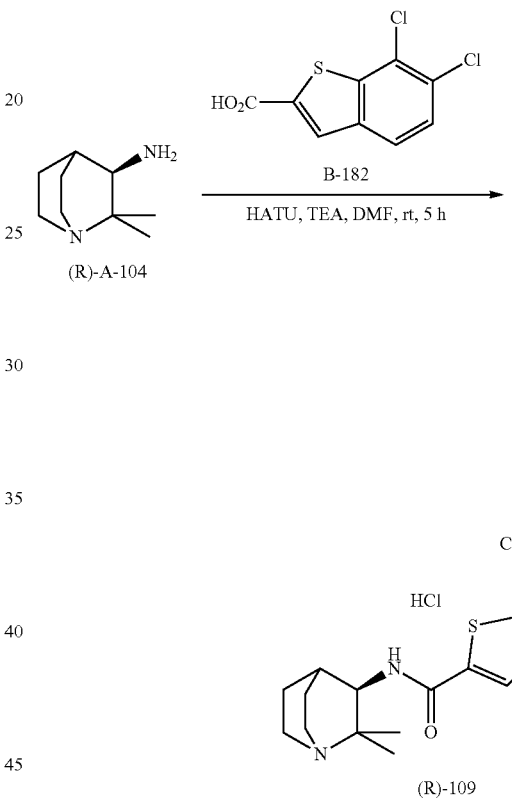

Following general procedure B, Compound (R)-109 was prepared from compound B-182 (120 mg, 0.49 mmol) and compound (R)-A-104 (75 mg, 0.49 mmol), with a reaction time of 5 hours. The product was purified by prep-HPLC [Instrument: GX-D; Column: Boston Symmetrix ODS-R C18 150×30 mm, particle size: 5 μm; Mobile phase: 25-55% acetonitrile in H₂O (add 0.225% FA, v/v)]. The resulting solid was dissolved in 0.2 M hydrochloric acid solution and again lyophilized to give:

(R)-6,7-dichloro-N-(2,2-dimethylquinuclidin-3-yl)benzo[b]thiophene-2-carboxamide-hydrochloride (compound (R)-109) (82 mg, 40% yield) as a white solid: cSFC analytical (A) tR=3.22 min., purity: 97.50%; LCMS (H): tR=1.786 min., (ES⁺) m/z (M+H)⁺=383.1; ¹H-NMR (CD₃OD, 400 MHz): δ 8.19 (s, 1H), 7.87 (d, J=8.4 Hz, 1H), 7.61 (d, J=8.4 Hz, 1H), 4.26 (s, 1H), 3.77-3.67 (m, 2H), 3.38-3.31 (m, 2H), 2.42-2.41 (m, 1H), 2.28 (d, J=2.8 Hz, 1H), 2.19-2.12 (m, 2H), 2.11-1.96 (m, 1H), 1.76 (s, 3H), 1.50 (s, 3H).

Example 110: (R)-6-chloro-N-(2,2-dimethylquinuclidin-3-yl)-7-fluorobenzo[b]thiophene-2-carboxamide hydrochloride ((R)-110)

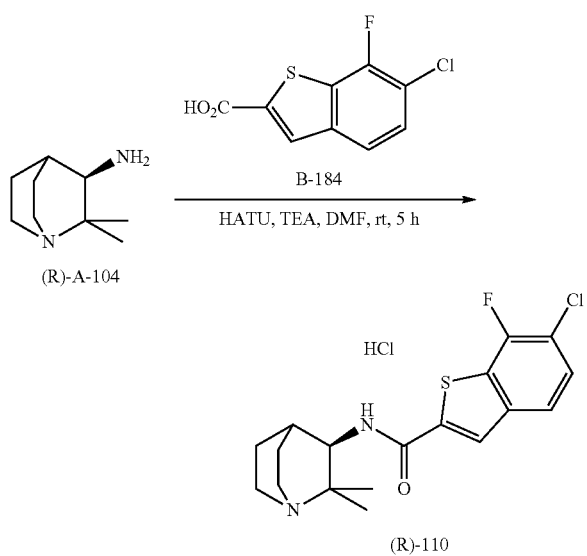

Following general procedure B, Compound (R)-110 was prepared from compound B-184 (120 mg, 0.52 mmol) and compound (R)-A-104 (80 mg, 0.52 mmol), with a reaction time of 5 hours. The product was purified by prep-HPLC [Instrument: GX-B; Column: YMC-pack ODS-AQ 150×30 mm, particle size: 5 μm; Mobile phase: 29-59% acetonitrile in H$_2$O (add 0.5% TFA, v/v)]. The resulting solid was dissolved in 0.2 M hydrochloric acid solution and again lyophilized to give:

(R)-6-chloro-N-(2,2-dimethylquinuclidin-3-yl)-7-fluorobenzo[b]thiophene-2-carboxamide-hydrochloride (compound (R)-110) (70 mg, 33% yield) as a white solid: cSFC analytical (A) tR=2.946 min., purity: 97.54%; LCMS (Y): tR=0.746 min., (ES$^+$) m/z (M+H)$^+$=367.0; $^1$H-NMR (CD$_3$OD, 400 MHz): δ 8.20 (d, J=3.2 Hz, 1H), 7.75 (d, J=8.4 Hz, 1H), 7.54 (dd, J$_1$=8 Hz, J$_2$=6.8 Hz, 1H), 4.26 (s, 1H), 3.75-3.67 (m, 2H), 3.38-3.35 (m, 2H), 2.42-2.41 (m, 1H), 2.28-2.27 (m, 1H), 2.18-2.09 (m, 2H), 1.95-1.91 (m, 1H), 1.75 (s, 3H), 1.49 (s, 3H).

Example 111: (R)-6-chloro-N-(2,2-dimethylquinuclidin-3-yl)-7-(trifluoromethyl)benzo[b]thiophene-2-carboxamide hydrochloride ((R)-111)

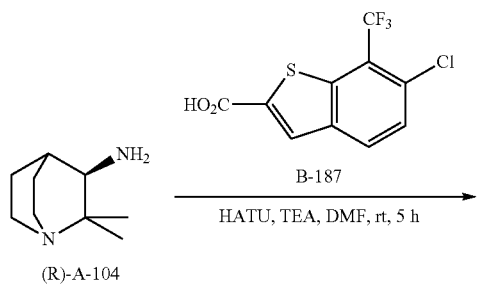

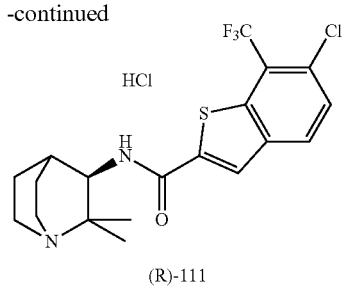

Following general procedure B, Compound (R)-111 was prepared from compound B-187 (146 mg, 0.52 mmol) and compound (R)-A-104 (80 mg, 0.52 mmol), with a reaction time of 5 hours. The product was purified by prep-HPLC [Instrument: GX-B; Column: YMC-Actus Pro C18 150×30 mm, particle size: 5 μm; Mobile phase: 30-60% acetonitrile in H$_2$O (add 0.1% TFA, v/v)]. The resulting solid was dissolved in 0.2 M hydrochloric acid solution and again lyophilized to give:

(R)-6-chloro-N-(2,2-dimethylquinuclidin-3-yl)-7-(trifluoromethyl)benzo[b]thiophene-2-carboxamide hydrochloride (compound (R)-111) (116 mg, 49% yield) as a white solid: cSFC analytical (A) tR=2.87 min., purity: 97.89%; LCMS (H): tR=1.766 min., (ES$^+$) m/z (M+H)$^+$=417.1; $^1$H-NMR (CD$_3$OD, 400 MHz): δ 8.24 (s, 1H), 8.14 (d, J=8.8 Hz, 1H), 7.67 (d, J=8.4 Hz, 1H), 4.26 (s, 1H), 3.75-3.66 (m, 2H), 3.37-3.32 (m, 2H), 2.41-2.39 (m, 1H), 2.27 (d, J=2.8 Hz, 1H), 2.17-2.10 (m, 2H), 1.97-1.80 (m, 1H), 1.75 (s, 3H), 1.49 (s, 3H).

Example 112: (R)-7-chloro-N-(2,2-dimethylquinuclidin-3-yl)-6-methoxybenzo[b]thiophene-2-carboxamide hydrochloride ((R)-112)

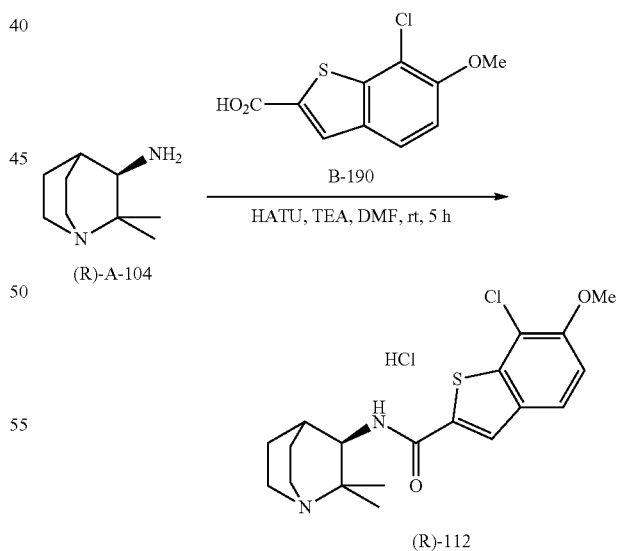

Following general procedure B, Compound (R)-112 was prepared from compound B-190 (126 mg, 0.52 mmol) and compound (R)-A-104 (80 mg, 0.52 mmol), with a reaction time of 5 hours. The product was purified by prep-HPLC [Instrument: GX-B; Column: YMC-pack ODS-AQ 150×30 mm, particle size: 5 μm; Mobile phase: 24-54% acetonitrile in H₂O (add 0.5% TFA, v/v)]. The resulting solid was dissolved in 0.2 M hydrochloric acid solution and again lyophilized to give:

(R)-7-chloro-N-(2,2-dimethylquinuclidin-3-yl)-6-methoxybenzo[b]thiophene-2-carboxamide-hydrochloride (compound (R)-112) (116 mg, 53% yield) as a white solid: cSFC analytical (A) tR=3.267 min., purity: 97.66%; LCMS (Y): tR=0.716 min., (ES⁺) m/z (M+H)⁺=379.0; ¹H-NMR (CD₃OD, 400 MHz): δ 8.12 (s, 1H), 7.86 (d, J=8.8 Hz, 1H), 7.32 (d, J=8.8, 1H), 4.25 (s, 1H), 4.00 (s, 3H), 3.76-3.66 (m, 2H), 3.37-3.36 (m, 2H), 2.41-2.40 (m, 1H), 2.27-2.26 (m, 1H), 2.18-2.04 (m, 2H), 1.94-1.90 (m, 1H), 1.75 (s, 3H), 1.49 (s, 3H).

Example 113: (R)—N-(2,2-dimethylquinuclidin-3-yl)-6-methyl-7-(trifluoromethyl)benzo[b]thiophene-2-carboxamide hydrochloride ((R)-113)

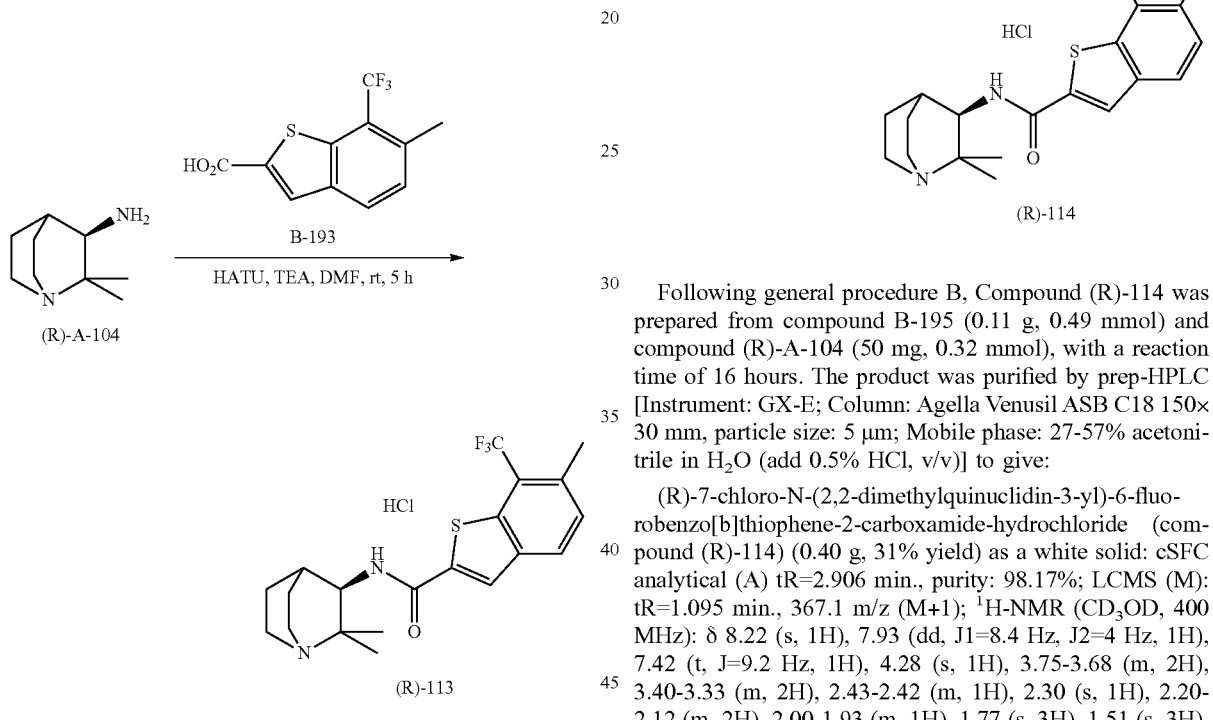

Following general procedure B, Compound (R)-113 was prepared from compound B-193 (0.12 g, 0.45 mmol) and compound (R)-A-104 (70 mg, 0.45 mmol), with a reaction time of 5 hours. The product was purified by prep-HPLC [Instrument: GX-B; Column: YMC-Actus Pro C18 150×30 mm, particle size: 5 μm; Mobile phase: 28-58% acetonitrile in H₂O (add 0.5% TFA, v/v)]. The resulting solid was dissolved in 0.2 M hydrochloric acid solution and again lyophilized to give:

(R)—N-(2,2-dimethylquinuclidin-3-yl)-6-methyl-7-(trifluoromethyl)benzo[b]thiophene-2-carboxamide-hydrochloride (compound (R)-113) (0.12 g, 69% yield) as a white solid: cSFC analytical (A) tR=2.59 min., purity: 97.70%; LCMS (DD): tR=0.861 min., 397.1 m/z (M+1); ¹H-NMR (CD₃OD, 400 MHz): δ 8.49 (d, J=7.6 Hz, 0.5H), 8.19 (s, 1H), 8.04 (d, J=8.0 Hz, 1H), 7.47 (d, J=8.4 Hz, 1H), 4.26 (s, 1H), 3.72-3.70 (m, 2H), 3.38-3.33 (m, 2H), 2.64 (d, J=2.0 Hz, 3H), 2.42-2.41 (m, 1H), 2.28-2.27 (m, 1H), 2.18-2.06 (m, 2H), 1.97-1.91 (m, 1H), 1.75 (s, 3H), 1.50 (s, 3H).

Example 114: (R)-7-chloro-N-(2,2-dimethylquinuclidin-3-yl)-6-fluorobenzo[b]thiophene-2-carboxamide hydrochloride ((R)-114)

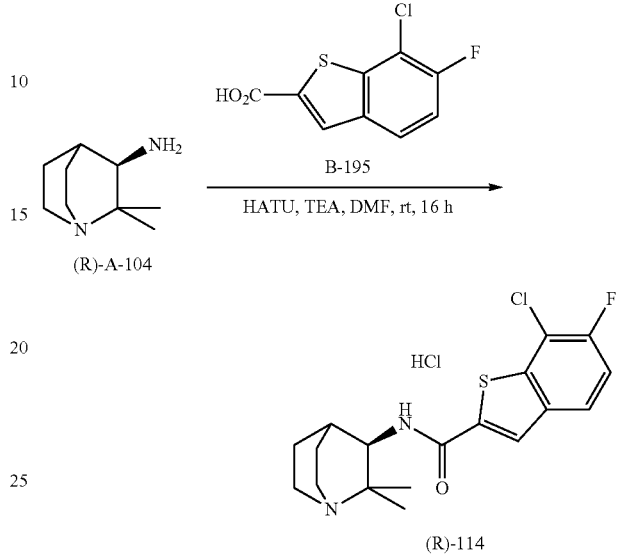

Following general procedure B, Compound (R)-114 was prepared from compound B-195 (0.11 g, 0.49 mmol) and compound (R)-A-104 (50 mg, 0.32 mmol), with a reaction time of 16 hours. The product was purified by prep-HPLC [Instrument: GX-E; Column: Agella Venusil ASB C18 150× 30 mm, particle size: 5 μm; Mobile phase: 27-57% acetonitrile in H₂O (add 0.5% HCl, v/v)] to give:

(R)-7-chloro-N-(2,2-dimethylquinuclidin-3-yl)-6-fluorobenzo[b]thiophene-2-carboxamide-hydrochloride (compound (R)-114) (0.40 g, 31% yield) as a white solid: cSFC analytical (A) tR=2.906 min., purity: 98.17%; LCMS (M): tR=1.095 min., 367.1 m/z (M+1); ¹H-NMR (CD₃OD, 400 MHz): δ 8.22 (s, 1H), 7.93 (dd, J1=8.4 Hz, J2=4 Hz, 1H), 7.42 (t, J=9.2 Hz, 1H), 4.28 (s, 1H), 3.75-3.68 (m, 2H), 3.40-3.33 (m, 2H), 2.43-2.42 (m, 1H), 2.30 (s, 1H), 2.20-2.12 (m, 2H), 2.00-1.93 (m, 1H), 1.77 (s, 3H), 1.51 (s, 3H).

Example 115: (R)-7-cyano-N-(2,2-dimethylquinuclidin-3-yl)benzo[b]thiophene-2-carboxamide hydrochloride ((R)-115)

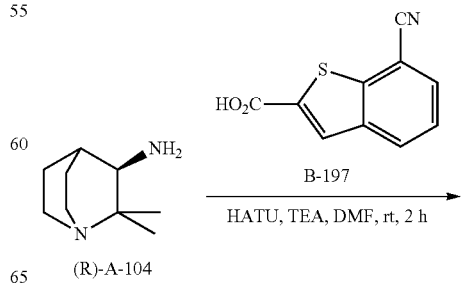

-continued

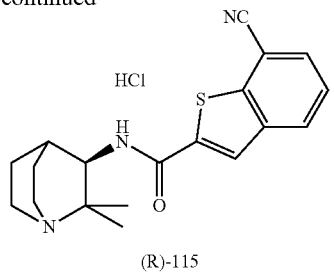

(R)-115

Following general procedure B, Compound (R)-115 was prepared from compound B-197 (as a mixture with compound B-198) (80 mg, 0.39 mmol) and compound (R)-A-104 (60 mg, 0.39 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)-7-cyano-N-(2,2-dimethylquinuclidin-3-yl)benzo[b]thiophene-2-carboxamide-hydrochloride (compound (R)-115) (15 mg, 32% yield) as a white solid: cSFC analytical (A) tR=2.30 min., purity: 99.66%; LCMS (M): tR=0.973 min., 340.1 m/z (M+1); $^1$H-NMR (CD$_3$OD, 400 MHz): 8.59 (d, J=7.2 Hz, 1H), δ 8.30 (s, 1H), 7.26 (d, J=7.6 Hz, 1H), 7.94 (d, J=7.2 Hz, 1H), 7.64 (t, J=8.0 Hz, 1H), 4.29 (s, 1H), 3.79-3.69 (m, 2H), 3.40-3.36 (m, 1H), 2.45-2.44 (m, 1H), 2.31-2.13 (m, 4H), 2.00-1.94 (m, 1H), 1.78 (s, 3H), 1.52 (s, 3H).

Example 116: (R)—N-(2,2-dimethylquinuclidin-3-yl)-7-methoxybenzo[b]thiophene-2-carboxamide hydrochloride ((R)-116)

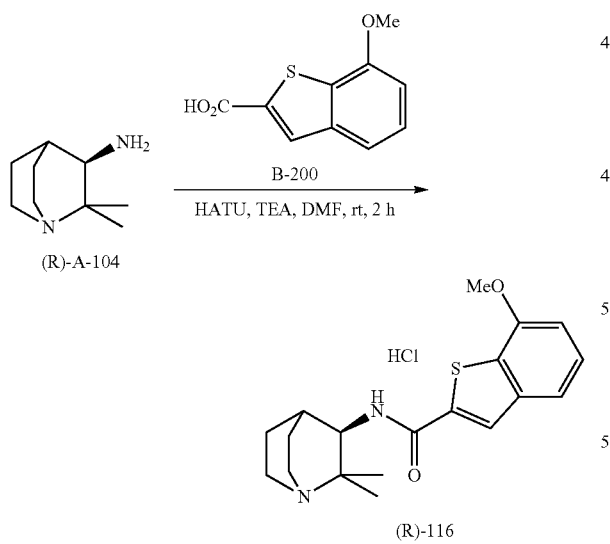

Following general procedure B, Compound (R)-116 was prepared from compound B-200 (67 mg, 0.32 mmol) and compound (R)-A-104 (50 mg, 0.32 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)—N-(2,2-dimethylquinuclidin-3-yl)-7-methoxybenzo[b]thiophene-2-carboxamide-hydrochloride (compound (R)-116) (72 mg, 65% yield) as a white solid: cSFC analytical (A) tR=3.35 min., purity: 99.66%; LCMS (M): tR=0.992 min., 345.1 m/z (M+1); $^1$H-NMR (CD$_3$OD, 400 MHz): δ 8.13 (s, 1H), 7.53 (d, J=8.0 Hz, 1H), 7.44 (t, J=7.6 Hz, 1H), 7.01 (d, J=3.6 Hz, 1H), 4.27 (s, 1H), 4.03 (s, 3H), 3.78-3.68 (m, 2H), 3.39-3.36 (m, 1H), 3.30 (m, 1H), 2.47-2.42 (m, 1H), 2.30-2.29 (m, 3H), 1.98-1.92 (m, 1H), 1.77 (s, 3H), 1.51 (s, 3H).

Example 117: (R)—N-(2,2-dimethylquinuclidin-3-yl)-6,7-difluorobenzo[b]thiophene-2-carboxamide hydrochloride ((R)-117)

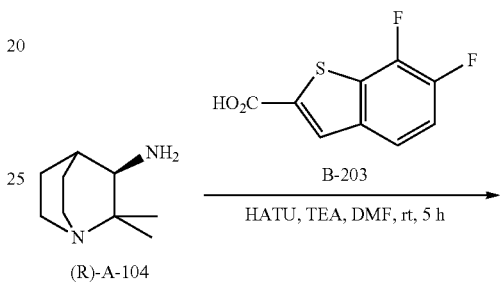

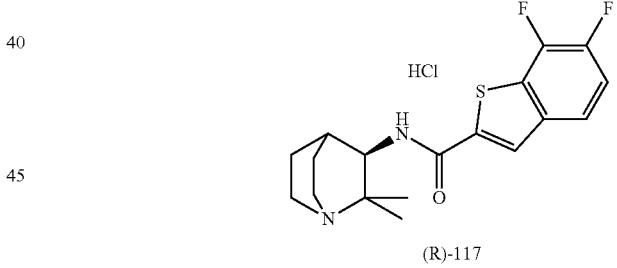

(R)-117

Following general procedure B, Compound (R)-117 was prepared from compound B-203 (60 mg, 0.34 mmol) and compound (R)-A-104 (50 mg, 0.32 mmol), with a reaction time of 5 hours. The product was purified by prep-HPLC [Instrument: GX-E; Column: Agella Venusil ASB C18 150× 21.2 mm, particle size: 5 μm; Mobile phase: 15-45% acetonitrile in H$_2$O (add 0.5% HCl, v/v)] to give:

(R)—N-(2,2-dimethylquinuclidin-3-yl)-6,7-difluorobenzo[b]thiophene-2-carboxamide-hydrochloride (compound (R)-117) (60 mg, 46% yield) as a white solid: cSFC analytical (A) tR=2.66 min., purity: 96.66%; LCMS (B): tR=0.702 min., 350.1 m/z (M+1); $^1$H-NMR (CD$_3$OD, 400 MHz): δ8.21 (d, J=3.2, 1H), 7.79-7.76 (m, 1H), 7.47-7.41 (m, 1H), 4.27 (s, 1H), 3.75-3.69 (m, 2H), 3.40-3.37 (m, 2H), 2.49-2.42 (m, 1H), 2.30 (d, J=2.8, 1H), 2.19-2.09 (m, 2H), 1.99-1.93 (m, 1H), 1.768 (s, 3H), 1.51 (s, 3H).

Example 118: (R)-7-cyclopropyl-N-(2,2-dimethylquinuclidin-3-yl)benzo[b]thiophene-2-carboxamide hydrochloride ((R)-118)

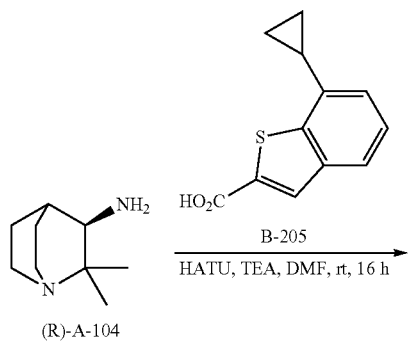

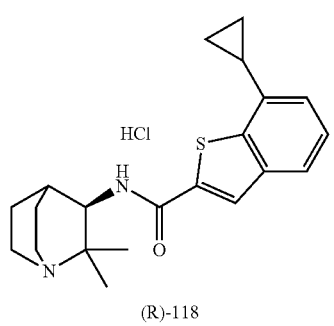

Following general procedure B, Compound (R)-118 was prepared from compound B-205 (0.12 g, 0.54 mmol) and compound (R)-A-104 (70 mg, 0.45 mmol), with a reaction time of 16 hours. The product was purified by prep-HPLC [Instrument: GX-B; Column: YMC-Actus Pro C18 150×30 mm, particle size: 5 μm; Mobile phase: 24-54% acetonitrile in H₂O (add 0.5% TFA, v/v)]. The resulting solid was dissolved in 0.2 M hydrochloric acid solution and again lyophilized to give:

(R)-7-cyclopropyl-N-(2,2-dimethylquinuclidin-3-yl)benzo[b]thiophene-2-carboxamide-hydrochloride (compound (R)-118) (75 mg, 42% yield) as a white solid: cSFC analytical (A) tR=3.228 min., purity: 100%; LCMS (B): tR=0.711 min., 355.2 m/z (M+1); ¹H-NMR (CD₃OD, 400 MHz): δ 8.45 (d, J=7.2 Hz, 1H), 8.17 (s, 1H), 7.76 (d, J=Hz, 1H), 7.39 (t, J=7.6 Hz, 1H), 7.16 (d, J=7.2 Hz, 1H), 4.29 (s, 1H), 3.77-3.69 (m, 2H), 3.40-3.37 (m, 2H), 2.44-2.43 (m, 1H), 2.30 (m, 1H), 2.20-2.11 (m, 2H), 1.99-1.93 (m, 1H), 1.74 (s, 3H), 1.52 (s, 3H).

Example 119: (R)—N-(2,2-dimethylquinuclidin-3-yl)-7-isopropylbenzo[b]thiophene-2-carboxamide hydrochloride ((R)-119)

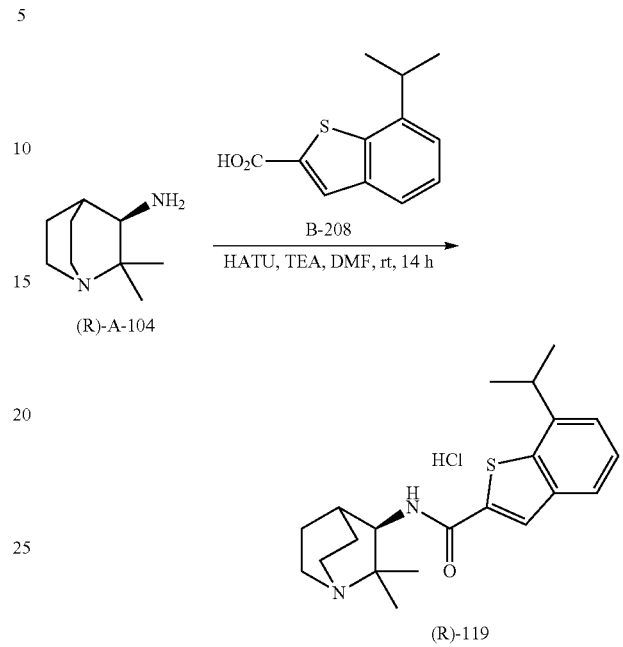

Following general procedure B, Compound (R)-119 was prepared from compound B-208 (0.11 g, 0.52 mmol) and compound (R)-A-104 (80 mg, 0.52 mmol), with a reaction time of 14 hours. The product was purified by prep-HPLC [Instrument: GX-E; Column: Phenomenex Synergi C18 150×30 mm, particle size: 5 μm; Mobile phase: 27-57% acetonitrile in H₂O (add 0.5% HCl, v/v)] to give:

(R)—N-(2,2-dimethylquinuclidin-3-yl)-7-isopropyl-benzo[b]thiophene-2-carboxamide hydrochloride (compound (R)-119) (0.10 g, 49% yield) as a white solid: cSFC analytical (B) tR=2.765 min., purity: 97.44%; LCMS (DD): tR=0.836 min., (ES⁺) m/z (M+H)⁺=357.2; ¹H-NMR (CD₃OD, 400 MHz): δ 8.46-8.44 (m, 1H), 7.18 (m, 1H), 7.79-7.77 (d, J=7.6 Hz, 1H), 7.47-7.39 (m, 2H), 4.28 (s, 1H), 3.78-3.68 (m, 2H), 3.40-3.35 (m, 2H), 3.28-3.23 (m, 1H), 2.44 (m, 1H), 2.30-2.20 (m, 1H), 2.16-2.11 (m, 2H), 2.09-1.93 (m, 1H), 1.78 (s, 3H), 1.52 (s, 3H), 1.44 (s, 3H), 1.43 (s, 3H).

Example 120: (R)—N-(1'-azaspiro[cyclopropane-1,2'-bicyclo[2.2.2]octan]-3'-yl)-7-(trifluoromethoxy)benzo[b]thiophene-2-carboxamide hydrochloride ((R)-120)

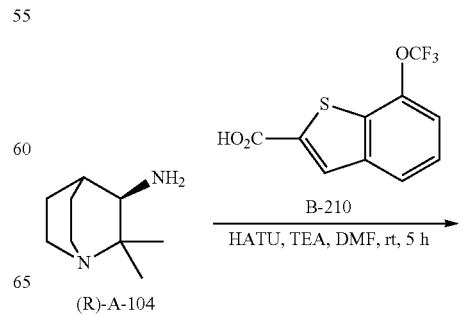

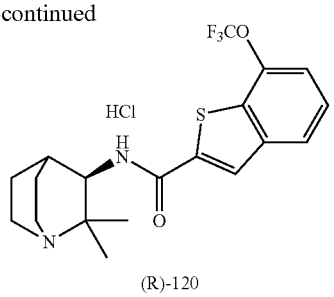

Following general procedure B, Compound (R)-120 was prepared from compound B-210 (136 mg, 0.26 mmol) and compound (R)-A-104 (80 mg, 0.26 mmol), with a reaction time of 5 hours. The product was purified by prep-HPLC [Instrument: GX-B; Column: YMC-Actus Pro C18 150*30, particle size: 5 μm; Mobile phase: 25-55% acetonitrile in H$_2$O (add 0.1% TFA, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-7-(trifluoromethoxy)benzo[b]thiophene-2-carboxamide hydrochloride (compound (R)-120) (130 mg, 57% yield) as a white solid: cSFC analytical (A) tR=2.346 min., purity: 98.01%; LCMS (B): tR=0.733 min., (ES$^+$) m/z (M+H)$^+$=399.1; $^1$H-NMR (CD$_3$OD, 400 MHz): δ8.23 (s, 1H), 7.94 (d, J=8.0 Hz, 1H), 7.55 (t, J=8.0 Hz, 1H), 7.44 (d, J=8.0 Hz, 1H), 4.26 (s, 1H), 3.76-3.67 (m, 2H), 3.38-3.33 (m, 2H), 2.42-2.41 (m, 1H), 2.29-2.28 (m, 1H), 2.19-2.10 (m, 2H), 1.99-1.95 (m, 1H), 1.75 (s, 3H), 1.50 (s, 3H).

Example 121: (R)—N-(2,2-dimethylquinuclidin-3-yl)-7-(tetrahydro-2H-pyran-4-yl)benzo[b]thiophene-2-carboxamide hydrochloride ((R)-121)

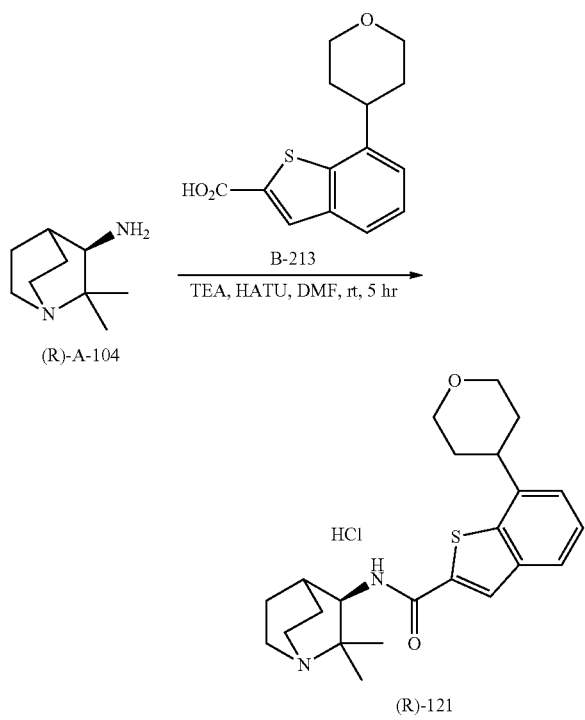

Following general procedure B, Compound (R)-121 was prepared from compound B-213 (119 mg, 0.45 mmol) and compound (R)-A-104 (70 mg, 0.45 mmol), with a reaction time of 5 hours. The product was purified by prep-HPLC [Instrument: GX-E; Column: Agella Venusil ASB C18 150× 30 mm, particle size: 5 μm; Mobile phase: 19-49% acetonitrile in H$_2$O (add 0.5% HCl, v/v)] to give:

(R)—N-(2,2-dimethylquinuclidin-3-yl)-7-(tetrahydro-2H-pyran-4-yl)benzo[b]thiophene-2-carboxamide hydrochloride (compound (R)-121) (60 mg, 33% yield) as a white solid: cSFC analytical (A) tR: 3.12 min., purity: 99.87%; LCMS (B): tR: 0.585 min., (ES$^+$) m/z (M+H)$^+$=399.1; $^1$H-NMR (CD$_3$OD, 400 MHz): δ 8.17 (s, 1H), 7.80 (dd, J$_1$=7.6 Hz, J$_2$=0.8 Hz, 1H), 7.47-7.43 (m, 1H), 7.39 (d, J=6.8 Hz, 1H), 4.27 (dd, J$_1$=4.8 Hz, J$_2$=1.2 Hz, 1H), 4.12-4.08 (m, 2H), 3.72-3.62 (m, 4H), 3.49-3.31 (m, 2H), 3.28-3.13 (m, 1H), 2.45-2.41 (m, 1H), 2.28-2.26 (m, 1H), 2.14-2.03 (m, 2H), 2.00-1.91 (m, 5H), 1.75 (s, 3H), 1.49 (m, 3H).

Example 122: (R)—N-(2,2-dimethylquinuclidin-3-yl)-1H-indole-2-carboxamide hydrochloride ((R)-122)

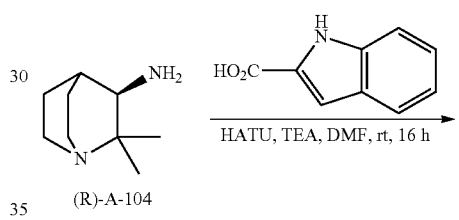

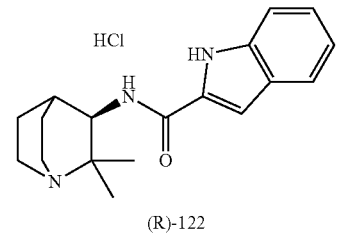

Following general procedure B, Compound (R)-122 was prepared from 1H-indole-2-carboxylic acid (80 mg, 0.50 mmol) and compound (R)-A-104 (70 mg, 0.45 mmol), with a reaction time of 16 hours. The product was purified by prep-HPLC [Instrument: GX-A; Column: Phenomenex Gemini C18 250*50, particle size: 10 μm; Mobile phase: 30-60% acetonitrile in H$_2$O (add 0.5% NH$_3$H$_2$O, v/v)]. The resulting solids were dissolved in 0.2 M hydrochloric acid solution and again lyophilized to give:

(R)—N-(2,2-dimethylquinuclidin-3-yl)-1H-indole-2-carboxamide hydrochloride (compound (R)-122) (50 mg, 37% yield) as a yellow solid: cSFC analytical (A) tR=2.99 min., purity: 98.13%; LCMS (G): tR=2.280 min., 298.1 m/z (M+1); $^1$H-NMR (CD$_3$OD, 400 MHz): δ 7.66-7.64 (d, J=8.0 Hz, 1H), 7.48-7.46 (d, J=8.4 Hz, 1H), 7.29-7.24 (m, 2H), 7.12-7.08 (t, J=7.2 Hz, 1H), 4.31 (s, 1H), 3.77-3.69 (m, 2H), 3.39-3.36 (m, 2H), 2.48-2.44 (m, 1H), 2.28-2.27 (m, 1H), 2.20-2.11 (m, 2H), 1.99-1.93 (m, 1H), 1.77 (s, 1H) 1.51 (s, 2H).

Example 123: (R)-6-chloro-N-(2,2-dimethylquinuclidin-3-yl)-5-fluorobenzo[b]thiophene-2-carboxamide hydrochloride ((R)-123)

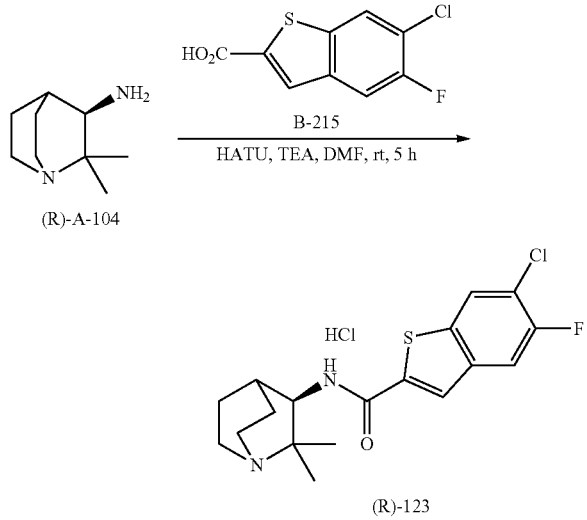 [SMILES: CC1(C)[C@H](N)C2CCN1CC2 ; O=C(O)c1cc2cc(F)c(Cl)cc2s1 ; CC1(C)[C@H](NC(=O)c2cc3cc(F)c(Cl)cc3s2)C2CCN1CC2 ; Cl]

Following general procedure B, Compound (R)-123 was prepared from compound B-215 (0.13 g, 0.54 mmol) and compound (R)-A-104 (70 mg, 0.45 mmol), with a reaction time of 5 hours. The product was purified by prep-HPLC [Instrument: GX-D; Column: Boston Green ODS C18 150× 30 mm, particle size: 5 μm; Mobile phase: 42-72% acetonitrile in H$_2$O (add 0.225% FA, v/v)]. The resulting solid was dissolved in 0.2 M hydrochloric acid solution and again lyophilized to give:

(R)-6-chloro-N-(2,2-dimethylquinuclidin-3-yl)-5-fluorobenzo[b]thiophene-2-carboxamide-hydrochloride (compound (R)-123) (73 mg, 40% yield) as a white solid: cSFC analytical (A) tR=2.98 min., purity: 96.51%; LCMS (B): tR=0.708 min., 367.1 m/z (M+1); $^1$H-NMR (CD$_3$OD, 400 MHz): δ 8.12-8.09 (m, 2H), 7.79-7.76 (d, J=9.6 Hz, 1H), 4.24 (m, 1H), 3.72-3.69 (m, 2H), 3.34-3.31 (m, 2H), 2.39 (m, 1H), 2.27 (m, 1H), 2.14-2.12 (m, 2H), 1.97-1.96 (m, 1H), 1.74 (s, 3H), 1.47 (s, 3H).

Example 124: (R)—N-(2,2-dimethylquinuclidin-3-yl)-5-fluoro-6-methoxybenzo[b]thiophene-2-carboxamide hydrochloride ((R)-124)

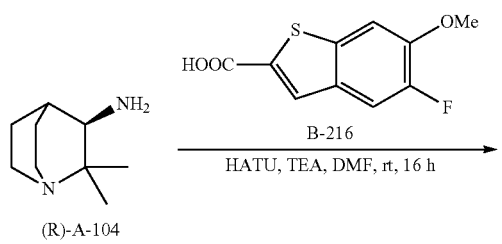

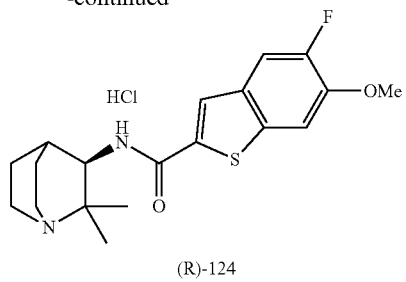

Following general procedure B, Compound (R)-124 was prepared from compound B-216 (120 mg, 0.53 mmol) and compound (R)-A-104 (82 mg, 0.53 mmol), with a reaction time of 16 hours. The product was purified by prep-HPLC [Instrument: GX-E; Column: Phenomenex SynergiC18 250*21.2 mm, particle size: 4 μm; Mobile phase: 15-45% acetonitrile in H$_2$O (add 0.05% HCl, v/v)] to give:

(R)—N-(2,2-dimethylquinuclidin-3-yl)-5-fluoro-6-methoxybenzo[b]thiophene-2-carboxamide-hydrochloride (compound (R)-124) (150 mg, 71% yield) as a white solid: cSFC analytical (A) tR=2.54 min., purity: 97.70%; LCMS (B): tR=0.646 min., 363.1 m/z (M+1); $^1$H-NMR (CD$_3$OD, 400 MHz): δ 8.04 (s, 1H), 7.65-7.61 (m, 2H), 4.26 (s, 1H), 3.98 (s, 3H), 3.80-3.68 (m, 2H), 3.39-3.36 (m, 2H), 2.42-2.41 (m, 1H), 2.29-2.28 (d, J=2.8 Hz, 1H), 2.19-2.12 (m, 2H), 1.99-1.93 (m, 1H), 1.76 (s, 3H), 1.50 (m, 3H).

Example 125: (R)-6-chloro-N-(2,2-dimethylquinuclidin-3-yl)-5,7-difluorobenzo[b]thiophene-2-carboxamide hydrochloride ((R)-125)

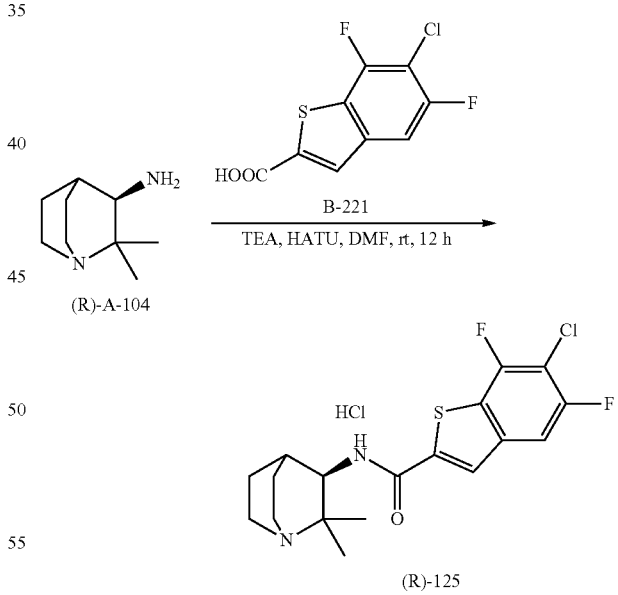

Following general procedure B, Compound (R)-125 was prepared from compound B-221 (70 mg, 0.28 mmol) and compound (R)-A-104 (43 mg, 0.28 mmol), with a reaction time of 12 hours. The product was purified by prep-HPLC [Instrument: GX-B; Column: YMC-Actus Pro C18 150×30 mm, particle size: 5 μm; Mobile phase: 25-55% acetonitrile in H$_2$O (add 0.5% TFA, v/v)]. The resulting solid was dissolved in 0.2 M hydrochloric acid solution and again lyophilized to give:

(R)-6-chloro-N-(2,2-dimethylquinuclidin-3-yl)-5,7-difluorobenzo[b]thiophene-2-carboxamide-hydrochloride (compound (R)-125) (55 mg, 46% yield) as a yellow solid: cSFC analytical (A) tR=2.960 min., purity: 98.11%; LCMS (FF): tR=2.570 min., 385.0 m/z (M+1); $^1$H-NMR (CD$_3$OD, 400 MHz): δ 8.22-8.21 (d, J=3.2 Hz, 1H), 7.73-7.71 (dd, J1=8.8 Hz, J2=1.2 Hz, 1H), 4.26 (m, 1H), 3.75-3.69 (m, 2H), 3.39-3.31 (m, 2H), 2.44-2.43 (m, 1H), 2.30 (m, 1H), 2.20-2.13 (m, 2H), 2.13-1.94 (m, 1H), 1.77 (s, 3H), 1.51 (s, 3H).

Example 126: (R)—N-(2,2-dimethylquinuclidin-3-yl)-7-methylbenzo[b]thiophene-2-carboxamide hydrochloride ((R)-126)

Example 127: (R)—N-(2,2-dimethylquinuclidin-3-yl)-7-(2,2,2-trifluoroethyl)benzo[b]thiophene-2-carboxamide hydrochloride ((R)-127)

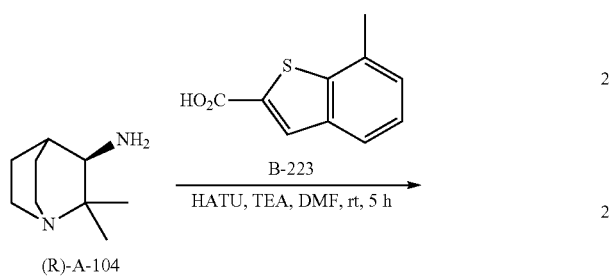

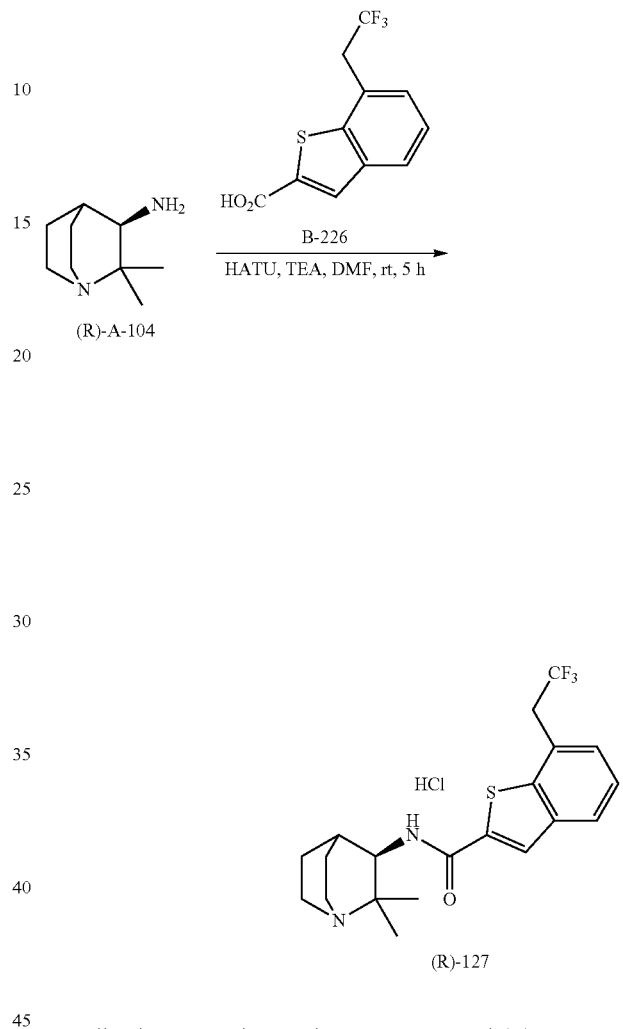

Following general procedure B, Compound (R)-126 was prepared from compound B-223 (98 mg, 0.52 mmol) and compound (R)-A-104 (80 mg, 0.52 mmol), with a reaction time of 5 hours. The product was purified by prep-HPLC [Instrument: GX-B; Column: YMC-Actus Pro C18 150×30 mm, particle size: 5 μm; Mobile phase: 29-59% acetonitrile in H$_2$O (add 0.1% TFA, v/v)]. The resulting solid was dissolved in 0.2 M hydrochloric acid solution and again lyophilized to give:

(R)—N-(2,2-dimethylquinuclidin-3-yl)-7-methylbenzo[b]thiophene-2-carboxamide hydrochloride (compound (R)-126) (70 mg, 37% yield) as a white solid: cSFC analytical (A) tR=3.023 min., purity: 98.27%; LCMS (B): tR=0.674 min., (ES$^+$) m/z (M+H)$^+$=329.2; $^1$H-NMR (CD$_3$OD, 400 MHz): δ 8.16 (s, 1H), 7.77 (d, J=8.0 Hz, 1H), 7.38 (t, J=7.6 Hz, 1H), 7.29 (d, J=7.2 Hz, 1H), 4.27 (d, J=4.0 Hz, 1H), 3.73-3.67 (m, 2H), 3.38-3.34 (m, 2H), 2.57 (s, 3H), 2.42-2.41 (m, 1H), 2.28-2.27 (m, 1H), 2.18-2.10 (m, 2H), 2.04-1.91 (m, 1H), 1.75 (s, 3H), 1.50 (s, 3H).

Following general procedure B, Compound (R)-127 was prepared from compound B-226 (84 mg, 0.32 mmol) and compound (R)-A-104 (50 mg, 0.32 mmol), with a reaction time of 5 hours. The product was purified by prep-HPLC [Instrument: GX-B; Column: YMC-Actus Pro C18 150×30 mm, particle size: 5 μm; Mobile phase: 25-55% acetonitrile in H$_2$O (add 0.1% TFA, v/v)]. The resulting solid was dissolved in 0.2 M hydrochloric acid solution and again lyophilized to give:

(R)—N-(2,2-dimethylquinuclidin-3-yl)-7-(2,2,2-trifluoroethyl)benzo[b]thiophene-2-carboxamide-hydrochloride (compound (R)-127) (69 mg, 54% yield) as a white solid: cSFC analytical (C) tR=0.71 min., purity: 98.06%; LCMS (DD): tR=0.806 min., 397.1 m/z (M+1); $^1$H-NMR (CD$_3$OD, 400 MHz): δ 8.49 (d, J=7.2 Hz, 0.1H), 8.21 (s, 1H), 7.95 (dd, J$_1$=6.4 Hz, J$_2$=2.8 Hz, 1H), 7.51-7.48 (m, 2H), 4.27 (s, 1H), 3.81 (q, J=11.2 Hz, 2H), 3.73-3.67 (m, 2H), 3.38-3.33 (m, 2H), 2.44-2.41 (m, 1H), 2.29-2.28 (m, 1H), 2.17-2.10 (m, 2H), 1.98-1.91 (m, 1H), 1.76 (s, 3H), 1.50 (s, 3H).

Example 128: (R)-7-(dimethylamino)-N-(2,2-dimethylquinuclidin-3-yl)benzo[b]thiophene-2-carboxamide hydrochloride ((R)-128)

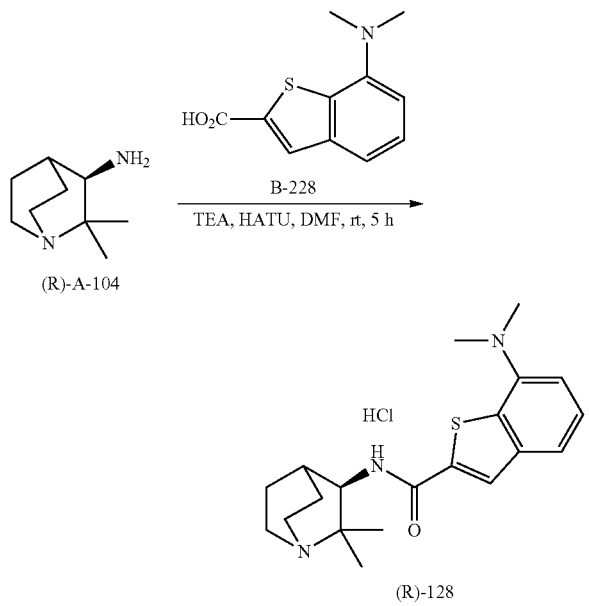

Following general procedure B, Compound (R)-128 was prepared from compound B-228 (149 mg, crude) and compound (R)-A-104 (104 mg, 0.67 mmol), with a reaction time of 5 hours. The product was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give:

(R)-7-(dimethylamino)-N-(2,2-dimethylquinuclidin-3-yl)benzo[b]thiophene-2-carboxamide-hydrochloride (compound (R)-128) (44 mg, 15% yield) as a white solid: cSFC analytical (A) tR=3.32 min., purity: 99.66%; LCMS (FF): tR=2.186 min., (ES$^+$) m/z (M+H)$^+$=358.1; $^1$H-NMR (CD$_3$OD, 400 MHz): δ 8.43 (s, 1H), 8.12 (d, J=8 Hz, 1H), 8.75 (d, J=7.6 Hz, 1H), 7.68-7.64 (m, 1H), 4.28 (s, 1H), 3.75-3.69 (m, 2H), 3.48 (s, 6H), 3.36-3.30 (m, 2H), 2.48-2.47 (m, 1H), 2.30-2.29 (m, 1H), 2.18-2.11 (m, 2H), 2.10-1.95 (m, 1H), 1.76 (s, 3H), 1.52 (m, 3H).

Example 129: (R)—N-(2,2-dimethylquinuclidin-3-yl)-7-(thiazol-2-yl)benzo[b]thiophene-2-carboxamide hydrochloride ((R)-129)

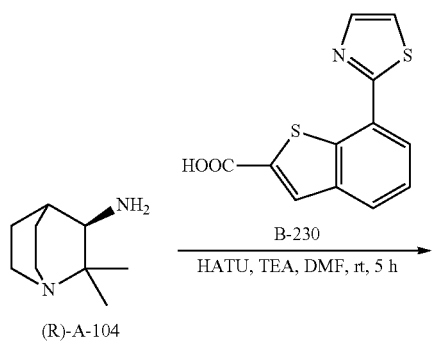

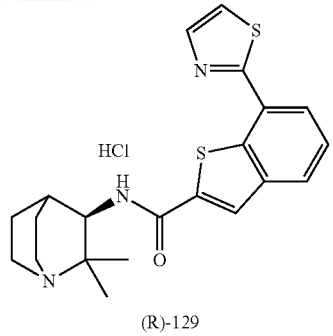

Following general procedure B, Compound (R)-129 was prepared from compound B-230 (119 mg, 0.45 mmol) and compound (R)-A-104 (70 mg, 0.45 mmol), with a reaction time of 5 hours. The product was purified by prep-HPLC [Instrument: GX-E; Column: Phenomenex Synergi C18 150×30 mm, particle size: 4 μm; Mobile phase: 20-50% acetonitrile in H$_2$O (add 0.05% HCl, v/v)] to give:

(R)—N-(2,2-dimethylquinuclidin-3-yl)-7-(thiazol-2-yl)benzo[b]thiophene-2-carboxamide-hydrochloride (compound (R)-129) (70 mg, 35% yield) as a yellow solid: cSFC analytical (C) tR=2.054 min., purity: 100%; LCMS (EE): tR=2.895 min., (ES$^+$) m/z (M+H)$^+$=398.1; $^1$H-NMR (CD$_3$OD, 400 MHz): δ 8.22 (s, 1H), 8.09-8.014 (m, 3H), 7.70 (d, J=3.6 Hz, 1H), 7.59 (t, J=8.0 Hz, 1H), 4.29 (s, 1H), 3.74-3.68 (m, 2H), 3.38-3.34 (m, 2H), 2.44-2.43 (m, 1H), 2.30-2.29 (m, 1H), 2.19-2.10 (m, 2H), 1.98-1.92 (m, 1H), 1.77 (s, 3H), 1.52 (s, 3H).

Example 130: (R)—N-(2,2-dimethylquinuclidin-3-yl)isoquinoline-3-carboxamide hydrochloride ((R)-130)

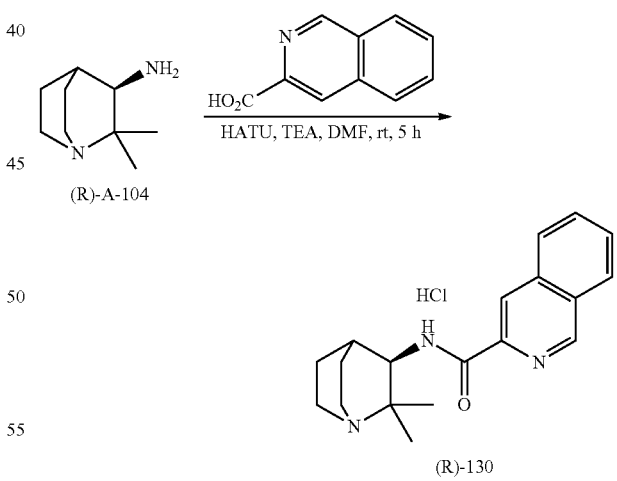

Following general procedure B, Compound (R)-130 was prepared from isoquinoline-3-carboxylic acid (90 mg, 0.52 mmol) and compound (R)-A-104 (80 mg, 0.52 mmol), with a reaction time of 5 hours. The product was purified by prep-HPLC [Instrument: GX-B; Column: YMC-Actus Pro C18 150×30 mm, particle size: 5 μm; Mobile phase: 10-40% acetonitrile in H$_2$O (add 0.1% TFA, v/v)]. The resulting solid was dissolved in 0.2 M hydrochloric acid solution and again lyophilized to give:

(R)—N-(2,2-dimethylquinuclidin-3-yl)isoquinoline-3-carboxamide-hydrochloride (compound (R)-130) (130 mg, 72% yield) as a white solid: cSFC analytical (A) tR=2.741 min., purity: 100%; LCMS (B): tR=0.575 min., (ES$^+$) m/z (M+H)$^+$=310.2; $^1$H-NMR (CD$_3$OD, 400 MHz): δ 9.69 (s, 1H), 9.14 (s, 1H), 8.52 (d, J=8.4 Hz, 1H), 8.37 (d, J=8.4 Hz, 1H), 8.22 (t, J=8.0 Hz, 1H), 8.08 (t, J=8.0 Hz, 1H), 4.38 (s, 1H), 3.76-3.73 (m, 2H), 3.41-3.37 (m, 2H), 2.54-2.47 (m, 1H), 2.35 (m, 1H), 2.22-2.14 (m, 2H), 2.03-1.96 (m, 1H), 1.80 (s, 3H), 1.56 (s, 3H).

Example 131: (R)-7-(tert-butyl)-N-(2,2-dimethylquinuclidin-3-yl)benzo[b]thiophene-2-carboxamide hydrochloride ((R)-131)

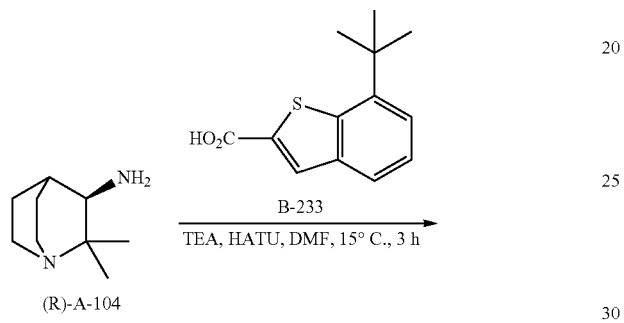

Following general procedure B, Compound (R)-131 was prepared from compound B-233 (96 mg, 0.49 mmol) and compound (R)-A-104 (63 mg, 0.41 mmol), with a reaction time of 3 hours. The product was purified by prep-HPLC [Instrument: GX-B; Column: Phenomenex Synergi C18 150×30 mm, particle size: 4 μm; Mobile phase: 32-62% acetonitrile in H$_2$O (add 0.1% TFA, v/v)]. The resulting solid was dissolved in 0.2 N hydrochloric acid and again lyophilized to give:

(R)-7-(tert-butyl)-N-(2,2-dimethylquinuclidin-3-yl)benzo[b]thiophene-2-carboxamide-hydrochloride (compound (R)-131) (90 mg, 45% yield) as a white solid: cSFC analytical (A) tR=2.71 min., purity: 96.96%; LCMS (FF): tR=2.668 min., 371.2 m/z (M+1); $^1$H-NMR (CD$_3$OD, 400 MHz): δ 8.45 (d, J=7.6 Hz, 1H), 8.17 (s, 1H), 7.81 (d, J=7.6 Hz, 1H), 7.52-7.48 (m, 1H), 7.45-7.41 (m, 1H), 4.29 (m, 1H), 3.78-3.69 (m, 2H), 3.40-3.35 (m, 2H), 2.47-2.30 (m, 1H), 2.20-1.93 (m, 4H), 1.74 (s, 3H), 1.59 (s, 1H), 1.52 (s, 3H).

Example 132: (R)—N-(2,2-dimethylquinuclidin-3-yl)-7-phenylbenzo[b]thiophene-2-carboxamide hydrochloride ((R)-132)

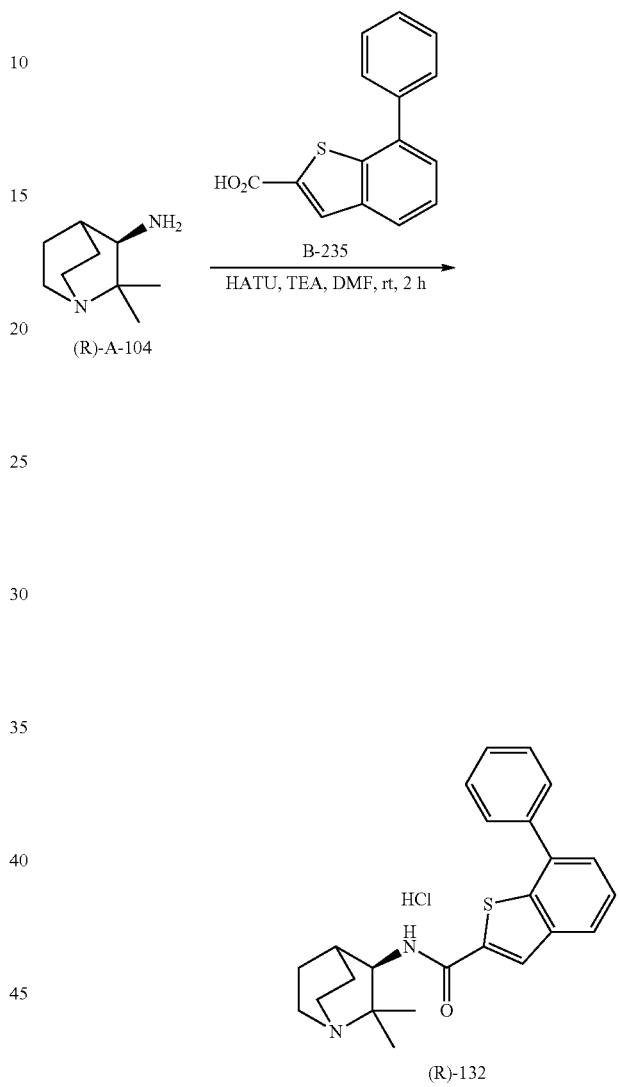

Following general procedure B, Compound (R)-132 was prepared from compound B-235 (99 mg, 0.39 mmol) and compound (R)-A-104 (60 mg, 0.39 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)—N-(2,2-dimethylquinuclidin-3-yl)-7-phenylbenzo[b]thiophene-2-carboxamide-hydrochloride (compound (R)-132) (70 mg, 46% yield) as a white solid: cSFC analytical (A) tR=3.57 min., purity: 100%; LCMS (Y): tR=0.754 min., 391.1 m/z (M+1); $^1$H-NMR (CD$_3$OD, 400 MHz): δ 8.44 (d, J=7.2 Hz, 1H), 8.22 (s, 1H), 7.94 (d, J=7.2 Hz, 1H), 7.73 (d, J=7.2 Hz, 2H), 7.60-7.46 (m, 5H), 4.27 (s, 1H), 3.83-3.69 (m, 2H), 3.40-3.37 (m, 1H), 2.46-2.42 (m, 1H), 2.30-2.12 (m, 3H), 1.99-1.93 (m, 1H), 1.76 (s, 3H), 1.50 (s, 3H).

Example 133: (R)—N-(2,2-dimethylquinuclidin-3-yl)-7-(1-methylcyclopropyl)benzo[b]thiophene-2-carboxamide hydrochloride ((R)-133)

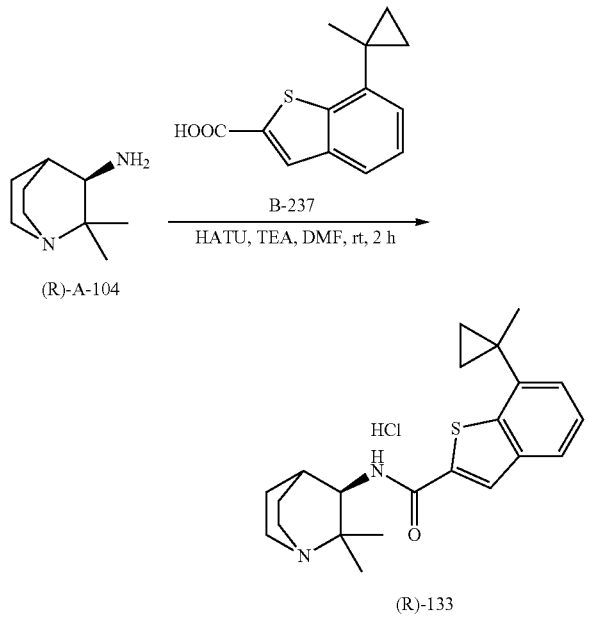

Compound (R)-133 was prepared from B-237 (90 mg, 0.39 mmol) and compound (R)-A-104 (60 mg, 0.39 mmol) using general procedure B with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)—N-(2,2-dimethylquinuclidin-3-yl)-7-(1-methylcyclopropyl)benzo[b]thiophene-2-carboxamide-hydrochloride (compound (R)-133) (62 mg, 47% yield) as a white solid: cSFC analytical (A) tR=2.76 min., purity: 98.18%; LCMS (GG): tR=2.298 min., 369.1 m/z (M+1); $^1$H-NMR (CD$_3$OD, 400 MHz): δ 8.42 (d, J=7.2 Hz, 1H), 8.16 (s, 1H), 7.80 (d, J=7.6 Hz, 1H), 7.46-7.39 (m, 2H), 4.29 (s, 1H), 3.79-3.69 (m, 2H), 3.40-3.37 (m, 1H), 2.47-2.42 (m, 1H), 2.31-2.30 (m, 1H), 2.20-2.10 (m, 3H), 2.00-1.94 (m, 1H), 1.78 (s, 3H), 1.51 (s, 3H), 1.48 (s, 3H), 0.96-0.92 (m, 2H), 0.89-0.86 (m, 2H).

Example 134: (R)—N-(2,2-dimethylquinuclidin-3-yl)-6-ethoxybenzo[b]thiophene-2-carboxamide hydrochloride ((R)-134)

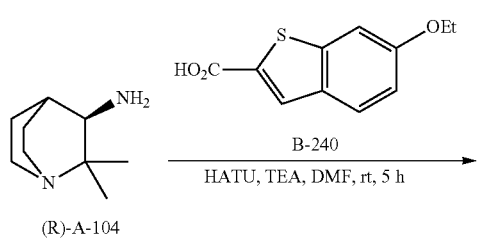

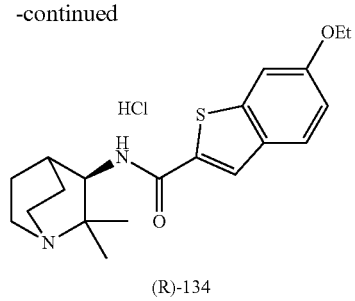

Following general procedure B, Compound (R)-134 was prepared from compound B-240 (115 mg, 0.52 mmol) and compound (R)-A-104 (80 mg, 0.52 mmol), with a reaction time of 5 hours. The product was purified by prep-HPLC [Instrument: GX-B; Column: Phenomenex Synergi C18 150×30 mm, particle size: 4 μm; Mobile phase: 25-55% acetonitrile in H$_2$O (add 0.1% TFA, v/v)]. The resulting solid was dissolved in 0.2 M hydrochloric acid solution and again lyophilized to give:

(R)—N-(2,2-dimethylquinuclidin-3-yl)-6-ethoxybenzo[b]thiophene-2-carboxamide-hydrochloride (compound (R)-134) (70 mg, 34% yield) as a white solid: cSFC analytical (A) tR=3.13 min., purity: 96.60%; LCMS (EE): tR=2.861 min., (ES$^+$) m/z (M+H)$^+$=359.1; $^1$H-NMR (CD$_3$OD, 400 MHz): δ 8.05 (s, 1H), 7.77 (d, J=8.8 Hz, 1H), 7.42 (d, J=1.6 Hz, 1H), 7.03 (dd, J=8.8, 2.0 Hz, 1H), 4.24-4.23 (m, 1H), 4.11 (q, J=6.8 Hz, 2H), 3.74-3.65 (m, 2H), 3.36-3.33 (m, 2H), 2.40-2.39 (m, 1H), 2.25 (d, J=2.8 Hz, 1H), 2.16-2.10 (m, 2H), 2.08-1.93 (m, 1H), 1.73 (s, 3H), 1.47 (s, 3H), 1.42 (t, J=6.8 Hz, 3H).

Example 135: (R)—N-(2,2-dimethylquinuclidin-3-yl)-7-ethoxybenzo[b]thiophene-2-carboxamide hydrochloride ((R)-135)

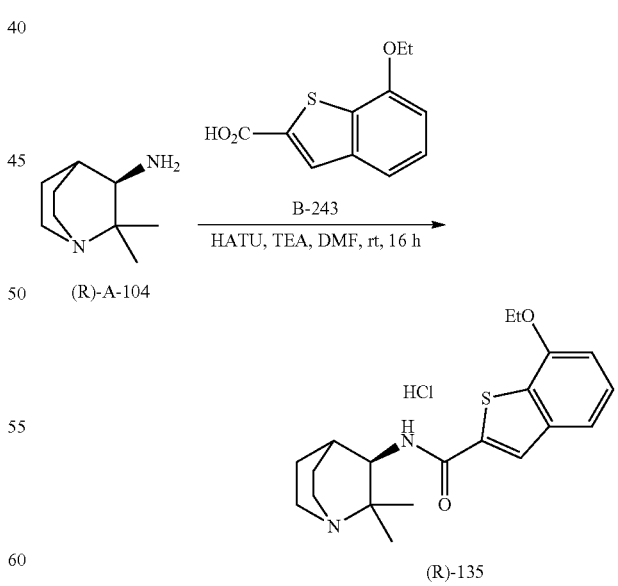

Following general procedure B, Compound (R)-135 was prepared from compound B-243 (101 mg, 0.45 mmol) and compound (R)-A-104 (117 mg, 0.45 mmol), with a reaction time of 16 hours. The product was purified by prep-HPLC [Instrument: GX-B; Column: YMC-Actus Pro C18 150×30 mm, particle size: 5 μm; Mobile phase: 25-55% acetonitrile in H$_2$O (add 0.5% HCl, v/v)] to give:

(R)—N-(2,2-dimethylquinuclidin-3-yl)-7-ethoxybenzo[b]thiophene-2-carboxamide-hydrochloride (compound (R)-135) (80 mg, 41% yield) as a white solid: cSFC analytical (A) tR=3.37 min., purity: 99.52%; LCMS (GG): tR=2.096 min., (ES$^+$) m/z (M+H)$^+$=359.2; $^1$H-NMR (CD$_3$OD, 400 MHz): 8.10 (s, 1H), 7.49 (d, J=8.0 Hz, 1H), 7.38 (m, 1H), 6.97 (d, J=7.6 Hz, 1H), 4.29-4.23 (m, 3H), 3.72-3.66 (m, 2H), 3.37-3.33 (m, 2H), 2.41-2.39 (m, 1H), 2.27-2.26 (m, 1H), 2.17-2.09 (m, 2H), 1.96-1.901 (m, 1H), 1.74 (s, 3H), 1.51-1.47 (m, 6H).

Example 136: (R)—N-(2,2-dimethylquinuclidin-3-yl)-7-isopropoxybenzo[b]thiophene-2-carboxamide hydrochloride ((R)-136)

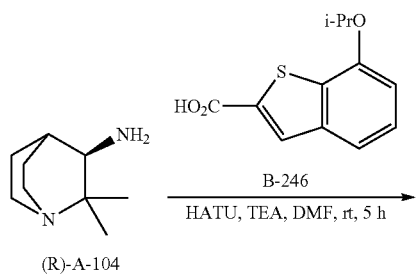

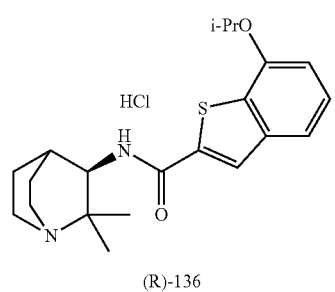

Following general procedure B, Compound (R)-136 was prepared from compound B-246 (107 mg, 0.45 mmol) and compound (R)-A-104 (70 mg, 0.45 mmol), with a reaction time of 5 hours. The product was purified by prep-HPLC [Instrument: GX-I; Column: Phenomenex Synergi C18 150×30 mm, particle size: 4 μm; Mobile phase: 28-58% acetonitrile in H$_2$O (add 0.1% TFA, v/v)]. The resulting solid was dissolved in 0.2 M hydrochloric acid solution and again lyophilized to give:

(R)—N-(2,2-dimethylquinuclidin-3-yl)-7-isopropoxybenzo[b]thiophene-2-carboxamide-hydrochloride (compound (R)-136) (101 mg, 54% yield) as a white solid: cSFC analytical (A) tR=2.970 min., purity: 98.63%; LCMS (EE): tR=3.041 min., (ES$^+$) m/z (M+H)$^+$=373.2; $^1$H-NMR (CD$_3$OD, 400 MHz): δ 8.09 (s, 1H), 7.49 (d, J=8.0 Hz, 1H), 7.38 (t, J=8.0 Hz, 1H), 7.00 (d, J=7.6 Hz, 1H), 4.87-4.81 (m, 1H), 4.25 (s, 1H), 3.76-3.67 (m, 2H), 3.38-3.31 (m, 2H), 2.44-2.40 (m, 1H), 2.28-2.27 (m, 1H), 2.19-2.10 (m, 2H), 1.97-1.91 (m, 1H), 1.75 (s, 3H), 1.49 (s, 3H), 1.42 (s, 3H), 1.41 (s, 3H).

Example 137: (R)-6-chloro-N-(2,2-dimethylquinuclidin-3-yl)-7-methoxybenzo[b]thiophene-2-carboxamide hydrochloride ((R)-137)

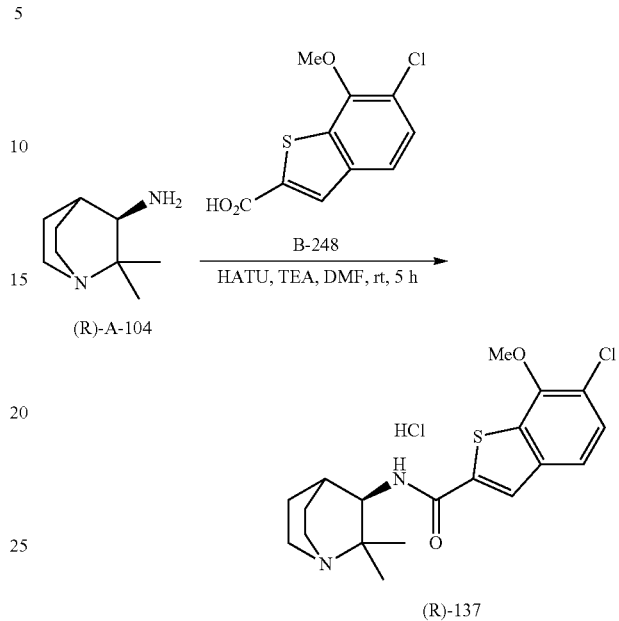

Following general procedure B, Compound (R)-137 was prepared from compound B-248 (110 mg, 0.45 mmol) and compound (R)-A-104 (70 mg, 0.45 mmol), with a reaction time of 5 hours. The product was purified by prep-HPLC [Instrument: GX-B; Column: YMC-Actus Pro C18 150×30 mm, particle size: 5 μm; Mobile phase: 38-68% acetonitrile in H$_2$O (add 0.1% TFA, v/v)]. The resulting solid was dissolved in 0.2 M hydrochloric acid solution and again lyophilized to give:

(R)-6-chloro-N-(2,2-dimethylquinuclidin-3-yl)-7-methoxybenzo[b]thiophene-2-carboxamide-hydrochloride (compound (R)-137) (72 mg, 38% yield) as a white solid: cSFC analytical (A) tR=2.982 min., purity: 98.64%; LCMS (FF): tR=2.455 min., (ES$^+$) m/z (M+H)$^+$=379.1; $^1$H-NMR (CD$_3$OD, 400 MHz): δ 8.13 (s, 1H), 7.66 (d, J=8.8 Hz, 1H), 7.48 (d, J=8.4 Hz, 1H), 4.25 (s, 1H), 4.04 (s, 3H), 3.76-3.66 (m, 2H), 3.38-3.33 (m, 2H), 2.42-2.39 (m, 1H), 2.28-2.27 (m, 1H), 2.17-2.09 (m, 2H), 2.04-1.91 (m, 1H), 1.75 (s, 3H), 1.48 (s, 3H).

Example 138: (R)—N-(2,2-dimethylquinuclidin-3-yl)-7-methoxy-6-methylbenzo[b]thiophene-2-carboxamide hydrochloride ((R)-138)

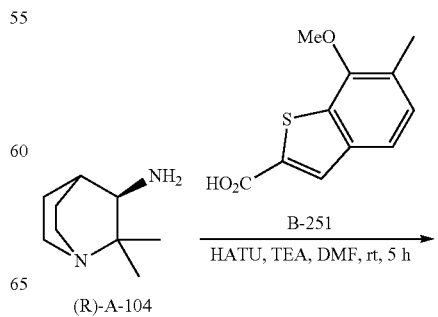

-continued

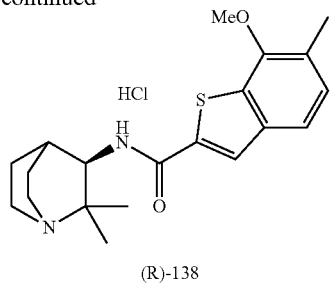

(R)-138

Following general procedure B, Compound (R)-138 was prepared from compound B-251 (0.10 g, 0.45 mmol) and compound (R)-A-104 (70 mg, 0.45 mmol), with a reaction time of 5 hours. The product was purified by prep-HPLC [Instrument: GX-B; Column: Phenomenex Synergi C18 150×30 mm, particle size: 4 μm; Mobile phase: 27-57% acetonitrile in H₂O (add 0.1% TFA, v/v)]. The resulting solid was dissolved in 0.2 M hydrochloric acid solution and again lyophilized to give:

(R)—N-(2,2-dimethylquinuclidin-3-yl)-7-methoxy-6-methylbenzo[b]thiophene-2-carboxamide-hydrochloride (compound (R)-138) (0.11 g, 59% yield) as a white solid: cSFC analytical (A) tR=2.89 min., purity: 97.99%; LCMS (EE): tR=2.864 min., 359.1 m/z (M+1); ¹H-NMR (CD₃OD, 400 MHz): δ 8.41 (d, J=7.2 Hz, 0.6H), 8.12 (s, 1H), 7.58 (d, J=8.0 Hz, 1H), 7.29 (d, J=8.0 Hz, 1H), 4.25 (s, 1H), 3.95 (s, 3H), 3.76-3.66 (m, 2H), 3.37-3.34 (m, 2H), 2.45-2.41 (m, 4H), 2.27-2.26 (m, 1H), 2.18-2.08 (m, 2H), 1.97-1.90 (m, 1H), 1.75 (s, 3H), 1.49 (s, 3H).

Example 139: (R)—N-(2,2-dimethylquinuclidin-3-yl)-1H-indazole-3-carboxamide hydrochloride ((R)-139)

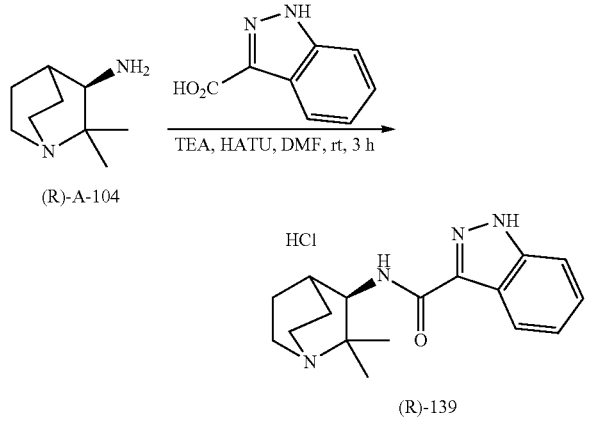

(R)-139

Following general procedure B, Compound (R)-139 was prepared from 1H-indazole-3-carboxylic acid d (0.10 g, 0.64 mmol) and compound (R)-A-104 (90 mg, 0.58 mmol), with a reaction time of 3 hours. The product was purified by prep-HPLC [Instrument: GX-B; Column: YMC-Actus Pro C18 150×30 mm, particle size: 5 μm; Mobile phase: 7-37% acetonitrile in H₂O (add 0.1% TFA, v/v)]. The resulting solid was dissolved in 0.2 M hydrochloric acid solution and again lyophilized to give:

(R)—N-(2,2-dimethylquinuclidin-3-yl)-1H-indazole-3-carboxamide-hydrochloride (compound (R)-139) (62 mg, 29% yield) as a white solid: cSFC analytical (A) tR=2.54 min., purity: 97.71%; LCMS (FF): tR=2.004 min, 299.1 m/z (M+1); ¹H-NMR (CD₃OD, 400 MHz): δ 8.23 (d, J=8.4 Hz, 1H), 7.63 (d, J=8.5 Hz, 1H), 7.47 (t, J=7.4 Hz, 1H), 7.31 (t, J=7.5 Hz, 1H), 4.34 (s, 1H), 3.79-3.71 (m, 2H), 3.41-3.36 (m, 2H), 2.39-2.29 (m, 2H), 2.22-2.14 (m, 2H), 2.01-1.95 (m, 1H), 1.80 (s, 3H), 1.54 (s, 3H).

Example 140: (R)-7-cyclopropyl-N-(2,2-dimethylquinuclidin-3-yl)-6-methylbenzo[b]thiophene-2-carboxamide hydrochloride ((R)-140)

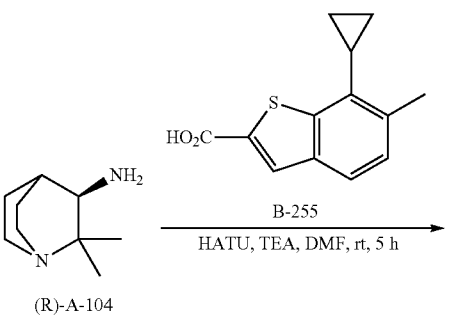

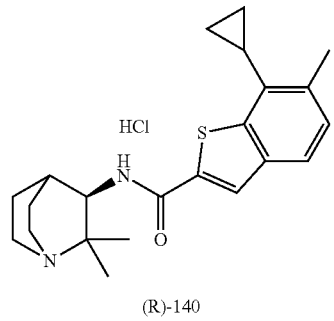

(R)-140

Following general procedure B, Compound (R)-140 was prepared from compound B-255 (0.14 g, 0.58 mmol) and compound (R)-A-104 (90 mg, 0.58 mmol), with a reaction time of 5 hours. The product was purified by prep-HPLC [Instrument: GX-B; Column: Phenomenex Synergi C18 150×30 mm, particle size: 4 μm; Mobile phase: 30-60% acetonitrile in H₂O (add 0.1% TFA, v/v)]. The resulting solid was dissolved in 0.2 M hydrochloric acid solution and again lyophilized to give:

(R)-7-cyclopropyl-N-(2,2-dimethylquinuclidin-3-yl)-6-methylbenzo[b]thiophene-2-carboxamide-hydrochloride (compound (R)-140) (0.14 g, 67% yield) as a white solid: cSFC analytical (A) tR=3.19 min., purity: 100%; LCMS (FF): tR=2.536 min., 369.1 m/z (M+1); ¹H-NMR (CD₃OD, 400 MHz): δ 8.36 (d, J=7.2 Hz, 0.5H), 8.08 (s, 1H), 7.68 (d, J=8.0 Hz, 1H), 7.27 (d, J=8.0 Hz, 1H), 4.25 (s, 1H), 3.76-3.67 (m, 2H), 3.37-3.34 (m, 2H), 2.57 (s, 3H), 2.42-2.41 (m, 1H), 2.27-2.26 (m, 1H), 2.17-2.06 (m, 3H), 1.97-1.90 (m, 1H), 1.75 (s, 3H), 1.49 (s, 3H), 1.17-1.12 (m, 2H), 0.82-0.78 (m, 2H).

Example 141: (R)—N-(2,2-dimethylquinuclidin-3-yl)-6-fluoro-7-methoxybenzo[b]thiophene-2-carboxamide hydrochloride ((R)-141)

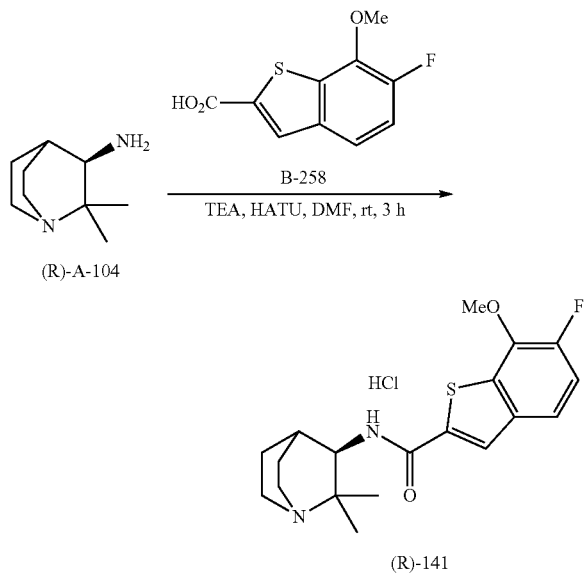

Following general procedure B, compound (R)-141 was prepared from compound B-258 (132 mg, 0.58 mmol) and compound (R)-A-104 (90 mg, 0.58 mmol), with a reaction time of 3 hours. The product was purified by prep-HPLC [Instrument: GX-E; Column: Phenomenex Synergi C18 250×21.2 mm, particle size: 4 μm; Mobile phase: 25-55% acetonitrile in H$_2$O (add 0.05% HCl, v/v)] to give:

(R)—N-(2,2-dimethylquinuclidin-3-yl)-6-fluoro-7-methoxybenzo[b]thiophene-2-carboxamide-hydrochloride (compound (R)-141) (119 mg, 56% yield) as a white solid: cSFC analytical (A) tR=2.71 min., purity: 98.06%; LCMS (FF): tR=2.356 min., 363.1 m/z (M+1); $^1$H-NMR (CD$_3$OD, 400 MHz): δ 8.11 (s, 1H), 7.60 (dd, J$_1$=8.4 Hz, J$_2$=4.0 Hz, 1H), 7.27 (dd, J$_1$=12 Hz, J$_2$=8.4 Hz, 1H), 4.23 (s, 1H), 4.12 (d, J=2.4 Hz, 3H), 3.72-3.65 (m, 2H), 3.38-3.28 (m, 2H), 2.40-2.38 (m, 1H), 2.27-2.25 (m, 1H), 2.15-2.10 (m, 2H), 1.97-1.93 (m, 1H), 1.74 (s, 3H), 1.47 (s, 3H).

Example 142: (R)-7-cyano-N-(2,2-dimethylquinuclidin-3-yl)-6-methylbenzo[b]thiophene-2-carboxamide hydrochloride ((R)-142)

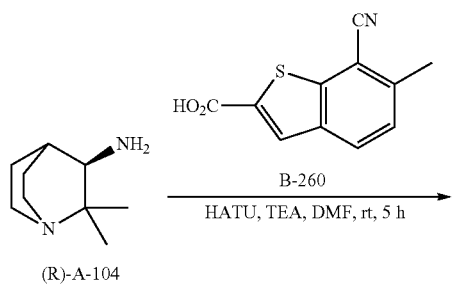

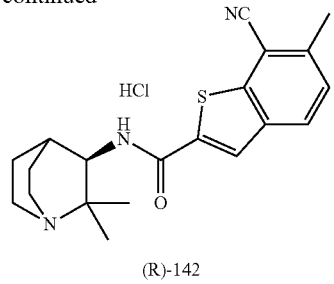

Following general procedure B, Compound (R)-142 was prepared from compound B-260 (0.11 g, 0.52 mmol) and compound (R)-A-104 (80 mg, 0.52 mmol), with a reaction time of 5 hours. The product was purified by prep-HPLC [Instrument: GX-B; Column: Welch Ultimate AQ-C18 150×30 mm, particle size: 5 μm; Mobile phase: 25-55% acetonitrile in H$_2$O (add 0.1% TFA, v/v)]. The resulting solid was dissolved in 0.2 M hydrochloric acid and again lyophilized to give:

(R)-7-cyano-N-(2,2-dimethylquinuclidin-3-yl)-6-methyl-benzo[b]thiophene-2-carboxamide-hydrochloride (compound (R)-142) (0.13 g, 71% yield) as a white solid: cSFC analytical (A) tR=3.05 min., purity: 100%; LCMS (GG): tR=2.065 min., 354.2 m/z (M+1); $^1$H-NMR (CD$_3$OD, 400 MHz): δ 8.53 (d, J=7.2 Hz, 0.6H), 8.22 (s, 1H), 8.09 (d, J=8.0 Hz, 1H), 7.50 (d, J=8.0 Hz, 1H), 4.26 (s, 1H), 3.76-3.67 (m, 2H), 3.38-3.33 (m, 2H), 2.69 (s, 3H), 2.46-2.41 (m, 1H), 2.29-2.28 (m, 1H), 2.18-2.10 (m, 2H), 1.98-1.91 (m, 1H), 1.75 (s, 3H), 1.50 (s, 3H).

Example 143: (R)—N-(2,2-dimethylquinuclidin-3-yl)-7-(methoxymethyl)benzo[b]thiophene-2-carboxamide hydrochloride ((R)-143)

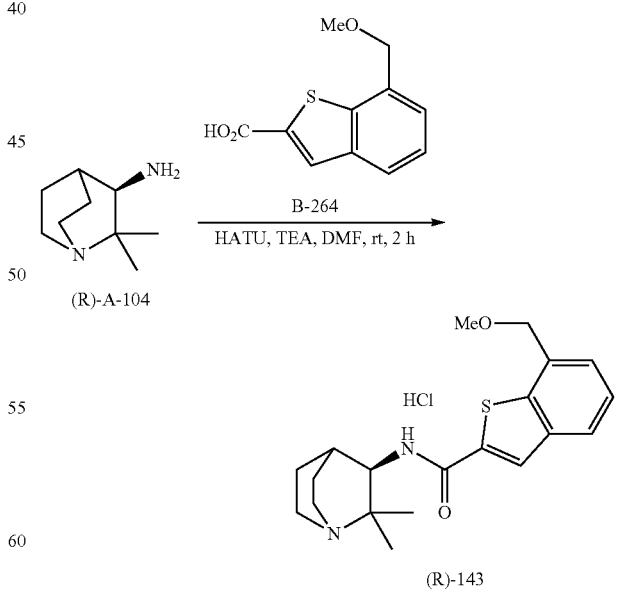

Following general procedure B, Compound (R)-143 was prepared from compound B-264 (0.13 g, 0.58 mmol) and compound (R)-A-104 (90 mg, 0.58 mmol), with a reaction time of 2 hours. The product was purified by prep-HPLC

[Instrument: GX-E; Column: Agella Venusil ASB C18 150×30 mm, particle size: 5 μm; Mobile phase: 27-57% acetonitrile in H₂O (add 0.5% HCl, v/v)] to give:

(R)—N-(2,2-dimethylquinuclidin-3-yl)-7-(methoxymethyl)benzo[b]thiophene-2-carboxamide-hydrochloride (compound (R)-143) (135 mg, 64% yield) as a white solid: cSFC analytical (A) tR=1.12 min., purity: 100%; LCMS (Y): tR=2.205 min., 359.1 m/z (M+1); $^{1}$H-NMR (CD$_3$OD, 400 MHz): δ 8.41 (d, J=7.2 Hz, 1H), 8.17 (s, 1H), 7.92-7.89 (m, 1H), 7.48-7.45 (m, 2H), 4.77 (s, 2H), 4.28 (d, J=6.8 Hz, 1H), 3.78-3.69 (m, 2H), 3.43 (s, 3H), 3.40-3.36 (m, 2H), 2.43-2.30 (m, 1H), 2.29-2.20 (m, 1H), 2.19-2.13 (m, 2H), 2.12-1.96 (m, 1H), 1.77 (s, 3H), 1.50 (s, 3H).

Example 144: (R)—N-(2,2-dimethylquinuclidin-3-yl)-3,4-dihydro-2H-thieno[3,2-h]chromene-8-carboxamide ((R)-144)

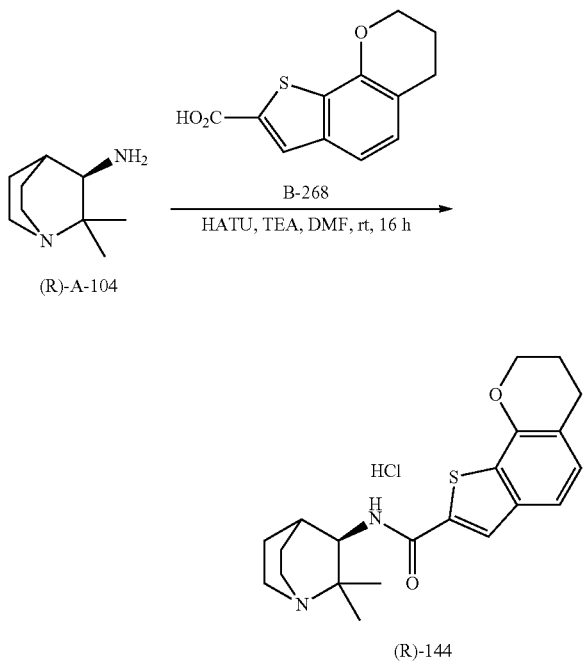 [SMILES: CC1(C)[C@H](N)C2CCN1CC2 ; O=C(O)c1cc2ccc3c(c2s1)OCCC3 ; CC1(C)[C@H](NC(=O)c2cc3ccc4c(c3s2)OCCC4)C2CCN1CC2 ; Cl]

Following general procedure B, Compound (R)-144 was prepared from compound B-268 (122 mg, 0.52 mmol) and compound (R)-A-104 (80 mg, 0.52 mmol), with a reaction time of 16 hours. The product was purified by prep-HPLC [Instrument: GX-E; Column: Phenomenex Synergi C18 150*30 mm, particle size: 4 μm; Mobile phase: 23-43% acetonitrile in H₂O (add 0.05% HCl, v/v)] to give:

(R)—N-(2,2-dimethylquinuclidin-3-yl)-3,4-dihydro-2H-thieno[3,2-h]chromene-8-carboxamide-hydrochloride (compound (R)-144) (150 mg, 71% yield) as a white solid: cSFC analytical (A) tR=3.62 min., purity: 100.00%; LCMS (FF): tR=2.391 min., (ES⁺) m/z (M+H)⁺=371.1; $^{1}$H-NMR (CD$_3$OD, 400 MHz): δ 8.06 (s, 1H), 7.41-7.39 (d, J=8.0 Hz, 1H), 7.17-7.15 (d, J=8.4 Hz, 1H), 4.39-4.36 (t, J=5.2 Hz, 2H), 4.26 (s, 1H), 3.77-3.68 (m, 2H), 3.39-3.36 (m, 2H), 2.94-2.91 (t, J=6.4 Hz, 2H), 2.45-2.40 (m, 1H), 2.29-2.28 (m, 1H), 2.19-2.10 (m, 4H), 1.98-1.92 (m, 1H), 1.76 (s, 3H), 1.50 (s, 3H).

Example 145: (R)—N-(2,2-dimethylquinuclidin-3-yl)-8,9-dihydro-7H-thieno[2,3-f]chromene-2-carboxamide hydrochloride ((R)-145)

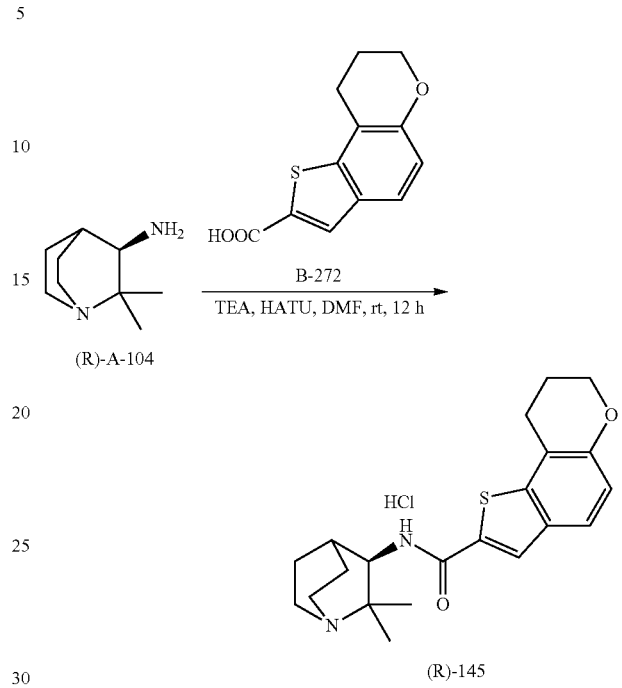

Following general procedure B, Compound (R)-145 was prepared from compound B-272 (0.14 g, 0.58 mmol) and compound (R)-A-104 (90 mg, 0.58 mmol), with a reaction time of 12 hours. The product was purified by prep-HPLC [Instrument: GX-B; Column: YMC-Actus Pro C18 150×30 mm, particle size: 5 μm; Mobile phase: 25-55% acetonitrile in H₂O (add 0.5% TFA, v/v)]. The resulting solid was dissolved in 0.2 M hydrochloric acid solution and again lyophilized to give:

(R)—N-(2,2-dimethylquinuclidin-3-yl)-8,9-dihydro-7H-thieno[2,3-f]chromene-2-carboxamide-hydrochloride (compound (R)-145) (70 mg, 32% yield) as a white solid: cSFC analytical (A) tR=3.308 min., purity: 96.94%; LCMS (GG): tR=2.058 min., 371.2 m/z (M+1); $^{1}$H-NMR (CD$_3$OD, 400 MHz): δ 8.09 (s, 1H), 7.66-7.64 (d, J=8.8 Hz, 1H), 6.94-6.92 (d, J=8.8 Hz, 1H), 4.29-4.26 (m, 3H), 3.74-3.68 (m, 2H), 3.39-3.30 (m, 2H), 2.89-2.86 (m, 2H), 2.43-2.42 (m, 1H), 2.28 (m, 1H), 2.19-2.14 (m, 4H), 1.99-1.92 (m, 1H), 1.76 (s, 3H), 1.51 (s, 3H).

Example 146: (R)—N-(2,2-dimethylquinuclidin-3-yl)-2-methylbenzo[b]thiophene-6-carboxamide-hydrochloride ((R)-146)

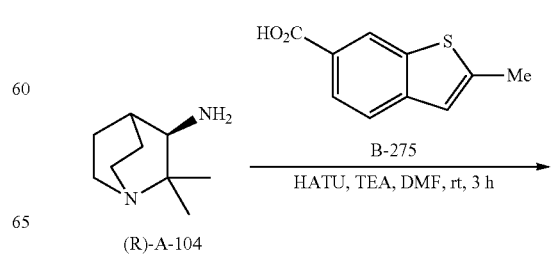

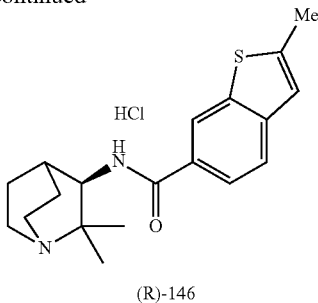

Following general procedure B, Compound (R)-146 was prepared from compound B-275 (123 mg, 0.64 mmol) and compound (R)-A-104 (90 mg, 0.58 mmol), with a reaction time of 3 hours. The product was purified by prep-HPLC [Instrument: GX-B; Column: Welch Ultimate AQ-C18 150× 30 mm, particle size: 5 μm; Mobile phase: 20-50% acetonitrile in H$_2$O (add 0.1% TFA, v/v)]. The resulting solid was dissolved in 0.2 N hydrochloric acid and again lyophilized to give:

(R)—N-(2,2-dimethylquinuclidin-3-yl)-2-methylbenzo[b]thiophene-6-carboxamide-hydrochloride (compound (R)-146) (110 mg, 49% yield) as a white solid: cSFC analytical (A) tR=2.79 min., purity: 98.20%; LCMS (GG): tR=1.946 min., 329.1 m/z (M+1); $^1$H-NMR (CD$_3$OD, 400 MHz): δ 8.33 (s, 1H), 7.81-7.76 (m, 2H), 7.15 (s, 1H), 4.29 (s, 1H), 3.74-3.67 (m, 2H), 3.39-3.29 (m, 2H), 2.65 (s, 3H), 2.43-2.07 (m, 4H), 1.97-1.90 (m, 1H), 1.79 (s, 3H), 1.51 (s, 3H).

Example 147: (R)-2-chloro-N-(2,2-dimethylquinuclidin-3-yl)benzo[b]thiophene-6-carboxamide hydrochloride ((R)-147)

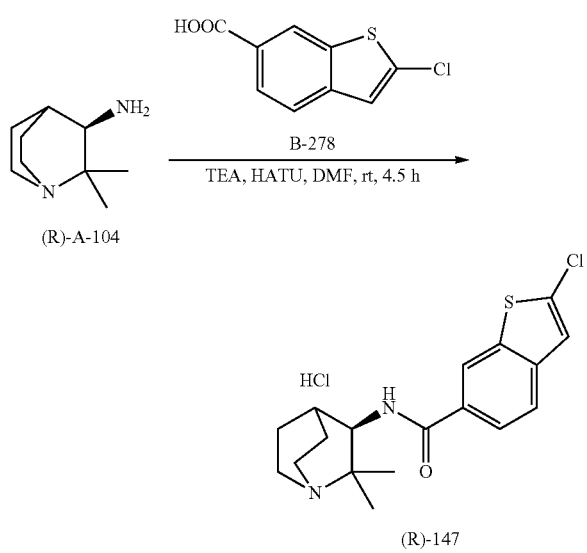

Following general procedure B, Compound (R)-147 was prepared from compound B-278 (69 mg, 0.32 mmol) and compound (R)-A-104 (50 mg, 0.32 mmol), with a reaction time of 4.5 hours. The product was purified by prep-HPLC [Instrument: GX-E; Column: Phenomenex Synergi C18 150×30 mm, particle size: 4 μm; Mobile phase: 25-45% acetonitrile in H$_2$O (add 0.05% HCl, v/v)]. The resulting solution was lyophilized to give:

(R)-2-chloro-N-(2,2-dimethylquinuclidin-3-yl)benzo[b]thiophene-6-carboxamide hydrochloride ((R)-147) (62 mg, 49% yield) as a white solid: cSFC analytical (A) tR=2.85 min., purity: 98.63%; LCMS (FF): tR=2.278 min., 349.1 m/z (M+1); $^1$H-NMR (D$_2$O, 400 MHz): δ 8.02 (s, 1H), 7.67-7.65 (d, J=8.0 Hz, 1H), 7.57-7.55 (d, J=8.0 Hz, 1H), 7.24 (s, 1H), 4.11 (s, 1H), 3.62-3.55 (m, 2H), 3.27-3.18 (m, 2H), 2.17 (s, 2H), 2.05-2.03 (m, 2H), 1.99-1.83 (m, 1H), 1.63 (s, 3H), 1.39 (s, 3H).

Example 148: (R)-6-chloro-N-(2,2-dimethylquinuclidin-3-yl)-7-methylbenzo[b]thiophene-2-carboxamide hydrochloride ((R)-148)

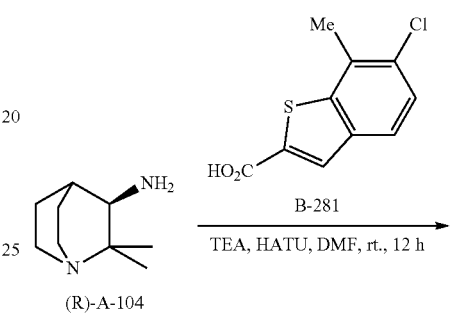

Following general procedure B, Compound (R)-148 was prepared from compound B-281 (0.15 g, 0.64 mmol) and compound (R)-A-104 (90 mg, 0.58 mmol), with a reaction time of 12 hours. The product was purified by prep-HPLC [Instrument: GX-B; Column: YMC-Actus Pro C18 150×30 mm, particle size: 5 μm; Mobile phase: 25-55% acetonitrile in H$_2$O (add 0.5% TFA, v/v)]. The resulting solid was dissolved in 0.2 M hydrochloric acid and again lyophilized to give:

(R)-6-chloro-N-(2,2-dimethylquinuclidin-3-yl)-7-methylbenzo[b]thiophene-2-carboxamide-hydrochloride (compound (R)-148) (70 mg, 30% yield) as a white solid: cSFC analytical (A) tR=2.921 min., purity: 97.21%; LCMS (FF): tR=2.508 min., 363.1 m/z (M+1); $^1$H-NMR (CD$_3$OD, 400 MHz): δ 8.17 (s, 1H), 7.78-7.75 (d, J=8.4 Hz, 1H), 7.49-7.47 (d, J=8.4 Hz, 1H), 4.27 (s, 1H), 3.78-3.69 (m, 2H), 3.40-3.35 (m, 2H), 2.63 (m, 3H), 2.42 (m, 1H), 2.30-2.29 (m, 1H), 2.19-2.12 (m, 2H), 1.99-1.96 (m, 1H), 1.77 (s, 3H), 1.51 (s, 3H).

Example 149: (R)-2-amino-N-(1'-azaspiro[cyclopropane-1,2'-bicyclo[2.2.2]octan]-3'-yl) thieno[2,3-d]pyrimidine-6-carboxamide hydrochloride ((R)-149)

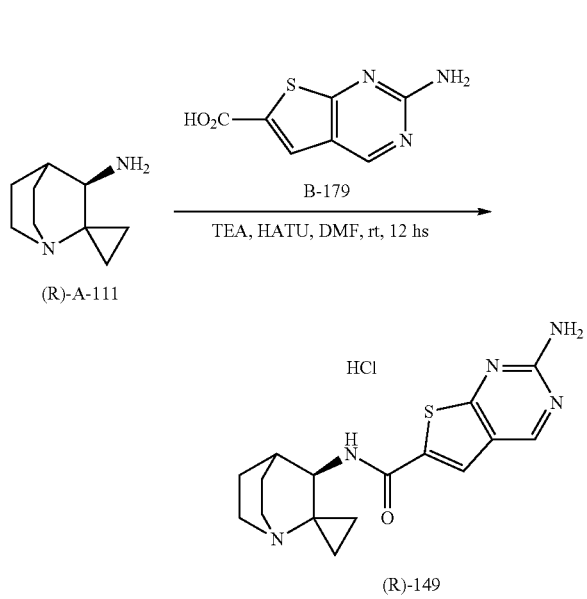

Following general procedure B, Compound (R)-149 was prepared from compound B-179 (60 mg, 0.31 mmol) and compound (R)-A-111 (47 mg, 0.31 mmol), with a reaction time of 12 hours. The product was purified by prep-HPLC [Instrument: GX-C; Column: Phenomenex Gemini C18 150×30 mm, particle size: 5 μm; Mobile phase: 35-65% acetonitrile in H$_2$O (add 0.5% NH$_3$.H$_2$O, v/v)]. The resulting solid was dissolved in 0.2 M hydrochloric acid solution and again lyophilized to give:

(R)-2-amino-N-(1'-azaspiro[cyclopropane-1,2'-bicyclo[2.2.2]octan]-3'-yl)thieno[2,3-d]pyrimidine-6-carboxamide-hydrochloride (compound (R)-149) (40 mg, 40% yield) as a white solid: cSFC analytical (A) tR=3.24 min., purity: 99.00%; LCMS (J): tR=0.880 min., 330.0 m/z (M+1); $^1$H-NMR (CD$_3$OD, 400 MHz): δ 9.04-9.04 (d, 1H), 8.27 (s, 1H), 4.56 (m, 1H), 3.81 (s, 1H), 3.58-3.33 (m, 3H), 2.44-2.37 (m, 2H), 2.21-2.19 (m, 2H), 2.01-1.99 (m, 1H), 1.43-1.27 (m, 3H), 1.19-1.16 (m, 1H).

Example 150: (R)-6,7-dichloro-N-(1'-azaspiro[cyclopropane-1,2'-bicyclo[2.2.2]octan]-3'-yl)benzo[b]thiophene-2-carboxamide hydrochloride ((R)-150)

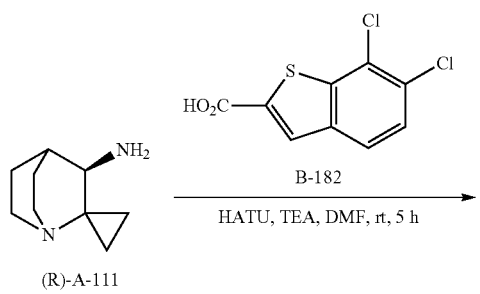

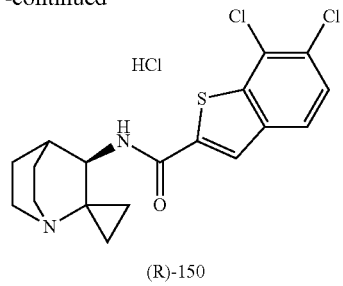

Following general procedure B, Compound (R)-150 was prepared from compound B-182 (97 mg, 0.39 mmol) and compound (R)-A-111 (60 mg, 0.39 mmol), with a reaction time of 5 hours. The product was purified by prep-HPLC [Instrument: GX-D; Column: Boston Symmetrix ODS-R C18 150×30 mm, particle size: 5 μm; Mobile phase: 25-55% acetonitrile in H$_2$O (add 0.225% FA, v/v)]. The resulting solid was dissolved in 0.2 M hydrochloric acid solution and again lyophilized to give:

(R)-6,7-dichloro-N-(1'-azaspiro[cyclopropane-1,2'-bicyclo[2.2.2]octan]-3'-yl)benzo[b]thiophene-2-carboxamide hydrochloride (compound (R)-150) (42 mg, 26% yield) as a white solid: cSFC analytical (A) tR=2.73 min., purity: 100%; LCMS (H): tR=1.791 min., (ES$^+$) m/z (M+H)$^+$= 381.0; $^1$H-NMR (CD$_3$OD, 400 MHz): δ 8.21 (s, 1H), 7.86 (d, J=8.4 Hz, 1H), 7.59 (d, J=8.8 Hz, 1H), 4.56 (d, J=2.4 Hz, 1H), 3.75-3.71 (m, 1H), 3.57 (m, 1H), 3.48-3.42 (m, 2H), 2.45 (d, J=2.8 Hz, 1H), 2.34 (m, 1H), 2.24-2.16 (m, 2H), 1.99-1.98 (m, 1H), 1.41-1.38 (m, 1H), 1.36-1.26 (m, 2H), 1.25-1.19 (m, 1H).

Example 151: (R)-6-chloro-7-fluoro-N-(1'-azaspiro[cyclopropane-1,2'-bicyclo[2.2.2]octan]-3'-yl)benzo[b]thiophene-2-carboxamide hydrochloride ((R)-151)

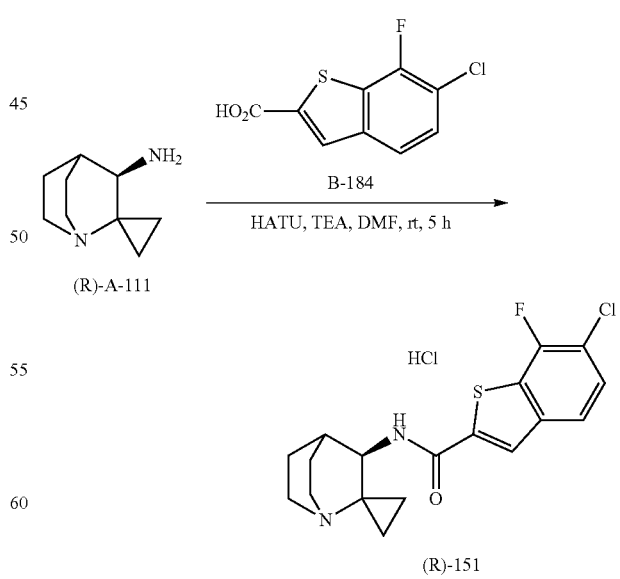

Following general procedure B, Compound (R)-151 was prepared from compound B-184 (76 mg, 0.33 mmol) and compound (R)-A-111 (50 mg, 0.33 mmol), with a reaction time of 5 hours. The product was purified by prep-HPLC [Instrument: GX-B; Column: YMC-pack ODS-AQ 150×30 mm, particle size: 5 μm; Mobile phase: 32-62% acetonitrile in H₂O (add 0.5% TFA, v/v)]. The resulting solid was dissolved in 0.2 M hydrochloric acid solution and again lyophilized to give:

(R)-6-chloro-7-fluoro-N-(1'-azaspiro[cyclopropane-1,2'-bicyclo[2.2.2]octan]-3'-yl)benzo[b]thiophene-2-carboxamide hydrochloride (compound (R)-151) (60 mg, 45% yield) as a white solid: cSFC analytical (A) tR=2.418 min., purity: 99.26%; LCMS (Y): tR=0.819 min., (ES⁺) m/z (M+H)⁺=364.9; ¹H-NMR (CD₃OD, 400 MHz): δ 8.17 (d, J=3.2 Hz, 1H), 7.75 (d, J=8.4 Hz, 1H), 7.54 (dd, J₁=8.4 Hz, J₂=7.2 Hz, 1H), 4.58 (d, J=2.4 Hz, 1H), 3.70-3.69 (m, 1H), 3.59-3.52 (m, 1H), 3.51-3.44 (m, 2H), 2.47-2.46 (m, 1H), 2.34-2.31 (m, 1H), 2.24-2.18 (m, 2H), 2.04-2.00 (m, 1H), 1.38-1.34 (m, 1H), 1.28-1.22 (m, 3H).

Example 152: (R)-6-chloro-N-(1'-azaspiro[cyclopropane-1,2'-bicyclo[2.2.2]octan]-3'-yl)-7-(trifluoromethyl)benzo[b]thiophene-2-carboxamide hydrochloride ((R)-152)

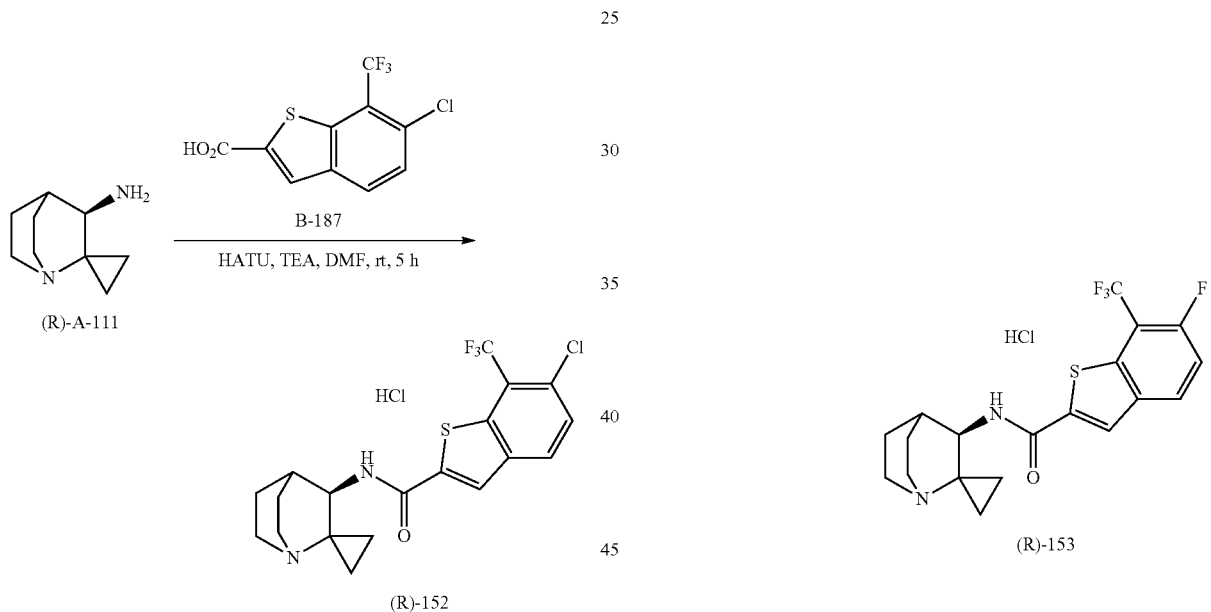

Following general procedure B, Compound (R)-152 was prepared from compound B-187 (110 mg, 0.39 mmol) and compound (R)-A-111 (60 mg, 0.39 mmol), with a reaction time of 5 hours. The product was purified by prep-HPLC [Instrument: GX-B; Column: YMC-Actus Pro C18 150×30 mm, particle size: 5 μm; Mobile phase: 30-60% acetonitrile in H₂O (add 0.1% TFA, v/v)]. The resulting solid was dissolved in 0.2 M hydrochloric acid solution and again lyophilized to give:

(R)-6-chloro-N-(1'-azaspiro[cyclopropane-1,2'-bicyclo[2.2.2]octan]-3'-yl)-7-(trifluoromethyl)benzo[b]thiophene-2-carboxamide hydrochloride (compound (R)-152) (72 mg, 40% yield) as a white solid: cSFC analytical (A) tR=2.34 min., purity: 98.48%; LCMS (H): tR=1.773 min., (ES⁺) m/z (M+H)⁺=415.0; ¹H-NMR (CD₃OD, 400 MHz): δ 8.25 (s, 1H), 8.13 (d, J=8.4 Hz, 1H), 7.66 (d, J=8.4 Hz, 1H), 4.57 (d, J=2.4 Hz, 1H), 3.74-3.72 (m, 1H), 3.58-3.57 (m, 1H), 3.50-3.42 (m, 2H), 2.45 (d, J=2.8 Hz, 1H), 2.34-2.33 (m, 1H), 2.22-2.17 (m, 2H), 2.03-1.99 (m, 1H), 1.42-1.37 (m, 1H), 1.31-1.21 (m, 2H), 1.20-1.19 (m, 1H).

Example 153: (R)-6-fluoro-N-(1'-azaspiro[cyclopropane-1,2'-bicyclo[2.2.2]octan]-3'-yl)-7-(trifluoromethyl)benzo[b]thiophene-2-carboxamide hydrochloride ((R)-153)

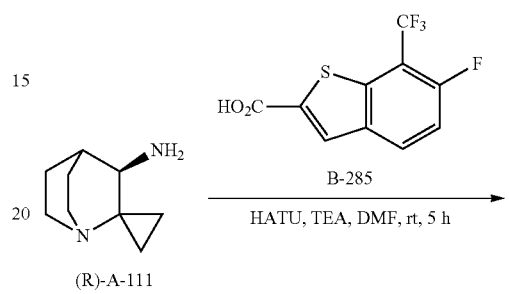

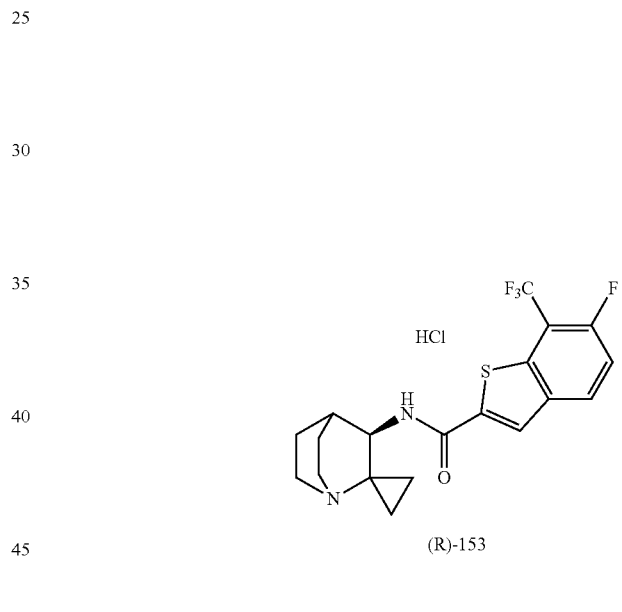

Following general procedure B, Compound (R)-153 was prepared from compound B-285 (87 mg, 0.33 mmol) and compound (R)-A-111 (50 mg, 0.33 mmol), with a reaction time of 5 hours. The product was purified by prep-HPLC [Instrument: GX-B; Column: P YMC-Actus Pro C18 150×30 mm, particle size: 5 μm; Mobile phase: 25-55% acetonitrile in H₂O (add 0.5% TFA, v/v)]. The resulting solid was dissolved in 0.2 M hydrochloric acid solution and again lyophilized to give:

(R)-6-fluoro-N-(1'-azaspiro[cyclopropane-1,2'-bicyclo[2.2.2]octan]-3'-yl)-7-(trifluoromethyl) benzo[b]thiophene-2-carboxamide-hydrochloride (compound (R)-153) (95 mg, 72% yield) as a white solid: cSFC analytical (A) tR=2.07 min., purity: 98.22%; LCMS (A): tR=1.686 min., 399.1 m/z (M+1); ¹H-NMR (CD₃OD, 400 MHz): δ 8.24-8.21 (m, 2H), 7.47 (t, J=10.0 Hz, 1H), 4.58 (d, J=2.0 Hz, 1H), 3.71-3.69 (m, 1H), 3.59-3.58 (m, 1H), 3.52-3.43 (m, 2H), 2.46-2.45 (m, 1H), 2.34-2.31 (m, 1H), 2.24-2.17 (m, 2H), 2.01-1.96 (m, 1H), 1.38-1.34 (s, 1H), 1.28-1.17 (s, 3H).

Example 154: (R)-7-chloro-6-methoxy-N-(1'-azaspiro[cyclopropane-1,2'-bicyclo[2.2.2]octan]-3'-yl)benzo[b]thiophene-2-carboxamide hydrochloride ((R)-154)

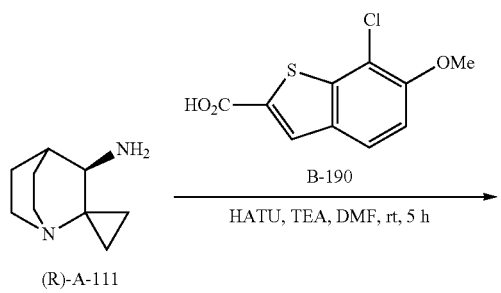

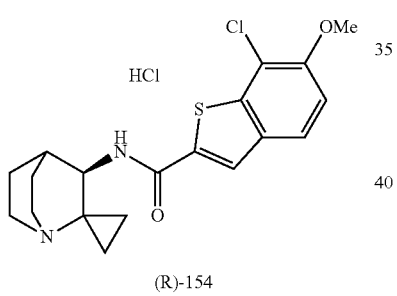

Following general procedure B, Compound (R)-154 was prepared from compound B-190 (96 mg, 0.39 mmol) and compound (R)-A-111 (60 mg, 0.39 mmol), with a reaction time of 5 hours. The product was purified by prep-HPLC [Instrument: GX-B; Column: YMC-pack ODS-AQ 150×30 mm, particle size: 5 μm; Mobile phase: 24-54% acetonitrile in H$_2$O (add 0.5% TFA, v/v)]. The resulting solid was dissolved in 0.2 M hydrochloric acid solution and again lyophilized to give:

(R)-7-chloro-6-methoxy-N-(1'-azaspiro[cyclopropane-1,2'-bicyclo[2.2.2]octan]-3'-yl)benzo[b]thiophene-2-carboxamide hydrochloride (compound (R)-154) (30 mg, 18% yield) as a white solid: cSFC analytical (A) tR=2.855 min., purity: 97.05%; LCMS (Y): tR=0.720 min., (ES$^+$) m/z (M+H)$^+$=377.0; $^1$H-NMR (CD$_3$OD, 400 MHz): δ 8.11 (s, 1H), 7.86 (d, J=8.4 Hz, 1H), 7.32 (d, J=8.8, 1H), 4.56 (s, 1H), 4.00 (s, 3H), 3.74-3.70 (m, 1H), 3.59-3.58 (m, 1H), 3.50-3.43 (m, 2H), 2.45-2.44 (m, 1H), 2.34 (m, 1H), 2.24-2.17 (m, 2H), 2.16-2.00 (m, 1H), 1.38-1.33 (m, 1H), 1.26-1.21 (m, 3H).

Example 155: (R)-7-fluoro-6-methoxy-N-(1'-azaspiro[cyclopropane-1,2'-bicyclo[2.2.2]octan]-3'-yl)benzo[b]thiophene-2-carboxamide hydrochloride ((R)-155)

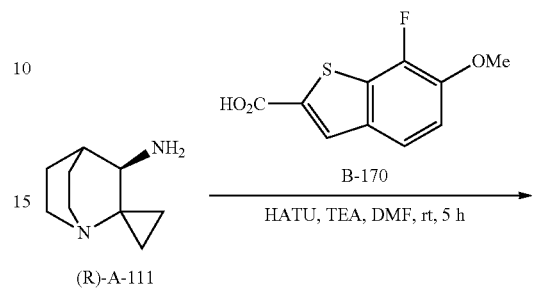

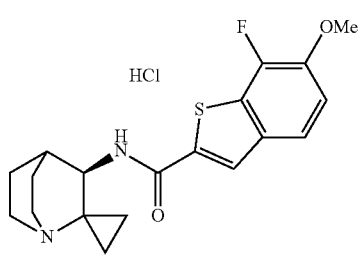

Following general procedure B, Compound (R)-155 was prepared from compound B-170 (74 mg, 0.33 mmol) and compound (R)-A-111 (50 mg, 0.33 mmol), with a reaction time of 5 hours. The product was purified by prep-HPLC [Instrument: GX-B; Column: YMC-pack ODS-AQ 150×30 mm, particle size: 5 μm; Mobile phase: 29-59% acetonitrile in H$_2$O (add 0.5% TFA, v/v)]. The resulting solid was dissolved in 0.2 M hydrochloric acid solution and again lyophilized to give:

(R)-7-fluoro-6-methoxy-N-(1'-azaspiro[cyclopropane-1,2'-bicyclo[2.2.2]octan]-3'-yl)benzo[b]thiophene-2-carboxamide hydrochloride (compound (R)-155) (40 mg, 31% yield) as a white solid: cSFC analytical (A) tR=2.535 min., purity: 98.25%; LCMS (Y): tR=0.768 min., (ES$^+$) m/z (M+H)$^+$=361.0; $^1$H-NMR (CD$_3$OD, 400 MHz): δ 8.11 (d, J=3.6 Hz, 1H), 7.70 (d, J=8.8 Hz, 1H), 7.34 (t, J=8.4 Hz, 1H), 4.56 (d, J=2.4 Hz, 1H), 3.99 (s, 3H), 3.70-3.61 (m, 1H), 3.59-3.58 (m, 1H), 3.48-3.43 (m, 2H), 2.45-2.44 (m, 1H), 2.34-2.33 (m, 1H), 2.24-2.16 (m, 2H), 2.00-1.96 (m, 1H), 1.38-1.34 (m, 1H), 1.27-1.20 (m, 3H).

Example 156: (R)-7-chloro-6-methyl-N-(1'-azaspiro[cyclopropane-1,2'-bicyclo[2.2.2]octan]-3'-yl)benzo[b]thiophene-2-carboxamide hydrochloride ((R)-156)

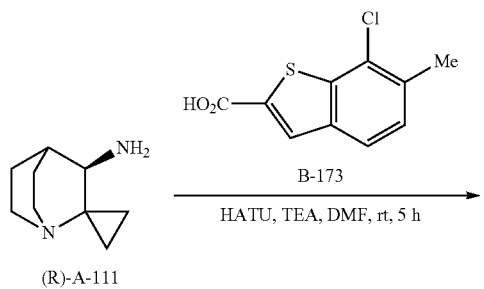

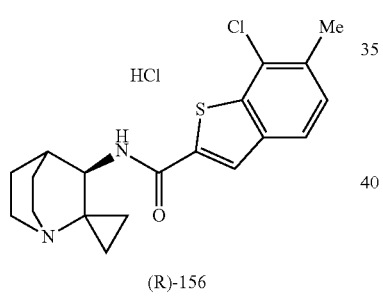

Following general procedure B, Compound (R)-156 was prepared from compound B-173 (74 mg, 0.33 mmol) and compound (R)-A-111 (50 mg, 0.33 mmol), with a reaction time of 5 hours. The product was purified by prep-HPLC [Instrument: GX-B; Column: YMC-pack ODS-AQ 150×30 mm, particle size: 5 μm; Mobile phase: 33-63% acetonitrile in H$_2$O (add 0.5% TFA, v/v)]. The resulting solid was dissolved in 0.2 M hydrochloric acid solution and again lyophilized to give:

(R)-7-chloro-6-methyl-N-(1'-azaspiro[cyclopropane-1,2'-bicyclo[2.2.2]octan]-3'-yl)benzo[b]thiophene-2-carboxamide hydrochloride (compound (R)-156) (55 mg, 42% yield) as a white solid: cSFC analytical (B) tR=2.594 min., purity: 97.66%; LCMS (B): tR=0.737 min., (ES$^+$) m/z (M+H)$^+$= 361.1; $^1$H-NMR (CD$_3$OD, 400 MHz): δ 8.13 (s, 1H), 7.77 (d, J=8.4 Hz, 1H), 7.40 (d, J=8.0 Hz, 1H), 4.57 (d, J=3.2 Hz, 1H), 3.74-3.70 (m, 1H), 3.59-3.50 (m, 1H), 3.48-3.43 (m, 2H), 2.53 (s, 3H), 2.46-2.45 (m, 1H), 2.37-2.34 (m, 1H), 2.24-2.15 (m, 2H), 2.00-1.99 (m, 1H), 1.38-1.34 (m, 1H), 1.27-1.19 (m, 3H).

Example 157: (R)-6-methyl-N-(1'-azaspiro[cyclopropane-1,2'-bicyclo[2.2.2]octan]-3'-yl)-7-(trifluoromethyl)benzo[b]thiophene-2-carboxamide hydrochloride ((R)-157)

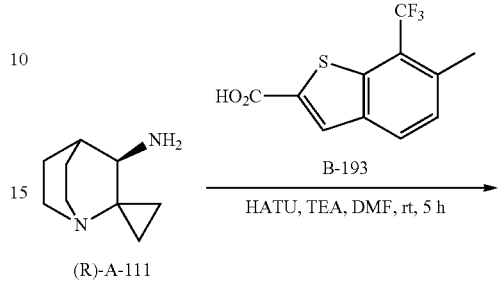

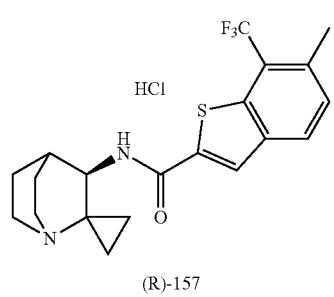

Following general procedure B, Compound (R)-157 was prepared from compound B-193 (85 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 250×50 mm, particle size: 10 μm; Mobile phase: 41-71% acetonitrile in H$_2$O (add 0.5% NH$_3$—H$_2$O, v/v)]. The resulting solid was dissolved in 0.2 M hydrochloric acid solution and again lyophilized to give:

(R)-6-methyl-N-(1'-azaspiro[cyclopropane-1,2'-bicyclo[2.2.2]octan]-3'-yl)-7-(trifluoromethyl) benzo[b]thiophene-2-carboxamide-hydrochloride (compound (R)-157) (50 mg, 35% yield) as a white solid: cSFC analytical (A) tR=2.12 min., purity: 97.64%; LCMS (DD): tR=0.829 min., 395.1 m/z (M+1); $^1$H-NMR (CD$_3$OD, 400 MHz): δ 8.21 (s, 1H), 8.06 (d, J=8.0 Hz, 1H), 7.49 (d, J=8.4 Hz, 1H), 4.59 (d, J=2.0 Hz, 1H), 3.78-3.74 (m, 1H), 3.61-3.59 (m, 1H), 3.52-3.42 (m, 2H), 2.66 (d, J=2.0 Hz, 3H), 2.47-2.46 (m, 1H), 2.39-2.34 (m, 1H), 2.26-2.18 (m, 2H), 2.05-1.98 (m, 1H), 1.41-1.37 (m, 1H), 1.31-1.20 (m, 3H).

Example 158: (R)-7-chloro-6-fluoro-N-(1'-azaspiro[cyclopropane-1,2'-bicyclo[2.2.2]octan]-3'-yl)benzo[b]thiophene-2-carboxamide hydrochloride ((R)-158)

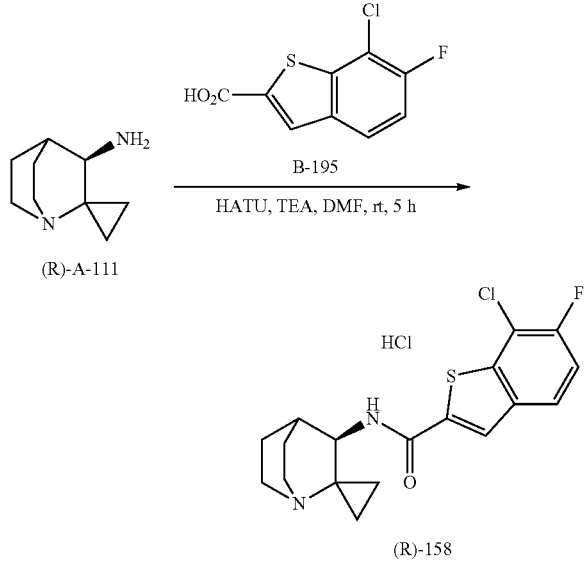

Following general procedure B, Compound (R)-158 was prepared from compound B-195 (91 mg, 0.39 mmol) and compound (R)-A-111 (50 mg, 0.33 mmol), with a reaction time of 16 hours. The product was purified by prep-HPLC [Instrument: GX-E; Column: Agella Venusil ASB C18 150×30 mm, particle size: 5 μm; Mobile phase: 26-56% acetonitrile in H$_2$O (add 0.5% HCl, v/v)] to give:

(R)-7-chloro-6-fluoro-N-(1'-azaspiro[cyclopropane-1,2'-bicyclo[2.2.2]octan]-3'-yl)benzo[b]thiophene-2-carboxamide-hydrochloride (compound (R)-158) (30 mg, 23% yield) as a white solid: cSFC analytical (A) tR=2.412 min., purity: 100%; LCMS (J): tR=1.471 min., 365.0 m/z (M+1); $^1$H-NMR (CD$_3$OD, 400 MHz): δ 8.72 (d, J=6.4 Hz, 1H), 8.228 (s, 1H), 7.94 (dd, J1=8.8 Hz, J2=4.4 Hz, 1H), 7.42 (t, J=8.8 Hz, 1H), 4.58 (s, 1H), 3.72 (m, 1H), 3.63-3.53 (m, 1H), 3.50-3.45 (m, 2H), 2.48-2.47 (m, 1H), 2.39-2.36 (m, 1H), 2.26-2.16 (m, 2H), 2.05-2.02 (m, 1H), 1.40-1.37 (m, 1H), 1.30-1.20 (m, 3H).

Example 159: (R)-6-cyclopropyl-7-fluoro-N-(1'-azaspiro[cyclopropane-1,2'-bicyclo[2.2.2]octan]-3'-yl)benzo[b]thiophene-2-carboxamide hydrochloride ((R)-159)

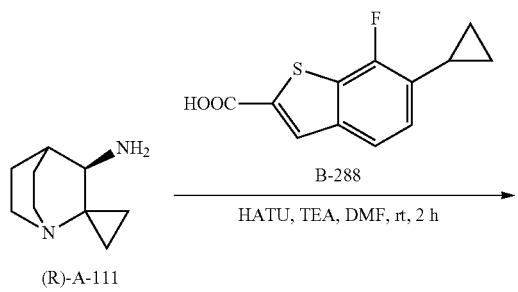

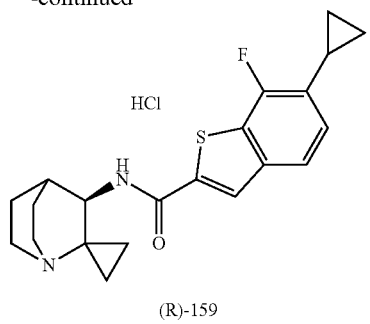

Following general procedure B, Compound (R)-159 was prepared from compound B-288 (78 mg, 0.33 mmol) and compound (R)-A-111 (50 mg, 0.33 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)-6-cyclopropyl-7-fluoro-N-(1'-azaspiro[cyclopropane-1,2'-bicyclo[2.2.2]octan]-3'-yl)benzo[b]thiophene-2-carboxamide hydrochloride (compound (R)-159) (68 mg, 56% yield) as a white solid: cSFC analytical (A) tR=2.55 min., purity: 97.97%; LCMS (M): tR=1.139 min., 371.2 m/z (M+1); $^1$H-NMR (CD$_3$OD, 400 MHz): δ 8.12 (d, J=3.6 Hz, 1H), 7.65 (d, J=8.0 Hz, 1H), 7.05 (t, J=7.2 Hz, 1H), 4.58 (s, 1H), 3.73-3.61 (m, 1H), 3.40-3.42 (m, 3H), 2.47-2.46 (m, 1H), 2.30-2.18 (m, 4H), 1.38-1.23 (m, 4H), 1.12-1.10 (m, 2H), 0.86-0.84 (m, 2H).

Example 160: (R)-7-cyano-N-(1'-azaspiro[cyclopropane-1,2'-bicyclo[2.2.2]octan]-3'-yl)benzo[b]thiophene-2-carboxamide hydrochloride ((R)-160)

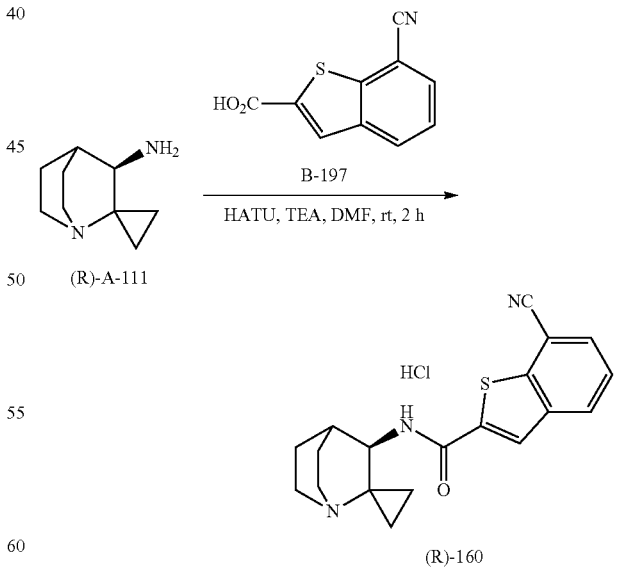

Following general procedure B, Compound (R)-160 was prepared from compound B-197 (as a mixture with compound B-198) (80 mg, 0.39 mmol) and compound (R)-A-111 (59 mg, 0.39 mmol), with a reaction time of 2 hours. The product was purified by prep-HPLC [Instrument: GX-E;

Column: Agella Venusil ASB C18 150×30 mm, particle size: 5 μm; Mobile phase: 27-57% acetonitrile in H$_2$O (add 0.5% HCl, v/v)] to give:

(R)-7-cyano-N-(1'-azaspiro[cyclopropane-1,2'-bicyclo[2.2.2]octan]-3'-yl)benzo[b]thiophene-2-carboxamide hydrochloride (compound (R)-160) (19 mg, 32% yield) as a white solid: cSFC analytical (A) tR=2.52 min., purity: 100%; LCMS (M): tR=0.860 min., 338.1 m/z (M+1); $^1$H-NMR (CD$_3$OD, 400 MHz): 8.25 (d, J=10.4 Hz, 2H), 7.92 (d, J=6.8 Hz, 1H), 7.63 (t, J=8.0 Hz, 1H), 7.64 (t, J=8.0 Hz, 1H), 4.34 (s, 1H), 3.42-3.37 (m, 1H), 3.25-3.22 (m, 1H), 3.13-3.06 (m, 2H), 2.24 (s, 1H), 2.14-1.93 (m, 3H), 1.73 (m, 1H), 1.14-0.85 (m, 4H).

Example 161: (R)-7-methoxy-N-(1'-azaspiro[cyclopropane-1,2'-bicyclo[2.2.2]octan]-3'-yl)benzo[b]thiophene-2-carboxamide hydrochloride ((R)-161)

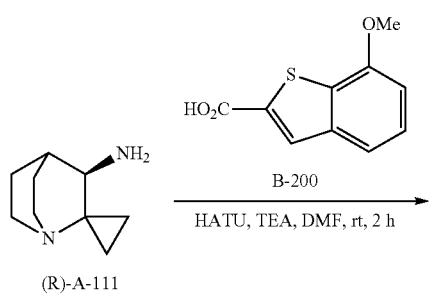

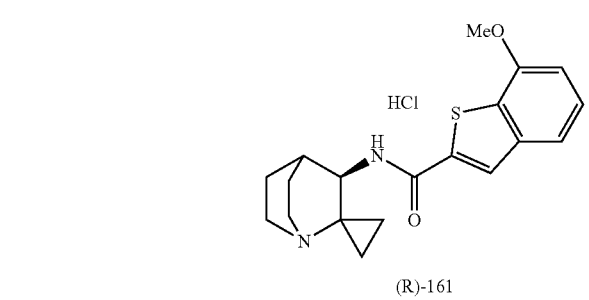

Following general procedure B, Compound (R)-161 was prepared from compound B-200 (68 mg, 0.33 mmol) and compound (R)-A-111 (50 mg, 0.33 mmol), with a reaction time of 2 hours. The product was purified by prep-HPLC [Instrument: GX-E; Column: Agella Venusil ASB C18 150× 30 mm, particle size: 5 μm; Mobile phase: 27-57% acetonitrile in H$_2$O (add 0.5% HCl, v/v)] to give:

(R)-7-methoxy-N-(1'-azaspiro[cyclopropane-1,2'-bicyclo[2.2.2]octan]-3'-yl)benzo[b]thiophene-2-carboxamide hydrochloride (compound (R)-161) (79 mg, 71% yield) as a white solid: cSFC analytical (A) tR=2.84 min., purity: 98.72%; LCMS (M): tR=0.993 min., 343.1 m/z (M+1); $^1$H-NMR (CD$_3$OD, 400 MHz): δ 8.15 (s, 1H), 7.53 (d, J=8.0 Hz, 1H), 7.42 (t, J=7.6 Hz, 1H), 7.01 (d, J=8.0 Hz, 1H), 4.58 (s, 1H), 4.02 (s, 3H), 3.77-3.59 (m, 3H), 3.59-3.41 (m, 3H), 2.46-2.33 (m, 2H), 2.25-2.18 (m, 2H), 2.04-2.00 (m, 1H), 1.41-1.20 (m, 4H).

Example 162: (R)-6,7-difluoro-N-(1'-azaspiro[cyclopropane-1,2'-bicyclo[2.2.2]octan]-3'-yl)benzo[b]thiophene-2-carboxamide hydrochloride ((R)-162)

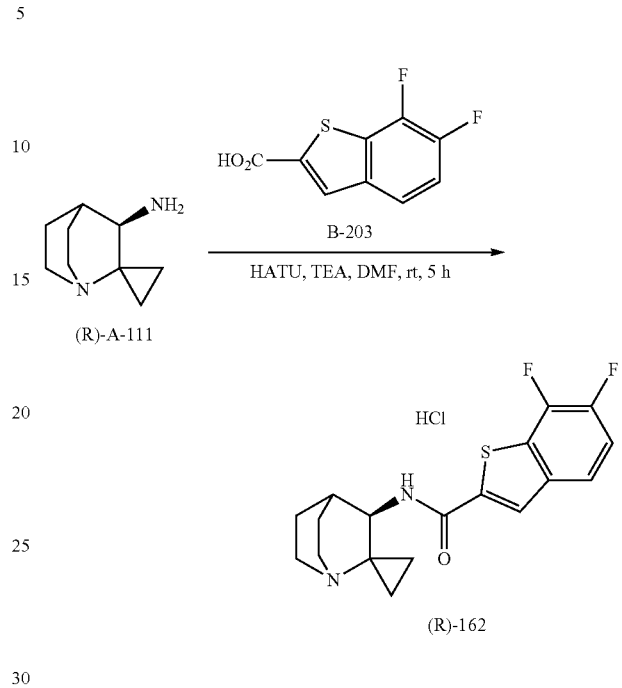

Following general procedure B, Compound (R)-162 was prepared from compound B-203 (60 mg, 0.34 mmol) and compound (R)-A-111 (50 mg, 0.33 mmol), with a reaction time of 5 hours. The product was purified by prep-HPLC [Instrument: GX-E; Column: Agella Venusil ASB C18 150× 21.2 mm, particle size: 5 μm; Mobile phase: 15-45% acetonitrile in H$_2$O (add 0.5% HCl, v/v)] to give:

(R)-6,7-difluoro-N-(1'-azaspiro[cyclopropane-1,2'-bicyclo[2.2.2]octan]-3'-yl)benzo[b]thiophene-2-carboxamide hydrochloride (compound (R)-162) (20 mg, 18.2% yield) as a white solid: cSFC analytical (A) tR=2.14 min., purity: 97.6%; LCMS (DD): tR=0.803 min., 348.1 m/z (M+1); $^1$H-NMR (CD$_3$OD, 400 MHz): δ8.21 (d, J=3.6, 1H), 7.80-7.77 (m, 1H), 7.47-7.41 (m, 1H), 4.59 (d, J=2.8, 1H), 3.73-3.72 (m, 1H), 3.3.61-3.60 (m, 1H), 3.54-3.42 (m, 2H), 2.47 (d, J=2.8, 1H), 2.36-2.33 (m, 1H), 2.26-2.19 (m, 2H), 1.98 (s, 1H), 1.42-1.36 (s, 1H), 1.30-1.21 (m, 3H).

Example 163: (R)-6-chloro-N-(1'-azaspiro[cyclopropane-1,2'-bicyclo[2.2.2]octan]-3'-yl)benzofuran-2-carboxamide hydrochloride ((R)-163)

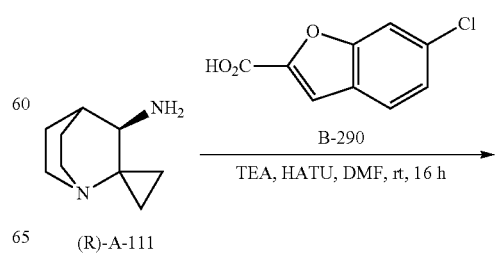

-continued

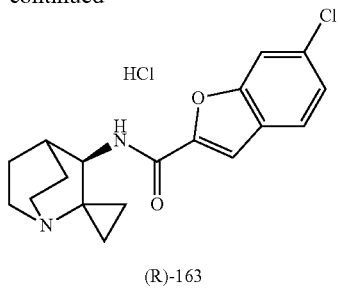

(R)-163

Following general procedure B, Compound (R)-163 was prepared from compound B-290 (77 mg, 0.39 mmol) and compound (R)-A-111 (50 mg, 0.33 mmol), with a reaction time of 16 hours. The product was purified by prep-HPLC [Instrument: GX-E; Column: Phenomenex Synergi C18 250×21.2 mm, particle size: 4 μm; Mobile phase: 10-40% acetonitrile in $H_2O$ (add 0.05% HCl, v/v)] to give:

(R)-6-chloro-N-(1'-azaspiro[cyclopropane-1,2'-bicyclo[2.2.2]octan]-3'-yl)benzofuran-2-carboxamide hydrochloride (compound (R)-163) (50 mg, 46% yield) as a white solid: cSFC analytical (A) tR=2.05 min., purity: 98.40%; LCMS (H): tR=2.503 min, 331.0 m/z (M+1); $^1$H-NMR (CD$_3$OD, 400 MHz): δ 7.74 (d, J=1H), 7.70 (s, 1H), 7.57 (s, 1H), 7.37 (dd, $J_1$=8.5 Hz, $J_2$=1.8 Hz, 1H), 4.60 (s, 1H), 3.76-3.75 (m, 1H), 3.59-3.33 (m, 3H), 2.44 (m, 1H), 2.32-2.14 (m, 3H), 2.00 (m, 1H), 1.35-1.18 (m, 4H).

Example 164: (R)-7-chloro-N-(1'-azaspiro[cyclopropane-1,2'-bicyclo[2.2.2]octan]-3'-yl)benzofuran-2-carboxamide hydrochloride ((R)-164)

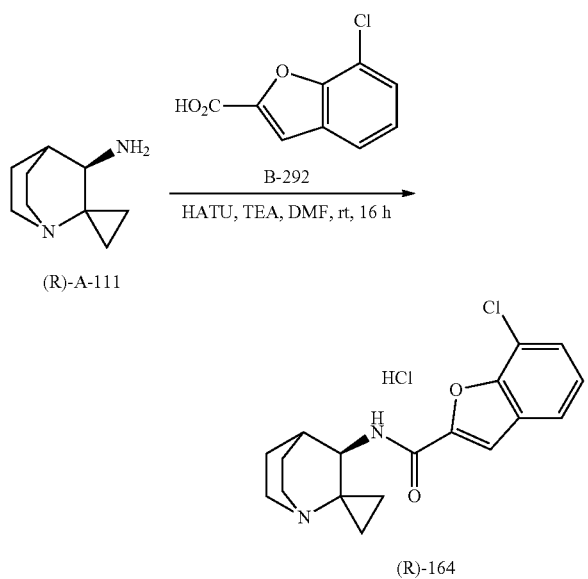

Following general procedure B, Compound (R)-164 was prepared from compound B-292 (77 mg, 0.39 mmol) and compound (R)-A-111 (50 mg, 0.33 mmol), with a reaction time of 16 hours. The product was purified by prep-HPLC [Instrument: GX-E; Column: Agella Venusil ASB C18 150× 30 mm, particle size: 5 μm; Mobile phase: 26-56% acetonitrile in $H_2O$ (add 0.5% HCl, v/v)] to give:

(R)-7-chloro-N-(1'-azaspiro[cyclopropane-1,2'-bicyclo[2.2.2]octan]-3'-yl)benzofuran-2-carboxamide-hydrochloride (compound (R)-164) (40 mg, 33% yield) as a white solid: cSFC analytical (A) tR=1.935 min., purity: 98.61%; LCMS (J): tR=1.341 min., 331.1 m/z (M+1); $^1$H-NMR (CD$_3$OD, 400 MHz): δ 7.72 (d, J=8 Hz, 1H), 7.67 (s, 1H), 7.54 (d, J=8 Hz, 1H), 7.35 (t, J=8 Hz, 1H), 4.63 (s, 1H), 3.80-3.77 (m, 1H), 3.61-3.53 (m, 1H), 3.51-3.44 (m, 2H), 2.49-2.48 (m, 1H), 2.36-2.33 (m, 1H), 2.27-2.19 (m, 2H), 2.03-2.01 (m, 1H), 1.40-1.20 (m, 4H).

Example 165: (R)-7-cyclopropyl-N-(1'-azaspiro[cyclopropane-1,2'-bicyclo[2.2.2]octan]-3'-yl)benzo[b]thiophene-2-carboxamide hydrochloride ((R)-165)

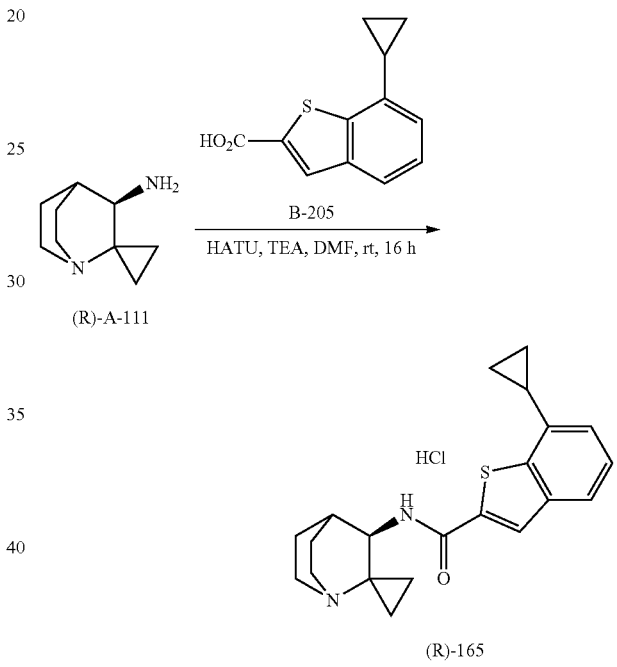

Following general procedure B, Compound (R)-165 was prepared from compound B-205 (86 mg, 0.39 mmol) and compound (R)-A-111 (50 mg, 0.33 mmol), with a reaction time of 16 hours. The product was purified by prep-HPLC [Instrument: GX-B; Column: YMC-Actus Pro C18 150×30 mm, particle size: 5 μm; Mobile phase: 25-55% acetonitrile in $H_2O$ (add 0.5% TFA, v/v)]. The resulting solid was dissolved in 0.2 M hydrochloric acid solution and again lyophilized to give:

(R)-7-cyclopropyl-N-(1'-azaspiro[cyclopropane-1,2'-bicyclo[2.2.2]octan]-3'-yl)benzo[b]thiophene-2-carboxamide-hydrochloride (compound (R)-165) (25 mg, 20% yield) as a white solid: cSFC analytical (A) tR=2.710 min., purity: 98.62%; LCMS (B): tR=0.719 min., 353.2 m/z (M+1); $^1$H-NMR (CD$_3$OD, 400 MHz): δ 8.19 (s, 1H), 7.77 (d, J=7.6 Hz, 1H), 7.39 (t, J=8 Hz, 1H), 7.15 (d, J=7.2 Hz, 1H), 4.60 (s, 1H), 3.78-3.74 (m, 1H), 3.61-3.59 (m, 1H), 3.50-3.45 (m, 2H), 2.48-2.47 (m, 1H), 2.37 (m, 1H), 2.25-2.12 (m, 3H), 2.03-2.02 (m, 1H), 1.42-1.40 (m, 1H), 1.31-1.26 (m, 3H), 1.11-1.09 (m, 2H), 0.85-0.83 (m, 2H).

367

Example 166: (R)-7-isopropyl-N-(1'-azaspiro[cyclopropane-1,2'-bicyclo[2.2.2]octan]-3'-yl)benzo[b]thiophene-2-carboxamide hydrochloride ((R)-166)

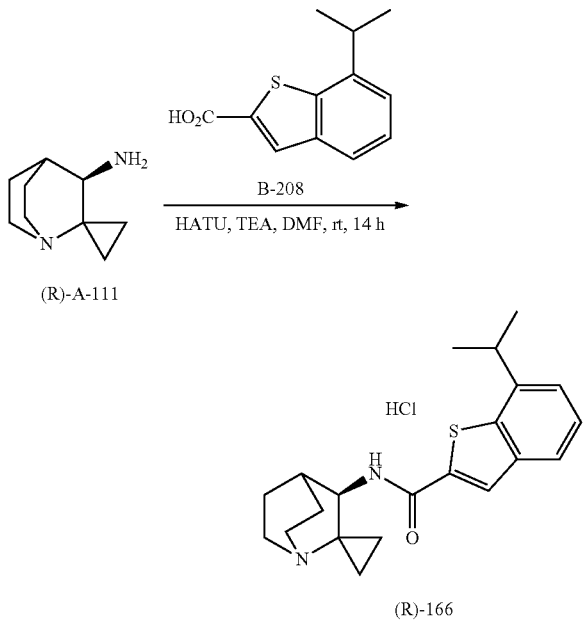

Following general procedure B, Compound (R)-166 was prepared from compound B-208 (86 mg, 0.40 mmol) and compound (R)-A-111 (60 mg, 0.40 mmol), with a reaction time of 14 hours. The product was purified by prep-HPLC [Instrument: GX-E; Column: Phenomenex Synergi C18 150×30 mm, particle size: 5 µm; Mobile phase: 27-57% acetonitrile in H$_2$O (add 0.5% HCl, v/v)] to give:

(R)-7-isopropyl-N-(1'-azaspiro[cyclopropane-1,2'-bicyclo[2.2.2]octan]-3'-yl)benzo[b]thiophene-2-carboxamide hydrochloride (compound (R)-166) (80 mg, 52% yield) as a white solid: cSFC analytical (B) tR=2.297 min., purity: 97.72%; LCMS (DD): tR=0.833 min., (ES$^+$) m/z (M+H)$^+$= 355.2; $^1$H-NMR (CD$_3$OD, 400 MHz): δ8.17-8.17 (d, J=2.8 Hz, 1H), 7.79-7.77 (d, J=8.0 Hz, 1H), 7.47-7.39 (m, 2H), 4.60-4.60 (d, J=2.0 Hz, 1H), 3.78-3.73 (m, 1H), 3.60-3.49 (m, 1H), 3.48-3.42 (m, 2H), 3.29-3.23 (m, 1H), 2.48-2.47 (m, 1H), 2.39-2.29 (m, 1H), 2.26-2.17 (m, 2H), 2.06-2.01 (m, 1H), 1.44-1.38 (m, 7H), 1.30-1.24 (m, 3H).

Example 167: (R)—N-(1'-azaspiro[cyclopropane-1,2'-bicyclo[2.2.2]octan]-3'-yl)-7-(trifluoromethoxy)benzo[b]thiophene-2-carboxamide hydrochloride ((R)-167)

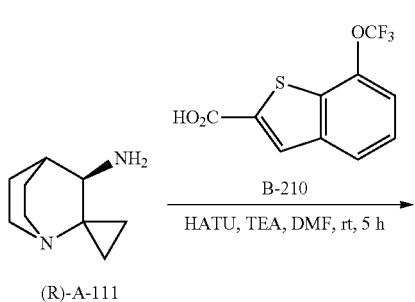

368

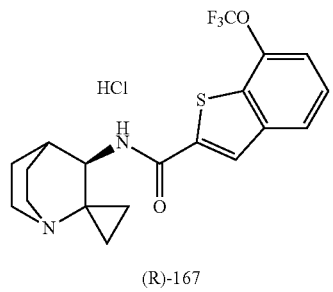

Following general procedure B, Compound (R)-167 was prepared from compound B-210 (103 mg, 0.39 mmol) and compound (R)-A-111 (60 mg, 0.39 mmol), with a reaction time of 5 hours. The product was purified by prep-HPLC [Instrument: GX-B; Column: YMC-Actus Pro C18 150×30 mm, particle size: 5 µm; Mobile phase: 25-55% acetonitrile in H$_2$O (add 0.1% TFA, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-7-(trifluoromethoxy)benzo[b]thiophene-2-carboxamide hydrochloride (compound (R)-167) (90 mg, 53% yield) as a white solid: cSFC analytical (A) tR=1.854 min., purity: 97.78%; LCMS (B): tR=0.723 min., (ES$^+$) m/z (M+H)$^+$=397.1; $^1$H-NMR (CD$_3$OD, 400 MHz): δ 8.23 (s, 1H), 7.94 (d, J=8.0 Hz, 1H), 7.54 (t, J=8.4 Hz, 1H), 7.44 (d, J=7.6 Hz, 1H), 4.58 (d, J=2.4 Hz, 1H), 3.72-3.71 (m, 1H), 3.59-3.51 (m, 1H), 3.49-3.40 (m, 2H), 2.46-2.45 (m, 1H), 2.34-2.32 (m, 1H), 2.24-2.17 (m, 2H), 2.04-2.01 (m, 1H), 1.39-1.35 (m, 1H), 1.28-1.19 (m, 3H).

Example 168: (R)—N-(1'-azaspiro[cyclopropane-1,2'-bicyclo[2.2.2]octan]-3'-yl)-7-(tetrahydro-2H-pyran-4-yl)benzo[b]thiophene-2-carboxamide hydrochloride ((R)-168)

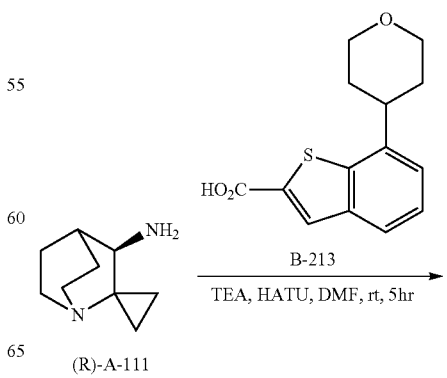

-continued

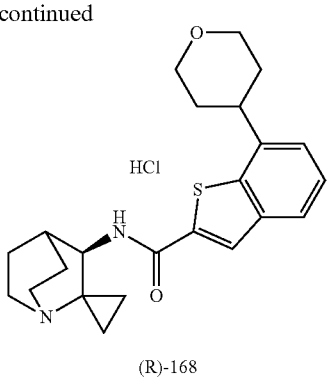

(R)-168

Following general procedure B, Compound (R)-168 was prepared from compound B-213 (86 mg, 0.33 mmol) and compound (R)-A-111 (50 mg, 0.33 mmol), with a reaction time of 5 hours. The product was purified by prep-HPLC [Instrument: GX-E; Column: Agella Venusil ASB C18 150× 30 mm, particle size: 5 μm; Mobile phase: 19-49% acetonitrile in H₂O (add 0.5% HCl, v/v)] to give:

(R)—N-(1'-azaspiro[cyclopropane-1,2'-bicyclo[2.2.2]octan]-3'-yl)-7-(tetrahydro-2H-pyran-4-yl)benzo[b]thiophene-2-carboxamide hydrochloride (compound (R)-168) (50 mg, 38% yield) as a white solid: cSFC analytical (A) tR=2.70 min., purity: 100%; LCMS (B): tR=0.570 min., (ES⁺) m/z (M+H)⁺=397.1; ¹H-NMR (CD₃OD, 400 MHz): δ 8.21 (s, 1H), 7.80 (dd, J₁=3.6 Hz, J₂=0.8 Hz, 1H), 7.46-7.42 (m, 1H), 7.37 (d, J=6.8 Hz, 1H), 4.56 (d, J=2.4 Hz, 1H), 4.11-4.07 (m, 2H), 3.75-3.76 (m, 1H), 3.69-3.64 (m, 2H), 3.61-3.60 (m, 1H), 3.59-3.40 (m, 2H), 3.12-3.08 (m, 1H), 2.45-2.43 (m, 1H), 2.21-2.20 (m, 1H), 2.19-2.17 (m, 2H), 1.98-1.92 (m, 5H), 1.41-1.39 (m, 1H), 1.33-1.25 (m, 2H), 1.23-1.17 (m, 1H).

Example 169: (R)—N-(1'-azaspiro[cyclopropane-1,2'-bicyclo[2.2.2]octan]-3'-yl)benzo[d]oxazole-2-carboxamide ((R)-169)

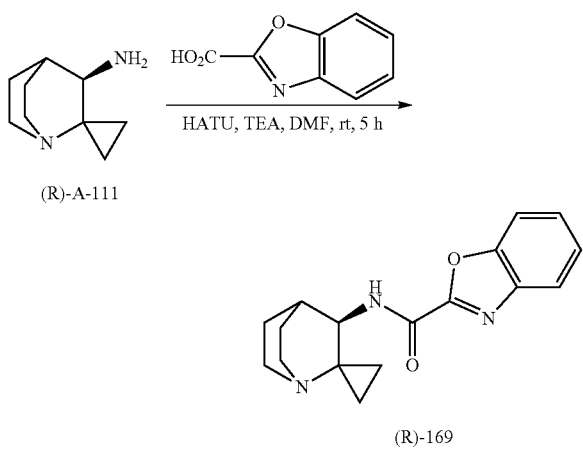

(R)-169

Following general procedure B, Compound (R)-169 was prepared from benzo[d]oxazole-2-carboxylic acid (53 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 250×50 mm, particle size: 10 μm; Mobile phase: 16-46% acetonitrile in H₂O (add 0.5% NH₃.H₂O, v/v)] to give:

(R)—N-(1'-azaspiro[cyclopropane-1,2'-bicyclo[2.2.2]octan]-3'-yl)benzo[d]oxazole-2-carboxamide (compound (R)-169) (50 mg, 51% yield) as a white solid: cSFC analytical (A) tR=1.77 min., purity: 97.86%; LCMS (J): tR=1.022 min., 298.1 m/z (M+1); ¹H-NMR (CD₃OD, 400 MHz): δ 7.87 (d, J=7.6 Hz, 1H), 7.75 (d, J=8.0 Hz, 1H), 7.56 (td, J₁=8.0 Hz, J₂=1.2 Hz, 1H), 7.50 (td, J₁=8.0 Hz, J₂=1.2 Hz, 1H), 4.22 (d, J=2.0 Hz, 1H), 3.23-3.22 (m, 1H), 3.08-3.05 (m, 1H), 2.94-2.86 (m, 2H), 2.15-1.13 (m, 1H), 1.97 (m, 1H), 1.87-1.83 (m, 2H), 1.58-1.54 (m, 1H), 0.92-0.88 (m, 2H), 0.77-0.74 (m, 1H), 0.70-0.65 (m, 1H).

Example 170: (R)—N-(1'-azaspiro[cyclopropane-1,2'-bicyclo[2.2.2]octan]-3'-yl)-1H-indole-2-carboxamide hydrochloride ((R)-170)

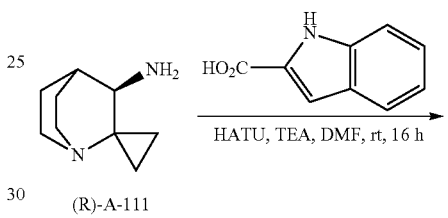

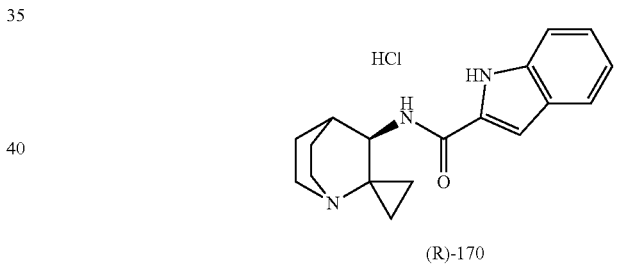

(R)-170

Following general procedure B, compound (R)-170 was prepared from 1H-indole-2-carboxylic acid (70 mg, 0.43 mmol) and compound (R)-A-111 (60 mg, 0.39 mmol), with a reaction time of 16 hours. The product was purified by prep-HPLC [Instrument: GX-A; Column: Phenomenex Gemini C18 250*50, particle size: 10 μm; Mobile phase: 30-60% acetonitrile in H₂O (add 0.5% NH₃H₂O, v/v)]. The resulting solids were dissolved in 0.2 M hydrochloric acid solution and again lyophilized to give:

(R)—N-(1'-azaspiro[cyclopropane-1,2'-bicyclo[2.2.2]octan]-3'-yl)-1H-indole-2-carboxamide hydrochloride (compound (R)-170) (40 mg, 35% yield) as a white solid: cSFC analytical (A) tR=2.56 min., purity: 98.54%; LCMS (J): tR=1.11 min., 296.2 m/z (M+1); ¹H-NMR (CD₃OD, 400 MHz): δ 7.66-7.64 (d, J=8.0 Hz, 1H), 7.48-7.46 (d, J=8.4 Hz, 1H), 7.30-7.24 (m, 2H), 7.11-7.08 (t, J=7.6 Hz, 1H), 4.62-4.61 (d, J=2.0 Hz, 1H), 3.75-3.74 (m, 1H), 3.60-3.59 (m, 1H), 3.51-3.44 (m, 2H), 2.45-2.37 (m, 2H), 2.24-2.18 (m, 2H), 2.04-2.00 (m, 1H), 1.39-1.37 (m, 1H) 1.30-1.16 (m, 3H).

Example 171: (R)—N-(1'-azaspiro[cyclopropane-1, 2'-bicyclo[2.2.2]octan]-3'-yl)thieno[2,3-c]pyridine-2-carboxamide hydrochloride ((R)-171)

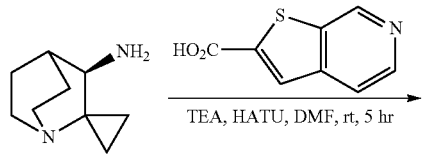

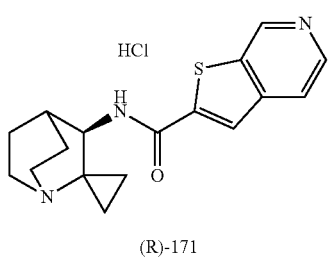

Following general procedure B, Compound (R)-171 was prepared from thieno[2,3-c]pyridine-2-carboxylic acid (59 mg, 0.33 mmol) and compound (R)-A-111 (50 mg, 0.33 mmol), with a reaction time of 5 hours. The product was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give:

(R)—N-(1'-azaspiro[cyclopropane-1,2'-bicyclo[2.2.2]octan]-3'-yl)thieno[2,3-c]pyridine-2-carboxamide hydrochloride (compound (R)-171) (40 mg, 39% yield) as a white solid: cSFC analytical (A) tR=2.41 min., purity: 100%; LCMS (K): tR=0.776 min., (ES$^+$) m/z (M+H)$^+$=314.1; $^1$H-NMR (CD$_3$OD, 400 MHz): δ 9.73 (s, 1H), 8.70 (s, 1H), δ 8.69 (s, 1H), 8.58 (d, J=6.4 Hz 1H), 4.61 (d, J=2.8 Hz 1H), 3.86-3.81 (m, 1H), 3.60-3.55 (m, 1H), 3.47-3.40 (m, 2H), 2.48-2.37 (m, 2H), 2.24-2.15 (m, 2H), 2.03-1.99 (m, 1H), 1.43-1.30 (m, 3H), 1.18-1.16 (m, 1H).

Example 172: (R)-6-chloro-5-fluoro-N-(1'-azaspiro[cyclopropane-1,2'-bicyclo[2.2.2]octan]-3'-yl)benzo[b]thiophene-2-carboxamide hydrochloride ((R)-172)

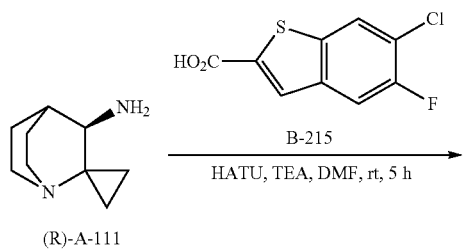

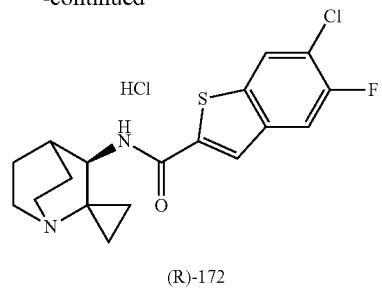

Following general procedure B, compound (R)-172 was prepared from compound B-215 (91 mg, 0.39 mmol) and compound (R)-A-111 (50 mg, 0.33 mmol), with a reaction time of 5 hours. The product was purified by prep-HPLC [Instrument: GX-D; Column: Boston Green ODS C18 150×30 mm, particle size: 5 μm; Mobile phase: 42-72% acetonitrile in H$_2$O (add 0.225% FA, v/v)]. The resulting solid was dissolved in 0.2 M hydrochloric acid solution and again lyophilized to give:

(R)-6-chloro-5-fluoro-N-(1'-azaspiro[cyclopropane-1,2'-bicyclo[2.2.2]octan]-3'-yl)benzo[b]thiophene-2-carboxamide hydrochloride (compound (R)-172) (50 mg, 38% yield) as a white solid: cSFC analytical (A) tR=2.50 min., purity: 100%; LCMS (B): tR=0.712 min., 365.1 m/z (M+1); $^1$H-NMR (CD$_3$OD, 400 MHz): δ 8.12-8.11 (d, J=6.8 Hz, 1H), 8.07 (s, 1H), 7.79-7.77 (d, J=9.6 Hz, 1H), 4.56-4.55 (m, 1H), 3.69-3.68 (m, 1H), 3.59-3.58 (m, 1H), 3.49-3.44 (m, 2H), 2.45-2.44 (m, 1H), 2.33-2.30 (m, 1H), 2.23-2.16 (m, 2H), 2.01 (m, 1H), 1.37-1.33 (m, 1H), 1.25-1.18 (m, 3H).

Example 173: (R)-5-fluoro-6-methoxy-N-(1'-azaspiro[cyclopropane-1,2'-bicyclo[2.2.2]octan]-3'-yl)benzo[b]thiophene-2-carboxamide hydrochloride ((R)-173)

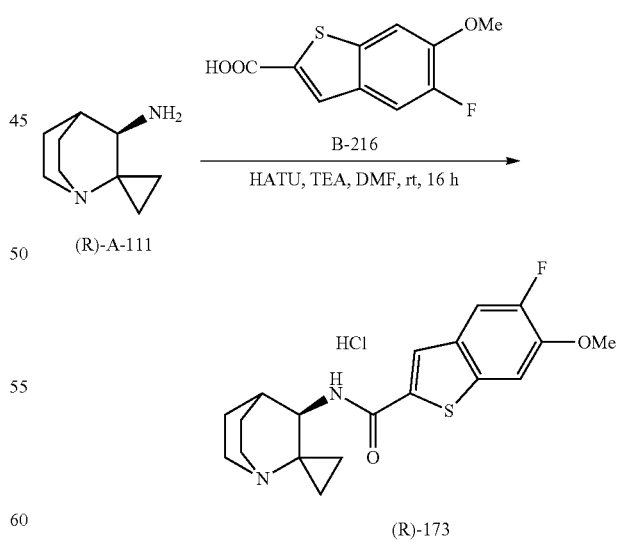

Following general procedure B, Compound (R)-173 was prepared from compound B-216 (60 mg, 0.27 mmol) and compound (R)-A-111 (40 mg, 0.27 mmol), with a reaction time of 16 hours. The product was purified by prep-HPLC [Instrument: GX-E; Column: Phenomenex SynergiC18

250*21.2 mm, particle size: 4 μm; Mobile phase: 15-45% acetonitrile in H₂O (add 0.05% HCl, v/v)] to give:

(R)-5-fluoro-6-methoxy-N-(1'-azaspiro[cyclopropane-1,2'-bicyclo[2.2.2]octan]-3'-yl)benzo[b]thiophene-2-carboxamide hydrochloride (compound (R)-173) (80 mg, 76% yield) as a white solid: cSFC analytical (A) tR=2.54 min., purity: 97.70%; LCMS (B): tR=0.649 min., 361.1 m/z (M+1); ¹H-NMR (CD₃OD, 400 MHz): δ 8.04 (s, 1H), 7.64-7.61 (m, 2H), 4.57-4.56 (d, J=2.0 Hz, 1H), 3.98 (s, 3H), 3.76-3.72 (m, 1H), 3.60-3.52 (m, 1H), 3.50-3.45 (m, 2H), 2.45-2.44 (m, J=2.8 Hz, 1H), 2.35-2.34 (m, 1H), 2.25-2.18 (m, 2H), 2.02-2.01 (m, 1H), 1.41-1.36 (m, 1H) 1.28-1.19 (m, 3H).

Example 174: (R)-5,6-difluoro-N-(1'-azaspiro[cyclopropane-1,2'-bicyclo[2.2.2]octan]-3'-yl)benzo[b]thiophene-2-carboxamide hydrochloride ((R)-174)

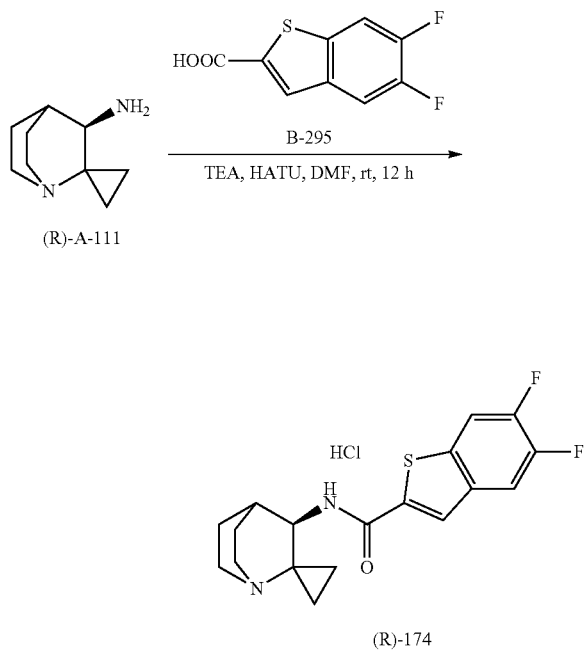

Following general procedure B, Compound (R)-174 was prepared from compound B-295 (0.10 g, 0.47 mmol) and compound (R)-A-111 (71 mg, 0.47 mmol), with a reaction time of 12 hours. The product was purified by prep-HPLC [Instrument: GX-A; Column: Phenomenex Gemini C18 250×50 mm, particle size: 10 μm; Mobile phase: 40-46% acetonitrile in H₂O (add 0.05% ammonia, v/v)]. The resulting solid was dissolved in 0.2 M hydrochloric acid solution and again lyophilized to give:

(R)-5,6-difluoro-N-(1'-azaspiro[cyclopropane-1,2'-bicyclo[2.2.2]octan]-3'-yl)benzo[b]thiophene-2-carboxamide-hydrochloride (compound (R)-174) (50 mg, 28% yield) as a white solid: cSFC analytical (A) tR=2.17 min., purity: 96.13%; LCMS (GG): tR=2.016 min., 349.1 m/z (M+1); ¹H-NMR (CD₃OD, 400 MHz): δ 8.14 (s, 1H), 7.93-7.89 (q, 1H), 7.86-7.82 (q, 1H), 4.59-4.57 (m, 1H), 3.77-3.73 (m, 1H), 3.60-3.59 (m, 1H), 3.50-3.45 (m, 2H), 2.46 (m, 1H), 2.36 (m, 1H), 2.25-2.18 (m, 2H), 2.02-2.01 (m, 1H), 1.40 (m, 1H), 1.39-1.19 (m, 3H).

Example 175: (R)-6-chloro-5,7-difluoro-N-(1'-azaspiro[cyclopropane-1,2'-bicyclo[2.2.2]octan]-3'-yl)benzo[b]thiophene-2-carboxamide hydrochloride ((R)-175)

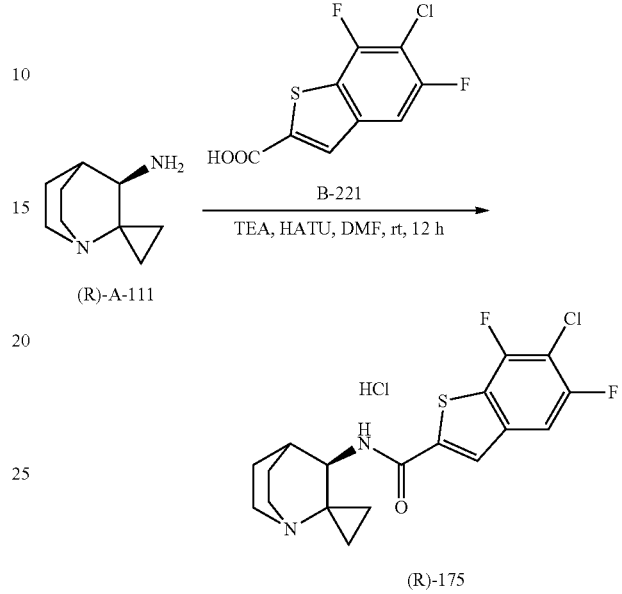

Following general procedure B, Compound (R)-175 was prepared from compound B-221 (40 mg, 0.16 mmol) and compound (R)-A-111 (24 mg, 0.16 mmol), with a reaction time of 12 hours. The product was purified by prep-HPLC [Instrument: GX-B; Column: YMC-Actus Pro C18 150×30 mm, particle size: 5 μm; Mobile phase: 25-55% acetonitrile in H₂O (add 0.5% TFA, v/v)]. The resulting solid was dissolved in 0.2 M hydrochloric acid and again lyophilized to give:

(R)-6-chloro-5,7-difluoro-N-(1'-azaspiro[cyclopropane-1,2'-bicyclo[2.2.2]octan]-3'-yl)benzo[b]thiophene-2-carboxamide-hydrochloride (compound (R)-175) (50 mg, 74% yield) as a yellow solid: cSFC analytical (A) tR=2.440 min., purity: 100.00%; LCMS (GG): tR=2.353 min., 383.1 m/z (M+1); ¹H-NMR (CD₃OD, 400 MHz): δ 8.20 (d, J=2.8 Hz, 1H), 7.76-7.73 (d, J=8.8 Hz, 1H), 4.59 (m, 1H), 3.73-3.71 (m, 1H), 3.60 (m, 1H), 3.54-3.42 (m, 2H), 2.47 (m, 1H), 2.38-2.33 (m, 1H), 2.23-2.20 (m, 2H), 2.02 (m, 1H), 1.39-1.37 (m, 1H), 1.29-1.21 (m, 3H).

Example 176: (R)-7-methyl-N-(1'-azaspiro[cyclopropane-1,2'-bicyclo[2.2.2]octan]-3'-yl)benzo[b]thiophene-2-carboxamide hydrochloride ((R)-176)

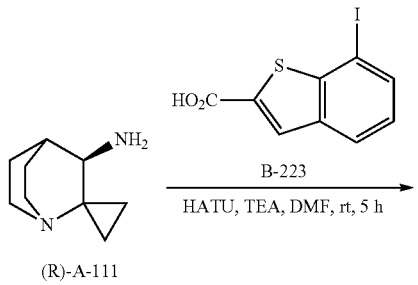

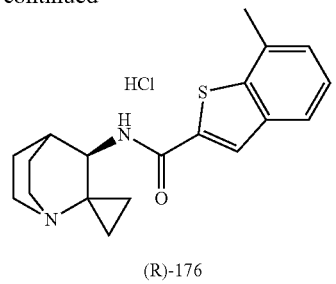

(R)-176

Following general procedure B, Compound (R)-176 was prepared from compound B-223 (51 mg, 0.26 mmol) and compound (R)-A-111 (40 mg, 0.26 mmol), with a reaction time of 5 hours. The product was purified by prep-HPLC [Instrument: GX-H; Column: Waters Xbridge 150×25, particle size: 5 μm; Mobile phase: 34-64% acetonitrile in H$_2$O (add 0.05% ammonia, v/v)]. The resulting solid was dissolved in 0.2 M hydrochloric acid solution and again lyophilized to give:

(R)-7-methyl-N-(1'-azaspiro[cyclopropane-1,2'-bicyclo[2.2.2]octan]-3'-yl)benzo[b]thiophene-2-carboxamide hydrochloride (compound (R)-176) (40 mg, 42% yield) as a white solid: cSFC analytical (A) tR=2.526 min., purity: 97.61%; LCMS (B): tR=0.677 min., (ES$^+$) m/z (M+H)= 327.2; $^1$H-NMR (CD$_3$OD, 400 MHz): δ 8.19 (s, 1H), 7.79 (d, J=8.0 Hz, 1H), 7.40 (t, J=7.2 Hz, 1H), 7.31 (d, J=7.2 Hz, 1H), 4.60 (d, J=3.6 Hz, 1H), 3.78-3.74 (m, 1H), 3.60-3.50 (m, 1H), 3.49-3.45 (m, 2H), 2.58 (s, 3H), 2.48-2.47 (m, 1H), 2.46-2.37 (m, 1H), 2.26-2.20 (m, 2H), 2.02-2.00 (m, 1H), 1.43-1.37 (m, 1H), 1.30-1.20 (m, 3H).

Example 177: (R)—N-(1'-azaspiro[cyclopropane-1,2'-bicyclo[2.2.2]octan]-3'-yl)-7-(2,2,2-trifluoroethyl)benzo[b]thiophene-2-carboxamide hydrochloride ((R)-177)

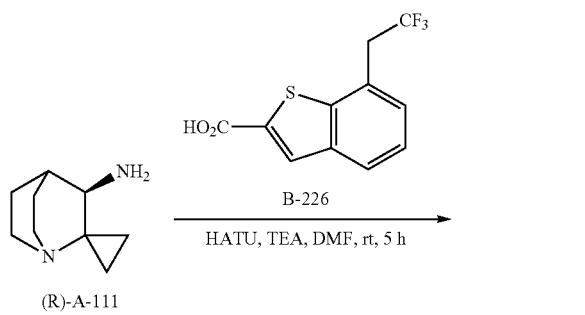

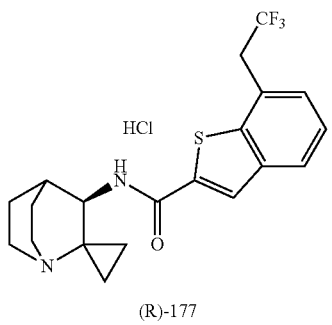

(R)-177

Following general procedure B, Compound (R)-177 was prepared from compound B-226 (68 mg, 0.26 mmol) and compound (R)-A-111 (40 mg, 0.26 mmol), with a reaction time of 5 hours. The product was purified by prep-HPLC [Instrument: GX-C; Column: Phenomenex Gemini C18 250×50 mm, particle size: 10 μm; Mobile phase: 42-72% acetonitrile in H$_2$O (add 0.05% NH$_3$.H$_2$O, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-7-(2,2,2-trifluoroethyl)benzo[b]thiophene-2-carboxamide-hydrochloride (compound (R)-177) (40 mg, 35% yield) as a white solid: cSFC analytical (A) tR=2.16 min., purity: 98.49%; LCMS (DD): tR=0.790 min., 395.1 m/z (M+1); $^1$H-NMR (CD$_3$OD, 400 MHz): δ 8.20 (s, 1H), 7.99-7.93 (m, 1H), 7.51-7.48 (m, 2H), 4.58 (d, J=3.0 Hz, 1H), 3.81 (q, J=10.8 Hz, 2H), 3.73 (m, 1H), 3.59-3.57 (m, 1H), 3.48-3.40 (m, 2H), 2.46-2.45 (m, 1H), 2.38-2.32 (m, 1H), 2.24-2.17 (m, 2H), 2.03-1.96 (m, 1H), 1.39-1.36 (m, 1H), 1.29-1.20 (m, 3H).

Example 178: (R)-7-(dimethylamino)-N-(1'-azaspiro[cyclopropane-1,2'-bicyclo[2.2.2]octan]-3'-yl)benzo[b]thiophene-2-carboxamide hydrochloride ((R)-178)

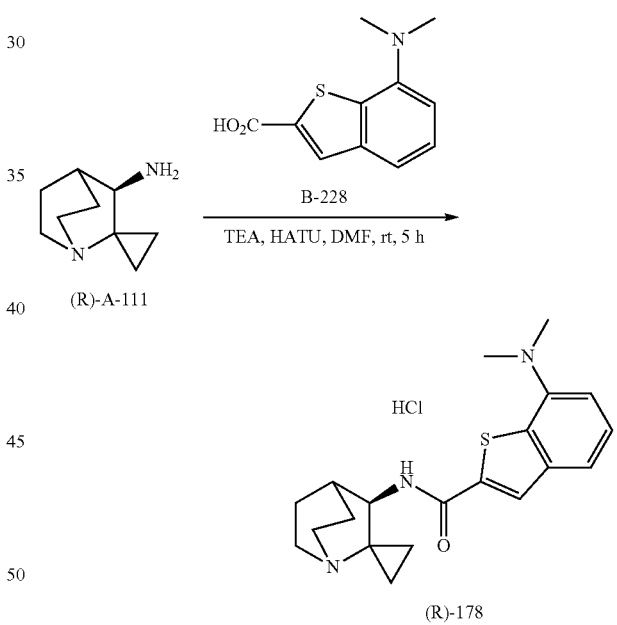

(R)-178

Following general procedure B, Compound (R)-178 was prepared from compound B-228 (110 mg, crude) and compound (R)-A-111 (75 mg, 0.49 mmol), with a reaction time of 5 hours. The product was purified by prep-HPLC [Instrument: GX-E; Column: Agella Venusil ASB C18 150×30 mm, particle size: 5 μm; Mobile phase: 19-49% acetonitrile in H$_2$O (add 0.5% HCl, v/v)] to give:

(R)-7-(dimethylamino)-N-(1'-azaspiro[cyclopropane-1,2'-bicyclo[2.2.2]octan]-3'-yl)benzo[b]thiophene-2-carboxamide hydrochloride (compound (R)-178) (38 mg, 18% yield) as a white solid: cSFC analytical (A) tR=2.86 min., purity: 99.74%; LCMS (FF): tR=2.147 min., (ES$^+$) m/z (M+H)$^+$=356.1; $^1$H-NMR (CD$_3$OD, 400 MHz): δ 8.45 (s, 1H), 8.15 (d, J=8 Hz, 1H), 7.88 (d, J=7.6 Hz, 1H), 7.69-7.65

(m, 1H), 4.59 (d, J=2.4 Hz, 1H), 3.79-3.77 (m, 1H), 3.58-3.57 (m, 1H), 3.49 (s, 6H), 3.48-3.43 (m, 2H), 2.47-2.38 (m, 2H), 2.24-2.17 (m, 2H), 2.00-1.99 (m, 1H), 1.42-1.26 (m, 3H), 1.18-1.16 (m, 1H).

Example 179: (R)-7-(methylsulfonyl)-N-(1'-azaspiro[cyclopropane-1,2'-bicyclo[2.2.2]octan]-3'-yl)benzo[b]thiophene-2-carboxamide hydrochloride ((R)-179)

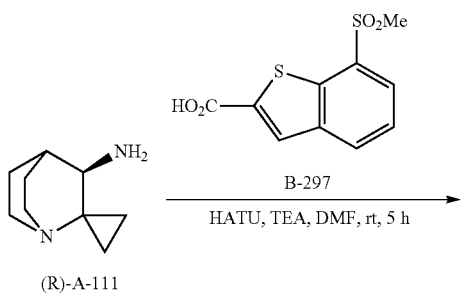

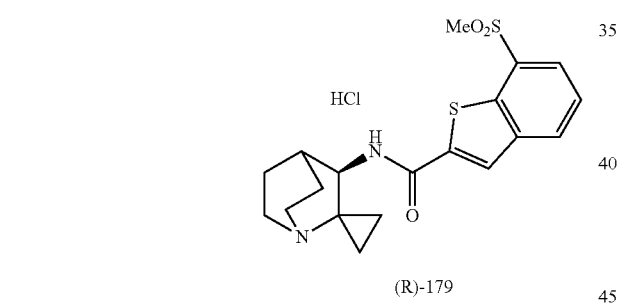

Following general procedure B, Compound (R)-179 was prepared from compound B-297 (101 mg, 0.39 mmol) and compound (R)-A-111 (60 mg, 0.39 mmol), with a reaction time of 5 hours. The product was purified by prep-HPLC [Instrument: GX-A; Column: Phenomenex Gemini C18 250×50 mm, particle size: 10 μm; Mobile phase: 23-53% acetonitrile in H$_2$O (add 0.05% ammonia, v/v)]. The resulting solid was dissolved in 0.2 M hydrochloric acid solution and again lyophilized to give:

(R)-7-(methylsulfonyl)-N-(1'-azaspiro[cyclopropane-1,2'-bicyclo[2.2.2]octan]-3'-yl)benzo[b]thiophene-2-carboxamide hydrochloride (compound (R)-179) (95 mg, 56% yield) as a white solid: cSFC analytical (A) tR=0.83 min., purity: 100%; LCMS (EE): tR=2.449 min., (ES$^+$) m/z (M+H)$^+$=391.0; $^1$H-NMR (CD$_3$OD, 400 MHz): δ 8.24 (d, J=6.4 Hz, 1H), 8.06 (d, J=7.2 Hz, 1H), 7.68 (t, J=7.6 Hz, 1H), 4.56 (d, J=2.4 Hz, 1H), 3.69-3.68 (m, 1H), 3.57-3.56 (m, 1H), 3.48-3.41 (m, 2H), 3.18 (s, 3H), 2.44 (d, J=3.2 Hz, 1H), 2.32-2.29 (m, 1H), 2.21-2.16 (m, 2H), 2.01-1.98 (m, 1H), 1.34-1.31 (m, 1H), 1.25-1.18 (m, 3H).

Example 180: (R)-7-morpholino-N-(1'-azaspiro[cyclopropane-1,2'-bicyclo[2.2.2]octan]-3'-yl)benzo[b]thiophene-2-carboxamide hydrochloride ((R)-180)

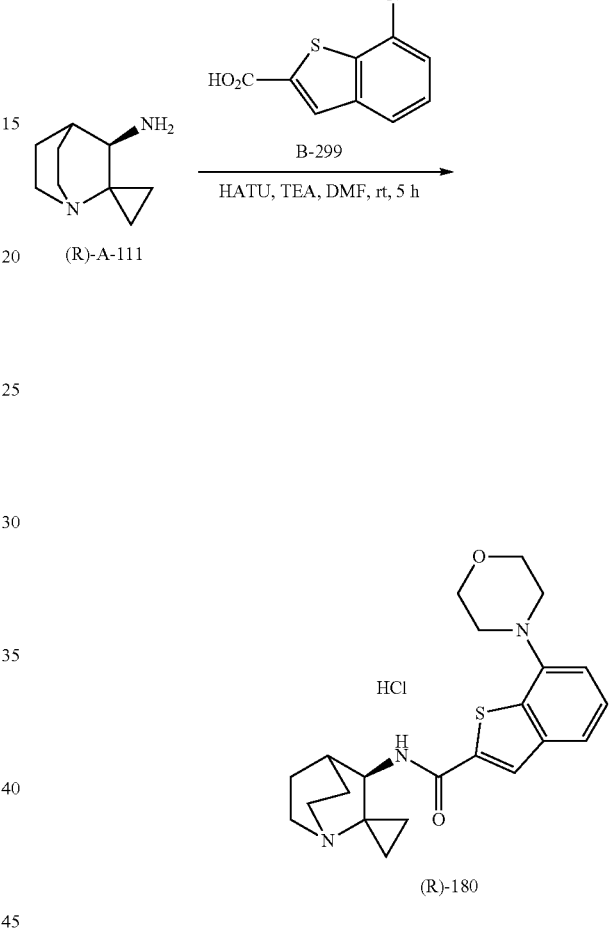

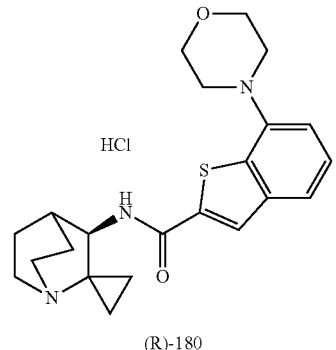

Following general procedure B, Compound (R)-180 was prepared from compound B-299 (104 mg, 0.39 mmol) and compound (R)-A-111 (60 mg, 0.39 mmol), with a reaction time of 5 hours. The product was purified by prep-HPLC [Instrument: GX-B; Column: YMC-Actus Pro C18 150×30 mm, particle size: 5 μm; Mobile phase: 18-48% acetonitrile in H$_2$O (add 0.1% TFA, v/v)]. The resulting solid was dissolved in 0.2 M hydrochloric acid solution and again lyophilized to give:

(R)-7-morpholino-N-(1'-azaspiro[cyclopropane-1,2'-bicyclo[2.2.2]octan]-3'-yl)benzo[b]thiophene-2-carboxamide hydrochloride (compound (R)-180) (30 mg, 18% yield) as a white solid: cSFC analytical (A) tR=2.88 min., purity: 99.09%; LCMS (Z): tR=1.424 min., (ES$^+$) m/z (M+H)$^+$= 398.2; $^1$H-NMR (CD$_3$OD, 400 MHz): δ 8.11 (d, J=7.2 Hz, 1H), 7.62 (d, J=8.0 Hz, 1H), 7.41 (t, J=8.0 Hz, 1H), 7.13 (d, J=7.2 Hz, 1H), 4.56 (s, 1H), 3.90 (t, J=4.2 Hz, 4H), 3.71-3.69 (m, 1H), 3.57 (m, 1H), 3.50-3.41 (m, 2H), 3.20 (s, 4H), 2.43 (d, J=2.4 Hz, 1H), 2.32-2.30 (m, 1H), 2.21-2.13 (m, 2H), 2.01-1.97 (m, 1H), 1.36-1.33 (m, 1H), 1.26-1.19 (m, 2H).

Example 181: (R)—N-(1'-azaspiro[cyclopropane-1,2'-bicyclo[2.2.2]octan]-3'-yl)-7-(thiazol-2-yl)benzo[b]thiophene-2-carboxamide hydrochloride ((R)-181)

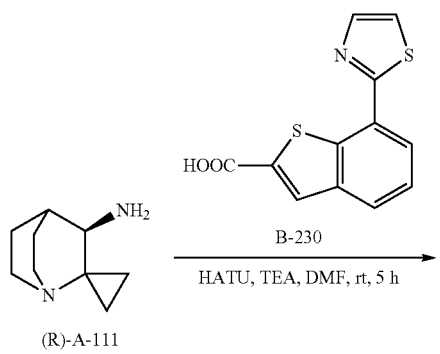

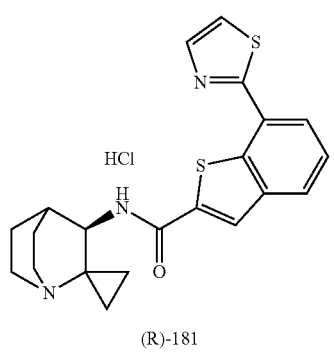

Following general procedure B, Compound (R)-181 was prepared from compound B-230 (69 mg, 0.26 mmol) and compound (R)-A-111 (40 mg, 0.26 mmol), with a reaction time of 5 hours. The product was purified by prep-HPLC [Instrument: GX-H; Column: Waters Xbridge 150×25 mm, particle size: 5 μm; Mobile phase: 32-62% acetonitrile in H$_2$O (add 0.05% ammonia, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-7-(thiazol-2-yl)benzo[b]thiophene-2-carboxamide-hydrochloride (compound (R)-181) (60 mg, 53% yield) as a white solid: cSFC analytical (A) tR=3.965 min., purity: 100%; LCMS (GG): tR=2.138 min., (ES$^+$) m/z (M+H)$^+$ =396.0; $^1$H-NMR (CD$_3$OD, 400 MHz): δ 8.20 (s, 1H), 8.08-8.03 (m, 3H), 7.68 (d, J=3.2 Hz, 1H), 7.59 (t, J=8.0 Hz, 1H), 4.60 (d, J=2.4 Hz, 1H), 3.77-3.73 (m, 1H), 3.59-3.48 (m, 1H), 3.46-3.44 (m, 2H), 2.48-2.47 (m, 1H), 2.36-2.35 (m, 1H), 2.24-2.17 (m, 2H), 2.07-2.00 (m, 1H), 1.38-1.36 (m, 1H), 1.30-1.22 (m, 3H).

Example 182: (R)—N-(1'-azaspiro[cyclopropane-1,2'-bicyclo[2.2.2]octan]-3'-yl)isoquinoline-3-carboxamide hydrochloride ((R)-182)

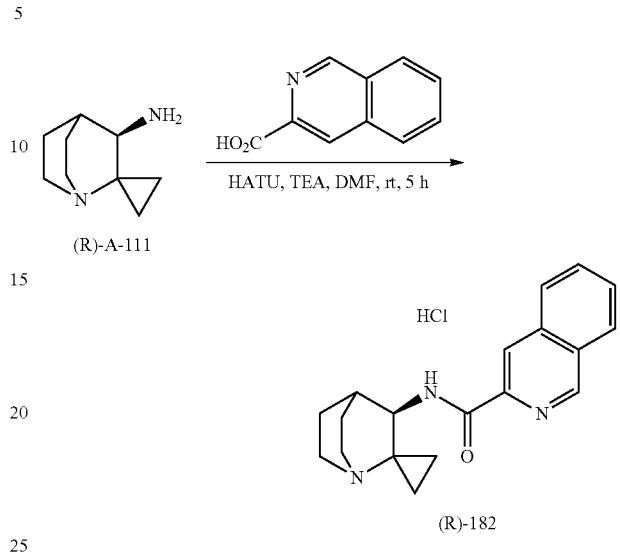

Following general procedure B, Compound (R)-182 was prepared from isoquinoline-3-carboxylic acid (68 mg, 0.39 mmol) and compound (R)-A-111 (60 mg, 0.39 mmol), with a reaction time of 5 hours. The product was purified by prep-HPLC [Instrument: GX-B; Column: YMC-Actus Pro C18 150×30 mm, particle size: 5 μm; Mobile phase: 10-40% acetonitrile in H$_2$O (add 0.1% TFA, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)isoquinoline-3-carboxamide-hydrochloride (compound (R)-182) (75 mg, 55% yield) as a white solid: cSFC analytical (A) tR=2.251 min., purity: 99.49%; LCMS (B): tR=0.562 min., (ES$^+$) m/z (M+H)$^+$=308.2; $^1$H-NMR (CD$_3$OD, 400 MHz): δ 9.71 (s, 1H), 9.20 (s, 1H), 8.54 (d, J=8.4 Hz, 1H), 8.40 (d, J=8.4 Hz, 1H), 8.25 (t, J=7.2 Hz, 1H), 8.10 (t, J=7.6 Hz, 1H), 4.70 (d, J=2.0 Hz, 1H), 3.89-3.85 (m, 1H), 3.63-3.62 (m, 1H), 3.56-3.48 (m, 2H), 2.55-2.54 (m, 1H), 2.45-2.43 (m, 1H), 2.29-2.22 (m, 2H), 2.09-2.04 (m, 1H), 1.46-1.34 (m, 3H), 1.26-1.23 (m, 1H).

Example 183: (R)-2-cyclopropyl-N-(1'-azaspiro[cyclopropane-1,2'-bicyclo[2.2.2]octan]-3'-yl)benzofuran-5-carboxamide hydrochloride ((R)-183)

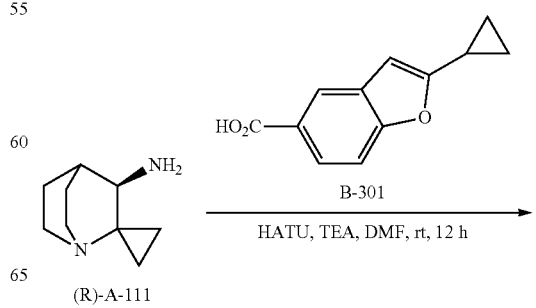

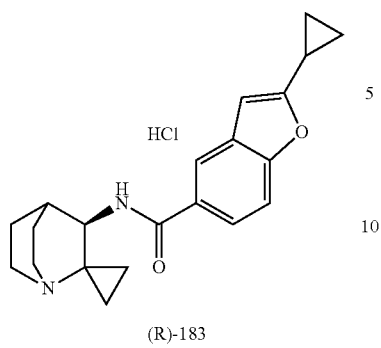

(R)-183

Following general procedure B, Compound (R)-183 was prepared from compound B-301 (66 mg, 0.33 mmol) and compound (R)-A-111 (50 mg, 0.33 mmol), with a reaction time of 12 hours. The product was purified by prep-HPLC [Instrument: GX-B; Column: YMC-Actus Pro C18 150×30 mm, particle size: 5 μm; Mobile phase: 20-50% acetonitrile in H2O (add 0.1% TFA, v/v)]. The resulting solid was dissolved in 0.2 M hydrochloric acid solution and again lyophilized to give:

(R)-2-cyclopropyl-N-(1'-azaspiro[cyclopropane-1,2'-bicyclo[2.2.2]octan]-3'-yl)benzofuran-5-carboxamide-hydrochloride (compound (R)-183) (50 mg, 45% yield) as a yellow solid: cSFC analytical (A) tR=2.40 min., purity: 97.21%; LCMS (BB): tR=0.944 min., 337.1 m/z (M+1); $^1$H-NMR (CD$_3$OD, 400 MHz): δ 7.99 (d, J=0.8 Hz, 1H), 7.72-7.69 (dd, J$_1$=8.4 Hz, J$_2$=1.6 Hz, 1H), 7.47-7.45 (d, J$_1$=8.8 Hz, 1H), 6.57 (s, 1H), 4.59-4.58 (d, J=2 Hz, 1H), 3.71-3.69 (m, 1H), 3.60-3.58 (m, 1H), 3.49-3.42 (m, 2H), 2.46-2.45 (m, 1H), 2.32 (m, 1H), 2.23-2.12 (m, 3H), 1.99 (m, 1H), 1.41-1.40 (m, 1H), 1.27-1.22 (m, 3H), 1.07-1.05 (m, 2H), 1.00-0.98 (m, 2H).

Example 184: (R)-7-(tert-butyl)-N-(1'-azaspiro[cyclopropane-1,2'-bicyclo[2.2.2]octan]-3'-yl)benzo[b]thiophene-2-carboxamide hydrochloride ((R)-184)

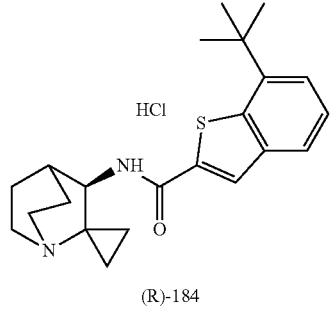

(R)-184

Following general procedure B, compound (R)-184 was prepared from compound B-233 (80 mg, 0.34 mmol) and compound (R)-A-111 (52 mg, 0.34 mmol), with a reaction time of 3 hours. The product was purified by prep-HPLC [Instrument: GX-B; Column: Phenomenex Gemini C18 150×30 mm, particle size: 4 μm; Mobile phase: 32-62% acetonitrile in H$_2$O (add 0.1% TFA, v/v)]. The resulting solid was dissolved in 0.2 N hydrochloric acid and again lyophilized to give:

(R)-7-(tert-butyl)-N-(1'-azaspiro[cyclopropane-1,2'-bicyclo[2.2.2]octan]-3'-yl)benzo[b]thiophene-2-carboxamide hydrochloride (compound (R)-184) (70 mg, 51% yield) as a white solid: cSFC analytical (A) tR=2.25 min., purity: 98.87%; LCMS (FF): tR=2.648 min, 369.2 m/z (M+1); $^1$H-NMR (CD$_3$OD, 400 MHz): δ 8.15 (s, 1H), 7.81 (d, J$_1$=7.6 Hz, 1H), 7.50-7.48 (m, 1H), 7.45-7.41 (m, 1H), 4.61 (s, 1H), 3.77-3.73 (m, 1H), 3.62-3.60 (m, 1H), 3.52-3.43 (m, 2H), 2.48-2.17 (m, 4H), 2.06-2.01 (m, 1H), 1.58 (s, 9H), 1.42-1.36 (m, 1H), 1.30-1.22 (m, 3H).

Example 185: (R)-7-(2-hydroxypropan-2-yl)-N-(1'-azaspiro[cyclopropane-1,2'-bicyclo[2.2.2]octan]-3'-yl)benzo[b]thiophene-2-carboxamide ((R)-185)

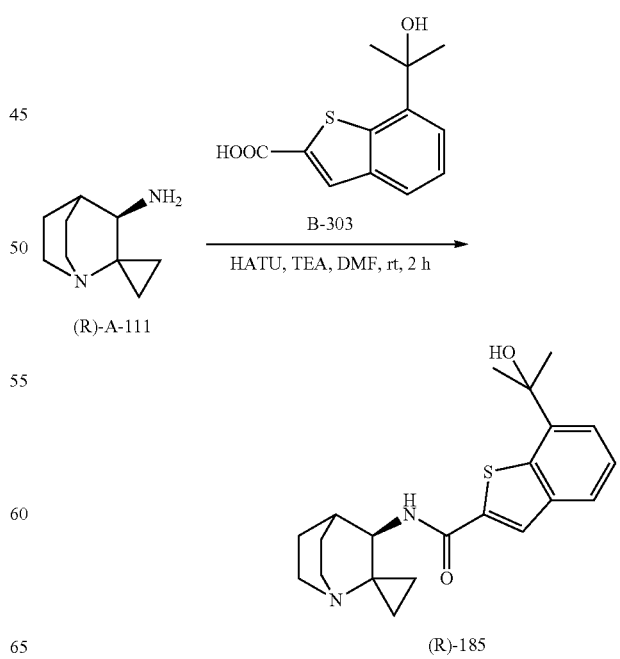

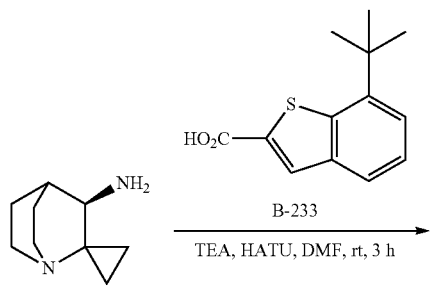

Following general procedure B, Compound (R)-185 was prepared from compound B-303 (78 mg, 0.33 mmol) and compound (R)-A-111 (50 mg, 0.33 mmol), with a reaction time of 2 hours. The product was purified by prep-HPLC [Instrument: GX-A; Column: Phenomenex Gemini C18 250×50 mm, particle size: 10 μm; Mobile phase: 32-62% acetonitrile in H₂O (add 0.05% NH₃.H₂O, v/v)] to give:

(R)-7-(2-hydroxypropan-2-yl)-N-(1'-azaspiro[cyclopropane-1,2'-bicyclo[2.2.2]octan]-3'-yl)benzo[b]thiophene-2-carboxamide (compound (R)-185) (20 mg, 17% yield) as a white solid: cSFC analytical (A) tR=2.63 min., purity: 95.08%; LCMS (EE): tR=2.611 min., 371.1 m/z (M+1); $^1$H-NMR (CD₃OD, 400 MHz): δ 8.07 (s, 1H), 7.80 (d, J=6.8 Hz, 1H), 7.44-7.38 (m, 2H), 4.23 (s, 1H), 3.28-3.26 (m, 1H), 3.13-3.06 (m, 1H), 2.94-2.87 (m, 2H), 2.12 (m, 1H), 2.03-1.97 (m, 1H), 1.89-1.85 (m, 2H), 1.71 (s, 6H), 1.58 (m, 1H), 0.93-0.87 (m, 2H), 0.80-0.67 (m, 2H).

Example 186: (R)-7-phenyl-N-(1'-azaspiro[cyclopropane-1,2'-bicyclo[2.2.2]octan]-3'-yl)benzo[b]thiophene-2-carboxamide hydrochloride ((R)-186)

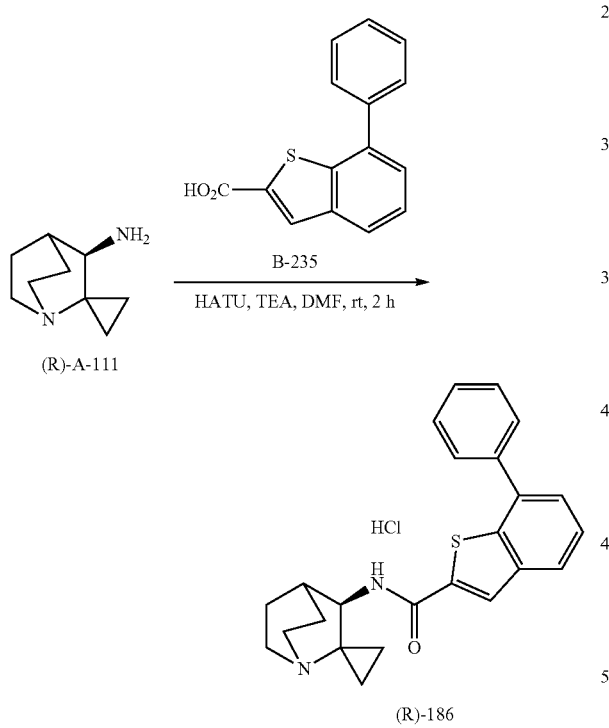

Following general procedure B, Compound (R)-186 was prepared from compound B-235 (99 mg, 0.39 mmol) and compound (R)-A-111 (60 mg, 0.39 mmol), with a reaction time of 2 hours. The product was purified by prep-HPLC [Instrument: GX-E; Column: Agella Venusil ASB C18 150× 30 mm, particle size: 5 μm; Mobile phase: 27-57% acetonitrile in H₂O (add 0.5% HCl, v/v)] to give:

(R)-7-phenyl-N-(1'-azaspiro[cyclopropane-1,2'-bicyclo[2.2.2]octan]-3'-yl)benzo[b]thiophene-2-carboxamide hydrochloride (compound (R)-186) (70 mg, 46% yield) as a white solid: cSFC analytical (A) tR=3.19 min., purity: 98.88%; LCMS (Y): tR=0.752 min., 389.1 m/z (M+1); $^1$H-NMR (CD₃OD, 400 MHz): 8.24 (s, 1H), 7.94 (d, J=8.0 Hz, 1H), 7.72 (d, J=7.2 Hz, 2H), 7.59-7.45 (m, 5H), 4.58 (s, 1H), 3.78-3.71 (m, 1H), 3.49-3.48 (m, 1H), 3.46-3.44 (m, 2H), 2.46-2.45 (m, 1H), 2.30-2.12 (m, 3H), 2.04-2.00 (m, 1H), 1.43-1.37 (m, 1H), 1.32-1.30 (m, 2H), 1.27-1.25 (m, 1H).

Example 187: (R)—N-(1'-azaspiro[cyclopropane-1,2'-bicyclo[2.2.2]octan]-3'-yl)-7-(1-(trifluoromethyl)cyclopropyl)benzo[b]thiophene-2-carboxamide hydrochloride ((R)-187)

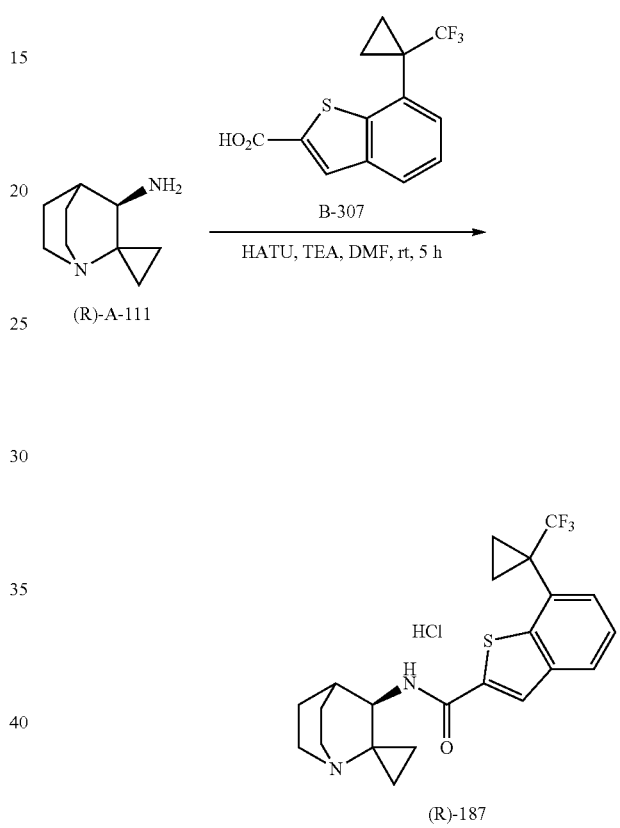

Following general procedure B, Compound (R)-187 was prepared from compound B-307 (94 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 250×50 mm, particle size: 10 μm; Mobile phase: 46-76% acetonitrile in H₂O (add 0.05% NH₃.H₂O, v/v)]. The resulting solid was dissolved in 0.2 M hydrochloric acid and again lyophilized to give:

(R)—N-(1'-azaspiro[cyclopropane-1,2'-bicyclo[2.2.2]octan]-3'-yl)-7-(1-(trifluoromethyl)cyclopropyl) benzo[b]thiophene-2-carboxamide-hydrochloride (compound (R)-187) (64 mg, 46% yield) as a white solid: cSFC analytical (A) tR=2.08 min., purity: 98.79%; LCMS (FF): tR=2.597 min., 421.1 m/z (M+1); $^1$H-NMR (CD₃OD, 400 MHz): δ 8.71 (d, J=8.0 Hz, 0.1H), 8.19 (s, 1H), 7.95 (d, J=7.6 Hz, 1H), 7.62 (d, J=7.2 Hz, 1H), 7.49 (t, J=7.6 Hz, 1H), 4.58 (d, J=2.0 Hz, 1H), 3.76-3.72 (m, 1H), 3.59-3.58 (m, 1H), 3.50-3.40 (m, 2H), 2.46-2.45 (m, 1H), 2.34-2.33 (m, 1H), 2.25-2.17 (m, 2H), 2.01-1.99 (m, 1H), 1.56-1.53 (m, 2H), 1.41-1.35 (m, 1H), 1.28-1.18 (m, 5H).

Example 188: (R)-7-(1-methylcyclopropyl)-N-(1'-azaspiro[cyclopropane-1,2'-bicyclo[2.2.2]octan]-3'-yl)benzo[b]thiophene-2-carboxamide-hydrochloride ((R)-188)

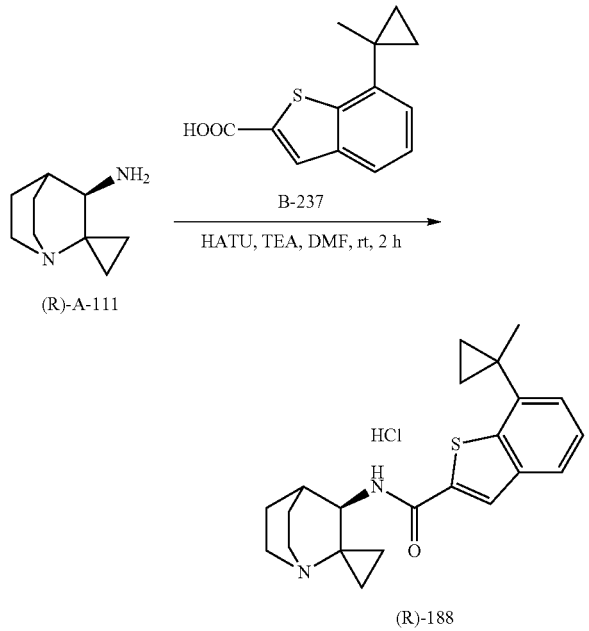

Following general procedure B, Compound (R)-188 was prepared from B-237 (76 mg, 0.39 mmol) and compound (R)-A-111 (50 mg, 0.33 mmol), with a reaction time of 2 hours. The product was purified by prep-HPLC [Instrument: GX-E; Column: Agella Venusil ASB C18 150×30 mm, particle size: 5 μm; Mobile phase: 27-57% acetonitrile in H$_2$O (add 0.5% HCl, v/v)] to give:

(R)-7-(1-methylcyclopropyl)-N-(1'-azaspiro[cyclopropane-1,2'-bicyclo[2.2.2]octan]-3'-yl)benzo[b]thiophene-2-carboxamide-hydrochloride (compound (R)-188) (29 mg, 24% yield) as a white solid: cSFC analytical (A) tR=2.30 min., purity: 95.77%; LCMS (GG): tR=3.152 min., 367.1 m/z (M+1); $^1$H-NMR (CD$_3$OD, 400 MHz): δ 8.65 (d, J=8.0 Hz, 1H), 8.17 (s, 1H), 7.80 (d, J=6.8 Hz, 1H), 7.45-7.39 (m, 2H), 4.60 (s, 1H), 3.78-3.71 (m, 1H), 3.60-3.52 (m, 1H), 3.50-3.44 (m, 2H), 2.48-2.34 (m, 2H), 2.26-2.19 (m, 2H), 2.02-2.01 (m, 1H), 1.48 (s, 3H), 1.38-1.21 (m, 4H), 0.96-0.93 (m, 2H), 0.88-0.85 (m, 2H).

Example 189: (R)-6-ethoxy-N-(1'-azaspiro[cyclopropane-1,2'-bicyclo[2.2.2]octan]-3'-yl)benzo[b]thiophene-2-carboxamide hydrochloride ((R)-189)

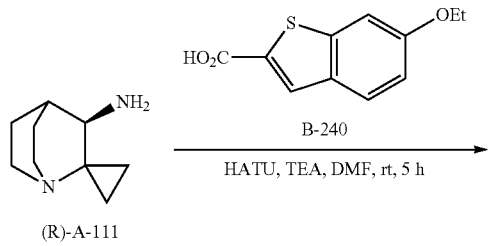

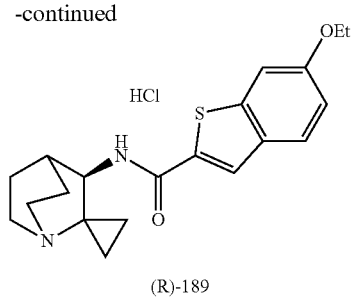

Following general procedure B, Compound (R)-189 was prepared from compound B-240 (88 mg, 0.39 mmol) and compound (R)-A-111 (60 mg, 0.39 mmol), with a reaction time of 5 hours. The product was purified by prep-HPLC [Instrument: GX-A; Column: Phenomenex Gemini C18 250×50 mm, particle size: 10 μm; Mobile phase: 34-64% acetonitrile in H$_2$O (add 0.05% ammonia, v/v)]. The resulting solid was dissolved in 0.2 M hydrochloric acid solution and again lyophilized to give:

(R)-6-ethoxy-N-(1'-azaspiro[cyclopropane-1,2'-bicyclo[2.2.2]octan]-3'-yl)benzo[b]thiophene-2-carboxamide-hydrochloride (compound (R)-189) (64 mg, 41% yield) as a white solid: cSFC analytical (A) tR=2.68 min., purity: 99.24%; LCMS (EE): tR=2.864 min., (ES$^+$) m/z (M+H)$^+$ =357.1; $^1$H-NMR (CD$_3$OD, 400 MHz): δ 8.01 (d, J=4.0 Hz, 1H), 7.76 (d, J=8.8 Hz, 1H), 7.41 (d, J=1.6 Hz, 1H), 7.02 (dd, J=8.8, 2.0 Hz, 1H), 4.53 (d, J=2.8 Hz, 1H), 4.10 (q, J=6.8 Hz, 2H), 3.69-3.67 (m, 1H), 3.55 (m, 1H), 3.49-3.41 (m, 2H), 2.41 (d, J=2.8 Hz, 1H), 2.32-2.29 (m, 1H), 2.20-2.13 (m, 2H), 1.97 (m, 1H), 1.41 (t, J=7.0 Hz, 3H), 1.34-1.31 (m, 1H), 1.24-1.18 (m, 3H).

Example 190: (R)-7-ethoxy-N-(1'-azaspiro[cyclopropane-1,2'-bicyclo[2.2.2]octan]-3'-yl)benzo[b]thiophene-2-carboxamide hydrochloride ((R)-190)

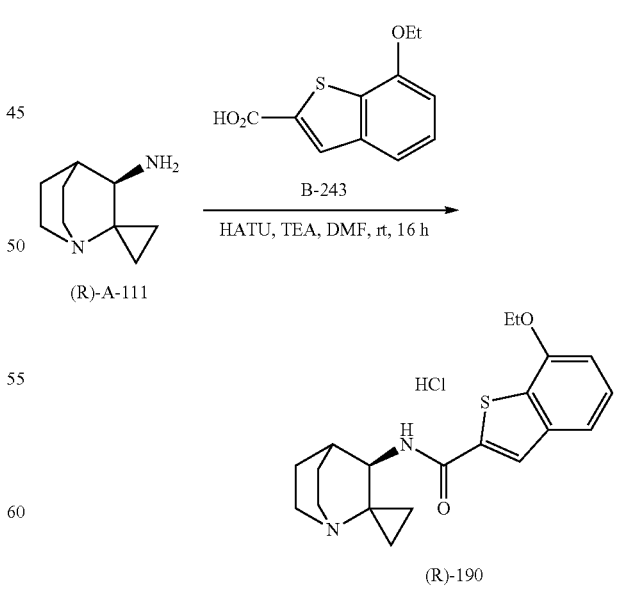

Following general procedure B, Compound (R)-190 was prepared from compound B-243 (73 mg, 0.33 mmol) and compound (R)-A-111 (50 mg, 0.33 mmol), with a reaction time of 16 hours. The product was purified by prep-HPLC [Instrument: GX-B; Column: YMC-Actus Pro C18 150×30 mm, particle size: 5 μm; Mobile phase: 25-55% acetonitrile in H$_2$O (add 0.5% HCl, v/v)] to give:

(R)-7-ethoxy-N-(1'-azaspiro[cyclopropane-1,2'-bicyclo[2.2.2]octan]-3'-yl)benzo[b]thiophene-2-carboxamide-hydrochloride (compound (R)-190) (22 mg, 19% yield) as a white solid: cSFC analytical (A) tR=2.81 min., purity: 99.20%; LCMS (EE): tR=2.914 min., (ES$^+$) m/z (M+H)$^+$= 357.1; $^1$H-NMR (CD$_3$OD, 400 MHz): 8.13 (s, 1H), 7.49 (d, J=7.6 Hz, 1H), 7.39-7.34 (m, 1H), 6.95 (d, J=7.6 Hz, 1H), 4.56 (d, J=2.4 Hz, 1H), 4.25 (dd, J$_1$=14 Hz, J$_2$=7.6 Hz, 2H), 3.76-3.71 (m, 1H), 3.57-3.55 (m, 1H), 3.50-3.40 (m, 2H), 2.44-2.43 (m, 1H), 2.37-2.33 (m, 1H), 2.22-2.15 (m, 2H), 2.02-1.98 (m, 1H), 1.50-1.46 (m, 3H), 1.39-1.38 (m, 1H), 1.31-1.53 (m, 3H).

Example 191: (R)-7-isopropoxy-N-(1'-azaspiro[cyclopropane-1,2'-bicyclo[2.2.2]octan]-3'-yl)benzo[b]thiophene-2-carboxamide hydrochloride ((R)-191)

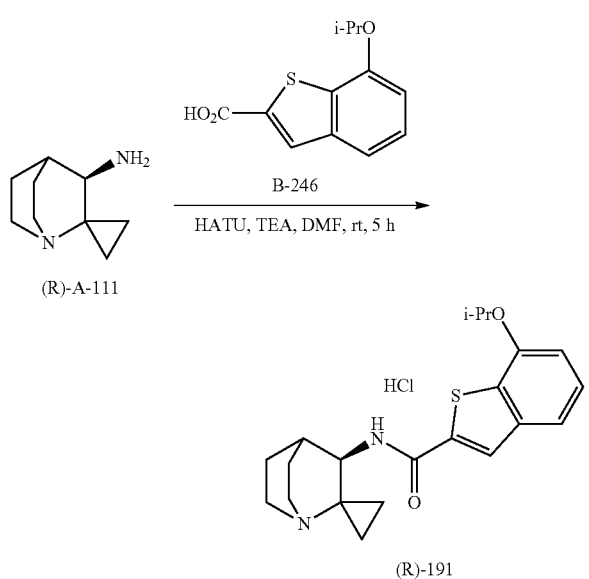

Following general procedure B, Compound (R)-191 was prepared from compound B-246 (63 mg, 0.26 mmol) and compound (R)-A-111 (40 mg, 0.26 mmol), with a reaction time of 5 hours. The product was purified by prep-HPLC [Instrument: GX-E; Column: Phenomenex Synergi C18 150×30 mm, particle size: 4 μm; Mobile phase: 23-48% acetonitrile in H$_2$O (add 0.05% HCl, v/v)] to give:

(R)-7-isopropoxy-N-(1'-azaspiro[cyclopropane-1,2'-bicyclo[2.2.2]octan]-3'-yl)benzo[b]thiophene-2-carboxamide-hydrochloride (compound (R)-191) (32 mg, 30% yield) as a white solid: cSFC analytical (A) tR=2.480 min., purity: 96.59%; LCMS (FF): tR=2.502 min., (ES$^+$) m/z (M+H)$^+$= 371.1; $^1$H-NMR (CD$_3$OD, 400 MHz): δ 8.09 (s, 1H), 7.49 (d, J=8.0 Hz, 1H), 7.38 (t, J=8.0 Hz, 1H), 6.99 (d, J=8.0 Hz, 1H), 4.86-4.80 (m, 1H), 4.57 (d, J=2.8 Hz, 1H), 3.74-3.71 (m, 1H), 3.59-3.57 (m, 1H), 3.50-3.43 (m, 2H), 2.45-2.44 (m, 1H), 2.36-2.34 (m, 1H), 2.24-2.16 (m, 2H), 2.03-1.98 (m, 1H), 1.42 (s, 3H), 1.40 (s, 3H), 1.38-1.36 (m, 1H), 1.37-1.16 (m, 3H).

Example 192: (R)-6-chloro-7-methoxy-N-(1'-azaspiro[cyclopropane-1,2'-bicyclo[2.2.2]octan]-3'-yl)benzo[b]thiophene-2-carboxamide hydrochloride ((R)-192)

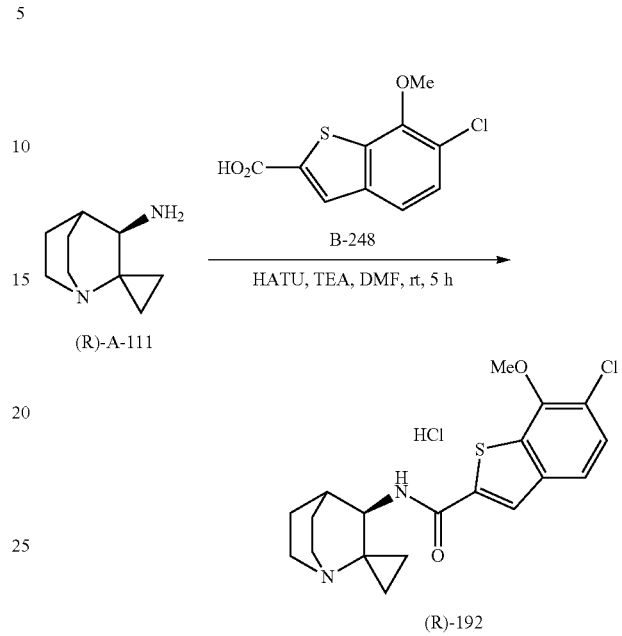

Following general procedure B, Compound (R)-192 was prepared from compound B-248 (64 mg, 0.26 mmol) and compound (R)-A-111 (40 mg, 0.26 mmol), with a reaction time of 5 hours. The product was purified by prep-HPLC [Instrument: GX-E; Phenomenex Synergi C18 C18 150×30 mm, particle size: 4 μm; Mobile phase: 23-48% acetonitrile in H$_2$O (add 0.05% HCl, v/v)] to give:

(R)-6-chloro-7-methoxy-N-(1'-azaspiro[cyclopropane-1,2'-bicyclo[2.2.2]octan]-3'-yl)benzo[b]thiophene-2-carboxamide-hydrochloride (compound (R)-192) (25 mg, 23% yield) as a white solid: cSFC analytical (A) tR=2.490 min., purity: 100%; LCMS (FF): tR=2.447 min., (ES$^+$) m/z (M+H)$^+$=377.0; $^1$H-NMR (CD$_3$OD, 400 MHz): δ 8.16 (s, 1H), 7.67 (d, J=8.8 Hz, 1H), 7.47 (d, J=8.4 Hz, 1H), 4.57 (d, J=2.4 Hz, 1H), 4.04 (s, 3H), 3.72-3.71 (m, 1H), 3.59-3.57 (m, 1H), 3.50-3.43 (m, 2H), 2.45-2.44 (m, 1H), 2.37-2.31 (m, 1H), 2.23-2.17 (m, 2H), 2.03-1.99 (m, 1H), 1.38-1.37 (m, 1H), 1.29-1.20 (m, 3H).

Example 193: (R)-7-methoxy-6-methyl-N-(1'-azaspiro[cyclopropane-1,2'-bicyclo[2.2.2]octan]-3'-yl)benzo[b]thiophene-2-carboxamide hydrochloride ((R)-193)

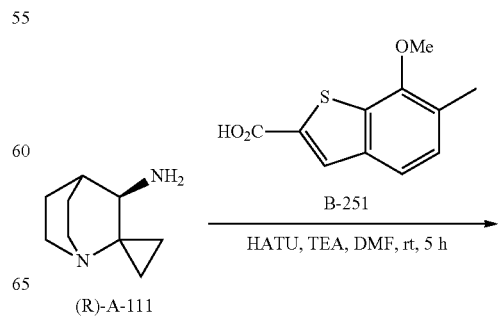

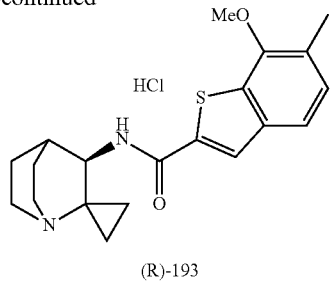

(R)-193

Following general procedure B, Compound (R)-193 was prepared from compound B-251 (73 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 250×50 mm, particle size: 10 μm; Mobile phase: 33-63% acetonitrile in H$_2$O (add 0.05% NH$_3$.H$_2$O, v/v)]. The resulting solid was dissolved in 0.2 M hydrochloric acid solution and again lyophilized to give:

(R)-7-methoxy-6-methyl-N-(1'-azaspiro[cyclopropane-1,2'-bicyclo[2.2.2]octan]-3'-yl)benzo[b]thiophene-2-carboxamide-hydrochloride (compound (R)-193) (58 mg, 45% yield) as a white solid: cSFC analytical (A) tR=2.48 min., purity: 94.50%; LCMS (EE): tR=2.842 min., 357.1 m/z (M+1); $^1$H-NMR (CD$_3$OD, 400 MHz): δ 8.11 (s, 1H), 7.58 (d, J=8.0 Hz, 1H), 7.29 (d, J=8.0 Hz, 1H), 4.56 (d, J=2.8 Hz, 1H), 3.95 (s, 3H), 3.76-3.71 (m, 1H), 3.58-3.57 (m, 1H), 3.49-3.40 (m, 2H), 2.44-2.43 (m, 1H), 2.41 (s, 3H), 2.34 (m, 1H), 2.23-2.16 (m, 2H), 2.01-1.95 (m, 1H), 1.38-1.36 (m, 1H), 1.28-1.19 (m, 3H).

Example 194: (R)—N-(1'-azaspiro[cyclopropane-1,2'-bicyclo[2.2.2]octan]-3'-yl)-1H-indazole-3-carboxamide hydrochloride ((R)-194)

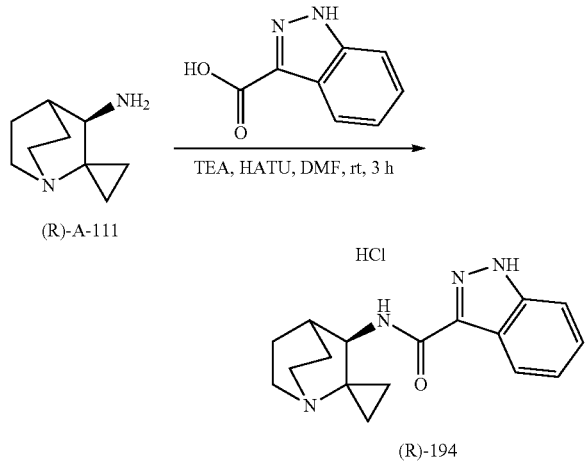

Following general procedure B, Compound (R)-194 was prepared from 1H-indazole-3-carboxylic acid (59 mg, 0.33 mmol) and compound (R)-A-111 (50 mg, 0.36 mmol), with a reaction time of 3 hours. The product was purified by prep-HPLC [Instrument: GX-F; Column: YMC-Actus Pro-C18 150×30 mm, particle size: 5 μm; Mobile phase: 12-37% acetonitrile in H$_2$O (add 0.1% TFA, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-1H-indazole-3-carboxamide-hydrochloride (compound (R)-194) (40 mg, 41% yield) as a white solid: cSFC analytical (A) tR=2.27 min., purity: 98.71%; LCMS (FF): tR=1.984 min., 297.1 m/z (M+1); $^1$H-NMR (CD$_3$OD, 400 MHz): δ 8.19 (d, J=8.4 Hz, 1H), 7.62 (d, J=8.8 Hz, 1H), 7.46 (t, J=7.4 Hz, 1H), 7.29 (t, J=7.6 Hz, 1H), 4.65 (s, 1H), 3.75-3.72 (m, 1H), 3.62-3.45 (m, 3H), 2.49-2.38 (m, 1H), 2.29-2.21 (m, 3H), 2.06-1.98 (m, 1H), 1.41-1.37 (m, 1H), 1.31-1.21 (m, 3H).

Example 195: (R)-1-methyl-N-(1'-azaspiro[cyclopropane-1,2'-bicyclo[2.2.2]octan]-3'-yl)-1H-indole-6-carboxamide ((R)-195)

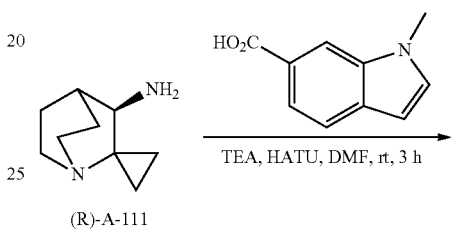

Following general procedure B, Compound (R)-195 was prepared from 1-methyl-1H-indole-6-carboxylic acid (60 mg, 0.39 mmol) and compound (R)-A-111 (69 mg, 0.39 mmol), with a reaction time of 3 hours. The product was purified by prep-HPLC [Instrument: GX-C; Column: Phenomenex Gemini C18 250×50 mm, particle size: 10 μm; Mobile phase: 27-57% acetonitrile in H$_2$O (add 0.05% NH$_3$—H$_2$O, v/v)] to give:

(R)-1-methyl-N-(1'-azaspiro[cyclopropane-1,2'-bicyclo[2.2.2]octan]-3'-yl)-1H-indole-6-carboxamide (compound (R)-195) (60 mg, 32% yield) as a yellow solid: cSFC analytical (A) tR=2.99 min., purity: 100.00%; LCMS (FF): tR=2.071 min., 310.0 m/z (M+1); $^1$H-NMR (CD$_3$OD, 400 MHz): δ 7.95 (s, 1H), 7.63-7.61 (m, 1H), 7.55 (dd, J$_1$=8.0 Hz, J$_1$=1.2 Hz, 1H), 7.35 (d, J=2.8 Hz, 1H), 6.51 (d, J=2.8 Hz, 1H), 4.27 (s, 1H), 3.91 (s, 3H), 3.28-3.25 (m, 1H), 3.10-2.87 (m, 3H), 2.14-2.12 (m, 1H), 2.03-1.85 (m, 3H), 1.59-1.53 (m, 1H), 0.92-0.89 (m, 2H), 0.77-0.70 (m, 2H).

Example 196: (R)-7-cyclopropyl-6-methyl-N-(1'-azaspiro[cyclopropane-1,2'-bicyclo[2.2.2]octan]-3'-yl)benzo[b]thiophene-2-carboxamide hydrochloride ((R)-196)

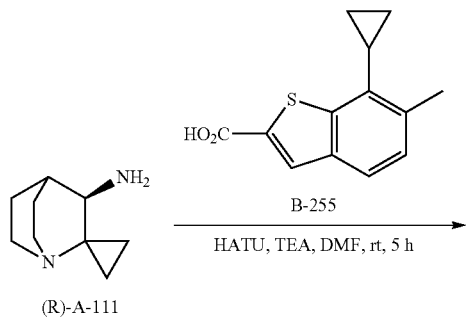

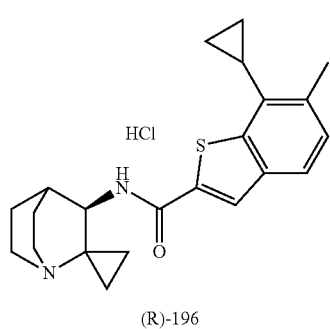

Following general procedure B, Compound (R)-196 was prepared from compound B-255 (76 mg, 0.33 mmol) and compound (R)-A-111 (50 mg, 0.33 mmol), with a reaction time of 5 hours. The product was purified by prep-HPLC [Instrument: GX-A; Column: Phenomenex Gemini C18 250×50 mm, particle size: 10 μm; Mobile phase: 44-74% acetonitrile in H$_2$O (add 0.05% NH$_3$H$_2$O, v/v)]. The resulting solid was dissolved in 0.2 M hydrochloric acid and again lyophilized to give:

(R)-7-cyclopropyl-6-methyl-N-(1'-azaspiro[cyclopropane-1,2'-bicyclo[2.2.2]octan]-3'-yl)benzo[b]thiophene-2-carboxamide-hydrochloride (compound (R)-196) (59 mg, 49% yield) as a white solid: cSFC analytical (A) tR=2.79 min., purity: 98.99%; LCMS (GG): tR=2.210 min., 367.2 m/z (M+1); $^1$H-NMR (CD$_3$OD, 400 MHz): δ 8.08 (s, 1H), 7.67 (d, J=8.0 Hz, 1H), 7.26 (d, J=8.0 Hz, 1H), 4.56 (d, J=2.0 Hz, 1H), 3.73-3.72 (m, 1H), 3.58-3.56 (m, 1H), 3.49-3.42 (m, 2H), 2.56 (s, 3H), 2.44-2.43 (m, 1H), 2.34-2.33 (m, 1H), 2.23-2.15 (m, 2H), 2.06-1.99 (m, 2H), 1.42-1.37 (m, 1H), 1.29-1.12 (m, 5H), 0.81-0.77 (m, 2H).

Example 197: (R)-6-fluoro-7-methoxy-N-(1'-azaspiro[cyclopropane-1,2'-bicyclo[2.2.2]octan]-3'-yl)benzo[b]thiophene-2-carboxamide hydrochloride ((R)-197)

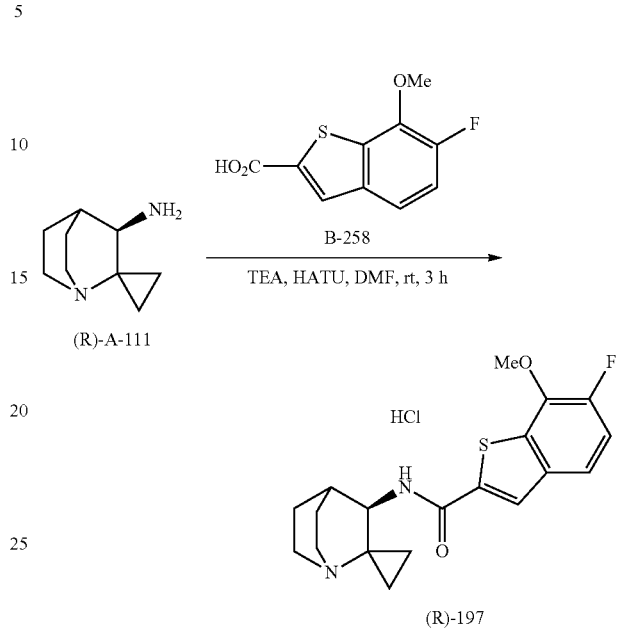

Following general procedure B, Compound (R)-197 was prepared from compound B-258 (74 mg, 0.33 mmol) and compound (R)-A-111 (50 mg, 0.33 mmol), with a reaction time of 3 hours. The product was purified by prep-HPLC [Instrument: GX-E; Column: Phenomenex Synergi C18 250×21.2 mm, particle size: 4 μm; Mobile phase: 25-55% acetonitrile in H$_2$O (add 0.05% HCl, v/v)] to give:

(R)-6-fluoro-7-methoxy-N-(1'-azaspiro[cyclopropane-1,2'-bicyclo[2.2.2]octan]-3'-yl)benzo[b]thiophene-2-carboxamide-hydrochloride (compound (R)-197) (55 mg, 42% yield) as a white solid: cSFC analytical (A) tR=2.27 min., purity: 100%; LCMS (GG): tR=1.936 min., 361.1 m/z (M+1); $^1$H-NMR (CD$_3$OD, 400 MHz): δ 8.11 (s, 1H), 7.60 (dd, J$_1$=8.4 Hz, J$_2$=4.0 Hz, 1H), 7.27 (dd, J$_1$=12 Hz, J$_2$=8.4 Hz, 1H), 4.56 (s, 1H), 4.12 (d, J=2.4 Hz, 3H), 3.71 (m, 1H), 3.57 (m, 1H), 3.49-3.39 (m, 2H), 2.44-2.32 (m, 2H), 2.22-2.16 (m, 2H), 2.00-1.95 (m, 1H), 1.40-1.34 (m, 1H), 1.27-1.17 (m, 3H).

Example 198: (R)-7-cyano-6-methyl-N-(1'-azaspiro[cyclopropane-1,2'-bicyclo[2.2.2]octan]-3'-yl)benzo[b]thiophene-2-carboxamide hydrochloride ((R)-198)

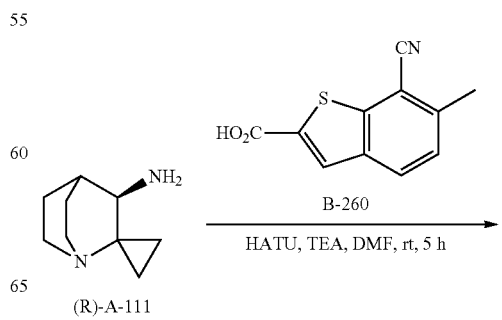

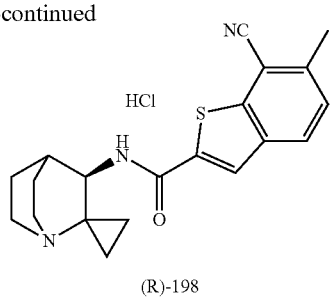

(R)-198

Following general procedure B, Compound (R)-198 was prepared from compound B-260 (64 mg, 0.30 mmol) and compound (R)-A-111 (45 mg, 0.30 mmol), with a reaction time of 5 hours. The product was purified by prep-HPLC [Instrument: GX-A; Column: Phenomenex Gemini C18 250×50 mm, particle size: 10 μm; Mobile phase: 34-64% acetonitrile in H$_2$O (add 0.05% NH$_3$H$_2$O, v/v)]. The resulting solid was dissolved in 0.2 M hydrochloric acid and again lyophilized to give:

(R)-7-cyano-6-methyl-N-(1'-azaspiro[cyclopropane-1,2'-bicyclo[2.2.2]octan]-3'-yl)benzo[b]thiophene-2-carboxamide-hydrochloride (compound (R)-198) (51 mg, 49% yield) as a white solid: cSFC analytical (A) tR=2.56 min., purity: 97.32%; LCMS (GG): tR=2.059 min., 352.1 m/z (M+1); $^1$H-NMR (CD$_3$OD, 400 MHz): δ 8.22 (s, 1H), 8.08 (d, J=8.0 Hz, 1H), 7.48 (d, J=8.0 Hz, 1H), 4.57 (d, J=2.4 Hz, 1H), 3.76-3.72 (m, 1H), 3.59-3.57 (m, 1H), 3.51-3.40 (m, 2H), 2.68 (s, 3H), 2.46-2.45 (m, 1H), 2.38-2.32 (m, 1H), 2.24-2.17 (m, 2H), 2.03-1.96 (m, 1H), 1.40-1.36 (m, 1H), 1.31-1.25 (m, 2H), 1.21-1.19 (m, 1H).

Example 199: (R)-7-(methoxymethyl)-N-(1'-azaspiro[cyclopropane-1,2'-bicyclo[2.2.2]octan]-3'-yl)benzo[b]thiophene-2-carboxamide hydrochloride ((R)-199)

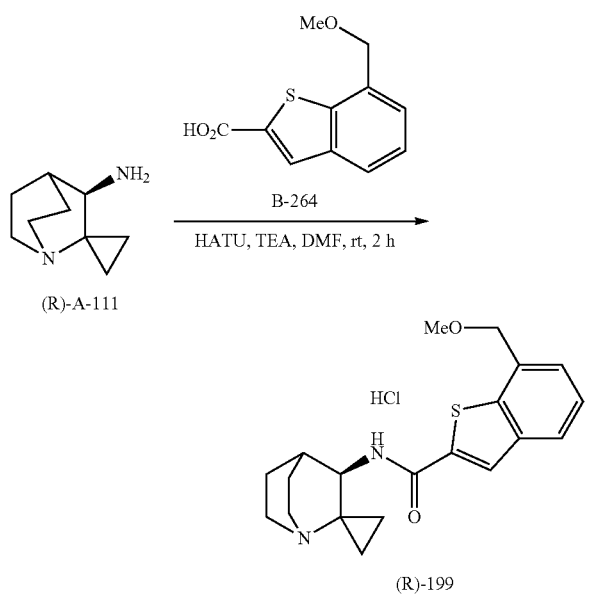

Following general procedure B, Compound (R)-199 was prepared from compound B-264 (0.11 g, 0.51 mmol) and compound (R)-A-111 (70 mg, 0.46 mmol), with a reaction time of 1 hour. The product was purified by prep-HPLC [Instrument: GX-E; Column: Agella Venusil ASB C18 150× 30 mm, particle size: 5 μm; Mobile phase: 27-57% acetonitrile in H$_2$O (add 0.5% HCl, v/v)] to give:

(R)-7-(methoxymethyl)-N-(1'-azaspiro[cyclopropane-1,2'-bicyclo[2.2.2]octan]-3'-yl)benzo[b]thiophene-2-carboxamide-hydrochloride (compound (R)-199) (98 mg, 60% yield) as a white solid: cSFC analytical (A) tR=2.88 min., purity: 99%; LCMS (Y): tR=2.265 min., 357.2 m/z (M+1); $^1$H-NMR (CD$_3$OD, 400 MHz): δ 8.59 (d, J=8.4 Hz, 1H), 8.17 (s, 1H), 7.92-7.89 (m, 1H), 7.48-7.45 (m, 2H), 4.77 (s, 2H), 4.60-4.59 (m, 1H), 3.77-3.72 (m, 1H), 3.61-3.60 (m, 1H), 3.51-3.50 (m, 2H), 3.43 (s, 3H), 2.47-2.39 (m, 1H), 2.36-2.33 (m, 1H), 2.26-2.20 (m, 2H), 2.19-1.98 (m, 1H), 1.37-1.22 (m, 4H).

Example 200: (R)-6-(methoxymethyl)-N-(1'-azaspiro[cyclopropane-1,2'-bicyclo[2.2.2]octan]-3'-yl)benzo[b]thiophene-2-carboxamide hydrochloride ((R)-200)

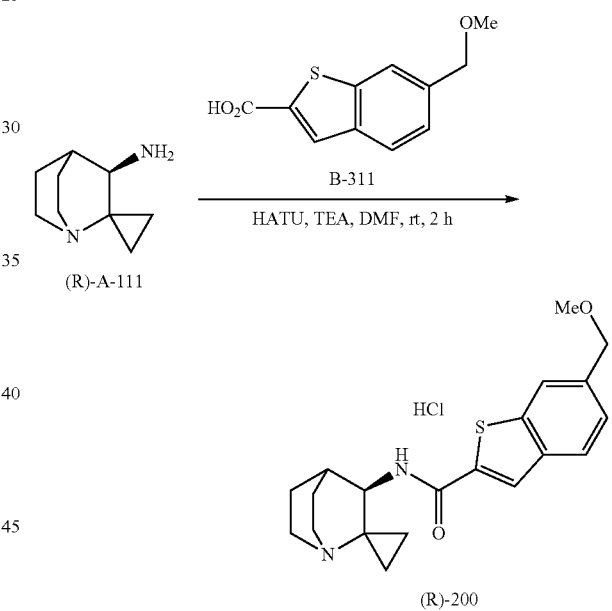

Following general procedure B, Compound (R)-200 was prepared from compound B-311 (96 mg, 0.43 mmol) and compound (R)-A-111 (60 mg, 0.39 mmol), with a reaction time of 5 hours. The product was purified by prep-HPLC [Instrument: GX-A; Column: Phenomenex Gemini C18 250×50 mm, particle size: 10 μm; Mobile phase: 31-61% acetonitrile in H$_2$O (add 0.05% ammonia, v/v)]. The resulting solid was dissolved in 0.2 M hydrochloric acid and lyophilized again to give:

(R)-6-(methoxymethyl)-N-(1'-azaspiro[cyclopropane-1, 2'-bicyclo[2.2.2]octan]-3'-yl)benzo[b]thiophene-2-carboxamide-hydrochloride (compound (R)-200) (75 mg, 39% yield) as a white solid: cSFC analytical (A) tR=2.64 min., purity: 98.75%; LCMS (FF): tR=2.253 min., 357.1 m/z (M+1); $^1$H-NMR (CD$_3$OD, 400 MHz): δ 8.18 (s, 1H), 7.93-7.91 (m, 2H), 7.43 (d, J=9.2 Hz, 1H), 4.60 (s, 2H), 4.58 (s, 1H), 3.76-3.74 (m, 1H), 3.59-3.57 (m, 1H), 3.52-3.43 (m, 5H), 2.46-2.45 (m, 1H), 2.37-2.34 (m, 1H), 2.24-2.18 (m, 2H), 2.01-1.97 (m, 1H), 1.42-1.39 (m, 1H), 1.34-1.25 (m, 2H), 1.21-1.18 (m, 1H).

Example 201: (R)—N-(1'-azaspiro[cyclopropane-1,2'-bicyclo[2.2.2]octan]-3'-yl)-3,4-dihydro-2H-thieno[3,2-h]chromene-8-carboxamide hydrochloride ((R)-201)

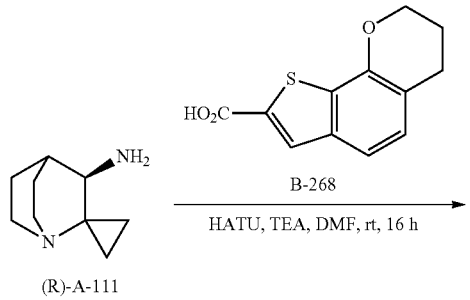

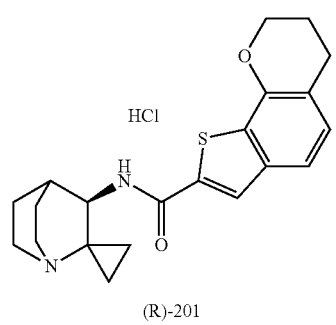

Following general procedure B, Compound (R)-201 was prepared from compound B-268 (92 mg, 0.39 mmol) and compound (R)-A-111 (60 mg, 0.39 mmol), with a reaction time of 16 hours. The product was purified by prep-HPLC [Instrument: GX-A; Column: Phenomenex Gemini C18 250*50 mm, particle size: 10 μm; Mobile phase: 36-66% acetonitrile in $H_2O$ (add 0.05% $NH_3H_2O$, v/v)]. The resulting solid was dissolved in 0.2 M hydrochloric acid and again lyophilized to give:

(R)—N-(1'-azaspiro[cyclopropane-1,2'-bicyclo[2.2.2]octan]-3'-yl)-3,4-dihydro-2H-thieno[3,2-h]chromene-8-carboxamide-hydrochloride (compound (R)-201) (40 mg, 28% yield) as a white solid: cSFC analytical (A) tR=3.18 min., purity: 94.85%; LCMS (GG): tR=1.978 min., (ES$^+$) m/z (M+H)$^+$=369.1; $^1$H-NMR (CD$_3$OD, 400 MHz): δ 8.06 (s, 1H), 7.41-7.39 (d, J=8.0 Hz, 1H), 7.17-7.15 (d, J=8.0 Hz, 1H), 4.58 (d, J=2.4 Hz, 1H), 4.38-4.36 (t, J=5.2 Hz, 2H), 3.73-3.70 (m, 1H), 3.60-3.59 (m, 1H), 3.52-3.43 (m, 2H), 2.94-2.91 (t, J=6.4 Hz, 2H), 2.46-2.45 (m, 1H), 2.38-2.35 (m, 1H), 2.24-2.19 (m, 2H), 2.15-2.11 (m, 2H), 2.10-1.97 (m, 1H), 1.41-1.35 (m, 1H), 1.28-1.19 (m, 3H).

Example 202: (R)-2-methyl-N-(1'-azaspiro[cyclopropane-1,2'-bicyclo[2.2.2]octan]-3'-yl)benzo[b]thiophene-6-carboxamide-hydrochloride ((R)-202)

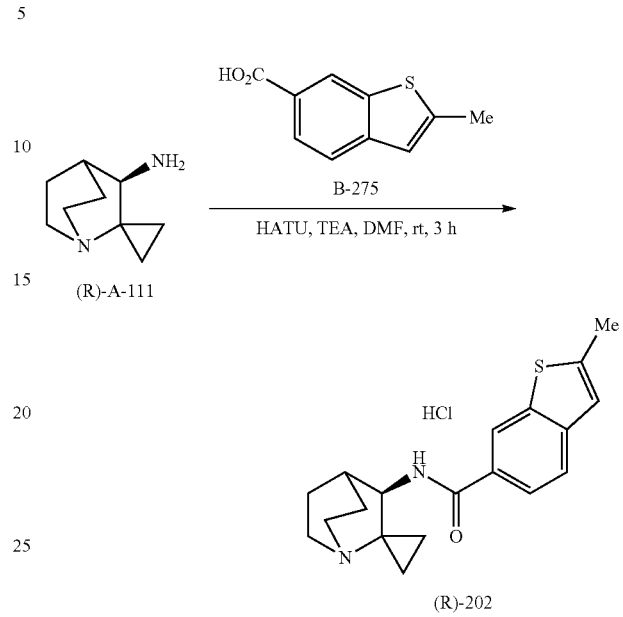

Following general procedure B, Compound (R)-202 was prepared from compound B-275 (63.13 mg, 0.33 mmol) and compound (R)-A-111 (50 mg, 0.33 mmol), with a reaction time of 3 hours. The product was purified by prep-HPLC [Instrument: GX-B; Column: Welch Ultimate AQ-C18 150× 30 mm, particle size: 5 μm; Mobile phase: 22-52% acetonitrile in $H_2O$ (add 0.1% TFA, v/v)]. The resulting solid was dissolved in 0.2 M hydrochloric acid and again lyophilized to give:

(R)-2-methyl-N-(1'-azaspiro[cyclopropane-1,2'-bicyclo[2.2.2]octan]-3'-yl)benzo[b]thiophene-6-carboxamide-hydrochloride (compound (R)-202) (50 mg, 22% yield) as a white solid: cSFC analytical (A) tR=2.42 min., purity: 100.00%; LCMS (GG): tR=1.970 min., 327.1 m/z (M+1); $^1$H-NMR (CD$_3$OD, 400 MHz): δ 8.32 (s, 1H), 7.78 (t, J=10 Hz, 1H), 7.15 (s, 1H), 4.60 (s, 1H), 3.74-3.51 (m, 2H), 3.50-3.41 (m, 2H), 2.65 (s, 3H), 2.47 (m, 1H), 2.36-2.16 (m, 3H), 2.03-2.00 (m, 1H), 1.40-1.21 (m, 4H).

Example 203: (R)-2-chloro-N-(1'-azaspiro[cyclopropane-1,2'-bicyclo[2.2.2]octan]-3'-yl)benzo[b]thiophene-6-carboxamide hydrochloride ((R)-203)

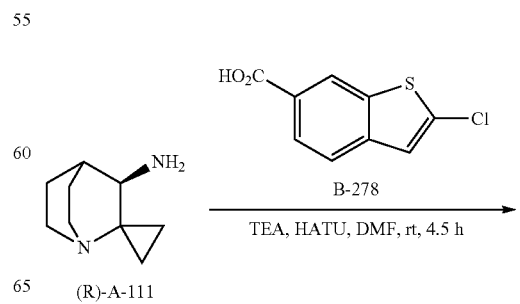

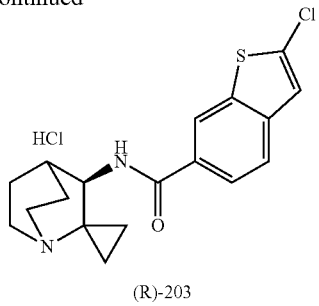

(R)-203

Following general procedure B, Compound (R)-203 was prepared from compound B-278 (70 mg, 0.33 mmol) and compound (R)-A-111 (50 mg, 0.33 mmol), with a reaction time of 4.5 hours. The product was purified by prep-HPLC [Instrument: GX-A; Column: Phenomenex Gemini C18 250*50 mm, particle size: 10 μm; Mobile phase: 38-68% acetonitrile in H₂O (add 0.05% NH₃H₂O, v/v)]. The resulting solids were dissolved in 0.2 M hydrochloric acid and again lyophilized to give:

(R)-2-chloro-N-(1'-azaspiro[cyclopropane-1,2'-bicyclo[2.2.2]octan]-3'-yl)benzo[b]thiophene-6-carboxamide hydrochloride ((R)-203) (45 mg, 39% yield) as a white solid: cSFC analytical (A) tR=2.47 min., purity: 99.28%; LCMS (FF): tR=2.342 min., 347.0 m/z (M+1); ¹H-NMR (CD₃OD, 400 MHz): δ 8.60-8.58 (d, J=8.0 Hz, 0.4H), 8.32 (s, 1H), 7.83 (s, 2H), 7.41 (s, 1H), 4.58 (s, 1H), 3.71-3.58 (m, 2H), 3.49-3.41 (m, 2H), 2.46 (s, 1H), 2.31-2.16 (m, 3H), 1.99-1.97 (m, 1H), 1.37-1.35 (m, 1H), 1.26-1.22 (m, 3H).

Example 204: (R)—N-(1'-azaspiro[cyclopropane-1,2'-bicyclo[2.2.2]octan]-3'-yl)-8,9-dihydro-7H-thieno[2,3-f]chromene-2-carboxamide hydrochloride ((R)-204)

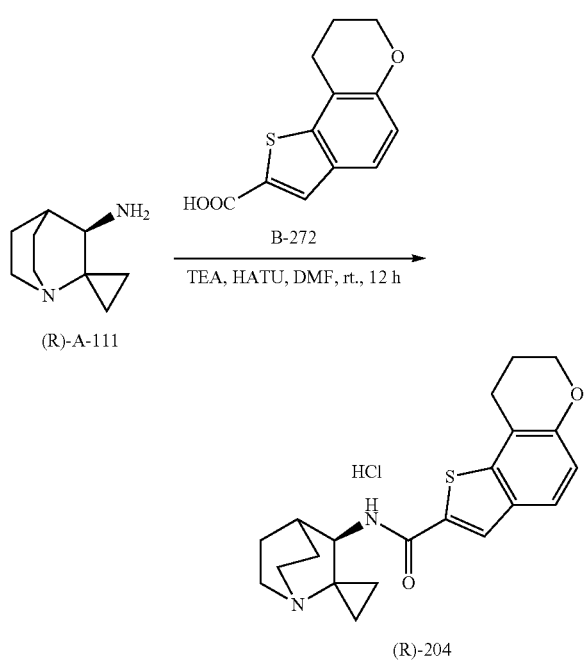

Following general procedure B, Compound (R)-204 was prepared from compound B-272 (77 mg, 0.33 mmol) and compound (R)-A-111 (50 mg, 0.33 mmol), with a reaction time of 12 hours. The product was purified by prep-HPLC [Instrument: GX-B; Column: Xtimate C18 150*25 mm, particle size: 5 μm; Mobile phase: 17-47% acetonitrile in H₂O (add 0.1% TFA, v/v)]. The resulting solid was dissolved in 0.2 M hydrochloric acid solution and again lyophilized to give:

(R)—N-(1'-azaspiro[cyclopropane-1,2'-bicyclo[2.2.2]octan]-3'-yl)-8,9-dihydro-7H-thieno[2,3-f]chromene-2-carboxamide-hydrochloride (compound (R)-204) (30 mg, 23% yield) as a yellow solid: cSFC analytical (A) tR=2.902 min., purity: 99.03%; LCMS (FF): tR=2.372 min., 369.1 m/z (M+1); ¹H-NMR (CD₃OD, 400 MHz): δ 8.09 (s, 1H), 7.66-7.64 (d, J=8.8 Hz, 1H), 6.94-6.92 (d, J=8.8 Hz, 1H), 4.58 (s, 1H), 4.29-4.26 (m, 2H), 3.74-3.73 (m, 1H), 3.59 (m, 1H), 3.52-3.41 (m, 2H), 2.88-2.85 (m, 2H), 2.36 (m, 1H), 2.33-2.23 (m, 1H), 2.21-2.14 (m, 4H), 2.04-2.01 (m, 1H), 1.39-1.37 (m, 1H), 1.28-1.20 (m, 3H).

Example 205: (R)-6-chloro-7-methyl-N-(1'-azaspiro[cyclopropane-1,2'-bicyclo[2.2.2]octan]-3'-yl)benzo[b]thiophene-2-carboxamide hydrochloride ((R)-205)

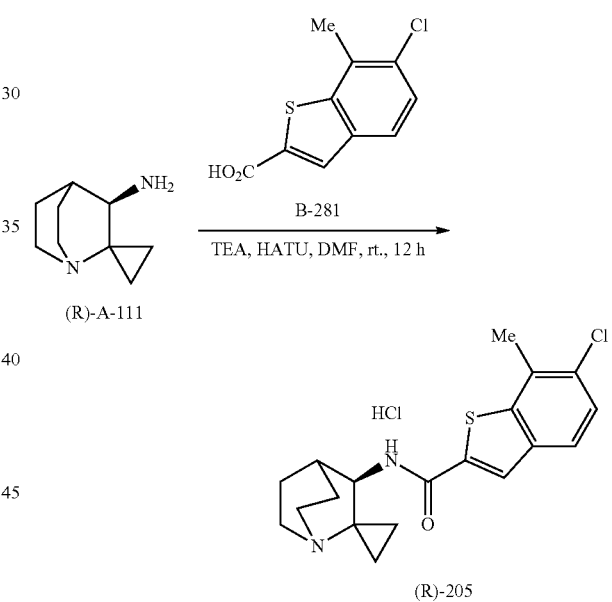

Following general procedure B, Compound (R)-205 was prepared from compound B-281 (82 mg, 0.33 mmol) and compound (R)-A-111 (50 mg, 0.33 mmol), with a reaction time of 12 hours. The product was purified by prep-HPLC [Instrument: GX-B; Column: Phenomenex Gemini C18 250*50 mm, particle size: 10 μm; Mobile phase: 41-71% acetonitrile in H2O (add 0.05% ammonia, v/v)]. The resulting solid was dissolved in 0.2 M hydrochloric acid solution and again lyophilized to give:

(R)-6-chloro-7-methyl-N-(1'-azaspiro[cyclopropane-1,2'-bicyclo[2.2.2]octan]-3' yl)benzo[b]thiophene-2-carboxamide-hydrochloride (compound (R)-205) (30 mg, 25% yield) as a white solid: cSFC analytical (A) tR=2.539 min., purity: 100.00%; LCMS (GG): tR=2.235 min., 361.1 m/z (M+1); ¹H-NMR (CD₃OD, 400 MHz): δ 8.17 (s, 1H), 7.78-7.75 (d, J=8.4 Hz, 1H), 7.49-7.47 (d, J=8.4 Hz, 1H), 4.60-4.58 (m, 1H), 3.74-3.73 (m, 1H), 3.59-3.46 (m, 3H), 2.62 (m, 3H), 2.47-2.46 (m, 1H), 2.36 (m, 1H), 2.26-2.20 (m, 3H), 2.18-2.00 (m, 1H), 1.39-1.37 (m, 1H), 1.30-1.20 (m, 3H).

Example 206

Following general procedure B, the following compounds listed in Table 2 were made in analogous fashion to the proceeding examples.

TABLE 2

| Compound | IUPAC Name | LCMS Conditions | LCMS tR (min.) | m/z (M + 1) |
|---|---|---|---|---|
| (S)-139 | (S)-N-(2,2-dimethylquinuclidin-3-yl)-1H-indazole-3-carboxamide hydrochloride | FF | 2.977 | 299.1 |
| (S)-194 | (S)-N-(1'-azaspiro[cyclopropane-1,2'-bicyclo[2.2.2]octan]-3'-yl)-1H-indazole-3-carboxamide hydrochloride | EE | 2.428 | 297.1 |
| (R)-206 | (R)-N-(2,2-dimethylquinuclidin-3-yl)-1-methyl-1H-benzo[d]imidazole-6-carboxamide hydrochloride | Q | 2.174 | 313.1 |
| (R)-207 | (R)-6-(tert-butyl)-N-(2,2-dimethylquinuclidin-3-yl)benzo[b]thiophene-2-carboxamide hydrochloride | B | 0.778 | 371.3 |
| (R)-208 | (R)-N-(2,2-dimethylquinuclidin-3-yl)-6-(1H-1,2,3-triazol-1-yl)benzo[b]thiophene-2-carboxamide hydrochloride | R | 0.728 | 382.1 |
| (R)-209 | (R)-N-(2,2-dimethylquinuclidin-3-yl)-6-(trifluoromethoxy)benzo[b]thiophene-2-carboxamide hydrochloride | B | 0.941 | 277.0 |
| (R)-210 | (R)-N-(2,2-dimethylquinuclidin-3-yl)-6-(oxetan-3-yl)benzo[b]thiophene-2-carboxamide | J | 1.274 | 317.2 |
| (R)-211 | (R)-N-(2,2-dimethylquinuclidin-3-yl)-6-fluoro-7-(trifluoromethyl)benzo[b]thiophene-2-carboxamide hydrochloride | A | 1.676 | 401.1 |
| (R)-212 | (R)-N-(2,2-dimethylquinuclidin-3-yl)-6-methoxy-7-(trifluoromethyl)benzo[b]thiophene-2-carboxamide hydrochloride | DD | 0.805 | 413.1 |
| (R)-213 | (R)-6-cyclopropyl-N-(2,2-dimethylquinuclidin-3-yl)-7-fluorobenzo[b]thiophene-2-carboxamide hydrochloride | M | 1.136 | 373.2 |
| (R)-214 | (R)-7-chloro-6-cyclopropyl-N-(2,2-dimethylquinuclidin-3-yl)benzo[b]thiophene-2-carboxamide hydrochloride | B | 0.770 | 389.1 |
| (R)-215 | (R)-N-(2,2-dimethylquinuclidin-3-yl)-2,3-dihydrobenzo[b][1,4]dioxine-6-carboxamide hydrochloride | M | 0.833 | 317.1 |
| (R)-216 | (R)-6-chloro-N-(2,2-dimethylquinuclidin-3-yl)benzofuran-2-carboxamide hydrochloride | H | 1.304 | 333.1 |
| (R)-217 | (R)-7-chloro-N-(2,2-dimethylquinuclidin-3-yl)benzofuran-2-carboxamide hydrochloride | M | 0.979 | 333.1 |
| (R)-218 | (R)-N-(2,2-dimethylquinuclidin-3-yl)benzo[d]oxazole-2-carboxamide | J | 1.196 | 300.2 |
| (R)-219 | (R)-N-(2,2-dimethylquinuclidin-3-yl)-1H-benzo[d]imidazole-2-carboxamide hydrochloride | CC | 0.867 | 299.1 |
| (R)-220 | (R)-N-(2,2-dimethylquinuclidin-3-yl)-1-methyl-1H-benzo[d]imidazole-2-carboxamide hydrochloride | J | 1.364 | 313.2 |
| (R)-221 | (R)-N-(2,2-dimethylquinuclidin-3-yl)-1-methyl-1H-indole-2-carboxamide hydrochloride | Y | 0.657 | 312.1 |
| (R)-222 | (R)-N-(2,2-dimethylquinuclidin-3-yl)thieno[2,3-c]pyridine-2-carboxamide hydrochloride | K | 0.702 | 316.1 |
| (R)-223 | (R)-3,4-dichloro-N-(2,2-dimethylquinuclidin-3-yl)benzamide hydrochloride | H | 1.214 | 327.1 |
| (R)-224 | (R)-N-(2,2-dimethylquinuclidin-3-yl)-4-methoxy-3-methylbenzamide hydrochloride | R | 0.637 | 303.2 |
| (R)-225 | (R)-N-(2,2-dimethylquinuclidin-3-yl)imidazo[1,2-a]pyrazine-6-carboxamide hydrochloride | M | 0.652 | 300.2 |
| (R)-226 | (R)-N-(2,2-dimethylquinuclidin-3-yl)-5,6-difluorobenzo[b]thiophene-2-carboxamide hydrochloride | GG | 2.348 | 351.1 |
| (R)-227 | (R)-N-(2,2-dimethylquinuclidin-3-yl)-7-(methylsulfonyl)benzo[b]thiophene-2-carboxamide hydrochloride | EE | 2.447 | 393.1 |
| (R)-228 | (R)-N-(2,2-dimethylquinuclidin-3-yl)-6-morpholinobenzo[b]thiophene-2-carboxamide hydrochloride | Z | 1.509 | 400.2 |
| (R)-229 | (R)-N-(2,2-dimethylquinuclidin-3-yl)quinoline-3-carboxamide hydrochloride | BB | 0.740 | 310.2 |
| (R)-230 | (R)-N-(2,2-dimethylquinuclidin-3-yl)quinoline-7-carboxamide hydrochloride | J | 1.14 | 310.2 |
| (R)-231 | (R)-N-(2,2-dimethylquinuclidin-3-yl)quinoline-6-carboxamide hydrochloride | M | 0.750 | 310.9 |
| (R)-232 | (R)-2-cyclopropyl-N-(2,2-dimethylquinuclidin-3-yl)benzofuran-5-carboxamide hydrochloride | BB | 0.913 | 339.2 |
| (R)-233 | (R)-N-(2,2-dimethylquinuclidin-3-yl)-7-(2-hydroxypropan-2-yl)benzo[b]thiophene-2-carboxamide | EE | 1.832 | 373.1 |
| (R)-234 | (R)-N-(2,2-dimethylquinuclidin-3-yl)-7-(1-(trifluoromethyl)cyclopropyl)benzo[b]thiophene-2-carboxamide hydrochloride | GG | 2.271 | 423.1 |
| (R)-235 | (R)-N-(2,2-dimethylquinuclidin-3-yl)-1H-indole-5-carboxamide | J | 1.091 | 298.2 |
| (R)-236 | (R)-6-cyclopropyl-N-(2,2-dimethylquinuclidin-3-yl)-7-methoxybenzo[b]thiophene-2-carboxamide hydrochloride | GG | 2.240 | 385.2 |
| (R)-237 | (R)-N-(2,2-dimethylquinuclidin-3-yl)benzo[d]isoxazole-5-carboxamide hydrochloride | EE | 2.411 | 314.1 |
| (R)-238 | (R)-N-(2,2-dimethylquinuclidin-3-yl)benzo[d]isoxazole-6-carboxamide hydrochloride | FF | 1.903 | 314.1 |
| (R)-239 | (R)-N-(2,2-dimethylquinuclidin-3-yl)-2,2-difluorobenzo[d][1,3]dioxole-5-carboxamide hydrochloride | EE | 2.680 | 339.1 |
| (R)-240 | (R)-N-(2,2-dimethylquinuclidin-3-yl)-1-methyl-1H-indazole-3-carboxamide hydrochloride | FF | 2.109 | 313.1 |
| (R)-241 | (R)-N-(2,2-dimethylquinuclidin-3-yl)benzo[d]isoxazole-3-carboxamide hydrochloride | FF | 2.006 | 300.1 |
| (R)-242 | (R)-N-(2,2-dimethylquinuclidin-3-yl)-1-methyl-1H-indole-5-carboxamide | FF | 2.025 | 312.2 |
| (R)-243 | (R)-N-(2,2-dimethylquinuclidin-3-yl)-1-methyl-1H-indole-6-carboxamide | FF | 2.049 | 312.1 |
| (R)-244 | (R)-6-(dimethylamino)-N-(2,2-dimethylquinuclidin-3-yl)benzo[b]thiophene-2-carboxamide hydrochloride | FF | 1.973 | 358.1 |
| (R)-245 | (R)-N-(2,2-dimethylquinuclidin-3-yl)-6-(methoxymethyl)benzo[b]thiophene-2-carboxamide hydrochloride | FF | 2.260 | 359.1 |
| (R)-246 | (R)-N-(2,2-dimethylquinuclidin-3-yl)-4,5,6,7-tetrahydrobenzo[b]thiophene-2-carboxamide hydrochloride | FF | 2.778 | 319.1 |
| (R)-247 | (R)-6-(tert-butyl)-N-(1'-azaspiro[cyclopropane-1,2'-bicyclo[2.2.2]octan]-3'-yl)benzo[b]thiophene-2-carboxamide hydrochloride | Z | 1.909 | 369.2 |
| (R)-248 | (R)-N-(1'-azaspiro[cyclopropane-1,2'-bicyclo[2.2.2]octan]-3'-yl)-6-(trifluoromethoxy)benzo[b]thiophene-2-carboxamide hydrochloride | H | 1.722 | 397.1 |
| (R)-249 | (R)-6-(oxetan-3-yl)-N-(1'-azaspiro[cyclopropane-1,2'-bicyclo[2.2.2]octan]-3'-yl)benzo[b]thiophene-2-carboxamide | J | 1.149 | 369.2 |
| (R)-250 | (R)-6-methoxy-N-(1'-azaspiro[cyclopropane-1,2'-bicyclo[2.2.2]octan]-3'-yl)-7-(trifluoromethyl)benzo[b]thiophene-2-carboxamide hydrochloride | DD | 0.805 | 411.1 |
| (R)-251 | (R)-7-chloro-6-cyclopropyl-N-(1'-azaspiro[cyclopropane-1,2'-bicyclo[2.2.2]octan]-3'-yl)benzo[b]thiophene-2-carboxamide hydrochloride | B | 0.764 | 387.1 |
| (R)-252 | (R)-N-(1'-azaspiro[cyclopropane-1,2'-bicyclo[2.2.2]octan]-3'-yl)-1H-benzo[d]imidazole-2-carboxamide hydrochloride | B | 0.975 | 297.1 |
| (R)-253 | (R)-1-methyl-N-(1'-azaspiro[cyclopropane-1,2'-bicyclo[2.2.2]octan]-3'-yl)-1H-benzo[d]imidazole-2-carboxamide hydrochloride | B | 0.553 | 311.2 |
| (R)-254 | (R)-1-methyl-N-(1'-azaspiro[cyclopropane-1,2'-bicyclo[2.2.2]octan]-3'-yl)-1H-indole-2-carboxamide hydrochloride | Y | 0.672 | 310.1 |
| (R)-255 | (R)-3,4-dichloro-N-(1'-azaspiro[cyclopropane-1,2'-bicyclo[2.2.2]octan]-3'-yl)benzamide hydrochloride | H | 1.200 | 325.0 |
| (R)-256 | (R)-4-methoxy-3-methyl-N-(1'-azaspiro[cyclopropane-1,2'-bicyclo[2.2.2]octan]-3'-yl)benzamide hydrochloride | R | 0.633 | 301.2 |
| (R)-257 | (R)-N-(1'-azaspiro[cyclopropane-1,2'-bicyclo[2.2.2]octan]-3'-yl)imidazo[1,2-a]pyrazine-6-carboxamide hydrochloride | M | 0.653 | 298.1 |
| (R)-258 | (R)-N-(1'-azaspiro[cyclopropane-1,2'-bicyclo[2.2.2]octan]-3'-yl)quinoline-3-carboxamide hydrochloride | BB | 0.740 | 308.1 |
| (R)-259 | (R)-N-(1'-azaspiro[cyclopropane-1,2'-bicyclo[2.2.2]octan]-3'-yl)quinoline-7-carboxamide hydrochloride | J | 0.980 | 308.2 |
| (R)-260 | (R)-N-(1'-azaspiro[cyclopropane-1,2'-bicyclo[2.2.2]octan]-3'-yl)quinoline-6-carboxamide hydrochloride | J | 0.960 | 308.2 |
| (R)-261 | (R)-N-(1'-azaspiro[cyclopropane-1,2'-bicyclo[2.2.2]octan]-3'-yl)-1H-indole-5-carboxamide | J | 0.968 | 296.2 |
| (R)-262 | (R)-6-cyclopropyl-7-methoxy-N-(1'-azaspiro[cyclopropane-1,2'-bicyclo[2.2.2]octan]-3'-yl)benzo[b]thiophene-2-carboxamide hydrochloride | EE | 3.018 | 383.1 |

TABLE 2-continued

| Compound | IUPAC Name | LCMS Conditions | LCMS tR (min.) | m/z (M + 1) |
|---|---|---|---|---|
| (R)-263 | (R)-N-(1'-azaspiro[cyclopropane-1,2'-bicyclo[2.2.2]octan]-3'-yl)benzo[d]isoxazole-5-carboxamide hydrochloride | EE | 2.361 | 312.1 |
| (R)-264 | (R)-N-(1'-azaspiro[cyclopropane-1,2'-bicyclo[2.2.2]octan]-3'-yl)benzo[d]isoxazole-6-carboxamide hydrochloride | FF | 1.901 | 312.1 |
| (R)-265 | (R)-2,2-difluoro-N-(1'-azaspiro[cyclopropane-1,2'-bicyclo[2.2.2]octan]-3'-yl)benzo[d][1,3]dioxole-5-carboxamide hydrochloride | EE | 2.668 | 337.1 |
| (R)-266 | (R)-1-methyl-N-(1'-azaspiro[cyclopropane-1,2'-bicyclo[2.2.2]octan]-3'-yl)-1H-indazole-3-carboxamide hydrochloride | FF | 2.079 | 311.1 |
| (R)-267 | (R)-N-(1'-azaspiro[cyclopropane-1,2'-bicyclo[2.2.2]octan]-3'-yl)benzo[d]isoxazole-3-carboxamide | EE | 2.423 | 299.1 |
| (R)-268 | (R)-1-methyl-N-(1'-azaspiro[cyclopropane-1,2'-bicyclo[2.2.2]octan]-3'-yl)-1H-indole-5-carboxamide | EE | 2.475 | 310.1 |
| (R)-269 | (R)-6-(dimethylamino)-N-(1'-azaspiro[cyclopropane-1,2'-bicyclo[2.2.2]octan]-3'-yl)benzo[b]thiophene-2-carboxamide hydrochloride | FF | 1.971 | 356.1 |
| (R)-270 | (R)-N-(1'-azaspiro[cyclopropane-1,2'-bicyclo[2.2.2]octan]-3'-yl)-4,5,6,7-tetrahydrobenzo[b]thiophene-2-carboxamide hydrochloride | FF | 2.259 | 317.1 |

Crystallization Experiments

Example 207: (R)-2,2-dimethyl-N—((R)-1-phenylethyl)quinuclidin-3-amine monofumarate ((R,R)-A-107 monofumarate)

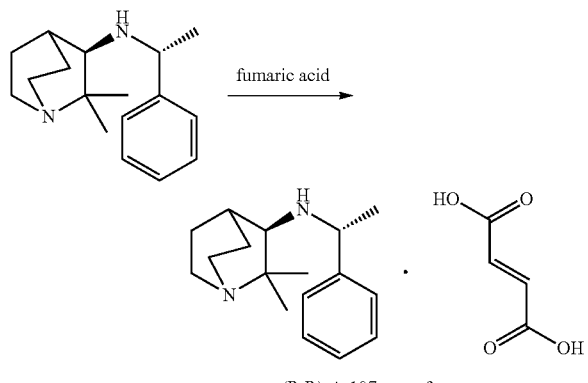

(R,R)-A-107 monofumarate

A solution of 2,2-dimethyl-N—((R)-1-phenylethyl)quinuclidin-3-amine (41 mg, 0.16 mmol, 1.6/98.4 mixture of diastereoisomers) in ethyl acetate was filtered through a 20 micron PTFE filter, concentrated and taken up in diethyl ether (4 mL). Next, a 0.8 M solution of fumaric acid in diethyl ether/methanol (9:1, v/v, 0.16 mmol, 2.0 mL) was added. An oily precipitate formed that turned into small needles. The mixture was concentrated and taken up in methanol (1 mL). Ethyl acetate (10 mL) was added, and the mixture was left to stand over weekend, during which time crystals formed. The solvent was decanted, and the crystals were washed with ethyl acetate (3×2 mL) and dried in vacuo to afford (R,R)-A-107 monofumarate (57 mg, 96% yield) as colorless crystals. 1H NMR (300 MHz, DMSO-$d_6$) δ 7.41-7.26 (m, 4H), 7.26-7.16 (m, 1H), 6.42 (s, 2H), 3.69 (q, J=6.5 Hz, 2H), 3.38-3.12 (m, 2H), 2.99-2.84 (m, 2H), 2.38-2.31 (m, 1H), 2.06-1.91 (m, 1H), 1.80-1.37 (m, 7H), 1.34 (s, 3H), 1.23 (d, J=6.6 Hz, 3H).

Single-crystal diffraction was performed on a Nonius KappaCCD single-crystal diffractometer using graphite monochromated Mo Kα radiation. During the measurement the crystal was cooled to −65° C. Diffraction images were integrated using Eval 14. Intensity data were corrected for Lorentz and polarization effects. A semi empirical multi scan absorption correction was applied (SADABS).

The structure was solved by SHELXT. This structure solution shows that the relative configuration of the bulk crystal is either (R,R) or (S,S) [and not (R,S) or (S,R)]. Refinement was performed with standard methods (refinement against F2 of all reflections with SHELXL97) with anisotropic displacement parameters for the non-hydrogen atoms. All hydrogen atoms were placed at calculated positions and refined riding on the parent atoms. The right enantiomer (the (R,R) versus the (S,S) form) was determined by careful examination of the Bijvoet pairs. This analysis showed that the vast majority of the crystal consists of the (R,R) form. Coordinate data from the X-ray analysis of the formed crystal of (R,R)-A-107 monofumarate are shown in Table 3, and its 3-D representation is shown in FIG. 1.

TABLE 3

X-ray Data:
Unit cell: 11.4272 12.7814 13.9040 90.000 90.000 90.000
Space group: P 21 21 21

| C1 | 0.382346 | 0.773501 | 0.978441 |
|---|---|---|---|
| H1 | 0.441086 | 0.824985 | 0.978134 |
| C2 | 0.389035 | 0.691661 | 1.042997 |
| H2 | 0.452287 | 0.687855 | 1.086078 |
| C3 | 0.303362 | 0.615194 | 1.044778 |
| H3 | 0.308259 | 0.559469 | 1.088714 |
| C4 | 0.210766 | 0.621504 | 0.981519 |
| H4 | 0.151757 | 0.570279 | 0.982616 |
| C5 | 0.204588 | 0.703345 | 0.916269 |
| H5 | 0.141569 | 0.706448 | 0.87291 |
| C6 | 0.289626 | 0.780722 | 0.913757 |
| C7 | 0.277321 | 0.871931 | 0.844143 |
| H7 | 0.227622 | 0.848412 | 0.789977 |
| C8 | 0.215153 | 0.963119 | 0.893086 |
| H8A | 0.260032 | 0.985387 | 0.948651 |
| H8B | 0.137825 | 0.941095 | 0.913533 |
| H8C | 0.208065 | 1.020869 | 0.848199 |
| N9 | 0.387075 | 0.91195 | 0.803634 |
| H09A | 0.428529 | 0.94322 | 0.851058 |
| C10 | 0.46518 | 0.834545 | 0.761719 |
| H10 | 0.464917 | 0.772012 | 0.803735 |
| C11 | 0.590972 | 0.877189 | 0.757592 |
| H11 | 0.610167 | 0.912196 | 0.819117 |
| C12 | 0.605827 | 0.954095 | 0.67511 |
| H12A | 0.68214 | 0.988741 | 0.679567 |
| H12B | 0.544643 | 1.007742 | 0.677811 |
| C13 | 0.596961 | 0.892436 | 0.580212 |
| H13A | 0.549106 | 0.93112 | 0.533774 |
| H13B | 0.67505 | 0.882408 | 0.552571 |
| N14 | 0.541888 | 0.788327 | 0.60147 |
| H14A | 0.525082 | 0.757863 | 0.544574 |
| C15 | 0.630396 | 0.723592 | 0.653638 |
| H15A | 0.696563 | 0.708187 | 0.611093 |
| H15B | 0.595231 | 0.657155 | 0.673706 |
| C16 | 0.673161 | 0.784434 | 0.742291 |
| H16A | 0.672575 | 0.738984 | 0.799054 |

TABLE 3-continued

X-ray Data:
Unit cell: 11.4272 12.7814 13.9040 90.000 90.000 90.000
Space group: P 21 21 21

| | | | |
|---|---|---|---|
| H16B | 0.753323 | 0.809268 | 0.731982 |
| C17 | 0.349716 | 0.877165 | 0.605596 |
| H17A | 0.271052 | 0.873601 | 0.631606 |
| H17B | 0.347983 | 0.859876 | 0.537681 |
| H17C | 0.38031 | 0.947384 | 0.613851 |
| C18 | 0.42793 | 0.799636 | 0.658441 |
| C19 | 0.367159 | 0.69317 | 0.659148 |
| H19A | 0.416303 | 0.642605 | 0.691936 |
| H19B | 0.353753 | 0.67037 | 0.593525 |
| H19C | 0.292837 | 0.698941 | 0.692432 |
| O20 | 0.534838 | 0.55045 | 0.500354 |
| O21 | 0.494626 | 0.700972 | 0.428969 |
| C22 | 0.508916 | 0.601753 | 0.429062 |
| C23 | 0.488106 | 0.548365 | 0.334472 |
| H23 | 0.44921 | 0.585217 | 0.28547 |
| C24 | 0.522344 | 0.451892 | 0.317715 |
| H24 | 0.565229 | 0.41667 | 0.365464 |
| C25 | 0.49606 | 0.396184 | 0.226392 |
| O26 | 0.544441 | 0.303217 | 0.223974 |
| H26 | 0.472243 | 0.766134 | 0.334473 |
| O27 | 0.437705 | 0.431251 | 0.163092 |

A large collection of crystals from the same batch was also analyzed with powder diffraction, in order to check the match between the crystal structure, obtained by single-crystal diffraction, with the characteristics of the whole batch of crystals. Powder diffraction was performed on a Bruker D8 Advance with a Vantec-1 detector with an effective angle of about 3 degrees with a step size of 0.0166 degrees. The pattern was measured in reflection mode in a Bragg-Brentano geometry using a Johansson monochromator with a focusing curved Ge 111 crystal. The diffraction pattern was measured at room temperature (20° C.) using monochromatic Cu Kalpha1 radiation in the range of 5-50 degrees 2theta with variable slits, resulting in a 12 mm constant footprint.

Combining SXRD and PXRD:

Using the data from single crystal diffraction a powder diffraction pattern was simulated with Cu Kalpha1 radiation in the range of 5-50 degrees 2theta with a step size of 0.02 degrees using Mercury software. Using the Bruker TOPAS software, for the calculated powder diffraction pattern the lattice cell parameters are adjusted to compensate for the temperature difference of Powder diffraction (20° C.) and the single crystal diffraction (−65° C.). Comparing the corrected calculated powder pattern with the measured powder pattern, we find an excellent fit leaving no measured diffraction peaks unassigned. Measuring extra diffraction peaks not corresponding to the corrected calculated powder pattern could indicate the presence of another chemical species/diastereomer [the (R,S) or (S,R) form]. If a significant/substantial amount of another diastereomer and/or species would be present, in a separate crystalline phase, this would most probably create new diffraction peaks, which we don't see. Therefore, there is no indication that a form different from the (R,R) form is present in the crystalline batch.

Example 208: (R)—N—((R)-1-phenylethyl)-1'-azaspiro[cyclopropane-1,2'-bicyclo[2.2.2]octan]-3'-amine bis(4-methylbenzenesulfonate) ((R,R)-A-113 bis(4-methylbenzenesulfonate))

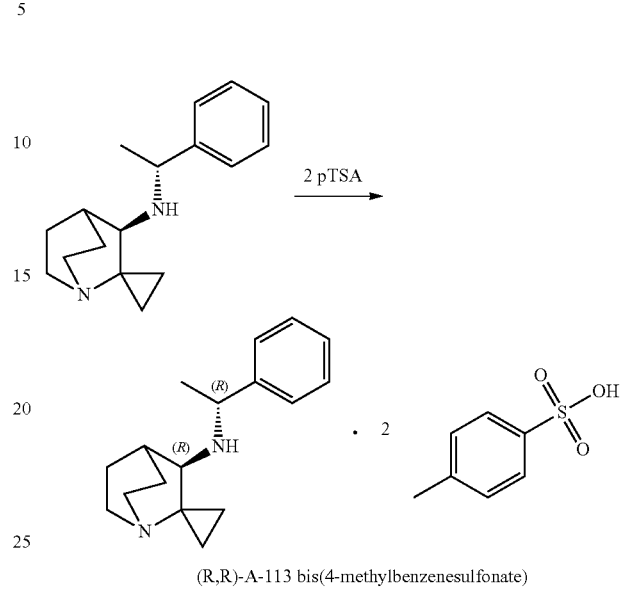

(R,R)-A-113 bis(4-methylbenzenesulfonate)

Figure 2:
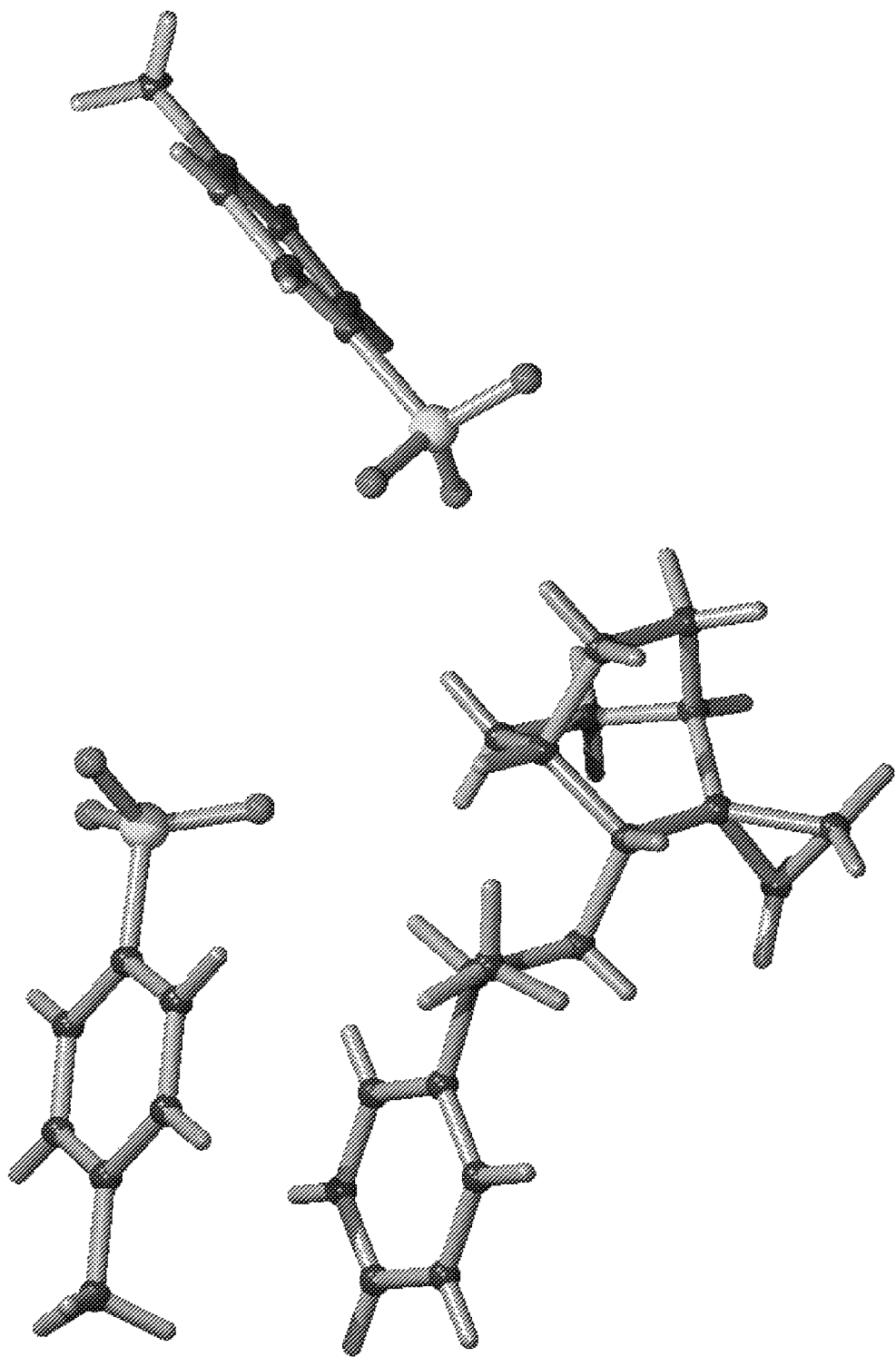
FIG. 2: Illustrates a 3-D representation of the formed crystal of (R)—N—((R)-1-phenylethyl)-1'-azaspiro[cyclopropane-1,2'-bicyclo[2.2.2]octan]-3'-amine bis(4-methylbenzenesulfonate).

To a solution of N—((R)-1-phenylethyl)-1'-azaspiro[cyclopropane-1,2'-bicyclo[2.2.2]octan]-3'-amine (100 mg, 0.39 mmol, 1.6/98.4 mixture of diastereoisomers) in ethyl acetate was added dropwise a solution of p-toluenesulfonic acid monohydrate (148 mg, 0.78 mmol). The resulting suspension was heated to reflux, and methanol was added until the precipitate had almost completely dissolved. The mixture was allowed to cool to room temperature and left to stand over weekend. The solvent was decanted, and the crystals were washed with ethyl acetate (5 mL) and dried in vacuo to afford compound (R,R)-A-113 bis(4-methylbenzenesulfonate) (180 mg, 77% yield) as colorless crystals. 1H NMR (300 MHz, DMSO-d6) δ 9.46 (br s, 1H), 9.14 (br s, 1H), 8.83 (br s, 1H), 7.64-7.53 (m, 2H), 7.53-7.37 (m, 7H), 7.19-7.10 (m, 4H), 4.60-4.38 (m, 1H), 3.91-3.72 (m, 1H), 3.61-3.21 (m, 4H), 2.72-2.58 (m, 1H), 2.30 (s, 6H), 2.08-1.80 (m, 4H), 1.53 (d, J=6.3 Hz, 3H), 1.47-1.02 (m, 4H). Single crystal X-ray analysis of (R,R)-A-113 bis(4-methylbenzenesulfonate) was performed by the same technique as in Example 108. This analysis showed the absolute configuration to be (R,R) form. Coordinate data from the X-ray analysis of the formed crystal are shown in Table 4, and its 3-D representation is shown in FIG. 2.

TABLE 4

X-ray Data:
Unit cell: 6.3474 7.2244 16.0360 86.00 81.74 83.81
Space group: P1

| | | | |
|---|---|---|---|
| C01 | 0.804341 | −0.177254 | 0.629535 |
| H01A | 0.698687 | −0.24098 | 0.606455 |
| H01B | 0.811861 | −0.205502 | 0.689765 |
| C02 | 1.008041 | −0.143845 | 0.573222 |
| H02A | 1.139692 | −0.151702 | 0.599133 |
| H02B | 1.026515 | −0.187182 | 0.51582 |
| C03 | 0.842241 | 0.015315 | 0.594449 |
| N04 | 0.71927 | 0.085105 | 0.524742 |
| H04 | 0.689495 | −0.019784 | 0.499645 |
| C05 | 0.84014 | 0.219849 | 0.466007 |
| H05A | 0.754593 | 0.270618 | 0.421916 |

TABLE 4-continued

X-ray Data:
Unit cell: 6.3474 7.2244 16.0360 86.00 81.74 83.81
Space group: P1

| | | | |
|---|---|---|---|
| H05B | 0.974034 | 0.156197 | 0.438879 |
| C06 | 0.888221 | 0.378212 | 0.517515 |
| H06A | 1.042812 | 0.374087 | 0.51816 |
| H06B | 0.839124 | 0.498969 | 0.491477 |
| C07 | 0.502405 | 0.176995 | 0.559251 |
| H07A | 0.423689 | 0.088676 | 0.597585 |
| H07B | 0.419399 | 0.216624 | 0.512973 |
| C08 | 0.534685 | 0.345601 | 0.606488 |
| H08A | 0.461284 | 0.334961 | 0.664456 |
| H08B | 0.473046 | 0.459735 | 0.578721 |
| C09 | 0.773988 | 0.356413 | 0.60767 |
| H09 | 0.794689 | 0.463512 | 0.639888 |
| C10 | 0.875901 | 0.1761 | 0.647124 |
| H10 | 1.031592 | 0.185032 | 0.643218 |
| N11 | 0.788382 | 0.142702 | 0.738391 |
| H11A | 0.65707 | 0.09706 | 0.743984 |
| H11B | 0.865823 | 0.052082 | 0.759138 |
| C12 | 0.77872 | 0.308263 | 0.793704 |
| H12 | 0.675254 | 0.408674 | 0.774181 |
| C13 | 0.996841 | 0.381607 | 0.784542 |
| H13A | 0.998788 | 0.466616 | 0.828587 |
| H13B | 1.024981 | 0.446913 | 0.729781 |
| H13C | 1.106018 | 0.278118 | 0.789409 |
| C14 | 0.696056 | 0.245364 | 0.883823 |
| C15 | 0.478603 | 0.272261 | 0.911931 |
| H15 | 0.383874 | 0.324746 | 0.874724 |
| C16 | 0.832113 | 0.168243 | 0.939809 |
| H16 | 0.979931 | 0.149786 | 0.921508 |
| C17 | 0.754286 | 0.118007 | 1.022058 |
| H17 | 0.848507 | 0.064564 | 1.059281 |
| C18 | 0.400266 | 0.222081 | 0.994679 |
| H18 | 0.252585 | 0.23986 | 1.013349 |
| C19 | 0.53849 | 0.14626 | 1.049525 |
| H19 | 0.485334 | 0.113759 | 1.105808 |
| S40 | 0.498256 | 0.69953 | 0.398074 |
| O41 | 0.363831 | 0.556807 | 0.432234 |
| O42 | 0.5702 | 0.794389 | 0.463747 |
| O43 | 0.670496 | 0.637166 | 0.336137 |
| C44 | 0.335563 | 0.873233 | 0.346304 |
| C45 | 0.148375 | 0.832254 | 0.320669 |
| H45 | 0.102025 | 0.71279 | 0.332608 |
| C46 | 0.3997 | 1.050889 | 0.329127 |
| H46 | 0.527559 | 1.07927 | 0.346229 |
| C47 | 0.028371 | 0.968926 | 0.276979 |
| H47 | −0.097946 | 0.939998 | 0.25878 |
| C48 | 0.277841 | 1.186772 | 0.287149 |
| H48 | 0.321841 | 1.307173 | 0.277075 |
| C49 | 0.091987 | 1.146817 | 0.259878 |
| C50 | −0.041675 | 1.298321 | 0.215853 |
| H50A | −0.091455 | 1.397477 | 0.253841 |
| H50B | −0.163659 | 1.246965 | 0.199416 |
| H50C | 0.044225 | 1.347845 | 0.166019 |
| S55 | 0.29597 | 0.82788 | 0.785536 |
| O56 | 0.062941 | 0.851015 | 0.792039 |
| O57 | 0.393757 | 0.673164 | 0.736701 |
| O58 | 0.385583 | 1.00313 | 0.756908 |
| C60 | 0.3539 | 0.773904 | 0.889816 |
| C61 | 0.191446 | 0.767955 | 0.956468 |
| H61 | 0.048387 | 0.79671 | 0.947195 |
| C62 | 0.56471 | 0.732661 | 0.903811 |
| H62 | 0.676677 | 0.737724 | 0.858718 |
| C63 | 0.238985 | 0.719703 | 1.03692 |
| H63 | 0.127138 | 0.715798 | 1.082109 |
| C64 | 0.608063 | 0.684134 | 0.984687 |
| H64 | 0.751042 | 0.655036 | 0.99401 |
| C65 | 0.447722 | 0.677031 | 1.052338 |
| C66 | 0.50188 | 0.626002 | 1.140419 |
| H66A | 0.607394 | 0.704208 | 1.152632 |
| H66B | 0.559396 | 0.496191 | 1.144137 |
| H66C | 0.373575 | 0.644888 | 1.180964 |

Example 209

Human α7 nAChR Binding Assay

The ability of compounds to displace binding of radioactive ligands from human α7 nAChR was determined, as a measure of the affinity of the compounds for these ligand-gated ion channels. The [$^{125}$I]-αBungarotoxin competition binding assay was performed under contract by Cerep Poitiers, France following published the methods (Sharpies et al., J Neurosci. 2000; 20(8):2783-91). "SH-SY5Y cells stably expressing human α7 nicotinic acetylcholine receptors, grown to confluency in 175 cm$^2$ flasks, were washed briefly with warm PBS containing (in mm): (150 NaCl, 8 K$_2$HPO$_4$, 2 KH$_2$PO$_4$, pH 7.4, 37° C.) and scraped into cold phosphate buffer. Cells were washed by centrifugation for 3 min at 500×g and resuspended in 10 mL of ice-cold phosphate buffer. The suspension was homogenized for 10 sec using an Ultraturax and centrifuged for 30 min at 45,000×g. The pellet was resuspended in phosphate buffer (0.5 mL per original flask). SH-SY5Y membranes (30 μg protein) were incubated in a total volume of 2 mL in 50 mM phosphate buffer with 0.05 nM [$^{125}$I]-αBgt and serial dilutions of test compound. Nonspecific binding was determined in the presence of α-bungarotoxin (1 μM). Samples were incubated for 120 min at 37° C. The reaction was terminated by filtration through Whatman GFA/E filter paper (presoaked overnight in 0.3% polyethyleneimine in PBS), using a Brandel Cell Harvester. Each condition was measured in duplicate. Filters were counted for radioactivity using a scintillation counter. The results were expressed as a percent inhibition of control specific binding obtained in the presence of the test compounds where Inhibition (%)=100−[(measured specific binding/control specific binding)×100].

The IC$_{50}$ values (concentration causing a half-maximal inhibition of control specific binding) and Hill coefficients (nH) were determined by non-linear regression analysis of the competition curves generated with mean replicate values using Hill equation:

$$Y = D + \left[\frac{A - D}{1 + (C/C_{50})^{nH}}\right]$$

where Y=specific binding, A=left asymptote of the curve, D=right asymptote of the curve, C=compound concentration, C$_{50}$=IC$_{50}$, and nH=slope factor.

This analysis was performed using software developed at Cerep (Hill software) and validated by comparison with data generated by the commercial software SigmaPlot® 4.0 for Windows® (© 1997 by SPSS Inc.). The inhibition constants (K$_i$) were calculated using the Cheng Prusoff equation:

$$K_i = \frac{IC_{50}}{(1 + L/K_D)}$$

where L=concentration of radioligand in the assay, and KD=affinity of the radioligand for the receptor.

A scatchard plot is used to determine the K$_d$. Results are provided in Table 5 (reported as h-α7 Ki (μM)).

[$^3$H]BRL 43694 Competition Binding (h-5HT$_3$ Ki (μM))

[$^3$H]BRL 43694 competition binding assay was performed under contract by Cerep Poitiers, France following the methods described in Hope, A. G et al., "*Characterization of a human 5-hydroxytryptamine*3 *receptor type A*

(h5-HT3R-AS) subunit stably expressed in HEK 293 cells," Brit. J. Pharmacol., (1996) 118: 1237-1245.

In brief, Chinese Hamster Ovary (CHO) cells stably expressing human 5-HT$_3$ serotonin receptors, grown to confluence in 175 cm$^2$ flasks. Following aspiration of the culture medium, cells were harvested by mechanical agitation in ice cold PBS containing (in mM): (150 NaCl, 8 K$_2$HPO$_4$, 2 KH$_2$PO$_4$, pH 7.4, 37° C.), centrifuged at 4,000 g for 10 min and subsequently stored as a cell pellet at −80 C. When required, the pellet was thawed and resuspended in ice cold homogenization buffer (Tris 50 mM, EGTA 5.0 mM, phenylmethylsulphonylfluoride 0.1 mM, pH 7.6) and homogenized. The homogenate was centrifuged at 48,000 g for 10 minutes at 40° C. The resulting pellet was resuspended in ice cold binding buffer comprising (in mM): NaCl 140, KCl 2.8, CaCl$_2$ 1.0; MgCl$_2$, 2.0; HEPES 10 (pH 7.4) and centrifuged as above. The pellet was resuspended in ice cold binding buffer and the protein concentration was determined by the method of Lowry et al., "Protein measurement with the Folin phenol reagent," J. Biol. Chem., (1953) 193, 265-275). The membrane homogenate was adjusted to a protein concentration of approximately 600 mg/mL in binding buffer. Assay tubes were loaded with equal volumes of binding buffer containing [$^3$H]BRL 43694 and test compound and 0.5 mL of membrane homogenate in a total reaction volume of 1 ml. Binding was initiated by the addition of the membrane homogenate and allowed to proceed for 120 min. at room temperature. Bound and free radioligand were separated by the addition of 3 ml of ice-cold binding buffer and immediate vacuum filtration through pre-soaked (0.1% (v/v) polyethyleneimine) Whatman GF/B filters. Filters were washed with a further 2×3 mL applications of binding buffer and counted for radioactivity using a scintillation counter.

The results were expressed as a percent inhibition of control specific binding obtained in the presence of the test compounds where Inhibition (%)=100−[(measured specific binding/control specific binding)×100].

The IC$_{50}$ values (concentration causing a half-maximal inhibition of control specific binding) and Hill coefficients (nH) were determined by non-linear regression analysis of the competition curves generated with mean replicate values using Hill equation $$Y = D + \left[ \frac{A - D}{1 + (C/C_{50})^{nH}} \right]$$

where Y=specific binding, A=left asymptote of the curve, D=right asymptote of the curve, C=compound concentration, C$_{50}$=IC$_{50}$, and nH=slope factor. This analysis was performed using software developed at Cerep (Hill software) and validated by comparison with data generated by the commercial software SigmaPlot® 4.0 for Windows® (© 1997 by SPSS Inc.).

The inhibition constants (K$_i$) were calculated using the Cheng Prusoff equation $$K_i = \frac{IC_{50}}{(1 + L/K_D)}$$

where L=concentration of radioligand in the assay, and KD=affinity of the radioligand for the receptor.

A scatchard plot is used to determine the K$_d$. Results are provided in Table 5 (reported as h-5HT$_3$ Ki (uM)).

Oocyte Electrophysiology Screen (% ACh @ 10 μM Oocyte)

The Oocyte Electrophysiology Screen studies were performed under contract by HiQScreen Geneva, Switzerland. All experiments were carried out at human α7 nAChRs transiently expressed in *Xenopus laevis* oocytes using the method of cDNA expression. Currents evoked by acetylcholine or other agonist ligands were recorded using the standard two-electrode voltage-clamp configuration (TEVC). *X. laevis* oocytes were prepared and injected using standard procedures. Briefly, ovaries were harvested from *X. laevis* females that were deeply anesthetized and pithed following the animal rights rule from the Geneva canton. A small piece of ovary was isolated for immediate preparation while the remaining part was placed at 4° C. in a sterile Barth solution containing in mM: NaCl 88, KCl 1, NaHCO$_3$ 2.4, HEPES 10, MgSO$_4$.7H2O 0.82, Ca(NO$_3$)$_2$.4H$_2$O 0.33, CaCl$_2$.6H$_2$O 0.41, at pH 7.4, and supplemented with 20 μg/mL of kanamycin, 100 unit/mL penicillin and 100 μg/mL streptomycin. On the second day following dissociation, oocytes were injected with 2 ng of cDNA per oocyte containing the gene encoding human α7 nicotinic acetylcholine receptor subunits using an automated injector (Hogg et al., 2008). All recordings were performed at 18° C. and cells were superfused with OR2 medium containing in mM: NaCl 82.5, KCl 2.5, HEPES 5, CaCl$_2$.2H$_2$O 2.5, pH 7.4. Cells were held at −80 mV. Data were filtered at 10 Hz, captured at 100 Hz and analyzed using proprietary data acquisition and analysis software running under Matlab (Mathworks Inc.).

Experimental Protocol and Analysis

After establishing a baseline transmembrane current, acetylcholine (ACh) was applied for 5 seconds at a concentration of 0.2 mM to establish a control ACh-evoked current response. Following a wash period of 90 s in OR2 medium (free of ACh), cells were then exposed for 30 s to the test compound applied at 0.01 mM. The same reference ACh test pulse was immediately given at the end of the compound exposure and again after 90 s of recovery in OR2 Medium (free of ACh or test compound). All data were determined in triplicate. The response evoked by the test compound was expressed as a percentage of that evoked by ACh:

Response (% ACh)=100×(I$_{test}$/I$_{ACh}$)

where I$_{test}$ is the peak inward current measured during exposure to 0.01 mM of test compound and I$_{ACh}$ is the peak inward current measured in the presence of ACh.

Results are provided in Table 5 (reported as % ACh @ 10 μM Oocyte).

TABLE 5

| Compound | h-a7 Ki (μM) | h-5HT$_3$ Ki (μM) | % ACh @ 10 μM Oocyte |
|---|---|---|---|
| 1a | 0.27 | 0.66 | 1470 |
| (R)-1 | 0.27 | | 401 |
| 1b | | 0.34 | 2 |
| 2a | 3.9 | >10 | 246 |
| 2b | | | 2 |
| (R)-3 | 0.11 | 0.27 | 304 |
| (S)-3 | 3.8 | | 22 |
| (R)-4 | 0.24 | 0.87 | 1060 |
| (S)-4 | 6.7 | | 17 |
| (R)-5 | 0.62 | 1.9 | 282 |
| (S)-5 | 14 | | 9 |
| (R)-6 | 0.925 | >10 | 374 |
| (S)-6 | >30 | | 2 |
| (R)-7 | 0.3 | 3.4 | 466 |
| (S)-7 | 14 | | 2 |

TABLE 5-continued

| Compound | h-a7 Ki (µM) | h-5HT₃ Ki (µM) | % ACh @ 10 µM Oocyte |
|---|---|---|---|
| (R)-8 | 0.83 | 6.5 | 480 |
| (S)-8 | 22 | | 1 |
| (R)-9 | 17 | >10 | 2 |
| (S)-9 | >30 | | 1 |
| (R)-10 | 23 | >10 | 1 |
| (S)-10 | >30 | | 1 |
| (R)-11 | 0.41 | 1.7 | 552 |
| (S)-11 | 11 | | 9 |
| (R)-12 | 0.495 | >10 | 765 |
| (S)-12 | 10 | | 3 |
| (R)-13 | 3 | 2.1 | 132 |
| (S)-13 | >30 | | 3 |
| (R)-14 | 25 | >10 | 3 |
| (S)-14 | >30 | | 3 |
| (R)-15 | 0.38 | >10 | 539 |
| (S)-15 | 14 | | 3 |
| (R)-16 | 3.5 | 2.5 | 74 |
| (S)-16 | >30 | | 2 |
| (R)-17 | >30 | >10 | 0 |
| (S)-17 | >30 | | 1 |
| (R)-18 | 0.355 | >10 | 422 |
| (S)-18 | 16 | | 1 |
| (R)-19 | 1.2 | 1.6 | 149 |
| (S)-19 | >30 | | 3 |
| (R)-20 | 0.33 | >10 | 558 |
| (S)-20 | 14 | | 5 |
| (R)-21 | 6.7 | | 73 |
| (S)-21 | >30 | | 1 |
| (R)-22 | 0.39 | 6.5 | 456 |
| (S)-22 | 10 | | 25 |
| (R)-23 | 9.6 | >10 | 82 |
| (S)-23 | >30 | | 0 |
| (R)-24 | 1.1 | 0.82 | 240 |
| (R)-25 | 9.8 | | 7 |
| (R)-26 | 1.1 | | 687 |
| (R)-27 | >30 | | 0 |
| (S)-27 | >30 | | 0 |
| (R)-28 | 5 | >10 | 321 |
| (S)-28 | >30 | | 1 |
| (R)-29 | 3 | | 448 |
| (S)-29 | >30 | | 2 |
| (R)-30 | 0.94 | 2.3 | 396 |
| (R)-31 | 3.1 | | 294 |
| (R)-32 | 11 | | 61 |
| (R)-33 | >30 | | 6 |
| (R)-34 | 4.6 | | 159 |
| (R)-35 | 7.5 | | 6 |
| (R)-36 | >30 | >10 | 1 |
| (R)-37 | >30 | | 5 |
| (R)-38 | 1.3 | | 339 |
| (R)-39 | 0.59 | | 697 |
| (R)-40 | 1.1 | | 517 |
| (R)-41 | 0.64 | | 384 |
| (R)-42 | >30 | | 0 |
| (R)-43 | 0.48 | 1.5 | 951 |
| (R)-44 | >30 | | 1 |
| (R)-45 | >30 | | 1 |
| (R)-46 | 0.46 | >10 | 301 |
| (R)-47 | 14 | | 1 |
| (R)-48 | >30 | >10 | 0 |
| (R)-49 | 0.55 | | 576 |
| (R)-50 | >30 | | 0 |
| (R)-51 | 1.7 | >10 | 326 |
| (R)-52 | 0.18 | 0.64 | 844 |
| (R)-53 | 0.38 | 5.9 | 576 |
| 54a | 20 | 0.44 | 4.5 |
| 54b | 0.061 | 0.39 | 1319 |
| 55a | | | 3 |
| 55b | 1.9 | >10 | 176 |
| 56a | 0.037 | 0.048 | 1231 |
| 56b | | | 0 |
| 57a | 0.075 | 0.11 | 386 |
| 57b | 11 | | 4 |
| 58a | 0.11 | 0.91 | 235 |
| 58b | | | 5 |
| 59a | 0.25 | 6.5 | 823 |
| (R)-59 | 0.4 | 6.8 | 374 |
| 59b | | | 27 |
| 60a | 0.098 | 1.01 | 501 |
| 60b | 21 | | 1 |
| 61a | 0.22 | 1.5 | 1493 |
| 61b | | | 1 |
| 62a | 6.6 | | 35 |
| 62b | 0.1 | 3.5 | 995 |
| 63a | | | 3 |
| 63b | | | 3 |
| 64a | 0.2 | 0.42 | 511 |
| 64b | | | 1 |
| 65a | 0.18 | >10 | 682 |
| 65b | 20 | | 1 |
| 66a | 3.1 | | 2 |
| 66b | 3.3 | 0.88 | 29 |
| 67a | >30 | | 1 |
| 67b | 14 | >10 | 1 |
| 68a | 0.18 | >10 | 769 |
| 68b | 4.6 | | 5 |
| 69a | 2.6 | 1.3 | 162 |
| 69b | >30 | | 1 |
| 70a | 16 | 3.2 | 2 |
| 70b | >30 | | 1 |
| 71a | 0.21 | >10 | 739 |
| 71b | >30 | | 2 |
| 72a | 0.89 | 1.5 | 188 |
| 72b | 16 | | 1 |
| 73a | 0.12 | >10 | 1036 |
| 73b | 21 | | 1 |
| 74a | 8.2 | 1.3 | 32 |
| 74b | 20 | | 4 |
| (R)-75 | 0.25 | 3.3 | 594 |
| (S)-75 | 11 | | 14 |
| (R)-76 | | >10 | 129 |
| (S)-76 | >30 | | 1 |
| (R)-77 | 0.76 | 0.66 | 547 |
| (R)-78 | 6.3 | 2.1 | 31 |
| (R)-79 | 0.24 | 0.75 | 758 |
| (R)-80 | >30 | | 0 |
| (S)-80 | >30 | | 2 |
| (R)-81 | 1.5 | | 449 |
| (S)-81 | >30 | | 1 |
| (R)-82 | 1.1 | | 239 |
| (S)-82 | >30 | | 2 |
| (R)-83 | 0.32 | 2.4 | 558 |
| (R)-84 | 1.3 | 4.7 | 341 |
| (R)-85 | 4.3 | >10 | 188 |
| (R)-86 | 15 | >10 | 67 |
| (R)-87 | 0.77 | | 341 |
| (R)-88 | 6.4 | | 133 |
| (R)-89 | >30 | | 0 |
| (R)-90 | 20 | | 3 |
| (R)-91 | 0.49 | >10 | 653 |
| (R)-92 | 0.33 | >10 | 532 |
| (R)-93 | 0.42 | | 516 |
| (R)-94 | 0.31 | 1.6 | 812 |
| (R)-95 | >30 | >10 | 0 |
| (R)-96 | 18 | | 0 |
| (R)-97 | 0.4 | 0.43 | 816 |
| (R)-98 | >30 | | 3 |
| (R)-99 | >30 | >10 | 1 |
| (R)-100 | 21 | | 1 |
| (R)-101 | 0.25 | >10 | 412 |
| (R)-102 | 10 | | 1 |
| (R)-103 | >30 | | 2 |
| (R)-104 | 7.9 | | 20 |
| (R)-105 | 20 | >10 | 2 |
| (R)-106 | 0.15 | >10 | 572 |
| (R)-107 | 3 | >10 | 414 |
| (R)-108 | 1.6 | | |
| (R)-109 | 0.11 | 4 | 432 |
| (R)-110 | 0.34 | >10 | 444 |
| (R)-111 | 0.5 | >10 | |
| (R)-112 | 1.2 | | 234 |
| (R)-113 | 0.71 | >10 | |
| (R)-114 | 0.42 | 0.62 | 703 |
| (R)-115 | 0.55 | | 215 |

TABLE 5-continued

| Compound | h-a7 Ki (μM) | h-5HT$_3$ Ki (μM) | % ACh @ 10 μM Oocyte |
|---|---|---|---|
| (R)-116 | 0.31 | 0.6 | 963 |
| (R)-117 | 1 | | |
| (R)-118 | 0.14 | 0.23 | |
| (R)-119 | 0.5 | | |
| (R)-120 | 0.52 | | |
| (R)-121 | 1.1 | | |
| (R)-122 | 1.1 | | |
| (R)-123 | 0.75 | >10 | |
| (R)-124 | 1.6 | | |
| (R)-125 | 1.1 | >10 | |
| (R)-126 | 0.14 | 0.17 | |
| (R)-127 | 0.505 | 1.1 | |
| (R)-128 | 1.6 | | |
| (R)-129 | 0.32 | 0.44 | |
| (R)-130 | 0.52 | | |
| (R)-131 | 0.63 | | |
| (R)-132 | 0.25 | 0.1 | |
| (R)-133 | 1.4 | 0.4 | |
| (R)-134 | 1.4 | | |
| (R)-135 | 0.58 | | |
| (R)-136 | 0.45 | | |
| (R)-137 | 0.55 | | |
| (R)-138 | 0.56 | | |
| (R)-139 | 0.57 | | |
| (S)-139 | 7.9 | | |
| (R)-140 | 0.38 | 22 | |
| (R)-141 | 0.57 | | |
| (R)-142 | 0.64 | | |
| (R)-143 | 0.155 | 0.74 | |
| (R)-144 | 0.81 | | |
| (R)-145 | 0.18 | | |
| (R)-146 | 0.57 | | |
| (R)-147 | 0.55 | | |
| (R)-148 | 0.092 | | |
| (R)-149 | 0.79 | >10 | 195 |
| (R)-150 | 0.0545 | 2.2 | 443 |
| (R)-151 | 0.24 | >10 | 409 |
| (R)-152 | 0.31 | >10 | |
| (R)-153 | 1.6 | | 114 |
| (R)-154 | 0.8 | 6.2 | |
| (R)-155 | 0.78 | >10 | 513 |
| (R)-156 | 0.16 | 0.3 | 403 |
| (R)-157 | 0.67 | | |
| (R)-158 | 0.2 | 0.37 | 180 |
| (R)-159 | 1.2 | >10 | 24 |
| (R)-160 | 0.11 | 0.26 | |
| (R)-161 | 0.058 | 0.66 | 493 |
| (R)-162 | 0.79 | | |
| (R)-163 | 0.86 | 2 | 446 |
| (R)-164 | 0.73 | | 266 |
| (R)-165 | 0.036 | 0.2 | |
| (R)-166 | 0.6233 | 0.325 | |
| (R)-167 | 0.28 | 0.895 | |
| (R)-168 | 1.2 | | |
| (R)-169 | 1.3 | | |
| (R)-170 | 0.81 | 0.8 | |
| (R)-171 | 0.9 | | |
| (R)-172 | 0.4452 | 4.9 | |
| (R)-173 | 0.565 | >10 | |
| (R)-174 | 1.1 | | |
| (R)-175 | 0.31 | >10 | |
| (R)-176 | 0.13 | 0.13 | |
| (R)-177 | 0.315 | 0.69 | |
| (R)-178 | 0.78 | 0.4 | |
| (R)-179 | 2.3 | | |
| (R)-180 | 1.1 | | |
| (R)-181 | 0.147 | 0.083 | |
| (R)-182 | 1.5 | | |
| (R)-183 | 0.62 | >10 | |
| (R)-184 | 0.48 | 0.11 | |
| (R)-185 | 1.4 | | |
| (R)-186 | 0.31 | 0.03 | |
| (R)-187 | 2.5 | | |
| (R)-188 | 0.54 | 0.2 | |
| (R)-189 | 1.2 | >10 | |
| (R)-190 | 0.2 | 0.29 | |
| (R)-191 | 0.22 | 0.16 | |
| (R)-192 | 0.22 | >10 | |
| (R)-193 | 0.3 | 6 | |
| (R)-194 | 0.35 | 0.079 | |
| (S)-194) | 14 | | |
| (R)-195 | 1.5 | | |
| (R)-196 | 0.24 | 0.61 | |
| (R)-197 | 0.16 | 2.8 | |
| (R)-198 | 0.19 | >10 | |
| (R)-199 | 0.42 | 0.58 | |
| (R)-200 | 1.8 | | |
| (R)-201 | 0.15 | 3.6 | |
| (R)-202 | 0.16 | | |
| (R)-203 | 0.29 | 2.3 | |
| (R)-204 | 0.1 | >10 | |
| (R)-205 | 0.047 | 2.6 | |
| (R)-206 | >30 | | 0 |
| (R)-207 | >30 | | |
| (R)-208 | >30 | | 0 |
| (R)-209 | 9.8 | | 1 |
| (R)-210 | >30 | | |
| (R)-211 | 3.6 | | 100 |
| (R)-212 | 8.4 | | |
| (R)-213 | 2.7 | | 60 |
| (R)-214 | 2.5 | | |
| (R)-215 | 12 | | 86 |
| (R)-216 | 4 | | 184 |
| (R)-217 | 3 | 1.1 | 473 |
| (R)-218 | 2.7 | | |
| (R)-219 | 15 | | |
| (R)-220 | >30 | | |
| (R)-221 | 5.4 | | 188 |
| (R)-222 | 5.4 | | |
| (R)-223 | 4.9 | | |
| (R)-224 | >30 | | |
| (R)-225 | >30 | | |
| (R)-226 | 2.7 | | |
| (R)-227 | 5.9 | | |
| (R)-228 | 3.5 | | |
| (R)-229 | >30 | | |
| (R)-230 | 19 | | |
| (R)-231 | >30 | | |
| (R)-232 | 2.2 | | |
| (R)-233 | 2.2 | | |
| (R)-234 | 2.9 | | |
| (R)-235 | 6.9 | | |
| (R)-236 | 6.5 | | |
| (R)-237 | >30 | | |
| (R)-238 | >30 | | |
| (R)-239 | >30 | | |
| (R)-240 | >30 | | |
| (R)-241 | 12 | | |
| (R)-242 | >30 | | |
| (R)-243 | 2 | | |
| (R)-244 | 8 | | |
| (R)-245 | 4.4 | | |
| (R)-246 | >30 | | |
| (R)-247 | >30 | | |
| (R)-248 | 8.2 | | 1 |
| (R)-249 | 11 | | |
| (R)-250 | 7.6 | | |
| (R)-251 | 3.4 | | |
| (R)-252 | 8.7 | | |
| (R)-253 | 20 | | |
| (R)-254 | 2.2 | | 447 |
| (R)-255 | 2 | | |
| (R)-256 | >30 | | |
| (R)-257 | >30 | | |
| (R)-258 | >30 | | |
| (R)-259 | 12 | | |
| (R)-260 | >30 | | |
| (R)-261 | 4 | | |
| (R)-262 | 2.6 | >10 | |
| (R)-263 | 19 | | |
| (R)-267 | >30 | | |
| (R)-265 | >30 | | |
| (R)-266 | >30 | | |
| (R)-267 | 9.6 | | |

TABLE 5-continued

| Compound | h-a7 Ki (µM) | h-5HT$_3$ Ki (µM) | % ACh @ 10 µM Oocyte |
|---|---|---|---|
| (R)-268 | 10 | | |
| (R)-269 | 6.9 | | |
| (R)-270 | 12 | | |

Example 210

Novel Object Recognition Task:

The Novel Object Recognition (NOR) task is a behavioral assay commonly used to evaluate cognition, particularly recognition memory, in rodent models of CNS disorders. This test is based on the spontaneous tendency of rodents to spend more time exploring a novel object compared to a familiar one. The choice to explore the novel object reflects the use of learning and recognition memory. The assay is commonly used to evaluate potential therapeutic agents for Alzheimer's disease, other neurodegenerative diseases and psychiatric disorders.

Procedure:

Male Wistar rats (Harlan Laboratories) weighing 350-400 grams were housed under a reversed light cycle and are tested during the dark cycle. Testing was done under low lux conditions, measured to be ~2-7 lux under red light. Animals were habituated and weighed one day prior to testing. During habituation, animals were placed in a cylindrical arena and allowed to explore for 3 minutes. Training (T1) was conducted approximately 24 hours later, with one set of identical objects placed on opposite sides of the arena. Animals were allowed to explore the objects in 3-minute sessions. Animals were dosed with a designated treatment 15-60 minutes prior to testing depending on the pharmacokinetic profile of the compound before the start of T1. Drug or vehicle was dosed subcutaneously based on body weight at 5 mL/kg. Testing (T2) was done at 48 hours after T1. During testing, one familiar object is replaced with a novel object. Animals were allowed to explore both objects in 3-minute sessions.

Equipment Specification:

Animals were tracked using Noldus Ethovision XT (EthoVision XT version: 8.5, Noldus Inc. Wageningen, Netherlands) tracking software, using a 2 centimeter (cm) perimeter for each object as a separate zone. The test arena consisted of a cylinder, 80 cm diameter with 40 cm high walls of black acrylic that was opaque and matte. Objects were custom fabricated shapes (cone and bullet) similar in overall size (8 cm high×8 cm diameter) and were counterbalanced between treatment groups.

Data Analysis and Statistics:

Contact time was defined as the amount of time (seconds) an animal spent within the 2 cm perimeter of an object. All animals that had <5 seconds total contact time were excluded from the study. Statistical significance was determined using a Mann Whitney U-test and the criterion was set at p<0.05.

Results:

Natural forgetting in an object recognition task in male Wistar rats (n=8-27/group). Test compound was administered via sub-cutaneous administration 30 minutes before T1. Test compounds improved object recognition using a 48-hour retention interval (mean±SEM). *p<0.05=novel (N) vs. familiar (F) object. Results are illustrated in Table 6.

TABLE 6

| Compound | Active doses (mg/kg) |
|---|---|
| 54b | 0.003, 0.01 |
| 65a | 0.3 |
| 68a | 0.001 |
| 71a | 0.01, 0.03 |
| 73a | 0.0003, 0.003 |
| (R)-1 | 0.03, 0.3, 1.0 |
| (R)-12 | 30 |
| (R)-22 | 0.0001, 0.0003, 0.003 |
| (R)-106 | 0.03, 0.1 |

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A geminal substituted quinuclidine amide compound represented by Formula (I):

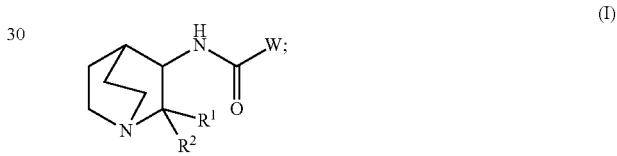

wherein:
R$^1$ and R$^2$ independently represent a branched or unbranched C$_1$-C$_4$-alkyl radical; or the C(R$^1$)(R$^2$) moiety forms a (3-4 membered)-carbocycle, wherein R$^1$ and R$^2$ taken together represent a C$_2$-C$_3$-alkyl di-radical; wherein the C$_1$-C$_4$-alkyl radical and the C$_2$-C$_3$-alkyl di-radical may be substituted with up to 4 radical substituents comprising: -D, —F, —Cl, —Br, —I, —CN, CH$_3$, CH$_2$CH$_3$, =O, —OR$^3$, or —OCF$_3$;
R$^3$ independently represents —H; a branched or unbranched C$_1$-C$_4$-alkyl radical; C$_3$-C$_4$-cycloalkyl radical; wherein the C$_1$-C$_4$-alkyl radical and the C$_3$-C$_4$-cycloalkyl radical may be substituted with up to 4 radical substituents comprising: -D, —F, —Cl, —Br, —I, —CN, =O, —OH, —OC$_1$-C$_4$-alkyl or —OCF$_3$; and
W represents a moiety represented by ring system M-I, M-II, M-III, M-IV, M-V, or M-VI:

-continued

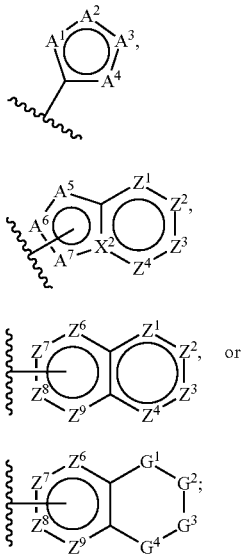

M-III

M-IV

M-V or

M-VI wherein:

$Z^1$, $Z^2$, $Z^3$, $Z^4$, and $Z^5$ independently represent N or $CR^4$; with the proviso that no more than two of $Z^1$, $Z^2$, $Z^3$, $Z^4$, and $Z^5$ are N;

$R^4$ independently represents —H; -D; —F; —Cl; —Br; —I; —CN; —NO$_2$; —OR$^5$; —N(R$^5$)(R$^6$); —SO$_2$(CH$_2$)$_m$ R$^5$; —(CO)(CH$_2$)$_m$R$^5$; —(CO)N(R$^5$)(R$^6$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; or when adjacent members of $Z^1$, $Z^2$, $Z^3$, $Z^4$, and $Z^5$, is (CR$^4$)(CR$^4$), the (CR$^4$)(CR$^4$) may form a cycle such that the adjacent $R^4$ substituents taken together represents a (3-6 membered)-heteroalkyl di-radical with at least one ring atom of the (3-6 membered)-heteroalkyl di-radical selected from the group consisting of oxygen, nitrogen, and sulfur, with the proviso that when the at least one ring atom is nitrogen, the nitrogen is substituted with —H, a branched or unbranched $C_1$-$C_4$-alkyl radical, a $C_3$-$C_4$-cycloalkyl radical, —(CO)-branched or unbranched $C_1$-$C_4$-alkyl, or —(SO$_2$)-branched or unbranched $C_1$-$C_4$-alkyl, wherein the $C_1$-$C_4$-alkyl radical and the $C_3$-$C_4$-cycloalkyl radical may be substituted with up to 4 radical substituents comprising: -D, halogen, =O, —OH, —OC$_1$-$C_4$-alkyl or —OCF$_3$, and with the further proviso that when the at least one ring atom is sulfur, the sulfur may substituted with 0 or 2=O; wherein the $C_1$-$C_6$-alkyl radical, the (3-6 membered)-heterocycloalkyl radical, the aryl radical, the heteroaryl radical, and the alkyl portion of the (3-6 membered)-heteroalkyl di-radical, may be substituted with up to 4 radical substituents comprising: -D, —F, —Cl, —Br, —I, —CN, —NO$_2$, —OR$^5$, —(CH$_2$)$_m$OR$^5$, —N(R$^5$)(R$^6$), —(CH$_2$)$_m$N(R$^5$)(R$^6$), —SO$_2$(CH$_2$)$_m$R$^5$, —(CO)(CH$_2$)$_m$R$^5$, —(CO)N(R$^5$)(R$^6$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^5$ and $R^6$ independently represent —H; a branched or unbranched $C_1$-$C_6$-alkyl radical; a $C_3$-$C_6$-cycloalkyl radical; or the N(R$^5$)(R$^6$) moiety forms a cycle, wherein $R^5$ and $R^6$ taken together represent a $C_2$-$C_6$-alkyl di-radical or a (3-6 membered)-heteroalkyl di-radical;

$Z^6$, $Z^7$, $Z^8$, and $Z^9$ independently represent N or $CR^7$; with the proviso that no more than two of $Z^6$, $Z^7$, $Z^8$, and $Z^9$ are N;

$R^7$ independently represents —H; -D; —F; —Cl; —Br; —I; —CN; —NO$_2$; —OR$^8$; —N(R$^8$)(R$^9$); —SO$_2$(CH$_2$)$_m$ R$^8$; —(CO)(CH$_2$)$_m$R$^8$; —(CO)N(R$^8$)(R$^9$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^8$, —(CH$_2$)$_m$OR$^8$, —N(R$^8$)(R$^9$), —(CH$_2$)$_m$N(R$^8$)(R$^9$), —SO$_2$(CH$_2$)$_m$R$^8$, —(CO)(CH$_2$)$_m$R$^8$, —(CO)N(R$^8$)(R$^9$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^8$ and $R^9$ independently represent —H; a branched or unbranched $C_1$-$C_6$-alkyl radical; a $C_3$-$C_6$-cycloalkyl radical; or the N(R$^8$)(R$^9$) moiety forms a cycle, wherein $R^8$ and $R^9$ taken together represent a $C_2$-$C_6$-alkyl di-radical or a (3-6 membered)-heteroalkyl di-radical;

$X^1$ independently represents N or C;

$A^1$, $A^2$, $A^3$ and $A^4$ independently represent N; NR$^{10}$; N(CH$_2$)$_m$R$^{10}$; O; S; or CR$^{11}$; with the proviso that only one $A^1$, $A^2$, $A^3$ and $A^4$ is NR$^{10}$, O, or S; with the further proviso that when $X^1$ is N, then $A^1$, $A^2$, and $A^3$ independently represent N or CR$^{11}$;

$R^{10}$ independently represents —H; -D; —SO$_2$(CH$_2$)$_m$R$^{12}$; —(CO)(CH$_2$)$_m$R$^{12}$; —(CO)N(R$^{12}$)(R$^{13}$); a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —NO$_2$, —OR$^{12}$, —(CH$_2$)$_m$OR$^{12}$, —N(R$^{12}$)(R$^{13}$), —(CH$_2$)$_m$N(R$^{12}$)(R$^{13}$), —SO$_2$(CH$_2$)$_m$R$^{12}$, —(CO)(CH$_2$)$_m$R$^{13}$, —(CO)N(R$^{12}$)(R$^{13}$), —OCF$_3$, a branched or unbranched $C_1$-$C_6$-alkyl radical, a $C_3$-$C_6$-cycloalkyl radical, a $C_1$-$C_6$-hydroxyalkyl radical, or a $C_1$-$C_6$-haloalkyl radical;

$R^{11}$ independently represents —H; -D; —F; —Cl; —Br; —I; —CN; —NO$_2$; —OR$^{12}$; —N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$); —OCF$_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —NO$_2$; —OR$^{12}$; —(CH$_2$)$_m$OR$^{12}$; —N(R$^{12}$)(R$^{13}$); —(CH$_2$)$_m$N(R$^{12}$)(R$^{13}$); —SO$_2$(CH$_2$)$_m$R$^{12}$; —(CO)(CH$_2$)$_m$R$^{12}$; —(CO)N(R$^{12}$)(R$^{13}$); —OCF$_3$; a branched or unbranched $C_1$-$C_6$-alkyl radical, a $C_3$-$C_6$-cycloalkyl radical, or a $C_1$-$C_6$-haloalkyl radical;

$R^{12}$ and $R^{13}$ independently represent —H; a branched or unbranched $C_1$-$C_6$-alkyl radical; a $C_3$-$C_6$-cycloalkyl radical; or the N(R$^{12}$)(R$^{13}$) moiety forms a cycle, wherein $R^{12}$ and $R^{13}$ taken together represent a $C_2$-$C_6$-alkyl di-radical or a (3-6 membered)-heteroalkyl di-radical;

$X^2$ independently represents N or C;

$A^5$, $A^6$, and $A^7$ independently represent N; $NR^{14}$; $N(CH_2)_m R^{14}$; O; S; or $CR^{15}$; with the proviso that only one $A^5$, $A^6$, and $A^7$ is $NR^{14}$, O, or S; with the further proviso that when $X^2$ is N, then $A^5$, $A^6$, and $A^7$ independently represent N or $CR^{15}$;

$R^{14}$ independently represents —H; -D; —$(CH_2)_m N(R^{16})(R^{17})$; —$SO_2(CH_2)_m R^{16}$; —$(CO)(CH_2)_m R^{16}$; —$(CO)N(R^{16})(R^{17})$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^{16}$, —$(CH_2)_m OR^{16}$, —$N(R^{16})(R^{17})$, —$(CH_2)_m N(R^{16})(R^{17})$, —$SO_2(CH_2)_m R^{16}$, —$(CO)(CH_2)_m R^{16}$, —$(CO)N(R^{16})(R^{17})$, —$OCF_3$, a branched or unbranched $C_1$-$C_6$-alkyl radical, a $C_3$-$C_6$-cycloalkyl radical, or a $C_1$-$C_6$-haloalkyl;

$R^{15}$ independently represents —H; -D; —F; —Cl; —Br; —I; —CN; —$NO_2$; —$OR^{16}$; —$N(R^{16})(R^{17})$; —$SO_2(CH_2)_m R^{16}$; —$(CO)(CH_2)_m R^{16}$; —$(CO)N(R^{16})(R^{17})$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; a heteroaryl radical; or the bond directly attaching the W moiety with the carbonyl moiety; wherein the $C_1$-$C_6$-alkyl radical, the (3-6 membered)-heterocycloalkyl radical, the aryl radical, and the heteroaryl radical may be substituted with up to 4 radical substituents comprising: -D; —F; —Cl; —Br; —I; —CN; —$NO_2$; —$OR^{16}$; —$(CH_2)_m OR^{16}$; —$N(R^{16})(R^{17})$; —$(CH_2)_m N(R^{16})(R^{17})$; —$SO_2(CH_2)_m R^{16}$; —$(CO)(CH_2)_m R^{16}$; —$(CO)N(R^{16})(R^{17})$; —$OCF_3$; a branched or unbranched $C_1$-$C_6$-alkyl radical, a $C_3$-$C_6$-cycloalkyl radical, or a $C_1$-$C_6$-haloalkyl radical;

$R^{16}$ and $R^{17}$ independently represent —H; a branched or unbranched $C_1$-$C_6$-alkyl radical; a $C_3$-$C_6$-cycloalkyl radical; or the $N(R^{16})(R^{17})$ moiety forms a cycle, wherein $R^{16}$ and $R^{17}$ taken together represent a $C_2$-$C_6$-alkyl di-radical or a (3-6 membered)-heteroalkyl di-radical;

$G^1$, $G^2$, $G^3$, and $G^4$ independently represent $C(R^{18})(R^{18})$; $N(R^{19})$; —$N(CH_2)_m R^{18}$; O; S; $SO_2$; or (C=O); with the proviso that no more than two of $G^1$, $G^2$, $G^3$, and $G^4$ represent $N(R^{19})$; —$N(CH_2)_m R^{18}$, O; S; $SO_2$; or (C=O);

$R^{18}$ independently represents —H; -D; —F; —Cl; —Br; —I; —CN; —$NO_2$; —$OR^{19}$; —$N(R^{19})(R^{20})$; —$SO_2(CH_2)_m R^{19}$; —$(CO)(CH_2)_m R^{19}$; —$(CO)N(R^{19})(R^{20})$; —$OCF_3$; a $C_1$-$C_6$-alkyl radical; a $C_1$-$C_6$-haloalkyl radical; a $C_3$-$C_6$-cycloalkyl radical; a (3-6 membered)-heterocycloalkyl radical; an aryl radical; or a heteroaryl radical; wherein the $C_1$-$C_6$-alkyl radical, the (3-6 membered)-heterocycloalkyl radical, the aryl radical, and the heteroaryl radical may be substituted with up to 4 radical substituents comprising: -D, —F, —Cl, —Br, —I, —CN, —$NO_2$, —$OR^{19}$, —$(CH_2)_m OR^{19}$, —$N(R^{19})(R^{20})$, —$(CH_2)_m N(R^{19})(R^{20})$, —$SO_2(CH_2)_m R^{19}$, —$(CO)(CH_2)_m R^{19}$, —$(CO)N(R^{19})(R^{20})$, —$OCF_3$, a branched or unbranched $C_1$-$C_6$-alkyl radical, a $C_3$-$C_6$-cycloalkyl radical, or a $C_1$-$C_6$-haloalkyl radical; and $R^{19}$ and $R^{20}$ independently represent —H; a branched or unbranched $C_1$-$C_6$-alkyl radical; a $C_3$-$C_6$-cycloalkyl radical; or the $N(R^{19})(R^{20})$ moiety forms a cycle, wherein $R^{19}$ and $R^{20}$ taken together represent a $C_2$-$C_6$-alkyl di-radical or a (3-6 membered)-heteroalkyl di-radical; or the $C(R^{19})(R^{20})$ moiety forms a cycle, wherein $R^{19}$ and $R^{20}$ taken together represent a $C_2$-$C_6$-alkyl di-radical or a (3-6 membered)-heteroalkyl di-radical;

m independently represents an integer from 1 to 6;

or a pharmaceutically acceptable salt thereof.

2. The compound of claim 1, wherein W represents the moiety represented by the ring system M-II.

3. The compound of claim 2, wherein M-II represents a moiety represented by ring system M-II-1:

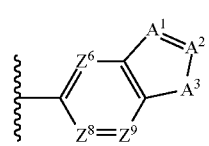

M-II-1 wherein:

$Z^6$, $Z^8$, and $Z^9$ independently represent $CR^7$;
$A^1$ and $A^2$ independently represent N or $CR^{11}$; and
$A^3$ represents $NR^{10}$; O; or S.

4. The compound of claim 2, wherein M-II represents a moiety represented by ring system M-II-2:

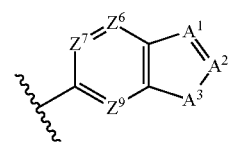

M-II-2 wherein:

$Z^6$, $Z^8$, and $Z^9$ independently represent $CR^7$;
$A^1$ and $A^2$ independently represent N or $CR^{11}$; and
$A^3$ represents $NR^{10}$; O; or S.

5. The compound of claim 2, wherein M-II represents a moiety represented by ring system M-II-6:

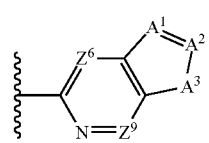

M-II-6 wherein:

$Z^6$ and $Z^9$ independently represent $CR^7$;
$A^1$ and $A^2$ independently represent N or $CR^{11}$; and
$A^3$ represents $NR^{10}$; O; or S.

6. The compound of claim 2, wherein the compound is selected from the group consisting of:

(R)—N-(2,2-dimethylquinuclidin-3-yl)benzofuran-5-carboxamide;

(R)—N-(1'-azaspiro[cyclopropane-1,2'-bicyclo[2.2.2]octan]-3'-yl)benzofuran-5-carboxamide;

(R)-2-chloro-N-(1'-azaspiro[cyclopropane-1,2'-bicyclo[2.2.2]octan]-3'-yl)benzofuran-5-carboxamide;
(R)—N-(1'-azaspiro[cyclopropane-1,2'-bicyclo[2.2.2]octan]-3'-yl)-1H-indole-6-carboxamide;
(R)—N-(1'-azaspiro[cyclopropane-1,2'-bicyclo[2.2.2]octan]-3'-yl)benzo[b]thiophene-6-carboxamide;
(R)-2-chloro-N-(1'-azaspiro[cyclopropane-1,2'-bicyclo[2.2.2]octan]-3'-yl)benzo[b]thiophene-6-carboxamide;
(R)—N-(2,2-dimethylquinuclidin-3-yl)furo[2,3-c]pyridine-5-carboxamide; and
(R)—N-(1'-azaspiro[cyclopropane-1,2'-bicyclo[2.2.2]octan]-3'-yl)furo[2,3-c]pyridine-5-carboxamide.

7. The compound of claim 1, wherein W represents the moiety represented by the ring system M-IV.

8. The compound of claim 7, wherein M-IV represents a moiety represented by one of the following:

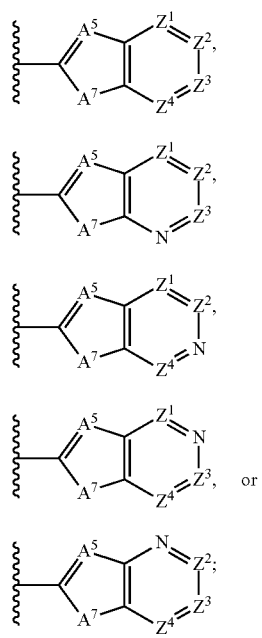

M-IV-1

M-IV-2

M-IV-3

M-IV-4

M-IV-5 wherein:
$A^5$ represents N or $CR^{15}$; and
$A^7$ represents $NR^{14}$; $N(CH_2)_m R^{14}$; O; or S.

9. The compound of claim 7, wherein the compound is selected from the group consisting of:
(R)—N-(2,2-dimethylquinuclidin-3-yl)benzo[b]thiophene-2-carboxamide;
(R)—N-(2,2-dimethylquinuclidin-3-yl)-7-fluoro-benzo[b]thiophene-2-carboxamide;
(R)-6-chloro-N-(2,2-dimethylquinuclidin-3-yl)benzo[b]thiophene-2-carboxamide;
(R)-7-chloro-N-(2,2-dimethylquinuclidin-3-yl)-6-methylbenzo[b]thiophene-2-carboxamide;
(R)—N-(2,2-dimethylquinuclidin-3-yl)-7-fluoro-6-methylbenzo[b]thiophene-2-carboxamide;
(R)—N-(1'-azaspiro[cyclopropane-1,2'-bicyclo[2.2.2]octan]-3'-yl)benzo[b]thiophene-2-carboxamide;
(R)-6-chloro-N-(1'-azaspiro[cyclopropane-1,2'-bicyclo[2.2.2]octan]-3'-yl)benzo[b]thiophene-2-carboxamide;
(R)-6-methyl-N-(1'-azaspiro[cyclopropane-1,2'-bicyclo[2.2.2]octan]-3'-yl)benzo[b]thiophene-2-carboxamide;
(R)-6-cyclopropyl-N-(1'-azaspiro[cyclopropane-1,2'-bicyclo[2.2.2]octan]-3'-yl)benzo[b]thiophene-2-carboxamide;
(R)-6-methoxy-N-(1'-azaspiro[cyclopropane-1,2'-bicyclo[2.2.2]octan]-3'-yl)benzo[b]thiophene-2-carboxamide;
(R)-6-bromo-N-(1'-azaspiro[cyclopropane-1,2'-bicyclo[2.2.2]octan]-3'-yl)benzo[b]thiophene-2-carboxamide;
(R)-7-fluoro-6-methyl-N-(1'-azaspiro[cyclopropane-1,2'-bicyclo[2.2.2]octan]-3'-yl)benzo[b]thiophene-2-carboxamide;
(R)-6,7-dichloro-N-(1'-azaspiro[cyclopropane-1,2'-bicyclo[2.2.2]octan]-3'-yl)benzo[b]thiophene-2-carboxamide;
(R)-6-chloro-7-fluoro-N-(1'-azaspiro[cyclopropane-1,2'-bicyclo[2.2.2]octan]-3'-yl)benzo[b]thiophene-2-carboxamide;
(R)-7-cyano-N-(1'-azaspiro[cyclopropane-1,2'-bicyclo[2.2.2]octan]-3'-yl)benzo[b]thiophene-2-carboxamide;
(R)-7-cyclopropyl-N-(1'-azaspiro[cyclopropane-1,2'-bicyclo[2.2.2]octan]-3'-yl)benzo[b]thiophene-2-carboxamide;
(R)—N-(1'-azaspiro[cyclopropane-1,2'-bicyclo[2.2.2]octan]-3'-yl)-7-(trifluoromethoxy)benzo[b]thiophene-2-carboxamide;
(R)-5-fluoro-6-methoxy-N-(1'-azaspiro[cyclopropane-1,2'-bicyclo[2.2.2]octan]-3'-yl)benzo[b]thiophene-2-carboxamide;
(R)-7-ethoxy-N-(1'-azaspiro[cyclopropane-1,2'-bicyclo[2.2.2]octan]-3'-yl)benzo[b]thiophene-2-carboxamide; and
(R)—N-(1'-azaspiro[cyclopropane-1,2'-bicyclo[2.2.2]octan]-3'-yl)-7-(2,2,2-trifluoroethoxy)benzo[b]thiophene-2-carboxamide.

10. The compound of claim 1, wherein:
$R^1$ and $R^2$ independently represent an unbranched $C_1$-alkyl radical and said compound is represented by Formula (II):

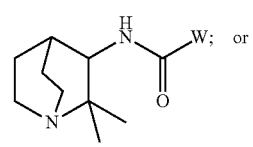

(II)

$R^1$ and $R^2$ taken together represent a $C_2$-alkyl di-radical and said compound is represented by Formula (III):

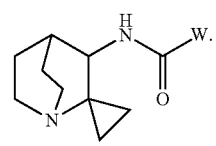

(III)

11. A pharmaceutical composition, comprising:
i) the compound, or pharmaceutically acceptable salt thereof, of claim 1; and
ii) at least one pharmaceutically acceptable carrier, excipient or diluent.

12. A method of improving cognition of a patient in need thereof, comprising: administering to the patient the compound, or pharmaceutically acceptable salt thereof, of claim 1.

13. The method of claim 12, wherein the patient suffers from a cognitive impairment, suffers from a cognitive loss associated with a cognitive impairment, or suffers from one or more symptoms associated with a cognitive impairment.

14. The method of claim 13, wherein the cognitive impairment comprises Limited Cognitive Impairment (LCI), Mild Cognitive Impairment (MCI), Alzheimer's disease, dementia of an Alzheimer's-type, schizophrenia, schizophreniform disorder, schizoaffective disorder, delusional disorder, positive symptoms of schizophrenia, negative symptoms of schizophrenia, or schizophrenia with dementia.

15. A method of treating or improving one or more symptoms associated with a cognitive disease and/or a cognitive impairment in a patient in need thereof, comprising: administering to the patient the compound, or pharmaceutically acceptable salt thereof, of claim 1.

* * * * *